(12) United States Patent
Banerjee et al.

(10) Patent No.: US 10,294,212 B2
(45) Date of Patent: May 21, 2019

(54) INHIBITORS OF THE KYNURENINE PATHWAY

(71) Applicant: CURADEV PHARMA PRIVATE LTD., Noida (IN)

(72) Inventors: Monali Banerjee, Greater Noida (IN); Sandip Middya, Greater Noida (IN); Ritesh Shrivastava, Greater Noida (IN); Sushil Raina, Noida (IN); Arjun Surya, New Delhi (IN); Dharmendra B. Yadav, Noida (IN); Veejendra K. Yadav, Kanpur (IN); Kamal Kishore Kapoor, Jammu (IN); Aranapakam Venkatesan, Rego Park, NY (US); Roger A. Smith, Chester Springs, PA (US); Scott K. Thompson, Phoenixville, PA (US)

(73) Assignee: CURADEV PHARMA, PVT. LTD., New Delhi (IN)

( * ) Notice: Subject to any disclaimer, the term of this patent is extended or adjusted under 35 U.S.C. 154(b) by 0 days.

(21) Appl. No.: 15/724,596

(22) Filed: Oct. 4, 2017

(65) Prior Publication Data
US 2018/0030026 A1    Feb. 1, 2018

Related U.S. Application Data

(62) Division of application No. 14/774,383, filed as application No. PCT/US2014/024920 on Mar. 12, 2014, now Pat. No. 9,815,811.

(60) Provisional application No. 61/782,841, filed on Mar. 14, 2013.

(51) Int. Cl.
| | |
|---|---|
| C07D 333/66 | (2006.01) |
| C07D 307/82 | (2006.01) |
| C07D 491/04 | (2006.01) |
| C07D 495/04 | (2006.01) |
| A61K 31/343 | (2006.01) |
| A61K 31/381 | (2006.01) |
| A61K 31/4355 | (2006.01) |
| A61K 31/4365 | (2006.01) |
| A61K 31/4436 | (2006.01) |
| A61K 31/444 | (2006.01) |
| A61K 31/4545 | (2006.01) |
| A61K 31/5377 | (2006.01) |
| A61K 31/704 | (2006.01) |
| C07D 409/04 | (2006.01) |
| C07D 409/12 | (2006.01) |
| C07D 491/048 | (2006.01) |
| C12Q 1/26 | (2006.01) |

(52) U.S. Cl.
CPC .......... *C07D 333/66* (2013.01); *A61K 31/343* (2013.01); *A61K 31/381* (2013.01); *A61K 31/4355* (2013.01); *A61K 31/4365* (2013.01); *A61K 31/444* (2013.01); *A61K 31/4436* (2013.01); *A61K 31/4545* (2013.01); *A61K 31/5377* (2013.01); *A61K 31/704* (2013.01); *C07D 307/82* (2013.01); *C07D 409/04* (2013.01); *C07D 409/12* (2013.01); *C07D 491/04* (2013.01); *C07D 491/048* (2013.01); *C07D 495/04* (2013.01); *C12Q 1/26* (2013.01); *G01N 2333/90241* (2013.01); *Y02A 50/411* (2018.01)

(58) Field of Classification Search
CPC .................................................. C07D 333/66
See application file for complete search history.

(56) References Cited

U.S. PATENT DOCUMENTS

| | | | |
|---|---|---|---|
| 9,059,412 | B2 | 6/2015 | Zeng et al. |
| 2007/0275962 | A1 | 11/2007 | Koul et al. |
| 2010/0125073 | A1 | 5/2010 | Weber et al. |
| 2012/0178748 | A1 | 7/2012 | Campbell et al. |

FOREIGN PATENT DOCUMENTS

| | | |
|---|---|---|
| WO | 9116325 | 10/1991 |
| WO | 9116325 A1 | 10/1991 |
| WO | 95/05079 | 2/1995 |
| WO | 2004/094409 | 11/2004 |
| WO | 2004094409 A1 | 11/2004 |
| WO | 2009073620 A2 | 6/2009 |
| WO | 2012/142237 | 10/2012 |

OTHER PUBLICATIONS

The Japanese Office Action, dated Mar. 13, 2018, in the related Japanese Patent Appl. No. 2016-501679.
Dash, B. et al., Mass spectrometry of some heterocytes, Journal of Teaching and Research in Chemistry, 1 9 9 4, vol. 1 No. 1, pp. 17-24.
Panda, D. et al., Synthesis of 2-amino-3-(2'-pyridylamino)benzofuran and kinetics of its rearrangement in the presence of akali and iron(III), Indian Journal of Chemistry, Section B: Organic Chemistry including Medicinal Chemistry , 1987, vol. 26B, No. 5, pp. 431-435.

(Continued)

*Primary Examiner* — David K O'Dell

(57) ABSTRACT

The present application provides novel inhibitors of indoleamine 2,3-dioxygenase-1 and/or indoleamine 2,3-dioxygenase-2 and/or tryptophan 2,3-dioxygenase, metabolites thereof, and pharmaceutically acceptable salts or prodrugs thereof. Also provided are methods for preparing these compounds. A therapeutically effective amount of one or more of the compounds of formula (I) is useful in treating diseases resulting from dysregulation of the kynurenine pathway. Compounds of formula (I) act by inhibiting the enzymatic activity or expression of indoleamine 2,3-dioxygenase-1 and/or indoleamine 2,3-dioxygenase-2 and/or tryptophan 2,3-dioxy-genase.

12 Claims, 2 Drawing Sheets

(56) References Cited

OTHER PUBLICATIONS

Cannizzo, Sergio et al., "Synthesis of substituted [1]benzothieno[2,3-b]pyrazines," Journal of Heterocyclic Chemistry, 1 9 9 0, vol. 27 No. 7, pp. 2175-2179.
Basavaraj, K. M. et al., "Synthesis and antimicrobial activity of some 3-methoxybenzofuran-2-carbamates and carbamides," Indian Journal of Heterocyclic Chemistry, 2 0 0 2, vol. 12 No. 1, pp. 1-4.
Wieland,et al., "Furoxane (II). Decomposition of furoxanedicarboxylic ester (glyoximeperoxidedicarboxylic ester)," Justus Liebigs Annalender Chemie, 1 9 0 9, vol. 367, pp. 52-79.
STN Registry No. 1379248-92-6, entered STN: Jun. 17, 2012.
STN Registry No. 202207-27-0, entered STN: Jun. 17, 2012.
STN Registry No. 33343-52-5, entered STN: Apr. 27, 2001.
Stone, T. W., Development and therapeutic potential of kynurenic acid and kynurenine derivatives for neuroprotection, Trends in Pharmacological Sciences, 2000, vol. 21 No. 4, pp. 149-154.
The Chinese Office Action, dated Sep. 9, 2016, in the related Chinese Appl. No. 201480028224.1.
STN-Registry Database, CAS RN:1384929-29-6, published on Jul. 31, 2012.
The Singapore Search Report and Written Opinion, dated Oct. 24, 2016, in the related Singapore Patent Appl. No. 11201507395P.
Guerrera et al., "Synthesis of 1H-Imidazo[3',4':4,5]thieno[2,3-b]pyridines. A New Ring System" Journal of Heterocyclic Chemistry 21(2):587-589 (Jul. 4, 1984).
The extended European Search Report, dated Jul. 1, 2016, in the corresponding European Patent Application No. 14797295.4.
D1: Lipunov M M et al: "Synthesis and reactivity of thieno[2,3-b]pyridine-2,3-diamines", Chemistry of Heterocyclic Compounds, Kluwer Academic Publishers—Plenum Publishers, NL, vol. 43, No. 9, Sep. 1, 2007 (Sep. 1, 2007), pp. 1189-1196, XP019550155.
D3: Database Caplus [Online] Chemical Abstracts Service, Columbus, Ohio, US; Dash, B. et al: "Mass spectrometry of some heterocycles", retrieved from STN Database accession No. 1995:57607 ; & Dash, B. et al: "Mass spectrometry of some heterocycles", Journal of Teaching and Research in Chemistry ( 1994 ), 1(1), 17-24.
D4: Database Caplus [Online] Chemical Abstracts Service; Columbus, Ohio, US; Toselli, Maurizio et al: "Thermal reactivity of 2-azido- and 3-azidobenzo[b]thiophene with dialkylarnines and alkanethiols", retrieved from STN Database accession No. 1990:118080 ; & Tosseli, Maurizio et al; "Thermal reactivity of 2-azido- and 3-azidobenzo[b]thiophene with dialkylamines and alkanethiols", Gazzetta Chimica Italiana ( 1989 ), 119(7), 411-13.
D5: Database Caplus [Online] Chemical Abstracts Service, Columbus, Ohio, US; Guerrera, Francesco et al: "A comparative study on the synthesis of the 1H[1] benzothieno[2,3-d]imidazole and 1H[1]benzothieno[2,3-d]-vtriazole", retrieved from STN Database accession No. 1987:84504 ; & Guerrera, Francesco et al: "A comparative study on the synthesis of the 1H[1]benzothieno[2,3-d]imidazole and 1 H[1]benzothieno[2,3-d]-v-triazole", Journal of Heterocyclic Chemistry ( 1986 ), 23(3), 951-3.
D6: Database Caplus [Online] Chemical Abstracts Service, Columbus, Ohio, US; Galvez, Carmen et al: "New routes to condensed thiophene ring systems from orthodiaminothiophene derivatives", retrieved from STN Database accession No. 1986:168301 ; & Galvez, Carmen et al: "New routes to condensed thiophene ring systems from orthodiaminothiophene derivatives", Journal of Chemical Research, Synopses ( 1985 ), (9), 296-7.
D7: Database Caplus [Online] Chemical Abstracts Service, Columbus, Ohio, US; Yoshino, Akio et al: "Crystal and molecular structure of the intermediate compound obtained in cyanide reaction of pyridoxal", retrieved from STN Database accession No. 1970:137515 ; & Yoshino, Akio et al: "Crystal and molecular structure of the intermediate compound obtained in cyanide reaction of pyridoxal", Acta Crystallographica, Section B: Structural Crystallography and Crystal Chemistry ( 1970 ), 26. (PT. 4), 394-402.
D8: Database Caplus [Online] Chemical Abstracts Service, Columbus, Ohio, US; Wieland et al: "Furoxane (H). Decomposition of Furoxanedicarboxylic Ester (Glyoximeperoxidedicarboxylic Ester)", retrieved from STN Database accession No. 1909:15872 ; & Wieland, H. et al: "Furoxane (H). Decomposition of Furoxanedicarboxylic Ester (Glyoximeperoxidedicarboxylic Ester)", Justus Liebigs Annalen Der Chemie ( 1909 ), 367, 52-79.
D9: Database Caplus [Online] Chemical Abstracts Service, Columbus, Ohio, US; Luk'yanchuk, V. D. et al: "Synthesis and study of the antioxidant properties of 5-hydroxy-4,6,7-trimethylbenzofurans", retrieved from STN Database accession No. 1991:101575 ; & Luk'yanchuk, V.D. et al: "Synthesis and study of the antioxidant properties of 5-hydroxy-4,6,7-trimethylbenzofurans", Farmatsevtichnii Zhurnal (KIEV) ( 1990 ), (5), 64-5.
D11: Database Caplus [Online] Chemical Abstracts Service, Columbus, Ohio, US; Cannizzo, Sergio et al; "Synthesis of substituted [1] benzothieno[2,3-b]pyrazines", retrieved from STN Database accession No. 1991:143350 ; & Cannizzo, Sergio et al: "Synthesis of substituted [1]benzothieno[2,3-b]pyrazines", Journal of Heterocyclic Chemistry ( 1990 ), 27(7), 2175-9.
D14: Stone T W: "Development and therapeutic potential of kynurenic acid and kynurenine derivatives for neuroprotection", Trends in Pharmacological Sciences, Elsevier, Haywarth, GB, vol. 21, No. 4, Apr. 1, 2000 (Apr. 1, 2000), pp. 149-154, XP004196017.
The Chinese Office Action, dated Jun. 19, 2017, in the related Chinese Appl. No. 201480028224.1.
Extracts from the STN-Registry Database, published on Jul. 31, 2012. (7 pages.).
The Indian Examination Report, dated Dec. 26, 2018, in the related Indian Appl. No. 5547/CHENP/2015.

INHIBITORS OF THE KYNURENINE PATHWAY

CROSS REFERENCE TO RELATED APPLICATIONS

This application is a Divisional of U.S. patent application Ser. No. 14/774,383, filed Sep. 10, 2015, which is a National Stage Application of PCT/US2014/024920, filed Mar. 12, 2014, which claims the benefit of U.S. Provisional Application Ser. No. 61/782,841, filed on Mar. 14, 2013, all of which are hereby incorporated by reference herein in their entireties.

FIELD OF INVENTION

The application generally relates to pharmaceutical compounds that regulate enzymes indoleamine 2,3-dioxygenase-1 and/or indoleamine 2,3-dioxygenase-2 and/or tryptophan 2,3-dioxygenase and are useful for the treatment of diseases and conditions with altered levels of the amino acid L-tryptophan and metabolites of the kynurenine pathway.

BACKGROUND

The essential amino acid Tryptophan (Trp) is catabolized through the kynurenine (KYN) pathway. The initial rate-limiting step in the kynurenine pathway is performed by heme-containing oxidoreductase enzymes, including tryptophan 2,3-dioxygenase (TDO), indoleamine 2,3-dioxygenase 1 (IDO1), and indoleamine 2,3-dioxygenase 2 (IDO2). IDO1 and IDO2 share very limited homology with TDO at the amino acid level and, despite having different molecular structures, each enzyme has the same biochemical activity in that they each catalyze tryptophan to form N-formylkynurenine. IDO1, IDO2, and/or TDO activity alter local tryptophan concentrations, and the build-up of kynurenine pathway metabolites due to the activity of these enzymes can lead to numerous conditions associated with immune suppression.

IDO1 and TDO are implicated in the maintenance of immunosuppressive conditions associated with the persistence of tumor resistance, chronic infection, HIV infection, malaria, schizophrenia, depression as well as in the normal phenomenon of increased immunological tolerance to prevent fetal rejection in utero. Therapeutic agents that inhibit IDO1, IDO2, and TDO activity can be used to modulate regulatory T cells and activate cytotoxic T cells in immunosuppressive conditions associated with cancer and viral infection (e.g. HIV-AIDS, HCV). The local immunosuppressive properties of the kynurenine pathway and specifically IDO1 and TDO have been implicated in cancer. A large proportion of primary cancer cells have been shown to overexpress IDO1. In addition, TDO has recently been implicated in human brain tumors.

The earliest experiments had proposed an anti-microbial role for IDO1, and suggested that localized depletion of tryptophan by IDO1 led to microbial death (Yoshida et al., Proc. Natl. Acad. Sci. USA, 1978, 75(8):3998-4000). Subsequent research led to the discovery of a more complex role for IDO1 in immune suppression, best exemplified in the case of maternal tolerance towards the allogeneic fetus where IDO1 plays an immunosuppressive role in preventing fetal rejection from the uterus. Pregnant mice dosed with a specific IDO1 inhibitor rapidly reject allogeneic fetuses through induction of T cells (Munn et al., Science, 1998, 281(5380):1191-3). Studies since then have established IDO1 as a regulator of certain disorders of the immune system and have discovered that it plays a role in the ability of transplanted tissues to survive in new hosts (Radu et al., Plast. Reconstr. Surg., 2007 June, 119(7):2023-8). It is believed that increased IDO1 activity resulting in elevated kynurenine pathway metabolites causes peripheral and ultimately, systemic immune tolerance. In-vitro studies suggest that the proliferation and function of lymphocytes are exquisitely sensitive to kynurenines (Fallarino et al., Cell Death and Differentiation, 2002, 9(10):1069-1077). The expression of IDO1 by activated dendritic cells suppresses immune response by mechanisms that include inducing cell cycle arrest in T lymphocytes, down regulation of the T lymphocyte cell receptor (TCR) and activation of regulatory T cells (T-regs) (Terness et al., J. Exp. Med., 2002, 196(4):447-457; Fallarino et al., J. Immunol., 2006, 176(11):6752-6761).

IDO1 is induced chronically by HIV infection and in turn increases regulatory T cells leading to immunosuppression in patients (Sci. Transl. Med., 2010; 2). It has been recently shown that IDO1 inhibition can enhance the level of virus specific T cells and concomitantly reduce the number of virus infected macrophages in a mouse model of HIV (Potula et al., 2005, Blood, 106(7):2382-2390). IDO1 activity has also been implicated in other parasitic infections. Elevated activity of IDO1 in mouse malaria models has also been shown to be abolished by in vivo IDO1 inhibition (Tetsutani K., et al., Parasitology. 2007 7:923-30.

More recently, numerous reports published by a number of different groups have focused on the ability of tumors to create a tolerogenic environment suitable for survival, growth and metastasis by activating IDO1 (Prendergast, Nature, 2011, 478(7368):192-4). Studies of tumor resistance have shown that cells expressing IDO1 can increase the number of regulatory T cells and suppress cytotoxic T cell responses thus allowing immune escape and promoting tumor tolerance.

Kynurenine pathway and IDO1 are also believed to play a role in maternal tolerance and immunosuppressive process to prevent fetal rejection in utero (Munn et al., Science, 1998, 281(5380):1191-1193). Pregnant mice dosed with a specific IDO1 inhibitor rapidly reject allogeneic fetuses through suppression of T cells activity (Munn et al., Science, 1998, 281(5380):1191-1193). Studies since then have established IDO1 as a regulator of immune-mediated disorders and suggest that it plays a role in the ability of transplanted tissues to survive in new hosts (Radu et al., Plast. Reconstr. Surg., 2007 June, 119(7):2023-8).

The local immunosuppressive properties of the kynurenine pathway and specifically IDO1 and TDO have been implicated in cancer. A large proportion of primary cancer cells overexpress IDO1 and/or TDO (Pilotte et al., Proc. Natl. Acad. Sci. USA, 2012, Vol. 109(7):2497-2502). Several studies have focused on the ability of tumors to create a tolerogenic environment suitable for survival, growth and metastasis by activating IDO1 (Prendergast, Nature, 2011, 478:192-4). Increase in the number of T-regs and suppression of cytotoxic T cell responses associated with dysregulation of the Kynurenine pathway by overexpression of IDO1 and/or TDO appears to result in tumor resistance and promote tumor tolerance.

Data from both clinical and animal studies suggest that inhibiting IDO1 and/or TDO activity could be beneficial for cancer patients and may slow or prevent tumor metastases (Muller et al., Nature Medicine, 2005, 11(3):312-319; Brody et al., Cell Cycle, 2009, 8(12):1930-1934; Witkiewicz et al., Journal of the American College of Surgeons, 2008, 206: 849-854; Pilotte et al., Proc. Natl. Acad. Sci. USA, 2012, Vol. 109(7):2497-2502). Genetic ablation of the IDO1 gene in mice (IDO1−/−) resulted in decreased incidence of DMBA-induced premalignant skin papillomas (Muller et al., PNAS, 2008, 105(44):17073-17078). Silencing of IDO1 expression by siRNA or a pharmacological IDO1 inhibitor 1-methyl tryptophan enhanced tumor-specific killing (Clin. Cancer Res., 2009, 15(2). In addition, inhibiting IDO1 in tumor-bearing hosts improved the outcome of conventional chemotherapy at reduced doses (Clin. Cancer Res., 2009, 15(2)). Clinically, the pronounced expression of IDO1 found in several human tumor types has been correlated with negative prognosis and poor survival rate (Zou, Nature Rev. Cancer, 2005, 5:263-274; Zamanakou et al., Immunol. Lett. 2007, 111(2):69-75). Serum from cancer patients has higher kynurenine/tryptophan ratio, a higher number of circulating T-regs, and increased effector T cell apoptosis when compared to serum from healthy volunteers (Suzuki et al., Lung Cancer, 2010, 67:361-365). Reversal of tumoral immune resistance by inhibition of tryptophan 2,3-dioxygenase has been studied by Pilotte et al. (Pilotte et al., Proc. Natl. Acad. Sci. USA, 2012, Vol. 109(7):2497-2502). Thus, decreasing the rate of kynurenine production by inhibiting IDO1 and/or TDO may be beneficial to cancer patients.

IDO1 and IDO2 are implicated in inflammatory diseases. IDO1 knock-out mice don't manifest spontaneous disorders of classical inflammation and existing kown small molecule inhibitors of IDO do not elicit generalized inflammatory reactions (Prendergast et al. Curr Med Chem. 2011; 18(15): 2257-62). Rather, IDO impairment alleviates disease severity in models of skin cancers promoted by chronic inflammation, inflammation-associated arthritis and allergic airway disease. Moreover, IDO2 is a critical mediator of autoantibody production and inflammatory pathogenesis in autoimmune arthritis. IDO2 knock-out mice have reduced joint inflammation compared to wild-type mice due to decreased pathogenic autoantibodies and Ab-secreting cells (Merlo et al. J. Immunol. (2014) vol. 192(5) 2082-2090). Thus, inhibitors of IDO1 and IDO2 are useful in the treatment of arthritis and other inflammatory diseases.

Kynurenine pathway dysregulation and IDO1 and TDO play an important role in the brain tumors and are implicated in inflammatory response in several neurodegenerative disorders including multiple sclerosis, Parkinson's disease, Alzheimer's disease, stroke, amyotrophic lateral schlerosis, dementia (Kim et al., J. Clin. Invest, 2012, 122(8):2940-2954; Gold et al., J. Neuroinflammation, 2011, 8:17; Parkinson's Disease, 2011, Volume 2011). Immunosuppression induced by IDO1 activity and the Kynurenine metabolites in the brain may be treated with inhibitors of IDO1 and/or TDO. For example, circulating T-reg levels were found to be decreased in patient with glioblastoma treated with anti-viral agent inhibitors of IDO1 (Soderlund, et al., J. Neuroinflammation, 2010, 7:44).

Several studies have found Kynurenine pathway metabolites to be neuroactive and neurotoxic. Neurotoxic kynurenine metabolites are known to increase in the spinal cord of rats with experimental allergic encephalomyelitis (Chiarugi et al., Neuroscience, 2001, 102(3):687-95). The neurotoxic effects of Kynurenine metabolites is exacerbated by increased plasma glucose levels. Additionally, changes in the relative or absolute concentrations of the kynurenines have been found in several neurodegenerative disorders, such as Alzheimer's disease, Huntington's disease and Parkinson's disease, stroke and epilepsy (Németh et al., Central Nervous System Agents in Medicinal Chemistry, 2007, 7:45-56; Wu et al. 2013; PLoS One; 8(4)).

Neuropsychiatric diseases and mood disorders such as depression and schizophrenia are also said to have IDO1 and Kynurenine dysregulation. Tryptophan depletion and defficiency of neurotransmitter 5-hydroxytryptamine (5-HT) leads to depression and anxiety. Increased IDO1 activity decreases the synthesis of 5-HT by reducing the amount of Tryptopan availability for 5-HT synthesis by increasing Tryp catabolism via the kynurenine pathway (Plangar et al. (2012) Neuropsychopharmacol Hung 2012; 14(4): 239-244). Increased IDO1 activity and levels of both kynurenine and kynurenic acid have been found in the brains of deceased schizophrenics (Linderholm et al., Schizophrenia Bulletin (2012) 38: 426-432)). Thus, inhibition of IDO1, IDO1, and TDO may also be an important treatment strategy for patients with neurological or neuropsychiatric disease or disorders such as depression and schizophrenia as well as insomnia.

Kynurenine pathway dysregulation and IDO1 and/or TDO activity also correlate with cardiovascular risk factors, and kynurenines and IDO1 are markers for Atherosclerosis and other cardiovascular heart diseases such as coronary artery disease (Platten et al., Science, 2005, 310(5749):850-5, Wirlietner et al. Eur J Clin Invest. 2003 Jul. 1; 33(7):550-4) in addition to kidney disease. The kynurenines are associated with oxidative stress, inflammation and the prevalence of cardiovascular disease in patients with end-stage renal disease (Pawlak et al., Atherosclerosis, 2009, (204)1:309-314). Studies show that kynurenine pathway metabolites are associated with endothelial dysfunction markers in the patients with chronic kidney disease (Pawlak et al., Advances in Medical Sciences, 2010, 55(2):196-203).

There is a need in the art for compounds that are inhibitors of the indoleamine 2,3-dioxygenase-1 and/or indoleamine 2,3-dioxygenase-2 and/or tryptophan 2,3-dioxygenase pathway, as well as for methods for treating diseases that can benefit from such inhibition.

SUMMARY OF THE INVENTION

In one aspect, the present invention provides a compound of formula (I) or a metabolite thereof, or a pharmaceutically acceptable salt or prodrug thereof, wherein $X^1$-$X^4$, Y, and Z are defined herein.

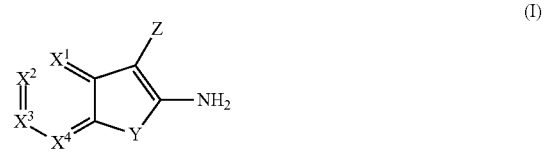

In another aspect, compounds of formulae (I-A), (I-AA), (I-AAA), (I-B), (I-BB), (I-BBB), (I-BBBB), (I-BBBBB), (I-BBBBBB), (I-C), (I-CC), (I-D), (I-DD), (I-E), (I-EE), (I-F), (I-FF), (I-G) and (I-GG) are provided, wherein $X^1$-$X^4$, $R^1$, $R^2$, $R^3$, $R^4$, $R^5$ and $R^6$ are defined herein.

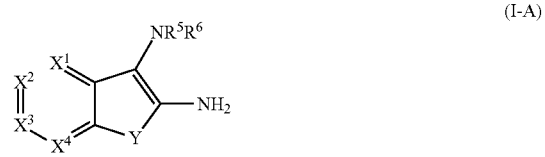

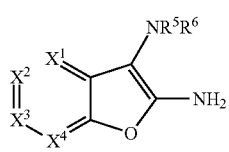 (I-AA)
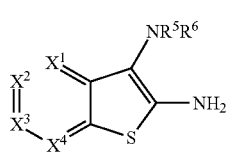 (I-AAA)
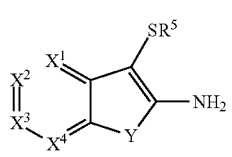 (I-B)
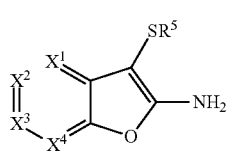 (I-BB)
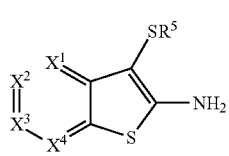 (I-BBB)
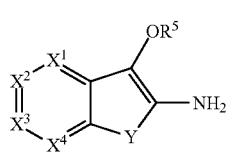 (I-BBBB)
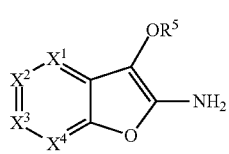 (I-BBBBB)
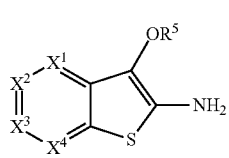 (I-BBBBBB)
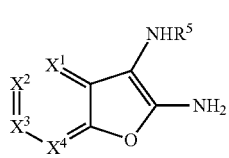 (I-C)
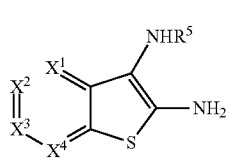 (I-CC)
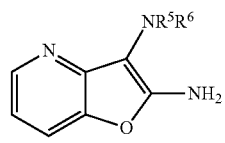 (I-D)
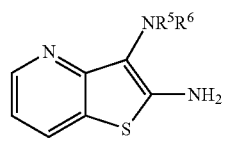 (I-DD)
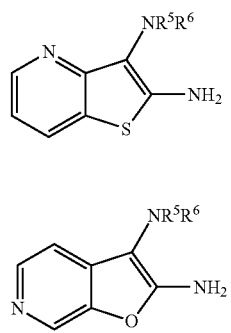 (I-E)
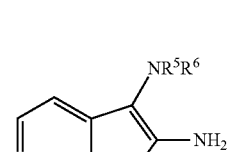 (I-EE)
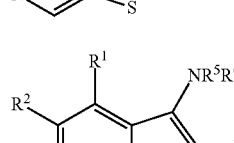 (I-F)
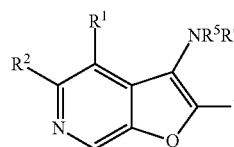 (I-FF)
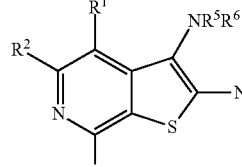 (I-G)
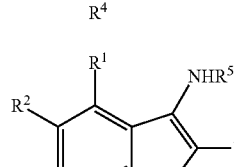 (I-GG)
In another aspect, the invention relates to prodrugs of compounds of formula (I) having a formula (II), (III) or (IV) are provided, wherein $R^9$-$R^{11}$ are defined herein

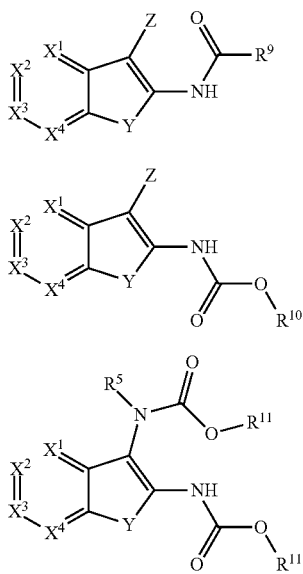

In one aspect, the invention relates to a metabolite of a compound of formula (I)-(IV) or a prodrug of said compound of formula (I), or a pharmaceutically acceptable salt or a prodrug thereof.

In a further aspect, a composition comprising a compound or prodrug thereof as described herein and a pharmaceutically acceptable carrier is provided.

In another aspect, a composition comprising a metabolite of a compound of formula (I)-(IV) or prodrug thereof as described herein and a pharmaceutically acceptable carrier is provided, In yet another aspect, a kit comprising a compound of formula (I) or a metabolite thereof, or a pharmaceutically acceptable salt or prodrug thereof described herein is provided.

In another aspect, a method for treating a disease treatable by inhibiting a kynurenine pathway is provided and includes administering a compound or a metabolite thereof, or a pharmaceutically acceptable salt or prodrug thereof to a subject in need thereof. In another aspect, a method for regulating a kynurenine pathway is provided and includes administering a compound or a metabolite thereof, or a pharmaceutically acceptable salt or prodrug thereof as described herein to a subject in need thereof.

In another aspect, a method of regulating one or more of a indoleamine 2,3-dioxygenase-1 or an indoleamine 2,3-dioxygenase-2 or a tryptophan 2,3-dioxygenase enzymes is provided and includes administering a compound of formula (I) or a metabolite thereof, or a pharmaceutically acceptable salt or prodrug thereof as described herein to a subject in need thereof. In another aspect, the regulating is inhibiting the kynurenine pathway or one or more of the enzymes.

In still a further aspect, a method of regulating the kynurenine pathway by inhibiting indoleamine 2,3-dioxygenase-1 and/or indoleamine 2,3-dioxygenase-2 and/or tryptophan 2,3-dioxygenase is provided and includes administering a compound or a metabolite thereof, or or a pharmaceutically acceptable salt or prodrug thereof as described herein to a subject in need thereof.

In one aspect, a method of reducing kynurenine pathway metabolites is provided and includes administering a compound or a metabolite thereof, or a pharmaceutically acceptable salt or prodrug thereof as described herein to a subject in need thereof.

In another aspect, a method of altering tryptophan levels in a subject and includes administering a compound of formula (I) or a metabolite thereof, or a pharmaceutically acceptable salt or prodrug thereof described herein is provided. In one aspect, the tryptophan levels are increased. In another aspect, kynurenine/tryptophan ratio is decreased.

In one aspect, a method of treating a disease associated with or resulting from dysregulation of a kynurenine pathway is provided and includes administering a compound of formula (I) or a metabolite thereof, or a pharmaceutically acceptable salt or prodrug thereof as described herein to a subject in need thereof.

In another aspect, a method for treating a disease caused by the dysregulation of the kynurenine pathway by inhibiting indoleamine 2,3-dioxygenase-1 and/or indoleamine 2,3-dioxygenase-2 and/or tryptophan 2,3-dioxygenase is provided and includes administering a compound or a pharmaceutically acceptable salt or prodrug thereof described herein to a subject in need thereof.

In yet another aspect, a method for treating a disease caused by activation of indoleamine 2,3-dioxygenase-1 or tryptophan 2,3-dioxygenase or both enzymes is provided and includes administering a compound of formula (I) or a metabolite thereof, or a pharmaceutically acceptable salt or prodrug thereof as described herein to a subject in need thereof. In yet another aspect, a method for treating a disease caused by activation of indoleamine 2,3-dioxygenase-2 or tryptophan 2,3-dioxygenase enzymes or both is provided and includes administering a compound of formula (I) or a metabolite thereof, or a pharmaceutically acceptable salt or prodrug thereof as described herein to a subject in need thereof.

In yet another aspect, a method for treating a disease caused by activation of indoleamine 2,3-dioxygenase-1 or indoleamine 2,3-dioxygenase-2 or both is provided and includes administering a compound of formula (I) or a metabolite thereof, or a pharmaceutically acceptable salt or prodrug thereof as described herein to a subject in need thereof.

In another aspect, a method of inhbiting activation of one or more of indoleamine 2,3-dioxygenase-1 or indoleamine 2,3-dioxygenase-2 or tryptophan 2,3-dioxygenase enzymes is provided and includes administering a compound of formula (I) or a metabolite thereof, or a pharmaceutically acceptable salt or prodrug thereof as described herein to a subject in need thereof In another aspect, a method for treating a disease associated with one or more of indoleamine 2,3-dioxygenase-1 or indoleamine 2,3-dioxygenase-2 or tryptophan 2,3-dioxygenase enzymes is provided and includes administering a compound of formula (I) or a metabolite thereof, or a pharmaceutically acceptable salt or prodrug thereof described herein to a subject in need thereof.

In yet a further aspect, a method is provided for treating a disease characterized by abnormal immune suppression resulting from dysregulation of a kynurenine pathway and includes administering a compound of formula (I) or a metabolite thereof, or a pharmaceutically acceptable salt or prodrug thereof described herein to a subject in need thereof.

In a further aspect, a method for regulating a disease characterized by abnormal immune suppression resulting from a dysregulated kynurenine due to activation any one or more of indoleamine 2,3-dioxygenase-1 or indoleamine 2,3-dioxygenase-2 or tryptophan 2,3-dioxygenase enzyme is provided and includes administering a compound, a metabolite thereof or a pharmaceutically acceptable salt or prodrug thereof as described herein to a subject in need thereof.

In one aspect, a method of treating immune suppression is provided and includes administering a compound or a metabolite thereof, or a pharmaceutically acceptable salt or prodrug thereof as described herein to a subject in need thereof In another aspect, the immune suppression is associated with increased kynurenine metabolite levels or enzymatic activity of one or more of indoleamine 2,3-dioxygenase-1 or indoleamine 2,3-dioxygenase-2 or tryptophan 2,3-dioxygenase enzymes. In yet another aspect, a method is provided for treating immune suppression associated with one or more of indoleamine 2,3-dioxygenase-1 or indoleamine 2,3-dioxygenase-2 or tryptophan 2,3-dioxygenase enzymes and includes administering a compound or a metabolite thereof, or a pharmaceutically acceptable salt or prodrug thereof to a subject in need thereof Thus, in an aspect, compounds of the invention for use in treatment of immunosuppression associated with one or more of indoleamine 2,3-dioxygenase-1 or indoleamine 2,3-dioxygenase-2 or tryptophan 2,3-dioxygenase enzymes are provided.

In yet another aspect, a method for treating immune suppression through inhibiting enzymatic activity of indoleamine 2,3-dioxygenase and/or tryptophan 2,3-dioxygenase is provided and includes administering a compound or a metabolite thereof, or a pharmaceutically acceptable salt or prodrug thereof described herein to a subject in need thereof In yet another aspect, a method of reducing or eliminating an immune mediated disorder is provided and includes administering a compound of formula (I)-(IV) or a metabolite thereof, or a pharmaceutically acceptable salt or prodrug thereof described herein to a patient.

In yet another aspect, a method of inhibiting an autoimmune reaction or autoimmune antibody production in a subject is provided and includes administering a compound or a metabolite thereof; or a pharmcetucially acceptable salt or prodrug thereof as described to a subject in need thereof. In another aspect, a method of inhibiting autoimmune reaction or autoimmune antibody production is inhibited by (i) inhibiting indoleamine 2,3-dioxygenase-2 or (ii) reducing kynurenine metabolites, and includes administering a compound or a metabolite thereof, or a pharmcetucially acceptable salt or prodrug thereof as described to a subject in need thereof. In one aspect, the foregoing reduction in autoimmune reaction or autoimmune antibody production is associated with inflammatory diseases, cancer or autoimminc disorders.

In one aspect, the list of diseases comprise cancer, bacterial infection, viral infection, parasitic infection, immune-mediated disorder, autoimmune disorder, inflammatory disease, central nervous system disease, peripheral nervous system disease, neurodegenerative disease, mood disorder, sleep disorder, cerebrovascular disease, peripheral artery disease, or cardiovascular disease. In another aspect, all foregoing methods comprise administration of one or more therapeutic agent or therapy. In one aspect, the therapeutic agent is a chemotherapeutic agent selected from a group further comprising a cancer vaccine, a targeted drug, a targeted antibody, an antibody fragment, an antimetabolite, an antineoplastic, an antifolate, a toxin, an alkylating agent, a DNA strand breaking agent, a DNA minor groove binding agent, a pyrimidine analog, a purine analog, a ribonucleotide reductase inhibitor, a tubulin interactive agent, an anti-hormonal agent, an immunomoldulator, an anti-adrenal agent, a cytokine, a radiation therapy, a cell therapy, or a hormone therapy.

In another aspect, a method of treating depression, Alzheimer's disease, dementia, schizophrenia, HIV inection, malaria, rheumatoid arthritis, insomnia or multiple sclierosis is provided and include administering a compound or a metabolite thereof; or a pharmaceutically acceptable salt or prodrug thereof described herein to a patient.

In one aspect, the disease is cancer. In another aspect, cancer disease is a cancer of squamous cell, peritoneum, prostate, head, neck, eye, mouth, throat, esophagus, bronchus, larynx, pharynx, thyroid cancer, chest, bone, lungs, colon, rectum, stomach, urinary bladder, gall bladder, uterus, cervix, breast, ovaries, uterus, vagina, vulva, testicles, penis, anus, skin, thyroid, blood, lymph nodes, kidney, liver, intestines, salivary gland, pancreas, brain, spine, adrenal gland, skin or leukemia. In another aspect, a method of treating tumor resistance is provided comprising administering a compound or a metabolite thereof; or a pharmaceutically acceptable salt or prodrug thereof described herein to a patient.

In another aspect, the viral infection is HIV infection. In another aspect, parasite infection is malaria or Leishmaniasis.

In another aspect, a method of preparing a compound of formula (I-C) is provided as described herein. In another aspect, compounds obtainable by the method of preparing a compound of formula (I-C) are provided.

In yet another aspect, a method for diagnosing and treating a disease associated with kynurenine pathway or one or more of indoleamine 2,3-dioxygenase-1 or an indoleamine 2,3-dioxygenase-2 or a tryptophan 2,3-dioxygenase enzymes in a subject is provided and includes: (i) assaying a blood and/or tissue sample from a subject; (ii) determining the subject's blood and/or tissue tryptophan or Kynurenine concentration or both in the sample; (iii) optionally determining the subject's Kynurnine/tryptophan ratio; and (iv) administering a compound or a metabolite thereof, or a pharmaceutically acceptable salt or prodrug thereof described herein to a subject.

In still another aspect, a method of monitoring a disease associated with kynurenine pathway or one or more of indoleamine 2,3-dioxygenase-1 or an indoleamine 2,3-dioxygenase-2 or a tryptophan 2,3-dioxygenase enzymes in a subject is provided and includes (i) dosing a subject having a disease associated with kynurenine pathway with a compound, (ii) analyzing a blood or tissue samples or both at one or more time points or continuously during a treatment regimen, (iii) determining a tryptophan and a kynurenine concentration in the blood or the tissue sample or both, (iv) optionally determining the subject's kynumine/tryptophan ratio, and (v) adjusting the treatment regimen or dosage of the compound.

In a further aspect, a method for diagnosing and treating a disease associated with kynurenine pathway or one or more of indoleamine 2,3-dioxygenase-1 or an indoleamine 2,3-dioxygenase-2 or a tryptophan 2,3-dioxygenase enzymes in a patient is provided and includes (i) analyzing a patient sample for the presence or absence of altered kynurenin/tryptophan ratio, wherein the patient is diagnosed with a disease associated with kynurenine pathway if altered kynurenine/tryptophan ratio is detected and (ii) administering a compound to the diagnosed patient.

In still a further aspect, a method for treating a disease associated with kynurenine pathway or one or more of an indoleamine 2,3-dioxygenase-1 or an indoleamine 2,3-dioxygenase-2 or a tryptophan 2,3-dioxygenase enzyme in a patient and includes (i) requesting a test providing the results of an analysis to determine whether the patient's kynurnine levels are altered, and (ii) administering a compound to the patient if the patient's kynurenine levels are altered.

In yet another aspect, a use of foregoing methods is provided wherein the disease is cancer, bacterial infection, viral infection, parasitic infection, immune-mediated disorder, autoimmune disorder, inflammatory disease, central nervous system disease, peripheral nervous system disease, neurodegenerative disease, mood disorder, sleep disorder, cerebrovascular disease, peripheral artery disease, or cardiovascular disease.

Other aspects and advantages of the invention will be readily apparent from the following detailed description of the invention.

DETAILED DESCRIPTION OF THE INVENTION

Definitions

Figure 1:
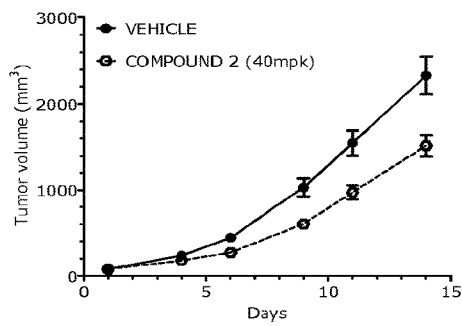
FIG. 1(a). Shows the mean tumor growth rate of CT-26 tumor cells in Balb/c mice when dosed orally BID with either test compound 2 (40 mg/kg in 30% PEG400+20% PG in NS) or vehicle alone.
FIG. 1(b). Shows the mean tumor growth rate of CT-26 tumor cells in Balb/c mice when dosed orally BID with either test compound 97 (75 mg/kg in 40% PEG400+20% PG+10% DACM in NS) or vehicle alone.
FIG. 1(c). Shows the mean tumor growth rate of CT-26 tumor cells in Balb/c mice when dosed orally BID with either test compound 166 (60 mg/kg in 40% PEG400+20% PG+10% DACM in NS) or vehicle alone.
FIG. 1(d). Shows the mean tumor growth rate of CT-26 tumor cells in Balb/c mice when dosed orally BID with either test compound 184 (50 mg/kg in 40% PEG400+20% PG+10% DACM in NS) or vehicle alone.
Figure 1:
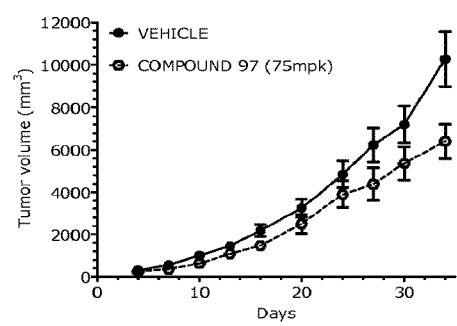
Figure 1:
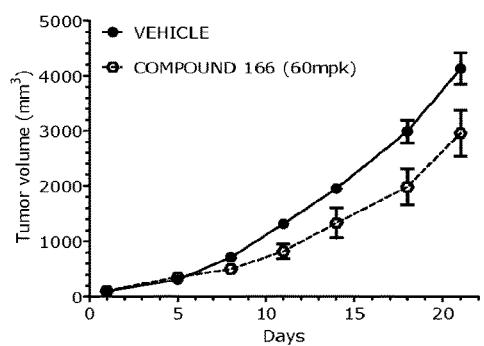
Figure 1:
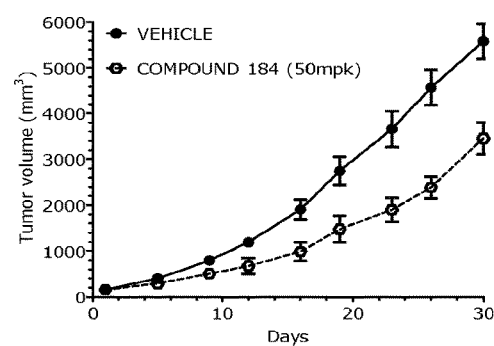

The following definitions are used in connection with the compounds of the present invention unless the context indicates otherwise.

Throughout the description and the claims of this specification the word "comprise" and other forms of the word, such as "comprising" and "comprises," means including but not limited to, and is not intended to exclude for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions.

"Optional" or "optionally" means that the subsequently described event or circumstances can or cannot occur, and that the description includes instances where the event or circumstance occurs and instances where it does not.

The following definitions are used in connection with the compounds of the present invention unless the context indicates otherwise. In general, the number of carbon atoms present in a given group is designated "$C_x$-$C_y$," where x and y are the lower and upper limits, respectively. For example, a group designated as "$C_1$-$C_6$" contains from 1 to 6 carbon atoms. The carbon number as used in the definitions herein refers to carbon backbone and carbon branching, but does not include carbon atoms of the substituents, such as alkoxy substitutions and the like. Unless indicated otherwise, the nomenclature of substituents that are not explicitly defined herein are arrived at by naming from left to right the terminal portion of the functionality followed by the adjacent functionality toward the point of attachment. For example, the substituent "arylalkyloxycarbonyl" refers to the group ($C_6$-$C_{14}$ aryl)-($C_1$-$C_6$ alkyl)-O—C(O)—. The term optionally substituted refers to replacing a hydrogen atom of a group with an alkyl, alkoxy, aryl, monocyclic or bicyclic cycloalkyl, mono or bicyclic heterocyclylalkyl, (aryl)alkyl, (alkoxy)carbonyl, (alkyl)amido, (alkyl)amino, —$NH_2$, aminoalkyl, alkylcarboxyl, (alkyl)carboxyamido, (aryl) amino, haloalkyl, heteroaryl, heterocyclyl, heteroaryl(alkyl), mono, di or perfluoroalkyl, halogen, CN, C(O)OH, amide, amide formed from a primary or secondary amine, $NO_2$, OH, mono-fluoroalkoxy, di-fluoroalkoxy, trifluoroalkoxy, and hydroxyalkyl. Terms not defined herein have the meaning commonly attributed to them by those skilled in the art.

"Alkyl" refers to a hydrocarbon chain that may be a straight chain or branched chain, containing the indicated number of carbon atoms, for example, a $C_1$-$C_{12}$ alkyl group may have from 1 to 12 (inclusive) carbon atoms in it. Examples of $C_1$-$C_6$ alkyl groups include, but are not limited to, methyl, ethyl, propyl, butyl, pentyl, hexyl, isopropyl, isobutyl , sec-butyl, tert-butyl, isopentyl, neopentyl, and isohexyl. Examples of $C_1$-$C_8$ alkyl groups include, but are not limited to, methyl, propyl, pentyl, hexyl, heptyl, 3-methylhex-1-yl, 2,3-dimethylpent-2-yl, 3-ethylpent-1-yl, octyl, 2-methylhept-2-yl, 2,3-dimethylhex-1-yl, and 2,3,3-trimethylpent-1-yl. An alkyl group can be unsubstituted or substituted with one or more of halogen, $NH_2$, (alkyl)NH, (alkyl)(alkyl)N—, —N(alkyl)C(O)(alkyl), —NHC(O)(alkyl), —NHC(O)H, —(CO)$NH_2$, —C(O)NH(alkyl), —(CO)N(alkyl)(alkyl), CN, OH, alkoxy, alkyl, C(O)OH, —(CO)O (alkyl), —C(O)(alkyl), aryl, heteroaryl, heterocyclyl, cycloalkyl, haloalkyl, aminoalkyl, —OC(O)(alkyl), carboxyamidoalkyl-, $NO_2$, and alkyl-CN.

"Alkoxy" refers to the group R—O— where R is an alkyl group, as defined above. Exemplary $C_1$-$C_6$ alkoxy groups include but are not limited to methoxy, ethoxy, n-propoxy, 1-propoxy, n-butoxy and t-butoxy. An alkoxy group can be unsubstituted or substituted with one or more of halogen, OH, alkoxy, $NH_2$, (alkyl)amino-, di(alkyl)amino-, (alkyl)C (O)N($C_1$-$C_3$ alkyl)-, (alkyl)carboxyamIDO1-, HC(O)NH—, $H_2$NC(O)—, (alkyl)NHC(O)—, di(alkyl)NC(O)—, CN, C(O)OH, (alkoxy)carbonyl-, (alkyl)C(O)—, aryl, heteroaryl, cycloalkyl, haloalkyl, amino($C_1$-$C_6$ alkyl)-, (alkyl) carboxyl-, or carboxyamidoalkyl-.

Aryl refers to an aromatic 6 to 14 membered hydrocarbon group. Examples of a $C_6$-$C_{14}$ aryl group include, but are not limited to, phenyl, α-naphthyl, β-naphthyl, biphenyl, anthryl, tetrahydronaphthyl, fluorenyl, indanyl, biphenylenyl, and acenanaphthyl. Examples of a $C_6$-$C_{10}$ aryl group include, but are not limited to, phenyl, α-naphthyl, β-naphthyl, biphenyl, and tetrahydronaphthyl. An aryl group can be unsubstituted or substituted with one or more of alkyl, halogen, haloalkyl, alkoxy, haloalkoxy, OH, hydroxyalkyl, O(hydroxyalkyl), —O(alkyl)C(O)OH, -(alkyl)(alkoxy)halogen, $NH_2$, aminoalkyl-, dialkylamino-, C(O)OH, —(CO)O (alkyl), —OC(O)(alkyl), —O(alkyl)N(alkyl)(alkyl), N-alkylamido-, —(CO)$NH_2$, (alkyl)amido-, $NO_2$, (aryl)alkyl, alkoxy, aryloxy, heteroaryloxy, (aryl)amino, (alkoxy) carbonyl-, (alkyl)amido-, (alkyl)amino, aminoalkyl-, alkylcarboxyl-, (alkyl)carboxyamido-, (aryl)alkyl-, (aryl)amino-, cycloalkenyl, di(alkyl)amino-, heteroaryl, (heteroaryl) alkyl-, heterocyclyl, —O(heterocyclyl), heterocyclyl (alkyl)-, (hydroxyalkyl)NH—, (hydroxyalkyl)$_2$N, —$SO_2$ (alkyl), —NHC(O)(aryl), —C(O)NH(aryl), —NHC(O) (heteroaryl), —(CO)NH(heteroaryl) or a spiro substituent.

The term "bicycle" or "bicyclic" as used herein refers to a molecule that features two fused rings, which rings are a cycloalkyl, heterocyclyl, or heteroaryl. In one embodiment, the rings are fused across a bond between two atoms. The bicyclic moiety formed therefrom shares a bond between the rings. In another embodiment, the bicyclic moiety is formed by the fusion of two rings across a sequence of atoms of the rings to form a bridgehead. Similarly, a "bridge" is an unbranched chain of one or more atoms connecting two bridgeheads in a polycyclic compound. In another embodiment, the bicyclic molecule is a "Spiro" or "spirocyclic" moiety. The spirocyclic group is a carbocyclic or heterocyclic ring which bound through a single carbon atom of the spirocyclic moiety to a single carbon atom of a carbocyclic or heterocyclic moiety. In one embodiment, the spirocyclic group is a cycloalkyl and is bound to another cycloalkyl. In another embodiment, the spirocyclic group is a cycloalkyl and is bound to a heterocyclyl. In a further embodiment, the spirocyclic group is a heterocyclyl and is bound to another heterocyclyl. In still another embodiment, the spirocyclic group is a heterocyclyl and is bound to a cycloalkyl.

"(Aryl)alkyl" refers to an alkyl group, as defined above, wherein one or more of the alkyl group's hydrogen atoms has been replaced with an awl group as defined above. ($C_6$-$C_{14}$ aryl)alkyl-moieties include benzyl, benzhydryl, 1-phenylethyl, 2-phenylethyl, 3-phenylpropyl, 2-phenylpropyl, 1-naphthylmethyl, 2-naphthylmethyl and the like. An (aryl)alkyl group can be unsubstituted or substituted with one or more of halogen, CN, $NH_2$, OH, (alkyl)amino-, di(alkyl)amino-, (alkyl)C(O)N(alkyl)-, (alkyl)carboxyamido-, HC(O)NH—, $H_2$NC(O)—, (alkyl)NHC(O)—, di(alkyl)NC(O)—, CN, OH, alkoxy, alkyl, C(O)OH, (alkoxy)carbonyl-, (alkyl)C(O)—, aryl, heteroaryl, cycloalkyl, haloalkyl, amino(alkyl)-, (alkyl)carboxyl-, carboxyamidoalkyl-, or $NO_2$.

"(Alkoxy)carbonyl-" refers to the group alkyl-O—C (O)—. Exemplary ($C_1$-$C_6$ alkoxy)carbonyl- groups include but are not limited to methoxy, ethoxy, n-propoxy, 1-propoxy, n-butoxy and t-butoxy. An (alkoxy)carbonyl group can be unsubstituted or substituted with one or more of halogen, OH, $NH_2$, (alkyl)amino-, di(alkyl)amino-, (alkyl)C(O)N(alkyl)-, (alkyl)carboxyamido-, HC(O)NH—, $H_2$NC(O)—, (alkyl)NHC(O)—, di(alkyl)NC(O)—, CN, alkoxy, C(O)OH, (alkoxy)carbonyl-, (alkyl)C(O)—, aryl, heteroaryl, cycloalkyl, haloalkyl, amino(alkyl)-, (alkyl)carboxyl-, carboxyamidoalkyl-, or $NO_2$.

"(Alkyl)amido-" refers to a —C(O)NH— group in which the nitrogen atom of said group is attached to a $C_1$-$C_6$ alkyl group, as defined above. Representative examples of a ($C_1$-$C_6$ alkyl)amido- group include, but are not limited to, —C(O)$NHCH_3$, —C(O)$NHCH_2CH_3$, —C(O) $NHCH_2CH_2CH_3$, —C(O)$NHCH_2CH_2CH_2CH_3$, —C(O)NH $CH_2CH_2CH_2CH_2CH_3$, —C(O)$NHCH(CH_3)_2$, —C(O) $NHCH_2CH(CH_3)_2$, —C(O)$NHCH(CH_3)CH_2CH_3$, —C(O) NH—C($CH_3$)$_3$ and —C(O)$NHCH_2$C($CH_3$)$_3$.

"(Alkyl)amino-" refers to an —NH group, the nitrogen atom of said group being attached to a alkyl group, as defined above. Representative examples of an ($C_1$-$C_6$ alkyl) amino-group include, but are not limited to $CH_3NH$—, $CH_3CH_2NH$—, $CH_3CH_2CH_2NH$—, $CH_3CH_2CH_2CH_2NH$—, ($CH_3$)$_2$CHNH—, ($CH_3$)$_2$CH$CH_2NH$—, $CH_3CH_2CH(CH_3)NH$— and ($CH_3$)$_3$CNH—. An (alkyl)amino group can be unsubstituted or substituted on the alkyl moiety with one or more of halogen, $NH_2$, (alkyl)amino-, di(alkyl)amino-, (alkyl)C(O)N(alkyl)-, (alkyl)carboxyamido-, HC(O)NH—, $H_2$NC(O)—, (alkyl) NHC(O)—, di(alkyl)NC(O)—, CN, OH, alkoxy, alkyl, C(O) OH, (alkoxy)carbonyl-, (alkyl)C(O)—, aryl, heteroaryl, cycloalkyl, haloalkyl, amino(alkyl)-, (alkyl)carboxyl-, carboxyamidoalkyl-, or $NO_2$.

"Aminoalkyl-" refers to an alkyl group, as defined above, wherein one or more of the alkyl group's hydrogen atoms has been replaced with —$NH_2$; one or both H of the $NH_2$ may be replaced by a substituent.

"Alkylcarboxyl-" refers to an alkyl group, defined above that is attached to the parent structure through the oxygen atom of a carboxyl (C(O)—O—) functionality. Examples of ($C_1$-$C_6$ alkyl)carboxyl- include acetoxy, propionoxy, propylcarboxyl, and isopentylcarboxyl.

"(Alkyl)carboxyamido-" refers to a —NHC(O)— group in which the carbonyl carbon atom of said group is attached to a $C_1$-$C_6$ alkyl group, as defined above. Representative examples of a ($C_1$-$C_6$ alkyl)carboxyamido-group include, but are not limited to, —NHC(O)$CH_3$, —NHC(O)$CH_2CH_3$, —NHC(O)$CH_2CH_2CH_3$, —NHC(O)$CH_2CH_2CH_2CH_3$, —NHC(O)$CH_2CH_2CH_2CH_2CH_3$, —NHC(O)CH($CH_3$)$_2$, NHC(O)$CH_2CH(CH_3)_2$, —NHC(O)CH($CH_3$)$CH_2CH_3$, —NHC(O)—C($CH_3$)$_3$ and —NHC(O)$CH_2$C($CH_3$)$_3$.

"(Aryl)amino" refers to a radical of formula (aryl)-NH—, wherein aryl is as defined above. "(Aryl)oxy" refers to the group Ar—O— where Ar is an aryl group, as defined above.

"Cycloalkyl" refers to a non-aromatic, saturated, partially saturated, monocyclic, bicyclic or polycyclic hydrocarbon 3 to 12 membered ring system. Representative examples of a $C_3$-$C_{12}$ cycloalkyl include, but are not limited to, cyclopropyl, cyclopentyl, cycloheptyl, cyclooctyl, decahydronaphthalen-1-yl, octahydro-1H-inden-2-yl, decahydro-1H-benzo [7]annulen-2-yl, and dodecahydros-indacen-4-yl. Representative examples of a $C_3$-$C_{10}$ cycloalkyl include, but are not limited to, cyclopropyl, cyclobutyl, cyclopentyl, cyclohexyl, cycloheptyl, cyclooctyl, decahydronaphthalen-1-yl, and octahydro-1H-inden-2-yl. Representative examples of a $C_3$-$C_8$ cycloalkyl include, but are not limited to, cyclopropyl, cyclobutyl, cyclopentyl, cyclohexyl, cycloheptyl, cyclooctyl, and octahydropentalen-2-yl. A cycloalkyl can be unsubstituted or substituted with one or more of halogen, $NH_2$, (alkyl)NH, (alkyl)(alkyl)N—, —N(alkyl)C (O)(alkyl), —NHC(O)(alkyl), —NHC(O)H, —C(O)$NH_2$, —C(O)NH(alkyl), —(CO)N(alkyl)(alkyl), CN, OH, alkoxy, alkyl, C(O)OH, —(CO)O(alkyl), —(CO) alkyl), aryl, heteroaryl, cycloalkyl, haloalkyl, aminoalkyl-, —OC(O) (alkyl), carboxyamidoalkyl-, and $NO_2$. Additionally, each of any two hydrogen atoms on the same carbon atom of the carbocyclic ring can be replaced by an oxygen atom to form an oxo (=O) substituent.

"Halo" or "halogen" refers to —F, —Cl, —Br and —I.

"$C_1$-$C_6$ haloalkyl" refers to a $C_1$-$C_6$ alkyl group, as defined above, wherein one or more of the $C_1$-$C_6$ alkyl group's hydrogen atoms has been replaced with F, Cl, Br, or I. Each substitution can be independently selected from F, Cl, Br, or I. Representative examples of an $C_1$-$C_6$ haloalkyl- group include, but are not limited to, —$CH_2F$, —$CCl_3$, —$CF_3$, $CH_2CF_3$, —$CH_2Cl$, —$CH_2CH_2Br$, —$CH_2CH_2I$, —$CH_2CH_2CH_2F$, —$CH_2CH_2CH_2Cl$, —$CH_2CH_2CH_2Br$, —$CH_2CH_2CH_2I$, —$CH_2CH_2CH_2CH_2Br$, —$CH_2CH_2CH_2CH_2I$, —$CH_2CH(Br)CH_3$, —$CH_2CH(Cl)CH_2CH_3$, —$CH(F)CH_2CH_3$ and —$C(CH_3)_2(CH_2Cl)$.

"Heteroaryl" refers to a monocyclic, bicyclic, or polycyclic aromatic ring system containing at least one ring atom selected from the heteroatoms oxygen, sulfur and nitrogen. Examples of $C_1$-$C_9$ heteroaryl groups include furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline. Bicyclic $C_1$-$C_9$ heteroaryl groups include those where a phenyl, pyridine, pyrimidine or pyridazine ring is fused to a 5 or 6-membered monocyclic heteroaryl ring having one or two nitrogen atoms in the ring, one nitrogen atom together with either one oxygen or one sulfur atom in the ring, or one O or S ring atom. Examples of monocyclic $C_1$-$C_4$ heteroaryl groups include 2H-tetrazole, 3H-1,2,4-triazole, furan, thiophene, oxazole, thiazole, isoxazole, isothiazole, imidazole, and pyrrole. A heteroaryl group can be unsubstituted or substituted with one or more of $C_1$-$C_6$ alkyl, halogen, haloalkyl, OH, CN, hydroxyalkyl, $NH_2$, aminoalkyl-, dialkylamino-, C(O)OH, —(CO)O-(alkyl), —OC(O)(alkyl), N-alkylamido-, —(CO)$NH_2$, (alkyl)amido-, —$NO_2$, (aryl)alkyl, alkoxy, aryloxy, heteroaryloxy, (aryl)amino, (alkoxy)carbonyl-, (alkyl)amido-, (alkyl)amino, aminoalkyl-, alkylcarboxyl-, (alkyl)carboxyamido-, (aryl)alkyl-, (aryl)amino-, cycloalkenyl, di(alkyl)amino-, heteroaryl, (heteroaryl)alkyl-, heterocyclyl, heterocyclyl(alkyl)-, (hydroxyalkyl)NH—, (hydroxyalkyl)$_2$N, —NHC(O)aryl, —(CO)NHaryl, —NHC(O)heteroaryl, —(CO)NH(heteroaryl), or a spiro substituent.

"Heterocycle" or "heterocyclyl" refers to monocyclic, bicyclic, polycyclic, or bridged head molecules in which at least one ring atom is a heteroatom. A heterocycle may be saturated or partially saturated. Exemplary $C_1$-$C_9$ heterocyclyl groups include but are not limited to aziridine, oxirane, oxirene, thiirane, pyrroline, pyrrolidine, dihydrofuran, tetrahydrofuran, dihydrothiophene, tetrahydrothiophene, dithiolane, piperidine, 1,2,3,6-tetrahydropyridine-1-yl, tetrahydropyran, pyran, thiane, thiine, piperazine, azepane, diazepane, oxazine, 5,6-dihydro-4H-1,3-oxazin-2-yl, 2,5-diazabicyclo[2.2.1]heptane, 2,5-diazabicyclo[2.2.2]octane, 3,6-diazabicyclo[3.1.1]heptane, 3,8-diazabicyclo[3.2.1]octane, 6-oxa-3,8-diazabicyclo[3.2.1]octane, 7-oxa-2,5-diazabicyclo[2.2.2]octane, 2,7-dioxa-5-azabicyclo[2.2.2]octane, 2-oxa-5-azabicyclo[2.2.1]heptane-5-yl, 2-oxa-5-azabicyclo[2.2.2]octane, 3,6-dioxa-8-azabicyclo[3.2.1]octane, 3-oxa-6-azabicyclo[3.1.1]heptane, 3-oxa-8-azabicyclo[3.2.1]octan-8-yl, 5,7-dioxa-2-azabicyclo[2.2.2]octane, 6,8-dioxa-3-azabicyclo[3.2.1]octane, 6-oxa-3-azabicyclo[3.1.1]heptane, 8-oxa-3-azabicyclo[3.2.1]octan-3-yl, 2-methyl-2,5-diazabicyclo[2.2.1]heptane-5-yl, 1,3,3-trimethyl-6-azabicyclo[3.2.1]oct-6-yl, 3-hydroxy-8-azabicyclo[3.2.1]octan-8-yl-, 7-methyl-3-oxa-7,9-diazabicyclo[3.3.1]nonan-9-yl, 9-oxa-3-azabicyclo[3.3.1]nonan-3-yl, 3-oxa-9-azabicyclo[3.3.1]nonan-9-yl, 3,7-dioxa-9-azabicyclo[3.3.1]nonan-9-yl, 4-methyl-3,4-dihydro-2H-1,4-benzoxazin-7-yl, thiazine, dithiane, and dioxane. The contemplated heterocycle rings or ring systems have a minimum of 3 members. Therefore, for example, $C_1$ heterocyclyl radicals would include but are not limited to oxaziranyl, diaziridinyl, and diazirinyl, $C_2$ heterocyclyl radicals include but are not limited to aziridinyl, oxiranyl, and diazetidinyl, $C_9$ heterocyclyl radicals include but are not limited to azecanyl, tetrahydroquinolinyl, and perhydroisoquinolinyl. A heterocyclyl group can be unsubstituted or substituted with one or more of alkyl, halogen, alkoxy, haloalkyl, OH, hydroxyalkyl, —(CO)-(hydroxyalkyl), $NH_2$, aminoalkyl-, dialkylamino-, C(O)OH, —(CO)O-(alkyl), —OC(O)(alkyl), N-alkylamido-, —(CO)$NH_2$, (alkyl)amido-, —(CO)-(alkyl)-CN, (alkyl)-CN, or $NO_2$.

"Heterocyclyl(alkyl)-" refers to an alkyl group, as defined above, wherein one or more of the alkyl group's hydrogen atoms has been replaced with a heterocycle group as defined above. Heterocyclyl($C_1$-$C_6$ alkyl)-moieties include 1-piperazinylethyl, 4-morpholinylpropyl, 6-piperazinylhexyl, and the like. A heterocyclyl(alkyl) group can be unsubstituted or substituted with one or more of halogen, $NH_2$, (alkyl)amino-, di(alkyl)amino-, (alkyl)C(O)N(alkyl)-, (alkyl)carboxyamido-, HC(O)NH—, $H_2$NC(O)—, (alkyl)NHC(O)—, di(alkyl)NC(O)—, CN, OH, alkoxy, alkyl, C(O)OH, (alkoxy)carbonyl-, (alkyl)C(O)—, 4- to 7-membered monocyclic heterocycle, aryl, heteroaryl, or cycloalkyl.

"Heteroaryl(alkyl)" refers to a heteroaryl which is attached to an alkyl group and the heteroaryl is defined above.

"Hydroxyalkyl" refers to a alkyl group, as defined above, wherein one or more of the alkyl group's hydrogen atoms has been replaced with OH groups. Examples of $C_1$-$C_6$ hydroxyalkyl moieties include, for example, —$CH_2OH$, —$CH_2CH_2OH$, —$CH_2CH_2CH_2OH$, —$CH_2CH(OH)CH_2OH$, —$CH_2CH(OH)CH_3$, —$CH(CH_3)CH_2OH$ and higher homologs.

"Perfluoroalkyl-" refers to alkyl group, defined above, having two or more fluorine atoms. Examples of a $C_1$-$C_6$ perfluoroalkyl- group include $CF_3$, $CH_2CF_3$, $CF_2CF_3$ and $CH(CF_3)_2$. This may also be referred to as mono or difluorine substituted alkyl group such as $CHF_2$ or $CH_2F$.

A "subject" is a mammal, including but not limited to a human, mouse, rat, guinea pig, dog, cat, horse, cow, pig, or non-human primate, such as a monkey, chimpanzee, baboon or gorilla. In certain embodiments, the subject is a human. In certain embodiments, the subject is a non-human animal. The terms "individual," "patient," and "subject" are used interchangeably herein.

"Effective amount" means the amount of a compound that when administered to a subject, tissue, cell, living organism, is sufficient to inhibit the kynurenine pathway or activity of IDO1 and/or IDO2 and/or TDO.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

As used herein, the terms "therapeutic," "therapeutic agent," "medication" and "medicament" may be used interchangeably throughout the specification.

A "chemotherapeutic agent" is a biological (large molecule) or chemical (small molecule) compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, proteins, antibodies, photosensitizers, and kinase inhibitors. Chemotherapeutic agents include compounds used in "targeted therapy" and non-targeted conventional chemotherapy.

As used herein, the term "isotopic variant" or "isotopically" or "radio-labeled" refers to a compound of the invention where one or more atoms are replaced or substitutd by an atom having an atomic mass or mass number different from the atomic mass or mass number typically found in nature (i.e., naturally occurring). For example, an "isotopic variant" of a compound or a "radio-labeled" compound can contain one or more non-radioactive isotopes, such as for example, Deuterium ($^2$H or D), Tritium ($^3$H), Carbon 11 ($^{11}$C) Carbon-13 ($^{13}$C), Carbon-14 ($^{14}$C), Nitrogen-15 ($^{15}$N), Oxygen-15 ($^{15}$O), Oxygen-17 ($^{17}$O), Oxygen-18 (18O), Fluorine-18 ($^{18}$F), Sulphur-35 ($^{35}$S), Chlorine-36 ($^{36}$Cl), Bromium-75 ($^{75}$Br), Bromium-76 ($^{76}$Br), Bromium-77 ($^{77}$Br), Bromium-82 ($^{82}$Br), Iodine-123 ($^{123}$I), Iodine-125 ($^{125}$I), Iodine-131 ($^{131}$I), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined by a person having the skill in the art. Likewise, the invention may include the preparation of isotopic variants with radioisotopes, in the instance for example, where the resulting compounds may be used for drug and/or substrate tissue distribution studies. The radioactive isotopes tritium, i.e., $^3$H, and carbon-14, i.e., $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy. All isotopic variants of the compounds provided herein, radioactive or not, are intended to be encompassed within the scope of the invention.

The term "prodrug" means compounds that are transformed in vivo to yield a compound of the present invention. The transformation can occur by various mechanisms, such as through hydrolysis, oxidation, or reduction in blood. A good discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association an Pergamon Press, 1987.

A "metabolite" is a product produced through metabolism in the body of a specified compound or salt thereof. Metabolites of a compound may be identified using routine techniques known in the art and their activities determined using tests such as those described herein. Such products may result for example from oxidation, reduction, hydrolysis, amidation, deamidation, esterification deesterification, enzymatic cleavage, and the like, of the administered compound.

"Salts" refers to derivatives of the disclosed compounds wherein the parent compound is modified by converting an existing acid or base moiety to its salt form. Examples of salts include, but are not limited to mineral acid (such as HCl, HBr, H$_2$SO$_4$) or organic acid (such as acetic acid, benzoic acid, trifluoroacetic acid), salts of basic residues such as amines (primary, secondary, and tertiary amines, substituted amines including naturally occurring substituted amines, cyclic amines (such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine), organic amines, for example, ethylamine, ethanolamine, triethanolamine or amino acids); alkali (such as Li, Na, K, Mg, Ca) or organic (such as trialkyammonium) salts of acidic residues such as carboxylic acids; alkyl or arylalkyl pyridinium salts; and the like. The salts of the present invention can be synthesized from the parent compound which contains a basic or acidic moiety by conventional chemical methods. Generally, such salts can be prepared by reacting the free acid or base forms of these compounds with a stoichiometric amounts of the appropriate base or acid in water or in an organic solvent, or in a mixture of the two; generally, non-aqueous media like ether, ethyl acetate, ethanol, isopropanol, or acetonitrile are preferred.

The phrase "pharmaceutically acceptable" indicates that the substance composition must be compatible chemically and/or toxicologically, with other ingredients comprising a formulation, and/or the mammal being treated therewith.

Representative "pharmaceutically acceptable salts" as used herein refers to a pharmaceutically acceptable organic or inorganic salts of a compound of the invention and include but are not limited to those of an acid or base. Lists of suitable salts are found in Remington's Pharmaceutical Sciences, 17$^{th}$ ed., Mack Publishing Company, Easton, Pa., 1985, p 1418 and Journal of Pharmaceutical Science, 66, 2 (1977), each of which is incorporated in its entirety. In one embodiment, the pharmaceutical salt is selected from amount water-soluble and water-insoluble salts, such as the acetate, benzenesulfonate, benzoate, bicarbonate, bisulfate, bitartrate, bromide, butyrate, calcium, chloride, choline, citrate, edisylate (camphorsulfonate), formate, fumarate, gluconate, glucuronate, glutamate, hydrobromide, hydrochloride, iodide, isonicotinate, lactate, lauryl sulfate, malate, maleate, mandelate, methylsufonate, mesylate, nitrate, oleate, oxalate, palmitatc, pantothcnatc, phosphate, acid phosphate, potassium, propionate, p-toluenesulfonate, salicylate, sodium, stearate, succinate, sulfate and tannate salts. A pharmaceutically acceptable salt may involve the inclusion of another molecule such as an acetate ion, a succinate in or other counter ion. The counter ion may be any organic or inorganic moiety that stabilizes the charges on the parent compound. Furthermore, a pharmaceutically acceptable salt can have multiple counter ions. Hence, a pharmaceutically acceptable salt can have one or more charged atoms and/or one or more counter ion.

A "solvate" refers to a physical association or complex of one or more solvent molecules and a compound of the invention. The compounds of the invention may exist in unsolvate as well as solvated forms. Examples of solvents that form solvates include but are not limited to water, isopropanol, ethanol, methanol, DMSO, ethyl acetate, acetic acid, and ethanolamine. The term "hydrate" refers to the complex where the solvent molecule is water. This physical association involves varying degrees of ionic and covalent bonding, including hydrogen bonding. In certain instances, the solvate will be capable of isolation, for example when one or more solvent molecules are incorporated in the crystal lattice of the crystalline solid. Preparation of solvates is generally known for example, M. Caira et al. J. Pharmaceutical Sci. 93(3), 601-611 (2004). Similar preparations of solvates, hemisolvates, hydrates, and the like are described by E. C. van Tonder et al. AAPS PharmSciTech, 5(1), article 12 (2004); and A. L. Bingham et al. Chem. Commun., 603-604 (2001). A typical, non-limiting, process involves dissolving a compound of the invention in desired amount of the desired solvent (organic or water or mixtures thereof) at a higher than ambient temperature, and cooling the solution at a rate sufficient to form crystals which are then isolated by standard methods. Analytical techniques such as, for example, I.R. spectroscopy, show the present of the solvent (or water in the crystal as solvate (or hydrate)).

The term "synergistic" as used herein refers to a therapeutic combination which is more effective than the additive effects of the two or more single agents. A determination of a synergistic interaction between one or more compounds of the invention, or a compound of the invention and one or more therapeutic agent may be based on the results obtained from the assays described herein. The combination therapy may provide "synergy" and prove "synergistic" i.e., the effect achieved when the active ingredients used together is greater than the sum of the effects that results from using the compounds separately. A synergistic effect may be attained wen the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, effective dosages of two or more active ingredients are administered together.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

Some compounds within the present invention may possess one or more chiral centers, and in some embodiments, each center exists in the R or S configuration. The present invention includes each separate enantiomer of such compounds as well as mixtures of the enantiomers. Where multiple chiral centers exist in compounds of the present invention, the invention includes each possible combination of chiral centers within a compound, as well as all possible enantiomeric and diastereomeric mixtures thereof. All chiral, diastereomeric, and racemic forms of a structure are intended, unless the specific stereochemistry or isomeric form is specifically indicated. It is well known in the art how to prepare optically active forms, such as by resolution of racemic forms or by synthesis from optically active starting materials. Compounds of the invention also include tautomeric forms. Tautomeric forms result from the swapping of a single bond with an adjacent double bond together the concomitant migration of a proton. For example, enols and ketones are tautomers because they are rapidly interconverted by treatment with either acid or base. Another example of tautomerism is the aci- and nitro- forms of phenylnitromethane, which are likewise formed by treatment with acid or base. Tautomeric forms may be relevant to the attainment of the optimal chemical reactivity and biological activity of a compound of interest.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2$H or $^2$D), carbon 13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e., $^3$H, and carbon-14, i.e., $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy. All isotopic variants of the compounds provided herein, radioactive or not, are intended to be encompassed within the scope of the invention.

For the purposes of the present disclosure, the terms "compound," "compound of the invention," "test compounds," and "composition of matter" stand equally well for inhibitors of kynurenine pathway- and/or the IDO1- and/or IDO2- and/or TDO and metabolites thereof described herein including all enantiomeric forms, diastereomeric forms, racemic forms, racemic-diastereomeric mixtures, optical isomers, tautomeric forms, salts, polymorphs, and the like. The terms "compound," "compound of the invention," "test compounds," and "composition of the matter" are used interchangeably throughout the present specification.

For the purposes of the present disclosure, the terms "disease," "condition," and "disorder" stand equally well for conditions where a subject may benefit from regulation of kynurenine pathway and/or IDO1, and/or IDO2, and/or TDO, and may be used interchangeably throughout the present specification.

The following abbreviations are used and have the indicated definitions:

| Abbreviation | Definition |
| --- | --- |
| TMSCN | trimethylsilyl nitrile |
| TFE | trifluoro ethanol |
| n-BuLi | n-butyl lithium |
| TMEDA | tetramethylene diamine |
| DMF | dimethylformamide |
| DCM | dichloromethane |
| LDA | lithium diisopropylamide |
| HCl | hydrochloric acid |
| NBS | N-bromosuccinimide |
| Bis-Pin | Bis(pinacolato) |
| ACN or MeCN | acetonitrile |
| THF | tetrahydrofuran |
| RT or rt | room temperature |
| DIPEA | N,N-diisopropylethylamine |
| IPA | isopropylamine |
| BINAP | 2,2'-bis(diphenylphosphino)-1,1'-binaphthyl |
| DMAP | 4-dimethylamino pyridine |
| DPPA | diphenylphosphoryl azide |
| PPA | phenylpropanol amine |
| TEA | triethylamine |
| SEM | trimethylsilylethoxy methyl |
| Pd(OAc)$_2$ | palladium acetate |
| DACM | Dimethyl acetamide |
| PG | Polypropyl glycol |
| DOXO | Doxorubicin |
| mpk | Mg/Kg |
| TDO | tryptophan 2,3-dioxygenase |
| Pd(dppf)Cl$_2$•DCM | [1,1'Bis(diphenylphosphino)ferrocene]-dichloropalladium(II), complex with dichloromethane |
| SEMCl | 2-(Trimethylsilyl)ethoxymethyl chloride |
| MOMCl | Methoxymethyl chloride |
| Dppf | bis(diphenylphosphino)ferrocene |

-continued

| Abbreviation | Definition |
| --- | --- |
| MTBE | methyl tertiary butyl ether |
| HEPES | 4-(2-hydroxyethyl)-1-piperazineethanesulfonic acid |
| ATCC | American Type Culture Collection |
| DMEM | Dulbecco's Modified Eagle Medium |
| TCA | trichloro acetic acid |
| hIDO | human indoleamine 2,3-dioxygenase |
| $CO_2$ | carbon dioxide |
| IFNγ | gamma-interferon |
| DMSO | dimethylsulfoxide |
| LTMS | lithium trimethylsilyl |
| $Pd(PPh_3)_4$ | tetrakis(triphenylphosphine) palladium (0) |
| TMS | trimethylsilane |
| $Pd_2(dba)_3$ | tris(dibenzylideneacetone) palladium (0) |
| Boc | butoxycarbonyl |
| TFA | trifluoroacetic acid |
| HMPA | hexamethylphosphoramide |
| MOM | methoxymethyl ether |
| LTMP | lithium 2,2,6,6-tetramethylpiperidide |
| TMP | 2,2,6,6,-tetramethylpiperidine |
| XPhos | 2-dicyclohexyl phosphino-2',4',6'-triisopropylbiphenyl |
| $Ni(dppp)Cl_2$ | dichloro(1,3-bis(diphenylphosphine) propane nickel |
| PEG | Polyethylene Glycol |
| PBS | Phosphate buffered saline |
| KYN | Kynurenine |
| IDO | indoleamine 2,3-dioxygenase |
| TFA | Trifluoroacetic acid |
| LHMDS | Lithium Hexamethyldisilazide |
| TMSOTf | Trimethylsilyl trifluoro methanesulfonate |
| PPA | Polyphosphoric acid |
| EtOH | Ethanol |
| CrEL | Cremophore Ethanol |

The invention provides compounds of formula (I) and metabolites thereof, or pharmaceutically acceptable salts or prodrugs thereof, and metabolites thereof, and pharmaceutical composition thereof (collectively "compounds of the invention," or "compounds," "test compounds," or "composition of matter"), which are capable of reducing or eliminating immune-mediated disorders as standalone therapy (monotherapy) or in combination with other therapies, incuding without limitation, antiviral therapy, anti-inflammation therapy, conventional chemotherapy, or in combination with anti-cancer vaccines or in combination with hormonal therapy to slow or prevent various conditions or diseases including tumor growth. The invention further provides compounds and compositions which function by decreasing levels of kynurenine and/or altering the levels of tryptophan in plasma and/or tissues through the inhibition of the enzymes indoleamine 2,3-dioxygenase-1 (IDO1) or indoleamine 2,3-dioxygenase-2 (IDO2) or tryptophan 2,3-dioxygenase (TDO) or any combination of the three enzymes.

In one embodiment, the compound is of formula (I) or a metabolite thereof, or a pharmaceutically acceptable salt or prodrug thereof.

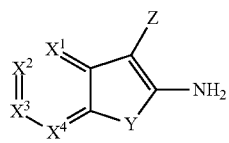

(I)

In this compound, $X^1$ is $CR^1$, N, or NO; $X^2$ is $CR^2$, N, or NO; $X^3$ is $CR^3$, N, or NO; $X^4$ is $CR^4$, N, or NO. In one embodiment, one or two of $X^1$, $X^2$, $X^3$ and $X^4$ is N. In another embodiment, $X^1$ is $CR^1$, $X^2$ is $CR^2$, $X^3$ is $CR^3$, and $X^4$ is $CR^4$.

Y is O, S, or $NR^8$ and Z is $OR^5$, $SR^5$ or $NR^5R^6$.

$R^1$, $R^2$, $R^3$ and $R^4$ are independently selected from the group consisting of H, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, mono or bicyclic optionally substituted $C_6$-$C_{14}$ aryl, mono or bicyclic optionally substituted heteroaryl, optionally substituted (aryl)alkyl, (alkoxy)carbonyl, (alkyl)amido, (alkyl)amino, optionally substituted mono or bicyclic cycloalkyl, optionally substituted mono or bicyclic heterocyclyl, aminoalkyl, alkylcarboxyl, (alkyl)carboxyamido, optionally substituted (aryl)amino, hydroxyl, halogen, $C_1$-$C_6$ haloalkyl, optionally substituted heterocyclyl(alkyl)-, optionally substituted heteroaryl(alkyl), hydroxyalkyl, perfluoroalkyl, optionally substituted aryloxy, optionally substituted heteroaryloxy, optionally substituted $C_3$-$C_8$ cycloalkoxy, $N(R^7)_2$, CN, $NO_2$, $CO_2H$, $CONR^AR^B$, $S(O)_nR^7$, and optionally substituted heterocyclyloxy having 1 to 2 heteroatoms selected from the group consisting of O, $S(O)_n$, and $NR^7$.

In one embodiment, $R^1$ is H, halogen, CN, $C_1$-$C_6$ hydroxyalkyl, $C_1$-$C_6$ alkoxy, or $C_1$-$C_6$ alkyl. In another embodiment, $R^1$ is H. In yet another embodiment, the $R^1$ is a halogen. In still another embodiment, $R^1$ is a Cl. In yet another embodiment, $R^1$ is a methoxy or a methyl. In still another embodiment, $R^1$ is CN.

In a further embodiment, $R^2$ is H, halogen, hydroxyl, CN, $N(R^7)_2$, mono or bicyclic optionally substituted $C_6$-$C_{14}$ aryl, optionally substituted $C_1$-$C_6$ alkoxy, optionally substitutd $C_1$-$C_6$ alkyl, or optionally substituted aryloxy. In a still further embodiment, $R^2$ is F, Cl, Br, or I. In yet another embodiment, $R^2$ is H or optionally substituted $C_1$-$C_6$ alkyl. In yet another embodiment, $R^2$ is optionally substituted C alkoxy or optionally substituted aryloxy. In still another embodiment, $R^2$ is $N(R^7)_2$ or mono or bicyclic optionally substituted $C_6$-$C_{14}$ aryl.

In another embodiment, $R^3$ is H, halogen, $NO_2$ or CN. In still a further embodiment, $R^3$ is H. In yet another embodiment, $R^3$ is $NO_2$ or CN.

H, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, mono or bicyclic optionally substituted $C_6$-$C_{14}$ aryl, $CH_2$-aryl, mono or bicyclic optionally substituted heteroaryl, optionally substituted (aryl)alkyl, (alkoxy)carbonyl, (alkyl)amido, (alkyl)amino, optionally substituted mono or bicyclic cycloalkyl, optionally substituted mono or bicyclic heterocyclyl, aminoalkyl, alkylcarboxyl, (alkyl)carboxyamido, optionally substituted (aryl)amino, hydroxyl, halogen, $C_1$-$C_6$ haloalkyl, optionally substituted heterocyclyl(alkyl)-, optionally substituted heteroaryl(alkyl), hydroxyalkyl, perfluoroalkyl, optionally substituted aryloxy, optionally substituted heteroaryloxy, optionally substituted $C_3$-$C_8$ cycloalkoxy, $N(R^7)_2$, CN, $NO_2$, $CO_2H$, CONRARB, $S(O)nR^7$, and optionally substituted heterocyclyloxy having 1 to 2 heteroatoms selected from the group consisting of O, S(O)n, and $NR^7$, and n is 0 to 2.

In yet a further embodiment, $R^4$ is H, halogen or CN. In still another embodiment, $R^4$ is optionally substituted phenyl. In a further embodiment, $R^4$ is phenyl substituted with one or more $C_1$-$C_6$ alkoxy or halogen. In a further embodiment, $R^4$ is phenyl substituted with F, Cl, Br or I.

In another embodiment, $R^4$ is optionally substituted alkyl, optionally substituted cycloalkyl, or optionally substituted arylalkyl. In still another embodiment, $R^4$ is $N(R^7)_2$. In yet another embodiment, $R^4$ is optionally substituted arylalkenyl or optionally substituted arylalkynyl. In still another embodiment, $R^4$ is optionally substituted diarylamine or optionally substituted diphenylamine. In a further embodiment, $R^4$ is optionally substituted aryl, optionally substituted bicylic aryl, heteroaryl, optionally substituted heteroaryl, or bicyclic heteroaryl. In a still further embodiment, $R^4$ is an optionally substituted heterocyclyl.

In another embodiment, $R^4$ is optionally substituted pyridine, optionally substituted picolyl, optionally substituted picolinamide. In yet another embodiment, $R^4$ is $R^4$ is optionally substituted (alkyl)carboxyamido, (aryl)carboxyamido, (alkyl)amido, alkylcarboxyl, (alkoxy)carbonyl, COOH, C1-C6 cyclyloxy, heterocyclyloxy, aryloxy, heteroaryloxy, perfluoroalkyl, $S(O)_nN(R^7)_2$, or pyrimidine.

$R^A$ and $R^B$ are independently selected from among H, optionally substituted $C_1$-$C_6$ alkyl, optionally substituted mono or bicyclic $C_6$-$C_{14}$ aryl, optionally substituted mono or bicyclic heteroaryl, optionally substituted (aryl)alkyl, optionally substituted mono or bicyclic $C_3$-$C_8$ cycloalkyl, optionally substituted mono or bicyclic heterocyclyl, $C_1$-$C_6$ haloalkyl, optionally substituted heterocyclyl(alkyl), optionally substituted heteroaryl(alkyl), hydroxyalkyl, and perfluoroalkyl.

In this compound, n is 0 to 2. In one embodiment, n is 0. In another embodiment, n is 1. In a further embodiment, n is 2.

$R^7$ is H, $C_1$-$C_6$ alkyl, mono or bicyclic $C_6$-$C_{14}$ aryl, mono or bicyclic heteroaryl, (aryl)alkyl, (alkoxy)carbonyl, (alkyl)amido, (alkyl)amino, mono or bicyclic cycloalkyl, mono or bicyclic heterocyclyl, alkylcarboxyl, heterocyclyl(alkyl), heteroaryl(alkyl), hydroxyalkyl, perfluoroalkyl, aryloxy, heteroaryloxy, $C_3$-$C_6$ cycloalkoxy, or heterocyclyloxy having 1 to 2 heteroatoms selected from the group consisting of O, $S(O)_n$, and $NR^A$. $R^A$ is H, $C_1$-$C_6$ alkyl, mono or bicyclic $C_6$-$C_{14}$ aryl, mono or bicyclic heteroaryl, (aryl)alkyl, (alkoxy)carbonyl, (alkyl)amido, (alkyl)amino, mono or bicyclic cycloalkyl, mono or bicyclic heterocyclyl, alkylcarboxyl, heterocyclyl(alkyl), heteroaryl(alkyl), hydroxyalkyl, perfluoroalkyl, aryloxy, heteroaryloxy, $C_3$-$C_6$ cycloalkoxy, or optionally substituted heterocyclyloxy.

$R^8$ is H or optionally substituted $C_1$-$C_6$ alkyl.

$R^5$ and $R^6$ are independently selected from among H, optionally substituted $C_1$-$C_6$ alkyl, optionally substituted mono or bicyclic $C_6$-$C_{14}$ aryl, optionally substituted mono or bicyclic heteroaryl, optionally substituted (aryl)alkyl, optionally substituted mono or bicyclic cycloalkyl, optionally substituted mono or bicyclic heterocyclyl, $C_1$-$C_6$ haloalkyl, optionally substituted heterocyclyl(alkyl), optionally substituted heteroaryl(alkyl), hydroxyalkyl, and perfluoroalkyl. In one embodiment, $R^5$ or $R^6$ is optionally substituted phenyl. In another embodiment, $R^5$ or $R^6$ is of the following structure, wherein, $R^C$ to $R^G$ are independently selected from among H, halogen, $C_1$-$C_6$ haloalkyl, $C_1$-$C_6$ alkoxy, heterocycle, optionally substituted $C_1$-$C_6$ alkyl, $C_3$-$C_8$ cycloalkyl, CN, —O(aryl), $C_2$-$C_6$ alkynyl, $C(O)C_1$-$C_6$ alkyl, —O—$C_1$-$C_6$ haloalkyl, and optionally substituted aryl.

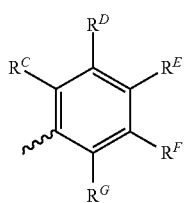

In a further embodiment, $R^5$ or $R^6$ is of the following structure, wherein, $R^C$ to $R^G$ are independently selected from among H, halogen, $CHF_2$, $C(CH_3)F_2$, $OCF_3$, $OCH_3$, $OCH(CH_3)_2$, morpholine, piperidine, $CH_3$, $C(CH_3)_3$, $CH_2CH_3$, $CH(CH_3)_2$, cyclopropyl, cyclohexyl, $CH_2$-cyclopropyl, $CH_2$-cyclobutyl, benzyl, CN, phenoxy, ethynyl, $C(O)CH_3$, and phenyl.

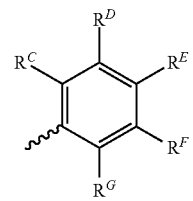

In yet another embodiment, $R^5$ or $R^6$ is of the following structure, wherein, $R^C$ to $R^G$ are independently selected from the group consisting of H and optionally substituted aryl. In one embodiment, $R^C$ to $R^G$ are independently selected from among H and aryl substituted with one or more halogen. In yet another embodiment, each halogen is independently selected from F, Cl, Br, or I. In another embodiment, $R^C$ to $R^G$ arc independently selected from among H and aryl substituted with one or more Cl or F.

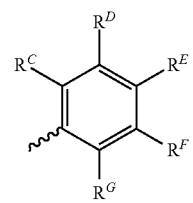

In still a further embodiment, $R^5$ or $R^6$ is phenyl, 2-Br-4-F-phenyl, 2,3,4-tri-Cl-phenyl, 2,3-di-Cl-4-F-phenyl, 2,4-di-Cl-phenyl, 2-Cl-4-F-phenyl, 2-Cl-phenyl, 2-Et-phenyl, 2,4-di-F-3-Cl-phenyl, 2-F-3-CN-phenyl, 2,4-di-F-phenyl, 2-tetralin, 2,3-di-Me-phenyl, 2-Me-4-Br-phenyl, 2,4-di-Me-phenyl, 2,4-di-OMe-phenyl, 2-piperidine-phenyl, 3-Br-4,5-di-F-phenyl, 3-Br-4-F-phenyl, 3-Br-4-Me-phenyl, 3-Br-phenyl, 3-acetylene-4-F-phenyl, 3-acetylene-phenyl, 3-$CF_2$Me-4-F-phenyl, 3-$CF_3$-4-Br-phenyl, 3-$CF_3$-4-Cl-phenyl, 3-$CF_3$-4-F-phenyl, 3-$CF_3$-phenyl, 3-$CH_2$-cyclobutyl-phenyl, 3-$CH_2$-cyclopropyl-phenyl, 3-$CH_2$Ph-phenyl, 3-CHF2-phenyl, 3,4-di-Cl-phenyl, 3,5-di-Cl-4-F-phenyl, 3-Cl-4,6-di-F-phenyl, 3-Cl-4-F-phenyl, 3-Cl-4-I-phenyl, 3-Cl-4-Me-phenyl, 3-Cl-5-Me-phenyl, 3,6-di-Cl-phenyl, 3-Cl-6-F-phenyl, 3-Cl-6-OMe-phenyl, 3-Cl-phenyl, 3-CN-phenyl, 3-cyclohexyl-phenyl, 3-cyclopropyl-phenyl, 3-Et-phenyl, 3,4,6-tri-F-phenyl, 3,4-di-F-phenyl, 3,5-di-F-phenyl, 3-F-phenyl, 3-tetralin, 3-I-phenyl, 3-iPr-phenyl, 3-Me-4-Cl-phenyl, 3-Me-4-F-phenyl, 3,4-di-Me-phenyl, 3,5-di-Me-phenyl, 3-Me-phenyl, 3-$OCF_3$-4-F-phenyl, benzo[d]dioxolane, 3-OiPr-phenyl, 3-OMe-4-Cl-phenyl, 3,5-di-OMe-phenyl, 3-OMe-phenyl, 3-Ph-phenyl, 3-chloropyridyl, 3-pyridyl, 3,5-di-tBu-phenyl, 3-tBu-phenyl, 4-Br-phenyl, 4-acetylene-phenyl, 4-$CF_3$-phenyl, 4-$CH_2$Ph-phenyl, 4-Cl-phenyl, 4-CN-phenyl, 4-COMe-phenyl, 4-F-phenyl, 4-Me-phenyl, 4-morpholine-phenyl, 4-$OCF_3$-phenyl, 4-OPh-phenyl, or 5-Cl-6-F-phenyl.

In yet another embodiment, $R^5$ or $R^6$ is optionally substituted heteroaryl.

In a further embodiment, $R^5$ or $R^6$ is pyridine optionally substituted with one or more halogen. In one embodiment, each halogen is independently selected from a group of F, Cl, Br and I.

In one embodiment, $R^5$ or $R^6$ is pyrrolyl, indolyl, pyrimidinyl, alkyl, benzyl, cycloalkylyl, heterocycloalkylyl, or heterocycloalkylylalkyl.

In another embodiment, $R^5$ or $R^6$ is benzo[d]dioxolane.

In yet a further embodiment, $R^5$ or $R^6$ is tetrahydronaphthalene.

In another embodiment, the compound is of formula (I-A), wherein $X^1$-$X^4$, Y, $R^5$ and $R^6$ are defined herein.

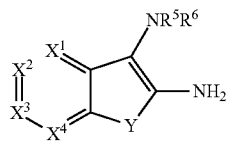
(I-A)

In a further embodiment, the compound is of formula (I-AA), wherein $X^1$-$X^4$, $R^5$ and $R^6$ are defined herein.

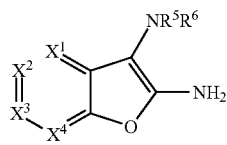
(I-AA)

In yet another embodiment, the compound is of formula (I-AAA), wherein $X^1$-$X^4$, $R^5$ and $R^6$ are defined herein.

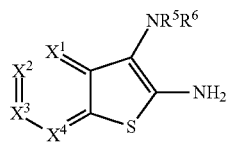
(I-AAA)

In still a further embodiment, the compound is of formula (I-B), wherein $X^1$-$X^4$, Y, and $R^5$ are defined herein.

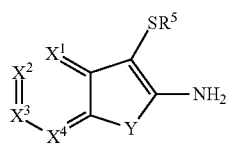
(I-B)

In another embodiment, the compound is of formula (I-BB), wherein $X^1$-$X^4$ and $R^5$ are defined herein.

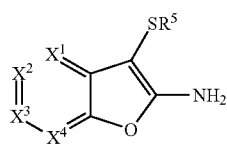
(I-BB)

In yet a further embodiment, the compound is of formula (I-BBB), wherein $X^1$-$X^4$ and $R^5$ are defined herein.

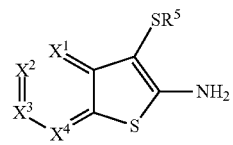
(I-BBB)

In still a further embodiment, the compound is of formula (I-BBBB), wherein $X^1$-$X^4$, Y, and $R^5$ are defined herein.

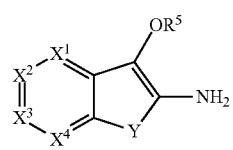
(I-BBBB)

In another embodiment, the compound is of formula (I-BBBBB), wherein $X^1$-$X^4$ and $R^5$ are defined herein.

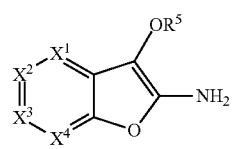
(I-BBBBB)

In yet a further embodiment, the compound is of formula (I-BBBBBB), wherein $X^1$-$X^4$ and $R^5$ arc defined herein.

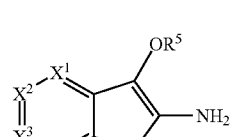
(I-BBBBBB)

In still another embodiment, the compound is of formula (I-C), wherein $X^1$-$X^4$ and $R^5$ are defined herein.

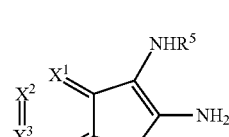
(I-C)

In a further embodiment, the compound is of formula (I-CC), wherein $X^1$-$X^4$ and $R^5$ are defined herein.

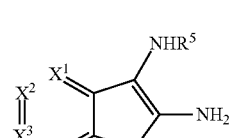
(I-CC)

In yet another embodiment, the compound is of formula (I-D), wherein $R^5$ and $R^6$ are defined herein.

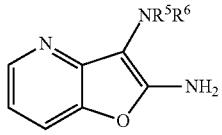

(I-D)

In still a further embodiment, the compound is of formula (I-DD), wherein $R^5$ and $R^6$ are defined herein.

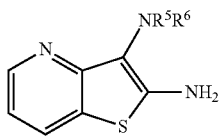

(I-DD)

In another embodiment, the compound is of formula (I-E), wherein $R^5$ and $R^6$ are defined herein.

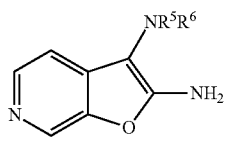

(I-E)

In a further embodiment, the compound is of formula (I-EE), wherein $R^5$ and $R^6$ are defined herein.

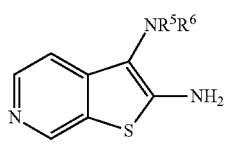

(I-EE)

In still another embodiment, the compound is of formula (I-F), wherein $R^1$, $R^2$, and $R^4$-$R^6$ are defined herein.

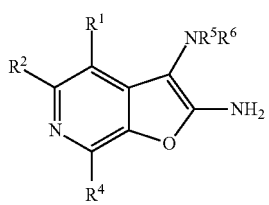

(I-F)

In yet a further embodiment, the compound is of formula (I-FF), wherein $R^1$, $R^2$, and $R^4$-$R^6$ are defined herein.

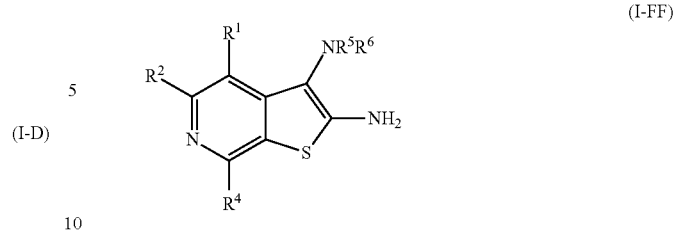

(I-FF)

In another embodiment, the compound is of formula (I-G), wherein $R^1$-$R^5$ are defined herein.

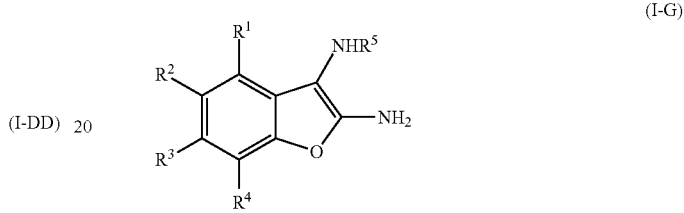

(I-G)

In still a further aspect, the compound is of formula (I-GG), wherein $R^1$-$R^5$ are defined herein.

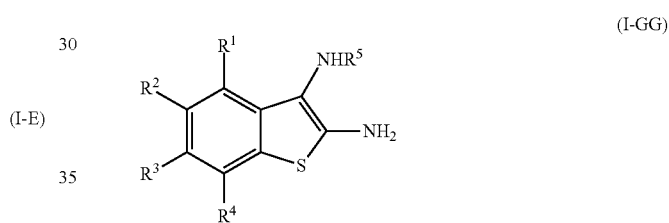

(I-GG)

Also falling within the scope of this invention are in vivo metabolic products of the compounds of formula (I) described herein and prodrugs thereof Such metabolic products may result from the oxidation, reduction, hydrolysis, amidation, deamidation, esterification, deesterification, enzymatic cleavage, and the like, of the administered compound. Accordingly, compounds of the invention include without limitation metabolites of compounds of formula (I) and prodrugs thereof. Further, the invention includes metabolites of compounds of formula (I), including compounds produced synthetically and/or by a process comprising contacting a compound of this invention with a mammal or a cell, for example, a mammalian cell (including without limitation, rat, mice, human, ape, monkey, rabbit, guinea pig, hamster, pig, cow, goat, sheep, cat, dog etc.) or a eukaryotic cell such as a yeast cell, for a period of time sufficient to yield a metabolic product thereof, and prodrug thereof.

Metabolic products typically are identified by preparing a radiolabeled (e.g., $^{14}$C or $^3$H) isotope of a compound of the invention, administering it parentally in a detectable dose (e.g., greater than about 0.5 mg/kg) to an animal such as a rat, mouse, guinea pig, monkey, rabbit, bovine such a cow, ape, goat, cat, or to human allowing sufficient time for metabolism to occur (typically about 30 seconds to 30 hours) and isolating its conversion products from urine, blood, or other biological samples. These products are easily isolated since they are labeled (others are isolated by the use of antibodies capable of binding epitopes surviving in the metabolite). Initial identification and analysis of the metabolites, however, may also be performed using non-radiolabeled compounds. In general, analysis of metabolites is done in the same way as conventional drug metabolisms studies well known to those skilled in the art. Metabolite structures are determined in conventional fashion, e.g., MS, LC/MS/MS or NMR analysis.

In one aspect, the invention relates to a purified and isolated metabolite of the compounds of formula (I) and prodrugs thereof, and pharmaceutically acceptable salts of the metabolites thereof In another aspect, the invention relates to pharmaceutically acceptable metabolites of compounds of formula (I) and prodrugs thereof. In one aspect of the invention, metabolites of compounds of formula (I) have a molecular mass less than that of a corresponding or parent compound of formula (I). In another aspect of the invention, the molecular mass of metabolites is greater than that of corresponding or parent compound of formula (I). In one embodiment of the invention, the molecular mass of metabolites of compounds of formula (I) is less by 1 or 2 units than that of corresponding or parent compound of formula (I). In another embodimentof the invention, the molecular mass of metabolites of compounds of formula (I) is less by 2 units. In yet another aspect of the invention, metabolites are capable of converting back to a corresponding (parent) compound in vitro and in vivo. The conversion may be complete or partial. Accordingly, metabolites of compounds of formula (I) are useful as prodrugs.

Compounds of formula (I) or metabolites thereof that are basic in nature are capable of forming a wide variety of different salts with various inorganic and organic acids. Although such salts must be pharmaceutically acceptable for administration to animals and mammals, it is often desirable in practice to initially isolate a compounds or metabolite from a reaction mixture as a pharmaceutically unacceptable salt and then simply convert the latter back to a free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of a chosen mineral or organic acid in an aqueous solvent medium or in a suitable organic solvent such as, but not limited to, methanol or ethanol. Upon careful evaporation of the solvent, the desired solid salt is obtained.

Acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nirate, sulfate or bisulfate, phosphate or acid phosphate, acetate, lactate, citrate or acid citrate, tartarate or bitartrate, succinate, maleate, fumarate, gluconate, saccharate, benzoate, methanesulfonate and palmoate (i.e., 1,1'-methylene-bis-(2-hydroxy-3-naphtoate)) salts and the like.

Compounds of formula (I) or metabolites thereof which are also acidic in nature, e.g., where $R^1$-$R^6$ includes a COOH or tetrazole moiety, are capable of forming base salts with various pharmacologically acceptable cations. Examples of such salts include the alkali metal or alkaline-earth metal salts and particularly, the sodium and potassium salts. These salts are prepared by conventional techniques. The chemical bases which arc used as reagents to prepare the pharmaceutically acceptable base salts of this invention are those which form non-toxic base salts with the herein described acidic metabolites of the compounds of formula (I). These non-toxic base salts include those derived from such pharmacologically acceptable cations as sodium, potassium, calcium, and magnesium etc. These salts can easily be prepared by treating the corresponding acidic compounds with an aqueous solution containing the desired acceptable cations, and then evaporating the resulting solution to dryness, preferably under reduced pressure. Alternatively, they can also be prepared by mixing lower alkanoic solutions of the acidic compounds and the desired alkali metal alkoxide together, and then evaporating the resulting solution to dryness in the same manner as before. In either case, stoichiometric quantitities of reagents are preferably employed in order to ensure completeness of reaction and maximum product yields.

One aspect of the invention is directed to prodrugs of compounds of the invention. In a further embodiment, a compound of the invention may be a prodrug of a compound of formula (I). Another aspect of the invention is directed to prodrugs of metabolites of the compounds.

In a one embodiment, a compound of the invention may be a prodrug of a compound of formula (I). Acetyl, amide, carbamate, carbonate, ester or carbonate prodrugs of compounds of formula (I) may be prepared using the methods described herein. In one embodiment, a compound of formula (I) may be reacted with an acyl chloride. In another embodiment, the acyl chloride may be $R^ZC(O)Cl$, where $R^Z$ is $C_1$-$C_6$ optionally substituted alkyl, $C_6$-$C_{10}$ optionally substituted aryl, or heteroaryl. In an embodiment, the prodrug is an acylated compound of formula (I) which has the formula (II), wherein $R^9$ is optionally-substituted $C_1$-$C_6$ alkyl.

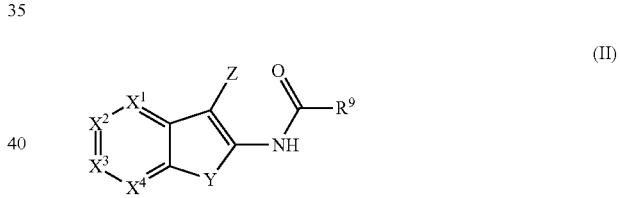

(II)

In one embodiment, the prodrug is of formula (II) wherein $R^9$ is methyl. In a further embodiment, the reaction may be performed in the presence of a base such as potassium tert-butoxide, to provide a prodrug of compound of formula (I). In a further embodiment, the reaction may be performed in the presence of a base such as pyridine. As well, acetyl amide prodrugs of compounds of formula (I) may be prepared by reaction of a compound of formula (I) with MeCN. In one embodiment, the reaction is performed under acidic conditions.

Thus, in one embodiment, the prodrug is an acetylated compound of formula (I). In a further embodiment, the prodrug is a phosphamide of the compound of formula (I). In still a further embodiment, the prodrug is an acetate of the compound of formula (I).

In another embodiment, the prodrug is a carbamate of the compound of formula (I) which has the formula (III), wherein $R^{10}$ is optionally-substituted $C_1$-$C_6$ alkyl, aryl, (aryl)alkyl, heteroaryl, or (heteroaryl)alkyl. In one embodiment, the prodrug structure is formula (III) wherein $R^{10}$ is selected from methyl, ethyl, benzyl, ($C_1$-$C_6$ alkoxy)methyl, and 1-($C_1$-$C_6$ alkoxy)ethyl.

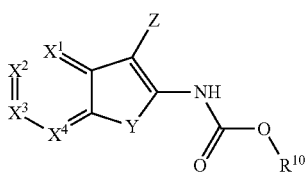

(III)

In yet another embodiment, the prodrug is a (bis)carbamate of the compound of formula (I) which has the formula (IV), wherein $R^{11}$ is optionally-substituted $C_1$-$C_6$ alkyl, aryl, (aryl)alkyl, heteroaryl, or (heteroaryl)alkyl. In one embodiment, the prodrug structure is formula (IV) wherein $R^{11}$ is selected from methyl, ethyl, benzyl, ($C_1$-$C_6$ alkoxy)methyl, and 1-($C_1$-$C_6$ alkoxy)ethyl.

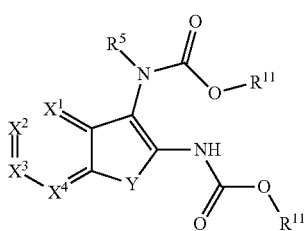

(IV)

Thus, in still a further embodiment, the carbamate group is selected from the following:

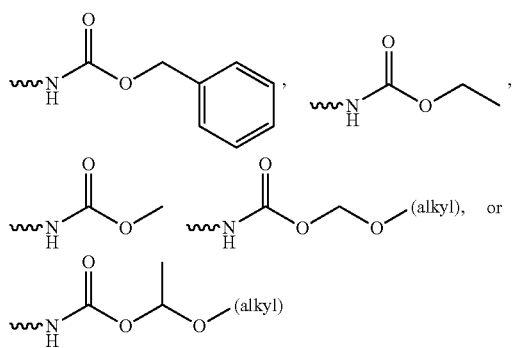

Prodrugs of compounds of formula (I) may be prepared and used as a means to modulate the pharmacokinetic properties, using various methods known to those skilled in the art. See, e.g., Rautio, Nature Reviews Drug Discovery, 7:255-270 (2008) and Ettmayer, J. Med. Chem., 47:2393-2404 (2004), which are hereby incorporated by reference. In the case of drugs containing a hydroxy moiety, acetyl and other ester analogs are contemplated for use as prodrugs. See, e.g., Beaumont, Current Drug Metabolism, 4:461-485 (2003), which is hereby incorporated by reference. In the case of drugs containing an amine moiety, prodrugs containing amides and carbamates are contemplated. See, e.g., Simplicio, Molecules, 13:519-547 (2008), which is hereby incorporated by reference. As specific examples, (alkoxycarbonyloxy)alkyl carbamates, (acyloxy)alkyl carbamates, and (oxodioxolenyl)alkyl carbamates may be utilized as effective prodrug strategies for amines. See, e.g., Li, Bioorg. Med. Chem. Lett., 7:2909-2912 (1997); Alexander, J. Med. Chem., 34:78-81 (1991); Alexander, J. Med. Chem., 31:318-322 (1988); and Alexander, J. Med. Chem., 39:480-486 (1996), all of which are incorporated by reference herein.

Compounds of formula (I) and metabolites thereof, and pharmaceutically acceptable salts and prodrugs thereof, as well as metabolites of prodrugs of compounds of formula (I) (collectively "compounds of the invention," "compounds" or "test compounds") are well within the scope of this invention.

Schemes for Preparation

The compounds of the invention may be synthesized by synthetic routes that include processes analogous to those well-known in the chemical arts and those included in the present application. Starting materials are generally available from commercial sources such as Sigma Aldrich Chemicals (Milwakee, Wis.) or are readily prepared using methods well known to those skilled in the art (e.g., prepared by methods generally described in Louis F. Fieser and Mary Fieser, Reagents for Organic Sythesis, v. 1-19, Wiley, N.Y. (1967-1999 ed.), or Vogel's Textbook of Practical Organic Chemistry (5th Edition) A. I. Vogel et al., or Beilsteins Handbuch der organischen Chemi, 4, Aufl. Ed. Springer-Verlag, Berlin, including supplements (also available via the Beilstein and Reaxys online database).

Compounds of the invention may be converted into a pharmaceutically acceptable salt, and a salt may be converted into the free base compound, by conventional methods. Compounds of the invention may be therapeutically effective as a free base or as a pharmaceutically acceptable salt, depending on the desired properties such as solubility, dissolution, hygroscopic nature, and pharmacokinetics. Examples of pharmaceutically acceptable salts include salts with inorganic acids, such as hydrochloric acids, trifluoroacetic acid, propprionic acid, oxalic acid, malonic acid, accinic acid, fumaric acid, maleic acid, lactic acid, malic acid, tartaric acid, citric acid, ethanesulfonic acid, aspartic acid and glutamic acid. The salt may be a mesylate, a hydrochloride, a phosphate, a benzenesulfonate, or a sulfate. Salts may be mono-salts or bis-salts. For example, the mesylate may be the monomesylate or the bismesylate.

Compounds of the invention may also exist as hydrates or solvates.

Protection of functional groups (e.g., primary or secondary amines) of the intermediates may be necessary in preparing compounds of formula (I)-(IV). The need for such protection will vary depending on the nature of the remote functionality and the conditions of the preparation methods. Suitable amino-protecting groups include acetyl, trifluoroacetyl, t-butoxycarbonyl (Boc), benzyloxycarbonyl (CBz) and 9-fluorenylethyleneoxycarbonyl (Fmoc). The need for such protection is readily determined by one skilled in the art. For a general description of protection groups and their use, see T.W. Greene, Protective groups in Organic Synthesis, John Wiley & Sons, New York, 1991.

Methods useful for making the compounds of formula (I) are set forth in the Examples below and generalized in Schemes 1-28. One of skill in the art will recognize that Schemes 1-28 can be adapted to produce other compounds of formula (I), prodrugs, metabolites, and pharmaceutically acceptable salts of compounds of formula (I) according to the present invention.

Scheme 1

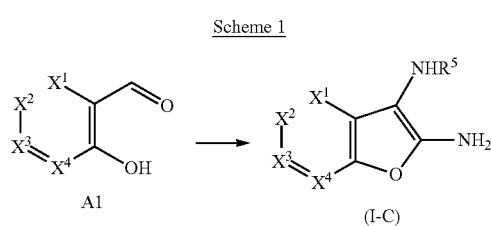

Scheme 1 depicts a synthesis of fluoropyridin derivative (I-C). Compound A1 was treated with an amine ($R^5$—$NH_2$). In one embodiment, the amine ($R^5$—$NH_2$) was an optionally substituted aniline. In another embodiment, the amine ($R^5$—$NH_2$) was a heterocyclic amine. In yet another embodiment, the amine ($R^5$—$NH_2$) was an alkylamine. After the complete disappearance of starting materials, an alkylsilyl cyanide was added to provide compound (I-C). In one embodiment, the alkylsilyl cyanide was TMSCN.

Scheme 1A

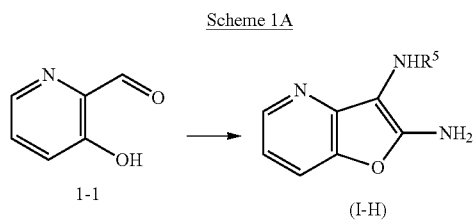

Scheme 1A depicts a synthesis of compound (I-H). 3-Hydroxy pyridine-2-carboxaldehyde 1-1 was treated with an amine ($R^5NH_2$). In one embodiment, the amine ($R^5$—$NH_2$) is an optionally substituted aniline. After the complete disappearance of starting materials, TMSCN was added to provide compound (I-H).

Scheme 1B

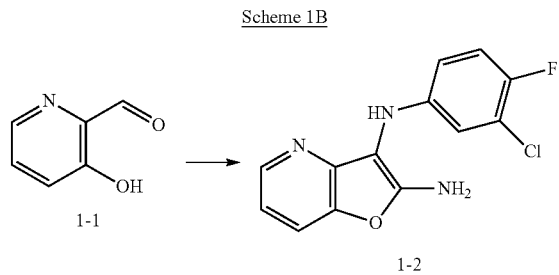

Scheme 1B depicts a synthesis of fluoropyridin derivative 1-2. 3-Hydroxy pyridine 2-carboxaldehyde 1-1 was treated with 3-chloro-4-fluoroaniline. After complete disappearance of starting materials, TMSCN was added to provide compound 1-2.

Scheme 2

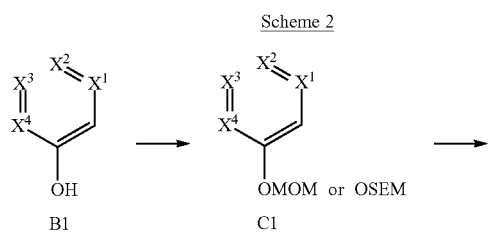

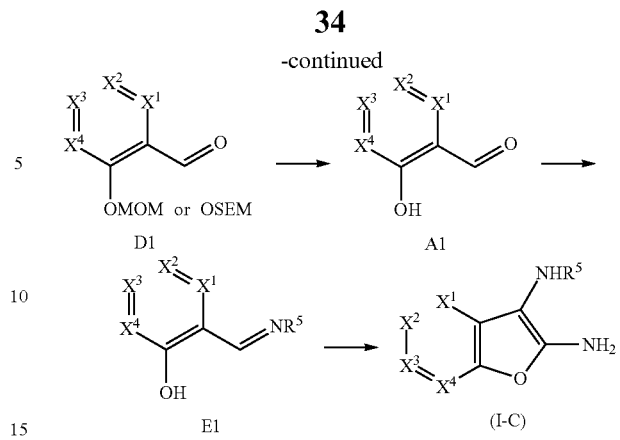

Scheme 2 provides the compounds of formula (I-C). A sodium or potassium alkoxide or NaH was added to a solution of compound B1. In one embodiment, the potassium alkoxide was potassium tert-butoxide. Compound B1 was reacted with methoxymethyl chloride or 2-(trimethylsilyl)ethoxymethyl chloride (SEMCl) to provide MOM or SEM protected compound C1. TMEDA, HMPA, TEA, or DIPEA was then added to a solution of compound C1, followed by addition of an alkyllithium reagent and then DMF, N-formylpiperidine or ethylformate to provide carbaldehyde D1. In one embodiment, the alkyl-lithium reagent was n-BuLi. Deprotection of the MOM or SEM group provided the 3-hydroxy carbaldehyde compound A1. Compound A1 was then treated with an amine ($R^5$—$NH_2$) in the presence of an acid to provide imine E1. Imine E1 then underwent Strecker reaction followed by intramolecular cyclization using TMSCN to form fluoropyridin compound (I-C).

Scheme 2A

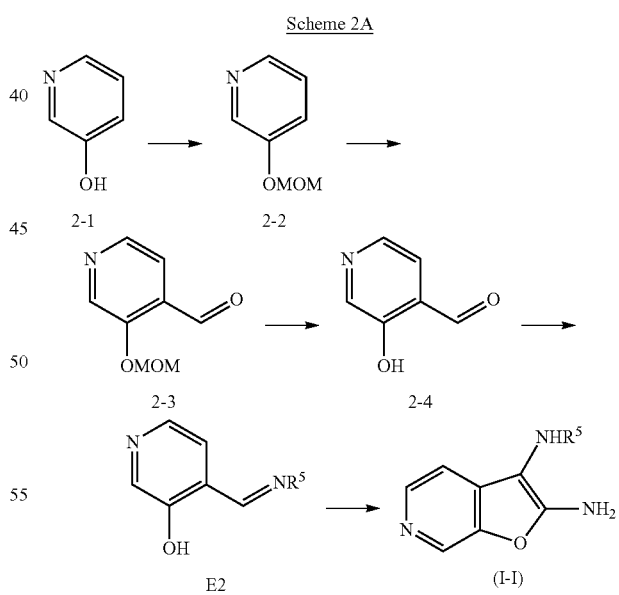

Scheme 2A provides compounds of formula (I-I). Potassium tert-butoxide was added to a solution of 3-hydroxypyridine 2-1. Methoxymethyl chloride was then added to afford the desired MOM protected compound 2-2. TMEDA was then added to compound 2-2. n-BuLi was then added to this solution. DMF was then added to provide the MOM protected carbaldehyde 2-3. Deprotection of the MOM group provided compound 2-4. In one embodiment, the deprotection was performed using 3N HCl/THF. Compound 2-4 was then treated with an amine (R⁵—NH₂) to provide imine E2 as the intermediate. In one embodiment, the amine (R⁵—NH₂) was an aniline. Imine E2 was then reacted with TMSCN to form fluoropyridin compound (I-I).

Scheme 2B

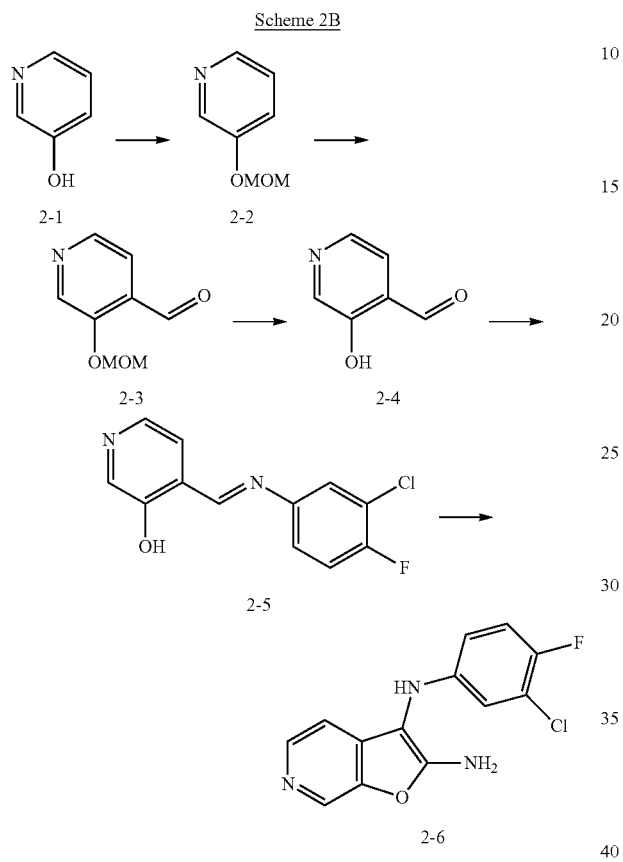

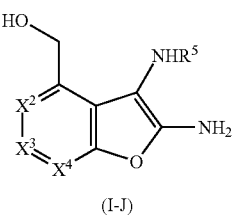

(I-J)

Scheme 3 shows the synthesis of compound (I-J). Compound F1 was coupled with an amine (R⁵—NH₂). In one embodiment, the amine (R⁵—NH₂) was an optionally substituted aniline to provide the corresponding imine compound G1. Compound G1 was reacted with TMSCN to provide target compound (I-J).

Scheme 3A

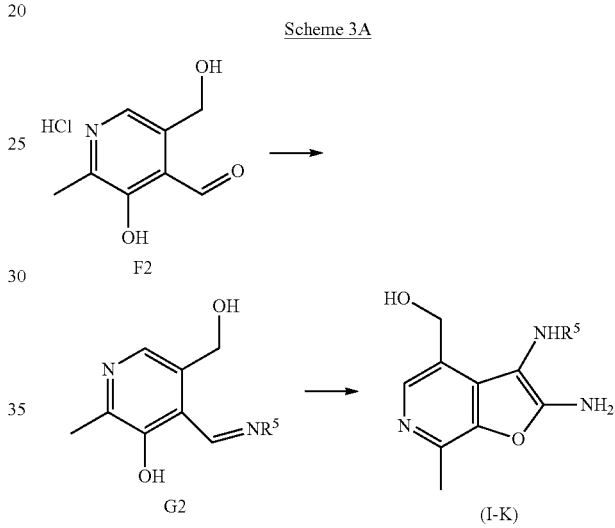

Scheme 2B provides the formation of compound 2-6. Potassium tert-butoxide was added to 3-hydroxypyridine 2-1. Methoxymethyl chloride was then added to afford the desired MOM protected compound 2-2. TMEDA was then added to compound 2-2 followed by addition of n-BuLi. DMF was then added to give the MOM protected carbaldehyde 2-3. Deprotection of the MOM group provided 3-hydroxypyridine-2-carbaldehyde 2-4. In one embodiment, the deprotection was performed using 3N HCl. Compound 2-4 was treated with 3-chloro-4-fluoroaniline to provide imine 2-5. The corresponding imine underwent Strecker reaction followed by intramolecular cyclization using TMSCN to form fluoropyridin 2-6.

Scheme 3A shows the synthesis of compound (I-K). First, compound F2 was coupled with an amine (R⁵—NH₂) to provide the corresponding G2 imine. Imine G2 was then reacted with TMSCN to provide compound (I-K).

Scheme 3B

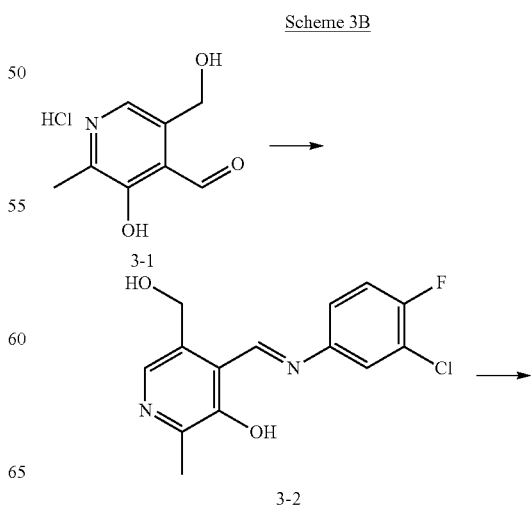

Scheme 3

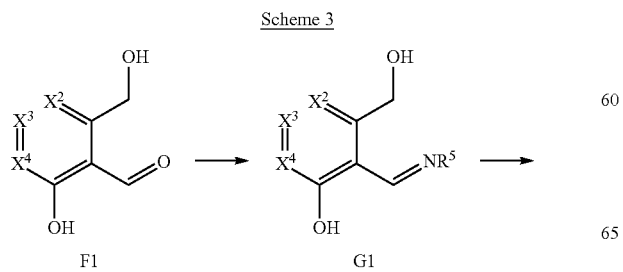

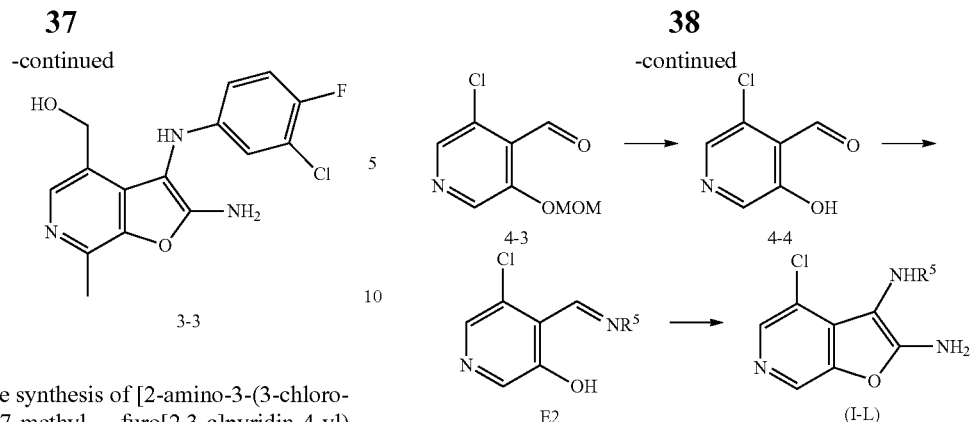

Scheme 3B shows the synthesis of [2-amino-3-(3-chloro-4-fluorophenyl)amino]-7-methyl furo[2,3-c]pyridin-4-yl)methanol 3-3. Pyridoxal hydrochloride 3-1 was reacted with 4-fluoro-3-chloro aniline to provide corresponding imine intermediate 3-2. Reaction with TMSCN provided compound 3-3.

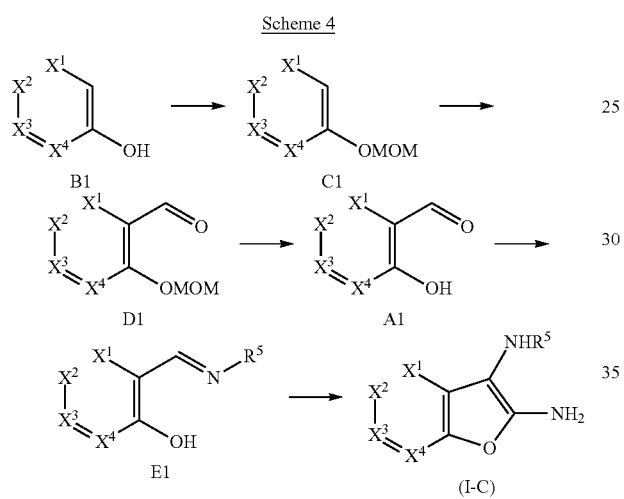

Scheme 4 depicts another synthesis of furopyridine derivative (I-C). To a stirred solution of compound B1 was added a potassium or sodium alkoxide to provide MOM protected compound C1. In one embodiment, the potassium alkoxide was potassium tert-butoxide. Methoxymethyl chloride was then added to form MOM protected compound C1. LDA or LTMP was added to the solution of compound C1, followed by N-formylpiperidine or DMF to provide compound D1. Aldehyde D1 was deprotected via its reaction with an acid. In one embodiment, the acid was HCl or TFA/DCM. Deprotected aldehyde A1 was coupled with an amine ($R^5$—$NH_2$) to provide imine intermediate E1. Imine intermediate E1 was treated with TMSCN to provide furopyridine (I-C).

Scheme 4A

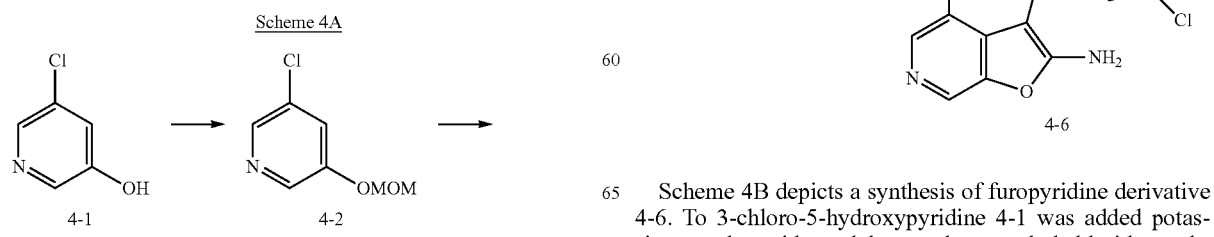

Scheme 4A depicts a synthesis of furopyridine derivative (I-L). To compound 4-1 was added potassium tert-butoxide. Methoxymethyl chloride was then added to form MOM protected compound 4-2. LDA was then added to the solution of compound 4-2. N-formylpiperidine was then added to this solution resulting in the formation of compound 4-3. Aldehyde 4-3 was then deprotected using an acid to compound 4-4. In one embodiment, the deprotection was performed using 3N HCl. Deprotected aldehyde 4-4 was coupled with an amine ($R^5$—$NH_2$) to provide imine intermediate E2. The corresponding imine intermediate was treated with TMSCN to provide furopyridine (I-L) via a Strecker reaction followed by intramolecular cyclization.

Scheme 4B

Scheme 4B depicts a synthesis of furopyridine derivative 4-6. To 3-chloro-5-hydroxypyridine 4-1 was added potassium tert-butoxide, and then methoxymethyl chloride resulting in the formation of MOM protected compound 4-2. LDA was added to compound 4-2. N-formylpiperidine was then added resulting in the formation of compound 4-3. The protected aldehyde 4-3 was deprotected to afford 3-chloro-5-hydroxy-pyridine-4-carbaldehyde 4-4 using HCl. The deprotected aldehyde 4-4 was coupled with 3-chloro-4-fluoroaniline to provide imine intermediate 4-5. The imine intermediate was then treated with TMSCN to provide furopyridine 4-6.

pound A1 was then reacted with an amine ($R^5$—$NH_2$) to provide imine intermediate E1. Corresponding imine E1 was converted to compound (I-C) using a trialkylsilyl cyanide such as TMSCN.

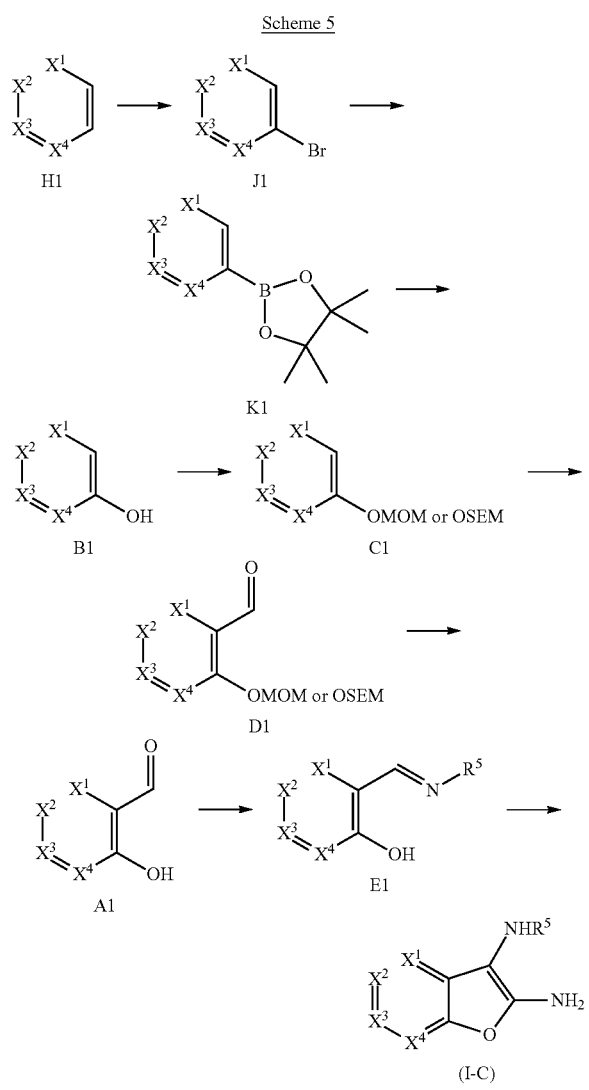

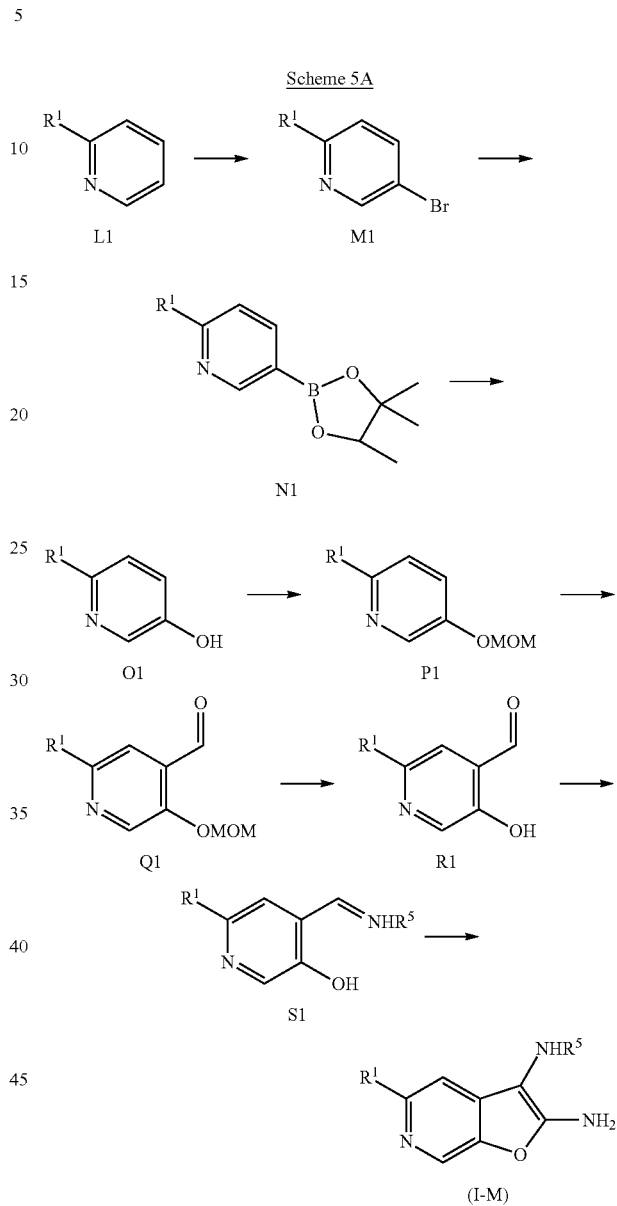

Scheme 5 depicts a synthesis of compound (I-C). NBS or N-iodosuccinimide was added to a compound H1 to afford compound J1. Compound J1 was then reacted with bis(pinacolato)diborane, potassium or sodium acetate, and Pd(dppf)Cl$_2$. DCM, Pd(OAc)$_2$, or Pd$_2$(dba)$_3$ to provide compound K1. Compound K1 was then reacted with sodium perborate tetrahydrate to provide compound B1 which was protected as the MOM ether using a potassium or sodium tert-butoxide and methoxymethylchloride or SEMCl. Resultant compound C1 was formylated via reaction with TMEDA or HMPA, followed by reaction with n-BuLi to provide compound D1. Corresponding aldehyde D1 was deprotected using an acid to provide compound A1. Com- Scheme 5A depicts the synthesis of compound (I-M). NBS was reacted with an $R^1$-substituted pyridine to afford compound M1. Compound M1, bis(pinacolato)diborane, potassium acetate, and Pd(dppf)Cl$_2$. DCM were reacted to provide compound N1. Compound N1 was reacted with sodium perborate tetrahydrate in water to provide compound O1 which was then protected as a MOM ether using potassium tert-butoxide and methoxymethylchloride. The resultant compound P1 was formylated via its reaction with TMEDA, followed by addition of n-BuLi to provide compound Q1. Corresponding aldehyde Q1 was then deprotected using an acid to provide compound R1. Compound R1 was then reacted with an amine ($R^5$—$NH_2$) to provide imine intermediate S1. The corresponding imine S1 was then converted to compound (I-M) using TMSCN.

Scheme 5B

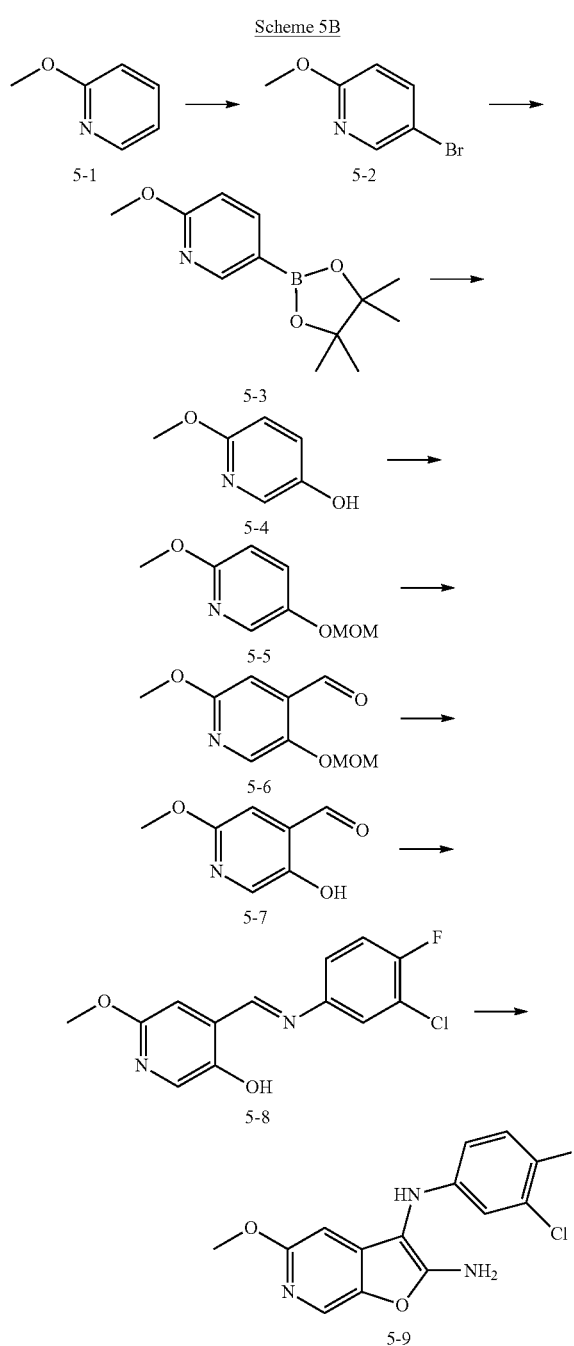

carbaldehyde 5-7. Compound 5-7 was then treated with 3-chloro-4-fluoroaniline to provide imine intermediate 5-8. The imine was converted to $N^3$-(3-chloro-4-fluoro-phenyl)-5-methoxy-furo[2,3-e]pyridine-2,3-diamine 5-9 using TMSCN.

Scheme 6

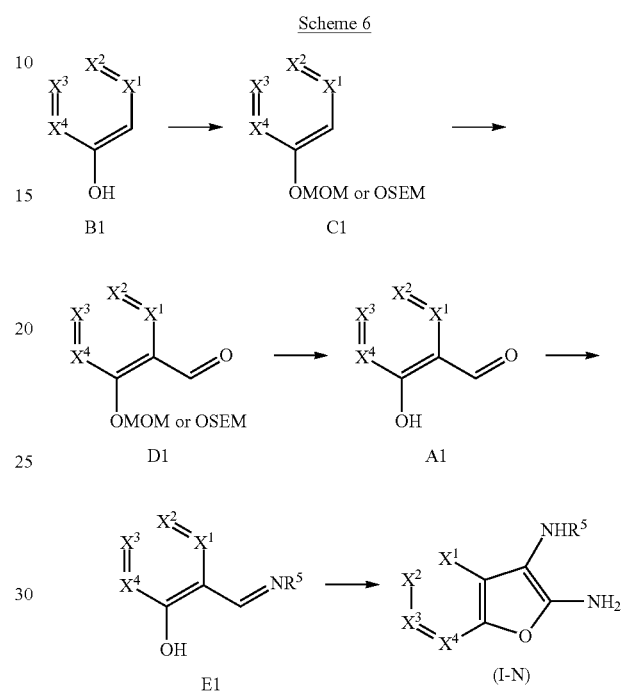

In Scheme 6, DIPEA or TEA was reacted with compound B1. The addition of methoxymethyl chloride or SEMCl provided the MOM or SEM protected compound C1. TMEDA was then added to compound C1, followed by an alkyl lithium reagent such as n-BuLi or sec-BuLi, and finally followed by DMF to provide MOM protected carbaldehyde D1. Compound D1 was deprotected using an acid to provide compound A1. Compound A1 was then treated with an amine ($R^5$—$NH_2$) to provide imine intermediate compound E1. Compound (I-N) was synthesized by treating corresponding imine E1 with a trialkylsilyl cyanide such as TMSCN.

Scheme 5B provides the synthesis of compound 5-9. NBS was added to 2-methoxypyridine in MeCN to afford compound 5-2. 5-Bromo-2-methoxypyridine on reaction with bis(pinacolato)diborane and potassium acetate in the presence of Pd(dppf)Cl$_2$. DCM provided 2-methoxy-5-(4,4,5,5-tetramethyl-[1,3,2]-dioxaborolan-2-yl)-pyridine 5-3. Compound 5-3 was added to a suspension of sodium perborate tetrahydrate in water to provide 6-methoxypyridin-3-ol 5-4. Compound 5-4 was protected as the MOM ether using potassium tert-butoxide and methoxymethylchloride. Compound 5-5 was then formylated by adding TMEDA, n-BuLi, and DMF to provide 2-methoxy-5-methoxymethoxy-pyridine-4-carbaldehyde 5-6. Aldehyde 5-6 was deprotected using 3N HCl to provide 5-hydroxy-2-methoxy-pyridine-4-

Scheme 6A

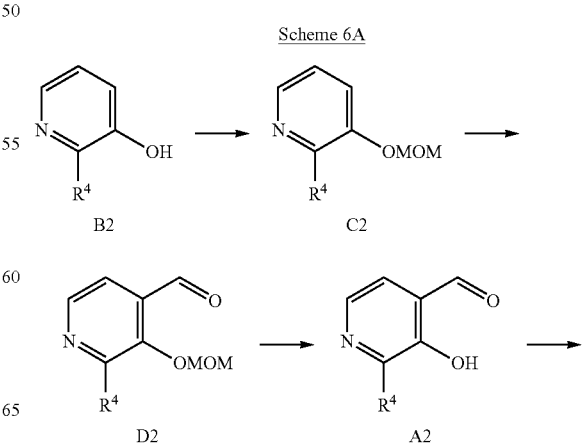

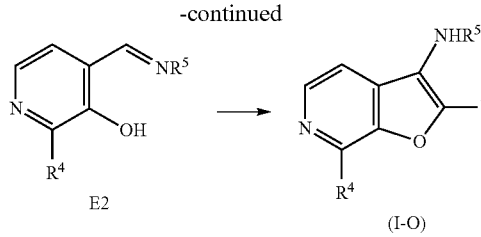

In Scheme 6A, DIPEA was added to 3-hydroxy-2-substituted pyridine B2. Methoxymethyl chloride was then added to provide the MOM protected compound C2. TMEDA was added to compound C2, followed by n-BuLi, which was followed by DMF to provide MOM protected carbaldehyde D2. Compound D2 was deprotected using 3N HCl to provide compound A2. Compound A2 was then reacted with an amine ($R^5$—$NH_2$) to provide imine intermediate E2. Compound (I-O) was synthesized by reacting imine E2 with TMSCN.

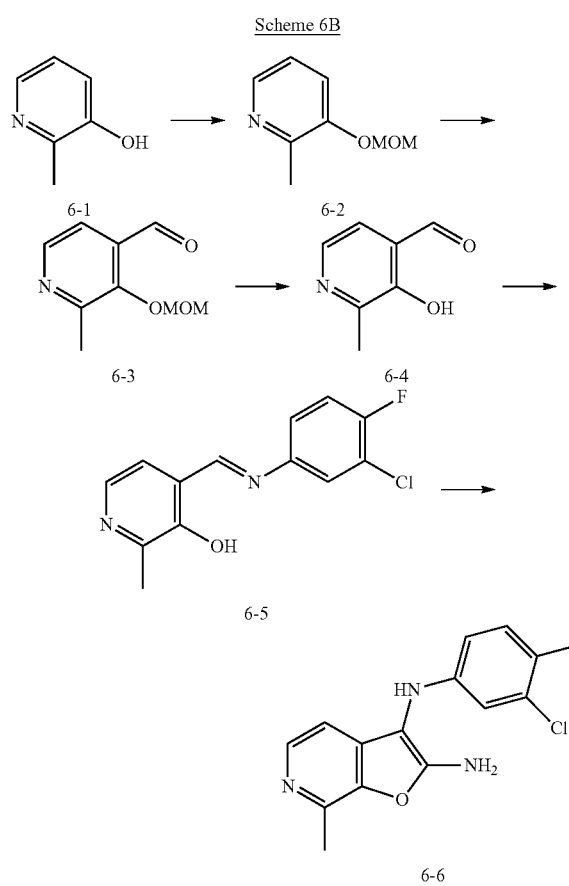

In Scheme 6B, DIPEA was added to 3-hydroxy-2-methylpyridine 6-1. Methoxymethyl chloride was then added to provide MOM protected compound 6-2. TMEDA was then added, n-BuLi (2.17 M in hexane) was added, and DMF was then added to provide the MOM protected carbaldehyde 6-3 which was deprotected using 3N HCl to provide 3-hydroxy-2-methylpyridine-4-carbaldehyde 6-4. Compound 6-4 was then treated with 3-chloro-4-fluoroaniline, resulting in the formation of imine intermediate 6-5. $N^3$-(3-chloro-4-fluorophenyl)-7-methyl-furo[2,3-c]pyridine-2,3-diamine 6-6 was synthesized by treating imine 6-5 with TMSCN.

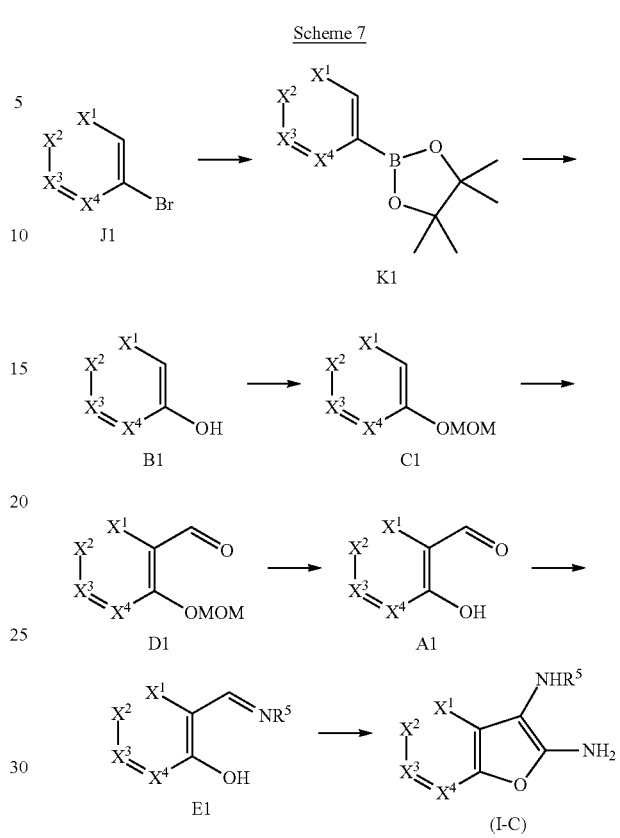

Scheme 7 provides the synthesis of compound (I-C). Specifically, compound J1, bis(pinacolato)diborane, potassium or sodium acetate, and Pd(dppf)Cl$_2$. DCM, Pd(OAc)$_2$, Pd(dba)$_3$, or Pd$_2$(dba)$_3$ were reacted to provide (4,4,5,5-tetramethyl-[1,3,2]dioxaborolan-2-yl)-pyridine K1. Compound K1 was reacted with sodium perborate tetrahydrate to provide pyridinol or phenol compound B1. Compound B1 was combined with potassium or sodium alkoxide such as potassium tert-butoxide, methoxymethyl chloride, and TMEDA or HMPA to provide compound C1. Compound C1 was then reacted with an alkyl lithium reagent such as n-BuLi or s-BuLi, followed by DMF or n-formylpiperidine to provide compound D1. Compound D1 was then deprotected using an acid to provide compound A1. Compound A1 was then treated with an amine ($R^5$—$NH_2$) to provide imine intermediate E1, which was treated with a trialkylsilyl cyanide such as TMSCN to provide compound (I-C).

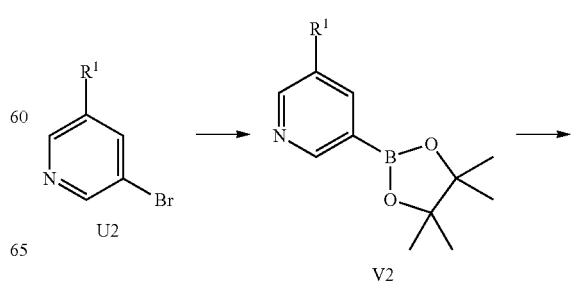

-continued

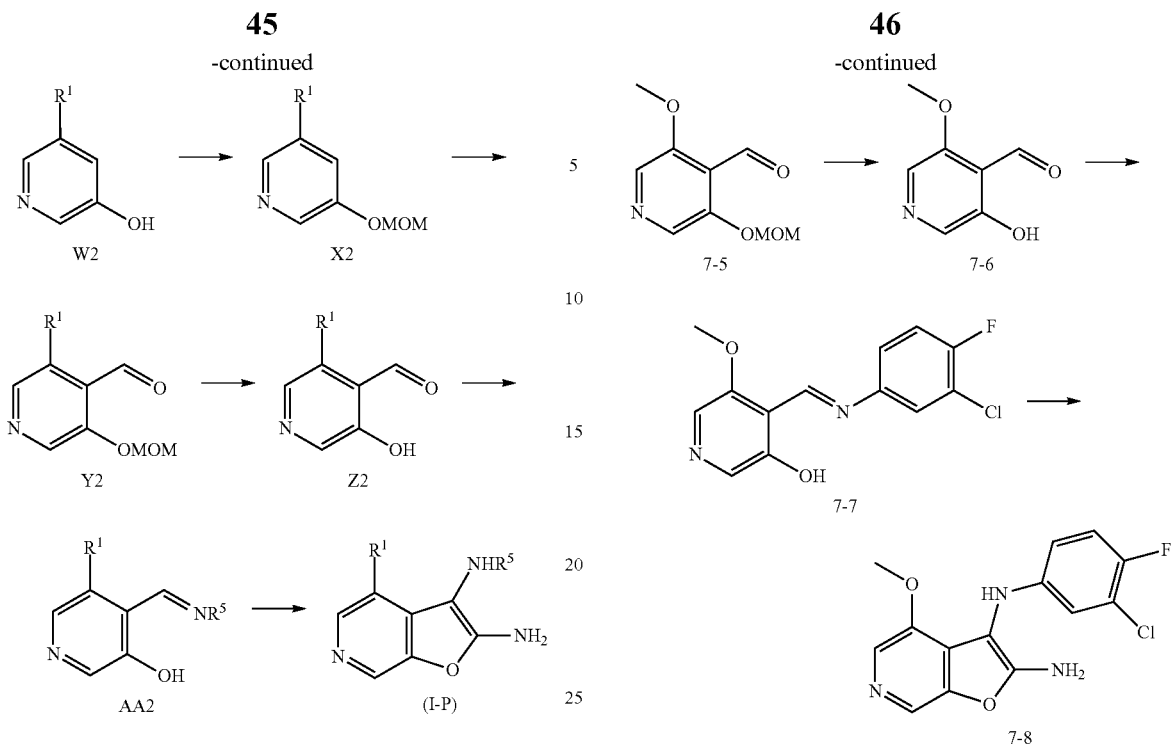

Scheme 7A provides the synthesis of compound (I-P). Specifically, $R^1$-substituted 3-bromo-pyridine U2, bis(pinacolato)diborane, potassium acetate, and Pd(dppf)Cl$_2$.DCM were reacted to provide 5-(4,4,5,5-tetramethyl-[1,3,2]dioxaborolan-2-yl)-pyridine V2. Compound V2 was reacted with sodium perborate tetrahydrate in water to provide $R^1$-substituted- pyridin-3-ol W2. Compound W2 was stepwise combined with potassium tert-butoxide, methoxymethyl chloride, and TMEDA to provide compound X2. Compound X2 was then reacted with n-BuLi, followed by DMF to provide compound Y2. Compound Y2 was then deprotected using an acid to provide compound Z2. Compound Z2 was then treated with an amine ($R^5$—NH$_2$) to provide imine intermediate AA2, which was treated with TMSCN to provide compound (I-P).

Scheme 7B provides the synthesis of compound 7-8. 3-Bromo-5-methoxypyridine 7-1, bis(pinacolato)diborane, potassium acetate, and Pd(dppf)Cl$_2$.DCM were reacted to provide 3-methoxy-5-(4,4,5,5-tetramethyl-[1,3,2]dioxaborolan-2-yl)-pyridine 7-2. Compound 7-2 was reacted with a suspension of sodium perborate tetrahydrate in water to provide 5-methoxy-pyridin-3-ol 7-3. Compound 7-4 was prepared by reacting compound 7-3, potassium tert-butoxide, and methoxymethyl chloride. Compound 7-4 was lithiated using n-BuLi and TMEDA and the resultant lithiated species was quenched with DMF to yield 3-methoxy-5-methoxymethoxy-pyridine-4-carbaldehyde 7-5. Compound 7-5 was deprotected using 3N HCl to provide 3-hydroxy-5-methoxy-pyridine-4-carbaldehyde 7-6. Compound 7-6 was then treated with 3-chloro-4-fluoroaniline to form imine intermediate 7-7 which was treated with TMSCN to provide $N^3$-(3-chloro-4-fluoro-phenyl)-4-methoxy-furo[2,3-c]pyridine-2,3-diamine 7-8.

Scheme 7B

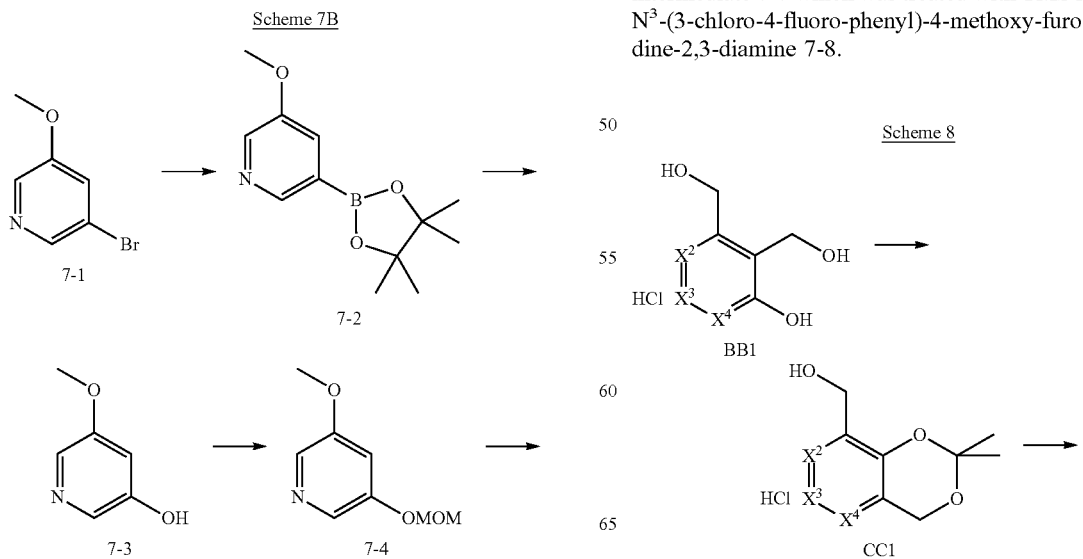

Scheme 8

47

-continued

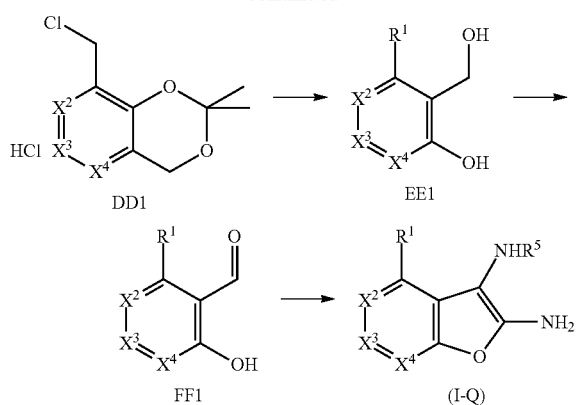

Scheme 8 describes the synthesis of compound (I-Q). Specifically, an acid was bubbled through compound BB1 to provide compound CC1 in acetone solution. In one embodiment, the acid was dry HCl. Thionyl chloride or oxalyl chloride in the presence of a catalytic amount of DMF was then added to compound CC1 to provide compound DD1. Compound DD1 was hydrogenated with hydrogen using a catalyst, such as Pd/C and sodium or potassium acetate to provide compound EE1. The alcoholic group of compound EE1 was oxidized to provide aldehyde FF1. In one embodiment, the oxidation was performed using manganese dioxide or pyridinium chloro chromate. Compound FF1 was then coupled with an amine ($R^5$—$NH_2$) to provide an imine intermediate which underwent in-situ Strecker reaction followed by intramolecular cyclization with TMSCN in the presence of acetic acid to afford compound (I-Q).

48

-continued

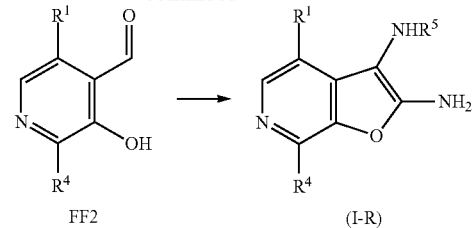

Scheme 8A describes the synthesis of compound (I-R) via treatment of an acetone solution of compound BB2 with an anhydrous acid such as HCl gas or sulfuric acid, to provide compound CC2. Thionyl chloride was then added to compound CC2 to provide compound DD2. Compound DD2 was hydrogenated with hydrogen gas using a catalyst, such as Pd/C and sodium acetate, to provide compound EE2. The alcoholic group of compound EE2 was oxidized with a reagent such as manganese dioxide to provide aldehyde FF2. Compound FF2 was then coupled with an amine ($R^5$—$NH_2$) to provide an imine intermediate which undergoes in-situ Strecker reaction followed by intramolecular cyclization with TMSCN in the presence of acetic acid to afford compound (I-R).

Scheme 8B

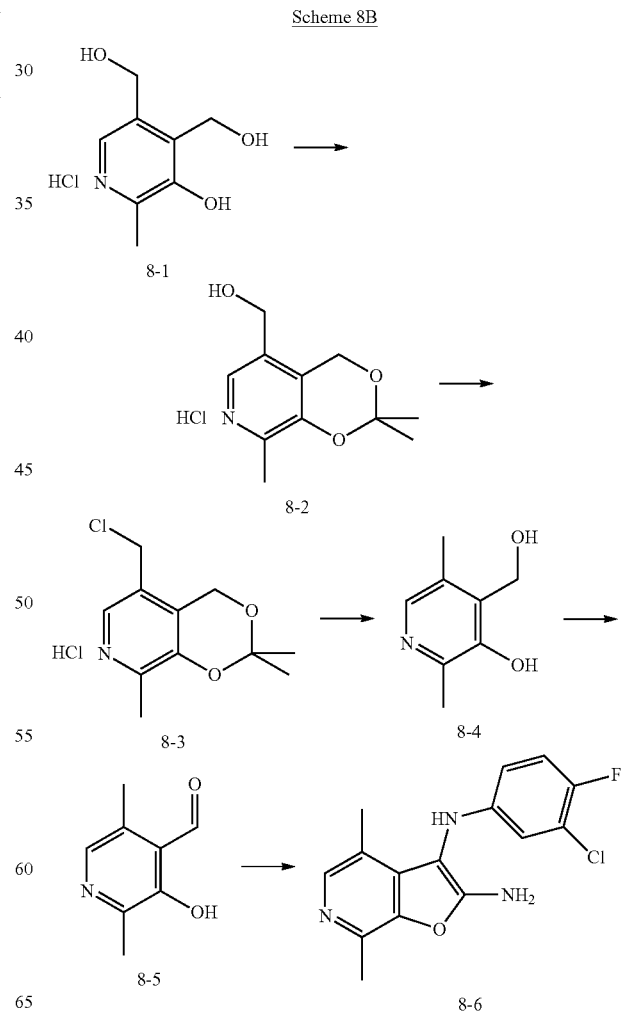

Scheme 8A

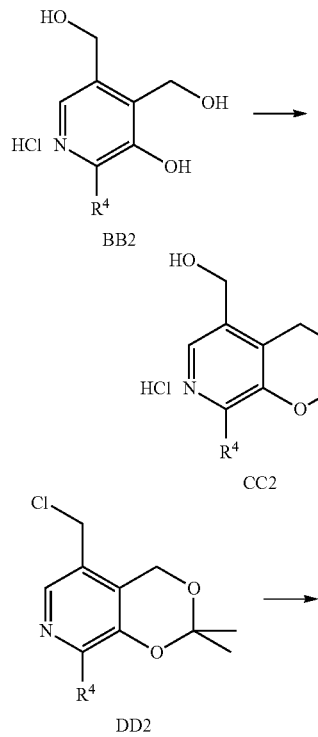

Scheme 8B describes the synthesis of $N^3$-(3-chloro-4-fluorophenyl)-4,7 dimethylfuro[2,3-c]pyridine-2,3-diamine 8-6. Dry HCl was bubbled through a suspension of pyridoxine hydrochloride 8-1 in acetone to afford 2,2-dimethyl-4H-[1,3]dioxino[4,5-c]pyridin-5-yl)methanol hydrochloride 8-2. Thionyl chloride was then added to the solution of compound 8-2 to afford 5-(chloromethyl)-2,2-dimethyl-4H-[1,3]dioxino[4,5-c]pyridine hydrochloride 8-3. Compound 8-3 was hydrogenated with Pd/C and sodium acetate under hydrogen, resulting in the formation of 4-(hydroxymethyl)-2,5-dimethylpyridin-3-ol 8-4. The alcoholic group of compound 8-4 was oxidized with manganese dioxide to give aldehyde 8-5. 3-Hydroxy-2,5-dimethylisonicotinaldehyde 8-5 was coupled with 3-chloro-4-fluoroaniline resulting in the formation of imine intermediate which undergoes in situ Strecker reaction followed by intramolecular cyclization with TMSCN to afford $N^3$-(3-chloro-4-fluorophenyl)-4,7-dimethylfuro[2,3-c]pyridine-2,3-diamine 8-6.

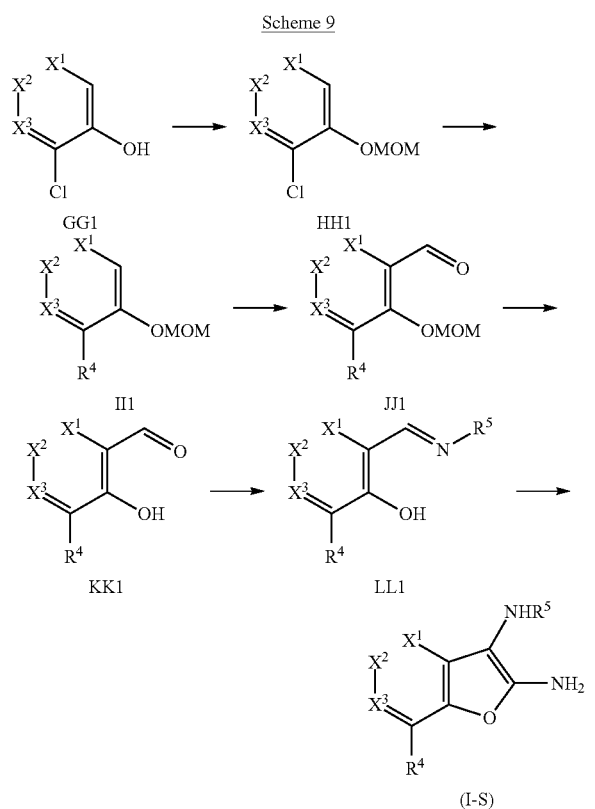

The synthesis of compound (I-S) is provided in Scheme 9. A strong base such as sodium or potassium alkoxide was added to compound GG1. In one embodiment, the strong base was potassium tert-butoxide. Methoxymethyl chloride was then added dropwise resulting in the formation of MOM protected compound HH1. To a stirred solution of compound HH1 was added an $R^4$-substituted alkylating agent and a catalyst to provide compound II1. In one embodiment, the alkylating agent was triethylborate. In another embodiment, the catalyst was Pd(PPh$_3$)$_4$. TMEDA or HMPA was then added to stirred solution of compound II1. n-BuLi, s-BuLi, LDA, or LTMP was then added, followed by DMF or N-formylpiperidine to afford compound JJ1. Compound JJ1 was deprotected to provide compound KK1. In one embodiment, this reaction was performed using an acid. In another embodiment, the acid was HCl. Compound KK1 was then treated with an amine ($R^5$—NH$_2$) to provide imine intermediate LL1. Compound LL1 was then converted to compound (I-S) using a trialkylsilyl cyanide such as TMSCN.

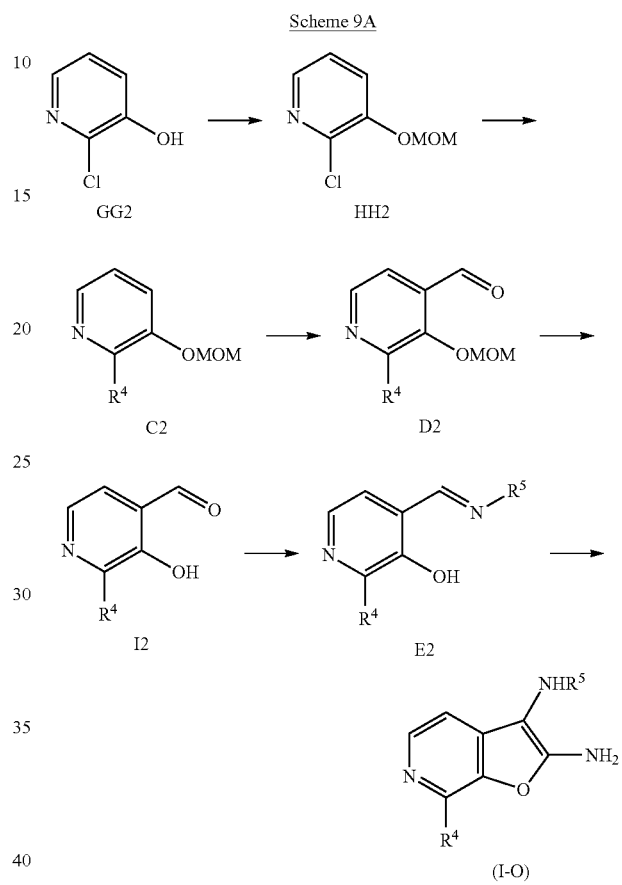

The synthesis of compound (I-O) is provided in Scheme 9A. Potassium tert-butoxide was added to a solution of compound GG2. Methoxymethyl chloride was then added resulting in the formation of MOM protected compound HH$_2$. To compound HH2 was added an $R^4$-substituted alkylating agent, such as triethylborate, K$_2$CO$_3$ and Pd(PPh$_3$)$_4$ to provide compound C2. TMEDA was then added to compound C2. n-BuLi was then added, followed by DMF to afford compound D2. Compound D2 was deprotected to provide compound I2. Compound I2 was then treated with an amine ($R^5$—NH$_2$) to provide imine intermediate E2. Compound E2 was then converted to compound (I-O) using TMSCN.

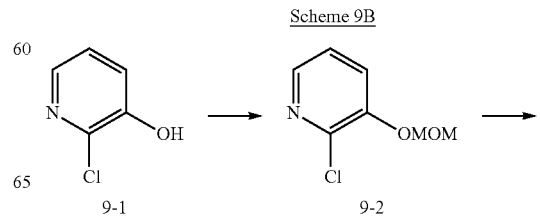

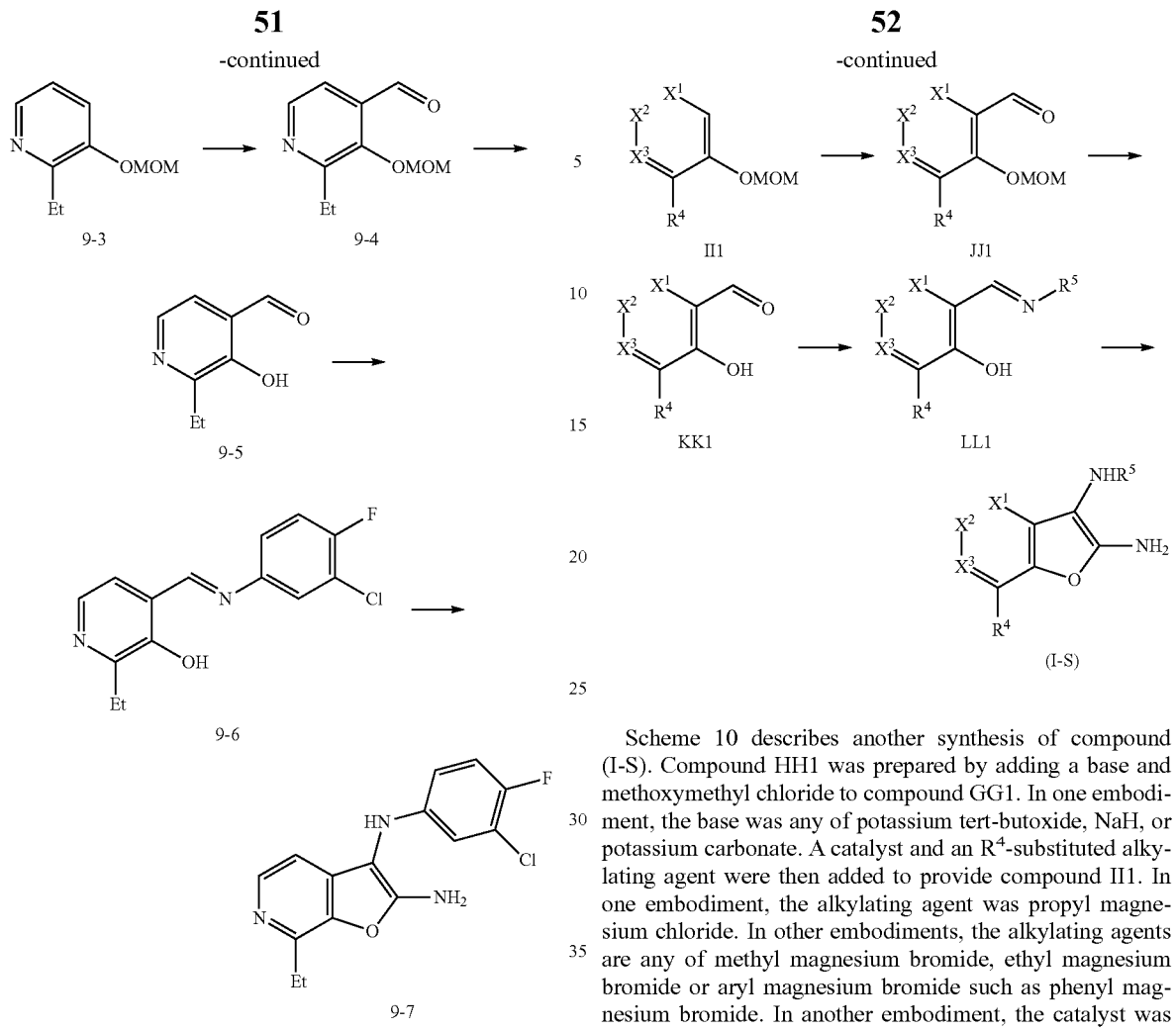

The synthesis of compound 9-7 is depicted in Scheme 9B. Potassium tert-butoxide was added to compound 9-1. Methoxymethyl chloride was then added, resulting in the formation of MOM protected compound 9-2. To a solution of 2-chloro-3-methoxymethoxy-pyridine 9-2 was added triethylborate, $K_2CO_3$ and $Pd(PPh_3)_4$ to afford 2-ethyl-3-methoxymethoxypyridine 9-3. TMEDA was added, followed by n-BuLi, and then DMF to afford 2-ethyl-3-methoxy methoxypyridine-4-carbaldehyde 9-4. Compound 9-4 was deprotected using 3N HCl to provide 2-ethyl-3-hydroxypyridine-4-carbaldehyde 9-5. Compound 9-5 was treated with 3-chloro-4-fluoroaniline to provide imine intermediate 9-6 which is in-turn converted to $N^3$-(3-chloro-4-fluoro-phenyl)-7-ethyl-furo[2,3-c]pyridine-2,3-diamine 9-7 in the presence of TMSCN.

Scheme 10 describes another synthesis of compound (I-S). Compound HH1 was prepared by adding a base and methoxymethyl chloride to compound GG1. In one embodiment, the base was any of potassium tert-butoxide, NaH, or potassium carbonate. A catalyst and an $R^4$-substituted alkylating agent were then added to provide compound II1. In one embodiment, the alkylating agent was propyl magnesium chloride. In other embodiments, the alkylating agents are any of methyl magnesium bromide, ethyl magnesium bromide or aryl magnesium bromide such as phenyl magnesium bromide. In another embodiment, the catalyst was $Ni(dppp)Cl_2$. TMEDA or LTMP was then added to compound II1. n-BuLi or s-BuLi was next added to the reaction mixture. To the lithiated species, DMF was added to provide an aldehyde compound JJ1. Aldehyde compound JJ1 was deprotected to provide compound KK1. In one embodiment, the deprotection was performed using an acid. In another embodiment, the acid was HCl. In another embodiment, the acid was TFA. Carbaldehyde KK1 was then treated with and an amine ($R^5$—$NH_2$) to provide imine intermediate LL1, which was converted to compound (I-S) using a trialkylsilyl cyanide such as TMSCN.

Scheme 10

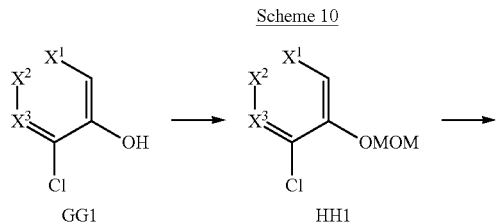

Scheme 10A

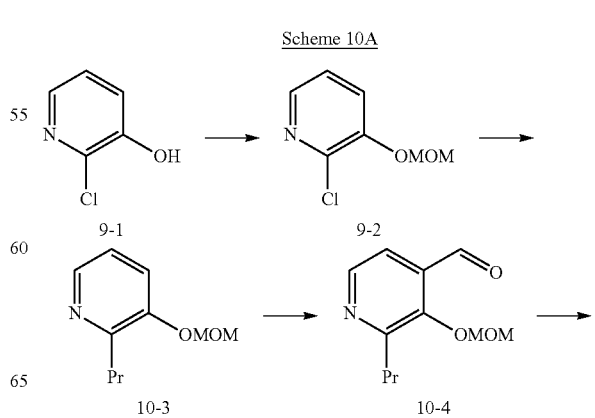

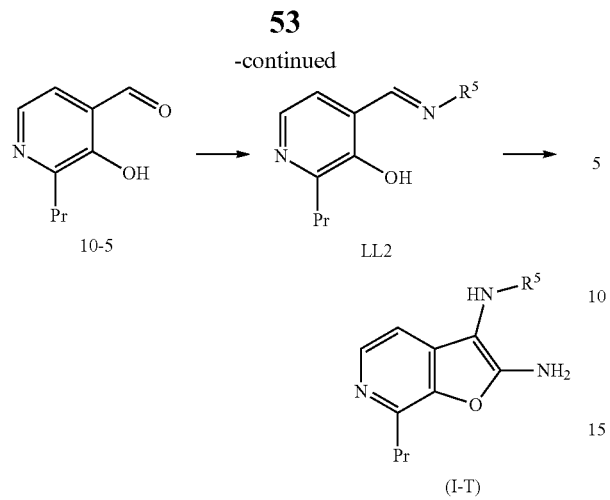

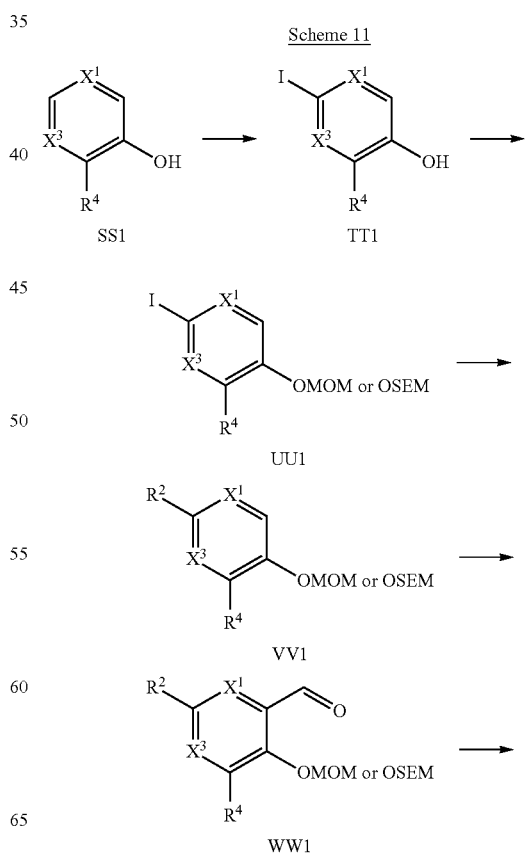

Scheme 10A describes the synthesis of (I-T). Compound 9-2 was prepared by adding potassium tert-butoxide and methoxymethyl chloride to a solution of compound 9-1. To a solution of 2-chloro-3-methoxy methoxypyridine 9-2, Ni(dppp)Cl$_2$ and propyl magnesium chloride (2M soln) were added to provide 3-methoxymethoxy-2-propylpyridine 10-3. TMEDA and n-BuLi was added to compound 10-3. To the resulting lithiated species, DMF was added to provide 3-methoxymethoxy-2-propylpyridine-4-carbaldehyde 10-4. Aldehyde 10-4 was deprotected to provide 3-hydroxy-2-propylpyridine-4-carbaldehyde 10-5 using 3N HCl. Carbaldehyde 10-5 was then treated with an amine (R$^5$—NH$_2$) to provide imine intermediate LL2. The compound LL2 was converted to compound (I-T) using TMSCN.

Scheme 10B describes the synthesis of N$^3$-(3-chloro-4-fluoro-phenyl)-7-propyl-furo[2,3-c]pyridine-2,3-diamine 10-7. Compound 9-2 was prepared by adding potassium tert-butoxide and methoxymethyl chloride to a solution of compound 9-1. To a solution of 2-chloro-3-methoxy methoxypyridine 9-2, Ni(dppp)Cl$_2$ and propyl magnesium chloride (2M soln) were added to provide 3-methoxymethoxy-2-propylpyridine 10-3. TMEDA was added to compound 10-3 and then n-BuLi added. To the lithiated species, DMF was added to provide 3-methoxymethoxy-2-propylpyridine-4-carbaldehyde 10-4. Aldehyde 10-4 was deprotected to provide 3-hydroxy-2-propylpyridine-4-carbaldehyde 10-5 using 3N HCl. Carbaldehyde 10-5 was then treated with 3-chloro-4-fluoroaniline to provide imine intermediate 10-6. 4-{[3-chloro-4-fluoro-phenylimino]-methyl}-2-propyl-pyridin-3-ol 10-6 was converted to N$^3$-(3-chloro-4-fluoro-phenyl)-7-propyl-furo[2,3-c]pyridine-2,3-diamine 10-7 using TMSCN.

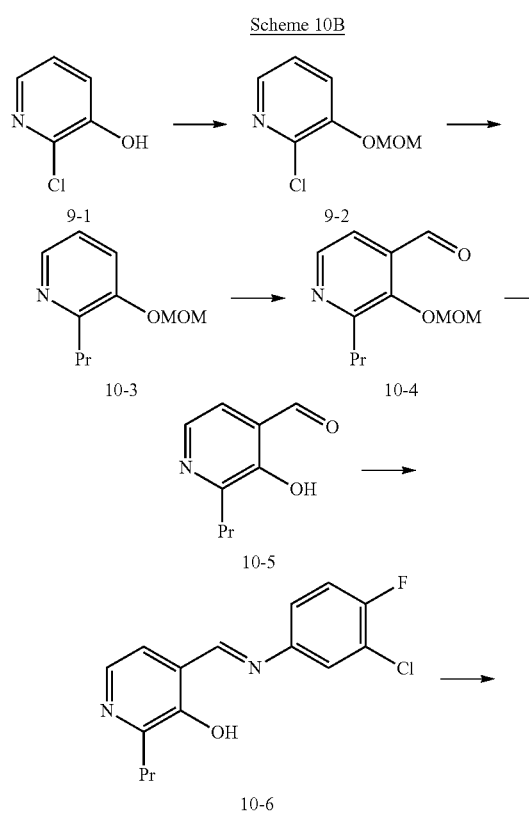

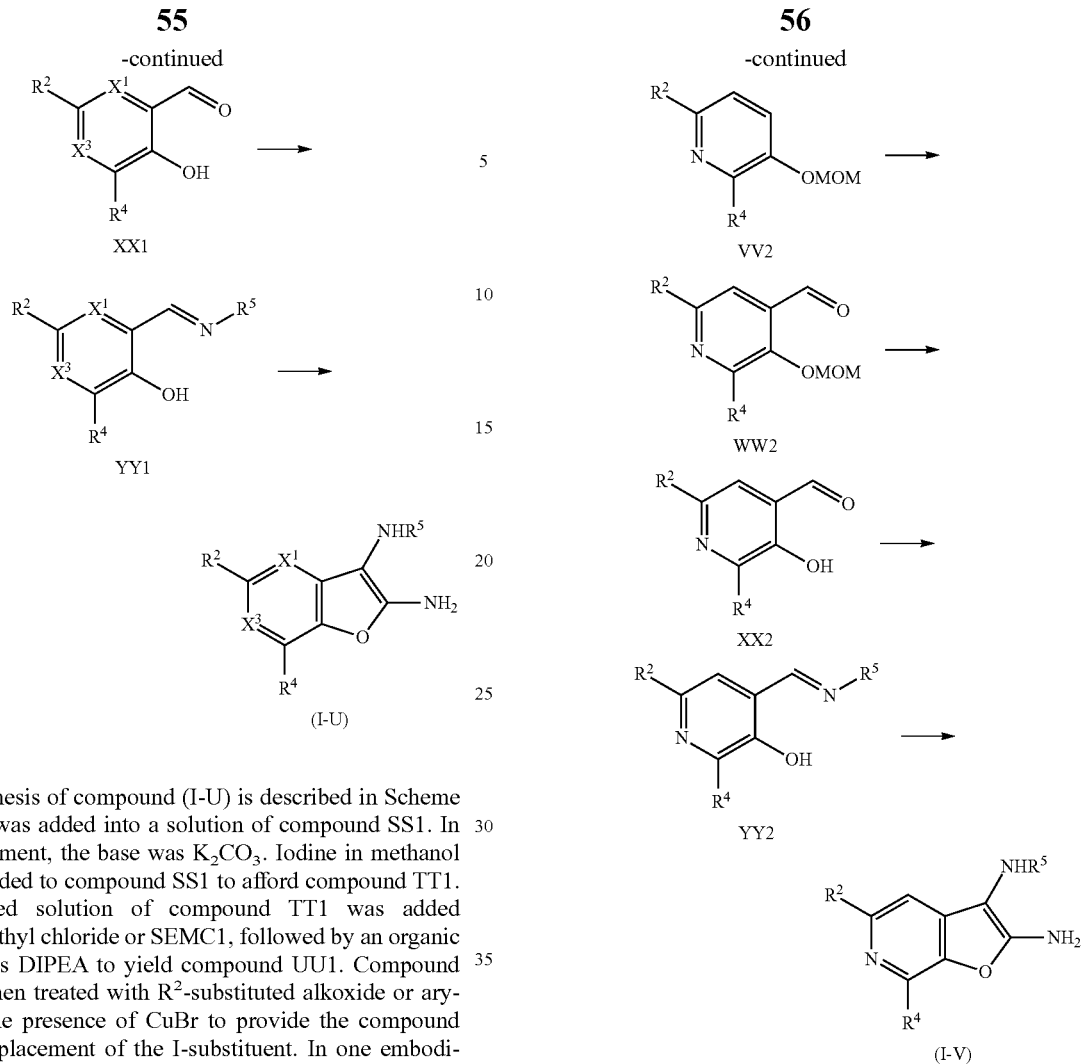

The synthesis of compound (I-U) is described in Scheme 11. A base was added into a solution of compound SS1. In one embodiment, the base was K₂CO₃. Iodine in methanol was then added to compound SS1 to afford compound TT1. To a stirred solution of compound TT1 was added methoxymethyl chloride or SEMC1, followed by an organic base such as DIPEA to yield compound UU1. Compound UU1 was then treated with $R^2$-substituted alkoxide or aryloxide in the presence of CuBr to provide the compound VV1 via replacement of the I-substituent. In one embodiment, the $R^2$-substituted alkoxide was sodium methoxide. TMEDA or HMPA was added to compound VV1 and n-BuLi or s-BuLi was added to provide the lithiated species. DMF was then added to provide carbaldehyde WW1, which was deprotected to provide compound XX1 using an acid. In one embodiment, the acid was HCl. Compound XX1 was reacted with an amine ($R^5$—NH₂) to provide imine intermediate YY1. Compound (I-U) was synthesized by reacting a trialkylsilyl cyanide such as TMSCN with compound YY1.

Scheme 11A

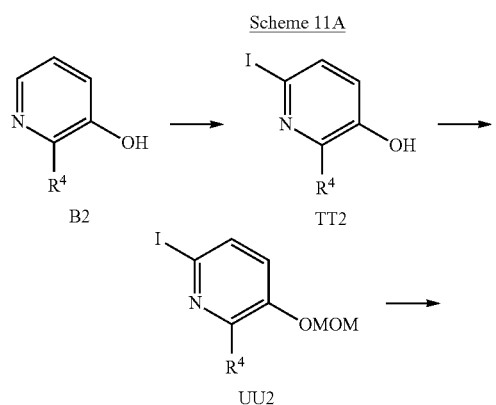

The synthesis of compound (I-V) is described in Scheme 11A. K₂CO₃ was added to compound B2. Iodine in methanol was then added to afford compound TT2. To a solution of compound TT2, methoxymethyl chloride was added followed by DIPEA to yield compound UU2. A solution of compound UU2 was added to freshly prepared sodium methoxide, followed by CuBr to yield compound VV2. TMEDA was added to compound VV2 and n-BuLi was added. DMF was then added to provide carbaldehyde WW2, which was deprotected to provide XX2 by using HCl. Compound XX2 was reacted with an amine ($R^5$—NH₂) to provide imine intermediate YY2. Compound (I-V) was synthesized by adding TMSCN to the solution of compound YY2.

Scheme 11B

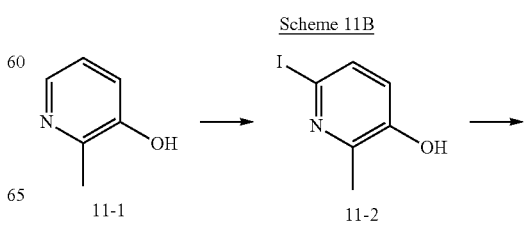

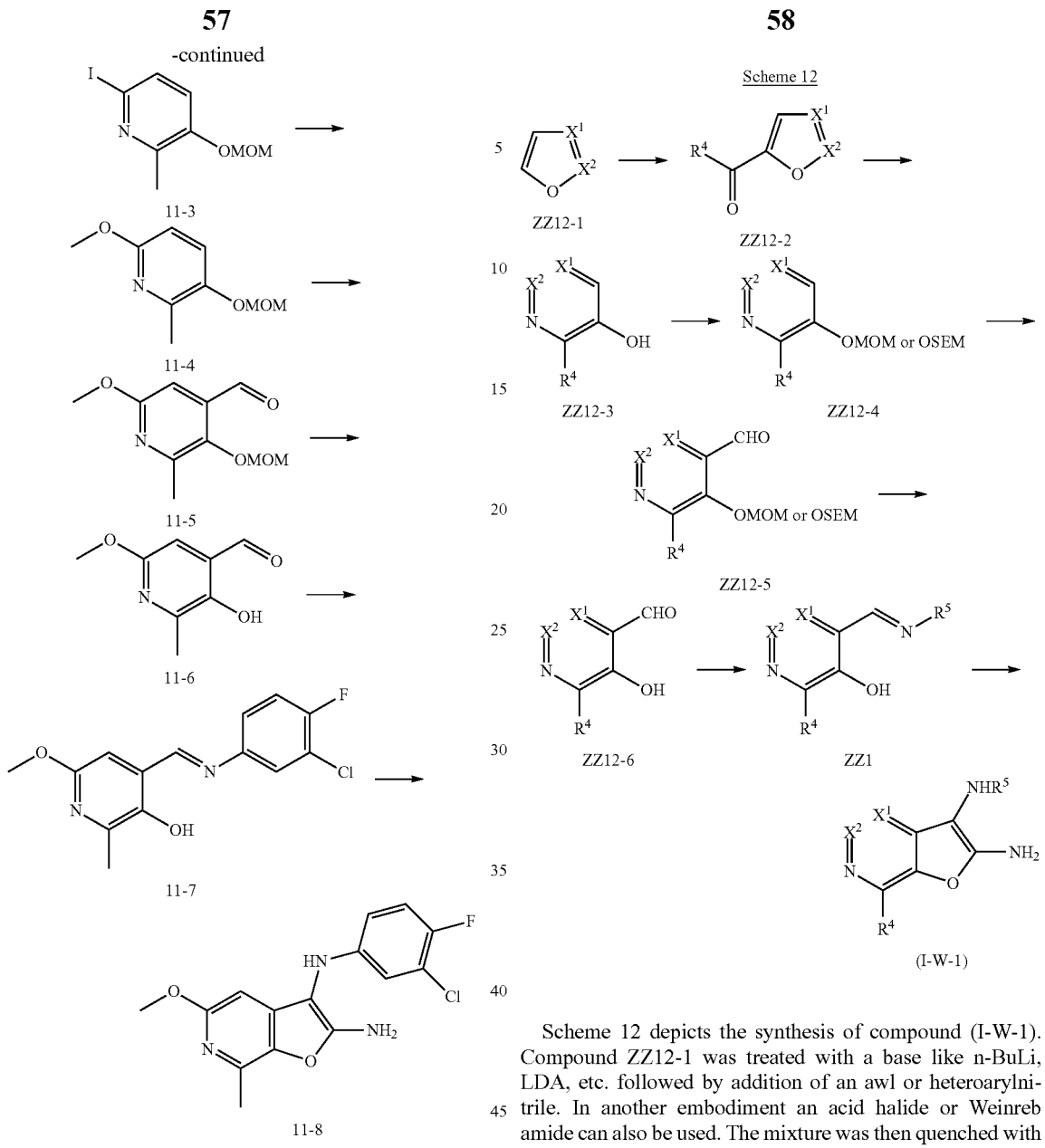

The synthesis of N³-(3-chloro-4-fluoro-phenyl)-5-methoxy-7-methyl-furo[2,3-c]pyridine-2,3-diamine 11-8 is described in Scheme 11B. K₂CO₃ was added to 2-methylpyridine-3-ol 11-1. Iodine in methanol was then added to afford 6-iodo-2-methylpyridine-3-ol 11-2. To compound 11-2, methoxymethyl chloride was added followed by DIPEA to yield 6-iodo-3-methoxymethoxy-2-methyl pyridine 11-3. Compound 11-3 was added to freshly prepared sodium methoxide followed by CuBr to yield compound 11-4. TMEDA was added to 6-methoxy-3-methoxy methoxy-2-methyl pyridine 11-4 and n-BuLi was added, followed by DMF to synthesize carbaldehyde 11-5. 6-M ethoxy-3-methoxymethoxy-2-methylpyridine-4-carbaldehyde 11-5 was then deprotected to provide 3-hydroxy-6-methoxy-2-methyl-pyridine-4-carbaldehyde 11-6. Compound 11-6 was then reacted with 4-fluoro-3-chloroaniline to give imine intermediate 11-7. The product 11-8 was synthesized by adding TMSCN to the solution of compound 11-7.

Scheme 12 depicts the synthesis of compound (I-W-1). Compound ZZ12-1 was treated with a base like n-BuLi, LDA, etc. followed by addition of an aryl or heteroarylnitrile. In another embodiment an acid halide or Weinreb amide can also be used. The mixture was then quenched with ammonium chloride and pH adjusted to about 2 to about 4 using an acid to provide compound ZZ12-2. In one embodiment, the pH was adjusted to 3. In another embodiment, the acid was 6N HCl. See, Chubb et al., J. Chem. Soc., Perkin. Trans., 1853-1854 (2001), which is hereby incorporated by reference.

Compound ZZ12-3 was obtained by treating compound ZZ12-2 with ammonium hydroxide in an autoclave at 100-140° C. Protection of the OH group in compound ZZ12-3 with MOM or SEM to provide compound ZZ12-4 was performed with a potassium or sodium alkoxide such as tert-BuOK and methoxymethyl chloride or SEMCl. Treatment of protected compound ZZ12-4 with TMP or TMEDA and n-BuLi followed by addition of DMF generated protected aldehyde ZZ12-5. Deprotection was done with an acid to provide compound ZZ12-6. In one embodiment, the acid is hydrochloric acid. Treatment of aldehyde ZZ12-6 with an amine (R⁵—NH₂) provided imine ZZ1 which was further reacted with TMSCN to provide target compound (I-W-1).

Scheme 12A

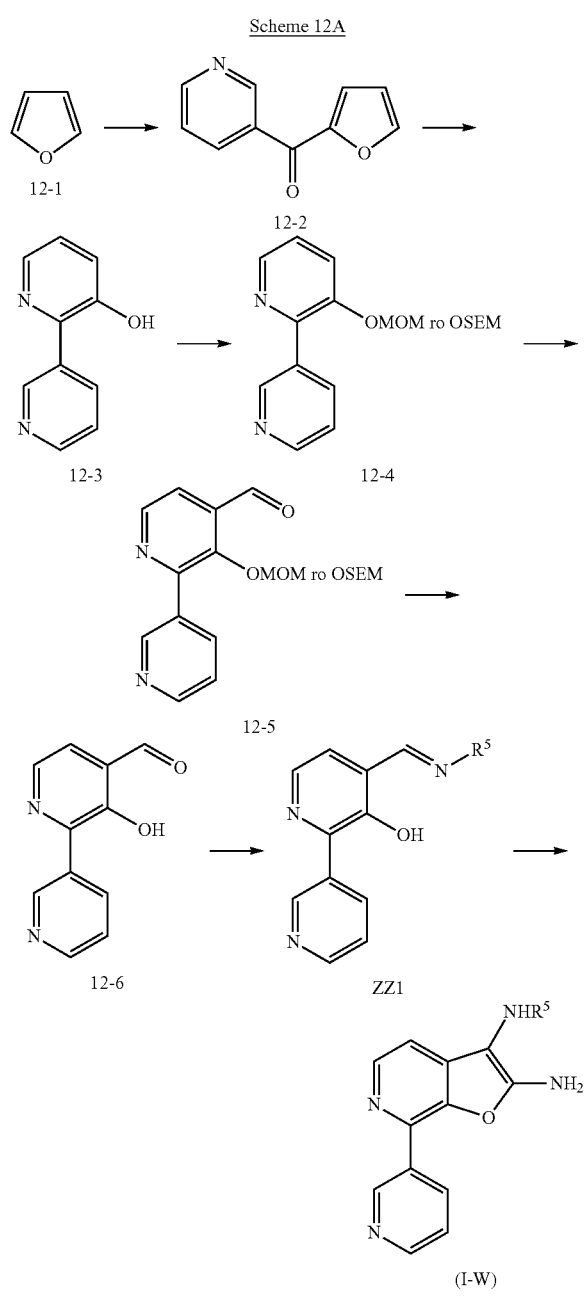

Scheme 12 depicts the synthesis of compound (I-W). Furan 12-1 was treated with n-BuLi, followed by addition of 3-cyanopyridine. The mixture was then quenched with ammonium chloride and pH adjusted to about 2 to about 4 using an acid to provide compound 12-2. In one embodiment, the pH was adjusted to 3. In another embodiment, the acid was 6N HCl. See, Chubb et al., J. Chem. Soc., Perkin. Trans., 1853-1854 (2001), which is hereby incorporated by reference. Compound 12-3 was obtained by treating compound 12-2 with ammonium hydroxide in an autoclave at 140° C. Protection of the OH group in compound 12-3 with MOM or SEM to provide compound 12-4 was performed with a potassium or sodium alkoxide such as tert-BuOK and methoxymethyl chloride or SEMCl. Treatment of protected compound 12-4 with TMP or TMEDA and n-BuLi followed by addition of DMF generated protected aldehyde 12-5.

Deprotection was done with an acid to provide compound 12-6. In one embodiment, the acid is hydrochloric acid. Treatment of aldehyde 12-6 with an amine ($R^5$—$NH_2$) provided imine intermediate ZZ1 which was further reacted with TMSCN to provide target compound (I-W).

Scheme 12B

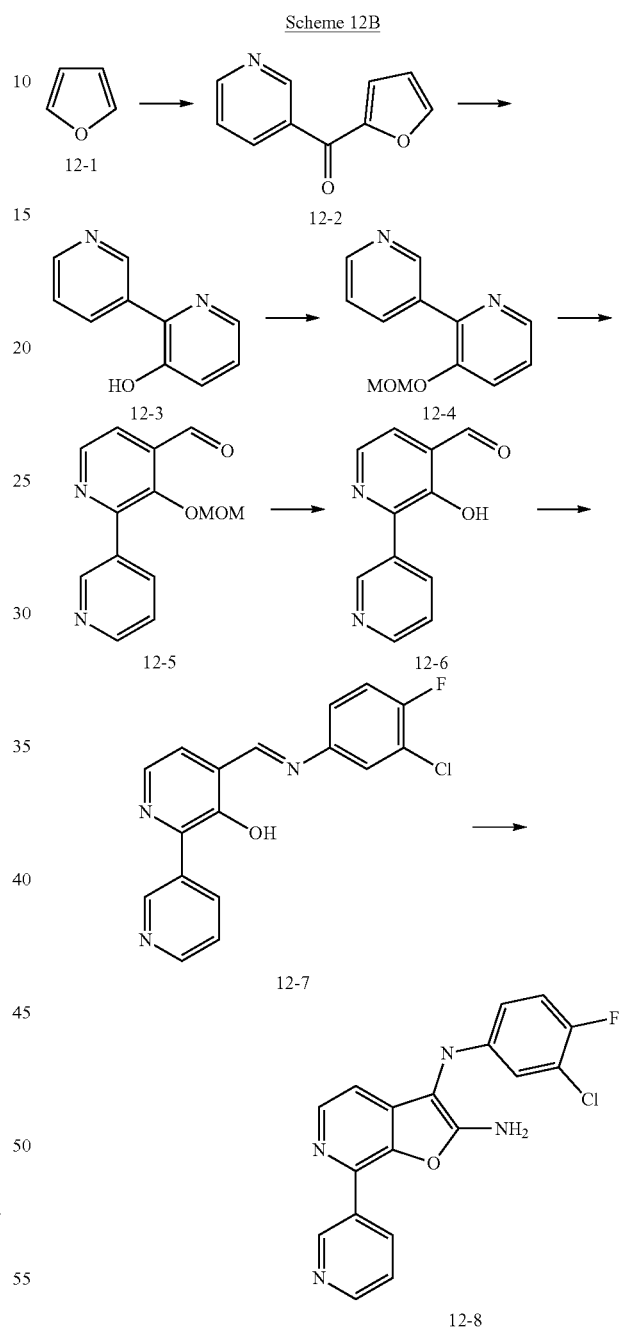

Scheme 12B depicts the synthesis of compound 12-8. Furan 12-1 was treated with n-BuLi, followed by addition of 3-cyanopyridine. The mixture was then quenched with ammonium chloride and pH adjusted to 3 using 6N HCl to provide compound 12-2. Compound 12-3 was obtained by treating compound 12-2 with ammonium hydroxide in an autoclave at 140° C. Protection of the c OH group in compound 12-3 with MOM to provide compound 12-4 was performed with tert-BuOK and methoxymethyl chloride.

Treatment of MOM protected compound 12-4 with TMP and n-BuLi followed by addition of DMF generated the MOM protected aldehyde 12-5. Deprotection was done with 3N HCl to provide compound 12-6. Treatment of aldehyde 12-6 with 4-fluoro-3-chlorophenylamine provided imine 12-7 which was further reacted with TMSCN to provide the target compound 12-8.

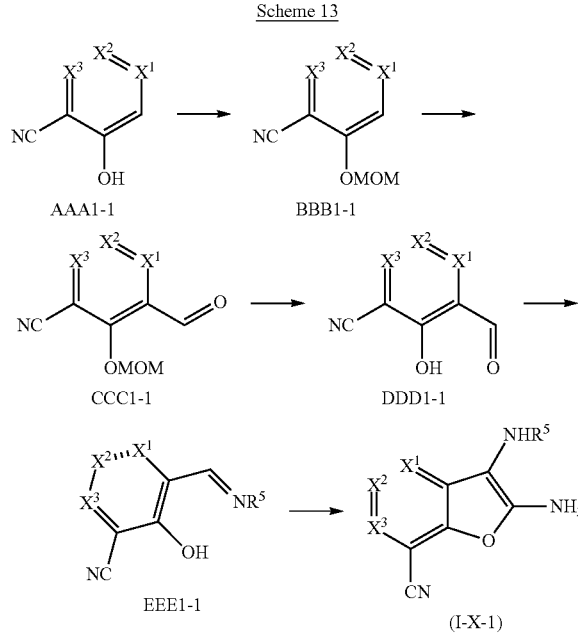

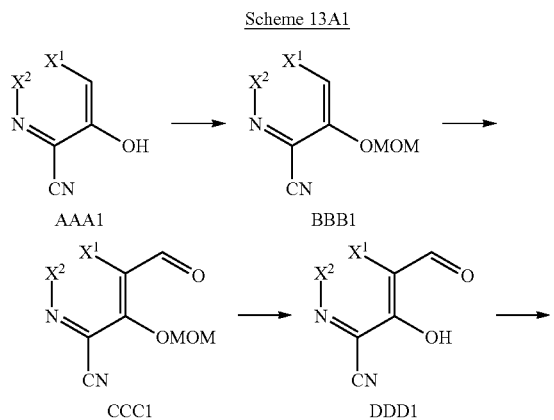

Scheme 13 shows the preparation of cyano-substituted compound (I-X-1). Compound AAA1-1 was treated with a base, followed by addition of methoxymethylchloride to provide the MOM protected product BBB1-1. In one embodiment, the base was sodium or potassium tert-butoxide. Compound BBB1-1 was treated with TMP or LDA and n-BuLi, followed by DMF or N-formylpiperidine to provide compound CCC1-1. Compound CCC1-1 was deprotected to DDD1-1, and then condensed with amine ($R^5$—$NH_2$) to provide compound EEE1-1. EEE1-1 was further reacted with TMSCN under Strecker reaction conditions to provide compound (I-X-1).

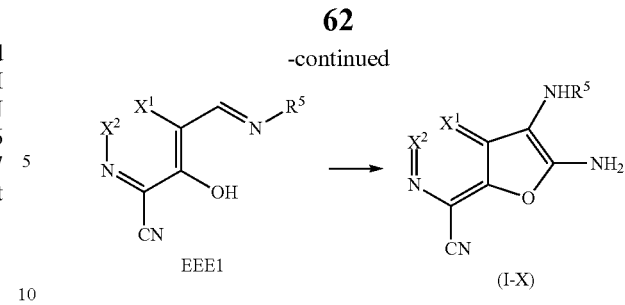

Scheme 13A1 shows the preparation of cyano-substituted compound (I-X). Compound AAA1 was treated with a base, followed by addition of methoxymethylchloride to provide the MOM protected product BBB1. In one embodiment, the base was sodium or potassium tert-butoxide. Compound BBB1 was treated with TMP or LDA and n-BuLi, followed by DMF or N-formylpiperidine to provide compound CCC1. Compound CCC1 was deprotected and condensed with an amine ($R^5$—$NH_2$) provide compound EEE 1 which was further reacted with TMSCN under Strecker reaction condition to provide compound (I-X).

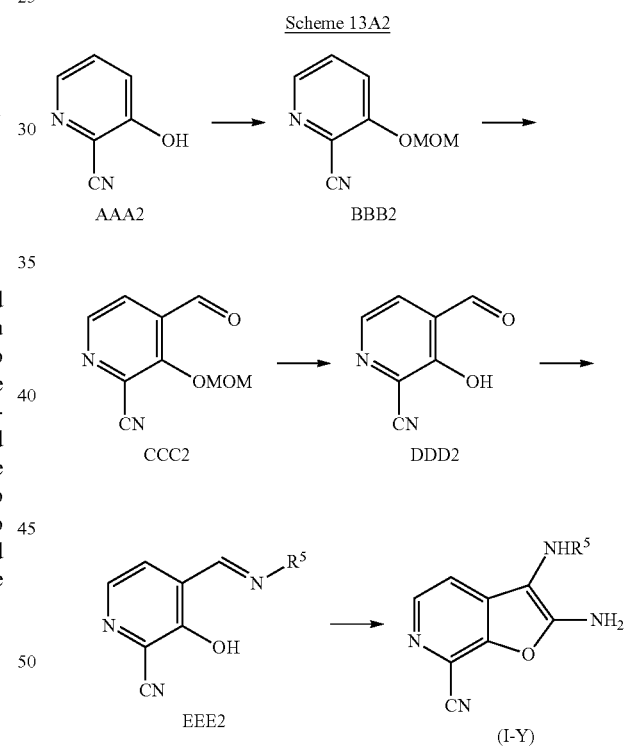

Scheme 13A2 shows the preparation of cyano-substituted compound (I-Y). Compound AAA2 was treated with potassium tert-butoxide, followed by addition of methoxymethylchloride to provide the MOM protected product BBB2. Compound BBB2 was treated with TMP and n-BuLi, followed by DMF to provide compound CCC2. Compound CCC2 was deprotected and condensed with an amine ($R^5$—$NH_2$) to provide compound EEE2 which was further reacted with TMSCN under Strecker reaction condition to provide compound (I-Y).

Scheme 13B

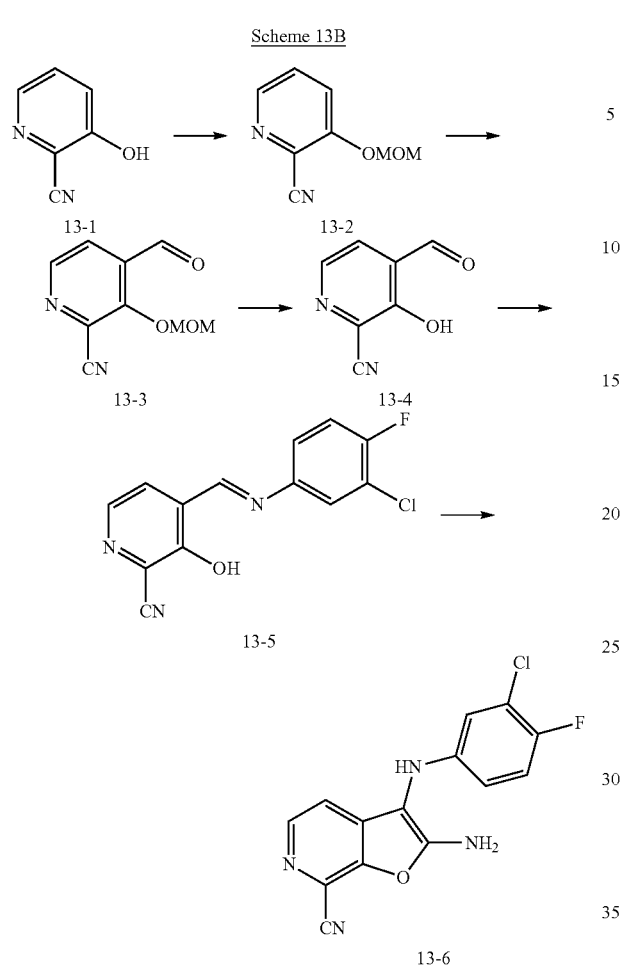

Scheme 13B shows the preparation of cyano-substituted compound 13-6. 2-Cyano-3-hydroxypyridine 13-1 was treated with potassium tert-butoxide, followed by addition of methoxymethylchloride to provide the MOM protected product 13-2. Compound 13-2 was treated with TMP and n-BuLi in THF followed by DMF to provide formylated product 13-3. Compound 13-3 was deprotected and condensed with 3-chloro-4-fluoroaniline to provide compound 13-5 which was further reacted with TMSCN under Strecker reaction condition to provide compound 13-6.

Scheme 14

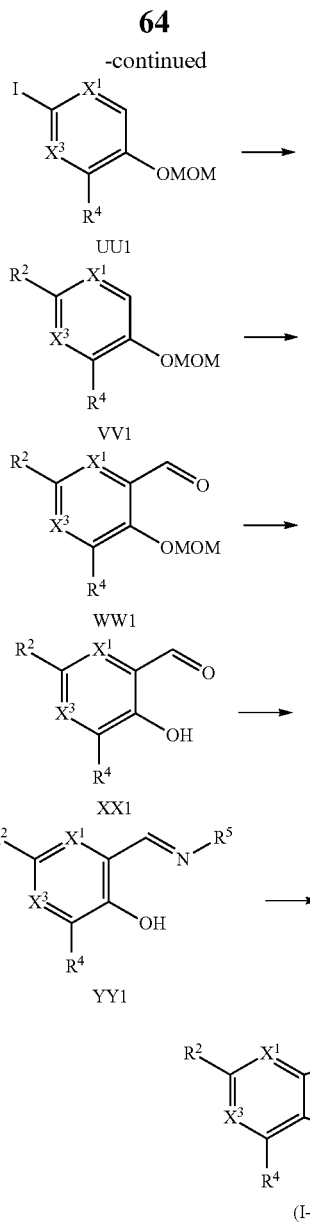

Scheme 14 provides the preparation of compound (I-U). Specifically, compound EEEE1-1 prepared as described above was reacted with an $R^4$-substituted boronic acid and a Pd catalyst. In one embodiment, the catalyst was $Pd(PPh_3)_4$. Product SS1 was iodinated to provide compound TT1. In one embodiment, the iodination was performed using with iodine. Iodo compound TT1 was protected by MOMCl and then $R^2$-substituted in presence of a Pd catalyst or [1,3-bis(diphenylphosphino)propane]dichloronickel (II) to provide compound VV1. In one embodiment, the catalyst was [1,3-bis(diphenylphosphino)propane]dichloronickel (II). In another embodiment, the $R^2$-substitution was performed using an alkylated borate such as triethylborate. Compound VV1 was lithiated using n-BuLi and formulated using DMF to provide compound XX1. In one embodiment, the formylation was performed in TMEDA using DMF as the formylating agent. The formylated product XX1 was converted to compound (I-U) via intermediate YY1 as described above.

Scheme 14A1

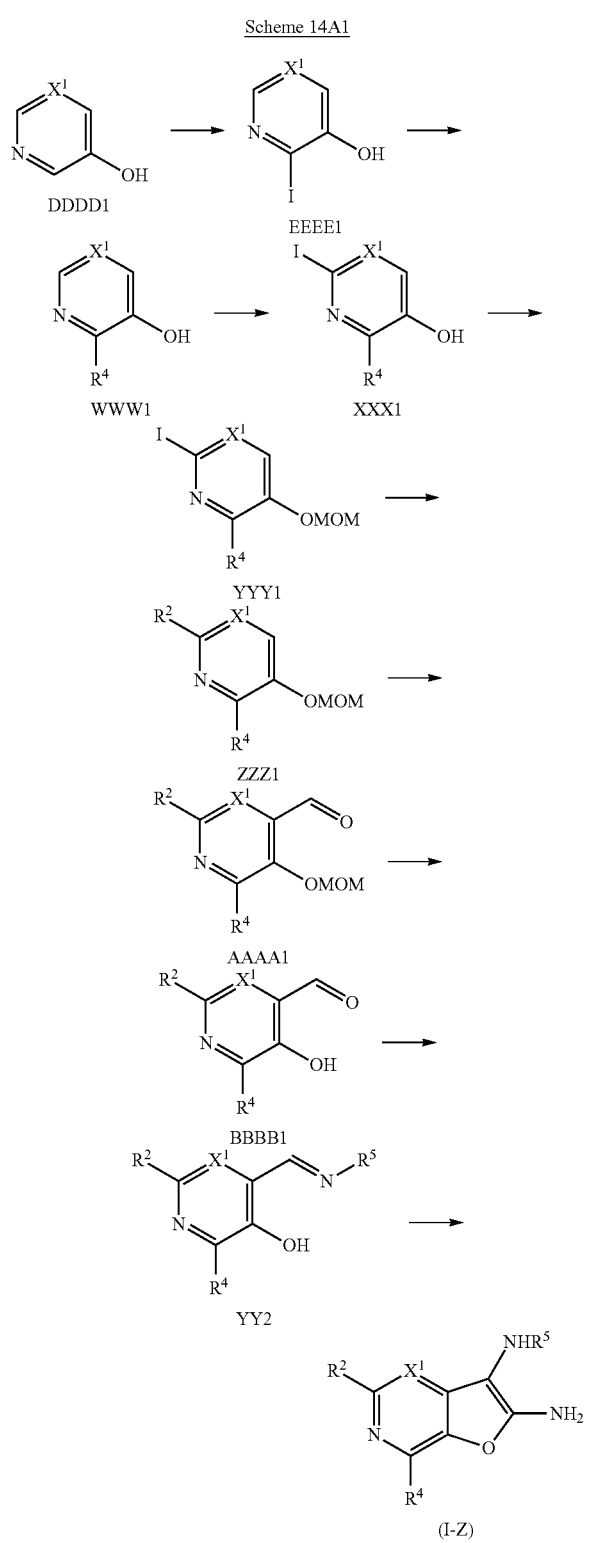

protected as a MOM ether and then $R^2$-substituted in presence of a Pd catalyst or [1,3-bis(diphenylphosphino)propane]dichloronickel (II) to provide compound ZZZ1. In one embodiment, the catalyst was [1,3-bis(diphenylphosphino)propane]dichloronickel (II). In another embodiment, the $R^2$ substitution was performed using an alkylated borate such as triethylborate. Compound ZZZ1 was lithiated using n-BuLi and formulated using DMF to provide compound BBBB1. In one embodiment, the formylation was performed in TMEDA using DMF as the formulation agent. The formylated product BBBB1 was converted to compound (I-Z) via intermediate YY2 as described above.

Scheme 14A2

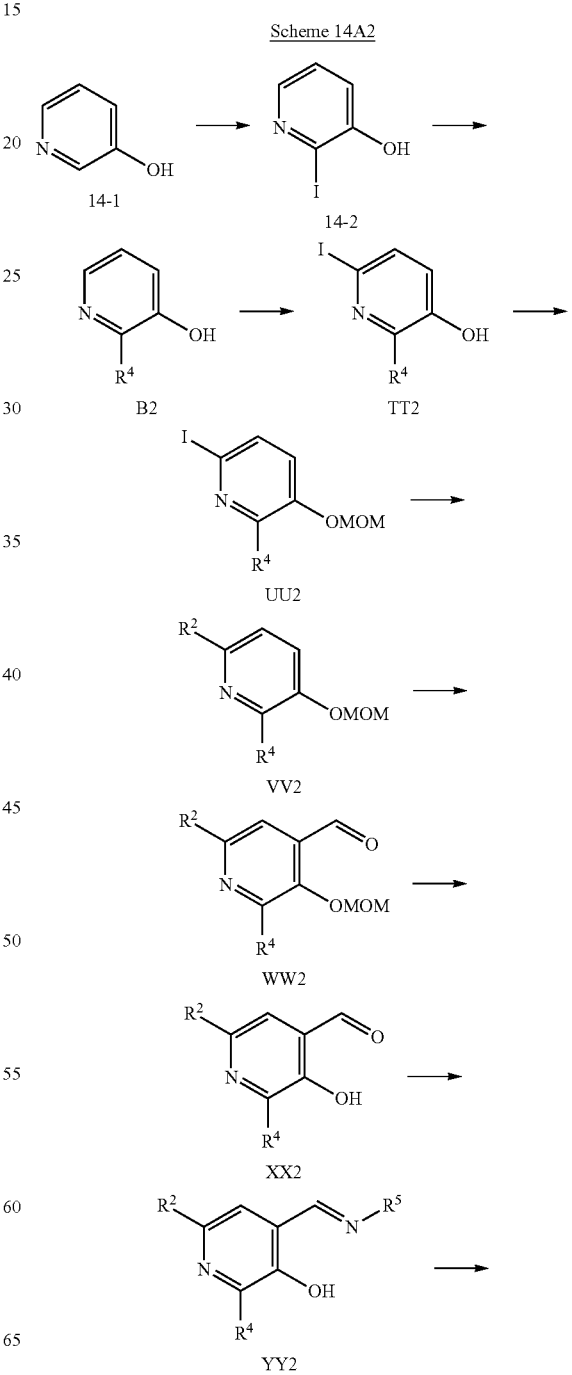

Scheme 14A1 provides the preparation of compound (I-Z). Specifically, compound EEEE1, prepared as described above was reacted with an $R^4$-substituted boronic acid and a Pd catalyst. In one embodiment, the catalyst was Pd(PPh$_3$)$_4$. Product WWW1 was iodinated to provide compound XXX1. In one embodiment, the iodination was performed using with iodine. Iodo compound XXX1 was

67

-continued

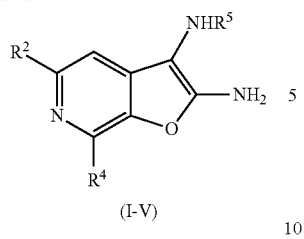

(I-V)

Scheme 14A2 provides the preparation of compound (I-V). Specifically, 2-iodo-3-hydroxypyridine 14-2 prepared as described above was reacted with an $R^4$-substituted boronic acid and a catalyst. In one embodiment, the catalyst was Pd(PPh$_3$)$_4$. Product B2 was iodinated with iodine to provide compound TT2. Compound TT2 was MOM protected via a coupling reaction and then $R^2$-substituted in presence of a catalyst to provide compound VV2. In one embodiment, the catalyst was [1,3-bis(diphenylphosphino)propane]dichloronickel (II). In another embodiment, the $R^2$-substitution was performed using triethylborate. Formylation of compound VV2 was done by reaction with n-BuLi and DMF to provide compound WW2. In one embodiment, the formylation was performed in TMEDA using N-formylpiperidide. The formylated product WW2 was converted to compound (I-V) via intermediate YY2 as described above.

Scheme 14B

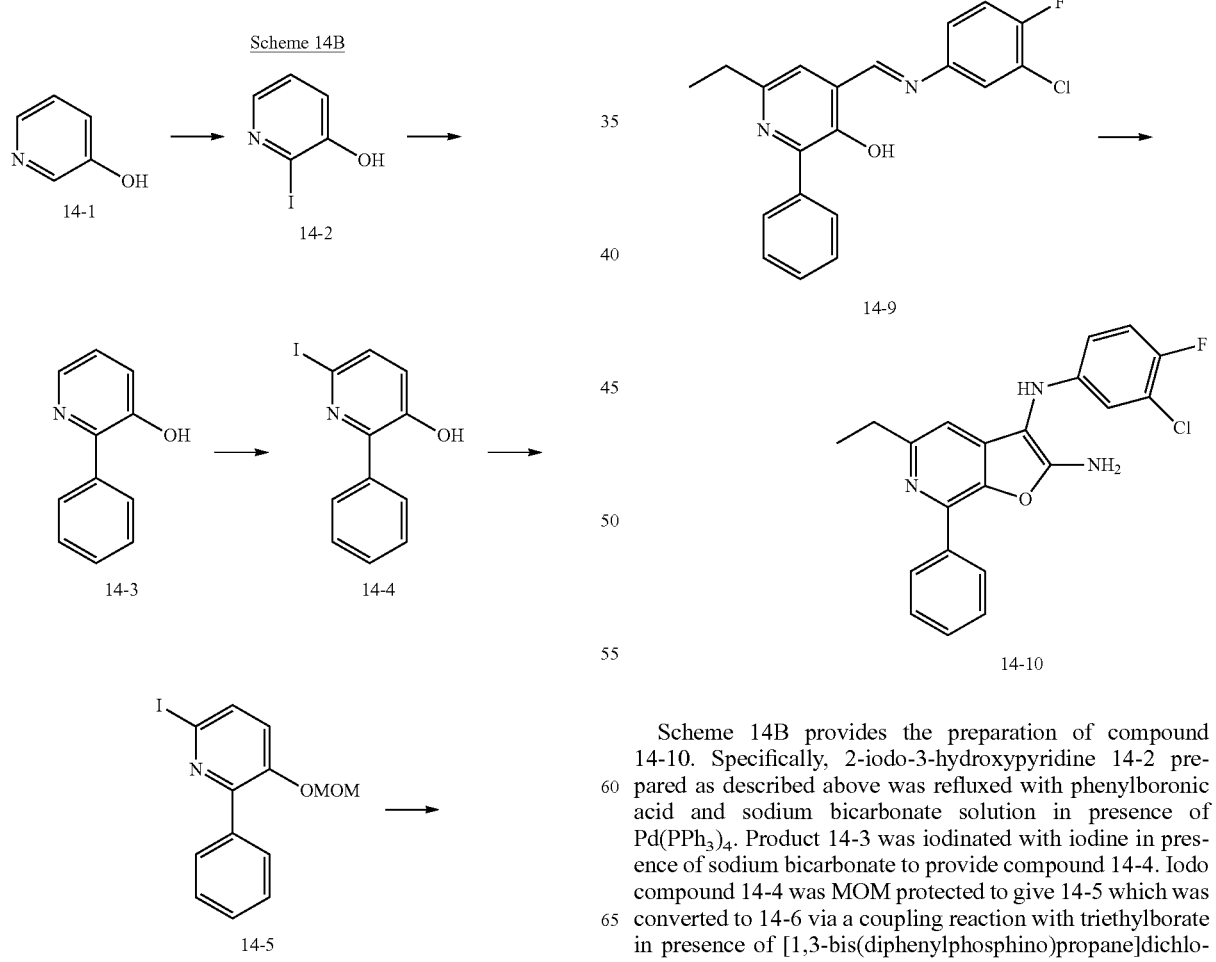

68

-continued

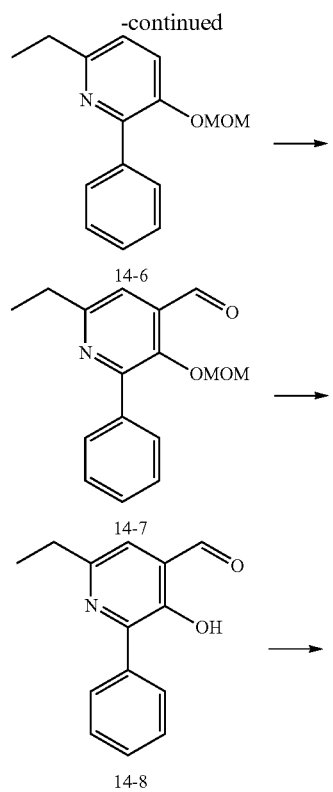

Scheme 14B provides the preparation of compound 14-10. Specifically, 2-iodo-3-hydroxypyridine 14-2 prepared as described above was refluxed with phenylboronic acid and sodium bicarbonate solution in presence of Pd(PPh$_3$)$_4$. Product 14-3 was iodinated with iodine in presence of sodium bicarbonate to provide compound 14-4. Iodo compound 14-4 was MOM protected to give 14-5 which was converted to 14-6 via a coupling reaction with triethylborate in presence of [1,3-bis(diphenylphosphino)propane]dichloronickel(II) to provide compound 14-6. Reaction of compound 14-6 with n-BuLi in TMEDA provided the lithiated species which was formylated using DMF. The formylated product 14-8 was converted to compound 14-10 via intermediate 14-9 as described herein.

acetic acid. Compound GGG1 was then nitrated using fuming nitric acid and acetic acid or fuming nitric acid and TFA or fuming nitric acid and sulfuric acid to afford compound HHH1. Compound HHH1 was $NHR^5$-substituted using an amine ($R^5$—$NH_2$) to form compound III1. Catalytic hydrogenation was then done on compound III1 using Pd/C (10%) under hydrogen gas in methanol, ethanol, isopropanol, or ethyl acetate to afford compound (I-HH).

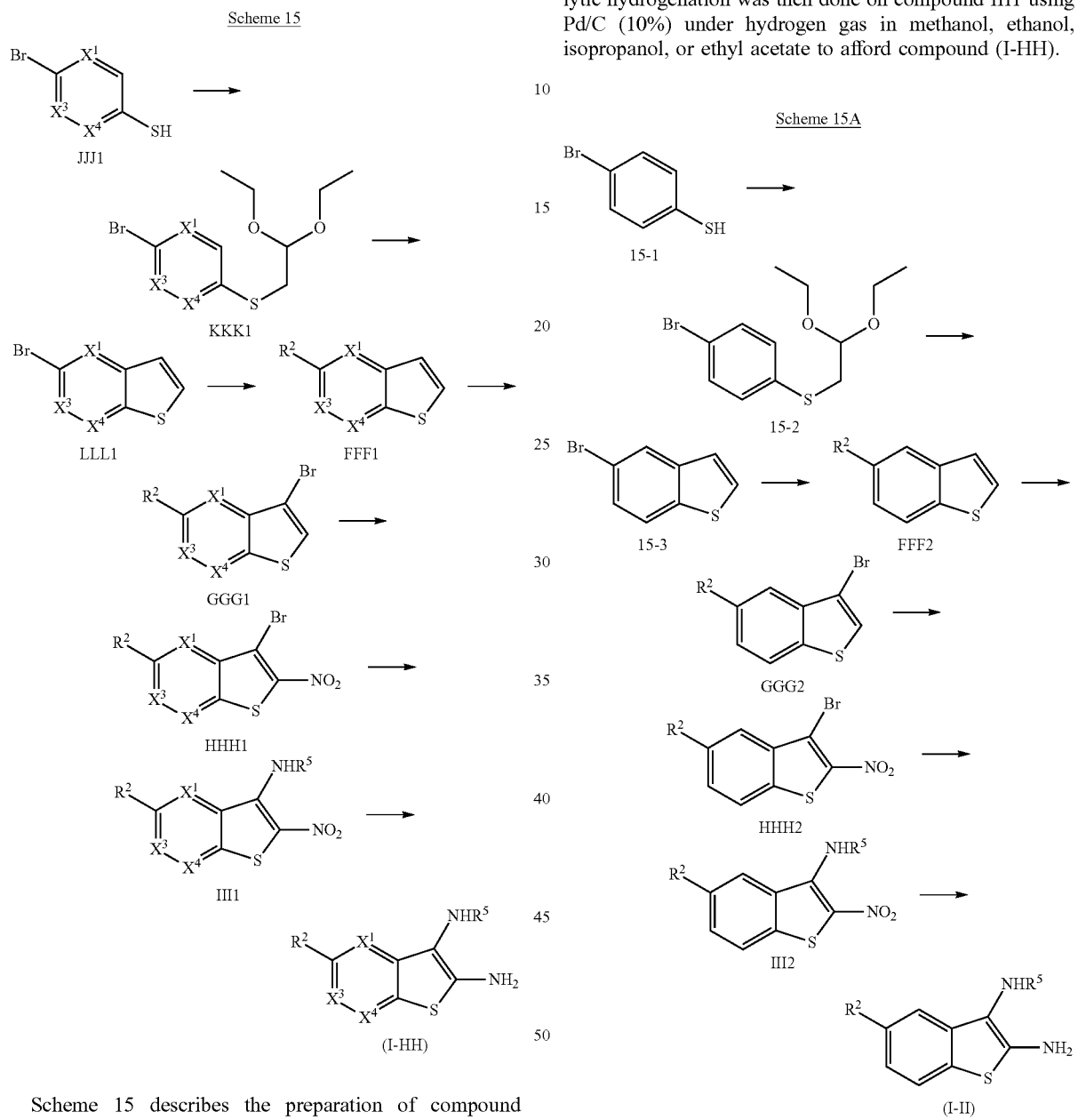

Scheme 15 describes the preparation of compound (I-HH). Compound JJJ1 was treated with bromoacetaldehyde diethyl acetal in the presence of potassium carbonate in DMF to afford compound KKK1. Compound KKK1 was refluxed in the presence of PPA or a Lewis acid such as $ZnCl_2$, $AlCl_3$, or $AlBr_3$ to give compound LLL1. In one embodiment, this reaction was performed in a high boiling aromatic solvent such as chlorobenzene, toluene, xylenes, or diphenylether. Compound LLL1 was then $R^2$-substituted via a Suzuki-Miyaura cross coupling reaction in the presence of a catalyst such as $Pd(PPh_3)_4$, $Pd(OAc)_2$, or $PdCl_2(PPh_3)_2$ in the presence of potassium carbonate in refluxing dioxane to afford compound FFF1. Compound FFF1 was brominated to give compound GGG1. In one embodiment, the bromination is performed using NBS in the presence of chloroform and Scheme 15A describes the preparation of compound (I-II). Commercially available 4-bromothiophenol 15-1 was treated with bromoacetaldehyde diethyl acetal in the presence of potassium carbonate in DMF to afford compound 15-2. 1-Bromo-4-[(2,2-diethoxyethyl)sulfanyl]benzene 15-2 was refluxed in the presence of PPA or a Lewis acid such as $ZnCl_2$, $AlCl_3$, or $AlBr_3$ to give 5-bromo-1-benzothiophene 15-3. In one embodiment, this reaction was performed in a high boiling aromatic solvent such as chlorobenzene, toluene, xylene, or diphenylether. Compound 15-3 was then $R^2$-substituted via a Suzuki-Miyaura cross coupling reaction in the presence of a catalyst such as $Pd(PPh_3)_4$, $Pd(OAc)_2$, or PdCl$_2$(PPh$_3$)$_2$ in the presence of potassium carbonate in refluxing dioxane to afford compound FFF2. Compound FFF2 was brominated to give compound GGG2. In one embodiment, the bromination is performed using NBS in the presence of chloroform and acetic acid. Compound GGG2 was then nitrated using fuming nitric acid and acetic acid or fuming nitric acid and TFA or fuming nitric acid and sulfuric acid to afford compound HHH$_2$. Compound HHH$_2$ was NHR$^5$-substituted using an amine (R$^5$—NH$_2$) to give compound III2. Catalytic hydrogenation was then done on compound III2 using Pd/C (10%) under hydrogen gas in methanol, ethanol, isopropanol or ethyl acetate to afford compound (I-II).

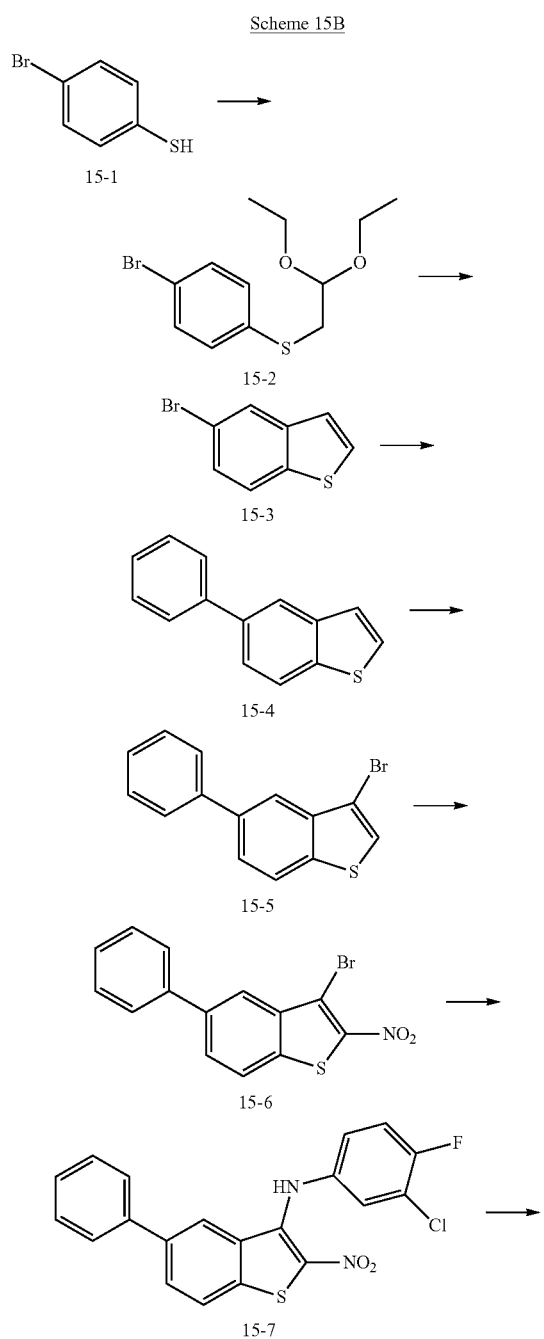

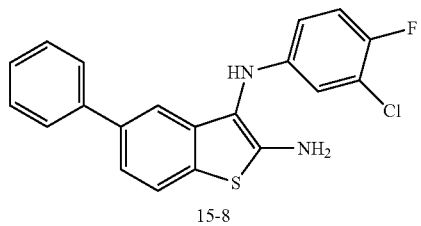

Scheme 15B describes the preparation of N$^3$-(3-chloro-4-fluorophenyl)-5-phenyl-1-benzothiophene-2,3-diamine 15-8. 4-Bromothiophenol 15-1 was treated with bromoacetaldehyde diethyl acetal in the presence of potassium carbonate in DMF to afford 15-2. 1-Bromo-4-[(2,2-diethoxyethyl)sulfanyl]benzene 15-2 was refluxed in the presence of PPA or a Lewis acid such as ZnCl$_2$, AlCl$_3$, or AlBr$_3$ to give 5-bromo-1-benzothiophene 15-3. In one embodiment, this reaction was performed in a high boiling aromatic solvent such as chlorobenzene, toluene, xylene, or diphenylether. Compound 15-3 was then subjected to Suzuki-Miyaura cross coupling reaction with phenylboronic acid in the presence of a catalyst such as Pd(PPh$_3$)$_4$, Pd(OAc)$_2$, or PdCl$_2$(PPh$_3$)$_2$ in the presence of potassium carbonate in refluxing dioxane to afford 5-phenyl-1-benzothiophene 15-4. Compound 15-4 was brominated to give 3-bromo-5-phenyl-1-benzothiophene 15-5. In one embodiment, the bromination is performed using NBS in the presence of chloroform or acetic acid. Compound 15-5 was then nitrated using fuming nitric acid and acetic acid or fuming nitric acid and TFA or fuming nitric acid and sulfuric acid to afford 3-bromo-2-nitro-5-phenyl-1-benzothiophene 15-6. Compound 15-6 was coupled with 3-chloro-4-fluoroaniline in DMF to give N-(3-chloro-4-fluorophenyl)-2-nitro-5-phenyl-1-benzothiophen-3-amine 15-7. Catalytic hydrogenation was then done on compound 1-7 using Pd/C (10%) under hydrogen gas in methanol, ethanol, isopropanol or ethyl acetate to afford N$^3$-(3-chloro-4-fluorophenyl)-5-phenyl-1-benzothiophene-2,3-diamine 15-8.

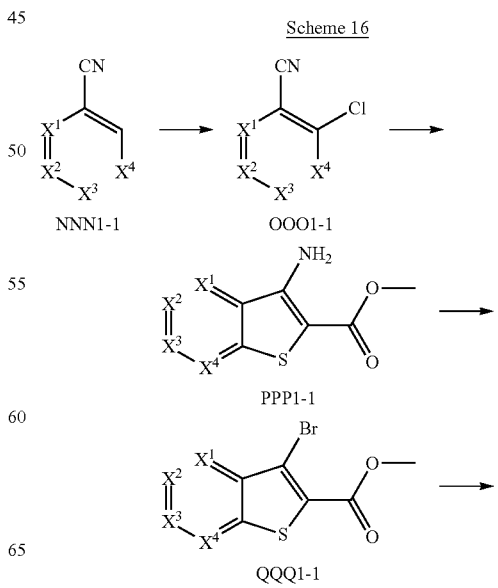

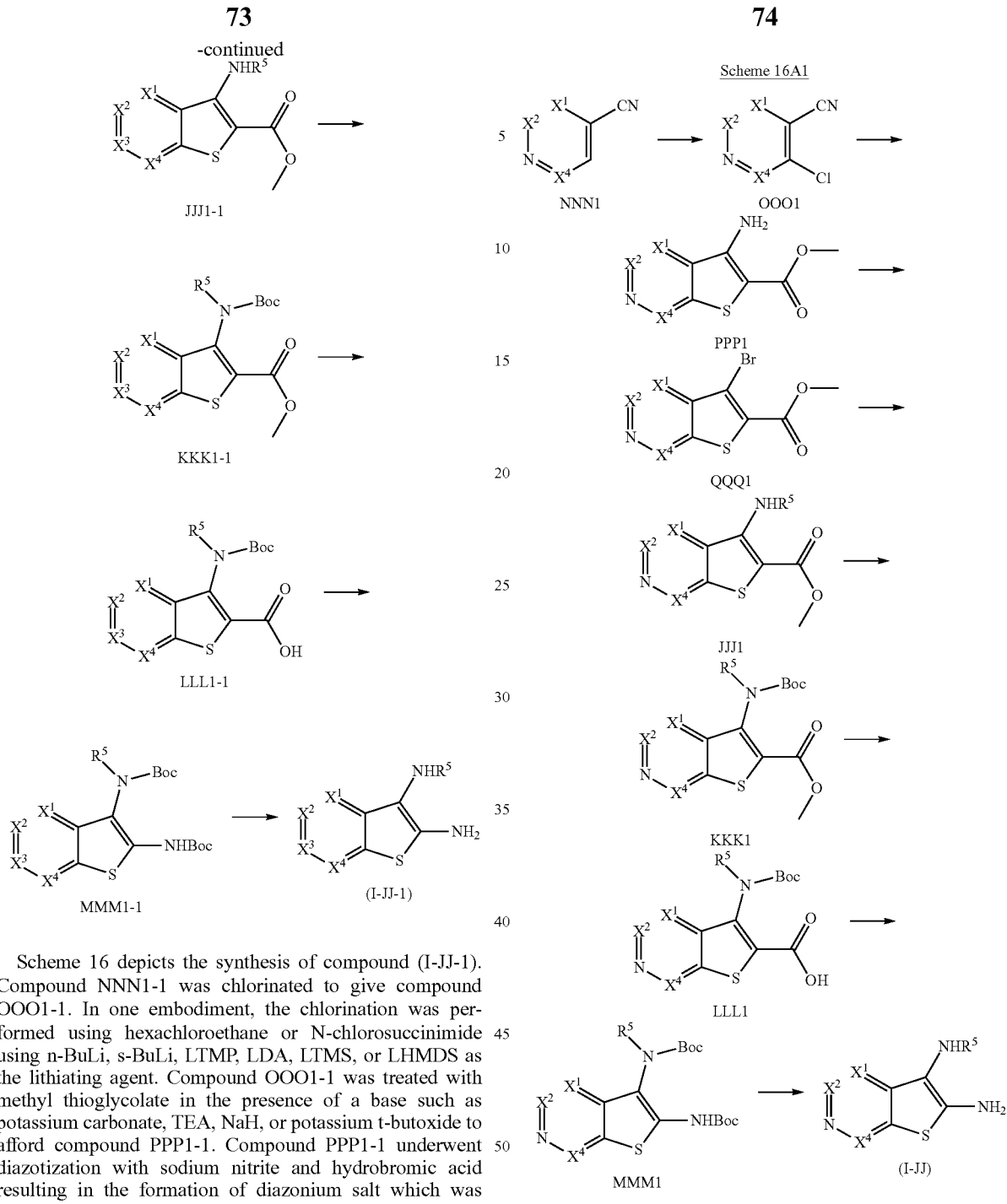

Scheme 16 depicts the synthesis of compound (I-JJ-1). Compound NNN1-1 was chlorinated to give compound OOO1-1. In one embodiment, the chlorination was performed using hexachloroethane or N-chlorosuccinimide using n-BuLi, s-BuLi, LTMP, LDA, LTMS, or LHMDS as the lithiating agent. Compound OOO1-1 was treated with methyl thioglycolate in the presence of a base such as potassium carbonate, TEA, NaH, or potassium t-butoxide to afford compound PPP1-1. Compound PPP1-1 underwent diazotization with sodium nitrite and hydrobromic acid resulting in the formation of diazonium salt which was reacted with copper bromide to give compound QQQ1-1. Compound QQQ1-1 was subjected to a Buchwald-Hertwig amination reaction with an amine ($R^5$—$NH_2$) in the presence of catalyst, such as $Pd_2(dba)_3$ or $Pd(dba)_2$, and BINAP or XPhos to afford compound JJJ1-1. Compound JJJ1-1 then underwent Boc protection with di-tent-butyl dicarbonate in the presence of a base such as TEA, potassium carbonate, DIPEA, sodium carbonate, NaH, sodium t-butoxide, or potassium t-butoxide followed by hydrolysis to give compound LLL1-1. Compound LLL1-1 was treated with an azide source such as DPPA and DIPEA under Curtius rearrangement condition to afford compound MMM1-1. Boc deprotection was then performed on compound MMM1-1 using hydrochloric acid or TFA in a solvent such as dioxane, THF, or DCM to afford compound (I-JJ-1).

Scheme 16A1 depicts the synthesis of compound (I-JJ). Compound NNN1 was chlorinated to give compound OOO1. In one embodiment, the chlorination was performed using hexachloroethane or N-chlorosuccinimide using n-BuLi, s-BuLi, LTMP, LDA, LTMS, or LHMDS as the lithiating agent. Compound OOO1 was treated with methyl thioglycolate in the presence of a base such as potassium carbonate, TEA, NaH, or potassium t-butoxide to afford compound PPP1. Compound PPP1 underwent diazotization with sodium nitrite and hydrobromic acid resulting in the formation of diazonium salt which was reacted with copper bromide to give compound QQQ1. Compound QQQ1 was subjected to a Buchwald-Hertwig amination reaction with an amine ($R^5$—$NH_2$) in the presence of catalyst, such as Pd₂(dba)₃ or Pd(dba)₂, and BINAP or XPhos to afford compound JJJ1. Compound JJJ1 then underwent Boc protection with di-tert-butyl dicarbonate in the presence of a base such as TEA, potassium carbonate, DIPEA, sodium carbonate, NaH, sodium t-butoxide, or potassium t-butoxide followed by hydrolysis to give compound LLL1. Compound LLL1 was treated with an azide source such as DPPA and DIPEA under Curtius rearrangement condition to afford compound MMM1. Boc deprotection was then performed on compound MMM1 using hydrochloric acid or TFA in a solvent such as dioxane, THF, or DCM to afford compound (I-JJ).

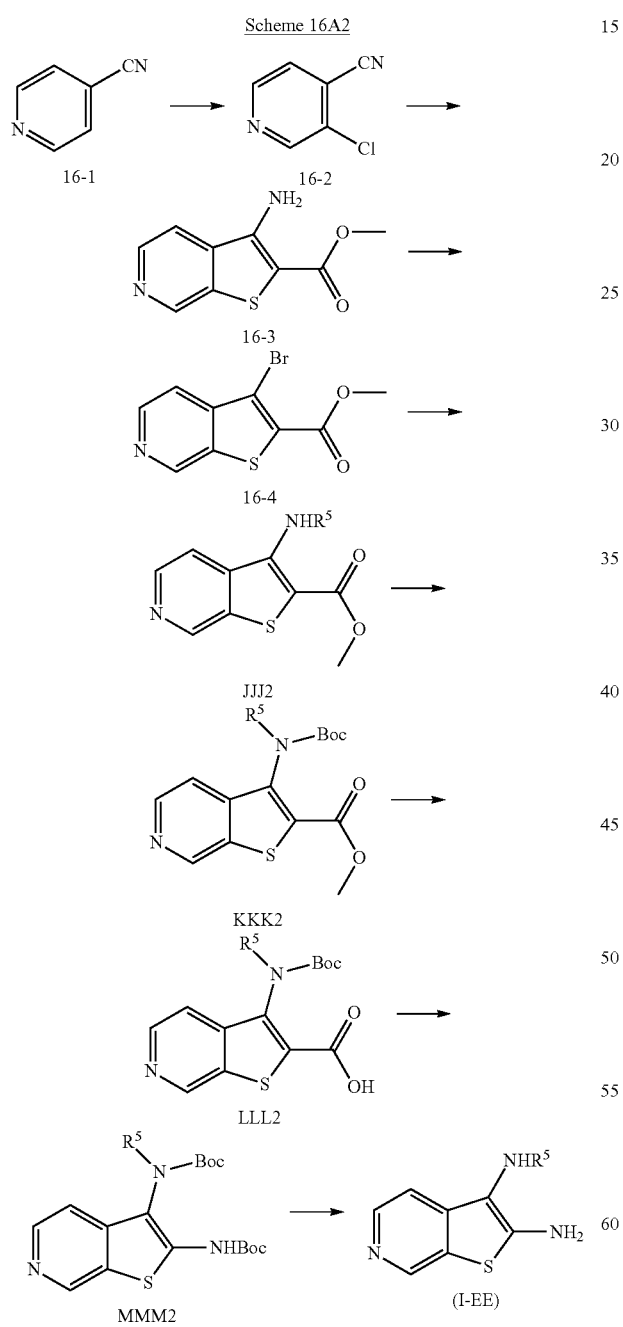

Scheme 16A2 depicts the synthesis of compound (1-EE). 4-Cyanopyridine 16-1 was chlorinated to give 3-chloropyridine-4-carbonitrile 16-2. In one embodiment, the chlorination was performed using hexachloroethane or N-chlorosuccinimide in the presence of a lithiating reagent such as n-BuLi, s-BuLi, LTMP, LDA, LTMS, or LHMDS as the lithiating agent. Compound 16-2 was treated with methyl thioglycolate in the presence of potassium carbonate, TEA, NaH, or potassium t-butoxide to afford methyl 3-bromothieno[2,3-c]pyridine-2-carboxylate 16-3. Compound 16-3 underwent diazotization with sodium nitrite and hydrobromic acid resulting in the formation of the diazonium salt which was reacted with copper bromide to give compound 16-4. Methyl-3-aminothieno [2,3-c]pyridine-2-carboxylate 16-4 was subjected to a Buchwald-Hertwig amination reaction with an amine (R⁵—NH₂) in the presence of catalyst such as Pd₂(dba)₃ or Pd(dba)₂ and BINAP or XPhos to afford compound JJJ2. Compound JJJ2 then underwent Boc protection with di-tent-butyl dicarbonate in the presence of a base such as TEA, potassium carbonate, DIPEA, sodium carbonate, NaH, sodium t-butoxide, or potassium t-butoxide followed by hydrolysis to give compound LLL2. Compound LLL2 was treated with an azide source such as DPPA and DIPEA under Curtius rearrangement condition to afford compound MMM2. Boc deprotection was then performed on compound MMM2 using hydrochloric acid or TFA in a solvent such as dioxane, THF, or DCM to afford compound (I-EE).

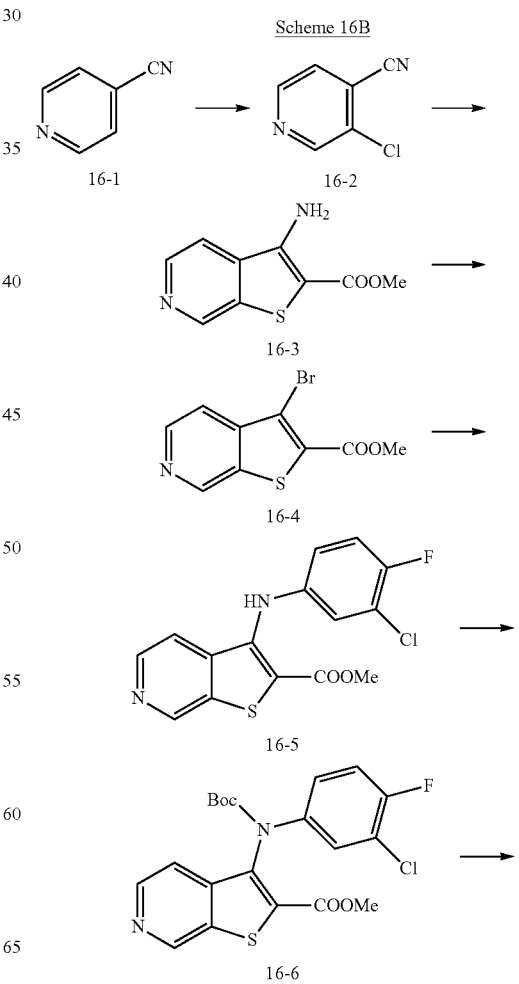

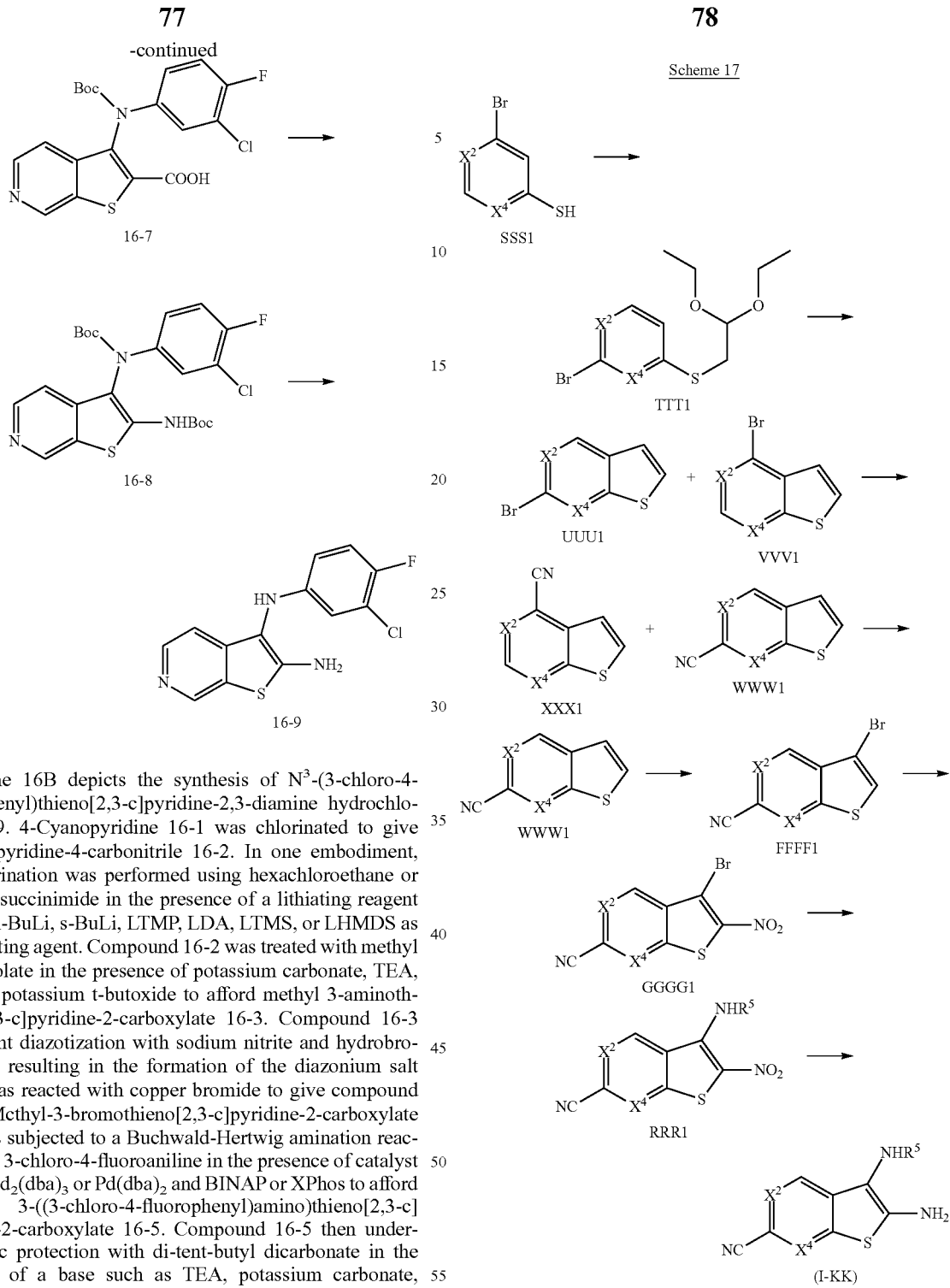

Scheme 16B depicts the synthesis of N³-(3-chloro-4-fluorophenyl)thieno[2,3-c]pyridine-2,3-diamine hydrochloride 16-9. 4-Cyanopyridine 16-1 was chlorinated to give 3-chloropyridine-4-carbonitrile 16-2. In one embodiment, the chlorination was performed using hexachloroethane or N-chlorosuccinimide in the presence of a lithiating reagent such as n-BuLi, s-BuLi, LTMP, LDA, LTMS, or LHMDS as the lithiating agent. Compound 16-2 was treated with methyl thioglycolate in the presence of potassium carbonate, TEA, NaH, or potassium t-butoxide to afford methyl 3-aminothieno [2,3-c]pyridine-2-carboxylate 16-3. Compound 16-3 underwent diazotization with sodium nitrite and hydrobromic acid resulting in the formation of the diazonium salt which was reacted with copper bromide to give compound 16-4. Methyl-3-bromothieno[2,3-c]pyridine-2-carboxylate 16-4 was subjected to a Buchwald-Hertwig amination reaction with 3-chloro-4-fluoroaniline in the presence of catalyst such as Pd₂(dba)₃ or Pd(dba)₂ and BINAP or XPhos to afford methyl 3-((3-chloro-4-fluorophenyl)amino)thieno[2,3-c]pyridine-2-carboxylate 16-5. Compound 16-5 then underwent Boc protection with di-tent-butyl dicarbonate in the presence of a base such as TEA, potassium carbonate, DIPEA, sodium carbonate, NaH, sodium t-butoxide, or potassium t-butoxide, followed by hydrolysis to give compound 16-7. 3-((Tert-butoxycarbonyl)(3-chloro-4-fluorophenyl)amino)thieno [2,3-c]pyridine-2-carboxylic acid 16-7 was treated with an azide source such as DPPA and DIPEA under Curtius rearrangement condition to afford tent-butyl (2-(((tert-butoxycarbonyl)amino)thieno[2,3-c]pyridin-3-yl) (3-chloro-4-fluorophenyl)carbamate 16-8. Boc de-protection was then performed on compound 16-8 using hydrochloric acid or TFA in a solvent such as dioxane, THF, or DCM to afford N³-(3-chloro-4-fluorophenyl)thieno[2,3-c]pyridine-2,3-diamine hydrochloride 16-9.

Scheme 17 describes the synthesis of compound (I-KK). Compound SSS1 was treated with bromoacetaldehyde diethylacetal in the presence of a base such as sodium hydride, potassium carbonate, sodium t-butoxide, potassium t-butoxide, or TEA in a solvent such as DMF, THF, dioxane, or toluene to afford compound TTT1. Compound TTT1 was added to a refluxed solution of PPA or a Lewis acid such as ZnCl₂, AlCl₃, or AlBr₃ and the resulting reaction mixture refluxed overnight to give a mixture of compounds UUU1 and VVV1. This mixture which was treated with copper cyanide in the presence of a catalyst such as Pd(PPh₃)₄, Pd(dba)₂, Pd₂(dba)₃, Pd(OAc)₂, PdCl₂(PPh₃)₂ in DMF, THF, or MeCN to afford a mixture of compounds XXX1 and WWW1. These compounds were separated using methods known in the art such as column chromatography or prep-HPLC. Compound WWW1 was brominated with NBS to give compound FFFF1. In one embodiment, the bromination was performed using NBS or bromine. Compound FFFF1 then underwent nitration to afford compound GGGG1. In one embodiment, the nitration was performed using with potassium nitrate/acetic anhydride or potassium nitrate/TFA. Compound GGGG1 was coupled with an amine (R⁵—NH₂) to give compound RRR1. Catalytic hydrogenation was then done on compound RRR1 to afford compound (I-KK). In one embodiment, this reaction was performed in the presence of Zn dust/NH₄Cl or Sn/acetic acid in methanol, ethanol, or butanol.

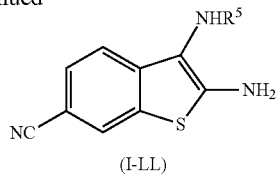

(I-LL)

Scheme 17A describes the synthesis of compound (I-LL). Commercially available 3-bromothiophenol 17-1 was treated with bromoacetaldehyde diethylacetal in the presence of a base such as sodium hydride, potassium carbonate, sodium t-butoxide, potassium t-butoxide, or TEA in a solvent such as DMF, THF, dioxane, or toluene to afford compound 17-2.1-Bromo-4-[(2,2-diethoxyethyl)sulfanyl]benzene 17-2 was added to a refluxed solution of PPA or a Lewis acid such as ZnCl₂, AlCl₃, or AlBr₃ and the resulting reaction mixture refluxed overnight to give a mixture of 6-bromobenzo[b]thiophene 17-3 and 4-bromobenzo[b]thiophene 17-4. This mixture which was treated with copper cyanide in the presence of a catalyst such as Pd(PPh₃)₄, Pd(dba)₂, Pd₂(dba)₃, Pd(OAc)₂, PdCl₂(PPh₃)₂ in a solvent such as DMF, THF, or MeCN to afford a mixture of benzo[b]thiophene-6-carbonitrile 17-5 and benzo[b]thiophene-4-carbonitrile 17-6. These compounds were separated using methods known in the art such as column chromatography or prep-HPLC. Compound 17-5 was brominated with NBS to give 3-bromobenzo[b]thiophene-6-carbonitrile 17-7. In one embodiment, the bromination was performed using NBS or bromine. Compound 17-7 then underwent nitration to afford 3-bromo-2-nitrobenzo[b]thiophene-6-carbonitrile 17-8. In one embodiment, the nitration was performed using with potassium nitrate/acetic anhydride or potassium nitrate/TFA. Compound 17-8 was coupled with an amine (R⁵—NH₂) to give compound RRR2. Catalytic hydrogenation was then done on compound RRR2 to afford compound (I-LL). In one embodiment, this reaction was performed in the presence of Zn dust/NH₄Cl or Sn/acetic acid in methanol ethanol, or butanol.

Scheme 17A

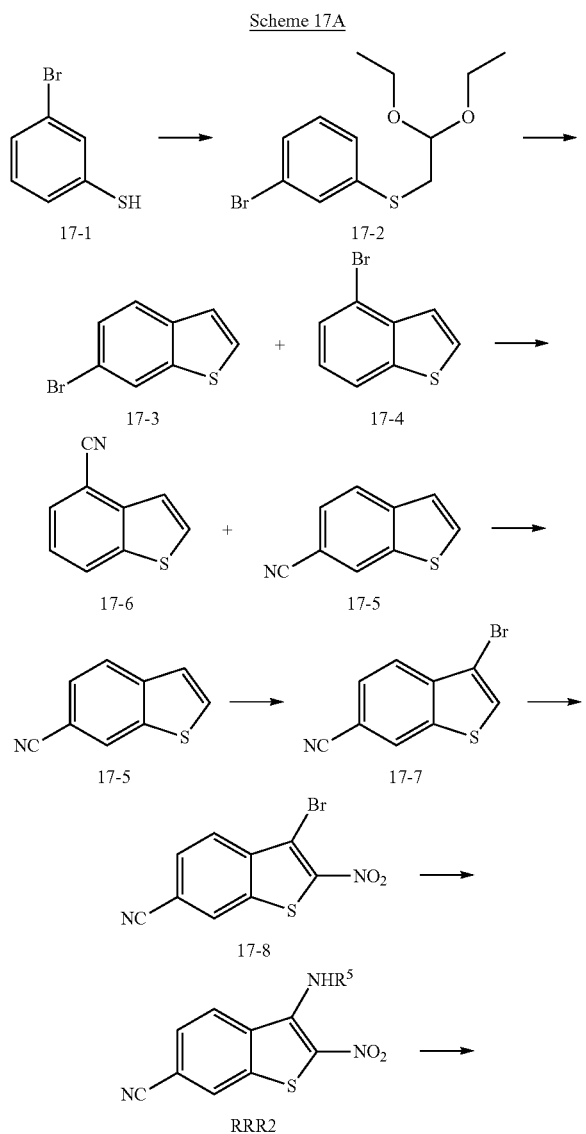

Scheme 17B

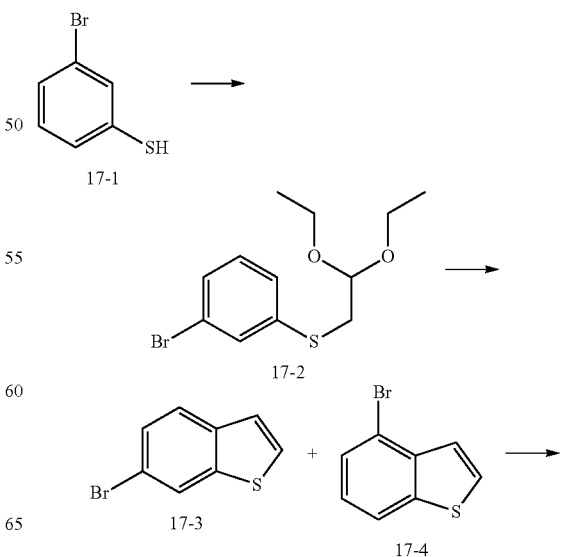

-continued

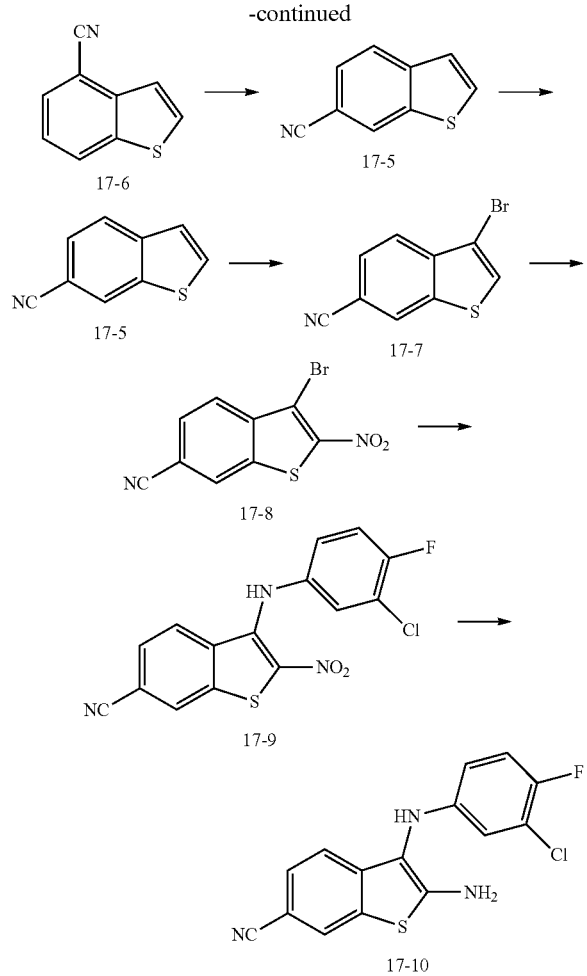

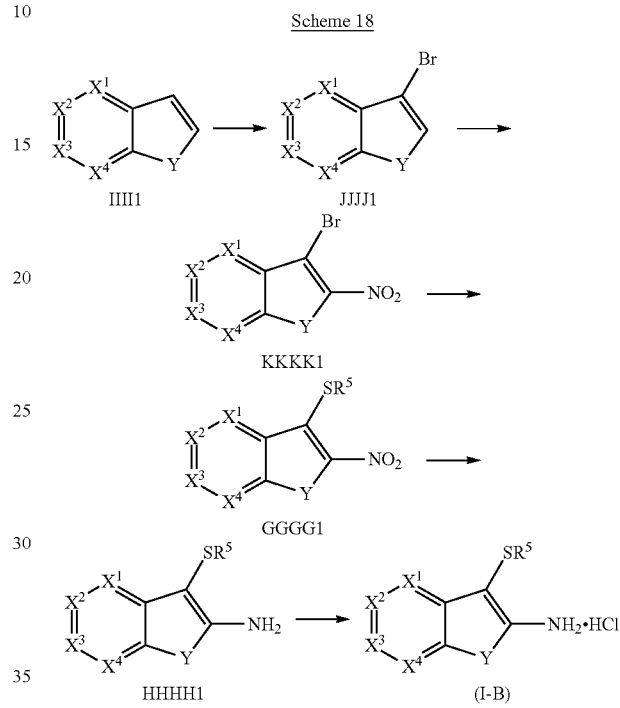

3-((3-chloro-4-fluorophenyl)amino)-2-nitrobenzo[b]thiophene-6-carbonitrile 17-9. Catalytic hydrogenation was then done on compound 17-9 to afford 2-amino-3-((3-chloro-4-fluorophenyl)amino)benzo[b]thiophene-6-carbonitrile 17-10. In one embodiment, this reaction was performed in the presence of Zn dust/NH$_4$Cl or Sn/acetic acid in methanol, ethanol, or butanol.

Scheme 17B describes the synthesis of 2-amino-3-((3-chloro-4-fluorophenyl)-amino)benzo[b]thiophene-6-carbonitrile 17-10. 3-Bromothiophenol 17-1 was treated with bromoacetaldehyde diethylacetal in the presence of a base such as sodium hydride, potassium carbonate, sodium t-butoxide, potassium t-butoxide, or TEA in a solvent such as DMF, THF, dioxane, or toluene to afford compound 17-2.1-Bromo-4-[(2,2-diethoxyethyl)sulfanyl]benzene 17-2 was added to a refluxed solution of PPA or a Lewis acid such as ZnCl$_2$, AlCl$_3$, or AlBr$_3$ and the resulting reaction mixture refluxed overnight to give a mixture of 6-bromobenzo[b]thiophene 17-3 and 4-bromobenzo[b]thiophene 17-4. This mixture which was treated with copper cyanide in the presence of a catalyst such as Pd(PPh$_3$)$_4$, Pd(dba)$_2$, Pd$_2$(dba)$_3$, Pd(OAc)$_2$, PdCl$_2$(PPh$_3$)$_2$ in a solvent such as DMF, THF, or MeCN to afford a mixture of benzo[b]thiophene-6-carbonitrile 17-5 and benzo[b]thiophene-4-carbonitrile 17-6. These compounds were separated using methods known in the art such as column chromatography or prep-HPLC. Compound 17-5 was brominated with NBS or bromine to give 3-bromobenzo[b]thiophene-6-carbonitrile 17-7. In one embodiment, the bromination was performed using NBS or bromine. Compound 17-7 then underwent nitration to afford 3-bromo-2-nitrobenzo[b]thiophene-6-carbonitrile 17-8. In one embodiment, the nitration was performed using with potassium nitrate/acetic anhydride or potassium nitrate/TFA. Compound 17-8 was coupled with 3-chloro-4-fluoroaniline in a solvent such as DMF to give Scheme 18 depicts the synthesis of compound (I-B). Compound IIII1 was brominated resulting in the formation of compound JJJJ1. In one embodiment, the bromination was performed using NBS or bromine. Compound JJJJ1 underwent nitration to afford nitro compound KKKK1. In one embodiment, the nitration was performed using fuming nitric acid and TFA, fuming nitric acid and acetic acid, or fuming nitric acid and sulfuric acid. Compound KKKK1 was reacted with R$^5$—SH to provide compound GGGG1. Compound GGGG1 was hydrogenated resulting in the formation of compound HHHH1. In one embodiment, the hydrogenation was performed using activated Pd/C under hydrogen gas or Zn/methanol or Sn/acetic acid. Compound HHHH1 underwent hydrochloride salt formation to afford compound (I-B). In one embodiment, salt formation was performed using hydrochloride gas absorbed in diethyl ether or hydrochloride gas absorbed in an alcohol such as methanol, ethanol, or isopropanol, EtOAc, or MTBE.

Scheme 18A

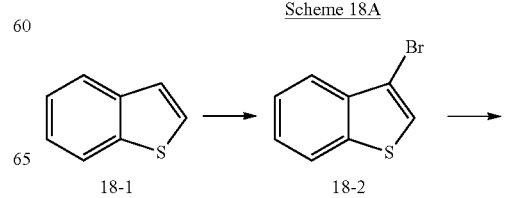

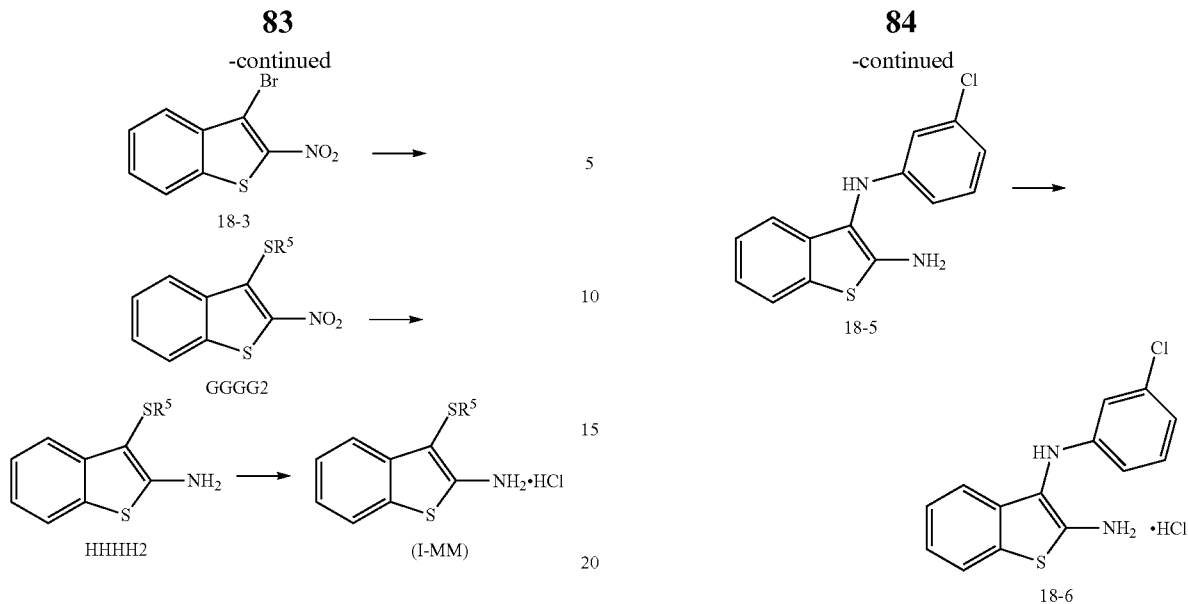

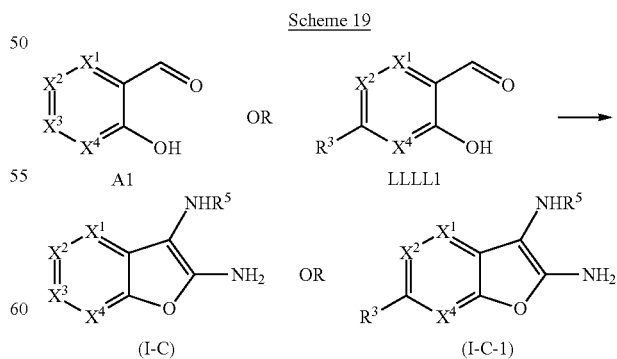

Scheme 18A depicts the synthesis of compound (I-MM). Commercially available benzothiophene 18-1 was brominated resulting in the formation of 3-bromo-benzothiophene 18-2. In one embodiment, the bromination was performed using NBS or bromine. Compound 18-2 underwent nitration to afford nitro compound 18-3. In one embodiment, the nitration was performed using fuming nitric acid and TFA, fuming nitric acid and acetic acid, or fuming nitric acid and sulfuric acid. 3-Bromo-2-nitrobenzothiophene 18-3 was reacted with $R^5$—SH to provide compound GGGG2. Compound GGGG2 was hydrogenated resulting in the formation of compound HHHH2. In one embodiment, the hydrogenation was performed using activated Pd/C under hydrogen gas, Zn/methanol or Sn/acetic acid. Compound HHHH2 underwent hydrochloride salt formation to afford compound (I-MM). In one embodiment, salt formation was performed using hydrochloride gas absorbed in diethyl ether or hydrochloride gas absorbed in an alcohol such as methanol, ethanol, or isopropanol, EtOAc, or MTBE.

Scheme 18B depicts the synthesis of 3-[(3-chlorophenyl)sulfanyl]-1-benzothiophen-2-amine hydrochloride 18-6. Compound 18-1 was brominated resulting in the formation of 3-bromo-benzothiophene 18-2. In one embodiment, the bromination was performed using NBS or bromine. Compound 18-2 underwent nitration to afford nitro compound 18-3. In one embodiment, the nitration was performed using fuming nitric acid and TFA, fuming nitric acid and acetic acid, or fuming nitric acid and sulfuric acid. 3-Bromo-2-nitrobenzothiophene 18-3 was reacted with 3-chlorothiophenol in NaOH to provide compound 18-4. 3-[(3-Chlorophenyl)sulfanyl]-2-nitro-1-benzothiophene 18-4 was hydrogenated resulting in the formation of 3-[(3-chlorophenyl)sulfanyl]-1-benzothiophen-2-amine 18-5. In one embodiment, the hydrogenation was performed using activated Pd/C under hydrogen gas, Zn/methanol or Sn/acetic acid. Compound 18-5 underwent hydrochloride salt formation to afford 3-[(3-chlorophenyl)sulfanyl]-1-benzothiophen-2-amine hydrochloride 18-6. In one embodiment, salt formation was performed using hydrochloride gas absorbed in diethyl ether or hydrochloride gas absorbed in an alcohol such as methanol, ethanol, or isopropanol, EtOAc, or MTBE.

Scheme 18B

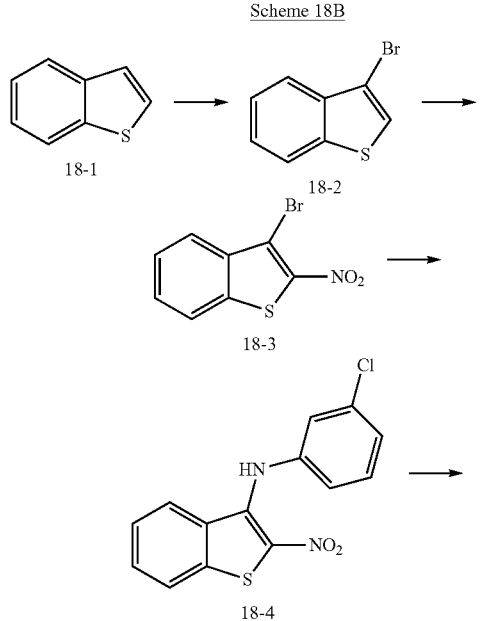

Scheme 19 describes the synthesis of compound (I-C) or (I-C-1). Compound A1 or LLLL1 was reacted with an amine ($R^5$—$NH_2$) resulting in the formation of the imine intermediate which underwent in situ Strecker reaction with a trialkylsilyl cyanide such as TMSCN or an inorganic cyanide salt such as NaCN, KCN, or Zn(CN)₂ followed by unexpected intramolecular cyclization in the presence of trimethylsilyl trifluoromethanesulfonate to afford compound (I-C) or (I-C-1).

Scheme 19A

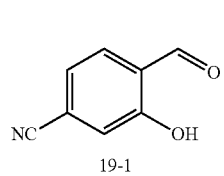
19-1

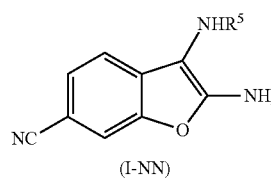
(I-NN)

Scheme 19A describes the synthesis of compound (I-NN). 4-Formyl-3-hydroxybenzonitrile 19-1 was reacted with an amine (R⁵—NH₂) resulting in the formation of the imine intermediate which underwent in situ Strecker reaction with a trialkylsilyl cyanide such as TMSCN or an inorganic cyanide salt such as NaCN, KCN, or Zn(CN)₂ followed by unexpected intramolecular cyclization in the presence of trimethylsilyl trifluoromethanesulfonate to afford compound (I-NN).

Scheme 19B

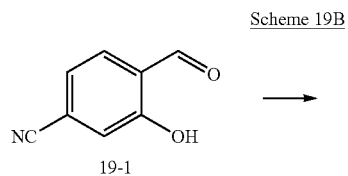
19-1

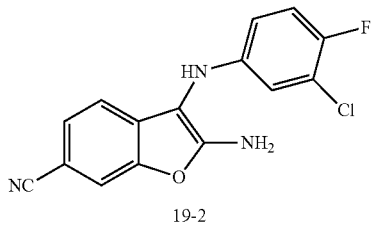
19-2

Scheme 19B describes the synthesis of 2-amino-3-((3-chloro-4-fluorophenyl)-amino)benzofuran-6-carbonitrile 19-2. 4-Formyl-3-hydroxybenzonitrile 19-1 was reacted with 3-chloro-4-fluoroaniline resulting in the formation of the imine intermediate which underwent in situ Strecker reaction with a trialkylsilyl cyanide such as TMSCN or an inorganic cyanide salt such as NaCN, KCN, or Zn(CN)₂ followed by unexpected intramolecular cyclization in the presence of trimethylsilyl trifluoromethanesulfonate to afford 2-amino-3-((3-chloro-4-fluorophenyl)amino)benzofuran-6-carbonitrile 19-2.

Scheme 20

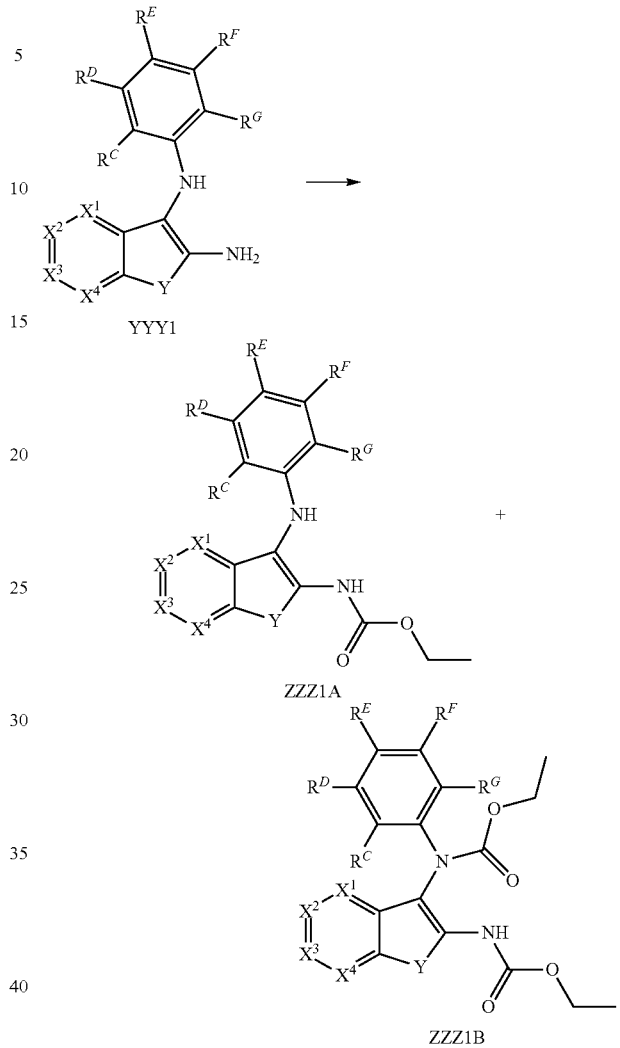

Scheme 20 describes the synthesis of compounds (ZZZ1A) and (ZZZ1B). Compound YYY1 was treated with an alkyl chloroformate in THF or DCM in the presence of pyridine or TEA to afford the title compounds. In one embodiment, the alkyl chloroformate was ethyl chloroformate. In other embodiments, the alkyl chloroformate were methyl chloroformate or benzyl chloroformate.

Scheme 20A

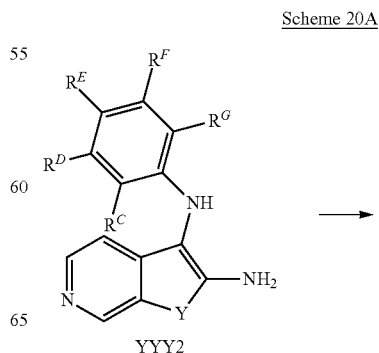
YYY2

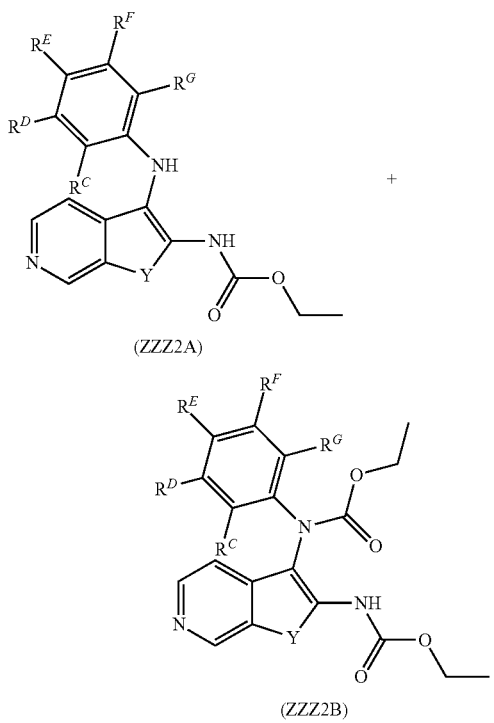

(ZZZ2A)

(ZZZ2B)

Scheme 20A describes the synthesis of compounds (ZZZ2A) and (ZZZ2B). Compound YYY2 was treated with an alkyl chloroformate in THF or DCM in the presence of pyridine or TEA to afford the title compounds. In one embodiment, the alkyl chloroformate was ethyl chloroformate. In other embodiments, the alkyl chloroformate were methyl chloroformate or benzyl chloroformate.

Scheme 20B

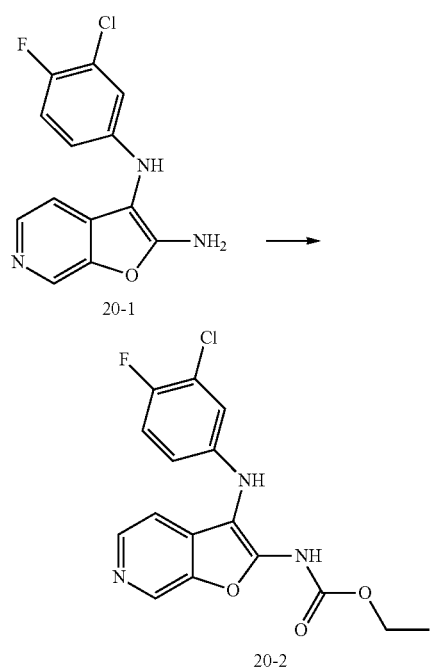

20-1

20-2

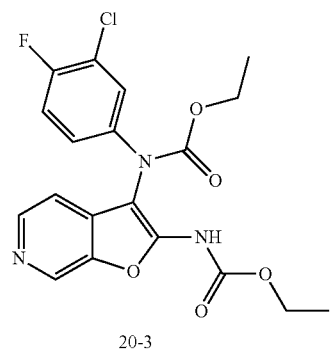

20-3

Scheme 20 describes the synthesis of mono-carbamate ethyl (3-((3-chloro-4-fluorophenyl)amino)furo[2,3-c]pyridin-2-yl)carbamate 20-2 and di-carbamate ethyl (3-chloro-4-fluorophenyl)(2-((ethoxycarbonyl)amino)furo[2,3-c]pyridin-3-yl)carbamate 20-3. $N^3$-(3-chloro-4-fluorophenyl)furo[2,3-c]pyridine-2,3-diamine 20-1 was treated with ethyl chloroformate in THF in the presence of pyridine to afford the mono-carbamate 20-2 and di-carbamate 20-3. One of skill in the art would be able to vary the reaction time and amounts of reagents utilize to prepare the mono-carbamate, di-carbamate, or a combination thereof, as needed.

Scheme 21

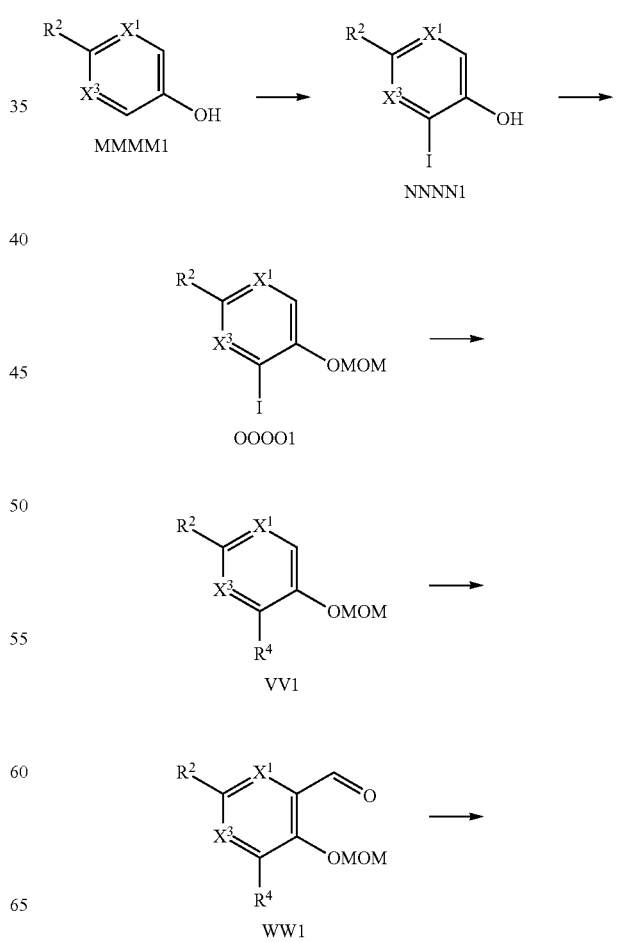

MMMM1

NNNN1

OOOO1

VV1

WW1

-continued

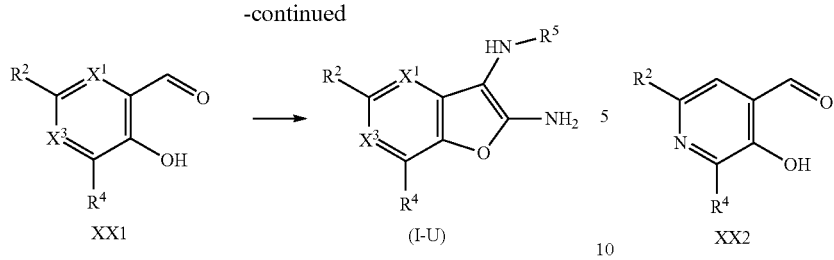

XX1     (I-U)

-continued

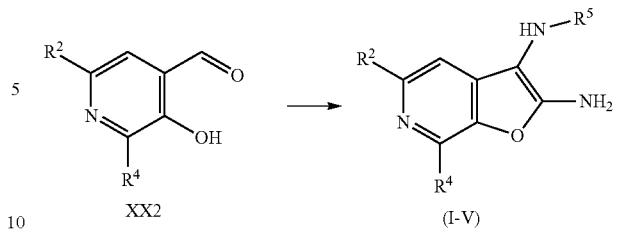

XX2     (I-V)

Scheme 21 provides the preparation of compound (I-U). The synthesis began with the iodination of hydroxy compound MMMM1. In one embodiment iodine and sodium carbonate was used as iodinating reagent. In another embodiment the iodination was performed in a mixture of solvents like tetrahydrofuran and water to afforded compound NNNN1. The resulting compound NNNN1 was forwarded to MOM protection or SEM protection using MOMCl or SEMCl respectively in the presence of a base to provide the product OOOO1. The compound OOOO1 was subjected to a metal catalyzed cross-coupling reaction to give compound VV1. In one embodiment, the catalyst was Pd(PPh$_3$)$_4$. In another embodiment the catalyst was Pd$_2$(dba)$_3$. The compound VV1 underwent formylation with DMF or N-formylpiperidine in the presence of base like n-BuLi, s-BuLi, LDA, or LTMP at −78° C. to give product WW1. The compound WW1 was deprotected in presence of a Lewis acid to provide XX1. In one embodiment the acid was TFA. The compound XX1 was treated with an amine (R$^5$NH$_2$), a cyanide ion source and a Lewis acid to provide the compound (I-U). In one embodiment the cyanide ion source was TMSCN. In another embodiment the Lewis acid was TMSOTf.

Scheme 21A provides the preparation of compound (I-V). The compound hydroxypyridine MMMM2 was iodinated using iodine and sodium carbonate in a mixture of solvents like tetrahydrofuran and water to afforded compound NNNN2. The resulting compound NNNN2 was forwarded to MOM protection or SEM protection using MOMCl or SEMCl respectively in the presence of a base product OOOO2. The compound OOOO2 was subjected to a metal catalyzed cross-coupling reaction to give compound VV2. In another embodiment, the catalyst was Pd(PPh$_3$)$_4$. In another embodiment the catalyst was Pd$_2$(dba)$_3$. The compound VV2 underwent formylation with DMF or N-formylpiperidine in the presence of base like n-BuLi, s-BuLi, LDA, or LTMP at −78° C. to give product WW2. The compound WW2 was deprotected under acidic conditions to provide XX2. In one embodiment the acid was TFA. The compound XX2 was treated with an amine (R$^5$NH$_2$), TMSCN and TMSOTf to provide the compound (I-V) via a sequence of reactions such as imine formation, Strecker reaction and intramolecular cyclization.

Scheme 21A

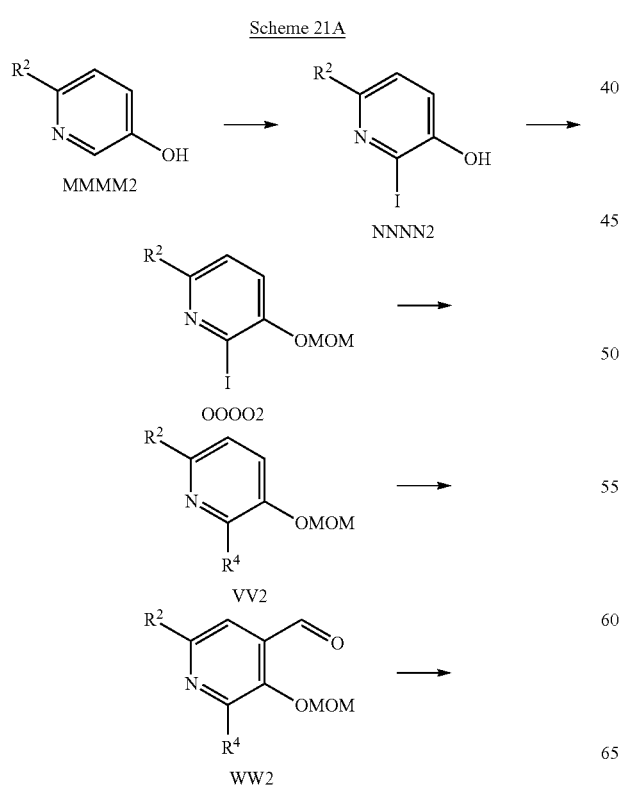

Scheme 21B

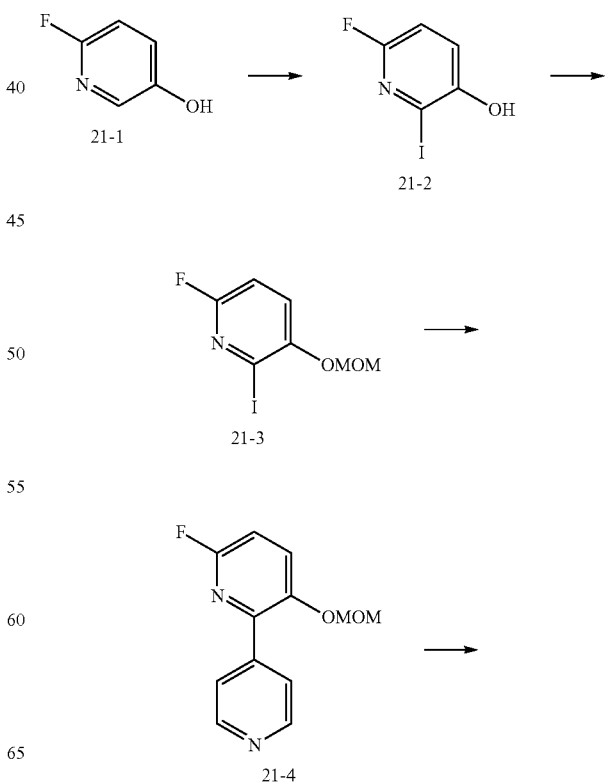

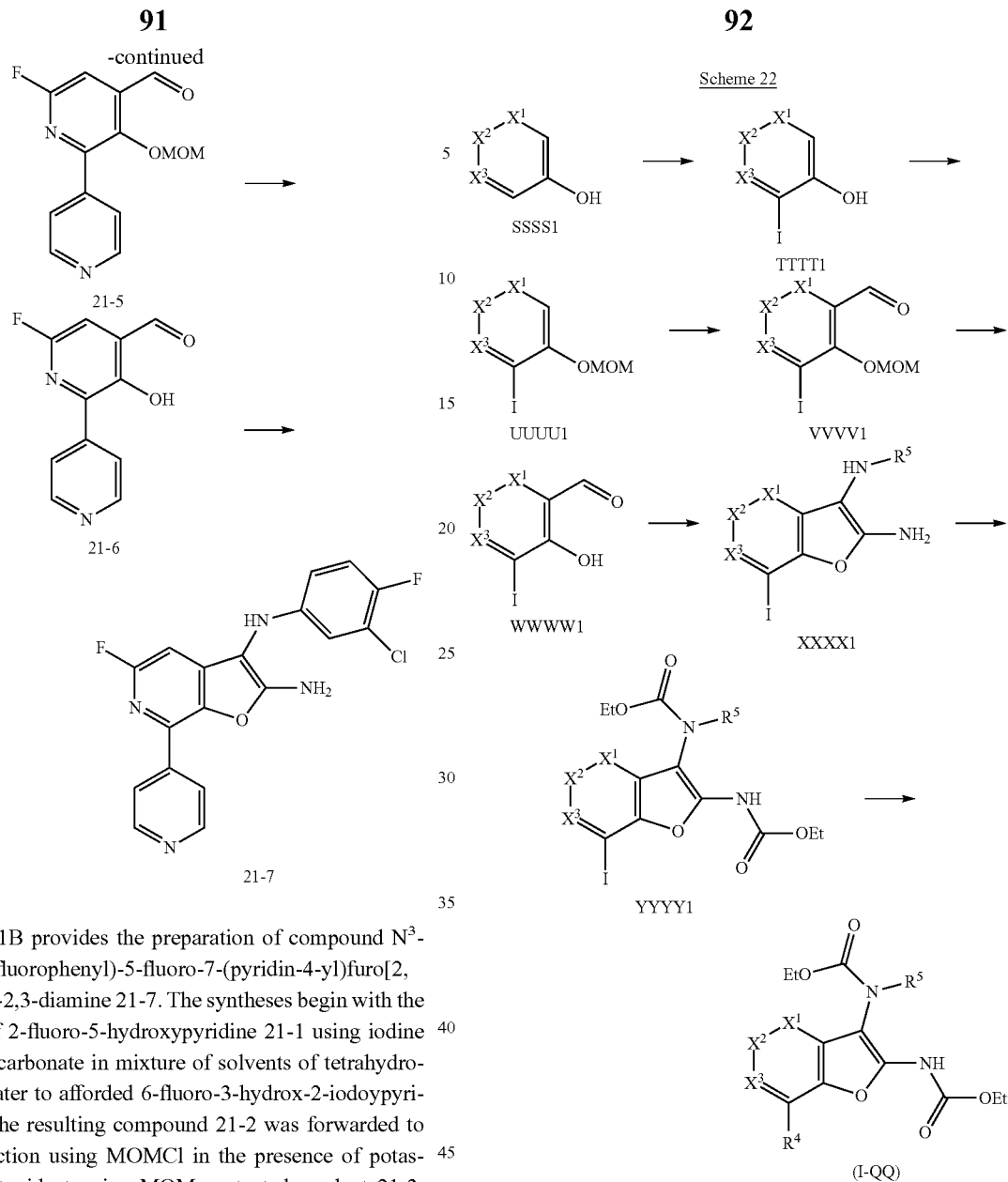

Scheme 21B provides the preparation of compound $N^3$-(3-chloro-4-fluorophenyl)-5-fluoro-7-(pyridin-4-yl)furo[2,3-c]pyridine-2,3-diamine 21-7. The syntheses begin with the iodination of 2-fluoro-5-hydroxypyridine 21-1 using iodine and sodium carbonate in mixture of solvents of tetrahydrofuran and water to afforded 6-fluoro-3-hydrox-2-iodoypyridine 21-2. The resulting compound 21-2 was forwarded to MOM protection using MOMCl in the presence of potassium tert-butoxide to give MOM protected product 21-3. The 6-fluoro-2-iodo-3-(methoxymethoxy)pyridine 21-3 was subjected to Suzuki-Miyaura cross-coupling reaction condition with 4-pyridinylboronic acid in the presence of tripotassium phosphate, tricyclohexylphosphine and $Pd_2(dba)_3$ in dioxane to afford 6-fluoro-3-(methoxymethoxy)-2,4'-bipyridine 21-4 which was undergoes formylation with DMF in the presence of n-BuLi at −78° C. to give formylated product 21-5. The compound 21-5 was treated with TFA-DCM solution to afford MOM-deproted compound 6-fluoro-3-hydroxy-[2,4'-bipyridine]-4-carbaldehyde 21-6. The compound 21-6 was treated with 3-chloro-4-fluoroaniline, TMSCN, TMSOTf and DCM in a single pot at room temperature to afford desired product $N^3$-(3-chloro-4-fluorophenyl)-5-fluoro-7-(pyridin-4-yl)furo[2,3-c]pyridine-2,3-diamine 21-7 as pale yellow solid via a sequence of reactions such as imine formation, Strecker reaction and intramolecular cyclization.

Scheme 22 provides the preparation of compound (I-QQ). The synthesis began with the iodination of hydroxy compound SSSS1. In one embodiment iodine and sodium carbonate was used as iodinating reagent. In another embodiment the iodination was performed in a mixture of solvents like tetrahydrofuran and water to afforded compound TTTT1. The resulting compound TTTT1 was forwarded to MOM protection or SEM protection using MOMCl or SEMC1 respectively in the presence of a base to provide the product UUUU1. The compound UUUU1 underwent formylation with DMF or N-formylpiperidine in the presence of base like n-BuLi, s-BuLi, LDA, or LTMP at −78° C. to give product VVVV1. The compound VVVV1 was deprotected in presence of a Lewis acid to provide WWWW1. In one embodiment the acid was TFA. The compound WWWW1 was treated with an amine ($R^5$—$NH_2$), a cyanide ion source and a Lewis acid to provide the compound XXXX1. In one embodiment the cyanide ion source was TMSCN. In another embodiment the Lewis acid was TMSOTf. The compound XXXX1 was converted to dicarbamate YYYY1. In one embodiment ethyl chloroformate in the presence of pyridine in THF was used for formation of monocarbamate or dicarbamate. The dicarbamate YYYY1 was converted to the product (I-QQ) under cross-coupling reaction conditions.

amine ($R^5$—$NH_2$), a cyanide ion source and a Lewis acid to provide the compound XXXX2. In one embodiment the cyanide ion source was TMSCN. In another embodiment the Lewis acid was TMSOTf. The compound XXXX2 was converted to dicarbamate YYYY2. In one embodiment ethyl chloroformate in the presence of pyridine in THF was used for formation of monocarbamate or dicarbamate. The dicarbamate YYYY2 was converted to the product (I-RR) under cross-coupling reaction conditions.

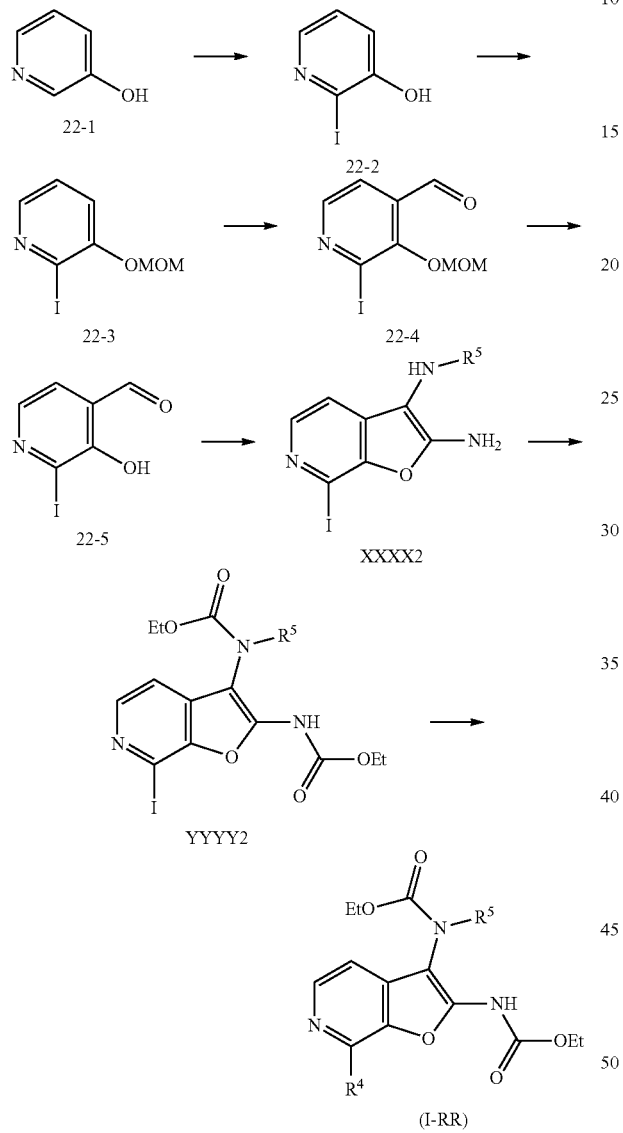

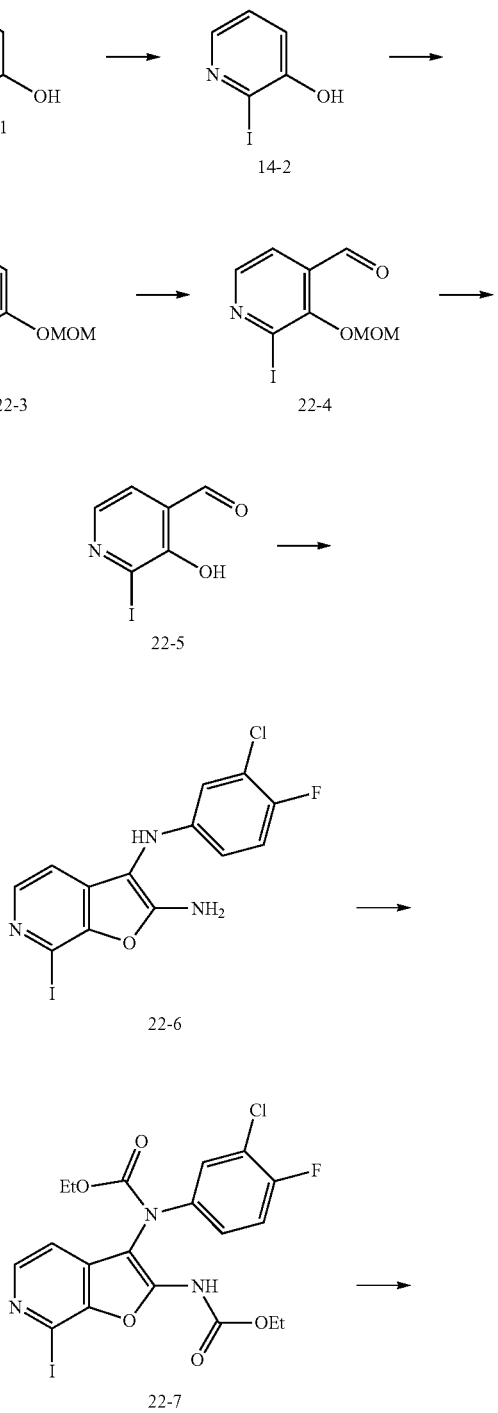

Scheme 22A provides the preparation of compound (I-RR). The synthesis began with the iodination of 3-hydroxypyridine 22-1 which was treated with iodine in the presence of sodium carbonate in water to afford 2-iodo-3-hydroxypyridine 22-2. The resulting compound 22-2 was forwarded to MOM protection using MOMCl in the presence of potassium tert-butoxide to give MOM protected product 22-3. The 2-iodo-3-(methoxymethoxy)pyridine 22-3 was formylated with DMF in the presence of LDA in THF at −78° C. to give 2-iodo-3-(methoxymethoxy)-isonicotinaldehyde 22-4 which was subjected to MOM-de-protection with TFA-DCM to afford 3-hydroxy-2-iodoisonicotinaldehyde 22-5. The compound 22-5 was treated with an -continued

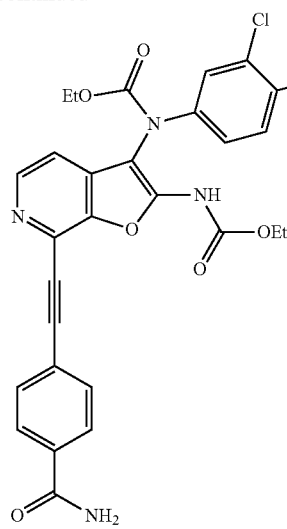

22-8

Scheme 22B described the synthesis of ethyl (7-((4-carbamoylphenyl)ethynyl)-2-((ethoxycarbonyl)amino)furo[2,3-c]pyridin-3-yl)(3-chloro-4-fluorophenyl)carbamate 22-8. The syntheses begin with the commercially available 3-hydroxypyridine 14-1 which was treated with iodine in the presence of sodium carbonate in water to afford 2-iodo-3-hydroxypyridine 14-2. The resulting compound 14-2 was forwarded to MOM protection using MOMCl in the presence of potassium tert-butoxide to give MOM protected product 22-3. The 2-iodo-3-(methoxymethoxy)pyridine 22-3 was formylated with DMF in the presence of LDA in THF at −78° C. to give 2-iodo-3-(methoxymethoxy)-isonicotinaldehyde 22-4 which was undergoes MOM-de-protection with TFA-DCM to afford 3-hydroxy-2-iodoisonicotinaldehyde 22-5. The compound 22-5 was treated in a one-pot with 3-chloro-4-fluoroaniline, TMSCN followed by TMSOTf in DCM at room temperature to afford $N^3$-(3-chloro-4-fluorophenyl)-7-iodofuro[2,3-c]pyridine-2,3-diamine 22-6 via a sequence of reactions such as imine formation, Strecker reaction and intramolecular cyclization. The compound 22-6 undergoes dicarbamate formation using ethylchloroformate in the presence of pyridine in THF to afford diethylcarbamate 22-7. The ethyl (3-chloro-4-fluorophenyl)(2-((ethoxycarbonyl)amino)-7-iodo furo[2,3-c]pyridin-3-yl)carbamate 22-7 was treated under Sonogashira reaction condition with 4-ethynylbenzamide in the presence of $PdCl_2(PPh_3)_2$, CuI and triethyl amine to give desired product ethyl (7-((4-carbamoylphenypethynyl)-2-((ethoxycarbonyl)amino)furo[2,3-c]pyridin-3-yl)(3-chloro-4-fluorophenyl)carbamate 22-8 as brown solid.

Scheme 23

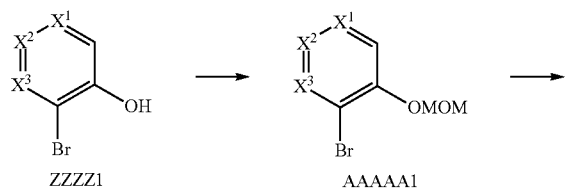

ZZZZ1      AAAAA1

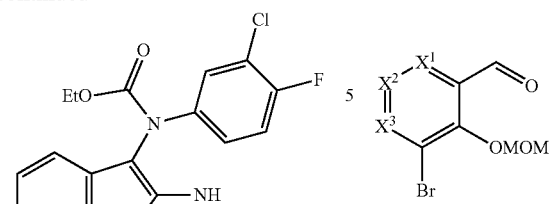

BBBBB1     CCCCC1

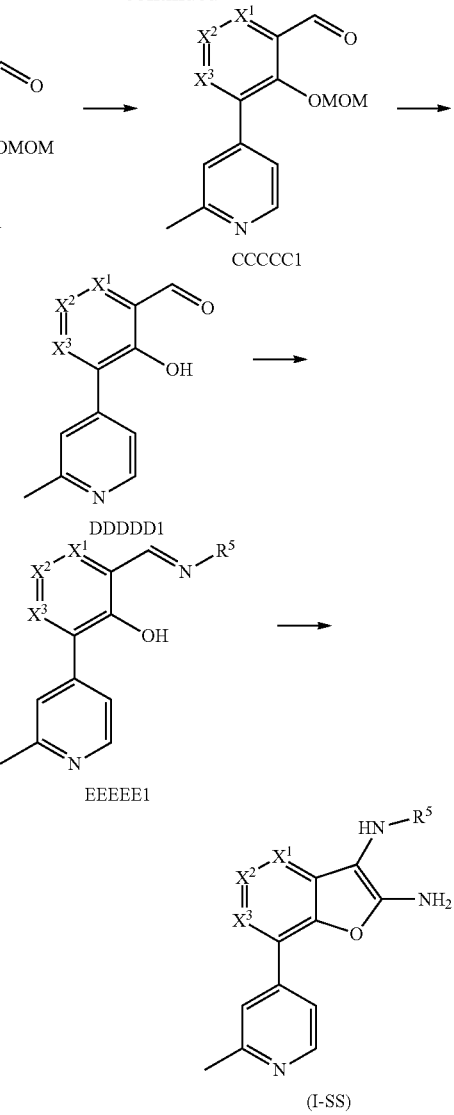

DDDDD1

EEEEE1

(I-SS)

Scheme 23 describes the synthesis of compound (I-SS). The starting bromohydroxy compound ZZZZ1 was subjected to MOM protection or SEM protection using MOMCl or SEMCl respectively in the presence of a base to provide the product AAAAA1 which in turn was formylated with DMF or N-formylpiperidine in the presence of base like n-BuLi, s-BuLi, LDA, or LTMP at −78° C. to give product BBBBB1. The cross coupling reaction was done on BBBBB1 with heteroaryl boronic acid or ester to provide the compound CCCCC1. In one embodiment the heteroarylboron was 2-methylpyridine-4-boronic acid. In another embodiment $Pd_2(dba)_3$ in dioxane in the presence of tripotassium phosphate and tricyclohexylphosphine was used as a catalyst. The product CCCCC1 was deprotected in presence of a Lewis acid to provide DDDDD1. In one embodiment the acid was TFA. The compound DDDDD1 was treated with an amine ($R^5$—$NH_2$) to provide imine EEEEE1. In one embodiment imine formation was done in a mixed solvents of TFE and MeCN. The imine EEEEE1 was allowed to react with a cyanide ion source to provide the product (I-SS). In one embodiment the cyanide ion source was TMSCN. In another embodiment the solvent was a mixture of DCM-TFE.

Scheme 23A

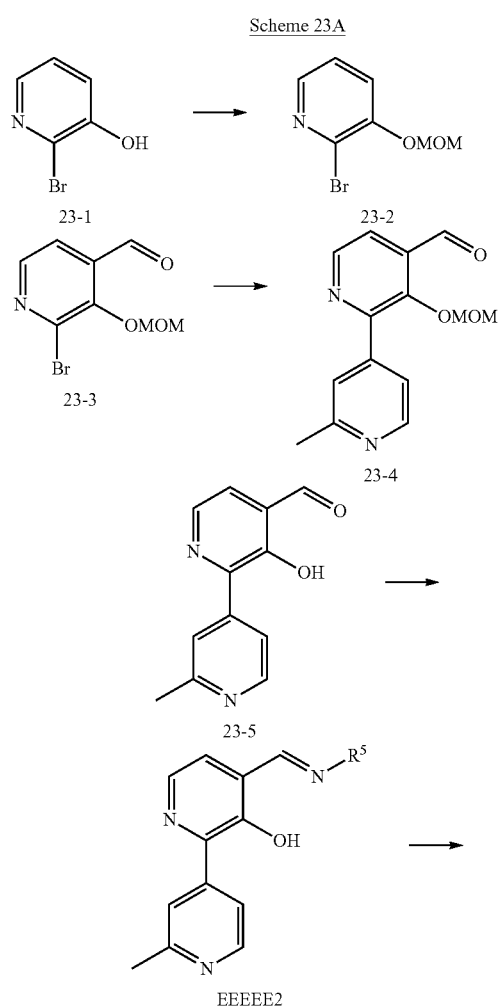

imine formation was done in a mixed solvent of TFE and MeCN. The imine EEEEE2 was allowed to react with a cyanide ion source to provide the product (I-TT). In one embodiment the cyanide ion source was TMSCN. In another embodiment the solvent was a mixture of DCM-TFE.

Scheme 23B

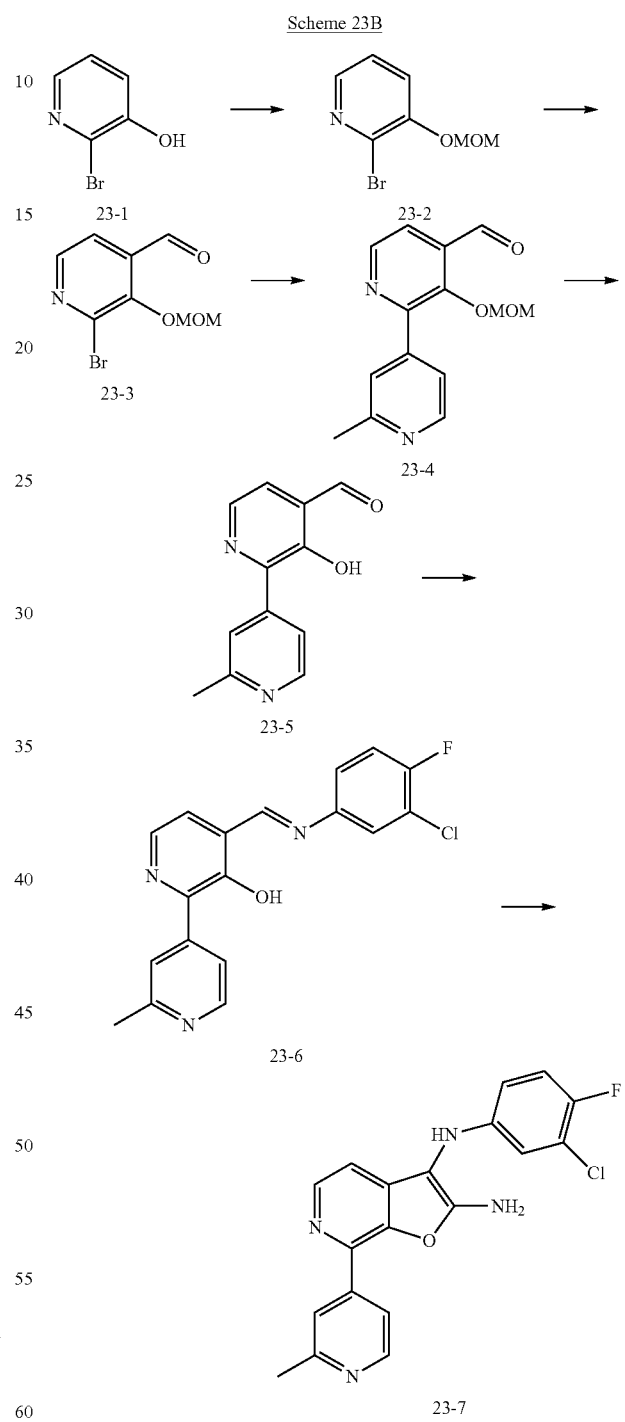

Scheme 23A described the synthesis of compound (I-TT). 2-Bromo-3-hydroxypyridine 23-1 was treated with MOMCl in the presence of t-BuOK in THF resulting in to the formation of 2-bromo-3-(methoxymethoxy)pyridine 23-2. The MOM protected compound underwent formylation with ethylformate in the presence of LDA at in THF at −78° C. to give 2-bromo-3-(methoxymethoxy)isonicotin aldehyde 23-3. The Suzuki cross coupling reaction was done on 23-3 with 2-methylpyridine-4-boronic acid in the presence of tripotassium phosphate, tricyclohexylphosphine and $Pd_2(dba)_3$ in dioxane to afford 3-(methoxymethoxy)-2'-methyl-[2,4'-bipyridine]-4-carbaldehyde 23-4 which was treated with TFA-DCM solution to give MOM-de-protected compound 23-5. The compound 23-5 was treated with amine ($R^5NH_2$) to provide imine EEEEE2. In one embodiment Scheme 23B described the synthesis $N^3$-(3-chloro-4-fluorophenyl)-7-(2-methylpyridin-4-yl)furo[2,3-c]pyridine-2,3-diamine 23-7. The 2-bromo-3-hydroxypyridine 23-1 was treated with MOMCl in the presence of t-BuOK in THF resulting in to the formation of 2-bromo-3-(methoxymethoxy)pyridine 23-2. The MOM protected compound underwent formylation with ethylformate in the presence of LDA in THF at −78° C. to give 2-bromo-3-(methoxymethoxy)isonicotinaldehyde 23-3. The Suzuki cross coupling reaction was done on 23-3 with 2-methylpyridine-4-boronic acid in the presence of tripotassium phosphate, tricyclohexylphosphine and Pd$_2$(dba)$_3$ in dioxane to afford 3-(methoxymethoxy)-2'-methyl-[2,4'-bipyridine]-4-carbaldehyde 23-4 which was treated with TFA-DCM solution to give MOM-de-protected compound 23-5. The compound 3-hydroxy-2'-methyl-[2,4'-bipyridine]-4-carbaldehyde 23-5 was treated with 3-chloro-4-fluoroaniline in a mixed solvents of TFE and MeCN to yield imine intermediate 23-6 which was further reacted with TMSCN in a mixed solvents of DCM-TFE to afford desired product N$^3$-(3-chloro-4-fluorophenyl)-7-(2-methylpyridin-4-yl)furo[2,3-c]pyridine-2,3-diamine 23-7 as a solid.

aryl- or heteroaryl boronic acid or ester under cross-coupling reaction conditions to provide compound FFFFF1. In one embodiment, the boronic ester used was N-methyl-4-(4,4,5,5-tetramethyl-1,3,2-dioxaborolan-2-yl)picolinamide . In another embodiment, the coupling reaction was done in presence of tripotassium phosphate, tricyclohexylphosphine and Pd$_2$(dba)$_3$ in dioxane. The compound FFFFF1 was deprotected in presence of a Lewis acid to provide GGGGG1. In one embodiment, the acid was TFA. The compound GGGGG1was next treated with an amine (R$^5$—NH$_2$), a cyanide ion source and a Lewis acid in sealed tube containing NH$_{40}$Ac buffer solution to provide the compound (I-UU). In one embodiment, the cyanide ion source was TMSCN. In another embodiment, the Lewis acid was TMSOTf.

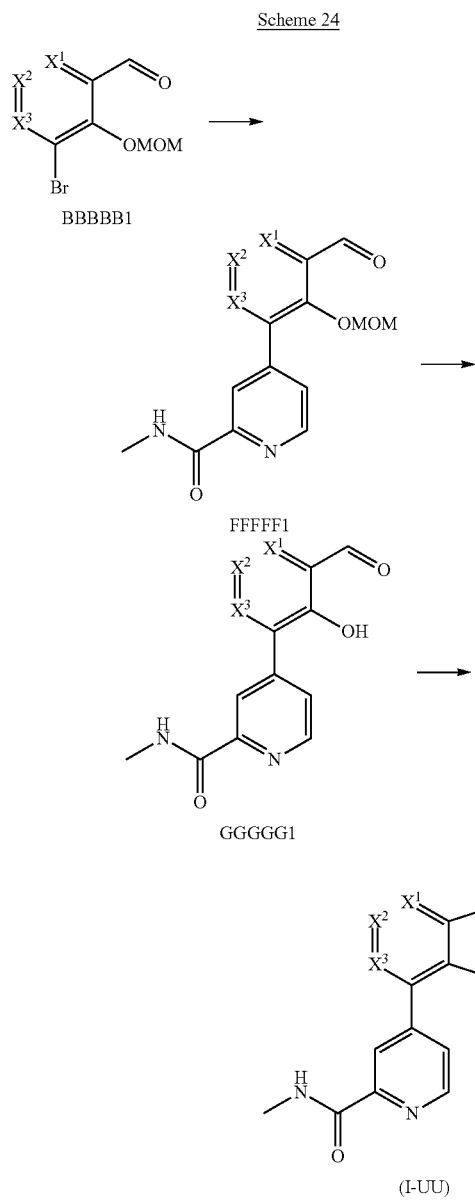

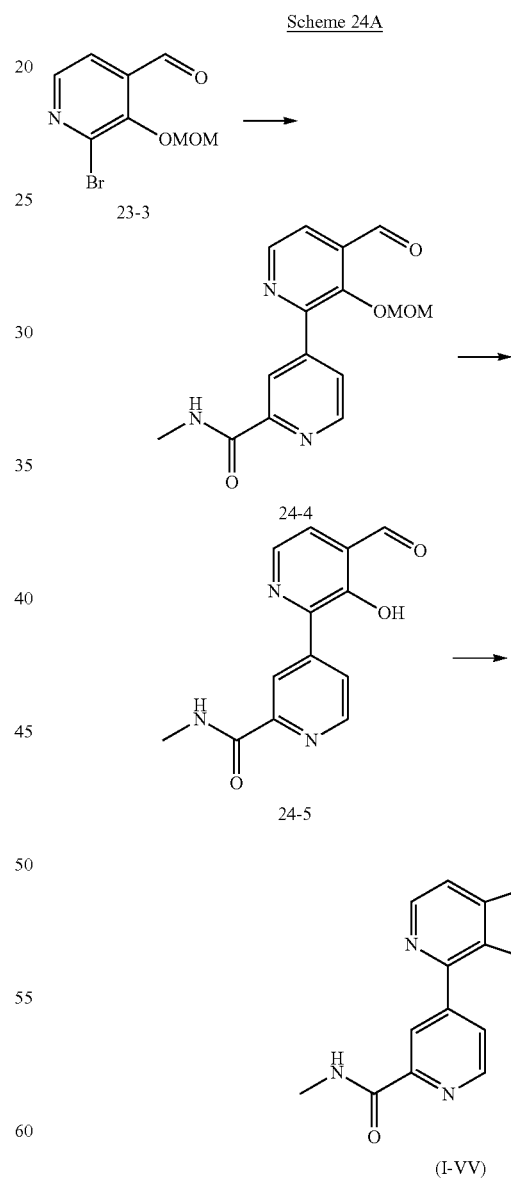

Scheme 24 depicts the synthesis of (I-UU). The compound BBBBB1 was coupled with a suitable substituted Scheme 24A depicts the synthesis of compound (I-VV). The compound 23-3 was coupled with N-methyl-4-(4,4,5,5-tetramethyl-1,3,2-dioxaborolan-2-yl)picolinamide under cross-coupling reaction conditions to provide 24-4. In one embodiment, the coupling reaction was done in presence of tripotassium phosphate, tricyclohexylphosphine and $Pd_2(dba)_3$ in dioxane. The compound 24-4 was deprotected in presence of a Lewis acid to provide 24-5. In one embodiment the acid was TFA. The compound 24-5 was treated with an amine ($R^5$—$NH_2$), a cyanide ion source and a Lewis acid in sealed tube containing $NH_4OAc$ buffer solution to provide the compound (I-VV). In one embodiment the cyanide ion source was TMSCN. In another embodiment the Lewis acid was TMSOTf.

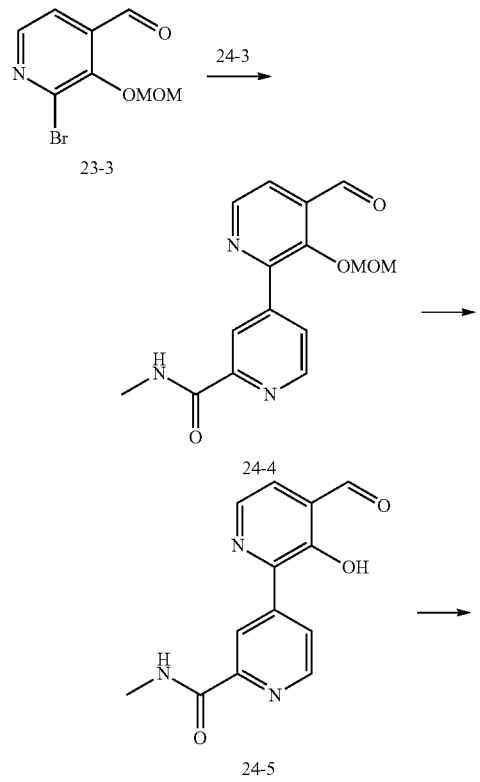

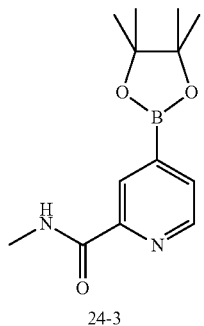

Scheme 24B depicts the synthesis of 4-(2-amino-3-((3-chloro-4-fluorophenyl)amino)furo[2,3-c]pyridin-7-yl)-N-methylpicolinamide 24-6. The commercially available 4-chloro-pyridine-2-carboxylic acid 24-1 was treated with thionyl chloride under refluxed to give intermediate 4-chloropicolinoyl chloride which in-situ reacted with methyl amine in THF to afforded amide 24-2. The compound 4-chloro-N-methylpicolinamide 24-2 was reacted with bis(pinacolato)diboron under palladium catalyst to give N-methyl-4-(4,4,5,5-tetramethyl-1,3,2-dioxaborolan-2-yl)picolinamide 24-3. The compound 24-3 was coupled with 2-bromo-3-(methoxymethoxy)isonicotinaldehyde 23-3 (prepared according to scheme 23B) in the presence of tripotassium phosphate, tricyclohexylphosphine and $Pd_2(dba)_3$ in dioxane to afford 4-formyl-3-(methoxymethoxy)-N-methyl [2,4'-bipyridine]-2'-carboxamide 24-4 which in turn underwent MOM-de-protection with TFA-DCM to form 4-formyl-3-hydroxy-N-methyl-[2,4'-bipyridine]-2'-carboxamide 24-5. The compound 24-5 was coupled with 3-chloro-4-fluoroaniline to form intermediate imine which was treated in-situ with TMSCN followed by TMSOTf in a sealed tube containing $NH_4OAc$ buffer solution to form cyclized product 4-(2-amino-3-((3-chloro-4-fluorophenyl)amino)furo[2,3-c]pyridin-7-yl)-N-methylpicolinamide 24-6 as a solid.

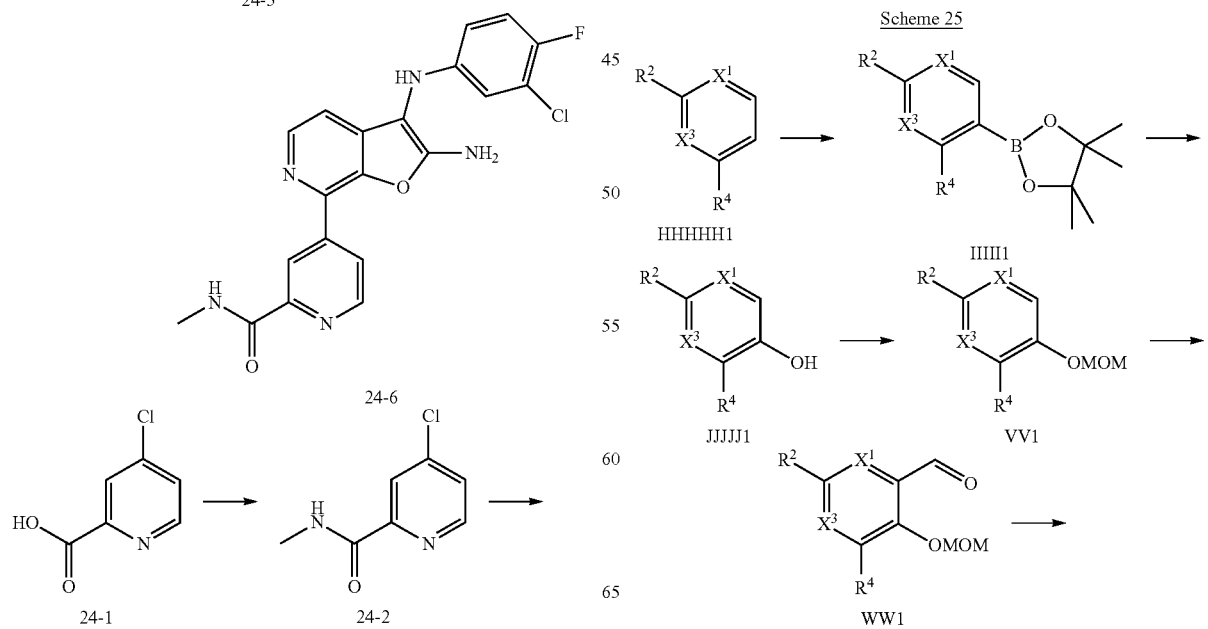

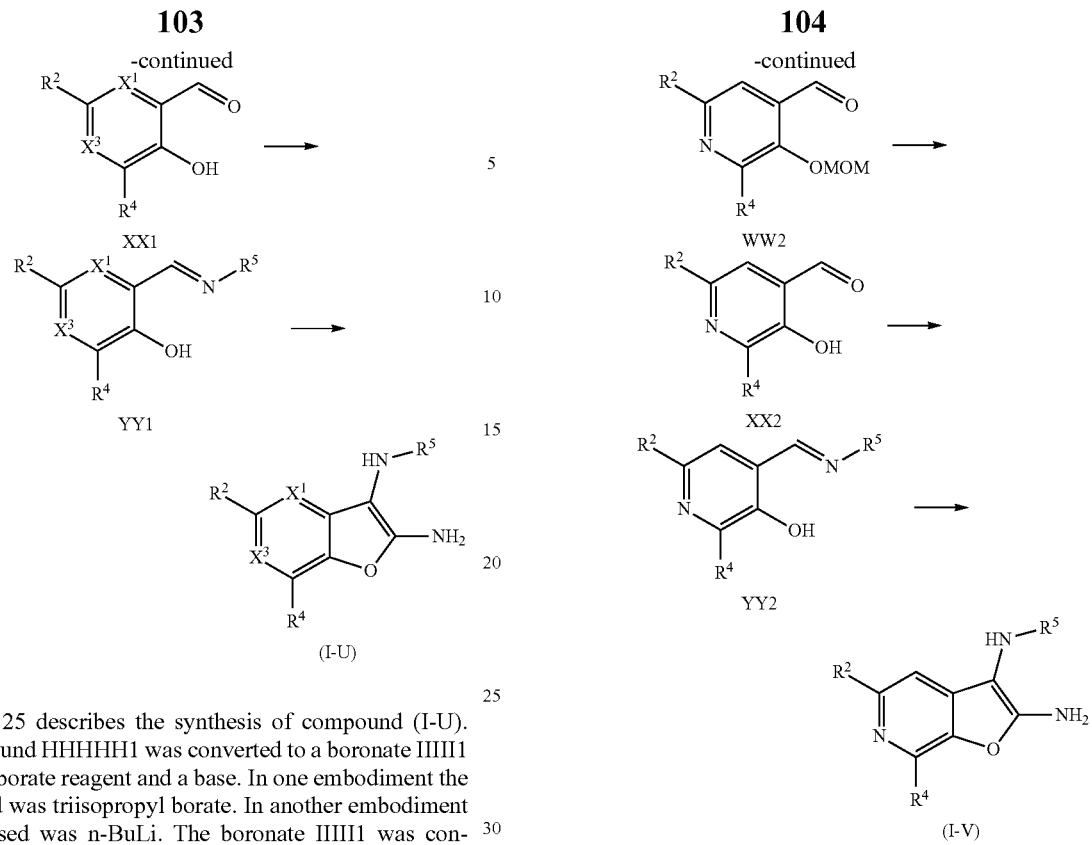

Scheme 25 describes the synthesis of compound (I-U). The compound HHHHH1 was converted to a boronate IIIII1 by using a borate reagent and a base. In one embodiment the borate used was triisopropyl borate. In another embodiment the base used was n-BuLi. The boronate IIIII1 was converted to hydroxyl compound JJJJJ1 in presence of an oxidizing reagent. In one embodiment the oxidizing reagent used was sodium perborate tetrahydrate in water. The resulting compound JJJJJ1 was forwarded to MOM protection or SEM protection using MOMCl or SEMCl respectively in the presence of a base to provide the product VV1. The compound VV1 was formylated with DMF or N-formylpiperidine in the presence of base like n-BuLi, s-BuLi, LDA, or LTMP at −78° C. to give product WW1. The compound WW1 was deprotected in presence of a Lewis acid to provide XX1. In one embodiment the acid was TFA. The compound XX1 was treated with an amine ($R^5NH_2$) to provide the imine YY1. The imine YY1 was treated with a cyanide ion source and a Lewis acid to provide the compound (I-U). In one embodiment the cyanide ion source was TMSCN. In another embodiment the Lewis acid was TMSOTf.

Scheme 25A describes the synthesis of compound (I-V). The compound HHHHH2 was converted to a boronate IIIII2 by using a borate reagent and a base. In one embodiment the borate used was triisopropyl borate. In another embodiment the base used was n-BuLi. The boronate IIIII2 was converted to hydroxyl compound JJJJJ2 in presence of an oxidizing reagent. In one embodiment the oxidizing reagent used was sodium perborate tetrahydrate in water. The resulting compound JJJJJ2 was forwarded to MOM protection or SEM protection using MOMCl or SEMCl respectively in the presence of a base to provide the product VV2. The compound VV2 was formylated with DMF or N-formylpiperidine in the presence of base like n-BuLi, s-BuLi, LDA, or LTMP at −78° C. to give product WW2. The compound WW2 was deprotected in presence of a Lewis acid to provide XX2. In one embodiment the acid was TFA. The compound XX2 was treated with an amine ($R^5NH_2$) to provide the imine YY2. The imine YY2 was treated with a cyanide ion source and a Lewis acid to provide the compound (I-V). In one embodiment the cyanide ion source was TMSCN. In another embodiment the Lewis acid was TMSOTf.

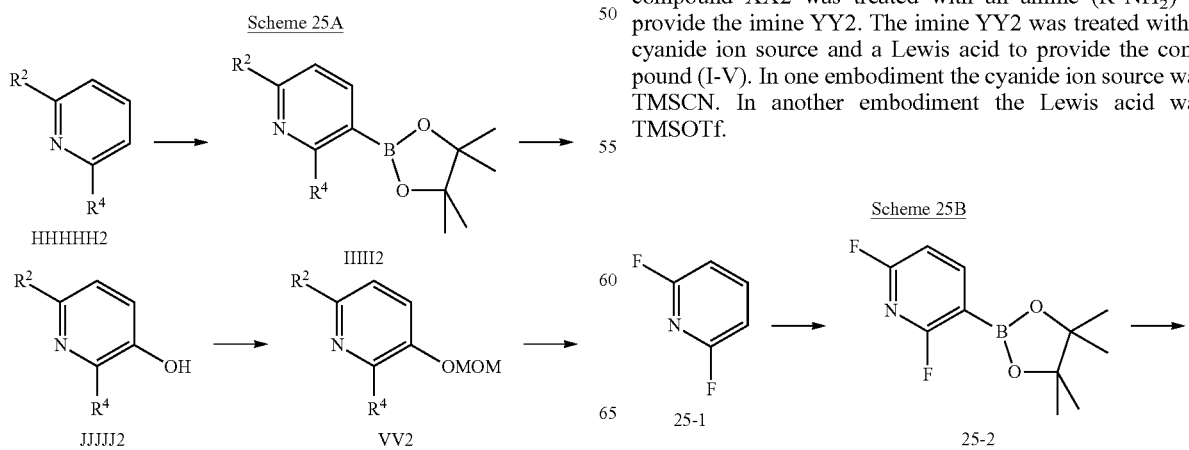

105

-continued

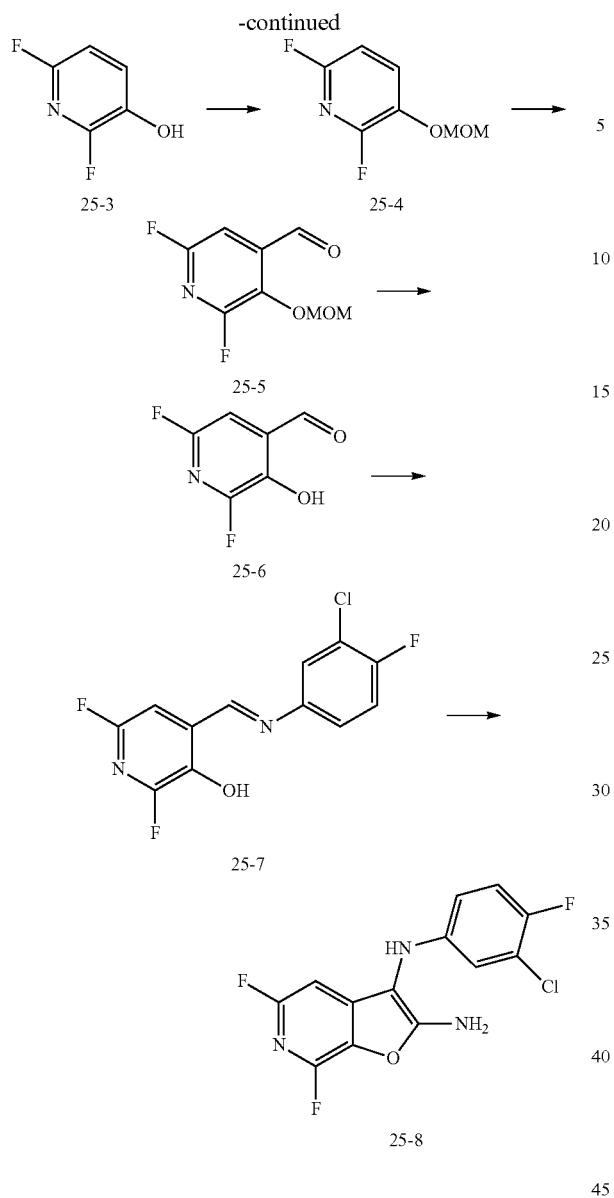

Scheme 25B describe the synthesis of N³-(3-chloro-4-fluorophenyl)-5,7-difluorofuro[2,3-c]pyridine-2,3-diamine 25-8. 2,6-Difluoropyridine 25-1 was treated with triisopropyl borate in the presence of n-BuLi to give 2,6-difluoro-3-(4,4,5,5-tetramethyl-1,3,2-dioxaborolan-2-yl)pyridine 25-2 which was further reacted with sodium perborate tetrahydrate in water to yield 2.6-difluoro-3-hydroxypyridine 25-3. The compound 25-3 underwent MOM protection with MOMCl in the presence of diisopropylamine to give MOM-protected compound 25-4. The 2,6-difluoro-3-(methoxymethoxy)pyridine 25-4 was formylated with DMF in the presence of n-BuLi to afford 2,6-difluoro-3-(methoxymethoxy)isonicotinaldehyde 25-5 which was deprotected by TFA-DCM to give 25-6. The 2,6-difluoro-3-hydroxyisonicotinaldehyde 25-6 was coupled with 3-chloro-4-fluoroaniline to give imine 25-7 which was further treated with TMSCN and TMSOTf resulting into the formation of first Strecker product which in-situ underwent intramolecular cyclization to afford N³-(3-chloro-4-fluorophenyl)-5,7-difluorofuro[2,3-c]pyridine-2,3-diamine 25-8 as brown solid.

106

Scheme 26

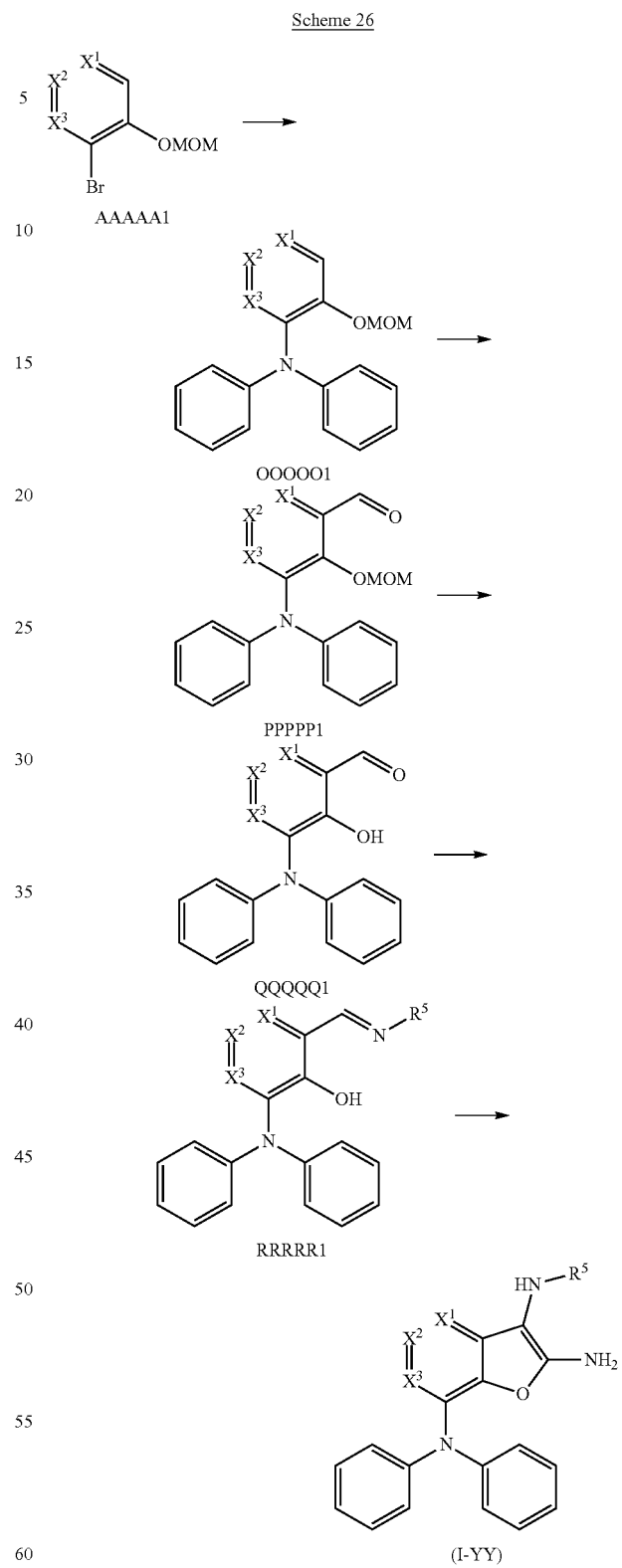

Scheme 26 depicts the synthesis of compound (I-YY). The compound AAAAA1 was converted to OOOOO1 by using an alkyl or aromatic amine under cross-coupling reaction conditions. In one embodiment Buchwald-Hartwig amination reaction was performed as cross-coupling reaction. In another embodiment diphenylamine was used an aryl amine. In yet another embodiment the catalysts used were Pd$_2$(dba)$_3$ and Dppf. The compound OOOOO1 underwent formylation with DMF or N-formylpiperidine in the presence of base like n-BuLi, s-BuLi, LDA, or LTMP at −78° C. to give product PPPPP1. The compound PPPPP1 was deprotected in presence of a Lewis acid to provide QQQQQ1. In one embodiment the acid was TFA. The compound QQQQQ1 was treated with an amine (R$^5$—NH$_2$) to provide imine RRRRR1. The amine RRRRR1 was treated with a cyanide ion source and a Lewis acid to provide the compound (I-YY). In one embodiment the cyanide ion source was TMSCN. In another embodiment the Lewis acid was TMSOTf.

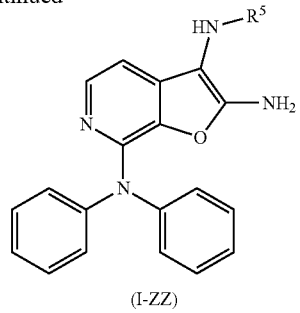

(I-ZZ)

Scheme 26A depicts the synthesis of compound (I-ZZ). The Buchwald-Hartwig amination reaction was done on 2-bromo-3-(methoxymethoxy)pyridine 23-2 with diphenyl amine in the presence of Pd$_2$(dba)$_3$ and Dppf to afford 3-(methoxymethoxy)-N,N-diphenylpyridin-2-amine 26-1. The compound 26-1 was formylated with DMF in the presence of n-BuLi to give 2-(diphenylamino)-3-(methoxymethoxy)isonicotinaldehyde 26-2 which underwent MOM-deprotection to yielded 2-(diphenylamino)-3-hydroxyisonicotinaldehyde 26-3. The compound 26-3 was treated with amine (R$^5$—NH$_2$) to provide imine RRRRR2. The amine RRRRR2 was treated with a cyanide ion source and a Lewis acid to provide the compound (I-ZZ). In one embodiment the cyanide ion source was TMSCN. In another embodiment the Lewis acid was TMSOTf.

Scheme 26A

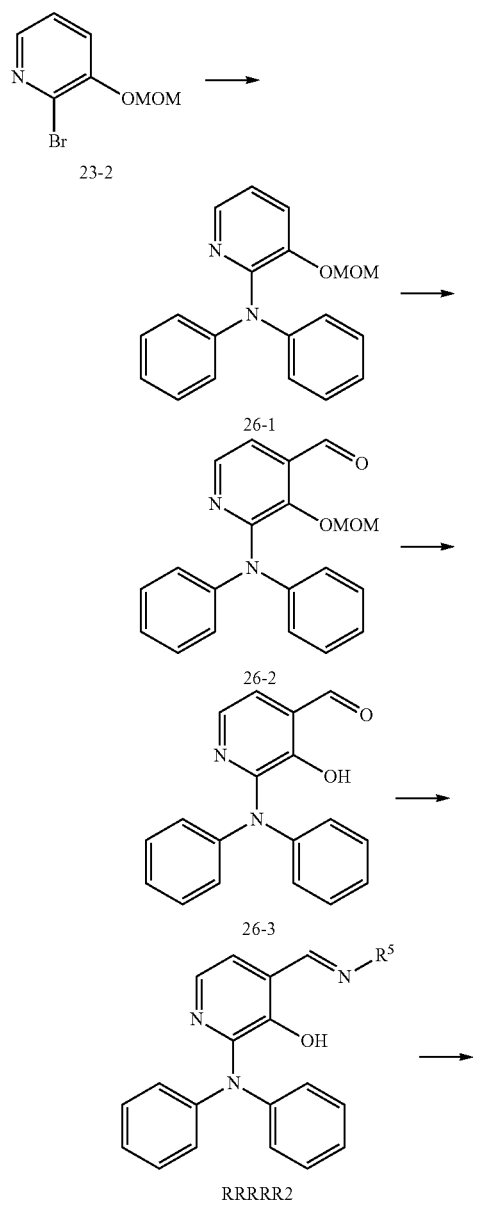

Scheme 26B

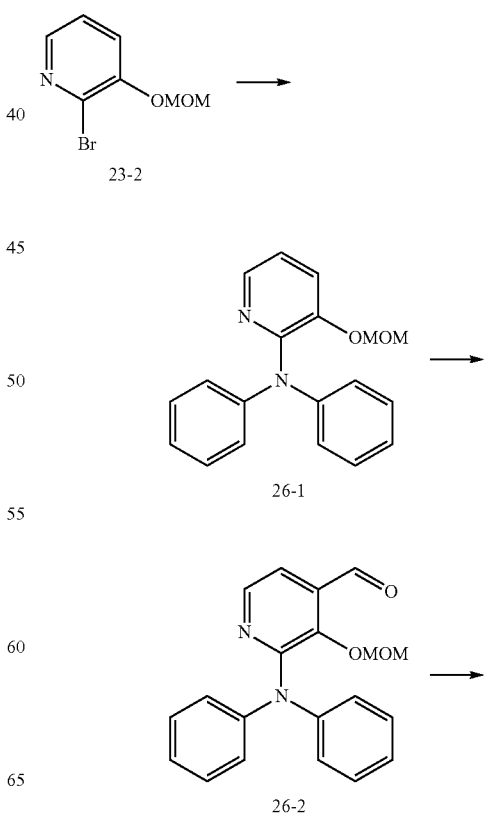

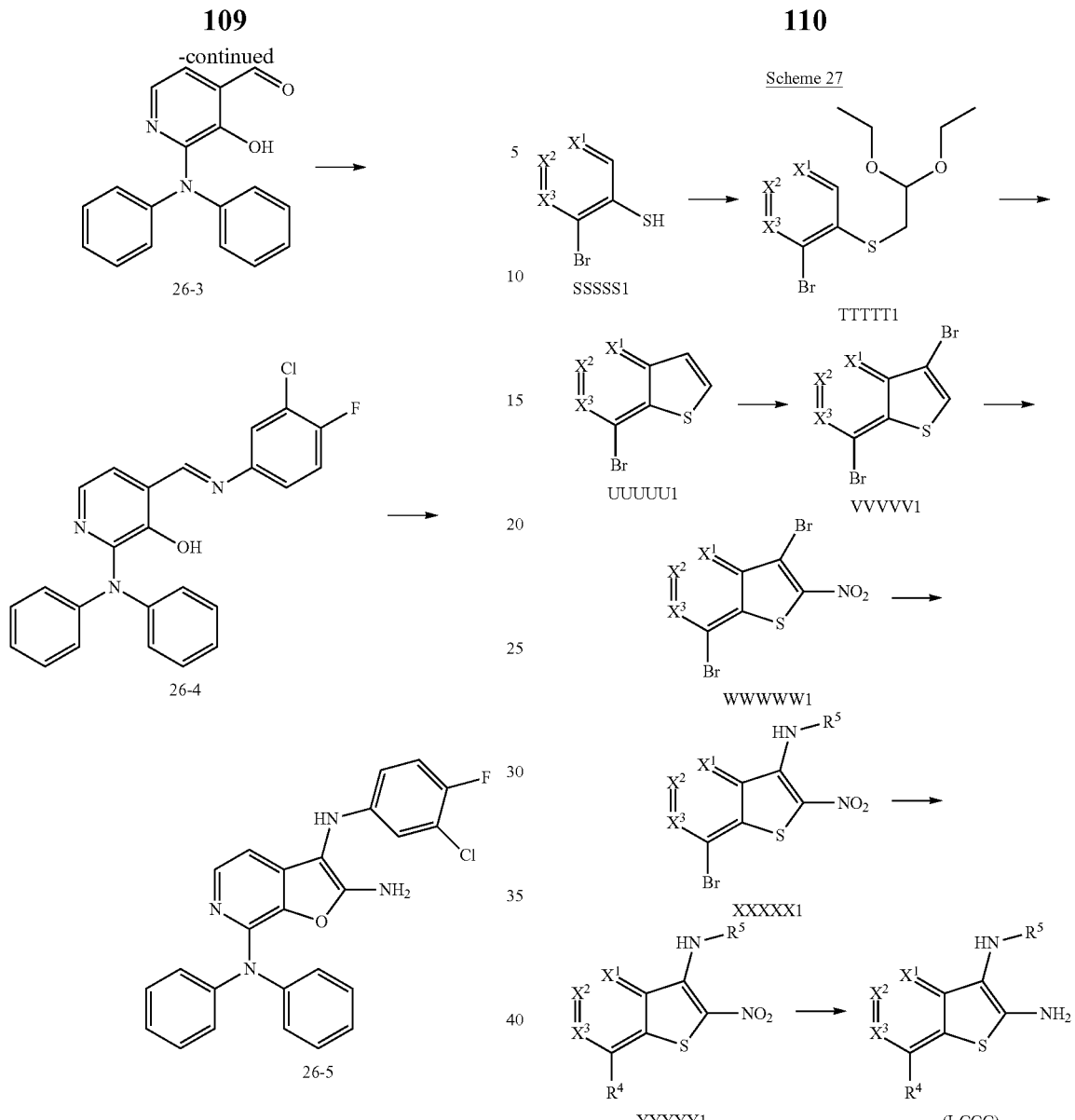

Scheme 26B depicts the synthesis of $N^3$-(3-chloro-4-fluorophenyl)-$N^7,N^7$-diphenylfuro[2,3-c]pyridine-2,3,7-triamine 26-5. The Buchwald-Hartwig amination reaction was performed on 2-bromo-3-(methoxymethoxy)pyridine 23-2 with diphenylamine in the presence of $Pd_2(dba)_3$ and Dppf to afford 3-(methoxymethoxy)-N,N-diphenylpyridin-2-amine 26-1. The compound 26-1 was formylated with DMF in the presence of n-BuLi to give 2-(diphenylamino)-3-(methoxymethoxy)isonicotinaldehyde 26-2. Compound 26-2h underwent MOM-deprotection to yield 2-(diphenylamino)-3-hydroxyisonicotinaldehyde 26-3. The compound 26-3 was coupled with 3-chloro-4-fluoroaniline to form an imine 26-4. The immune 26-4 was further treated with TMSCN in TFE resulting into the formation of a first Strecker product which underwent in-situ intramolecular cyclization to form $N^3$-(3-chloro-4-fluorophenyl)-$N^7,N^7$-diphenylfuro[2,3-c]pyridine-2,3,7-triamine 26-5 as a solid.

Scheme 27 depicts the preparation of compound (I-CCC). The starting compound SSSSS1 was treated with a base and then allowed to react with a suitable alkyl halide to form a compound TTTTT1. The compound TTTTT1 was converted to a compound UUUUU1 under acid catalysis. In one embodiment, PPA in chlorobenzene was used as an acid catalyst. The compound UUUUU1 was halogenated to provide a compound VVVVV1. In one embodiment, NBS, in a mixture chloroform and acetic acid, was used for halogenation. The compound VVVVV1 was nitrated to provide a nitro compound WWWWW1. In one embodiment, nitric acid was used for nitration. The compound WWWWW1 was treated with an amine ($R^5$—$NH_2$) to provide a compound XXXXX1. The compound XXXXX1 was reacted with an aryl or heteroaryl boronic acid or ester in a cross-coupling reaction to provide a compound YYYYY1. In one embodiment, a mixture of DMF and water was used a solvent. In another embodiment, $Pd(PPh_3)_4$ and an inorganic base were used as catalysts. In another embodiment, the inorganic base was any of $K_2CO_3$, $KHCO_3$, or CsF or $K_3PO_4$. In yet another embodiment, the boronic acid was 2-methyl-4-pyridinylboronic acid. Next, nitro compound YYYYY1 was reduced to an amine to provide a compound (I-CCC). In one embodiment, Pd/C and hydrogen were used for reduction.

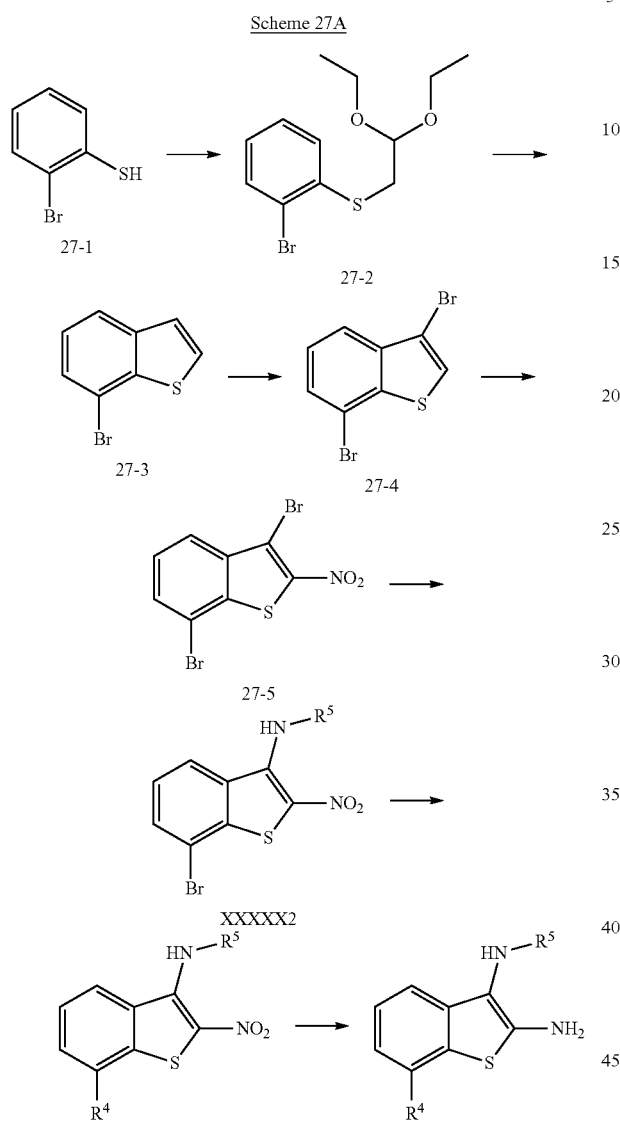

Pd(PPh$_3$)$_4$ and an inorganic base were used as catalysts. In another embodiment, the inorganic base was any one of K$_2$CO$_3$, KHCO$_3$, CsF or K$_3$PO$_4$. In yet another embodiment, the boronic acid was 2-methyl-4-pyridinylboronic acid. Next, nitro compound YYYYY2 was reduced to a amine to provide a compound (I-DDD). In one embodiment, Pd/C and hydrogen were used for reduction.

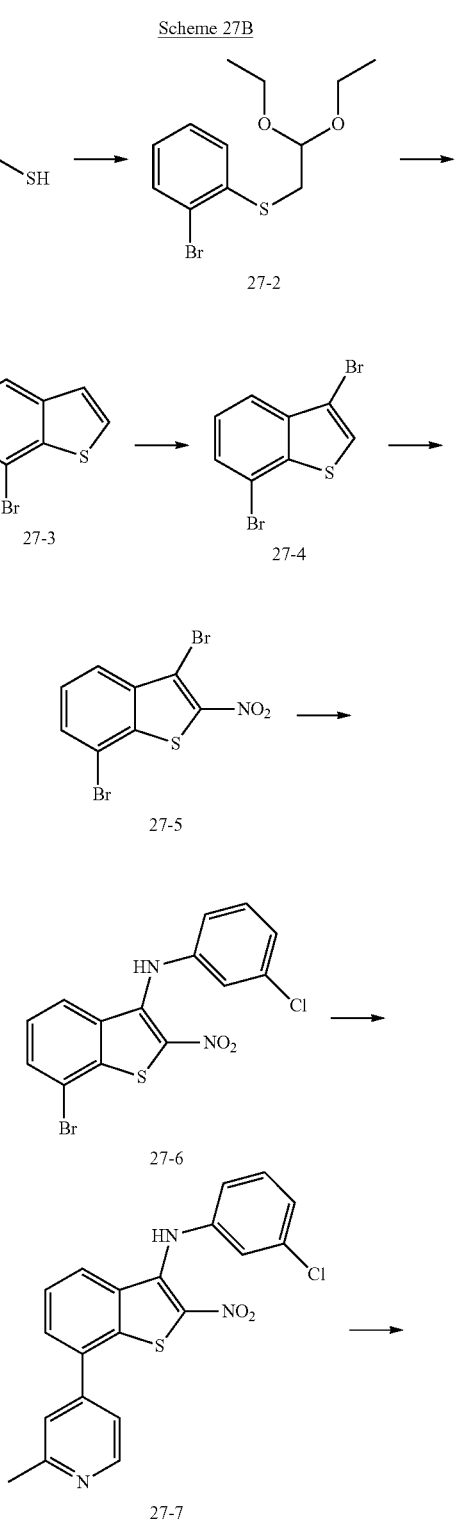

Scheme 27A describes the preparation of compound (I-DDD). Compound 2-bromothiophenol was treated with potassium carbonate in acetone and then allowed to react with bromoacetaldehyde diethylacetal to form (2-bromophenyl)(2,2-diethoxyethyl)sulfane 27-2. The compound 27-2 was allowed to react with PPA in chlorobenzene to provide 7-bromobenzo[b]thiophene 27-3. Compound 27-3 in turn was brominated to form 3,7-dibromobenzo[b]thiophene 27-4 by using NBS in a mixture chloroform and acetic acid. This was followed by nitration of 27-4 to provide 3,7-dibromo-2-nitrobenzo[b]thiophene (27-5). The compound 27-5 was treated with an amine (R$^5$—NH$_2$) to provide a compound XXXXX2. The compound XXXXX2 was reacted with an optionally substituted aryl or heteroaryl boronic acid or ester in a cross-coupling reaction to provide a compound YYYYY2. In one embodiment, a mixture of DMF and water was used a solvent. In another embodiment,

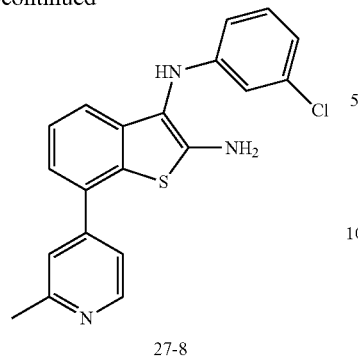

27-8

Scheme 27B describes the preparation of compound N³-(3-chlorophenyl)-7-(2-methylpyridin-4-yl)benzo[b]thiophene-2,3-diamine 27-8. 2-bromothiophenol was treated with potassium carbonate in acetone and then allowed to react with bromoacetaldehyde diethylacetal to form (2-bromophenyl)(2,2-diethoxyethyl)sulfane 27-2. The compound 27-2 was allowed to react with PPA in chlorobenzene to form 7-bromobenzo[b]thiophene 27-3. The compound 27-3 in turn was brominated to form 3,7-dibromobenzo[b]thiophene 27-4 by using NBS in a mixture chloroform and acetic acid. This was followed by nitration of compound 27-4 to provide 3,7-dibromo-2-nitrobenzo[b]thiophene 27-5. The compound 27-5 was treated with 3-chloroaniline in DMF to provide 7-bromo-N-(3-chlorophenyl)-2-nitrobenzo[b]thiophen-3-amine 27-6. The compound 27-6 was reacted with 2-methyl-4-pyridinylboronic acid in a mixture of DMF and water in the presence of $K_3PO_4$ and $Pd(PPh_3)_4$ to form N-(3-chlorophenyl)-7-(2-methylpyridin-4-yl)-2-nitrobenzo[b]thiophen-3-amine 27-7. Next, nitro compound 27-7 was reduced to an amine by using Pd/C and hydrogen to form N³-(3-chlorophenyl)-7-(2-methylpyridin-4-yl)benzo[b]thiophene-2,3-diamine 27-8.

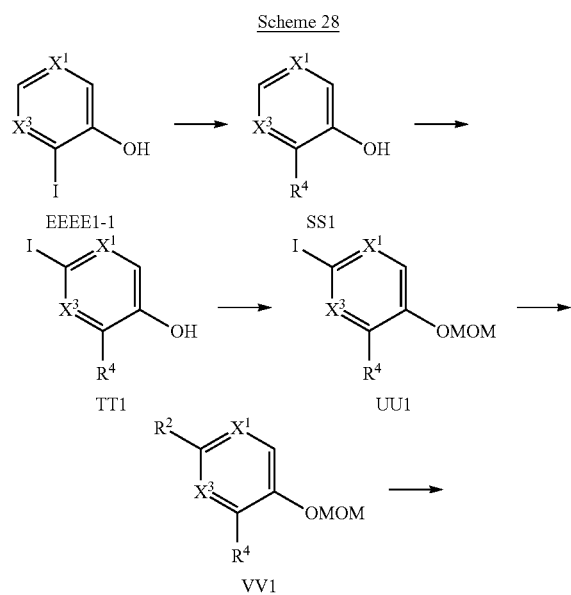

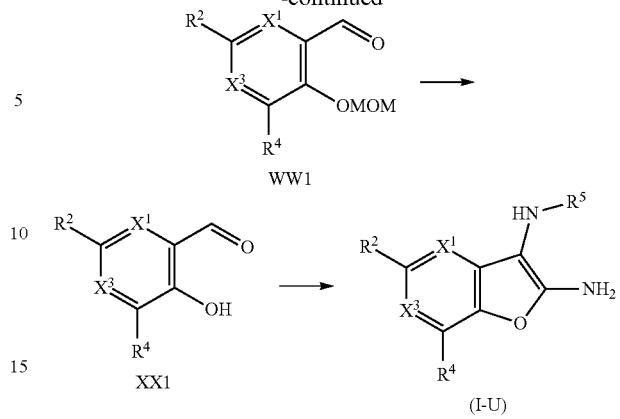

Scheme 28 depicts the synthesis of compound (I-U). Compound EEEE1-1 was coupled with arylboronic acid under Suzuki cross-coupling reaction condition to form compound SS1. In one embodiment, a mixture of DMF and water was used as a solvent. In another embodiment, the solvent was 1,4-dioxane. In yet another embodiment, $Pd(PPh_3)_4$ and an inorganic base were used as catalysts. In still another embodiment, the catalyst was $Pd_2(dba)_3$. In a further embodiment, the inorganic base was any of $K_2CO_3$, $KHCO_3$, CsF or $K_3PO_4$. In yet another embodiment, the arylboronic acid was phenylboronic acid. The compound SS1 was treated with iodine in basic medium to provide compound TT1. In one embodiment, the base was $Na_2CO_3$. The compound TT1 was MOM-protected with MOMCl in the presence of a base to form a MOM-protected compound UU1. In one embodiment, the base was potassium tert-butoxide. The compound UU1 was added to a freshly prepared sodium alkoxide or aryloxide solution. Next, to the resulting mixture was addedCuBr to form a compound VV1. In one embodiment, the sodium aryloxide was sodium phenoxide. The compound VV1 was formylated with DMF in the presence of any on or more or n-BuLi, s-BuLi, LDA, and TMEDA to form compound WW1. Compound WW1 next under went deprotection under acidic conditions to yield a compound XX1. In one embodiment, the acid was HCl. In another embodiment the acid was TFA. Compound XX1 was first coupled with an amine ($R^5$—$NH_2$) and then treated with trialkylsilyl cyanide. The resulting mixture was next treated with a Lewis acid to form compound (I-U) as a solid. In one embodiment, the cyanide source was TMSCN. In another embodiment the cyanide source was NaCN. In another embodiment, the Lewis acid was any of TMSOTf, $Sc(OTO_3$, $Fe(OTf)_2$, $Ni(OTf)_2$ or $In(OTf)_3$.

Scheme 28A

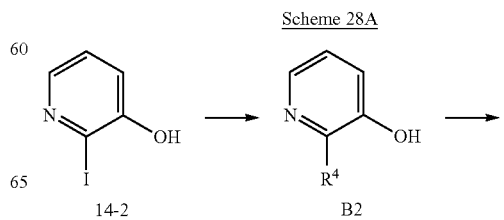

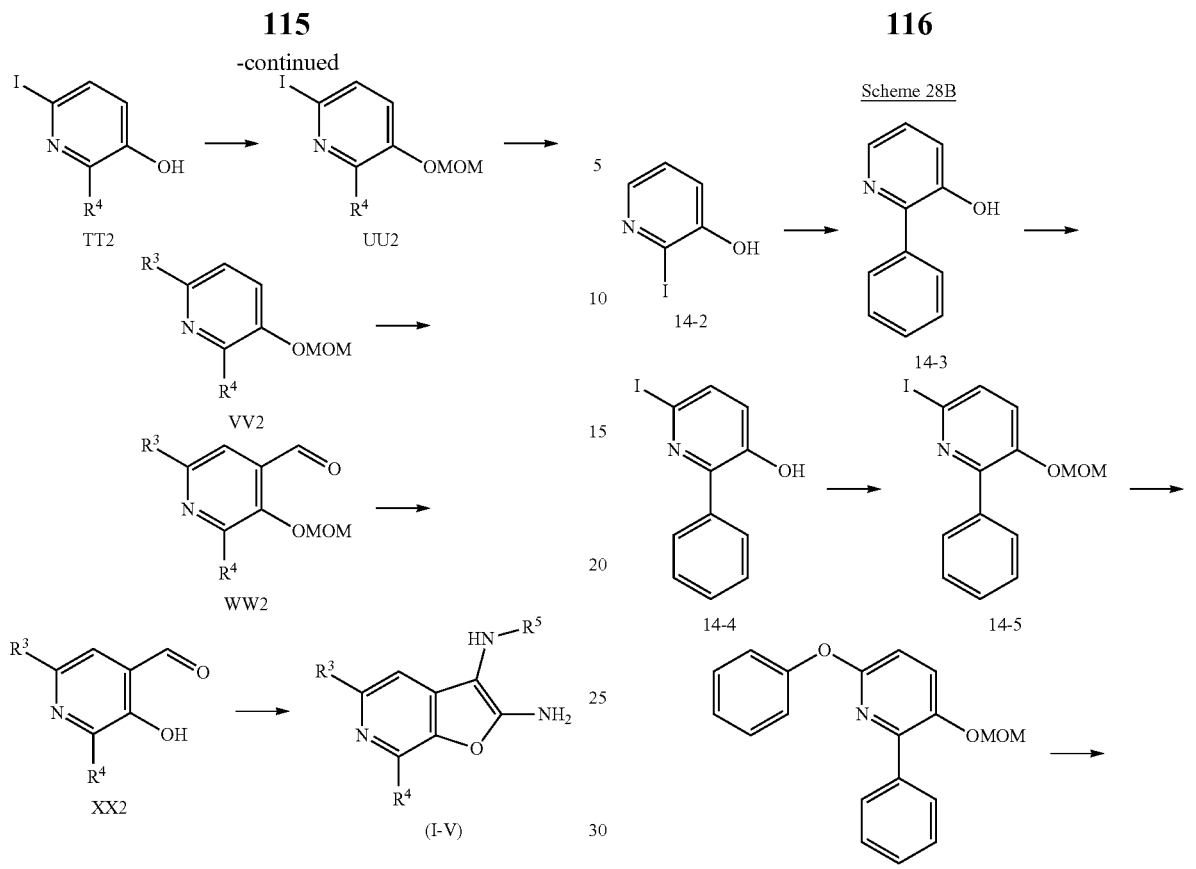

Scheme 28A describes the synthesis of compound (I-V). 2-Iodo-3-hydroxypyridine 14-2 was coupled with arylboronic acid under Suzuki cross coupling reaction condition to form compound B2. In one embodiment, a mixture of DMF and water was used a solvent. In another embodiment, Pd(PPh$_3$)$_4$ and an inorganic base were used as catalysts. In still another embodiment, the inorganic base was any of K$_2$CO$_3$, KHCO$_3$, CsF, or K$_3$PO$_4$. In yet another embodiment, the arylboronic acid was phenylboronic acid. Compound B2 was treated with iodine in basic medium to provide compound TT2. In one embodiment, the base used in the basic medium was Na$_2$CO$_3$. The compound TT2 was MOM-protected with MOMCl in the presence of potassium tert-butoxide to form a MOM-protected compound UU2. The compound UU2 was added to freshly prepared sodium aryloxide solution. Next, to the reaction mixture was added CuBr to form a compound VV2. In one embodiment, the sodium aryloxide was sodium phenoxide. The compound VV2 was formylated with DMF in the presence of any of n-BuLi, s-BuLi, or LDA, and TMEDA to form compound WW2. Next, compound WW2 underwent deprotection under acidic conditions to yield a compound XX2. In one embodiment, the acid used was HCl. The compound XX2 was coupled with an amine (R$^5$—NH$_2$) and then treated first with trialkylsilyl cyanide and then with a Lewis acid to form a compound (I-V) as a solid. In one embodiment, the cyanide source was TMSCN. In another embodiment, the lewis acid was TMSOTf.

Scheme 28B describes the synthesis of compound $N^3$-(3-chloro-4-fluorophenyl)-5-phenoxy-7-phenylfuro[2,3-c]pyridine-2,3-diamine 28-4.2-Iodo-3-hydroxypyridine 14-2 was coupled with phenylboronic acid under Suzuki cross-coupling reaction to form 2-Phenyl-3-hydroxypyridine 14-3. Compound 14-3 was treated with iodine in basic medium to provide 6-iodo-2-phenylpyridin-3-ol 14-4 which underwent MOM-protection with MOMCl in the presence of potassium tert-butoxide to form a MOM-protected compound 6-iodo-3-(methoxymethoxy)-2-phenylpyridine 14-5. The compound 14-5 was added to freshly prepared sodium phenoxide solution followed by the addition of CuBr. The resulting reaction mixture was refluxed for 16 h forming 3-(methoxymethoxy)-6-phenoxy-2-phenylpyridine 28-1. The compound 28-1 was formylated with DMF in the presence of n-BuLi and TMEDA to form 3-(methoxymethoxy)-6-phenoxy-2-phenylisonicotinaldehyde 28-2. Compound 28-2 underwent deprotection to yield 3-hydroxy-6-phenoxy-2-phenylisonicotinaldehyde 28-3. The compound 28-3 was first coupled with 4-fluoro-3-chloroaniline and then treated with TMSCN. The resulting mixture was next treated with TMSOTf resulting in the formation of $N^3$-(3-chloro-4-fluorophenyl)-5-phenoxy-7-phenylfuro[2,3-c]pyridine-2,3-diamine 28-4 as a solid.

Accordingly, the invention also relates to a method of preparing a compound of formula (I-C), said method comprising:

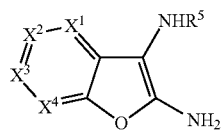

(I-C)

wherein:
$X^1$ is $CR^1$, N, or NO;
$X^2$ is $CR^2$, N, or NO;
$X^3$ is $CR^3$, N, or NO;
$X^4$ is $CR^4$, N, or NO; and
$R^5$ is selected from the group consisting of H, optionally substituted $C_1$-$C_6$ alkyl, optionally substituted mono or bicyclic $C_6$-$C_{14}$ aryl, optionally substituted mono or bicyclic heteroaryl, optionally substituted (aryl)alkyl, optionally substituted mono or bicyclic cycloalkyl, optionally substituted mono or bicyclic heterocyclyl, $C_1$-$C_6$haloalkyl, optionally substituted heterocyclyl(alkyl), optionally substituted heteroaryl(alkyl), hydroxyalkyl, and perfluoroalkyl;
(i) reacting

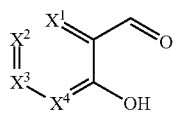

with an amine ($R^5$—$NH_2$);
(ii) reacting the product of step (i) with a cyanide salt; and
(iii) reacting the product of step (ii) with a Lewis acid.

In a further embodiment, the Lewis acid is trimethylsilyl trifluoromethanesulfonate, Sc(OTf)$_3$, Fe(OTf)$_2$, Ni(OTf)$_2$, or In(OTf)$_3$. In a still further embodiment, the cyanide salt is selected from group consisting of a trialkyl silyl cyanide, NaCN, KCN, and Zn(CN)$_2$. In yet another embodiment, the trialkyl silyl cyanide is TMSCN. In a still further embodiment, the reaction of step (iii) is performed in the presence of a buffer solution. In one embodiment, the buffer solution is ammonium acetate buffer.

Also falling within the scope of the invention are compounds that are obtainable by the practice of methods disclosed herein. In an embodiment, the invention relates to a compound obtainable by a method of preparing a compound of formula (I-C), said method comprising:

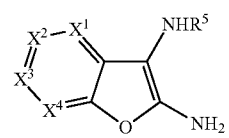

(I-C)

wherein:
$X^1$ is $CR^1$, N, or NO;
$X^2$ is $CR^2$, N, or NO;
$X^3$ is $CR^3$, N, or NO;
$X^4$ is $CR^4$, N, or NO; and
$R^5$ is selected from the group consisting of H, optionally substituted $C_1$-$C_6$ alkyl, optionally substituted mono or bicyclic $C_6$-$C_{14}$ aryl, optionally substituted mono or bicyclic heteroaryl, optionally substituted (aryl)alkyl, optionally substituted mono or bicyclic cycloalkyl, optionally substituted mono or bicyclic heterocyclyl, $C_1$-$C_6$ haloalkyl, optionally substituted heterocyclyl (alkyl), optionally substituted heteroaryl(alkyl), hydroxyalkyl, and perfluoroalkyl;
(i) reacting

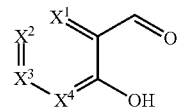

with an amine ($R^5$—$NH_2$);
(ii) reacting the product of step (i) with a cyanide salt; and
(iii) reacting the product of step (ii) with a Lewis acid.

In a further embodiment, the Lewis acid is trimethylsilyl trifluoromethanesulfonate, Sc(OTf)$_3$, Fe(OTf)$_2$, Ni(OTf)$_2$, or In(OTf)$_3$. In a still further embodiment, the cyanide salt is selected from group consisting of a trialkyl silyl cyanide, NaCN, KCN, and Zn(CN)$_2$. In yet another embodiment, the trialkyl silyl cyanide is TMSCN. In a still further embodiment, the reaction of step (iii) is performed in the presence of a buffer solution. In one embodiment, the buffer solution is ammonium acetate buffer.

In still another embodiment, invention relates to intermediate compounds that are products of one or more of steps (i) (iii) of the method of preparing a compound of formula (I-C). In one embodiment, the product or intermediate of step (i) is an imine.

Pharmaceutical Compositions

Pharmaceutical compositions useful herein contain a compound of formula (I) or metabolites thereof, or prodrugs thereof ("compounds of the invention" or "compounds") in a pharmaceutically acceptable carrier optionally with other pharmaceutically inert or inactive ingredients. In another embodiment, a compound of formulae (I)-(IV) is present in a single composition. In another embodiment, a metabolite of a compound of formulae (I)-(IV) is present in a single composition. In yet another embodiment, a prodrug of a compound of formula (I), including without limitation, a compound having any one of the formulae (II)-(IV) is present in a single composition. In a further embodiment, a compound of formula (I) or a metabolite thereof, or a pharmaceutically accetable salt or prodrug thereof is combined with one or more excipients and/or one or more of other therapeutic agents as described below.

Pharmaceutical compositions comprise an amount of a compound of formula (I) or a metabolite thereof, or prodrug thereof, or pharmaceutically acceptable salt thereof that is effective for regulating one or more of indoleamine 2,3-dioxygenase-1 or indoleamine 2,3-dioxygense-2 or tryptophan 2,3-dioxygenase enzymes. Pharmaceutical compositions comprise an amount of compound of formula (I) or a metabolite thereof, or a pharmaceutical salt or prodrug thereof that is effective for regulating the kynurenine pathway. The pharmaceutical compositions useful herein comprise an amount of a compound of formula (I) or a metabolite thereof, or prodrug thereof, or a pharmaceutically acceptable salt thereof that is effective for regulating the kynurenine pathway by inhibiting one or more of indoleamine 2,3-dioxygenase-1 or indoleamine 2,3-dioxygenase-2 or tryptophan 2,3-dioxygenase enzymes in a subject. The pharmaceutical compositions comprise an amount of a compound of formula (I) or a metabolite thereof, or a pharmaceutically acceptable salt or prodrug thereof that is effective for regulating one or more of indoleamine 2,3-dioxygenase-1 or indoleamine 2,3-dioxygenase-2 or tryptophan 2,3-dioxygenase enzyme in a subject. In one aspect, the pharmaceutical compositions comprise an amount of a compound or a metabolite thereof, or a pharmaceutically acceptable salt or prodrug thereof that is effective for reducing kynurenine pathway metabolites and/or altering (for example increasing) tryptophan levels and/or reducing kynurenine/tryptophan ratio in a subject. The pharmaceutical compositions comprise an amount of a compound of Formula (I) or a metabolite thereof, or a pharmaceutically acceptable salt or prodrug thereof that is effective for reducing or eliminating autoimmune antibody in a subject. In another aspect, pharmaceutical compositions comprise an amount of a compound of formula (I) or a metabolite thereof, or a pharmaceutically acceptable salt or prodrug thereof that is effective for reducing immune suppression in a subject.

Specifically, the dosage of the compound of formula (I) or a metabolite thereof, or a pharmaceutically acceptable salt or prodrug thereof to achieve a therapeutic effect will depend on the formulation, age, weight and sex of the patient and route and frequency of delivery. It is also contemplated that the treatment and dosage of the compound of formula (I) or a metabolite thereof, or a pharmaceutically acceptable salt or prodrug thereof may be administered in unit dosage form and that one skilled in the art would adjust the unit dosage form accordingly to reflect the relative level of activity. The decision as to the particular dosage to be employed (and the number of times to be administered per day) is within the discretion of the ordinarily-skilled physician, and may be varied by titration of the dosage to the particular circumstances to produce the desired therapeutic effect. In one embodiment, the therapeutically effective amount is about 0.01 mg/kg to 10 mg/kg body weight. In another embodiment, the therapeutically effective amount is less than about 5 g/kg, about 500 mg/kg, about 400 mg/kg, about 300 mg/kg, about 200 mg/kg, about 100 mg/kg, about 50 mg/kg, about 25 mg/kg, about 10 mg/kg, about 1 mg/kg, about 0.5 mg/kg, about 0.25 mg/kg, about 0.1 mg/kg, about 100 µg/kg, about 75 µg/kg, about 50 µg/kg, about 25 µg/kg, about 10 µg/kg, or about 1 µg/kg. However, the therapeutically effective amount of the compound of formula (I) or a metabolite thereof, or a pharmaceutically acceptable salt or prodrug thereof can be determined by the attending physician and depends on the condition or disease treated, the compound administered, the route and frequency of delivery, the age, weight, severity of the patient's symptoms and response pattern of the patient.

The therapeutically effective amounts may be provided on regular schedule, i.e., daily, weekly, monthly, or yearly basis or on an irregular schedule with varying administration days, weeks, months, etc. Alternatively, the therapeutically effective amount to be administered may vary. In one embodiment, the therapeutically effective amount for the first dose is higher than the therapeutically effective amount for one or more of the subsequent doses. In another embodiment, the therapeutically effective amount for the first dose is lower than the therapeutically effective amount for one or more of the subsequent doses. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, about every two months, about every four months, about every six months, about every 9 months, and about every year. The number and frequency of dosages corresponding to a completed course of therapy will be determined according to the judgment of a health-care practitioner. The therapeutically effective amounts described herein refer to total amounts administered for a given time period; that is, if more than one compound of formula (I) or a metabolite thereof, or prodrug thereof, or a pharmaceutically acceptable salt thereof is administered, the therapeutically effective amounts correspond to the total amount administered.

The pharmaceutical compositions containing a compound of formula (I) may be formulated neat or with one or more pharmaceutical carriers for administration. The amount of the pharmaceutical carrier(s) is determined by the solubility and chemical nature of the compound of formula (I) or a metabolite thereof, or prodrug thereof, chosen route of administration and standard pharmacological practice. The pharmaceutical carrier(s) may be solid or liquid and may incorporate both solid and liquid carriers. A variety of suitable liquid carriers are known and may be readily selected by one of skill in the art. Such carriers may include, for example, DMSO, saline, buffered saline, hydroxypropylcyclodextrin, and mixtures thereof. Similarly, a variety of solid carriers and excipients are known to those of skill in the art. The compounds of formula (I) may be administered by any route, taking into consideration the specific condition or disease for which it has been selected. The compounds of formula (I) or a metabolite thereof, or prodrug thereof may, be delivered orally, by injection, inhalation (including orally, intranasally and intratracheally), ocularly, transdermally, intravascularly, subcutaneously, intramuscularly, sublingually, intracranially, epidurally, rectally, and vaginally, among others.

Although the compound of formula (I) or a metabolite thereof, or a pharmaceutically salt thereof or prodrug thereof may be administered alone, it may also be administered in the presence of one or more pharmaceutical carriers that are physiologically compatible. The carriers may be in dry or liquid form and must be pharmaceutically acceptable. Liquid pharmaceutical compositions are typically sterile solutions or suspensions. When liquid carriers are utilized for parenteral administration, they are desirably sterile liquids. Liquid carriers are typically utilized in preparing solutions, suspensions, emulsions, syrups and elixirs. In one embodiment, the compound of formula (I) or a metabolite thereof, or a pharmaceutically salt thereof or prodrug thereof is dissolved a liquid carrier. In another embodiment, the compound of formula (I) or a metabolite thereof, or a pharmaceutically salt thereof or prodrug thereof is suspended in a liquid carrier. One of skill in the art of formulations would be able to select a suitable liquid carrier, depending on the route of administration. The compound of formula (I) or a metabolite thereof, or a pharmaceutically salt thereof or prodrug thereof may alternatively be formulated in a solid carrier. In one embodiment, the composition may be compacted into a unit dose form, i.e., tablet or caplet. In another embodiment, the composition may be added to unit dose form, i.e., a capsule. In a further embodiment, the composition may be formulated for administration as a powder. The solid carrier may perform a variety of functions, i.e., may perform the functions of two or more of the excipients described below. For example, solid carrier may also act as a flavoring agent, lubricant, solubilizer, suspending agent, filler, glidant, compression aid, binder, disintegrant, or encapsulating material.

The composition may also be sub-divided to contain appropriate quantities of the compound of formula (I) or a metabolite thereof, or a pharmaceutically salt thereof or prodrug thereof. For example, the unit dosage can be packaged compositions, e.g., packeted powders, vials, ampoules, prefilled syringes or sachets containing liquids.

Examples of excipients which may be combined with one or more compound of formula (I) or a metabolite thereof, or prodrug thereof include, without limitation, adjuvants, antioxidants, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, preservatives, solubilizers, sorbents, stabilizers, sweeteners, surfactants, suspending agents, syrups, thickening agents, or viscosity regulators. See, for example, the excipients described in the "Handbook of Pharmaceutical Excipients", $5^{th}$ Edition, Eds.: Rowe, Sheskey, and Owen, APhA Publications (Washington, D.C.), Dec. 14, 2005, which is incorporated herein by reference.

In one embodiment, the compositions may be utilized as inhalants. For this route of administration, compositions may be prepared as fluid unit doses using a compound of formula (I) or a metabolite thereof, or a pharmaceutically acceptable salt or prodrug thereof, and a vehicle for delivery by an atomizing spray pump or by dry powder for insufflation.

In another embodiment, the compositions may be utilized as aerosols, i.e., oral or intranasal. For this route of administration, the compositions are formulated for use in a pressurized aerosol container together with a gaseous or liquefied propellant, e.g., dichlorodifluoromethane, carbon dioxide, nitrogen, propane, and the like. Also provided is the delivery of a metered dose in one or more actuations.

In another embodiment, the compositions may be administered by a sustained delivery device. "Sustained delivery" as used herein refers to delivery of a compound of formula (I) or a metabolite thereof, or a pharmaceutically acceptable salt or prodrug thereof which is delayed or otherwise controlled. Those of skill in the art know suitable sustained delivery devices. For use in such sustained delivery devices, the compound of formula (I) or a metabolite thereof, or a pharmaceutically acceptable salt or prodrug thereof is formulated as described herein.

Labeled Compounds and Assay Methods

Another aspect of the present invention relates to fluorescent dyes, spin label, heavy metal, or isotopically- or radio-labeled compounds of the invention that would be useful not only in imaging but also in assays both in vitro and in vivo, for localizing and quantitating one or more of IDO1 or IDO2 or TDO enzymes in blood or tissue samples of mammals or in cells, and for identifying or screening for ligands of one or more of IDO1 or IDO2 or TDO by inhibition binding of a labeled compound. Compounds of the invention may also be conjugated to other therapeutics or assay reagents, for example, to biotherapeutics such as targeted antibodies or antibody fragments, or drug targets or antibodies, antibody fragment or a protein as reagents for research or test purposes or for any other purpose. Accordingly, the present invention includes enzyme assays for one or more of IDO1 or IDO2 or TDO enzymes that contain such labeled compounds. Examples of assays include without limitation ELISA, RIA, ELTSPOT etc.

One aspect of the invention includes isotopically-labeled compounds, which are identical to those shown in formula (I) or metabolites thereof, or pharmaceutically acceptable salts or prodrugs thereof, but for the fact that one or more atoms are replaced by an atom having an atomic mass or mass number usually different from the atomic mass or mass number usually found in nature. Examples of isotopes that can be incorporated into compounds of the invention include isotopes of hydrogen, carbon, nitrogen, oxygen, phosphorus, sulfur, fluorine, and chlorine, such as $^2H$, $^3H$, $^{13}C$, $^{15}N$, $^{18}O$, $^{17}O$, $^{31}P$, $^{32}P$, $^{35}S$, $^{18}F$, and $^{36}Cl$, respectively. Compounds of the invention which contain the aforementioned isotopes and other isotopes of other atoms are within the scope this of invention.

Synthetic methods for incorporating radio-isotopes into organic compounds are applicable to compounds of the invention and are well-known in the art. The radionucliide that is incorporated in the instant radio-labeled compounds will depend on the specific application of that radiolabeled compound. It will be understood that, in a compound where such isotopic substitution is made, the following atoms, where present, may vary, so that for example, any hydrogen may be $^2H$/D, any carbon may be $^{13}C$, or any nitrogen may be $^{15}N$, and that the presence and placement of such atoms may be determined by a person having skill in the art. For example, for an IDO1, IDO2, or TDO enzyme labeling and competition assays, compounds that are incorporate $^2H$/D, $^3H$, $^{14}C$ $^{82}Br$, $^{125}I$, $^{131}I$, $^{35}S$ will generally be most useful. The radioactive isotopes $^3H$, and $^{14}C$, are particularly useful for this purpose in view of their ease of incorporation and ready means of detection.

Likewise, the compounds of the invention may include the preparation of isotopic variants with radioisotopes, in the instance for example, where the resulting compounds may be used for drug and/or substrate tissue distribution studies. For example, in radio-imaging applications $^{11}C$, $^{18}F$, $^{125}I$, $^{123}I$, $^{124}I$, $^{131}I$, $^{75}Br$, $^{77}Br$ will generally be most useful. Further, compounds may be prepared that are substituted with positron emitting isotopes, such as $^{11}C$, $^{18}F$, $^{15}O$, and $^{13}N$, and would be useful in Positron Emission Topography (PET) studies for examining substrate receptor occupancy. In some embodiments, the radionuclide is selected from a group of $^3$H, $^{14}$C, $^{125}$I, $^{35}$S, $^{82}$Br. Tritiated $^3$H and carbon 14 i.e., $^{14}$C, are preferred for their ease of preparation and detectability. Further, substitution with heavier isotopes such as deuterium, i.e. $^2$H/D, can afford certain therapeutic advantages resulting from greater metabolic stability, for example, increased in vivo half life or reduced dosage requirements, and hence can be preferred in some circumstances. All isotopic variants of the compounds provided herein, radioactive or not, are intended to be encompassed within the scope of the invention.

A isotopically- or radio-labeled compound can be used in a screening assay to identify or evaluate compounds or drug targets. In general terms, a newly synthesized or identified compound (i.e., test compound) can be evaluated for its ability to reduce binding of the radio-labeled compound to one or more of IDO1 or IDO2 or TDO enzymes. Accordingly, the ability of a test compound to compete with an labeled compound such as isotopically including radiolabeled compound or fluroscein-labeled compound for binding to one or more of IDO1, IDO2, or TDO enzymes directly correlates to its binding activity.

Articles Of Manufacture

Also provided herein are kits or packages of pharmaceutical formulations containing the compounds of formula (I) or a metabolite thereof, or a pharmaceutically acceptable salt or prodrug thereof, or compositions described herein. The kits may be organized to indicate a single formulation or combination of formulations to be taken at each desired time.

Suitably, the kit contains packaging or a container with the compound of formula (I) or a metabolite thereof, or a pharmaceutically acceptable salt or prodrug thereof formulated for the desired delivery route. Suitably, the kit contains instructions on dosing and an insert regarding the active agent. Optionally, the kit may further contain instructions for monitoring circulating levels of product and materials for performing such assays including, e.g., reagents, well plates, containers, markers or labels, and the like. Such kits are readily packaged in a manner suitable for treatment of a desired indication. For example, the kit may also contain instructions for use of a spray pump or other delivery device. Other suitable components to include in such kits will be readily apparent to one of skill in the art, taking into consideration the desired indication and the delivery route.

The compounds of formula (I) or a metabolite thereof, or a pharmaceutically acceptable salt or prodrug thereof, or compositions described herein can be a single dose or for continuous or periodic discontinuous administration. For continuous administration, a package or kit can include the compound of formula (I) or a metabolite thereof, or a pharmaceutically acceptable salt or prodrug thereof, in each dosage unit (e.g., solution, lotion, tablet, pill, or other unit described above or utilized in drug delivery), and optionally instructions for administering the doses daily, weekly, or monthly, for a predetermined length of time or as prescribed. When the compound of formula (I) or a metabolite thereof, or a pharmaceutically acceptable salt or prodrug thereof is to be delivered periodically in a discontinuous fashion, a package or kit can include placebos during periods when the compound of formula (I) or a metabolite thereof, or a pharmaceutically acceptable salt or prodrug thereof is not delivered. When varying concentrations of a composition, of the components of the composition, or the relative ratios of the compounds of formula (I) or a metabolite thereof, or a pharmaceutically acceptable salt or prodrug thereof, or therapeutic agents within a composition over time is desired, a package or kit may contain a sequence of dosage units which provide the desired variability.

A number of packages or kits are known in the art for dispensing pharmaceutical agents for periodic oral use. In one embodiment, the package has indicators for each period. In another embodiment, the package is a labeled blister package, dial dispenser package, or bottle.

The packaging means of a kit may itself be geared for administration, such as an inhalant, syringe, pipette, eye dropper, or other such apparatus, from which the formulation may be applied to an affected area of the body, such as the lungs, injected into a subject, or even applied to and mixed with the other components of the kit.

The compositions of these kits also may be provided in dried or lyophilized forms. When reagents or components are provided as a dried form, reconstitution generally is by the addition of a suitable solvent. It is envisioned that the solvent also may be provided in another package.

The kits of the present invention also will typically include a means for containing the vials in close confinement for commercial sale such as, e.g., injection or blow-molded plastic containers into which the desired vials are retained. Irrespective of the number or type of packages and as discussed above, the kits also may include, or be packaged with a separate instrument for assisting with the injection/administration or placement of the composition within the body of an animal. Such an instrument may be an inhalant, syringe, pipette, forcep, measuring spoon, eye dropper or any such medically approved delivery means.

In one embodiment, a kit is provided and contains a compound of formula (I). In another embodiment the kit comprises a compound of formula (I) or a metabolite thereof, or a pharmaceutically acceptable salt or prodrug thereof. In yet another embodiment, the kit comprises a metabolite of a compound of formulae (I)-(IV). In yet another embodiment, the kit contains a prodrug of a compound of formulae (I)-(IV). The compound of formula (I) or a metabolite thereof, or a pharmaceutically acceptable salt or prodrug thereof may be in the presence or absence of one or more of the carriers or excipients described above. In still another embodiment, the kit contains a compound of formula (I) or a metabolite thereof, or a pharmaceutically acceptable salt or prodrug thereof may be in one or more of other therapeutic agents as described herein. The kit may optionally contain instructions for administering the medication and the compound of formula (I) or a metabolite thereof, or a pharmaceutically acceptable salt or prodrug thereof to a subject having a disease characterized by (i) the dysregulation of the kynurenine pathway caused by dysregulated indoleamine 2,3-dioxygenase-1 and/or indoleamine 2,3-dioxygenase-2 and/or tryptophan 2,3-dioxygenase activity, or (ii) immune suppression or (iii) autoimmunity, or (iv) increased kynurenine metabolites or (v) decreased tryptophan or (vi) increased kynurenine/tryptophan ratio or (vii) with inflammation.

In a further embodiment, a kit is provided and contains a compound of formula (I) or a metabolite thereof, or prodrug thereoof in a second dosage unit, and one or more of the carriers or excipients described above in a third dosage unit. The kit may optionally contain instructions for administering the medication and the compound of formula (I) or a metabolite thereof, or a pharmaceutically acceptable salt or prodrug thereof to a subject having a disease characterized by (i) abnormal immune suppression resulting from dysregulation of the kynurenine pathway, or (ii) autoimmunity, or (iii) increased kynurenine metabolites, or (iv) decreased tryptophan, or (v) increased kynurenine/tryptophan ratio.

In a further embodiment, a kit is provided and contains a compound of formula (I) or a metabolite thereof, or a pharmaceutically acceptable salt or prodrug thereof in a second dosage unit, and one or more of the carriers or excipients described above in a third dosage unit. The kit may optionally contain instructions for administering the medication and the compound of formula (I) or a metabolite thereof, or a pharmaceutically acceptable salt or prodrug thereof to a subject having a disease characterized by abnormal immune suppression resulting from enzymatic activity of indoleamine 2,3-dioxygenase-1 and/or indoleamine 2,3-dioxygenase-2 and/or tryptophan 2,3-dioxygenase.

Methods of Use

The compounds of formula (I) or metabolites thereof, or a pharmaceutically acceptable salt or prodrugs thereof, and pharmaceutical compositions described herein are useful in treating or regulating diseases or conditions associated with kynurenine pathway. Specifically, the compounds are useful in treating or regulating diseases or conditions associated with increased kynurenine pathway metabolites, for e.g., kynurenine or altered (for example, decreased) tryptophan levels. The compounds are useful for the treatment of disease or condition associated with one or more of indoleamine 2,3-dioxygenase-1 or indoleamine 2,3-disoxygenase-2 or tryptophan 2,3-dioxygenase enzymes. The compounds of the invention are useful in the treatement of immune suppression. In one aspect, the immune suppression is associated with one or more of indoleamine 2,3-dioxygenase-1 or indoleamine 2,3-disoxygenase-2 or tryptophan 2,3-dioxygenase enzymes. The compounds and pharmaceutical compositions described herein are useful in regulating diseases which are associated with increased immune suppression resulting from dysregulation of the kynurenine pathway due to activation of one or more of indoleamine 2,3-dioxygenase-1 or indoleamine 2,3-dioxygenase-2 or tryptophan 2,3-dioxygenase enzymes. The compounds of the invention are useful in the treatement of immune autoimmunity. In one aspect, autoimmunity are associated with one or more of indoleamine 2,3-dioxygenase-1 or indoleamine 2,3-disoxygenase-2 or tryptophan 2,3-dioxygenase enzymes.

The term "regulation" or variations thereof as used herein refers to the ability of a compound of formula (I) to inhibit one or more components of a biological pathway. In one embodiment, "regulation" refers to a decrease in plasma and/or tissue concentrations of kynurenine. In another embodiment, "regulation" refers to a decrease in plasma and/or tissue concentrations of kynurenine/tryptophan (kyn/trp) ratio. In yet another embodiment, "regulation" referes to an increase in plasma and/or tissue concentations of tryptophan. In still another embodiment, "regulation" refers to (i) a decrease in concentrations of kynurenine and/or kyn/trp ratio, and/or (ii) increase in tryptophan concentration in an in vitro assay, for example, using cell culture system.

In another embodiment, "regulation" refers to inhibition of indoleamine 2,3-dioxygenase-1 activity. In yet another embodiment, "regulation" refers to inhibition of indoleamine 2,3-dioxygenase-2 activity. In another embodiment, "regulation" refers to inhibition of tryptophan 2,3-dioxygenase activity. In a further embodiment, "regulation" refers to dual inhibition of indoleamine 2,3-dioxygenase-1 and tryptophan 2,3-dioxygenase activity. In a yet further embodiment, "regulation" refers to dual inhibition of indoleamine 2,3-dioxygenase-2 and tryptophan 2,3-dioxygenase activity. In a still further embodiment, "regulation" refers to dual inhibition of indoleamine 2,3-dioxygenase-1 and indoleamine 2,3-dioxygenase-2 activity. In a still further embodiment, "regulation" refers to triple inhibition of indoleamine 2,3-dioxygenase-1, indoleamine 2,3-dioxygenase-2 and tryptophan 2,3-dioxygenase activity.

The utility of the compounds can be illustrated, for example, by their activity in in vitro and in vivo assays known in the art and as described herein. The compounds of formula (I) or metabolites thereof, or a pharmaceutically accetable salt or prodrug thereof exhibit indoleamine 2,3-dioxygense-1 and/or indoleamine 2,3-disoxygenase-2 and/or tryptophan 2,3-dioxygenase inhibitory activity, and decrease the production of kynurenine pathway metabolites. Accordingly, compounds of the invention can be used as therapeutic agents for the treatment of a disease, disorder, or condition directly or indirectly related to or associated with kynurenine pathway metabolites and/or one or more of indoleamine 2,3-dioxygenase-1, indoleamine 2,3-dioxygenase-2 and tryptophan 2,3-dioxygenase enzymes.

As used herein, "disease," "disorder" and "condition" are used interchangeably, to indicate an abnormal state in a subject. Kynurenine pathway associated disease is a disease that can be treated, prevented, ameliorated or cured by reducing kynurenine pathway metabolite levels or increasing tryptophan levels or both. IDO1-, IDO2-, and/or TDO-associated disease can be any disease that can be treated, prevented, ameliorated or cured by regulating enzyme expression and/or activity. The association may be direct or indirect. Accordingly, the compounds described herein are useful for treating diseases associated directly or indirectly with IDO1, IDO2 or TDO or any combination these enzymes, or with kynurenine pathway.

In one embodiment, such a disease is associated with abnormal cellular proliferation. The term "abnormal cellular proliferation" refers to the uncontrolled growth of cells which are naturally present in a mammalian body. In one embodiment, a disease which is characterized by abnormal cellular proliferation is cancer, including, without limitation, squamous cell cancer (e.g., epithelial squamous cell cancer), cancer of the peritoneum, prostate, head, neck, eye, mouth, throat, esophagus, bronchus, larynx, pharynx, thyroid cancer, chest, bone, lung including small-cell lung cancer ("SCLC"), non-small cell lung cancer ("NSCLC"), adenocarcinoma of the lung and squamous carcinoma of the lung, colon, rectum, gastric or stomach including gastrointestinal cancer, bladder, uterus, cervix, breast, ovaries, uterus including endometrial or uterine carcinoma, vagina, vulval cancer, testicles, penile carcinoma, anal carcinoma, skin, thyroid, blood, lymph nodes, kidney or renal, liver including hepatocellular cancer, hepatic carcinoma, and hepatoma, intestines, salivary gland carcinoma, pancreas, brain including glioblastoma, central nervous system, adrenal gland, skin or leukemia. Accordingly, the use of compounds for treating cancer is provided. One of skill in the art would understand that there is an established link between decreased kynurenine levels and anti-tumor activity in the clinical setting.

As described herein, a therapeutically effective amount of a compound when used for the treatment of cancer is an amount which may reduce the number of cancer cells, reduce tumor size, inhibit metastasis, inhibit or reduce tumor growth, reduce tumor resistance, reduce tumor evasion, and/or ameliorate one or more of the symptoms of the cancer. For cancer therapy, efficacy can be measured for example, by assessing the time to disease progression and/or determining the response rate.

In one embodiment, the condition is immunosuppression. The terms "immune suppression" or "immunosuppression" used throughout the present disclosure refers to suppression of the body's immune system and its ability to fight infections and other diseases. The suppression of the immune system may be partial or complete. Immunosuppression may result from certain diseases, for example without limitation, abnormal cell proliferation or cancer, acute and chronic infections including but not limited to bacterial infections such as tuberculosis, viral infections such as AIDS, HIV, HCV, HPV infection and parasitic infections such as malaria and Leishmaniasis. In addition, immunosuppression may result from disease treatment, for example, from treatment with anticancer drugs such as tetracycline or its analogs. The compounds as described herein are useful for treating immunosuppression. More specifically, the compounds can be utilized in order to reduce immune suppression associated with abnormal cell growth in which one or more of indoleamine 2,3-disoxygenase-1 or indoleamine 2,3-disoxygenase-2 or tryptophan 2,3-disoxygenase plays a role. Thus, the compounds are effective in the treatment of diseases, disorders or conditions such as cancer, associated with increased kynurenine levels due to the actions of indoleamine 2,3-dioxygenase-1 and/or indoleamine 2,3-dioxygenase-2 and/or tryptophan 2,3-dioxygenase.

Where immunosuppression is desired for treatment of a condition or disease or for a procedure such as preparation for bone marrow or other organ transplantation, immunosuppression is generally induced with drugs to prevent rejection of the donor tissue. Examples include without limitation allogeneic hematopoietic stem cell transplantation (HSCT), graft-versus-host disease (GvHD), organ transplant etc. The present invention also provides for use of the compounds of the invention and pharmaceutical compositions for inducing faster recovery from immunosuppression after bone marrow treatment or other organ transplantation to fight infection post-procedure. The timing for the use of the compounds will be determined by a healthcare professional or a physician. The compounds may also be used as adjuvants after bone marrow transplantation or peripheral blood stem cells transplantation and in immunotherapy by adoptive transfer. Accordingly, the use of compounds as described herein for treating conditions with immune suppression is provided.

In another embodiment, the disease is infectious disease. In one embodiment, infectious disease is a bacterial infection. Examples of bacterial infections treatable include but are not limited to *Mycobacteria* infection and *Streptococcus pyrogens* infection. Particular intracellular bacterial infections may be selected from the group consisting of *Mycobacterium leprae, Mycobacterium tuberculosis, Listeria monocytogens* and *Toxoplasma gondii*. Accordingly, use of compounds for the treatment of bacterial infection is provided herein.

In a further embodiment, the disease is a viral infection (for example HIV, HPV, or HCV infection). Examples of viral infections that may be treated using compounds of the invention include but not limited to are Human immunodeficiency (HIV)/AIDS virus, human parainfluenza virus, human papilloma virus, Hepatitis C, Hepatitis B, influenza, SARS, cytomegalovirus, viral hemorrhagic fevers (Ebola, Marburg, Lassa and yellow fever virus), polio virus, Epstein Barr virus, Varicella zoster virus and Coxsackie virus. In another embodiment, the viral infection is HCV infection. In another embodiment, the viral infection is HIV infection. Accordingly, the use of compounds as described herein for treating viral infections, such as HIV, HPV, or HCV infection, is provided.

In still another embodiment, the disease is a parasitic disease. Examples of parasitic diseases that may be treated using compounds of the invention include but not limited to are Leishmaniasis and Malaria. The compounds of the invention and pharmaceutical compositions are useful in the treatment against parasites that include but are not limited to *Leishmania donovani, Leishmania tropica, Leishmania major, Leishmania aethiopica, Leishmania maxicana, Plasmodium falciparum, Plasmodium vivax, Plasmodium ovale* and *Plasmodium malariae*. Accordingly, the use of compounds as described herein for treating parasitic disease such as Leishmaniasis and malaria is provided.

In a still further embodiment, the disease is an immune mediated disorder (for example a B-cell mediated disorder or a macrophage-mediated disorder, or a T-cell mediated immune disease). IDO1, for example, is induced by pro-inflammatory cytokines such as Interferon gamma and to a lesser extent by TNF-alpha, IL-1, IFN-alpa and beta. IDO2 is a critical mediator of inflammatory pathogenesis and autoreactive responses in autoimmune arthritis. Accordingly, in one embodiment, the disease is an inflammatory disease. Examples of inflammatory disorders or conditions include, without limitation, arthritis, pulomonary disease, allergic airway disease, asthma, cardiovascular and neurovascular diseases such as Atherosclerosis, coronary artery disease, peripheral artery disease, ischemia, Alzheimer's disease, and stroke, Irritable bowel syndrome, Crohn's disease, and pelvic inflammatory disorder. In one embodiment, the disease is arthritis. In another embodiment, arthritis is selected from a group consisting of osteoarthritis, rheumatoid arthritis, juvenile arthritis, ankylosing spondylitis, gout, and psoriatic arthritis. One of skill in the art will recognize that inhibition of IDO 1 activity reduces circulating T-rcgs and effector T-cell apoptosis in subjects with inflammatory disorders and promotes immune tolerance. Thus, the compounds described herein are useful for treating or regulating inflammatory disorders associated with one or more of IDO1 or IDO2 or TDO enzymes. The compounds are used for treating or regulating inflammatory disorders associated with kynurenine pathway metabolites. In one embodiment, the compounds are useful for treating IDO 1 associated immune-mediated diseases. In another embodiment, the compounds are useful for treating IDO2 associated immune-mediated disorders. In another embodiment, the compounds are useful for treating or regulating IDO2 associated inflammatory diseases. In another embodiment, the compounds are useful for treating TDO associated immune-mediated disorders. In yet another embodiment, the compounds are useful for treating or regulating one or more of (i) T-cell mediated immune disorders, or (ii) B-cell mediated immune disorders, or (iii) macrophage- or mast-cell mediated immune disorders. Accordingly, the use of compounds as described herein for treating immune-mediated disorders, including inflammatory diseases, is provided. In one embodiment, the compounds are useful for treating or regulating osteoarthritis, rheumatoid arthritis, juvenile arthritis, anklylosing spondylitis, and psoriatic arthritis. In another embodiment, compounds are useful for treating or regulating Alzheimer's disease.

IDO2 has been shown to inhibit the production of auto-immune antibodies in mouse model of autoimmune arthritis (Merlo et al. J. Immunol. (2014), 192(5), 2082-2090). Accordingly in one embodiment, the disease is autoimmune disorder. Examples of autoimmune disorders that may be treated using the compounds of the invention include, without limitation, multiple sclerosis, ulcerative colitis, rheumatoid arthritis, asthma, psoriasis, inflammatory bowel disease, primary sclerosing cholangitis, Hashimoto's thyroiditis, Sjogren's syndrome, systemic lupus erythematosus, antiphospholipid syndrome—primary and secondary, primary biliary cirrhosis, autoimmune hepatitis, encephalomyelitis, Graves' disease, autoimmune retinopathy—also called recoverin-associated retinopathy, scleroderma, autoimmune thrombocytopenic purpura, Addison's disease, celiac disease—sprue, dermatomyositis, chronic inflammatory demyelinating polyradiculoneuropathy, acute inflammatory demyelinating polyneuropathy, Isaacs' syndrome, Moersch-Woltmann syndrome, Lambert-Eaton myasthenic syndrome, and myasthenia gravis. In one embodiment, the disease is rheumatoid arthritis. In another embodiment, the disease is multiple sclerosis. In yet another embodiment, the disease is lupus erythromatosis. Accordingly, the use of compounds as described herein for treating autoimmune disease is provided. In one aspect, the use of compounds as described herein for treating multiple sclerosis is provided. In another aspect, the use of compounds as described herein for treating rheumatoid arthristis is provided.

IDO1 and TDO are expressed in the brain and are highly expressed in brain tumors. IDO1 activity in brain tumors negatively impacts survival (Wainright, et al. Clin Cancer Res. 2012 Nov. 15; 18(22):6110-21). Brain IDO1 contributes to the comorbidity of pain and depression (Kim et al. J Clin Invest. 2012; 122(8):2940-2954). Accordingly in another embodiment, the disease is a disease of the nervous system. Examples of diseases of central and peripheral nervous system that may be treated using the compounds of the invention include, without limitation, brain tumors such as glioma, giobastoma, neuroma, neuroinflammatory and neurodegenerative diseases such as Alzheimer's disease, Huntington's disease, multiple sclerosis, amyotrophic lateral sclerosis, and Parkinson's disease, lyme neuroborreliosis, late lyme encephalopathy, Tourette's syndrome, systemic sclerosis, Guillain-Barr syndrome, muscular dystrophy, acute disseminated encephalomyelitis, and optic neuritis, transverse myelitis, neuromyelitis optica. Examples of diseases also include without limitation neuropsychiatric diseases, including mood disorders and sleep disorders. In another embodiment, the disease is depression. In another embodiment, the disease is schizophrenia. In yet another embodiment, the sleep disorder is insomnia. In still another embodiment, the sleep disorder is sleep apnea. Accordingly, the use of compounds as described herein for treating diseases of the nervous system is provided. In one aspect, the use of compounds as described herein for treating multiple sclerosis is provided. In one aspect, the use of compounds as described herein for treating Alzheimer's disease is provided. In another aspect, the use of compounds as described herein for treating depression is provided. In yet another aspect, the use of compounds as described herein for treating schizophrenia or sleep disorder is provided.

In another aspect, a method for regulating a kynurenine pathway is provided and includes administering a compound a metabolite thereof, or a pharmaceutically acceptable salt or prodrug thereof as described herein to a subject in need thereof In one aspect, the disease may be any disease treatable by adminstering a compound or a metabolite thereof, or a pharmaceutically acceptable salt or prodrug thereof is provided. In another aspect, a method for treating a disease treatable by inhibiting a kynurenine pathway is provided and includes administering a compound, a metabolite thereof, or a pharmaceutically acceptable salt or prodrug thereof to a subject in need thereof.

In another aspect, a method of regulating any one or more of any one or more of indoleamine 2,3-dioxygenase-1 or an indoleamine 2,3-dioxygenase-2 or a tryptophan 2,3-dioxygenase enzymes is provided and includes administering a compound of formula (I)-(IV), a metabolite thereof, or a pharmaceutically acceptable salt or prodrug thereof as described herein to a subject in need thereof In another aspect, the regulating is inhibiting the kynurenine pathway or one or more of the enzymes.

In still a further aspect, a method of regulating the kynurenine pathway by inhibiting indoleamine 2,3-dioxygenase-1 and/or tryptophan 2,3-dioxygenase is provided and includes administering a compound as described herein to a subject in need thereof.

In still a further aspect, a method of regulating the kynurenine pathway by inhibiting indoleamine 2,3-dioxygenase-2 and/or tryptophan 2,3-dioxygenase is provided and includes administering a compound as described herein to a subject in need thereof.

In still a further aspect, a method of regulating the kynurenine pathway by inhibiting indoleamine 2,3-dioxygenase-1 and/or indoleamine 2,3-dioxygenase-2 is provided and includes administering a compound as described herein to a subject in need thereof.

In one aspect, a method of reducing kynurenine pathway metabolites is provided and includes administering a compound or a metabolite thereof, or a pharmaceutically acceptable salt or prodrug thereof as described herein to a subject in need thereof In another aspect, a method of altering tryptophan levels in a subject and includes administering a compound of formula (I) or a metabolite thereof, or a pharmaecuticallly acceptable salt or prodrug thereof described herein is provided. In one aspect, the tryptophan levels are increased. In another aspect, kynurenine/tryptophan ratio is decreased.

In yet another aspect, a method for increasing tryptophan levels is provided by inhibiting one or more of indoleamine 2,3-dioxygenase-1 or indoleamine 2,3-dioxygenase-2 or tryptophan 2,3-dioxygenase is provided and includes administering a compound as described herein to a subject in need thereof.

In one aspect, a method of treating a disease associated with or resulting from dysregulation of a kynurenine pathway is provided and includes administering a compound of formula ((I) or a metabolite thereof, or a pharmaceutically acceptable salt or prodrug thereof as described herein to a subject in need thereof.

In another aspect, a method for treating a disease caused by the dysregulation of the kynurenine pathway by inhibiting indoleamine 2,3-dioxygenase-1 and/or indoleamine 2,3-dioxygenase-2 and/or tryptophan 2,3-dioxygenase is provided and includes administering a compound or prodrug thereof described herein to a subject in need thereof In yet another aspect, a method for treating a disease caused by activation of indoleamine 2,3-dioxygenase-1 or tryptophan 2,3-dioxygenase or both enzymes is provided and includes administering a compound of formula (I) or a metabolite thereof, or a pharmaceutically acceptable salt or propdrug thereof as described herein to a subject in need thereof.

In yet another aspect, a method for treating a disease caused by activation of indoleamine 2,3-dioxygenase-2 or tryptophan 2,3-dioxygenase enzymes or both is provided and includes administering a compound of formula (I) or a metabolite thereof, or a pharmaceutically acceptable salt or propdrug thereof as described herein to a subject in need thereof.

In yet another aspect, a method for treating a disease caused by activation of indoleamine 2,3-dioxygenase-1 or indoleamine 2,3-dioxygenase-2 or both is provided and includes administering a compound of formula (I) or a metabolite thereof, or a pharmaceutically acceptable salt or propdrug thereof as described herein to a subject in need thereof.

In another aspect, a method of inhbiting activation of one or more of indoleamine 2,3-dioxygenase-1 or indoleamine 2,3-dioxygenase-2 or tryptophan 2,3-dioxygenase enzymes is provided and includes administering a compound of formula (I) or a metabolite thereof, or a pharmaceutically acceptable salt or prodrug thereof as described herein to a subject in need thereof.

In another aspect, a method for treating a disease associated with any one or more of indoleamine 2,3-dioxygenase-1 or indoleamine 2,3-dioxygenase-2 or tryptophan 2,3-dioxygenase enzymes is provided and includes administering a compound of formula (I) or a metabolite of the compound, or a pharmaceutically acceptable salt or prodrug thereof described herein to a subject in need thereof.

In yet a further aspect, a method is provided for treating a disease characterized by abnormal immune suppression, for example, increased immune suppression resulting from dysregulation of the kynurenine pathway and includes administering a compound of formula (I) or a metabolite thereof, or pharmaceutically acceptable or prodrug thereof described herein to a subject in need thereof.

In a further aspect, a method for regulating a disease characterized by abnormal immune suppression resulting from a dysregulated kynurenine due to activation one or more of indoleamine 2,3-dioxygenase-1 or indoleamine 2,3-dioxygenase-2 or tryptophan 2,3-dioxygenase enzyme is provided and includes administering a compound or a metabolite thereof, or a pharmaceutically acceptable salt or prodrug thereof as described herein to a subject in need thereof.

In one aspect, a method of treating immune suppression is provided and includes administering a compound or a metabolite thereof or a pharmaceutically acceptable salt or prodrug thereof as described herein to a subject in need thereof. In another aspect, the immune suppression is associated with increased kynurenine metabolite levels or enzymatic activity of one or more of indoleamine 2,3-dioxygenase-1 or indoleamine 2,3-dioxygenase-2 or tryptophan 2,3-dioxygenase enzymes. In yet another aspect, a method is provided for treating immune suppression associated with one or more of indoleamine 2,3-dioxygenase-1 or indoleamine 2,3-dioxygenase-2 or tryptophan 2,3-dioxygenase enzymes and includes administering a compound or a metabolite thereof, or pharmaceutically acceptable salt or prodrug thereof to a subject in need thereof. Thus, in an aspect, compounds of the invention for use in the treatment of immunosuppression associated with one or more of indoleamine 2,3-dioxygenase-1 or indoleamine 2,3-dioxygenase-2 or tryptophan 2,3-dioxygenase enzymes are provided.

In yet another aspect, a method for treating immune suppression through inhibiting enzymatic activity of indoleamine 2,3-dioxygenase and/or tryptophan 2,3-dioxygenase is provided and includes administering a compound or a metabolite thereof, or a pharmaceutically acceptable salt or prodrug thereof described herein to a subject in need thereof.

In yet another aspect, a method of reducing or eliminating an immune mediated disorder is provided and includes administering a compound or a metabolite thereof, or a pharmaceutically acceptable salt or prodrug thereof described herein to a patient.

In yet another aspect, a method of inhibiting an autoimmune reaction or autoimmune antibody production in a subject is provided and includes administering a compound or a metabolite thereof, or a pharmaceutically acceptable salt or prodrug thereof as described to a subject in need thereof. In another aspect, a method of inhibiting autoimmune reaction or autoimmune antibody production is provided wherein (i) indoleamine 2,3-dioxygenase-2 is inhibited or (ii) kynurenine metabolites are reduced, and includes administering a compound or a metabolite thereof, or a pharmaceutically acceptable salt or prodrug thereof as described to a subject in need thereof. In one aspect, the foregoing reduction in autoimmune reaction or autoimmune antibody production is associated with inflammatory diseases, cancer or autoimmine disorders.

In one aspect, diseases that can be treated using compounds of the invention comprise cancer, bacterial infection, viral infection, parasitic infection, immune-mediated disorder, autoimmune disorder, inflammatory disease, central nervous system disease, peripheral nervous system disease, neurodegenerative disease, mood disorder, sleep disorder, cerebrovascular disease, peripheral artery disease, or cardiovascular disease. In another aspect, all foregoing methods comprise administration of one or more additional medication or therapeutic agent or therapy. In one aspect, the therapeutic agent is a chemotherapeutic agent selected from a group further comprising a cancer vaccine, a targeted drug, a targeted antibody, an antibody fragment, an antimetabolite, an antineoplastic, an antifolate, a toxin, an alkylating agent, a DNA strand breaking agent, a DNA minor groove binding agent, a pyrimidine analog, a purine analog, a ribonucleotide reductase inhibitor, a tubulin interactive agent, an anti-hormonal agent, an immunomoldulator, an anti-adrenal agent, a cytokine, a radiation therapy, a cell therapy, cell depletion therapy such as B-cell depletion therapy, or a hormone therapy.

In another aspect, a method of treating depression, Alzheimer's disease, dementia, multiple sclerosis, schizophrenia, HIV inection, malaria, rheumatoid arthritis, or insomnia is provided and includes administering a compound or a metabolite thereof, or a pharmaceutically acceptable salt or prodrug thereof described herein to a patient.

In one aspect, the disease is cancer. In another aspect, cancer disease is a cancer of squamous cell, peritoneum, prostate, head, neck, eye, mouth, throat, esophagus, bronchus, larynx, pharynx, thyroid cancer, chest, bone, lungs, colon, rectum, stomach, urinary bladder, gall bladder, uterus, cervix, breast, ovaries, uterus, vagina, vulva, testicles, penis, anus, skin, thyroid, blood, lymph nodes, kidney, liver, intestines, salivary gland, pancreas, brain, spine, adrenal gland, skin or leukemia. In another aspect, a method of treating tumor resistance is provided comprising administering a compound or a metabolite thereof, or a pharmaceutically acceptable salt or prodrug thereof described herein to a patient.

In another aspect, the viral infection is HIV infection. In another aspect, parasite infection is malaria or Leishmaniasis.

In a further aspect, a method of treating a viral infection is provided and includes administering a compound described herein to a patient.

In another aspect, a method of treating depression is provided and includes administering a compound described herein to a patient.

In still another aspect, a method of treating schizophrenia is provided and includes administering a compound described herein to a patient.

In still another aspect, a method of treating Alzheimer's disease is provided and includes administering a compound described herein to a patient.

In one embodiment, methods for regulating the kynurenine pathway by inhibiting indoleamine 2,3-dioxygenase-1 or indoleamine 2,3-dioxygenase-2 or tryptophan 2,3-dioxygenase are provided and include administering a compound or a metabolite thereof, or a pharmaceutically acceptable salt or a prodrug thereof to a patient in need thereof.

In another embodiment, methods for treating a disease characterized by abnormal immune suppression resulting from a dysregulated kynurenine pathway due to activation of indoleamine 2,3-dioxygenase-1 or indoleamine 2,3-dioxygenase-2 or tryptophan 2,3-dioxygenase arc provided and include administering of a compound or a metabolite thereof, or a pharmaceutically acceptable salt or a prodrug thereof to a patient in need thereof.

In another embodiment, methods for treating a disease characterized by an abnormal immune suppression resulting from a dysregulated kynurenine pathway due to activation of one or more of indoleamine 2,3-dioxygenase-1 or or indoleamine 2,3-dioxygenase-2 or tryptophan 2,3-dioxygenase are provided and include administering of a compound or a metabolite thereof, or a pharmaceutically acceptable salt or a prodrug thereof to a patient in need thereof.

In yet another aspect, a method for diagnosing and treating a disease associated with kynurenine pathway or any one or more of indoleamine 2,3-dioxygenase-1 or an indoleamine 2,3-dioxygenase-2 or a tryptophan 2,3-dioxygenase enzymes in a subject is provided and includes: (i) assaying a blood and/or tissue sample from a subject; (ii) determining the subject's blood and/or tissue tryptophan or Kynurenine concentration or both in the sample; (iii) optionally determining the subject's Kynurnine/tryptophan ratio; and (iv) administering a compound or a metabolite thereof, or a pharmaceutically acceptable salt or prodrug thereof described herein to a subject.

In still another aspect, a method of monitoring a disease associated with kynurenine pathway or one or more of indoleamine 2,3-dioxygenase-1 or an indoleamine 2,3-dioxygenase-2 or a tryptophan 2,3-dioxygenase enzymes in a subject is provided and includes (i) dosing a subject having a disease associated with kynurenine pathway with a compound or a metabolite thereof, or a pharmaceutically acceptable salt or prodrug thereof, (ii) analyzing a blood or tissue sample or both at one or more time points or continuously during a treatment regimen, (iii) determining a tryptophan and a kynurenine concentration in the blood or the tissue sample or both, (iv) optionally determining the subject's kynurnine/tryptophan ratio, and (v) adjusting the treatment regimen or dosage of the compound.

In a further aspect, a method for diagnosing and treating a disease associated with kynurenine pathway or any one or more of indoleamine 2,3-dioxygenase-1 or an indoleamine 2,3-dioxygenase-2 or a tryptophan 2,3-dioxygenase enzymes in a patient is provided and includes (i) analyzing a patient sample for the presence or absence of altered kynurenin/tryptophan ratio, wherein the patient is diagnosed with a disease associated with kynurenine pathway if altered kynurenine/tryptophan ratio is detected and (ii) administering a compound or a metabolite thereof, or a pharmaceutically acceptable salt or prodrug to the diagnosed patient.

In still a further aspect, a method for treating a disease associated with kynurenine pathway or one or more of an indoleamine 2,3-dioxygenase-1 or an indoleamine 2,3-dioxygenase-2 or a tryptophan 2,3-dioxygenase enzyme in a patient and includes (i) requesting a test providing the results of an analysis to determine whether the patient's kynurninc levels arc altered, and (ii) administering a compound or a metabolite thereof, or a pharmaceutically acceptable salt or prodrug thereof to the patient if the patient's kynurenine levels are altered.

In another aspect, provided herein are compounds for use in a disease associated with kynurenine pathway in a subject comprising: assaying a blood sample from a patient; determining if a patient has high blood and/or tissue kynurenine levels; and administering a compound as described herein to the patient if blood and/or tissue kynurenine levels are high.

In one aspect, provided herein are compounds for use for treating disease associated with kynurenine pathway in a patient comprising: assaying a blood sample from a patient; determining if a patient has low blood and/or tissue tryptophan levels; and administering a compound as described herein to the patient if blood and/or tissue tryptophan levels are low.

In one aspect, provided herein are compounds for use for treating a disease associated with one or more indoleamine 2,3-dioxygenase-1 or or indoleamine 2,3-dioxygenase-2 or tryptophan 2,3-dioxygenase in a patient comprising: assaying a blood sample from a patient; determining if a patient has high blood and/or tissue kynurenine levels or low blood and/or tissue tryptophan levels; and administering an amount of a compound as described herein to the patient if blood and/or tissue kynurenine levels are high or blood and/or tissue tryptophan levels are low.

In yet another aspect, a use of foregoing methods is provided wherein the disease is cancer, bacterial infection, viral infection, parasitic infection, immune-mediated disorder, autoimmune disorder, inflammatory disease, central nervous system disease, peripheral nervous system disease, neurodegenerative disease, mood disorder, sleep disorder, cerebrovascular disease, peripheral artery disease, or cardiovascular disease.

In one aspect, provided herein are compounds for use in treating immune suppression in a patient comprising: assaying a blood sample from a patient; determining if a patient has high blood and/or tissue kynurenine levels, and/or low blood and/or tissue tryptophan levels; and administering a compound as described herein to the patient if blood and/or tissue kynurenine levels are high, and/or blood and/or tissue tryptophan levels are low.

In another aspect, a method for treating a disease associated with kynurenine pathway in a mammal is provided, said method comprising: assaying a blood and/or tissue sample from a mammal; determining the mammal's blood and/or tissue tryptophan and kynurenine concentrations; optionally determining the mammal's kynurnine/tryptophan ratio; and administering an amount of a compound described herein.

In one aspect, a method for treating a disease associated with kynurenine pathway in a mammal is provided, said method comprising: assaying blood and/or tissue sample from a subject; determining the patient's IDO1 and/or IDO2 and/or TDO expression and/or activity in tissue sample; and administering an amount of a compound as described herein.

In yet another aspect, a method of monitoring or tracking a disease associated with kynurenine pathway in a mammal is provided, said method comprising: dosing a mammal having a disease associated with kynurenine pathway with a compound in combination with one or more therapeutic agent; analyzing a blood and/or tissue samples at one or more time points or continuously during the treatment regimen; determining the mammal's blood and/or tissue tryptophan and kynurenine concentrations and/or determining the kynurenine/tryptophan ratio; adjusting the treatment regimen or dosage of the compound or the second therapeutic agent.

In another aspect, a method of monitoring or tracking a disease associated with kynurenine pathway in a mammal is provided, said method comprising: dosing a mammal having a disease associated with kynurenine pathway with a compound as described herein; analyzing a blood and/or tissue sample of the mammal at one or more time points or continuously during the treatment regimen; determining the blood and/or tissue dosed compound's metabolite concentration; and adjusting the treatment regimen or therapeutic dosage.

The compounds of the invention may used in combination with one or more therapeutic agents as described herein. The compounds of the invention are thus useful in the treatment and monitoring the progression of disease associated with kynurenine pathway.

In yet another aspect, a method for diagnosing and treating a disease associated with kynurenine pathway in a patient comprising: analyzing a patient sample for the presence or absence of altered kynurenine and/or tryptophan and/or kynuren i n/tryptoph an ratio, wherein the patient is diagnosed with a disease associated with kynurenine pathway if altered kynurenine and/or tryptophan and/or kynurenine/ratio is detected, and administering therapeutically effective amount of a compound to the diagnosed patient.

In yet another aspect, a method for treating a disease associated with kynurenine pathway in a patient comprising: requesting a test providing the results of an analysis to determine whether the patient's kynurnine and/or tryptophan levels and/or kynurenine/tryptophan ratio are altered and administering therapeutically effectively amount of a compound to the patient if the patient's kynurenine and/or tryptophan levels and/or kynurenine/tryptophan ratio are altered.

In a further aspect, a method for diagnosing and treating cancer associated with IDO1 or IDO2 or TDO in a subject, wherein the cancer is characterized by increased expression and/or activity of one or more of IDO1 or IDO2 or TDO biomarkers, said method comprising: i) obtaining a biological sample from the subject; ii) applying a monoclonal antibody specific for IDO1 or IDO2 or TDO to the sample, wherein presence of IDO 1 or IDO2 or TDO creates an antibody-IDO1 or an antibody-IDO2 or antibody-TDO biomarker complex; iii) applying a detection agent that detects the antibody-biomarker complex; iv) diagnosing cancer associated with one or more of IDO1 or IDO2 or TDO wherein the detection agent of step iii) is detected; and v) administering to the subject a compound or a metabolite thereof, or a pharmaceutically acceptable salt or prodrug thereof.

In yet another aspect, a method for treating a disease associated with kynurenine pathway in a patient comprising: requesting a test providing a result of an analysis to determine whether the patient's IDO 1 and/or IDO2 and/or TDO expression and/or activity are increased and administering therapeutically effectively amount of a compound to the patient if the patient's IDO1 and/or IDO2 and/or TDO expression and/or activity are increased. Measurement of tryptophan, kynurenine pathway metabolites such as kynurenine, and/or metabolites of the compounds of the invention can be done vivo or in vitro using methods known in the art, including without limitation, HPLC, LC/MS/MS, Fluorescence, ELISA, RIA techniques and continuous monitoring sensor technologies using devices placed over the skin or eye, or inserted into the skin or tissue. Measurement of IDO1 and/or IDO2 and/or TDO expression and/or activity can be done as a non-limiting example using in vitro assays known in the art such as PCR, ELISA, enzymatic assays and as described herein.

The present invention, thus, also provides compounds and methods of assaying the activity IDO1 and/IDO2 and/or TDO in a cell-free system or in a system containing cells expressing IDO1 and/or IDO2 and/or TDO (such as a cell culture system, tissue, living organism such as a mammal, or in plasma or serum) comprising contacting test sample with a compound of the invention and measuring the inhibition of tryptophan degradation or catabolism and the reduction in kynurenine pathway metabolite levels as compared to a control treated samples.

Combination Therapy

It is within the scope of the invention to combine one or more compounds of formula (I)-(IV) with one or more metabolite of the compounds of the formula (I)-(IV) and/or with one or more prodrug of the compounds of formula (I). In addition to the components described above for use in compositions and the compound of formula (I) or a metabolite thereof, or pharmaceutically acceptable salts or prodrug thereof, the compositions may contain one or more medications or therapeutic agents which are used to treat solid tumors and other diseases described herein. Therapeutically effective amounts of the additional medication(s) or therapeutic agents are well known to those skilled in the art. However, it is well within the attending physician or healthare procssional to determine the amount of other medication to be delivered.

Combination therapy for the treatment of Cancer

In one embodiment, the additional medication is a chemotherapeutic. Examples of chemotherapeutics include those recited in the "Physician's Desk Reference", 64$^{th}$ Edition, Thomson Reuters, 2010, which is hereby incorporated by reference. Methods for the safe and effective administration of most of these chemotherapeutic agents are known to those skilled in the art. In addition, their administration is described in the standard literature. For example, the administration of many chemotherapeutic agents is described in "Physician's Desk Reference" (PDR, e.g., 2010 edition, PDR Network, Montvale, N.J.), the disclosure of which is also incorporated by reference in its entirety. In one aspect, the chemotherapeutic is doxorubicin, paclitaxel or derivative thereof, 5-FU, and carboplatin or a derivative thereof.

Suitable antineoplastic chemotherapeutic agents that can be dosed in combination with the compounds of invention can include, for example without limitation, alkylating agents (including without limitation, nitrogen mustards, ethylenimine derivatives, alkyl sulfonates, nitrosoureas, and triazine), uracil mustard, cyclophosphamide (Cytoxan™), chlormethine, ifosfamide, melphala, chlorambucil, pipobroman, triethylene melamine, triethylenethiophosphoramine, busulfan, carmustine, lomustine, streptozocin, dacarbazine, temozoloide, and combinations thereof.

Other chemotherapeutic or anti-cancer agents include, for example without limitation, antimetabolites (including without limitation, folic acid antagonists or antifolates, pyrimidine analogs, purine analogs, and adenosine deaminase inhibitors) such as methotrexate, fluorouracil, gemcitabine, and combinations thereof. Suitable chemotherapeutic or anti-cancer agents further include certain natural products and their derivatives, for example without limitation, vinca alkaloids, anti-tumor antibiotics, enzymes, lymphokines, and epipodohyllotoxins) such as vinblastine, doxorubicin, vincristine, vindesine, bleomycin, dactinomycin, daunorubicin, epirubicin, idarubicin, ara-C, paclitaxel (TAXOL™), deoxycoformycin, mitomycin-C, mithramycin, L-asparagine, interferons (particularly IFN-a), etoposide, and teniposide and combinations thereof.

The compounds may be used to augment the effects of therapeutic vaccination against various tumors. When the compounds are used in combination, then at least one additional therapeutic agent may be a vaccine. The vaccine may also be a tumor vaccine or a melanoma vaccine. Preferably, the tumor vaccine comprises genetically modified tumors cells or genetically modified tumors cell lines. In such cases, preferably the genetically modified tumors cells or genetically modified cell lines has been transfected to express granulocyte-macrophage stimulating factor (GM-CSF). Alternatively, the vaccine may comprise one or more immunogenic peptides, preferably immunogenic peptides of cancer testis antigen (CTAgs). Such CTAgs and immunogenic peptides thereof are well known in the art. CTAgs protein include MAGE, BAGE, GAGE, SSX, NY-ESO-1, LAGE, SCP, CTSP, CT7, CT8, CT9, CT10, CT11, SAGE, OY-TES-1, NY-SAR-35 and NY-BR-1. Several MAGe proteins are known, including MAGE-A I , A3, A4, A5, A6, A8, A10, A12, B1, B2, B2, B4, C1, C2 and C3 proteins. Several SSX proteins exist, including SSX1 and SSX2, SSX3 and SSX5. Vaccine may comprise one of more DNA vaccines and recombinant viruses. Further the tumor vaccine may comprise dendritic cells. In another embodiment, the additional medication is a cancer vaccine. In an aspect, the cancer vaccine is a dendritic cell based vaccine. In one aspect, the cancer vaccine is the Provenge® vaccine (Dendreon Corp).

The present invention also contemplates that compounds of invention may be used in combination with other anti-cancer agents such as antibody therapeutics. In a further embodiment, the additional medication is a targeted antibody, i.e., an antibody which targets a specific tumor type. The term "antibody" is used in the broadest sense and specifically covers intact monoclonal antibodies, polyclonal antibodies, chimeric antibodies, humanized antibodies, multispecific antibodies (e.g. bispecific antibodies) formed from at least two intact antibodies, and antibody fragments so long as they exhibit the desired biological activity. The term "Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al. Protein Eng. 8(10):1057-1062, 1995); single-chain antibody molecules; and multispecific antibodies formed from antibody fragments. The targeted antibody may be a monoclonal or polyclonal antibody and may be selected from those described in Pasquetto et al., "Targeted Drug Delivery Using Immunoconjugates: Principles and Applications", J. Immunother., 34(9):611-628 (November-December 2011), which is hereby incorporated by reference.

In one aspect, the targeted antibody is one or more of gemtuzumab (Mylotarg), alemtuzmab (CAMPATH™), rituximab (Rituxin, Mabthera), trastuzumab (Herceptin™) nimotuxumab, cetuximab (Erbitux), erlotinib (TARCEVA.®., Genentech/OSI Pharm.), bevacizumab (Avastin™), pertuzumab (OMNITARG.®., rhuMab 2C4, Genentech), Brentuximab vedotin (Adcetris™), Ipilimumab (MDX-101 and also known as Yervoy), Ofatumumab (Arzerra), Panitumumab (Vectibix), and Tositumomab (Bexxar), among others. In another aspect, the targeted antibody is one or more of alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.ln another embodiment, an additional medication includes antibodies to immune co-stimulatory molecules including but not limited to CTLA-4, 4-1BB and PD-1, antibodies to cytokines (including but not limited to IL-10, TGF-beta, etc.), and chemokine receptors including but not limited to CCR2, CCR4 etc., among others. In yet another embodiment, the additional medication is a targeted drug. The term "targeted drug" as used herein refers to a medication that blocks cancer cell growth by interfering specific "targeted" molecules which are required for tumor growth. See, Pasquetto cited above, which is hereby incorporated by reference. In one aspect, the targeted drug includes, without limitation, dasatnib, imatinib, nilotinib, bosutnib, lcstaurtinib, ruxolitinib, crizotinib, vandetabib, cabozantinib, afibercept, adipotide, denileukin diftitox, everolimus, and temosirolimus, among others.

Other chemotherapeutic or anti-cancer agents include, for example, cytotoxic agents such as platinum coordination agents (for e.g., cisplastin, and carboplatin), antineoplastic enzymes, topoisomerase inhibitors, biological response modifiers, growth inhibitors, hematopoetic growth factors, immune modulators, chemokines, cytokines (for example a granulocyte-macrophage colony stimulating factor (GM-CSF) or FLT3-ligand), cell migration blockers, and inhibitors of angiogenesis. Angiogenesis inhibitors include, but are not limited to, angiostatin, endostatin, thrombospondin, platelet factor 4, Cartilage-derived inhibitor (CDI), retinoids, Interleukin-12, tissue inhibitor of metalloproteinase 1, 2 and 3 (TIMP-1, TIMP-2, and TIMP-3) and proteins that block the angiogenesis signaling cascade, such as anti-VEGF (Vascular Endothelial Growth Factor) and IFN-alpha.

Alternatively, the compounds may be used to augment the effects of radiation therapy, which may be delivered locally to the tumor or to the whole body. In yet another embodiment, the additional medication is hormonal therapy. The term "hormonal therapy" as used herein refers to a medication that blocks cancer cell growth by interfering with the activity of specific hormones such as estrogen, testosterone, or dihydrotestosterone.

Combination Therapy for Viral Infections

When the compounds are used in combination, then at least one additional therapeutic agent may be an anti-viral vaccine, for example without limitation, anti-HIV-vaccine, anti-HCV vaccine, and anti-HPV vaccine. Other suitable antiviral agents contemplated for use in combination with the compounds of the present invention comprise nucleoside and nucleotide reverse transcriptase inhibitors (NRTIs), non-nucleoside reverse transcriptase inhibitors (NNRTIs), protease inhibitors, and other anti-viral drugs. Examples of NRTIs include zIDO1 vuine (AZT); didanosine (ddI); zalcitabine (ddC); stavudine (d4T); lamivudine (3TC); abacavir (1592U89); adefovir diplovixil [bis(POM)-PMEA]; lobucavir (BMS-180194); BCH-10652; emitricitabine [(−)-FTC]; beta-L-FD4 (also known as beta-L-D4C and beta-L-2',3'dicleoxy-5-fluoro-cytidene); DAPD, ((−)0b eta-D-2,6,-diamino-purine dioxolane,); and Iodenosine (FddA). Typical suitable NNRTIs include nevirpine (BI-RG-587); delaviradine (BHAP, U-90152); efavirnz (DP-266); PNU-142721; AG-1549; MKC-442 (1-(ethoxy-methyl)-5-(1-methylethyl)-6-(phyenylmethyl)-2,4(1H,3H)-pyrimedinedione); and (+)-calanolide A(NSC-675451) and B. Typical suitable protease inhibitors include saquinavir (Ro 31-8959); ritonavir (ABT-538); indinavir (MK-639); nclfnavir (AG-1343); amprenavir (141W94); lasinavir (BMS-234475); DMP-450; BMS-2322623; ABT-378; and AG-1 549. Other antiviral agents include hydroxyurea, ribavarin, IL-2, IL12, perntasufide and Yissum Project No. 11607. In one aspect, the viral vaccine is an anti-HPV vaccine.

Combination Therapy for Bacteria and Parasitic Infections

When the compounds are used in combination, then at least one additional therapeutic agent may be a anti-bacterial agent (including without limitation, a vaccine against tuberculosis or antibitoics) or an anti-parasitic therapeutic agent, such as anti-parasitic vaccine, for example without limitation, a vaccine against malaria. Other compounds that may be used in combination with compounds of the invention include without limitation chloroquinine, hydrocholoroquinine, ferroquinine, Artemisinin, Atovaquone/Proguanil, Doxycycline, Mefloquine (Lariam), and Primaquine. Antimalarial vaccines include but are not limited to RTS,S malaria vaccine, RTS,S-AS01 delayed fractional third dose, Adenovirus (Ad35) vectored CS and RTS,S-AS01 in heterologous prime-boost regimen, ChAd63/MVA ME-TRAP, ChAd63/MVA ME-TRAP+Matrix M™, PfSPZ, polyepitope DNA EP1300, PfCelTOS FMP012, CSVAC, ChAd63/MVA (CS; ME-TRAP), ChAd63/MVA (CS; ME-TRAP, AMA-1), RTS,S/AS$_{01}$B+ChAd63 and MVA encoding ME-TRAP, EBA175 RII, FMP2.1/AS01B (AMA-13D7 *E. coli* expressed in AS01B adjuvant), GMZ2, pfAMA1-DiCo, P27A, MSP3 [181-276] field, SE36, ChAd63 AMAl/MVA AMA1, NMRC-M3V-Ad-PfCA, NMRC-M3V-D/Ad- PfCA Prime/Boost, PfPEBS, ChAd63/AMA MVA/AMA1 +alhydrogel/CPG7909, ChAd63 MSP1/MVA MSP1, Pfs25-EPA, Pfs25 VLP, ChAd63/MVA PvDBP. Anti-tuberculosis vaccines include but are not limited to bacilli Calmetter-Guérin (BCG), MVA85A, rBCG30, 72F fusion protein, ESAT6-Ag85b fusion protein, *M. tuberculosis* antigens—antigens 85A, 85B and TB10.4. In one aspect, the anti-parasitic vaccine is an anti-malaria vaccine.

Combination Therapy—other Diseases

The present invention also relates to the use of compounds of the invention to be used with one or more medicaments or therapies to treat any disease that is treateable by use of the compounds of the invention. For example, the compounds may be used in combination with B-cell depletion therapy, targeted drug, targeted antibody, vaccines, or other therapeutic agents for inflammatory diseases, including without limitation, arthritis, osteoarthrisitis, rheumatoid arthritis, juvenile arthritis, spinal arthritis, psoriatic arthritis, ankylosing spondylitis, fibromyaligia, gout, etc. Non-limiting examples of therapies used in combination with compounds of the invention include steroids (such as prednisone, dexamethasone), NSAIDS (such as Celebrex, Meloxicam, ibuprofen), targeted antibodies or antibody fragments such (Enbrel, Remicade/Infliximab, Humira, Rituxan/antiCD20), antimetabolites and antifolates (such as Methotrexate) etc. Compounds of the invention may also be used in combination for treatment of autoimmune diseases (for example, Alzheimer's disease, Huntington's disease, Parkinson's disease, multiple sclerosis etc), cardiovascular diseases (for example, coronary artery disease, peripheral artery disease, atherosclerosis and ischemia), and kidney disease (such as end stage renal disease). It is intended that where appropriate that combination therapies described elsewhere in the specification is to be used in combination or the treatment of the diseases listed herein.

The compounds or a metabolite thereof, or a pharmaceutically acceptable salt or prodrug thereof, and/or other medication(s) or therapeutic agent(s) may be administered in a single composition. However, the present invention is not so limited. The compounds of the invention may be administered sequentially, consecutively, alternatingly, or in any manner a healthcare professional or a physician deems appropriate. In other embodiments, the compounds or a metabolite thereof, or a pharmaceutically acceptable salt or prodrug thereof may be administered in one or more separate formulations from other compounds of the invention or chemotherapeutic agents, cancer vaccine, targeted drug, targeted antibody, hormonal therapy or other agents as desired.

Reference are made in detail to certain embodiments of the invention, examples of which are illustrated in the accompanying structures and formulae. It is intended that any part of the disclosure may be read in combination with any other part of the disclosure, unless otherwise apparent from the text. While the invention is described in conjunction with the enumerated embodiments, it will be understood that they are not intended to limit the invention to those embodiments. It is specifically intended to cover all alternatives, modifications, and equivalents which maybe included within the scope of the present invention as defined by the claims. At various places in the present specification, substituents of compounds of the invention may be disclosed in groups. It is specifically intended that the invention include each and every individual sub combination of the members of such groups.

It is further appreciated that certain features of the invention, which are, for clarity, described in the context of separate embodiments, can also be provided in combination in a single embodiment. Conversely various features of the invention which are, for brevity, described in the context of a single embodiment can also be provided separately or in any suitable subcombination.

Furthermore, where the claims recite a composition, it is to be understood that methods of using the composition for any of the purposes disclosed herein are included, and methods of making the composition according to any of the methods of making disclosed herein or other methods known in the art arc included, unless otherwise indicated or unless it would be evident to one of ordinary skill in the art that a contradiction or inconsistency would arise. In addition, the invention encompasses compositions made according to any of the methods for preparing compounds and compositions disclosed herein.

EXAMPLES

The following examples are illustrative only and are not intended to limit the present invention. The following examples are only meant to suggest a method of practicing the invention. One of skill in the art will recognize that the chemical reactions described may be readily adapted prepare a number of other compounds of the invention, and alternative methods for preparing the compounds of this invention are deemed to be within the scope of this invention. For example, the synthesis of the non-exemplified compounds according to the invention may be successfully performed by modifications apparent to the skilled in the art, e.g., by appropriately protecting the interfering groups, by utilizing other suitable reagents known in the art than those described, and or making routine modifications of reaction conditions. Alternatively, other reactions disclosed herein or known in the art will be recognized as having applicability for preparing other compounds of the invention.

| General abbreviations and symbols | |
|---|---|
| g | gram |
| mg | milligram |
| ng | nano gram |
| L | liter |
| mL | milliliter |
| mol | mole |
| mmol | millimole |
| min | minutes |
| h | hour |
| °C. | degrees Celsius |
| EtOAc | Ethyl acetate |
| HRMS | High resolution mass spectrometry |
| % | percent |
| μM | micromolar |
| mM | millimolar |
| TLC | thin-layer chromatography |
| HPLC | high-performance liquid chromatography |
| GCMS | gas chromatography-mass spectrometry |
| LCMS | liquid chromatography-mass spectrometry |
| GCFID | gas chromatography-flame ionisation detector |
| SM | starting material |
| eq. | equivalent |
| Pd/C | Palladium on charcoal |
| nM | nanomolar |

| Spectroscopic abbreviations and symbols | |
|---|---|
| $^1$H NMR | proton nuclear magnetic resonance spectrum |
| δ (ppm) | chemical shift relative to tetramethylsilane ($\delta_{TMS}$ = 0) |
| s | singlet |
| d | doublet |
| dd | doublet of doublet |
| t | triplet |
| dt | doublet of triplets |
| q | quartet |
| m | multiplet |
| br | broad |
| Hz | Hertz |
| J | coupling constant |
| ddd | double doublet of doublet |
| MHz | Mega Hertz |

General Synthetic Procedures

Procedure A:

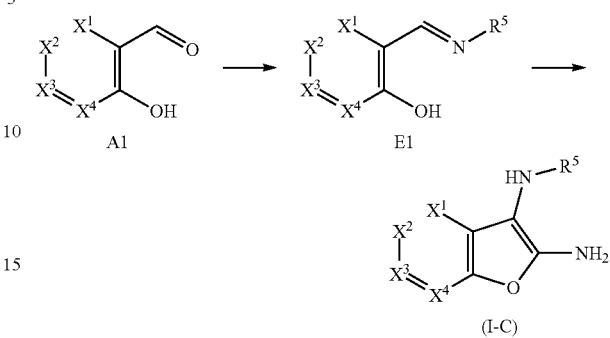

A mixture of compound A1 (1.0 mmol equiv.) and an amine ($R^5$—$NH_2$) (1.0 mmol equiv.) was combined in mixed solvents of TFE (20 mL):McCN (20 mL)) and stirred at 25° C. for 1 hr. At the end, the reaction mixture was concentrated and purified by triturating with n-pentane to afford compound E1.

To a stirred solution of E1 (1.0 mmol equiv.) in mixed solvent [DCM (10 mL): TFE (10 mL)] was added TMSCN (3.4 mmol equiv.) at 25° C. The reaction mixture was stirred for 3 h at 25° C. and concentrated. Crude material was triturated with n-pentane to provide (I-C) as solid. A similar procedure can be followed to prepare target molecules of formula (I) starting from optionally substituted amines ($R^5$—$NH_2$) and/or pyridine derivatives, wherein the hydroxyl and the aldehyde functionalities are adjacent to each other.

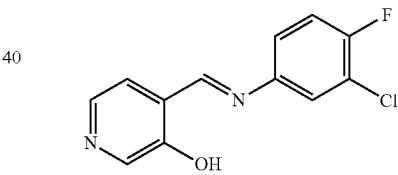

A mixture of 3-hydroxypyridine-4-carboxaldehyde (3 g, 24.39 mmol) and 4-fluoro-3-chloro phenyl amine (3.55 g, 24.39 mmol) was combined in mixed solvents of TFE (20 mL):MeCN (20 mL) and stirred at 25° C., for 1 hr. At the end, the reaction mixture was concentrated and purified by triturating with n-pentane to afford 6 g of 4-{[3-chloro-4-fluorophenylimino]-methyl}-pyridin-3-ol.

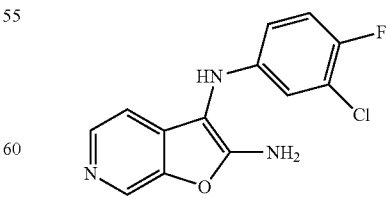

To a stirred solution of 4-{[3-chloro-4-fluoro-phenylimino]-methyl}-pyridin-3-ol (6 g, 24 mmol) in mixed solvent [DCM (10 mL): TFE (10 mL)] was added TMSCN (10.5 mL, 84 mmol) at 25° C. The reaction mixture was stirred for 3 hr at 25° C. and concentrated. Crude material was triturated with n-pentane to provide 4.9 g of $N^3$-(3-chloro-4-fluoro-phenyl)-furo[2,3-c]pyridine-2,3-diamine as a pale pink solid. A similar procedure can be followed to prepare target molecules of formula (I) starting from from optionally substituted amines ($R^5$—$NH_2$) and/or pyridine derivatives, wherein the hydroxyl and the aldehyde functionalities are adjacent to each other.

Procedure B:

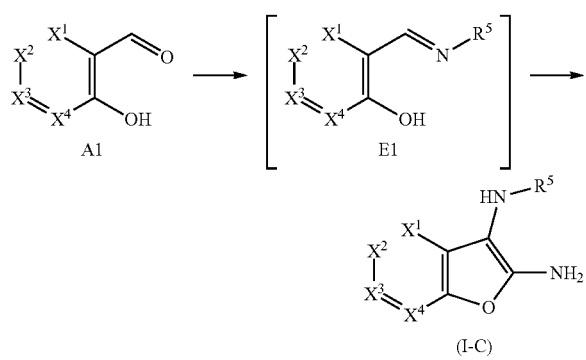

A mixture of compound Al (1.0 mmol quiv.) and an amine ($R^5$—$NH_2$)(1.0 mmol equiv.) was combined in mixed solvents of TFE (20 mL):MeCN (20 mL) and stirred at 25° C., for 2 h. The reaction was monitored by TLC $SiO_2$. At the end, reaction mixture was diluted with DCM (10 mL) and TMSCN (3.4 mmol) was added, and the resulting reaction mixture was stirred for 12 h and concentrated and triturated with EtOAc/pentane to provide compound (I-C) as solid. A similar procedure can be followed to preparetarget molecules of formula (I) starting from optionally substituted amines ($R^5$—$NH_2$) and/or pyridine derivatives, wherein the hydroxyl and the aldehyde functionalities are adjacent to each other.

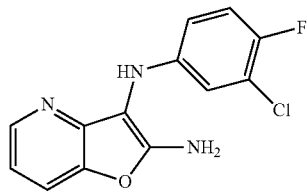 [SMILES: Nc1oc2cccnc2c1Nc1ccc(F)c(Cl)c1]

A mixture of 3-hydroxy pyridine 2-carboxaldehyde (500 mg, 4.065 mmol) and 3-chloro-4-fluoroaniline (591 mg, 4.065 mmol) was combined in TFE (10 mL):MeCN (10 mL) and stirred at 25° C. for 2 hr. The reaction was monitored by TLC SiO2. At the end, reaction mixture was diluted with DCM and TMSCN (2.6 mL, 21.78 mmol) was added. The resulting reaction mixture was stirred for 12 hr and concentrated and triturated with EtOAc/pentane to provide 450 mg of $N^3$-(3-chloro-4-fluorophenyl)-furo[3,2-b]pyridine-2,3-diamine. A similar procedure can be followed to prepare target molecules of formula (1) starting from optionally substituted amine ($R^5$—$NH_2$) and/or pyridine derivatives, wherein the hydroxyl and the aldehyde functionalities are adjacent to each other.

Procedure C:

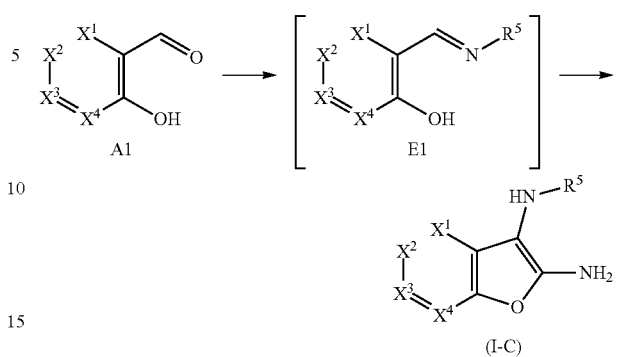

A mixture of compound Al (1.0 mmol eq.) and an amine ($R^5$—$NH_2$) (1 mmol eq.) was combined in solvent mixtures of TFE (20 mL):MeCN (20 mL)) and stirred at 25° C., for 2 h. The reaction was monitored by TLC. At the end of reaction period, reaction mixture was diluted with DCM (10 mL). Next, TMSCN (3.4 mmol eq.) followed by TMSOTf (0.2 mmol eq.) were added to the resulting reaction mixture. The reaction mixture was stirred for 12 h and concentrated under reduced pressure to provide a crude mass which was purified by trituration with EtOAc/pentane forming compound (I-C). A similar procedure can be followed to prepare target molecules of formula (I) starting from from optionally substituted amines ($R^5$—$NH_2$) and/or pyridine derivatives, wherein the hydroxyl and the aldehyde functionalities are adjacent to each other.

Procedure D:

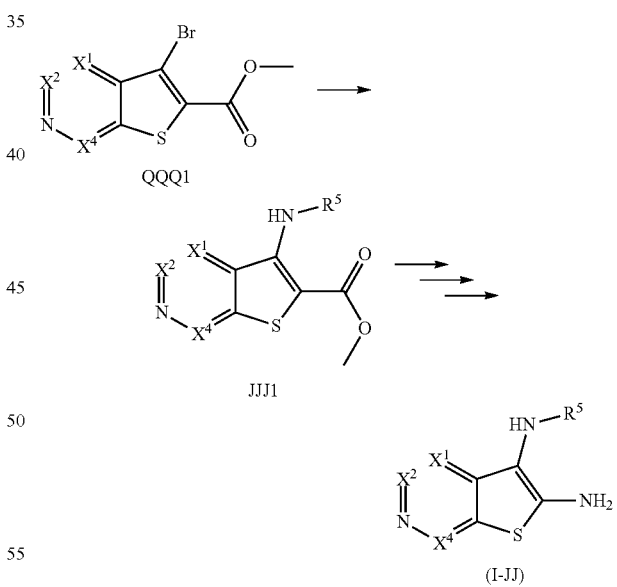

The compound QQQ1 was prepared according to scheme 16 (European Journal of Medicinal Chemistry, 2009, 44, 1893-1899). To a stirred solution of bromo-ester compound QQQ1 (1.0 mmol eq.) dissolved in toluene (5 mL) was added an amine ($R^5$—$NH_2$) (1.4 mmol eq.), $Cs_2CO_3$ (1.5 mmol eq.), BINAP (0.2 mmol eq.) and degassed for 20 min. Next, $Pd_2(dba)_3$ (0.048 mmol eq.) was added to the reaction mixture. The reaction mixture was heated at 100-105° C. for 16 h. The reaction mixture was filtered through a bed of Celite and washed with ethyl acetate. The filtrate was diluted with water and extracted with EtOAc. The combined organic layer was dried over sodium sulfate and further concentrated under reduced pressure resulting in the formation of a crude mass. The resulting mass was purified by column chromatography on silica gel using solvent mixtures of EtOAc and hexane as eluent resulting in the formation of the compound JJJ1 as a solid.

Next, the compound JJJ1 was dissolved in THF (10 mL), TEA (2.5 mmol eq.), and DMAP (0.6 mmol eq.) at 0° C.-5° C. After 10 minutes, Boc-anhydride (2.2 mmol eq.) was added dropwise to the reaction mixture and heated at 50° C.-60° C. for 4 h. After completion of the reaction, water was added to the reaction mixture. The reaction mixture was further extracted with EtOAc. The combined organic layer was dried over sodium sulfate, concentrated under reduced pressure resulting in the formation of a crude mass which was purified by column chromatography on silica gel using solvent mixtures of EtOAc and hexanes as eluent to form Boc-protected compound.

The Boc-protected compound was dissolved in a solvent-mixture of THF (15 mL):MeOH (9 mL):H$_2$O (3 mL) to which LiOH (2.0 mmol eq.) was added at 0° C.-5° C. The reaction mixture was continuously stirred at 0° C.-5° C. for 16 h. Next, the reaction mixture was concentrated under reduced pressure. The resulting residue was diluted with water and acidified with 5% citric acid solution (pH=4.0). The resulting solid precipitate was filtered, washed with water and dried under vacuum forming a corresponding carboxylic acid.

The resulting carboxilic acid was dissolved in tert-BuOH (10 mL). Next DPPA (1.2 mmol eq.) and DIPEA (1.1 mmol eq.) were added to the aforementioned solution at room temperature and the resulting reaction mixture was heated at 100° C. for 2 h. After completion of reaction, the mixture was concentrated under reduced pressure to form a residue which was diluted with water, neutralized with saturated NaHCO$_3$ solution, and extracted with EtOAc. The combined organic layer was dried over sodium sulfate and concentrated under reduced pressure resulting in the formation of a crude mass. The mass was purified by column chromatography on silica gel using solvent mixture of MeOH and DCM as eluent to form the corresponding carbamate.

The resulting carbamate was dissolved in dioxane to which dioxane-HCl solution (4 M; 9.0 mmol eq) was added at 0° C.-5° C. The resulting mixture was stirred for 8 h at 25° C. After completion of the reaction, the reaction mass was concentrated under reduced pressure resulting in the formation of a residue which was diluted with DCM and basified with liq. NH$_3$. The DCM layer was dried over sodium sulfate, concentrated under reduced pressure forming a crude mass which was subsequently purified by column chromatography on silica gel using solvent mixtures of MeOH and DCM as eluent resulting in the formation of a compound (I-JJ) as a solid.

Procedure E:

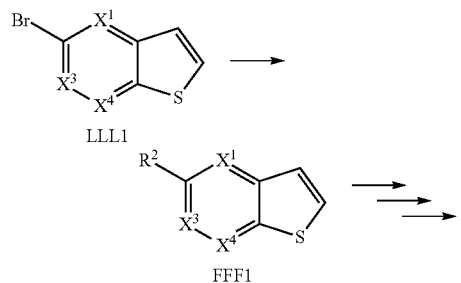

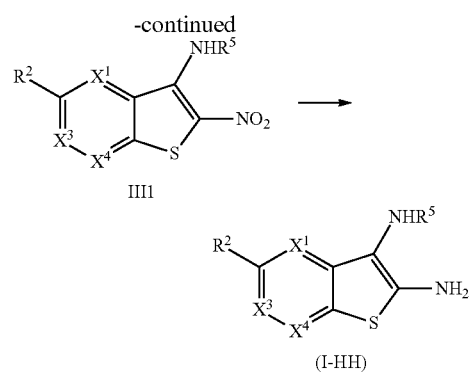

The compound LLL1 was prepared according to scheme 15. A solution of compound LLL1 (1.0 mmol eq.), R$^2$-substituted aryl/heteroarylboronic acid/ester (1.05 mmol eq.), Pd(PPh$_3$)$_4$, (0.05 mmol eq.), potassium carbonate (1.5 mmol eq.) in toluene:water (1:1 mL) mixture was refluxed overnight at 100° C. After completion of the reaction, the mixture was cooled to room temperature, diluted with ethyl acetate, filtered through a Celite bed, and washed with ethyl acetate. The combined filtrates were washed with water and brine. The organic layer was dried over sodium sulfate and concentrate under reduced pressure to give residue which was purified by column chromatography using hexane as eluent on silica gel to form compound FFF1 as a solid.

The compound FFF1 was dissolved in mixture of chloroform:acetic acid (1:1 mL) and cooled to 0° C.-5° C. To the above solution, NBS (1.26 mmol eq.) was added portion wise. The reaction mixture was stirred at room temperature for 48 h. After completion of the reaction, the mass was quenched by a saturated solution of sodium thiosulfate and extracted with chloroform. The combined organic layers were washed with saturated solution of sodium bicarbonate and brine, dried over sodium sulfate and concentrated under reduced pressure forming a residue. The residue was purified by column chromatography using hexane as eluent on silica gel forming a corresponding 3-bromo-compound.

The resulting 3-bromo-compound was dissolved in acetic anhydride (12.7 mmol eq.)the solution was cooled to 0° C. A mixture of fuming nitric acid (6.8 mmol eq.) in acetic acid (3.4 mmol eq.) was added to the above solution and the resulting mass was stirred for 2 h. After completion of reaction, the mixture was quenched in ice-cold water, extracted with DCM, dried over anhydrous sodium sulfate, and concentrated under reduced pressure and formed a residue. The resulting residue was purified by column chromatography using hexane as eluent on silica gel to provide a corresponding 2-bromo-3-nitro compound as solid.

Next, the 2-bromo-3-nitro compound was dissolved in DMF (10 mL) to which an amine (R$^5$—NH$_2$) (2.0 mmol eq.) was added. The reaction mixture was heated at 120° C. for 1 h. After completion of the reaction, the mixture was poured into ice-cold water while stirring resulting in the precipitation of a solid. The solid precipitate was filtered and washed with water. The precipitate was next dried under vacuum and recrystallized with a mixture of DCM and hexane resulting in the formation of compound III1.

Activated 10% Pd/C was added under nitrogen gas at room temperature to a solution of compound III1 in methanol. The reaction mass was stirred for 3-4 h under hydrogen gas (balloon). The reaction mixture was filtered through a Celite bed under nitrogen and washed with methanol. The filtrate was distilled generating a residue which was then crystallized with a DCM and hexane mixture to form compound (I-HH) as a solid.

Procedure F:

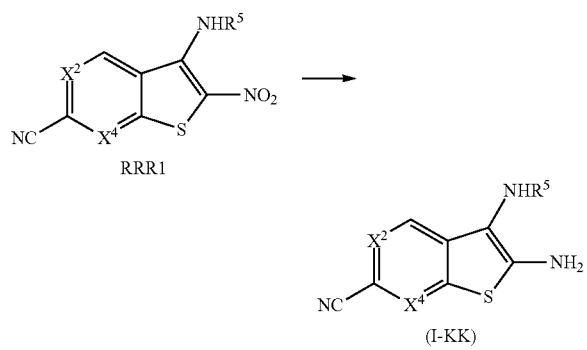

To a stirred solution of compound RRR1 (1.0 mmol eq.) in THF (2 mL) and methanol (2 mL) was added zinc dust (2.0 mmol eq.) and NH$_4$Cl (1.0 mmol eq.) at room temperature. The mixture was stirred for 3 h. The mixture was filtered through a pad of Celite and washed with ethyl acetate. The filtrate was diluted with EtOAc, and then washed with water and brine. The organic layer was dried over sodium sulfate, concentrated under reduced pressure generating a crude mass. The mass was purified by triturating with MTBE and pentane to form a compound (I-KK) as a solid.

Procedure G:

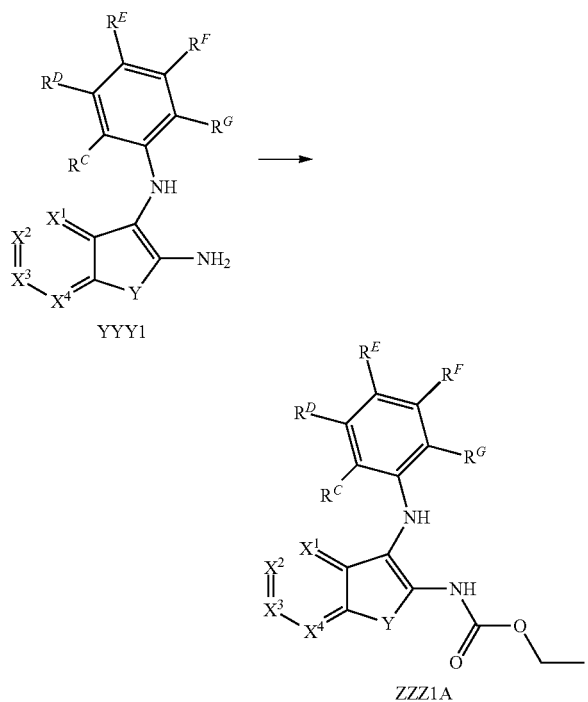

To a stirred solution of compound YYY1 (1.0 mmol eq.) in THF was added pyridine (1.3 mmol eq.) followed by the addition of ethyl chloroformate (1.1 mmol eq.) at 25° C. The reaction mixture was stirred for 3-10 h at 25° C. and concentrated. The crude mass was dissolved in EtOAc and washed first with water followed by a second wash with brine. The mass was next dried over Na$_2$SO$_4$ and concentrated. The mass was subjected to Prep-TLC/trituration to form a solid monocarbamate compound ZZZ1A with a trace of dicarbamate.

Procedure H:

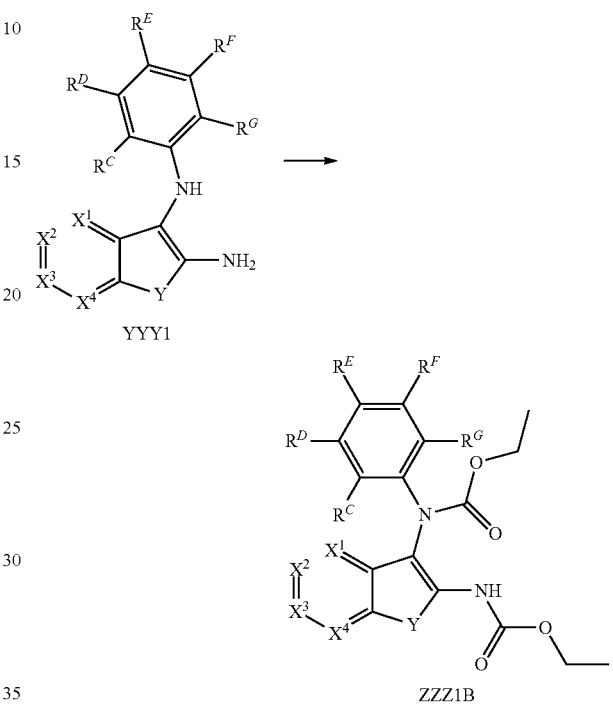

To a stirring solution of compound YYY1 (1.0 mmol eq.) dissolved in THF was added pyridine (10.0 mmol eq.) followed by ethyl chloroformate (8.0 mmol eq.) at 25° C. Reaction mixture was stirred for 20 h at 25° C. and concentrated. The crude material was dissolved in EtOAc, washed thoroughly with water followed by brine, dried over Na$_2$SO$_4$ and concentrated. The crude mass was subjected to Prep-TLC/trituration to afford the major desired dicarbamate compound ZZZ1B along with monocarbamate as a solid.

Procedure I:

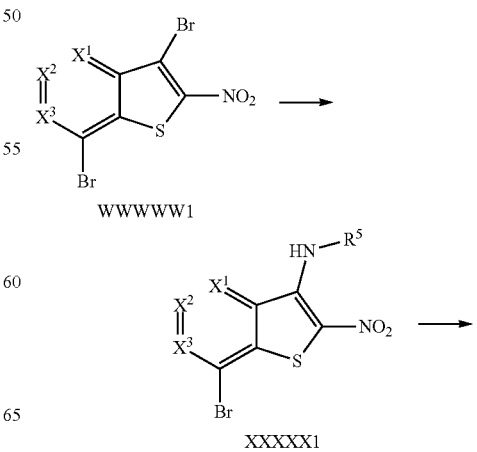

-continued

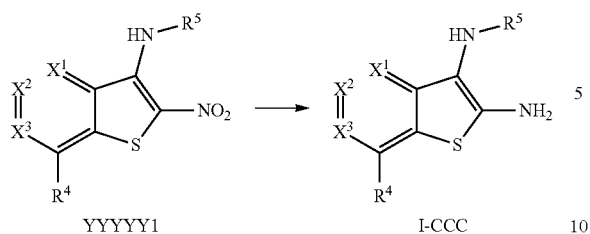

YYYYY1    I-CCC

The compound WWWWW1 was prepared according to scheme 27. Briefly, to a stirred solution of compound WWWWW1 (1.0 mmol eq.) in DMF (5 mL) was added an amine ($R^5$—$NH_2$) (3.0 mmol eq.) (0.672 g, 4.62 mmol) at room temperature. The reaction mass was heated at 100-120° C. and stirring continued for 12 h. After completion of reaction, the reaction mass was quenched with ice-water. The solid was precipitated, filtered and washed with water to generate a wet solid mass which was dried under hot air oven to afford compound ,0000(1 as a solid.

The compound XXXXX1 was dissolved in a mixture of DMF (5 mL) and $H_2O$ (1 mL). $R^4$-substituted aryl/heteroarylboronic acid/ester (1.3 mmol eq.), $K_3PO_4$ (3.0 mmol eq.) and Pd(PPh$_3$)$_4$ (0.09 mmol eq.) were added to XXXXX1 at room temperature. The resulting reaction mixture was stirred at 100-120° C. for 2 h. Completion of the reaction was monitored by TLC. After completion of reaction, the reaction mass was cooled to room temperature and filtered through Celite bed. The filtrate was extracted with ethyl acetate. The extract was washed with brine and dried over sodium sulfate to remove moisture. The extract as further concentrated under reduced pressure to remove solvents yielding a crude mass which was purified by column chromatography on silica gel using solvent mixture of EtOAc/hexane as eluent to form YYYYY1 as a solid.

10% Pd/C was added under nitrogen gas at room temperature to a stirring solution of compound YYYYY1 (1.0 mmol eq.) dissolved in methanol (8 mL). Then nitrogen gas was replaced by hydrogen gas balloon and stirring was further continued at ambient temperature for 3-4 h. After completion of reaction, the reaction mixture was filtered through Hyflo bed and washed with methanol. The filtrate was evaporated under reduce pressure to give rise to a crude mass which was purified by trituration using pentane to form a compound (I-CCC) as a solid.

Procedure J:

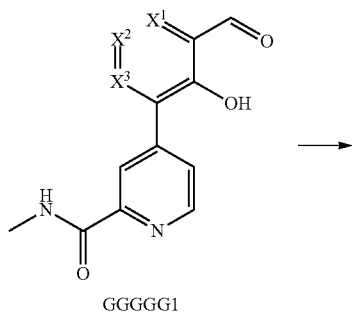

GGGGG1

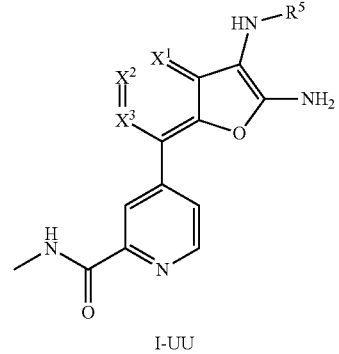

I-UU

An amine ($R^5$—$NH_2$) (1 mmol eq.), TMSCN (5.2 mmol eq.), and TMSOTf (0.2 mmol eq.) were added at room temperature in a sealed tube to a stirred solution of compound GGGGG1 (1 mmol eq.) in DCM (6.0 mL). The reaction mixture was stirred for 1 h at 40° C., followed by addition of 10 mmol NH$_4$OAc buffer (3.0 mL). The reaction mixture was stirred for 12 h and was filtered through a sintered funnel. The filtered solid was washed with MTBE, hexanes, Ethyl Acetate or mixtures thereof to remove trace impurities to generate compound (I-UU) as solid.

Procedure K:

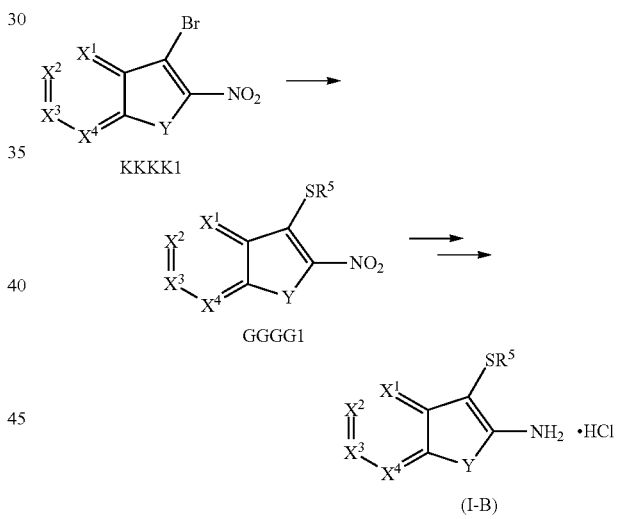

The compound KKKK1 was prepared according to scheme 18. Briefly, to a stirred solution of KKKK1 (1.0 mmol eq.) in dioxane (1 mL) was added dropwise $R^5$-substituted thiophenol or phenol in a mixture of solution of NaOH (1.1 mmol eq.), H2O (1 mL) and dioxane (10 mL) at 0° C., and the reaction mixture was stirred for 1-2 h. Reaction mass was diluted with water, extracted with ethyl acetate and washed with brine. The organic layers were dried over sodium sulfate, concentrated under reduced pressure to give residue which was purified by column chromatography on silica gel using suitable mixture of solvents to afford GGGG1 as solid.

10% Pd/C was added under nitrogen gas at room temperature to a stirring solution of compound GGGG1 (1.0 mmol eq.) dissolved in ethyl acetate (8 mL). Then, nitrogen gas was replaced by hydrogen gas balloon and stirring was further continued at ambient temperature for 10-12 h. After completion of reaction, the reaction mixture was filtered through Hyflo bed and washed with methanol. The filtrate was evaporated under reduced pressure to form to a crude mass which was purified by column chromatography on silica gel using solvent mixtures to form an amine compound. The amine compound was dissolved in diethyl ether (5 mL). To this solution was added a saturated solution (10 mL) of HCl in diethyl ether. The reaction mass was stirred at room temperature resulting in precipitation of a solid. The precipitate was separated by decantation and the solid precipitate was dried under vacuum to form compound (I-B).

Example 1

Synthesis of $N^3$-(3-chloro-4-fluorophenyl)furo pyridine-2,3-diamine (Compound 1)

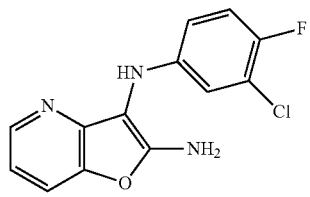

3-Hydroxypyridine-2-carboxaldehyde (500 mg, 4.065 mmol) was taken in mixed solvent (TFE (10 mL): MeCN (10 mL)) and 3-chloro-4-fluoroaniline (591 mg, 4.065 mmol) was added to it at 25° C., resulting mixture was stirred at this temperature for 2 hr. TLC indicated no SM remained, to this imine was added TMSCN (2.6 mL, 21.138 mmol) at 25° C. After stirring the reaction mixture for 12 hr at 25° C., it was concentrated and triturated with EtOAc/pentane to yield 450 mg of $N^3$-(3-chloro-4-fluoro-phenyl)-furo[3,2-b]pyridine-2,3-diamine (39% Yield) LCMS: 278 (M+H), HPLC: 98.64%, $^1$H-NMR (DMSO-d$_6$, 400 MHz): δ 8.07 (d,1H, J=4.8 Hz), 7.52 (d, 1H, J=7.8 Hz), 7.12-7.07 (m, 2H,), 6.87-6.85 (m, 1H), 6.77 (s, 2H), 6.56-6.55 (m, 1H), 6.51-6.49 (m, 1H).

Example 2

Synthesis of $N^3$-(3-Chloro-4-fluoro-phenyl)-furo[2,3-c]pyridine-2,3-diamine (Compound 2)

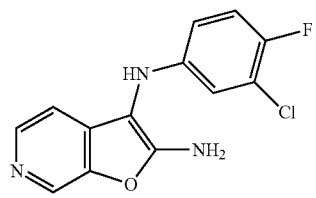 [SMILES: Nc1oc2cnccc2c1Nc1ccc(F)c(Cl)c1]

Step 1: 3-Methoxymethoxy-pyridine

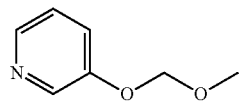

To a stirred solution of 3-hydroxypyridine (60 g, 662.9 mmol) in THF:DMF (120:280 mL) at 0° C. was added t-BuOK (81.8 μm, 729.28 mmol) portion-wise. After stirring the reaction mixture for 15 min, methoxymethyl chloride (52 mL, 696.13 mmol) was added to it at 0° C. and the resulting mixture was stirred for 1 hr at 25° C. Reaction mixture was diluted with water and extracted with ethyl acetate (4×500 mL). The organic layer was dried over anhydrous sodium sulfate, concentrated under reduced pressure to afford 100 g crude which was purified by column chromatography using silica (100-200 mesh) and 10% EtOAc-hexane as eluent to afford 3-methoxymethoxy-pyridine (54 g) as pale brown liquid. LCMS: 140 (M+H).

Step 2: 3-Methoxymethoxy-pyridine-4-carbaldehyde

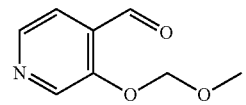

To a stirred solution of 3-methoxymethoxypyridine (2 g, 14.3885 mmol) in anhydrous THF (40 mL) was added TMEDA (1.83 g, 15.82 mmol) at 25° C. The reaction mixture was cooled to −78° C., n-BuLi (7.3 mL, 15.82 mmol, 2.17 M in hexane) was added dropwise manner maintaining the temperature −78° C. After stirring for 2 hr at −78° C., DMF (1.52g, 20.86 mmol) was added to it and stirred for 2 hr at 25° C. Reaction mixture was cooled to −40° C. and saturated ammonium chloride solution was added drop wise. The reaction mass was extracted with ethyl acetate (250 mL×2), EtOAc part was washed with water followed by brine, dried over sodium sulfate and concentrated under reduced pressure to afford 3 g of crude product which was passed through a pad of silica (100-200 mesh) using 10% EtOAc-hexane as eluent to afford 1.6 g of 3-methoxymethoxy-pyridine-4-carbaldehyde as pale yellow liquid. GC-MS: 167 (m/z).

Step 3: 3-Hydroxy-pyridine-4-carbaldehyde

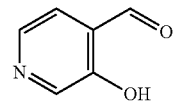

To a stirred solution of 3-methoxymethoxypyridine-4-carbaldehyde (11 g, 65.83 mmol) in THF (50 mL) was added 3N HCl (100 mL) and stirred at 60° C. for 1 hr. The reaction mixture was cooled under ice bath and pH was adjusted to 7 with solid K$_2$CO$_3$. Resulting mixture was extracted with EtOAc (250 mL×5). The organic layer was dried over sodium sulfate, concentrated under reduced pressure to afford 15g of crude which was purified by column chromatography using silica gel (100-200 mesh) and 23% EtOAc/hexane as eluent to afford 4 g of 3-hydroxy-pyridine-4-carbaldehyde as pale yellow solid. GC-MS: 123 (m/z), $^1$H-NMR (DMSO-d$_6$, 400 MHz): δ 11.04 (bs, 1H), 10.37 (s, 1H), 8.46 (s, 1H), 8.20 (d, 1H, J=4.88 Hz), 7.46 (d, 1H, J=4.88Hz). GC-FID: 99.51%.

153

Step 4: 4-{[3-Chloro-4-fluoro-phenylimino]-methyl}-pyridin-3-ol

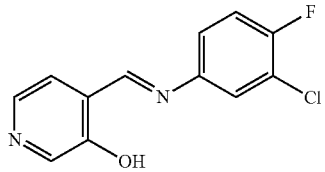 [SMILES: Oc1cnccc1/C=N/c1ccc(F)c(Cl)c1]

3-Hydroxypyridine-4-carbaldehyde (3 g, 24.39 mmol) was taken in mixed solvent (TFE (20 mL):MeCN(20 mL)) and 4-fluoro-3-chloroaniline (3.55 g, 24.39 mmol) was added to it at 25° C. The resulting mixture was stirred at this temperature for 1 hr. The reaction mass was concentrated and purified by triturating with n-pentane to afford 6 g of 4-{[3-chloro-4-fluoro-phenylimino]-methyl}-pyridin-3-o 1) LCMS: 251.2 (M+H).

Step 5: $N^3$-(3-Chloro-4-fluoro-phenyl)-furo[2,3-c]pyridine-2,3-diamine

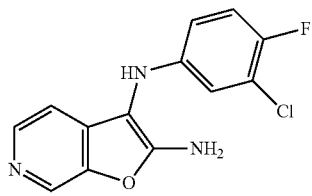

To a stirred solution of 4-{[3-chloro-4-fluoro-phenylimino]-methyl}-pyridin-3-ol (6 g, 24 mmol) in mixed solvent [DCM (10 mL):TFE (10 mL)] was added TMSCN (10.5 mL, 84 mmol) at 25° C. The reaction mixture was stirred 3 hr at 25° C., concentrated, and the crude material was triturated with n-pentane to provide 4.9 g (73% yield) of $N^3$-(3-chloro-4-fluoro-phenyl)-furo[2,3-c]pyridine-2,3-diamine as pale pink solid. LCMS: 278 (M+H), HPLC: 98.65%, $^1$H-NMR (DMSO-$d_6$, 400 MHz): δ 8.41 (s, 1H), 8.06 (d, 1H, J=5.08Hz), 7.14-7.10 (m, 2H), 6.91 (s, 2H), 6.86 (d, 1H, J=5.08 Hz), 6.56-6.54 (m, 1H), 6.48-6.45 (m, 1H).

Example 3

Synthesis of (2-amino-3-((3-chloro-4-fluorophenyl)amino)-7-methylfuro[2,3-c]pyridin-4-yl)methanol (Compound 56)

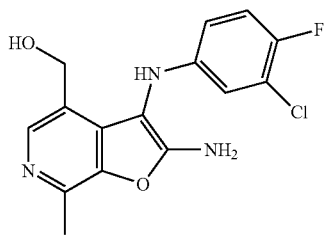 [SMILES: Cc1ncc(CO)c2c(Nc3ccc(F)c(Cl)c3)c(N)oc12]

154

Step 1: 4-{[(E)-3-Chloro-4-fluoro-phenylimino]-methyl}-5-hydroxymethyl-2-methyl-pyridin-3-ol

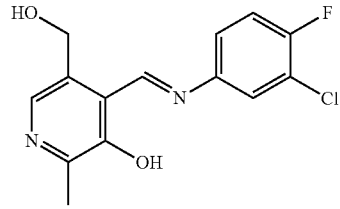 [SMILES: Cc1ncc(CO)c(/C=N/c2ccc(F)c(Cl)c2)c1O]

3-Hydroxy-5-hydroxymethyl-2-methyl-pyridine-4-carbaldehyde hydrochloride (250 mg, 1.2277 mmol) was taken in mixed solvent (TFE (3 mL):MeCN (3 mL)), 4-fluoro-3-chlorophenylamine (178 mg, 1.2277 mmol) was added to it at 25° C., and the resulting mixture was stirred at this temperature for 3 hr. The reaction mass was concentrated, dissolved in EtOAc, washed with sodium bicarbonate solution, dried over $Na_2SO_4$, and concentrated to afford 100 mg of 4-{[(E)-3-chloro-4-fluoro-phenylimino]-methyl}-5-hydroxymethyl-2-methyl-pyridin-3-ol. LCMS: 295 (M+H)

Step 2: (2-amino-3-((3-chloro-4-fluorophenyl)amino)-7-methylfuro[2,3-c]pyridin-4-yl)methanol

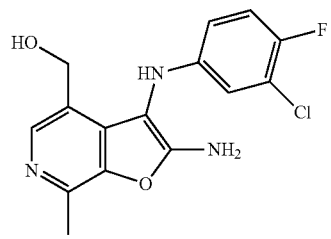 [SMILES: Cc1ncc(CO)c2c(Nc3ccc(F)c(Cl)c3)c(N)oc12]

To a stirred solution of 4-{[(E)-3-chloro-4-fluoro-phenylimino]-methyl}-5-hydroxymethyl-2-methyl-pyridin-3-ol (100 mg, 0.3401 mmol) in mixed solvent [DCM (2 mL):TFE (2 mL)] was added TMSCN (0.149 mL, 1.19 mmol) at 25° C. The reaction mixture was stirred for 4 hr at 2° C. and concentrated. The crude material was triturated with n-pentane followed by MTBE to yield 30 mg (27% yield) of [2-amino-3-(3-chloro-4-fluoro-phenylamino)-7-methyl-furo[2,3-c]pyridin-4-yl]-methanol. LCMS: 322 (M+H), HPLC: 98.82%, $^1$H-NMR (DMSO-$d_6$, 400 MHz): δ 7.94 (s, 1H), 7.12 (t, 1H, J=9 Hz), 6.89 (s, 1H), 6.78 (s, 2H), 6.54-6.53 (m, 1H), 6.45-6.43 (m, 1H), 4.92 (s, 1H), 4.45 (s, 2H), 2.46 (s, 3H).

Example 4

Synthesis of 4-Chloro-$N^3$-(3-chloro-4-fluoro-phenyl)-furo[2,3-c]pyridine-2,3-diamine (Compound 57)

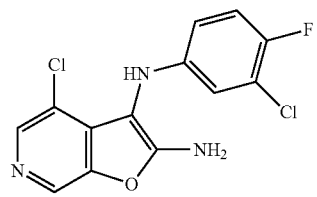 [SMILES: Nc1oc2cncc(Cl)c2c1Nc1ccc(F)c(Cl)c1]

Step 1: 3-chloro-5-methoxymethoxy-pyridine

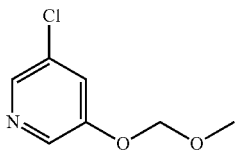

To a stirred solution of 3-chloro-5-hydroxypyridine (500 mg, 3.86 mmol) in THF:DMF (1 mL:2.3 mL) at 0° C. was added SuOK (480 mg, 4.24 mmol) portion-wise. After stirring the reaction mixture for 15 min, methoxymethyl chloride (320 mg, 4.05 mmol) was added to it at 0° C. and the resulting mixture was stirred for 0.5 hr at 25° C. The reaction mixture was diluted with water and extracted with ethyl acetate (2×50 mL). The organic layer was dried over anhydrous sodium sulfate, concentrated under reduced pressure to afford the crude which was purified by column chromatography using silica (100-200 mesh) and 10% EtOAc-hexane as eluent to afford 3-chloro-5-methoxymethoxy-pyridine (200 mg) as pale brown liquid.

Step 2: 3-Chloro-5-methoxymethoxy-pyridine-4-carbaldehyde

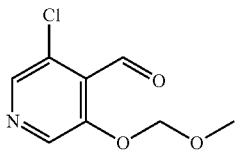

To a stirred solution of 3-chloro-5-methoxymethoxypyridine (500 mg, 2.89 mmol) in anhydrous THF (5 mL) was added LDA (1 M soln, 4.05 mL) at −78° C. After stirring for 30 min at −78° C., N-formyl-piperidine (650 mg, 5.78 mmol) was added to it and stirred for 2 hr at −78° C. The reaction mixture was quenched with water, extracted with ethyl acetate (50 mL×2). The EtOAc part was washed with water followed by brine, dried over sodium sulfate and concentrated under reduced pressure to afford the crude which was passed through a pad of silica (100-200 mesh) using 10% EtOAc-hexane as eluent to afford 250 mg of crude 3-chloro-5-methoxymethoxy-pyridine-4-carbaldehyde as pale yellow liquid. GCMS: 201 (m/z).

Step 3: 3-Chloro-5-hydroxy-pyridine-4-carbaldehyde

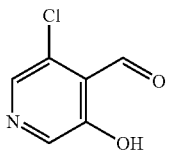

To a stirred solution of 3-chloro-5-methoxymethoxypyridine-4-carbaldehyde (450 mg, 2.2388 mmol) in THF (4 mL) was added 3N HCl (4 mL) and stirred at 60° C. for 2 hr. The reaction mixture was cooled under ice bath and pH was adjusted to 7 with solid $K_2CO_3$. The resulting mixture was extracted with EtOAc (50 mL×3). The organic layer was dried over sodium sulfate, concentrated under reduced pressure to afford the crude which was purified by column chromatography using silica gel (100-200 mesh) and 7% EtOAc/hexane as eluent to afford 110 mg of 3-chloro-5-hydroxy-pyridine-4-carbaldehyde. LCMS: 156 (M−H).

Step 4: 5-Chloro-4-{[3-chloro-4-fluoro-phenylimino]-methyl}-pyridin-3-ol

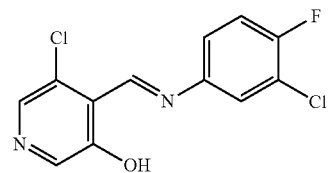 [SMILES: Oc1cncc(Cl)c1/C=N/c1ccc(F)c(Cl)c1]

3-Chloro-5-hydroxy-pyridine-4-carbaldehyde (110 mg, 0.69 mmol) was taken in mixed solvent [TFE (1.5 mL): MeCN(1.5 mL)] and 4-fluoro-3-chloro phenyl amine (100 mg, 0.69 mmol) was added to it at 25° C., and the resulting mixture was stirred at this temperature for 2 hr. The reaction mass was concentrated and purified by triturating with n-pentane to afford 100 mg of 5-chloro-4-{[3-chloro-4-fluoro-phenylimino]-methyl}-pyridin-3-ol. LCMS: 285 (M+H).

Step 5: 4-Chloro-$N^3$-(3-chloro-4-fluoro-phenyl)-furo[2,3-c]pyridine-2,3-diamine

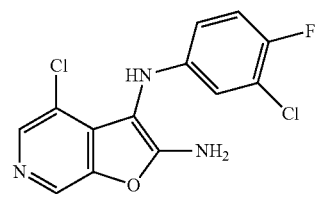 [SMILES: Nc1oc2cncc(Cl)c2c1Nc1ccc(F)c(Cl)c1]

To a stirred solution of 5-chloro-4-{[3-chloro-4-fluoro-phenylimino]-methyl}-pyridin-3-ol (100 mg, 0.35 mmol) in mixed solvent [DCM (1.5 mL): TFE (1.5 mL)] was added TMSCN (120 mg, 1.23 mmol) at 25° C. The reaction mixture was stirred for 3 hr at 25° C., concentrated, and crude material was triturated with DCM/MeCN to yield 20 mg (18% yield) of 4-chloro-$N^3$-(3-chloro-4-fluoro-phenyl)-furo[2,3-c]pyridine-2,3-diamine as off white solid. LCMS: 312 (M+H), HPLC: 97.01%, $^1$H-NMR (DMSO-$d_6$, 400 MHz): δ 8.37 (s, 1H), 8.03 (s, 1H), 7.25 (s, 2H), 7.11(t, 1H, J=9.04 Hz), 7.06 (s, 1H), 6.58-6.57 (m, 1H), 6.47-6.45 (m, 1H).

Example 5

Synthesis of N³-(3-Chloro-4-fluoro-phenyl)-5-methoxy-furo[2,3-c]pyridine-2,3-diamine (Compound 64)

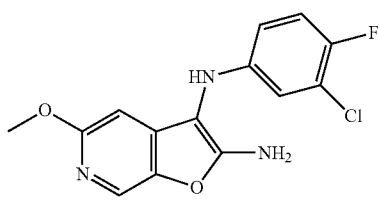 [SMILES: COc1cc2c(Nc3ccc(F)c(Cl)c3)c(N)oc2cn1]

Step 1: 5-Bromo-2-methoxy-pyridine

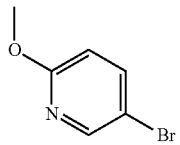

To a stirred solution of 2-methoxypyridine (2 g, 18.33 mmol) in MeCN (54 mL) was added NBS (3.9 g, 21.998 mmol) at 0° C. The reaction mixture was stirred for 16 hr. The reaction mass was filtered through a pad of silica and the filtrate was evaporated to provide the crude product. Column chromatography rendered 2 g of 5-bromo-2-methoxypyridine.

Step 2: 2-Methoxy-5-(4,4,5,5-tetramethyl-[1,3,2]dioxaborolan-2-yl)-pyridine

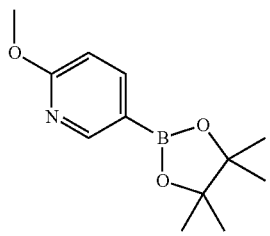 [SMILES: COc1ccc(B2OC(C)(C)C(C)(C)O2)cn1]

5-Bromo-2-methoxypyridine (5 g, 26.59 mmol), bis(pinacolato)diborane (10.13 g, 39.89 mmol) and potassium acetate (10.44 g, 106 mmol) were taken in dry toluene (60 mL) and degassed with nitrogen for 20 min. Pd(dppf)Cl₂.DCM (2.17 g, 2.66 mmol) was added to the reaction under nitrogen atmosphere and the resulting mixture was refluxed for 2 hr. The reaction progress was monitored by TLC. After completion of the reaction, the mixture was cooled to 25° C. and filtered through a Celite® reagent pad. Filtrate was diluted with ethyl acetate (200 mL), washed with water followed by brine, dried over Na₂SO₄ and concentrated under reduced pressure to provide the crude which was purified by silica gel (100-200 mesh) column chromatography using 10% EtOAc in hexane as eluent to afford 3.6 g of 2-methoxy-5-(4,4,5,5-tetramethyl-[1,3,2]dioxaborolan-2-yl)-pyridine.

Step 3: 6-Methoxy-pyridin-3-ol

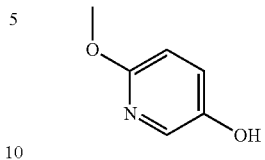

To a stirred suspension of sodium perborate tetrahydrate (6.87 g, 44.68 mmol) in water was added 2-methoxy-5-(4,4,5,5-tetramethyl-[1,3,2]dioxaborolan-2-yl)-pyridine (3.5 g, 14.68 mmol) in THF (70 mL) at room temperature. The resulting reaction mixture was stirred for 2 hr at room temperature. The reaction mass was extracted with ethyl acetate (200 mL), washed with brine dried over Na₂SO₄ and concentrated under reduced pressure to provide the crude which was purified by silica gel (100-200 mesh) column chromatography using 20% EtOAc in hexane as eluent to afford 2.4 g of 6-methoxy-pyridin-3-ol. LCMS: 126 (M+H).

Step 4: 2-Methoxy-5-methoxymethoxy-pyridine

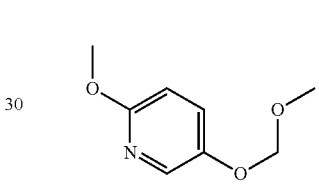

To stirred solution of 6-methoxypyridin-3-ol (2.4 g, 19.20 mmol) in THF:DMF (4 mL: 9 mL) was added potassium tert-butoxide (2.37 g, 21.12 mmol) at 0° C. The reaction mixture was stirred for 15 min at 0° C. and methoxymethylene chloride (1.6 g, 20.16 mmol) was added dropwise at 0° C. The reaction mixture was allowed to stir 40 min at room temperature. The reaction mass was diluted with ethyl acetate (100 mL), washed with water followed by brine dried over Na₂SO₄ and concentrated under reduced pressure to provide the crude which was purified by silica gel (100-200 mesh) column chromatography by using 10% EtOAc in hexane as eluent to afford 2 g of 2-methoxy-5-methoxymethoxypyridine. LCMS: 170 (M+H).

Step 5: 2-Methoxy-5-methoxymethoxy-pyridine-4-carbaldehyde

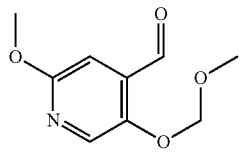

To a stirred solution of 2-methoxy-5-methoxymethoxy-pyridine (1.7g, 10.05 mmol) in THF (17 mL) was added TMEDA (1.65 mL, 11.05 mmol) and reaction mixture was cooled to −78° C. n-BuLi (2.17 M, 5.09 mL) was then added in dropwise at −78° C. Then reaction mixture was stirred for 1 hr at −78° C. DMF (1.2 mL, 14.57 mmol) was then added in dropwise at −78° C. Then reaction mixture was stirred for 1 hr at −78° C. The reaction progress was monitored by TLC. The reaction mixture was cooled to room temperature and extracted with ethyl acetate (100 mL). The combined organic layer was dried over Na$_2$SO$_4$ and concentrated under reduced pressure to crude material. The crude material was purified by silica gel (100-200 mesh) column chromatography by eluting with 8% EtOAc in hexane. The collected fractions were evaporated to afford 1.4 g of 2-methoxy-5-methoxymethoxy-pyridine-4-carbaldehyde. GCMS: 197 (m/z).

Step 6:
5-Hydroxy-2-methoxy-pyridine-4-carbaldehyde

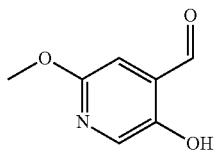

To a stirred solution of 2-methoxy-5-methoxymethoxy-pyridine-4-carbaldehyde (1.5 g, 7.61 mmol) in THF (3 mL) was added 3N HCl (15 mL) at room temperature and the reaction mixture was heated to 70° C. for 2 hr. The reaction mixture was cooled under ice bath, neutralized with K$_2$CO$_3$ and extracted with ethyl acetate (50 mL×2). The combined organic layer was dried over Na$_2$SO$_4$ and concentrated under reduced pressure to provide the crude product which was purified by column chromatography to afford 600 mg of 5-hydroxy-2-methoxy-pyridine-4-carbaldehyde. $^1$H-NMR (DMSO-d$_6$, 400 MHz): δ 10.33 (s, 1H), 10.30 (s, 1H), 8.02 (s, 1H), 6.88 (s, 1H), 3.79 (s, 3H).

Step 7: 4-{[3-Chloro-4-fluoro-phenylimino]-methyl}-6-methoxy-pyridin-3-ol

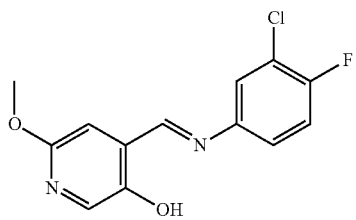 [SMILES: COc1cc(/C=N/c2ccc(F)c(Cl)c2)c(O)cn1]

5-Hydroxy-2-methoxypyridine-4-carbaldehyde (250 mg, 1.63 mmol) was taken in mixed solvent (TFE (2.5 mL): MeCN (2.5 mL)) and 4-fluoro-3-chlorophenyl amine (240 mg, 1.63 mmol) was added to it at 25° C. and the resulting mixture was stirred at this temperature for 2 hr. The reaction mass was concentrated and purified by triturating with n-pentane to afford 350 mg of 4-{-chloro-4-fluoro-phenylimino-methyl}-6-methoxy-pyridin-3-ol. LCMS: 281 (M+H).

Step 8: N$^3$-(3-Chloro-4-fluoro-phenyl)-5-methoxy-furo[2,3-c]pyridine-2,3-diamine

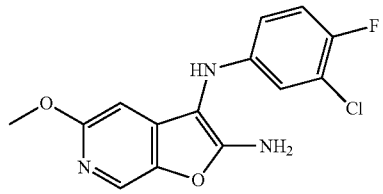

To a stirred solution of 4-{[3-chloro-4-fluoro-phenylimino]-methyl}-6-methoxy-pyridin-3-ol (350 mg, 1.25 mmol) in mixed solvent [DCM (3.5 mL): TFE (3.5 mL)] was added TMSCN (0.6 mL, 4.37 mmol) at 25° C. The reaction mixture was stirred 8 hr at 25° C., concentrated, and crude material was triturated with n-pentane to provide 70 mg (18% Yield) of N$^3$-(3-chloro-4-fluoro-phenyl)-5-methoxy-furo[2,3-c]pyridine-2,3-diamine as off white solid. LCMS: 308 (M+H), HPLC: 99.02%, $^1$H-NMR (DMSO-d$_6$, 400 MHz): δ 7.97 (s, 1H), 7.12 (t, 1H, J=9.1 Hz), 7.02 (s, 1H), 6.93 (s, 2H), 6.55-6.53 (m, 1H), 6.47-6.44 (m, 1H), 6.06 (s, 1H), 3.75 (s, 3H).

Example 6

Synthesis of N$^3$-(3-Chloro-4-fluoro-phenyl)-7-methyl-furo[2,3-c]pyridine-2,3-diamine (Compound 66)

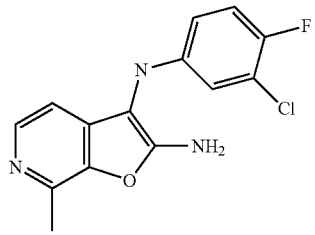 [SMILES: Cc1nccc2c(Nc3ccc(F)c(Cl)c3)c(N)oc12]

Step 1: 3-Methoxymethoxy-2-methyl-pyridine

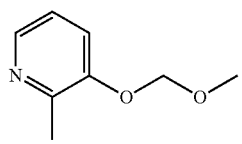

To a stirred solution of 3-hydroxy-2-methyl pyridine (1.5 g, 13.745 mmol) in DCM (20 mL) at 0° C. was added DIPEA (2.8 mL, 16.494 mmol). After stirring the reaction mixture for 10 min, methoxymethyl chloride (1.2 mL, 16.494 mmol) was added to it at 0° C. and the resulting mixture was stirred for 16 hr at 25° C. The reaction mixture was diluted with water and extracted with DCM (2×50 mL). The organic layer was dried over anhydrous sodium sulfate and concentrated under reduced pressure to afford crude material which was purified by column chromatography using silica (100-200 mesh) and 10% EtOAc-hexane as eluent to afford 3-methoxymethoxy-2-methyl-pyridine (1.1 g) as pale yellow liquid. LCMS: 154 (M+H).

Step 2: 3-Methoxymethoxy-2-methyl-pyridine-4-carbaldehyde

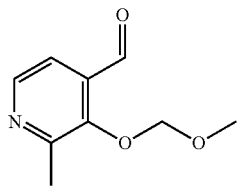

To a stirred solution of 3-methoxymethoxy-2-methyl-pyridine (1.1 g, 7.1895 mmol) in anhydrous THF (20 mL) was added TMEDA (1.1 mL, 7.9084 mmol) at 25° C. The reaction mixture was cooled to −78° C., n-BuLi (3.6 mL, 7.9084 mmol, 2.17 M in hexane) was added dropwise maintaining the temperature −78° C. After stirring for 2 hr at −78° C., DMF (0.80 mL, 10.4247 mmol) was added to it and stirred for 1 hr at −78° C. The temperature was then slowly raised to 25° C. The reaction mixture was quenched with saturated ammonium chloride solution, extracted with ethyl acetate (30 mL×2), EtOAc part was washed with water followed by brine, dried over sodium sulfate and concentrated under reduced pressure to afford crude material which was passed through a pad of silica (100-200 mesh) using 10% EtOAc-hexane as eluent to afford 250 mg of crude 3-methoxymethoxy-2-methylpyridine-4-carbaldehyde as pale yellow liquid. GCMS: 181 (m/z).

Step 3: 3-Hydroxy-2-methylpyridine-4-carbaldehyde

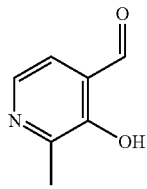

To a stirred solution of 3-methoxymethoxy-2-methylpyridine-4-carbaldehyde (250 mg, 1.3812 mmol) in THF (0.5 mL) was added 3N HCl (2.5 mL) and stirred at 60° C. for 2 hr. The reaction mixture was cooled under ice bath and pH was adjusted to 7 with solid K₂CO₃. The resulting mixture was extracted with EtOAc (20 mL×2). The organic layer was dried over sodium sulfate, concentrated under reduced pressure to afford crude which was purified by column chromatography using silica gel (100-200 mesh) and 23% EtOAc/hexane as eluent to afford 100 mg of 3-hydroxy-2-methyl-pyridine-4-carbaldehyde as pale yellow solid. GCMS: 137 (m/z).

Step 4: 4-{[3-Chloro-4-fluoro-phenylimino]-methyl}-2-methyl-pyridin-3-ol

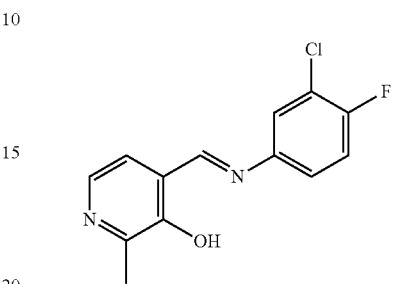

3-Hydroxy-2-methylpyridine-4-carbaldehyde (100 mg, 0.7299 mmol) was taken in mixed solvent [TFE (1 mL): MeCN (1 mL)] and 4-fluoro-3-chlorophenyl amine (106 mg, 0.7299 mmol) was added to it at 25° C. The resulting mixture was stirred at this temperature for 3 hr. The reaction mass was concentrated and purified by triturating with n-pentane to afford 150 mg of 4-{[3-chloro-4-fluoro-phenylimino ]-methyl}-2-methyl-pyridin-3-ol. LCMS: 262.8 (M−H).

Step 5: N³-(3-Chloro-4-fluoro-phenyl)-7-methyl-furo[2,3-c]pyridine-2,3-diamine

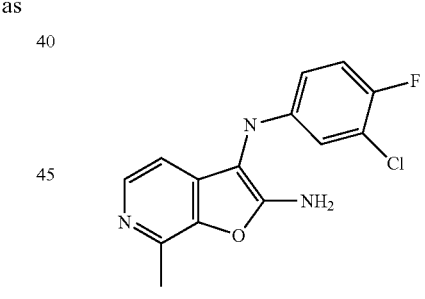

To a stirred solution of 4-{[3-chloro-4-fluoro -phenylimino]-methyl}-2-methyl-pyridin-3-ol (150 mg, 0.5681 mmol) in mixed solvent [DCM (2 mL): TFE (2 mL)] was added TMSCN (0.25 mL, 1.989 mmol) at 25° C. Reaction mixture was stirred for 5 hr at 25° C., concentrated, and the crude material was triturated with MeCN/pentane to yield 40 mg (24% Yield) of N³-(3-chloro-4-fluoro-phenyl)-7-methyl-furo[2,3-c]pyridine-2,3-diamine as reddish brown solid. LCMS: 292 (M+H), HPLC: 99.06%, ¹H-NMR (DMSO-d₆, 400 MHz): δ 7.93 (d, 1H, J=5.1 Hz), 7.13-7.08 (m, 2H), 6.82 (s, 2H), 6.71 (d, 1H, J=5.1 Hz), 6.54-6.52 (m, 1H), 6.48-6.45 (m, 1H), 2.49 (s, 3H).

Example 7

Synthesis of N³-(3-Chloro-4-fluoro-phenyl)-4-methoxy-furo[2,3-c]pyridine-2,3-diamine (Compound 67)

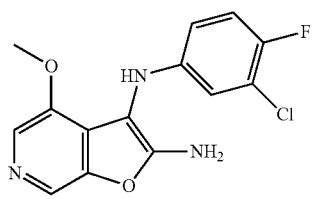 [SMILES: COc1cncc2oc(N)c(Nc3ccc(F)c(Cl)c3)c12]

Step 1: 3-Methoxy-5-(4,4,5,5-tetramethyl41,3,21dioxaborolan-2-yl)-pyridine

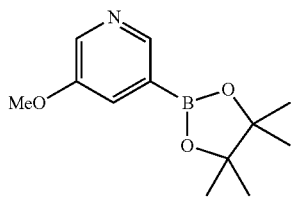 [SMILES: COc1cncc(B2OC(C)(C)C(C)(C)O2)c1]

3-Bromo-5-methoxypyridine (2g, 10.63 mmol), bis(pinacolato)diborane (4.05 g, 15.98 mmol) and potassium acetate (4.78 g, 42.55 mmol) were taken in dry toluene (25 mL) and degassed with nitrogen for 20 min. Pd(dppf)Cl$_2$. DCM (0.87 g, 0.10 mmol) was added to the reaction under nitrogen atmosphere and the resulting mixture was refluxed for 2 hr. The reaction progress was monitored by TLC. After completion of the reaction, the reaction mixture was cooled to 25° C. and filtered through a Celite® reagent pad. The filtrate was diluted with ethyl acetate (100 mL) washed with water followed by brine, dried over Na$_2$SO$_4$ and concentrated under reduced pressure to provide the crude which was purified by silica gel (100-200 mesh) column chromatography using 10% EtOAc in hexane as eluent to afford 2.6 g of 3-methoxy-5-(4,4,5,5-tetramethyl-[1,3,2]dioxaborolan-2-yl)-pyridine LCMS: 236 (M+H).

Step 2: 5-Methoxy-pyridin-3-ol

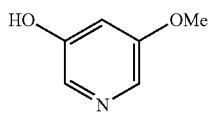

To a stirred suspension of sodium-perborate-tetrahydrate (7.86 g, 51.06 mmol) in water was added 3-methoxy-5-(4,4,5,5-tetramethyl-[1,3,2]dioxaborolan-2-yl)-pyridine (4 g, 17.02 mmol) in THF/H$_2$O (80 mL: 80 mL) at room temperature. The resulting reaction mixture was stirred for 2 hr at room temperature. The reaction mass was extracted with ethyl acetate (200 mL), washed with brine dried over Na$_2$SO$_4$ and concentrated under reduced pressure to provide the crude product which was purified by silica gel (100-200 mesh) column chromatography using 20% EtOAc in hexane as eluent to afford 1.5 g of 5-methoxypyridin-3-ol. LCMS: 126 (M+H).

Step 3: 3-Methoxy-5-methoxymethoxy-pyridine

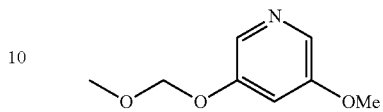

To stirred solution of 5-methoxypyridin-3-ol (1.9 g, 15.20 mmol) in THF:DMF (4 mL: 9 mL) was added potassium tert-butoxide (1.86 g, 16.72 mmol) at 0° C. The reaction mixture was stirred for 15 min at 0° C. and methoxymethylene chloride (1.28 g, 15.96 mmol) was added dropwise. The reaction mixture was allowed to stir 40 min at room temperature. The reaction mass was diluted with ethyl acetate (100 mL) washed with water followed by brine dried over Na$_2$SO$_4$ and concentrated under reduced pressure to provide the crude product which was purified by silica gel (100-200 mesh) column chromatography by using 10% EtOAc in hexane as eluent to afford 1.5 g of 3-methoxy-5-methoxymethoxypyridine. LCMS: 170 (M+H).

Step 4: 3-Methoxy-5-methoxymethoxy-pyridine-4-carbaldehyde

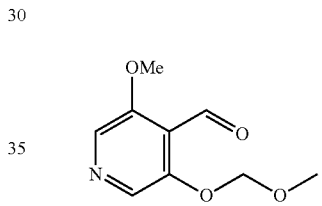

To a stirred solution of 3-methoxy-5-methoxymethoxy-pyridine (1.5 g, 8.86 mmol) in THF (15 mL) was added TMEDA (1.45 mL, 9.75 mmol) and reaction mixture was cooled to −78° C. n-BuLi (2.17 M, 4.49 mL) was then added dropwise at −78° C. and the reaction mixture was allowed to stir 1 hr at this temperature. DMF (1 mL, 12.85 mmol) was then added at −78° C. and the resulting mixture was stirred for 1 hr at the same temperature. The reaction mass was quenched with saturated NH$_4$Cl solution, extracted with ethyl acetate (100 mL×2). The combined organic layer was dried over Na$_2$SO$_4$ and concentrated under reduced pressure to provide the crude product which was purified by silica gel (100-200 mesh) column chromatography eluting with 8% EtOAc in hexane to afford 0.7 g of 3-methoxy-5-methoxymethoxy-pyridine-4-carbaldehyde. GCMS: 197 (m/z).

Step 5: 3-Hydroxy-5-methoxy-pyridine-4-carbaldehyde

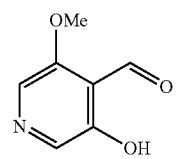 [SMILES: COc1cncc(O)c1C=O]

To a stirred solution of 3-methoxy-5-methoxymethoxy-pyridine-4-carbaldehyde (0.7 g, 3.55 mmol) in THF (3 mL) was added 3N HCl (7 mL) at room temperature and the reaction mixture was heated to 70° C. for 2 hr. The reaction mixture was cooled under ice bath, neutralized with K₂CO₃ and extracted with ethyl acetate (50 mL×2). The combined organic layer was dried over Na₂SO₄ and concentrated under reduced pressure to provide the crude product which was purified by column chromatography to afford 300 mg of 3-hydroxy-5-methoxypyridine-4-carbaldehyde. GCMS: 153 (m/z).

Step 6: 4-{[-3-Chloro-4-fluoro-phenylimino]-methyl}-4-methoxy-pyridin-3-ol

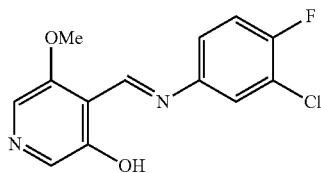 [SMILES: COc1cncc(O)c1/C=N/c1ccc(F)c(Cl)c1]

3-Hydroxy-5-methoxypyridine-4-carbaldehyde (100 mg, 0.65 mmol) was taken in mixed solvent [TFE (1.0 mL): MeCN (1.0 mL)] and 4-fluoro-3-chloro phenyl amine (95 mg, 0.65 mmol) was added at 25° C. The resulting mixture was stirred at this temperature for 2 hr. The reaction mass was concentrated and purified by triturating with n-pentane to afford 150 mg of 4-{[-3-Chloro-4-fluoro-phenylimino]-methyl}-4-methoxy-pyridin-3-ol. LCMS: 281 (M+H).

Step 6: $N^3$-(3-Chloro-4-fluoro-phenyl)-4-methoxy-furo[2,3-c]pyridine-2,3-diamine

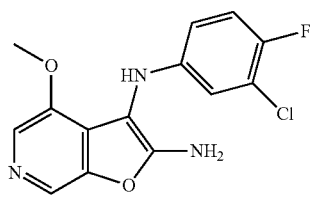

To a stirred solution 4-{[-3-chloro-4-fluoro-phenylimino]-methyl}-4-methoxy-pyridin-3-ol (150 mg, 0.53 mmol) in mixed solvent [DCM (1.5 mL): TFE (1.5 mL)] was added TMSCN (0.25 mL, 1.87 mmol) at 25° C. The reaction mixture was stirred 3 hr at 25° C., concentrated, and the crude material was triturated with DCM/MeCN to yield 60 mg (37% Yield) of $N^3$-(3-Chloro-4-fluoro-phenyl)-4-methoxy-furo[2,3-c]pyridine-2,3-diamine as pale yellow solid. LCMS: 308 (M+H), HPLC: 98.47%, ¹H-NMR (DMSO-d₆, 400 MHz): δ 8.18 (s, 1H), 7.86 (s, 1H), 7.09 (t, 1H, J=9.1 Hz), 6.99 (s, 1H), 6.68 (s, 2H), 6.55-6.52 (m, 1H), 6.47-6.44 (m, 1H), 3.68 (s, 3H).

Example 8

Synthesis of $N^3$-(3-chloro-4-fluorophenyl)-4,7-dimethylfuro[2,3-c]pyridine-2,3-diamine (Compound 72)

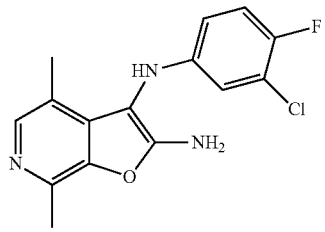 [SMILES: Cc1ncc(C)c2c(Nc3ccc(F)c(Cl)c3)c(N)oc12]

Step 1: 2,2-Dimethyl-4H-[1,3]dioxino[4,5-c]pyridin-5-yl)methanol hydrochloride

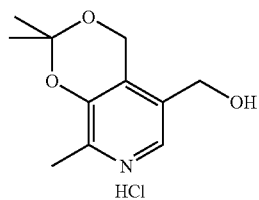

Dry HCl was bubbled to a cooled suspension of pyridoxine hydrochloride (4.0 g) in dry acetone (100 mL) for 1.5 hr. The solution was stirred for another 1 hr and then kept at cold condition for overnight. White crystals appeared at this stage which was separated out and re-crystallization in EtOH to afford 2,2-dimethyl-4H-[1,3]dioxino[4,5-c]pyridin-5-yl)methanol hydrochloride (3.70 g, yield 90.9%.) as white solid. HRMS [M+H]: 210.113; ¹H-NMR (400 MHz, DMSO-d₆): δ 7.90 (s, 1H), 5.13 (t, J=5.4 Hz, 1H), 4.86 (s, 2H), 4.40 (d, J=5.4 Hz, 2H), 2.26 (s, 3H), 1.47 (s, 6H).

Step 2: 5-(Chloromethyl)-2,2-dimethyl-4H-[1,3]dioxino[4,5-c]pyridine hydrochloride

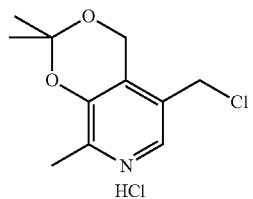

Thionyl chloride (9 mL) was added to a stirred suspension (3.7 g, 17.683 mmol) of 2,2-dimethyl-4H-[1,3]dioxino[4,5-c]pyridin-5-yl)methanol hydrochloride in anhydrous ether (250 mL) at 0° C. After refluxing for 5 hr, the precipitate was filtered, washed with ether, and dried under vacuum. The crude product was recrystallized with boiling absolute ethanol to give 5-(chloromethyl)-2,2-dimethyl-4H-[1,3]dioxino[4,5-c]pyridine hydrochloride (2.5 g, yield 80%) as white solid. HRMS [M+H] 228.079; $^1$H-NMR (400 MHz, CDCl$_3$): δ 7.97 (s, 1H), 4.92 (s, 2H), 4.45 (s, 2H), 2.39 (s, 3H), 1.54 (s, 6H).

Step-3: 4-(Hydroxymethyl)-2,5-dimethylpyridin-3-ol

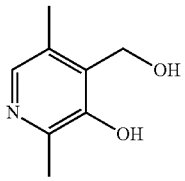

A solution of 5-(chloromethyl)-2,2-dimethyl-4H-[1,3]dioxino[4,5-c]pyridine hydrochloride (1.0 g, 4.403 mmol) in MeOH (10 mL) was hydrogenated in the presence of Pd/C (100 mg) and anhydrous NaOAc (366 mg, 4.403 mmol) at room temperature under hydrogen for 2 hr. After completion of reaction, the mixture was filtered off through a Celite® reagent bed and the bed was washed with methanol. The filtrate was collected and concentrated under reduce pressure to give the crude mass which was diluted with 1N HCl (20 mL) and held overnight at room temperature. After filtering out a slight precipitate, the solution was heated at 80° C. for 15 min and concentrated under reduce pressure up to dryness. The residue was triturated with ethanol and the product was crystallized by adding diethyl ether in the ethanol extract. The solid was filtered off and basified by saturated solution of sodium bicarbonate. The basic aqueous mass was extracted with ethyl acetate, washed with brine, dried over anhydrous sodium sulfate and concentrated under reduce pressure to give crude mass which was purified by column chromatography using ethyl acetate on silica gel to afford 4-(hydroxymethyl)-2,5-dimethylpyridin-3-ol (470 mg, yield 69.77%) as white solid. HRMS [M+H] 154.086; $^1$H-NMR (500 MHz, DMSO-d$_6$): δ 9.10 (s, 1H), 7.68 (s, 1H), 5.65 (s, 2H), 2.26 (s, 3H), 2.12 (s, 3H).

Step-4: 3-Hydroxy-2,5-dimethylisonicotinaldehyde

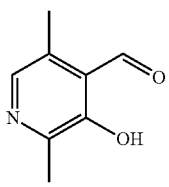

To a stirred solution of 4-(hydroxymethyl)-2,5-dimethylpyridin-3-ol (470 mg, 3.070 mmol) in chloroform (20 mL) was added MnO$_2$ (5.338 g, 61.406 mmol) at room temperature under nitrogen. The reaction mixture was stirred at room temperature for 20 hr under nitrogen. The catalyst was filtered off through a Celite® reagent bed and washed with chloroform. The filtrate was concentrated in vacuum. The crude product was purified by column chromatography on silica gel using 50% ethyl acetate and hexane mixture to afford 3-hydroxy-2,5-dimethylisonicotinaldehyde (200 mg, 44.1%) as white solid and taken directly to the next step.

Step-5: N$^3$-(3-Chloro-4-fluorophenyl)-4,7-dimethylfuro[2,3-c]pyridine-2,3-diamine

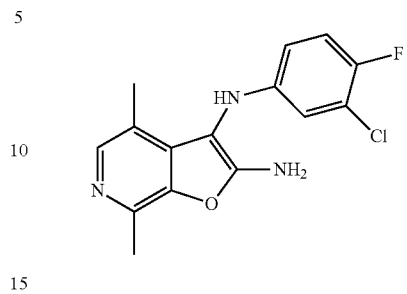

To stirred solution of 3-hydroxy-2,5-dimethylisonicotinaldehyde (200 mg, 1.323 mmol) in MeOH (2 mL) was added 3-chloro-4-fluoroaniline (193 mg, 1.323 mmol) and two drops of acetic acid at room temperature under nitrogen. The resulting reaction mixture was stirred at 50° C. for 15 min. Progress of the reaction was monitor by TLC. After consumption of aldehyde, TMSCN (263 mg, 2.646 mmol) was added dropwise at 50° C. and the reaction mass was stirred for further 20 min. The reaction mass was cooled to room temperature and solvent was removed by vacuum distillation. The crude mass was diluted with ethyl acetate, filtered through a cotton plug and concentrated under reduced pressure to give the crude product which was recrystallized by ethyl acetate and hexane mixture to afford N$^3$-(3-chloro-4-fluorophenyl)-4,7-dimethylfuro[2,3-c]pyridine-2,3-diamine (80 mg, yield 25%) as off white solid. HRMS [M+H] 306.080; $^1$H-NMR (500 MHz, DMSO-d$_6$): δ 7.67 (s, 1H), 7.08 (t, J=9.0 Hz, 1H), 7.03 (s, 1H), 6.73 (bs, 2H), 6.50-6.48 (m, 1H), 6.42-6.40 (m, 1H), 2.41 (s, 3H), 2.06 (s, 3H).

Example 9

Synthesis of N$^3$-(3-Chloro-4-fluoro-phenyl)-7-ethylfuro[2,3-c]pyridine-2,3-diamine (Compound 73)

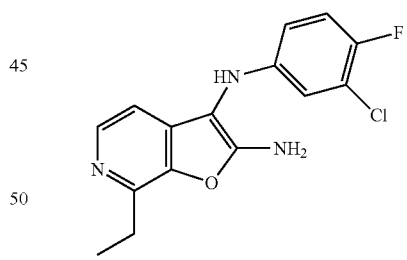

Step 1: 2-Chloro-3-methoxymethoxy-pyridine

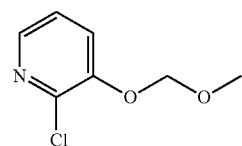

To a stirred solution of 2-chloro-3-hydroxy-pyridine (5 g, 38.59 mmol) in THF: DMF (10:25 mL) at 0° C. was added t-BuOK (4.763 g, 42.45 mmol) portionwise. After stirring the reaction mixture for 15 min, methoxymethylchloride (3.062 mL, 40.5 mmol) was added to it at 0° C. and the resulting mixture was stirred for 1 hr at 25° C. The reaction mixture was diluted with water and extracted with ethyl acetate (3×150 mL). The combined organic layer was dried over anhydrous sodium sulfate, concentrated under reduced pressure to afford crude which was purified by column chromatography using silica (100-200 mesh) and 10% EtOAc-hexane as eluent to afford 2-chloro-3-methoxymethoxypyridine (5.4 g) as pale brown liquid. LCMS: 174 (M+H).

Step 2: 2-Ethyl-3-methoxymethoxy-pyridine

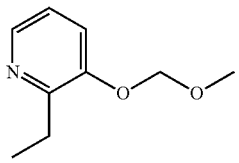

To a stirred solution of 2-chloro-3-methoxymethoxy-pyridine (3 g, 17.341 mmol) in DMF (10 mL) was added triethylborate (1.78 g, 18.208 mmol) and K$_2$CO$_3$ (3.58 g, 26.011 mmol), the reaction mass was degassed with argon, Pd(PPh$_3$)$_4$ (0.5 g, 0.4336 mmol) was then added and heated at 80° C. for 3 hr. The reaction mass was filtered through Celite® reagent, the filtrate was diluted with water and acidified to pH 4 using 1N HCl, and the resulting mixture was stirred for 15 min. To this suspension was added saturated NaHCO$_3$ solution to make a pH 9. The solution was extracted with MTBE (200 mL×2). The combined organic part was dried over Na$_2$SO$_4$, evaporated to dryness and the crude product was purified by column chromatography to provide 1.3 g of 2-ethyl-3-methoxymethoxy-pyridine. LCMS: 168 (M+H).

Step 3: 2-Ethyl-3-methoxymethoxy-pyridine-4-carbaldehyde

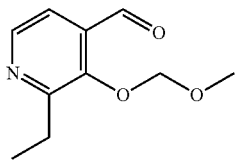

To a stirred solution of 2-ethyl-3-methoxymethoxypyridine (1 g, 5.988 mmol) in anhydrous THF (10 mL) was added TMEDA (1 mL, 6.58 mmol) at 25° C. The reaction mixture was cooled to −78° C., n-BuLi (2.17 M in hexane; 3.03 mL, 6.58 mmol) was added dropwise, maintaining the temperature at −78° C. After stirring for 2 hr at −78° C., DMF (0.67 mL, 8.68 mmol) was added, the solution stirred for 1 hr at −78° C. and the temperature slowly raised to 25° C. The reaction mixture was quenched with saturated ammonium chloride solution, extracted with ethyl acetate (100 mL×2), the EtOAc part was washed with water followed by brine, dried over sodium sulfate and concentrated under reduced pressure to afford crude material which was passed through a pad of silica (100-200 mesh) using 10% EtOAc-hexane as eluent to afford 900 mg of crude 2-ethyl-3-methoxymethoxy-pyridine-4-carbaldehyde. GCMS: 195 (m/z).

Step 4: 2-Ethyl-3-hydroxy-pyridine-4-carbaldehyde

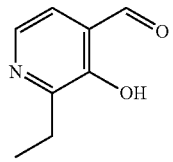

To a stirred solution of 2-ethyl-3-methoxymethoxypyridine-4-carbaldehyde (900 mg, 4.615 mmol) in THF (3 mL) was added 3N HCl (5 mL) and stirred at 60° C. for 2hr. The reaction mixture was cooled under ice bath and pH was adjusted to 7 with solid K$_2$CO$_3$. The resulting mixture was extracted with EtOAc (50 mL×2). The organic layer was dried over sodium sulfate, concentrated under reduced pressure to afford crude which was purified by column chromatography using silica gel (100-200 mesh) and 5% EtOAc/hexane as eluent to afford 300 mg of 2-ethyl-3-hydroxypyridine-4-carbaldehyde. GCMS: 151 (m/z).

Step 5: 4-{[3-Chloro-4-fluoro-phenylimino]-methyl}-2-ethyl-pyridin-3-ol

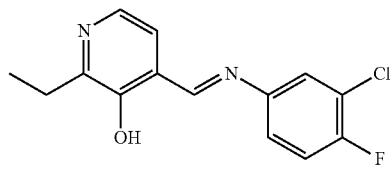 [SMILES: CCc1nccc(/C=N/c2ccc(F)c(Cl)c2)c1O]

2-Ethyl-3-hydroxy-pyridine-4-carbaldehyde (200 mg, 1.3245 mmol) was taken in mixed solvent [TFE (2 mL): MeCN (2 mL)] and 4-fluoro-3-chloro phenyl amine (192 mg, 1.3245 mmol) was added at 25° C. The resulting mixture was stirred at this temperature for 2 hr. The reaction mass was concentrated to afford 350 mg of 4-{[3-chloro-4-fluoro-phenylimino]-methyl}-2-ethyl-pyridin-3-ol (crude). LCMS: 279 (M+H).

Step 6: N$^3$-(3-Chloro-4-fluoro-phenyl)-7-ethyl-furo[2,3-c]pyridine-2,3-diamine

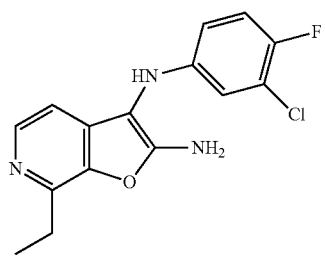 [SMILES: CCc1nccc2c(Nc3ccc(F)c(Cl)c3)c(N)oc12]

To a stirred solution of 4-{[3-chloro-4-fluoro-phenylimino]-methyl}-2-ethyl-pyridin-3-ol (crude) (300 mg, 1.0701 mmol) in mixed solvent [DCM (2 mL): TFE (2 mL)] was added TMSCN (0.5 mL, 3.777 mmol) at 25° C. The reaction mixture was stirred for 2 hr at 25° C., concentrated, and the crude material was purified by column chromatography to yield 80 mg (24% yield) of $N^3$-(3-chloro-4-fluoro-phenyl)-7-ethyl-furo[2,3-c]pyridine-2,3-diamine as a light brown solid. HPLC: 95.02%, LCMS: 306 (M+H), $^1$H-NMR (DMSO-$d_6$, 400 MHz): δ 7.97 (d, 1H, J=5.1 Hz), 7.14-7.08 (m, 2H), 6.81 (s, 2H), 6.72 (d, 1H, J=5.1 Hz), 6.55-6.53 (m, 1H), 6.48-6.44 (m, 1H), 2.88-2.83 (q, 2H), 1.28 (t, 3H, J=7.6 Hz).

Example 10

Synthesis of $N^3$-(3-Chloro-4-fluoro-phenyl)-7-propyl-furo[2,3-c]pyridine-2,3-diamine (Compound 77)

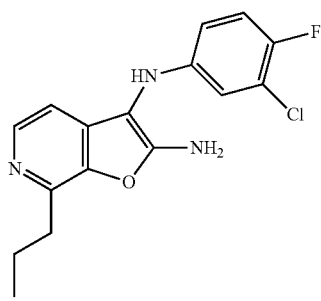 [SMILES: CCCc1nccc2c(Nc3ccc(F)c(Cl)c3)c(N)oc12]

Step 1: 2-Chloro-3-methoxymethoxypyridine

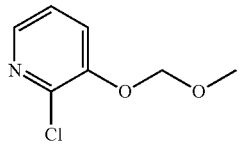

To a stirred solution of 2-chloro-3-hydroxypyridine (5 g, 38.59 mmol) in THF: DMF (10:25 mL) at 0° C. was added t-BuOK (4.763 g, 42.45 mmol) portionwise. After stirring the reaction mixture for 15 min, methoxymethyl chloride (3.062 mL, 40.5 mmol) was added at 0° C. and the resulting mixture was stirred for 1 hr at 25° C. The reaction mixture was diluted with water and extracted with ethyl acetate (3×150 mL). The combined organic layer was dried over anhydrous sodium sulfate, concentrated under reduced pressure to afford crude which was purified by column chromatography using silica (100-200 mesh) and 10% EtOAc-hexane as eluent to afford 2-chloro-3-methoxymethoxypyridine (5.4 g) as a pale brown liquid. LCMS: 174 (M+H).

Step 2: 3-Methoxymethoxy-2-propyl-pyridine

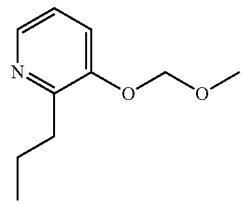

To a stirred solution of 2-chloro-3-methoxymethoxypyridine (500 mg, 2.89 mmol) in Et$_2$O (5 mL) was added Ni(dppp)Cl$_2$ (15 mg, 0.028 mmol). The reaction mixture was cooled to 0° C., propylmagnesium chloride (2 M, 4.3 mL, 8.6 mmol) was added and resulting mixture was refluxed for 3 hr. The reaction mass was allowed to come to rt (25° C.), acidified with 2 N HCl, and washed with MTBE. The aqueous part was basified with solid K$_2$CO$_3$, extracted with EtOAc (50 mL×2). The combined organic part was washed with water, followed by brine, dried over Na$_2$SO$_4$, and evaporated to dryness to provide crude 3-methoxymethoxy-2-propylpyridine (430 mg). LCMS: 182 (M+H).

Step 3: 3-Methoxymethoxy-2-propyl-pyridine-4-carbaldehyde

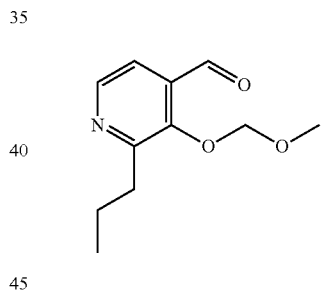

To a stirred solution of 3-methoxymethoxy-2-propylpyridine (650 mg, 3.591 mmol) in anhydrous THF (6 mL) was added TMEDA (0.6 mL, 3.95 mmol) at 25° C. The reaction mixture was cooled to −78° C. and n-SuLi (2.17 M in hexane; 1.82 mL, 3.95 mmol) was added dropwise maintaining the temperature at −78° C. After stirring for 2 hr at −78° C., DMF (0.4 mL, 5.207 mmol) was added, the reaction stirred for 1 hr at −78° C., and the temperature slowly raised to 25° C. The reaction mixture was quenched with saturated ammonium chloride solution, extracted with ethyl acetate (50 mL×2), the EtOAc part was washed with water followed by brine, dried over sodium sulfate and concentrated under reduced pressure to afford crude material which was purified by column chromatography to afford 480 mg of 3-methoxymethoxy-2-propyl-pyridine-4-carbaldehyde as a pale yellow liquid. GCMS: 209 (m/z).

Step 4: 3-Hydroxy-2-propyl-pyridine-4-carbaldehyde

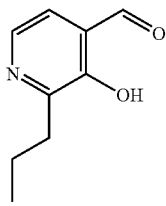

To a stirred solution of methoxymethoxy-2-propylpyridine-4-carbaldehyde (450 mg, 2.153 mmol) in THF (5 mL) was added 3N HCl (6 mL) and the mixture stirred at 60° C. for 2 hr. The reaction mixture was cooled under ice bath and pH was adjusted to 7 with solid $K_2CO_3$. The resulting mixture was extracted with EtOAc (25 mL×2). The organic layer was dried over anhydrous sodium sulfate, concentrated under reduced pressure to afford crude product which was purified by column chromatography using silica gel (100-200 mesh) and EtOAc/hexane as eluent to afford 285 mg of 3-hydroxy-2-propyl-pyridine-4-carbaldehyde. $^1$H-NMR (DMSO-$d_6$, 400 MHz): δ 10.34 (bs, 1H), 10.24 (s, 1H), 8.17(d, 1H), 4.43 (d, 1H), 2.80 (t, 2H), 1.69 (m, 2H), 0.92 (t, 3H).

Step 5: 4-{[3-Chloro-4-fluoro-phenylimino]-methyl}-2-propyl-pyridin-3-ol

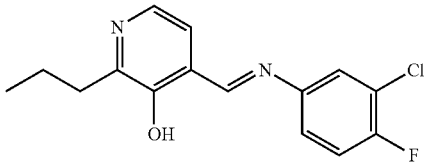 [SMILES: CCCc1nccc(/C=N/c2ccc(F)c(Cl)c2)c1O]

3-Hydroxy-2-propylpyridine-4-carbaldehyde (274 mg, 1.66 mmol) was taken in mixed solvent [TFE (2 mL): MeCN(2 mL)], 4-fluoro-3-chlorophenyl amine (265 mg, 1.82 mmol) was added at 25° C., and the resulting mixture was stirred at this temperature for 2 hr. The reaction mass was concentrated to afford 520 mg of 4-{[3-chloro-4-fluoro-phenylimino]-methyl}-2-propylpyridin-3-ol. LCMS: 292.8 (M+H).

Step 6: $N^3$-(3-Chloro-4-fluoro-phenyl)-7-propyl-furo[2,3-c]pyridine-2,3-diamine

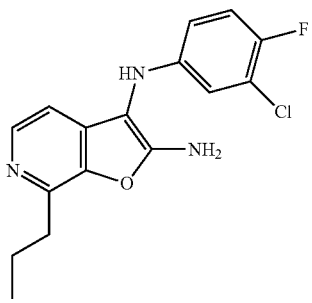 [SMILES: CCCc1nccc2c(Nc3ccc(F)c(Cl)c3)c(N)oc12]

To a stirred solution of 4-{[3-chloro-4-fluoro-phenylimino]-methyl}-2-propyl-pyridin-3-ol (492 mg, 1.684 mmol) in mixed solvent [DCM (4 mL): TFE (4 mL)] was added TMSCN (1.09 mL, 8.76 mmol) at 25° C. The reaction mixture was stirred for 4 hr at 25° C., concentrated, and crude material was triturated with MTBE/pentane to provide 120 mg (22% Yield) of $N^3$-(3-chloro-4-fluoro-phenyl)-7-propyl-furo[2,3-c]pyridine-2,3-diamine as brown solid. HPLC: 96.27%, LCMS: 320 (M+H), $^1$H-NMR (DMSO-$d_6$, 400 MHz): δ 7.96 (d, 1H, J=51 Hz), 7.14-7.07 (m, 2H), 6.81 (s, 2H), 6.71 (d, 1H, J=5.1 Hz), 6.55-6.53 (m, 1H), 6.47-6.44 (m, 1H), 2.81 (t, 2H, J=7.4 Hz), 1.79-1.71 (m, 2H), 0.94 (t, 3H, J=7.4 Hz).

Example 11

Synthesis of $N^3$-(3-Chloro-4-fluoro-phenyl)-5-methoxy-7-methyl-furo[2,3-c]pyridine-2,3-diamine (Compound 85)

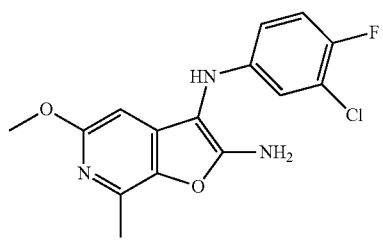 [SMILES: COc1cc2c(Nc3ccc(F)c(Cl)c3)c(N)oc2c(C)n1]

Step 1: 6-Iodo-2-Methyl-Pyridine-3-ol

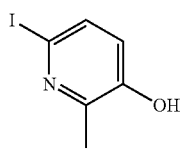

To a stirred solution of 2-methylpyridine-3-ol (500 mg, 4.5816 mmol) in water (10 mL) was added $K_2CO_3$ (2.2 g, 16.0359 mmol) and the mixture stirred at room temperature for 10 min. The reaction mass was cooled in an ice bath, iodine (1.4 g, 5.4980 mmol, dissolved in methanol (3 mL)) was added in dropwise manner and the resulting mixture was allowed to stir at room temperature for 16 hr. The reaction mass was cooled under ice bath, sodium thiosulphate solution was added and the mixture stirred for 5 min. The reaction mixture was diluted with water (50 mL), and extracted with ethyl acetate (4×50 mL). The combined organic part was dried over anhydrous sodium sulfate, and concentrated under reduced pressure to afford 400 mg crude product. Precipitation/trituration using DCM:pentane (1:1) afforded 6-iodo-2-methylpyridine-3-ol 200 mg as white solid. LCMS: 234 (M–H).

Step 2: 6-Iodo-3-methoxymethoxy-2-methyl pyridine

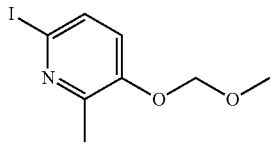

To a stirred solution of 6-iodo-2-methylpyridine-3-ol (200 mg, 0.851 mmol) in DCM (5 mL) under nitrogen atmosphere at −78° C. was added methoxymethyl chloride (0.077 mL, 1.0212 mmol) dropwise followed by DIPEA (0.218 mL, 1.2765 mmol) and the mixture was stirred for 3 hr. The reaction mixture was diluted with water and extracted with DCM (4×20 mL). The combined organic part was dried over anhydrous sodium sulfate, concentrated under reduced pressure to afford 250 mg crude which was purified by column chromatography using silica (100-200 mesh) and 10% EtOAc-hexane as eluent to afford 6-iodo-3-methoxy methoxy-2-methyl pyridine (200 mg) as colorless liquid. GCMS: 279 (m/z).

Step 3: 2-Methoxy-3-methoxymethoxy-pyridine-4-carbaldehyde

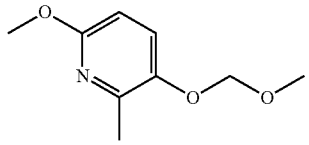

Na metal (86 mg, 3.5842 mmol) was added portion wise to methanol (5 mL) at 0° C. and the solution stirred for 30 min. 6-Iodo-3-methoxymethoxy-2-methylpyridine (200 mg, 0.7168 mmol) in methanol (5 mL) was added to the reaction mixture followed by CuBr (20.5 mg, 0.1433 mmol), and the resulting mixture was refluxed for 16 hr. The reaction mixture was cooled to room temperature, filtered through a Celite® reagent bed and the filtrate was concentrated. The residue was extracted with EtOAc (20 mL×5) washed with water followed by brine, dried over sodium sulfate and concentrated under reduced pressure to afford 200 mg of crude which was purified by column chromatography to afford 80 mg of 6-methoxy-3-methoxymethoxy-2-methyl-pyridine as colorless liquid. GCMS: 183 (m/z).

Step 4: 6-Methoxy-3-methoxymethoxy-2-methyl-pyridine-4-carbaldehyde

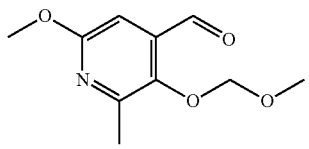

To a stirred solution of 6-methoxy-3-methoxymethoxy-2-methylpyridine (1 g, 5.4644 mmol) in anhydrous THF (20 mL) was added TMEDA (0.9 mL, 6.0109 mmol) at 25° C. The reaction mixture was cooled to −78° C., and n-BuLi (2.7 mL, 6.0109 mmol, 2.17 M in hexane) was added dropwise maintaining the temperature at −78° C. After stirring for 2 hr at −78° C., DMF (0.6 mL, 7.9233 mmol) was added and the mixture stirred for 2 hr at 25° C. The reaction mixture was cooled to −40° C. and saturated ammonium chloride solution was added dropwise. The reaction mass was extracted with ethyl acetate (100 mL×2), the EtOAc part was washed with water followed by brine, dried over sodium sulfate and concentrated under reduced pressure to afford 1.5 g of crude product which was passed through a pad of silica (100-200 mesh) using 5% EtOAc-hexane as eluent to afford 1 g of crude 6-methoxy-3-methoxymethoxy-2-methylpyridine-4-carbaldehyde as a pale yellow liquid. GCMS: 211 (m/z).

Step 5: 3-hydroxy-6-methoxy-2-methyl-pyridine-4-carbaldehyde

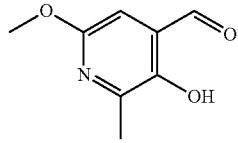

To a stirred solution of 6-methoxy-3-methoxymethoxy-2-methylpyridine-4-carbaldehyde (1g, 4.7393 mmol) in THF (3 mL) was added 3N HCl (10 mL) and the mixture stirred at 60° C. for 1 hr. The reaction mixture was cooled under ice bath and pH adjusted to 7 with solid $K_2CO_3$. The resulting mixture was extracted with EtOAc (50 mL×5). The organic layer was dried over sodium sulfate, concentrated under reduced pressure to afford 700 mg of crude product which was purified by column chromatography using silica gel (100-200 mesh) and 5% EtOAc/hexane as eluent to afford 350 mg of 3-hydroxy-6-methoxy-2-methylpyridine-4-carbaldehyde as pale yellow solid. GCMS: 167 (m/z).

Step 6: 4-{[3-Chloro-4-fluoro-phenylimino]-methyl}-6-methoxy-2-methyl-pyridin-3-ol

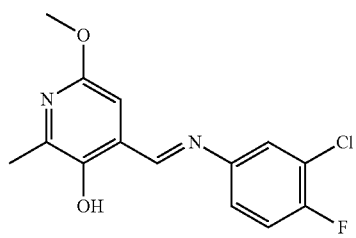 [SMILES: COc1cc(/C=N/c2ccc(F)c(Cl)c2)c(O)c(C)n1]

To a stirred solution of 3-hydroxy-6-methoxy-2-methyl-pyridine-4-carbaldehyde (150 mg, 0.8982 mmol) was taken in mixed solvent [TFE (2 mL):MeCN (2 mL)], 4-fluoro-3-chlorophenylamine (130 mg, 0.8982 mmol) was added at 25° C., and the resulting mixture was stirred at this temperature for 1 hr. The reaction mass was concentrated and purified by triturating with n-pentane to afford 200 mg of 4-{[3-chloro-4-fluoro-phenylimino]-methyl}-6-methoxy-2-methyl-pyridin-3-ol as yellow solid. LCMS: 293 (M−H).

Step 7: N³-(3-Chloro-4-fluoro-phenyl)-5-methoxy-7-methyl-furo[2,3-c]pyridine-2,3-diamine

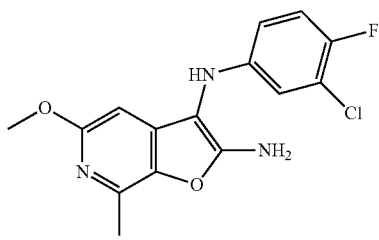 [SMILES: COc1cc2c(Nc3ccc(F)c(Cl)c3)c(N)oc2c(C)n1]

To a stirred solution of 4-{[3-chloro-4-fluoro-phenylimino]-methyl}-6-methoxy-2-methylpyridin-3-ol (200 mg, 0.6802 mmol) in mixed solvent [DCM (2 mL): TFE (2 mL)] was added TMSCN (0.297 mL, 2.3809 mmol) at 25° C. The reaction mixture was stirred 3 hr at 25° C., concentrated, and the crude material was triturated with n-pentane to yield 80 mg (36% Yield) of N³-(3-chloro-4-fluoro-phenyl)-5-methoxy-7-methyl-furo[2,3-c]pyridine-2,3-diamine as a brown solid. HPLC: 98.54%, LCMS: 320 (M–H), ¹H-NMR (DMSO-d₆, 400 MHz): δ 7.11 (t, 1H, J=9.04 Hz), 7.01 (bs, 1H), 6.84 (bs, 2H), 6.54-6.51 (m, 1H), 6.47-6.43 (m, 1H), 5.92 (s, 1H), 3.73 (s, 3H), 2.40 (s, 3H).

Example 12

Synthesis of N³-(3-chloro-4-fluorophenyl)-7-(pyridin-3-yl)furo[2,3-c]pyridine-2,3-diamine (Compound 94)

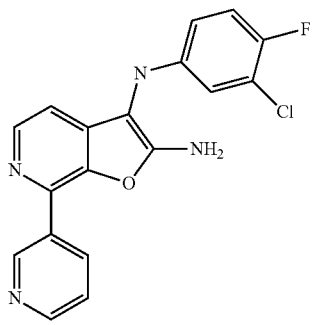 [SMILES: Nc1oc2c(-c3cccnc3)nccc2c1Nc1ccc(F)c(Cl)c1]

Step 1: Furan-2-ylpyridin-3-ylmethanone

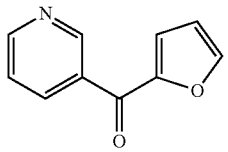 [SMILES: O=C(c1cccnc1)c1ccco1]

To a stirred solution of furan (5 g, 5.37 mL, 73.44 mmol) in anhydrous THF (80 mL) was added n-BuLi (37.2 mL, 80.79 mmol, 2.17 M in hexane) by dropwise maintaining the temperature at −78° C. After stirring for 20 min at −78° C., 3-cyanopyridine (7.64 g, 73.44 mmol) in THF (20 mL) was added dropwise and the mixture stirred for 1 hr at −78° C. Ammonium chloride was added dropwise to the reaction mixture and acidified with 6N HCl to pH 3. The reaction mass was extracted with ethyl acetate (150 mL×4), the EtOAc part was dried over sodium sulfate and concentrated under reduced pressure to afford the crude product which was passed through a pad of silica (100-200 mesh) using 10% EtOAc-hexane as eluent to afford 5.2 g of furan-2-ylpyridin-3-yl-methanone as a pale yellow solid. LCMS: 174.1 (M+H).

Step 2: [2,3']Bipyridinyl-3-ol

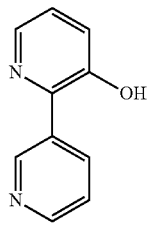 [SMILES: Oc1cccnc1-c1cccnc1]

The solution of furan-2-ylpyridin-3-ylmethanone (4.7 g, 27.167 mmol) in CH₃OH (15 mL) and NH₄OH (40 mL) was charged in an autoclave chamber and allowed to stir for 24 hr at 140° C. The reaction mixture was cooled to 25° C., concentrated under reduced pressure, the crude residue was taken in DCM and washed with 8N NaOH solution (40 mL×2). The aqueous part was neutralized with 6N HCl solution to pH 7 and extracted with ethyl acetate (100 mL×5). The EtOAc part was dried over sodium sulfate and concentrated under reduced pressure to afford 2.6 g crude [2,3']bipyridinyl-3-ol as a pale yellow solid. LCMS: 173 (M+H).

Step 3: 3-Methoxymethoxy-[2,3']bipyridinyl

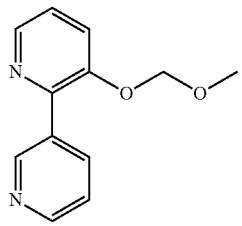 [SMILES: COCOc1cccnc1-c1cccnc1]

To a stirred solution of [2,3']bipyridinyl-3-ol (0.5 g, 2.906 mmol) in THF (10 mL) at 0° C. was added t-BuOK (0.358 g, 3.197 mmol) portionwise. After stirring the reaction mixture for 20 min, methoxy methyl chloride (0.23 mL, 3.052 mmol) was added at 0° C. and the resulting mixture was stirred for 2 hr at 25° C. The reaction mass was concentrated under reduced pressure and the crude residue was taken in 10% IPA/DCM (50 mL) and basified with NH₄OH solution. The organic part was separated, dried over anhydrous sodium sulfate, concentrated under reduced pressure to afford crude which was purified by column chromatography using silica (100-200 mesh) and 30% EtOAc-hexane as eluent to afford 3-methoxymethoxy-[2,3'] bipyridinyl (0.3 g) as a pale yellow liquid. LCMS: 217 (M+H).

Step 4: 3-Methoxymethoxy-[2,3]bipyridinyl-4-carbaldehyde

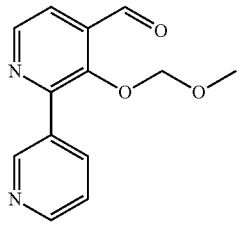 [SMILES: COCOc1c(C=O)ccnc1-c1cccnc1]

To a stirred solution of TMP (0.33 mL, 1.944 mmol) in anhydrous THF (4 mL) was added n-BuLi (0.85 mL, 1.85 mmol, 2.17 M in hexane) dropwise maintaining the temperature −30° C. and the temperature was slowly raised to 0° C. After stirring the mixture for 30 min at 0° C., 3-methoxymethoxy-[2,3']bipyridinyl (0.2 g, 0.925 mmol) in anhydrous THF (2 mL) was added dropwise maintaining the temperature −78° C. The mixture was stirred for 1 hr at −78° C., DMF (0.149 mL, 1.944 mmol) was added and the mixture stirred for 30 min at −78° C. The reaction mixture was cooled to −40° C. and saturated ammonium chloride solution was added dropwise. the reaction mass was extracted with ethyl acetate (5×25 mL), the EtOAc part was washed with water followed by brine, dried over sodium sulfate and concentrated under reduced pressure to afford 150 mg crude 3-methoxymethoxy-[2,3']bipyridinyl-4-carbaldehyde as pale yellow liquid. The crude product was used without further purification.

Step 5: 3-Hydroxy-[2,3']bipyridinyl-4-carbaldehyde

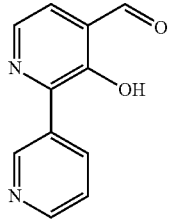 [SMILES: O=Cc1ccnc(-c2cccnc2)c1O]

To a stirred solution of 3-methoxymethoxy-[2,3']bipyridinyl-4-carbaldehyde (0.15 g, 0.614 mmol) in THF (1 mL) was added 3N HCl (2 mL) and the mixture stirred at 50° C. for 1 hr. The reaction mixture was cooled in an ice bath and pH was adjusted to 7 with solid $K_2CO_3$. The resulting mixture was extracted with EtOAc (25 mL×5). The organic layer was dried over sodium sulfate, concentrated under reduced pressure to afford crude product which was purified by column chromatography using silica gel (100-200 mesh) and 5% methanol in DCM as eluent to afford 70 mg 3-hydroxy-[2,3']bipyridinyl-4-carbaldehyde as a pale yellow solid. GCMS: 201.2 (M+H).

Step 6: 4-{[3-Chloro-4-fluoro-phenylimino]-methyl}-[2,3]bipyridinyl-3-ol

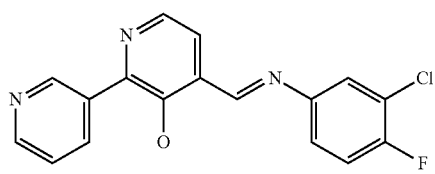 [SMILES: Oc1c(/C=N/c2ccc(F)c(Cl)c2)ccnc1-c1cccnc1]

3-Hydroxy-[2,3']bipyridinyl-4-carbaldehyde (70 mg, 0.35 mmol) was taken in mixed solvent [TFE (1 mL): McCN (1 mL)], 4-fluoro-3-chloro phenyl amine (50 mg, 0.35 mmol) was added at 25° C., and the resulting mixture stirred at this temperature for 2 hr. The reaction mass was concentrated and purified by triturating with n-pentane to afford 50 mg of 4-{[3-chloro-4-fluoro-phenylimino]-methyl}-[2,3']bipyridinyl-3-ol as a yellow solid. LCMS: 328 (M+H).

Step 7: $N^3$-(3-Chloro-4-fluoro-phenyl)-7-pyridin-3-yl-furo[2,3-c]pyridine-2,3-diamine

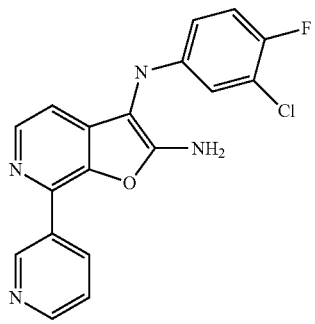 [SMILES: Nc1oc2c(-c3cccnc3)nccc2c1Nc1ccc(F)c(Cl)c1]

To a stirred solution of 4-{[3-chloro-4-fluoro-phenylimino]-methyl}-[2,3']bipyridinyl-3-ol (50 mg, 0.1529 mmol) in mixed solvent [DCM (1 mL):TFE (1 mL)] was added TMSCN (0.065 mL, 0.519 mmol) at 25° C. The reaction mixture was stirred 3 hr at 25° C., and concentrated, crude material was triturated with n-pentane and $CH_3CN$ to yield 25 mg (Yield: 46%) of $N^3$-(3-chloro-4-fluoro-phenyl)-7-pyridin-3-yl-furo[2,3-c]pyridine-2,3-diamine as brown solid. HPLC: 99.46%. LCMS: 355 (M+H). $^1$H-NMR ($CD_3CN$, 400 MHz): δ 9.51 (s, 1H), 8.63 (m, 2H), 8.25 (m, 1H), 7.51 (m, 1H), 7.03-6.99 (m, 2H), 6.66-6.59 (m, 2H), 5.73 (s, 1H), 5.51 (s, 2H).

Example 13

Synthesis of 2-Amino-3-((3-chloro-4-fluorophenyl)amino)furo[2,3-c]pyridine-7-carbonitrile (Compound 106)

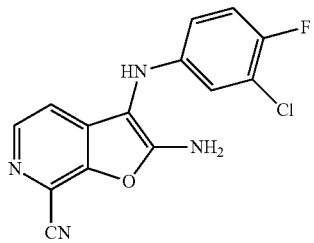 [SMILES: N#Cc1nccc2c(Nc3ccc(F)c(Cl)c3)c(N)oc12]

Step 1: 3-(Methoxymethoxy)picolinonitrile

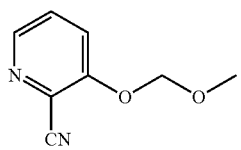

To a stirred solution of 2-cyano-3-hydroxypyridine (500 mg, 4.162 mmol, 1 eq) in THF:DMF (1:3; 2 mL/mmol) at 0° C. was added $^t$BuOK (510 mg, 4.579 mmol, 1.1 eq) portionwise. After stirring the reaction mixture for 15 min, methoxymethylchloride (0.33 mL, 4.37 mmol, 1.05 eq) was added at 0° C. and the resulting mixture was stirred for 1 hr at 25° C. The reaction mixture was diluted with water and extracted with ethyl acetate (3×30 mL). The organic layer was dried over anhydrous sodium sulfate, concentrated under reduced pressure to afford the crude mixture, which was purified by column chromatography to afford 400 mg of the product. Yield=58%. LCMS: 165.4 (M+H).

Step 2: 4-Formyl-3-(methoxymethoxy)picolinonitrile

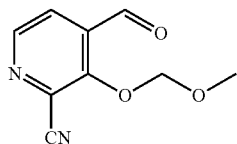

To a stirred solution of TMP (0.43 mL, 2.50 mmol, 2.05 eq) in anhydrous THF (3 mL/mmol) was added n-BuLi (1.12 mL, 2.43 mmol, 2 eq, 2.17 M in hexane) dropwise at −40° C. After stirring for 10 min at −40° C., the reaction mixture was warmed to 0° C. and stirred for 20 min. The reaction mixture was cooled to −78° C. and 3-(methoxymethoxy)picolinonitrile (200 mg, 1.219 mmol, 1 eq) in THF (2.5 mL/mmol) was added slowly. After stirring for 30 min at −78° C., DMF (0.19 mL, 2.50 mmol, 2.05 eq) was added and stirred for another 30 min at −78° C. Saturated ammonium chloride solution was then added dropwise below −50° C. and the reaction mass was cooled to 0° C. The reaction mass was extracted with ethyl acetate (3×30 mL). The organic layer was washed with water followed by brine, dried over sodium sulfate and concentrated under reduced pressure to afford the crude product which was used for next step without purification.

Step 3: 4-Formyl-3-hydroxypicolinonitrile

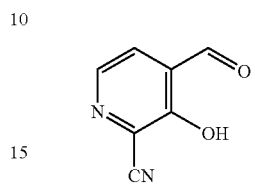

To a stirred solution of crude 4-formyl-3-(methoxymethoxy)picolinonitrile (200 mg, 1 eq) in THF (3 mL/mmol) was added 3N HCl (2 mL) and the mixture stirred at 60° C. for 1 hr. The reaction mixture was cooled under ice bath and pH was adjusted to 7 with solid $K_2CO_3$. The resulting mixture was extracted with ethyl acetate (2×50 mL). The organic layer was dried over sodium sulfate, concentrated under reduced pressure to afford the crude which was purified by column chromatography to afford 80 mg of crude product.

Step 4: (E)-4-(((3-Chloro-4-fluorophenyl)imino)methyl)-3-hydroxypicolinonitrile

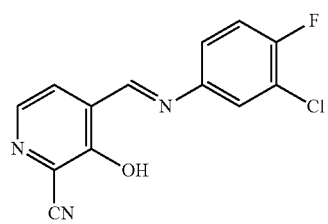 [SMILES: N#Cc1nccc(/C=N/c2ccc(F)c(Cl)c2)c1O]

This compound was prepared according to Procedure-A and was carried forward to next step as such without further purification.

Step 5: 2-Amino-3-((3-chloro-4-fluorophenyl)amino)furo[2,3-c]pyridine-7-carbonitrile

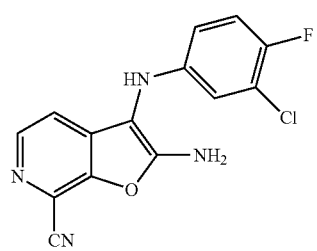 [SMILES: N#Cc1nccc2c(Nc3ccc(F)c(Cl)c3)c(N)oc12]

Following general procedure A, 2-amino-3-((3-chloro-4-fluorophenyl)amino) furo[2,3-c]pyridine-7-carbonitrile was prepared (7 mg). HPLC: 95.29%; LCMS: 303 (M+H);

$^1$H-NMR (CD$_3$CN, 400 MHz): δ 8.19 (d, 1H), 7.15 (d, 1H), 7.03 (t, 1H), 6.63-6.61 (m, 1H), 6.56-6.52 (m, 1H), 5.81 (s, 2H), 5.71 (s, 1H).

Example 14

Synthesis of N$^3$-(3-Chloro-4-fluorophenyl)-5-phenoxy-7-phenylfuro[2,3-c]pyridine-2,3-diamine (Compound 104)

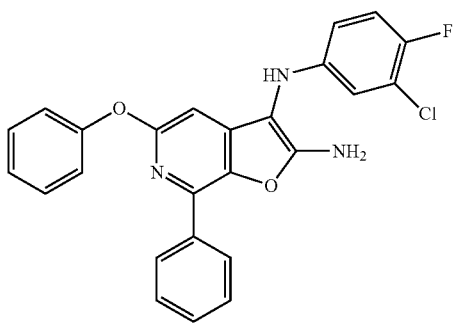 [SMILES: Nc1oc2c(-c3ccccc3)nc(Oc3ccccc3)cc2c1Nc1ccc(F)c(Cl)c1]

Step 1: 2-Phenylpyridin-3-ol

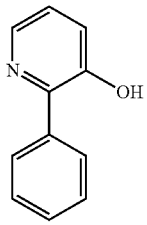

To a stirred solution of 2-iodo-3-hydroxypyridin (5.0 g, 22.624 mmol) in benzene (50 ml) was added phenylboronic acid (3.03 g, 24.85 mmol) and 2M Na$_2$CO$_3$ solution (20 mL) at 25° C. and the reaction mixture was degassed with argon for 15 min. Then added Pd(PPh$_3$)$_4$ (1.3 g, 5 mol %) and further degassed for 10 min. The resulting reaction mixture was refluxed for 4 h. After completion of reaction the reaction mixture was cooled to room temperature, water was added to it and extracted with EtOAc. Organic layer was dried over anhydrous sodium sulphate, concentrated under reduced pressure to afford the crude which was purified by trituration with MTBE/DCM to afford 2-phenylpyridin-3-ol (3.2 g). LCMS: 172 (M+H).

Step 2: 6-Iodo-2-phenylpyridin-3-ol

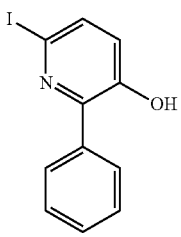 [SMILES: Oc1ccc(I)nc1-c1ccccc1]

To a stirred solution of 2-phenylpyridin-3-ol (3.0 g, 17.524 mmol) in THF (75 mL) was added Na$_2$CO$_3$ (3.9 g, 36.792 mmol) in 75 ml water and stirred at room temperature for 10 min. Reaction mass was cooled under ice bath, then iodine (4.45 g, 35.066 mmol) was added portion wise and the resulting mixture was allowed to stir at room temperature for 16 h. Reaction mass was cooled under ice-bath and sodium thiosulphate solution was added to it and stirred for 5 min. Reaction mixture was diluted with water, extracted with ethyl acetate. Combined organic part was dried over anhydrous sodium sulphate, concentrated under reduced pressure to afford the crude material which was purified by column chromatography to afforded 6-iodo-2-phenylpyridin-3-ol (1.6 g). LCMS: 297.8 (M+H).

Step 3:
6-Iodo-3-(methoxymethoxy)-2-phenylpyridine

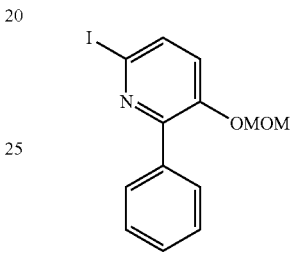

To a stirred solution of 6-iodo-2-phenylpyridin-3-ol (3.3 g, 11.107 mmol) in a mixture of solvents THF (6 mL):DMF (15 mL) at 0° C. was added t-BuOK (1.5 g, 13.368 mmol) portion wise. After stirring the reaction mixture for 15 mins, methoxymethyl chloride (0.98 mL, 12.173 mmol) was added to it at 0° C. and the resulting mixture was stirred for 1 h at 25° C. Reaction mixture was diluted with water and extracted with ethyl acetate. Organic layer was dried over anhydrous sodium sulphate, concentrated under reduced pressure to afford the crude mass which was purified by column chromatography to afford 6-iodo-3-(methoxymethoxy)-2-phenylpyridine (2.4 g). LCMS: 341.8 (M+H).

Step 4:
3-(Methoxymethoxy)-6-phenoxy-2-phenylpyridine

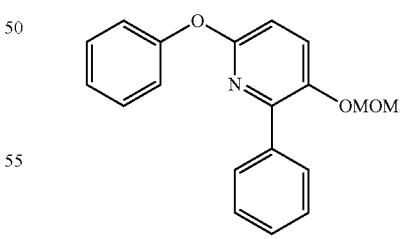

Na metal (0.38 g, 17.272 mmol) was added portionwise to phenol (20 mL) at 0° C. and stirred for 30 min at room temperature, then 6-iodo-3-(methoxymethoxy)-2-phenyl pyridine (1.2 g, 3.517 mmol) was added followed by CuBr (0.096 g, 0.669 mmol), the resulting reaction mixture was refluxed for 16 h and after completion of reaction the reaction mixture was cooled to room temperature and filtered through celite bed and the filtrate was concentrated.

Residue was extracted with EtOAc, washed with water followed by brine, dried over sodium sulphate and concentrated under reduced pressure to afford the crude material which was purified by column chromatography to get 3-(methoxymethoxy)-6-phenoxy-2-phenylpyridine (0.8 g). LCMS: 308 (M+H).

Step 5: 3-(Methoxymethoxy)-6-phenoxy-2-phenylisonicotinaldehyde

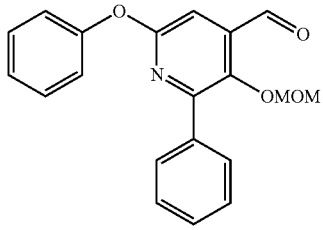

To a stirred solution of 3-(methoxymethoxy)-6-phenoxy-2-phenylpyridine (0.2 g, 0.65 mmol) in anhydrous THF (3 mL) was added TMEDA (0.107 mL, 0.920 mmol) at 25° C. The reaction mixture was cooled to −78° C. and then added n-BuLi (0.3 mL, 2.2 M) by dropwise at −78° C. and stirred for 1 h at −78° C. DMF (0.072 mL) was added to it at −78° C. and the resulting mixture was allowed to stirred for 1 h at −78° C. Saturated ammonium chloride solution was then added drop wise below −50° C. and the reaction mass was diluted with ethyl acetate, extracted with ethyl acetate, washed with brine and dried over sodium sulphate and concentrated to afford crude 3-(methoxymethoxy)-6-phenoxy-2-phenylisonicotinaldehyde (0.15 g) which was used in next step without purification. LCMS: 336.2 (M+H).

Step 6: 3-Hydroxy-6-phenoxy-2-phenylisonicotinaldehyde

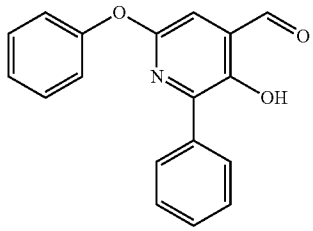 [SMILES: O=Cc1cc(Oc2ccccc2)nc(-c2ccccc2)c1O]

To a stirred solution of crude 3-(methoxymethoxy)-6-phenoxy-2-phenylisonicotinaldehyde (0.15 g, 0.447 mmol) in THF (2 mL) was added 3N HCl (3 mL) and stirred at 60° C. for 1 h. Reaction mixture was cooled under ice-bath and pH was adjusted to 7 with solid $K_2CO_3$. The resulting mixture was extracted with EtOAc, washed with brine, dried over sodium sulphate and concentrated under reduced pressure to afford the crude material which was purified by column chromatography to afford 3-hydroxy-6-phenoxy-2-phenylisonicotinaldehyde (0.055 g). LCMS: 289.6 (M−H).

Step 7: $N^3$-(3-Chloro-4-fluorophenyl)-5-phenoxy-7-phenylfuro[2,3-c]pyridine-2,3-diamine (Procedure C)

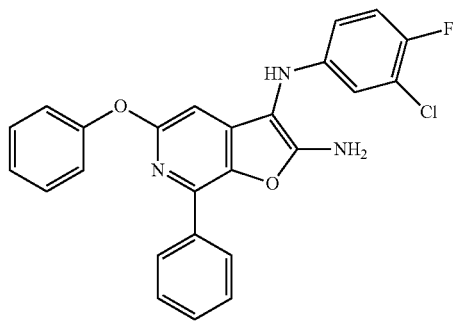 [SMILES: Nc1oc2c(-c3ccccc3)nc(Oc3ccccc3)cc2c1Nc1ccc(F)c(Cl)c1]

To a solution of 3-hydroxy-6-phenoxy-2-phenyl-pyridine-4-carbaldehyde (0.050 g, 0.171 mmol) in DCM (2 mL) was added 4-fluoro-3-chloroaniline (0.025 g, 0.171 mmol), TMSOTf (0.006 mL, 0.0343 mmol) and TMSCN (0.11 mL, 0.893 mmol). The resulting mixture was stirred for 6 h at room temperature. After completion of reaction the reaction mass was diluted with DCM, washed with water followed by brine and dried over anhydrous $Na_2SO_4$ and was evaporated to provide a brown crude material which was further purified by column chromatography/trituration to afford $N^3$-(3-chloro-4-fluoro-phenyl)-5-phenoxy-7-phenyl-furo[2,3-c]pyridine-2,3-diamine (0.015 g, 0.033 mmol, yield 20%). $^1$H-NMR (400 MHz, DMSO-$d_6$): δ 8.11 (d, J=6.6 Hz, 2H), 7.47-7.37 (m, 5H), 7.15-7.11 (m, 7H), 6.60 (bs, 1H), 6.52 (bs, 1H), 6.26 (s, 1H); LCMS: 444.2 (M+H).

Example 15

Synthesis of $N^3$-(3-chloro-4-fluorophenyl)-5-ethyl-7-phenylfuro[2,3-c]pyridine-2,3-diamine (Compound 109)

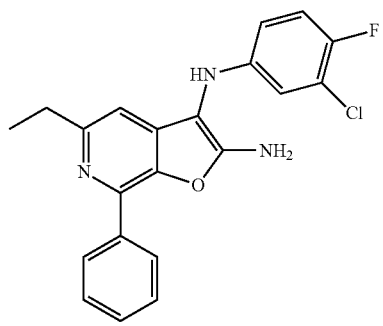 [SMILES: CCc1cc2c(Nc3ccc(F)c(Cl)c3)c(N)oc2c(-c2ccccc2)n1]

Step 1: 2-Phenylpyridin-3-ol

To a stirred solution of 2-iodo-3-hydroxypyridine, prepared as described above, (5 g, 22.62 mmol, 1 eq) in DME (2 mL/mmol) was added phenylboronic acid (3.03 g, 24.88 mmol, 1.1 eq) and 2M Na$_2$CO$_3$ solution (20 mL, 1.7 eq) at 25° C. and the reaction mixture was degassed with argon for 15 min. Pd(PPh$_3$)$_4$ (1.3 g, 5 mol %) was then added, the mixture was further degassed for 10 min, and the reaction mixture refluxed for 4 hr. The reaction mixture was cooled to RT, filtered through a pad of Celite® reagent and the filtrate was concentrated. The residue was diluted with ethyl acetate (2×50 mL) and washed with water and brine. The organic layer was dried over anhydrous sodium sulfate, concentrated under reduced pressure to afford the crude which was purified by column chromatography to afford 1.6 g of 2-phenylpyridin-3-ol (Yield: 41%). LCMS: 172 (M+H).

Step 2: 6-Iodo-2-phenylpyridin-3-ol

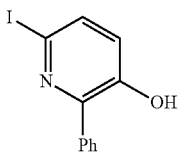 [SMILES: Oc1ccc(I)nc1-c1ccccc1]

To a stirred solution of 2-phenylpyridin-3-ol (3 g, 17.54 mmol, 1 eq) in THF (4 mL/mmol) was added Na$_2$CO$_3$ (3.9 g, 36.83 mmol, 2.1 eq; 0.5 M in water) and stirred at room temperature for 10 min. The reaction mass was cooled under ice bath. Iodine (4.45 g, 17.54 mmol, 1 eq) was added portionwise and the resulting mixture was allowed to stir at room temperature for 16 hr. The reaction mass was cooled under ice bath, sodium thiosulphate solution was added to it and stirred for 5 min. The reaction mixture was diluted with water, and extracted with ethyl acetate. The combined organic part was dried over anhydrous sodium sulfate, and concentrated under reduced pressure to afford the crude product. Purification of the crude material by column chromatography afforded 1.6 g of 6-iodo-2-phenylpyridin-3-ol (Yield: 31%). LCMS: 297.8 (M+H).

Step 3: 6-Iodo-3-(methoxymethoxy)-2-phenylpyridine

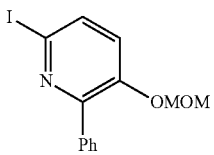

To a stirred solution of 6-iodo-2-phenylpyridin-3-ol (3.3 g, 11.11 mmol, 1 eq) in THF:DMF (1:3, 2 mL/mmol) at 0° C. was added t-BuOK (1.5 g, 13.33 mmol, 1.2 eq) portionwise. After stirring the reaction mixture for 15 min, methoxymethylchloride (0.91 mL, 12.17 mL, 1.1 eq) was added at 0° C. and the resulting mixture was stirred for 1 hr at 25° C. The reaction mixture was diluted with water and extracted with ethyl acetate (2×100 mL). The organic layer was dried over anhydrous sodium sulfate, concentrated under reduced pressure to afford the crude product, which was purified by column chromatography to afford 2.4 g of 6-oodo-3-(methoxymethoxy)-2-phenylpyridine (Yield: 63%). LCMS: 341.8 (M+H).

Step 4:
6-Ethyl-3-(methoxymethoxy)-2-phenylpyridine

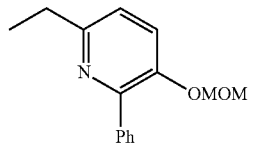

To a stirred solution of 6-iodo-3-(methoxymethoxy)-2-phenylpyridine (900 mg, 2.63 mmol, 1 eq) in DMF (10 mL/mmol) was added triethylborate (5.27 mL, 5.27 mmol, 1M in THF, 2 eq) and K$_2$CO$_3$ (546 mg, 3.95 mmol, 1.5 eq) at 0° C. The reaction mixture was degassed with argon and [1,3-bis(diphenylphosphino)propane]dichloronickel (II) (76 mg, 0.0659 mmol, 2.5 mol %) was added. The reaction mixture was heated at 80° C. for 16 hr. The reaction mass was cooled to room temperature, filtered through Celite® reagent, filtrate was diluted with water and acidified (pH 4) using 1N HCl and stirred for 15 min. To this suspension saturated NaHCO$_3$ solution was added to make the pH 9, extracted with MTBE, organic part was dried over Na$_2$SO$_4$, evaporated to dryness and the crude product was purified by column chromatography to yield 500 mg of 6-ethyl-3-(methoxymethoxy)-2-phenylpyridine (Yield: 77%). LCMS: 243.8 (M+H).

Step 5: 6-Ethyl-3-(methoxymethoxy)-2-phenylisonicotinaldehyde

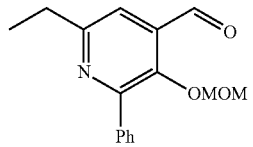

To a stirred solution of 6-ethyl-3-(methoxymethoxy)-2-phenylpyridine (200 mg, 0.8230 mmol, 1 eq) in anhydrous THF (3 mL/mmol) was added TMEDA (0.135 mL, 0.9053 mmol, 1.1 eq) at 25° C. The reaction mixture was cooled to −78° C., n-BuLi (0.417 mL, 0.9053 mmol, 2.17M, 1.1 eq) was added by dropwise at −78° C. and stirred for 1 hr at −78° C. DMF (0.091 mL, 1.1934 mmol, 1.45 eq) was added to it at −78° C. and the resulting mixture was allowed to stir for 1 hr at −78° C. Saturated ammonium chloride solution was then added dropwise below −50° C. and the reaction mass was diluted with ethyl acetate. The organic layer was separated, washed with brine and dried over sodium sulfate. The organic layer was filtered and concentrated to afford 200 mg of crude 6-ethyl-3-(methoxymethoxy)-2-phenylisonicotinaldehyde which was used for next step without purification. LCMS: 271.8 (M+H).

Step 6:
6-Ethyl-3-hydroxy-2-phenylisonicotinaldehyde

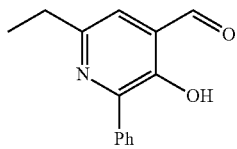 [SMILES: CCc1cc(C=O)c(O)c(-c2ccccc2)n1]

To a stirred solution of crude 6-ethyl-3-(methoxymethoxy)-2-phenylisonicotinaldehyde (200 mg, 0.7380 mmol, 1 eq) in THF (3 mL/mmol) was added 3N HCl (6 mL/mmol) and stirred at 60° C. for 1 hr. The reaction mixture was cooled under ice bath and pH was adjusted to 7 with solid $K_2CO_3$. The resulting mixture was extracted with ethyl acetate (2×50 mL). The organic layer was dried over sodium sulfate and concentrated under reduced pressure to afford the crude product which was purified by column chromatography to afford 120 mg of 6-ethyl-3-hydroxy-2-phenylisonicotinaldehyde (Yield: 64% after two steps). LCMS: 226.2 (M–H).

Step 7: (E)-4-(((3-Chloro-4-fluorophenyl)imino)methyl)-6-ethyl-2-phenylpyridin-3-ol

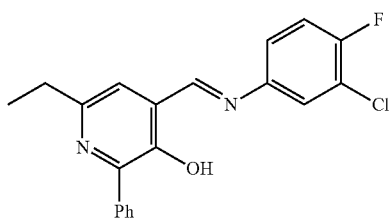 [SMILES: CCc1cc(/C=N/c2ccc(F)c(Cl)c2)c(O)c(-c2ccccc2)n1]

(E)-4-(((3-Chloro-4-fluorophenyl)imino)methyl)-6-ethyl-2-phenylpyridin-3-ol (50 mg) was prepared by following general procedure A. LCMS: 355.0 (M+H).

Step 8: N3-(3-Chloro-4-fluorophenyl)-5-ethyl-7-phenylfuro[2,3-c]pyridine-2,3-diamine

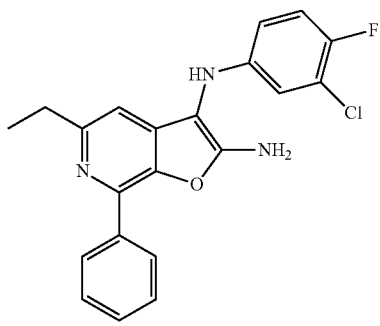 [SMILES: CCc1cc2c(Nc3ccc(F)c(Cl)c3)c(N)oc2c(-c2ccccc2)n1]

$N^1$-(3-chloro-4-fluorophenyl)-5-ethyl-7-phenylfuro[2,3-c]pyridine-2,3-diamine (15 mg) was prepared by following general procedure A. HPLC: 97.61%; LCMS: 382 (M+H); $^1$H-NMR (CDCl$_3$, 400 MHz): δ 8.25 (d, 2H), 7.50 (t, 2H), 7.42 (m, 1H), 6.96 (t, 1H), 6.81 (s, 1H), 6.65 (m, 1H), 6.51 (m, 1H), 4.74 (s, 1H), 4.49 (s, 2H), 2.84 (q, 2H), 1.32 (t, 3H).

Example 16

Synthesis of 2-Amino-3-((3-chloro-4-fluorophenyl)amino)benzofuran-6-carbonitrile (Compound 112) (Procedure A, B)

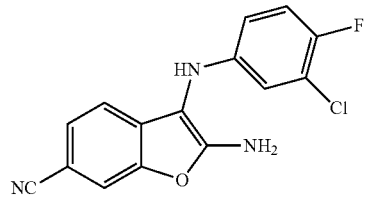 [SMILES: N#Cc1ccc2c(Nc3ccc(F)c(Cl)c3)c(N)oc2c1]

To a stirred solution of 4-formyl-3-hydroxybenzonitrile (0.2 g, 1.36 mmol) in DCM (4 mL) was added 3-chloro-4-fluoroaniline (0.198 g, 1.36 mmol) followed by the addition of TMSCN (0.89 mL, 7.074 mmol) and TMS-OTf (0.049 mL, 0.272 mmol). The resulting mixture was stirred in a sealed tube at 25° C. for 16 hr. After completion of reaction the reaction mixture was diluted with diethyl ether, washed with water, dried over sodium sulfate and evaporated under reduced pressure to give crude material obtained was purified by column chromatography over alumina using acetone/hexane as eluent to afford 2-amino-3-(3-chloro-4-fluorophenylamino)-benzofuran-6-carbonitrile (0.03 g, 0.103 mmol, 8%) as reddish brown solid. $^1$H-NMR (400 MHz, DMSO-d$_6$): δ 7.75 (s, 1H), 7.39 (d, J=8.1 Hz, 1H), 7.14-7.10 (m, 2H), 6.96 (bs, 2H), 6.92 (d, J=8.0 Hz, 1H), 6.56 (dd, J'=6.3 Hz, J"=2.7 Hz, 1H), 6.47 (dt, J'=8.8 Hz, J"=6.6 Hz, J'''=3.2 Hz, 1H); LCMS: 300 (M–H).

Example 17

Synthesis of $N^3$-(3-chloro-4-fluorophenyl)thieno[2,3-c]pyridine-2,3-diamine (Compound 121)

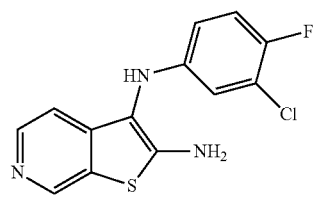 [SMILES: Nc1sc2cnccc2c1Nc1ccc(F)c(Cl)c1]

Step 1: 3-Chloropyridine-4-carbonitrile

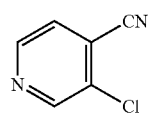

To a stirred solution of 2,2,6,6-tetramethyl piperidine (17.16 mL, 100.854 mmol) in THF (100 mL) was added n-BuLi (2.17 M, 44.26 mL, 96.052 mmol) at –30° C. After stirring the mixture for 15 min at 25° C., it was cooled to −78° C. and 4-cyanopyridine (5 g, 48.026 mmol) in THF (40 mL) was added dropwise. After stirring the reaction mixture for 30 min at −78° C., hexachloroethane (23.87 g, 100.854 mmol) in THF (50 mL) was added at −78° C. The resulting mixture was stirred for 30 min at −78° C. and was quenched with saturated $NH_4Cl$ solution. Water (100 mL) was added to the reaction mixture and extracted with ethyl acetate (4×300 mL). The combined organic layer was dried over anhydrous sodium sulfate, concentrated under reduced pressure to afford the crude material which was purified by column chromatography using silica (100-200 mesh) and 5% EtOAc-hexane as eluent to afford 3-chloropyridine-4-carbonitrile (3.5 g, 25.261 mmol, 53%) as pale white solid. GCMS: 138 (m/z).

Step 2: Methyl 3-aminothieno[2,3-c]pyridine-2-earboxylate

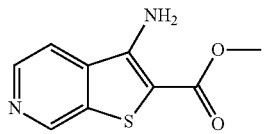

To a stirred solution of 3-chloropyridine-4-carbonitrile (6.2 g, 44.92 mmol) in MeCN (60 mL) was added mercaptoacetic acid methyl ester (4.26 mL, 47.173 mmol) and $K_2CO_3$ (12.4 g, 89.855 mmol) at 25° C. The reaction mixture was refluxed for 3 hr and was concentrated under reduced pressure. The resulting residue was diluted with water (100 mL) and extracted with EtOAc (4×200 mL). The combined organic layer was dried over sodium sulfate and was concentrated under reduced pressure to afford the crude material which was purified by trituration with n-pentane to afford methyl 3-aminothieno[2,3-c]pyridine-2-carboxylate (7.5 g, 36.016 mmol, 80%) as pale yellow solid. LCMS: 209 (M+H).

Step 3: Methyl 3-bromothieno[2,3-c]pyridine-2-carboxylate

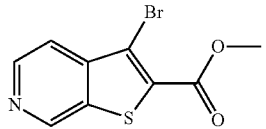

To a stirred solution of CuBr (2.71 g, 18.930 mmol) in aqueous HBr (46 mL, 48%) was added methyl 3-aminothieno[2,3-c]pyridine-2-carboxylate (3.75 g, 18.028 mmol) at −10° C. $NaNO_2$ (1.49 g, 21.634 mmol) in water (43 mL) was added dropwise at −10° C. and the resulting mixture was stirred for 30 min at −10° C. Solid $NaNO_2$ (0.149 g, 2.163 mmol) was then added to the reaction mass at −10° C. After stirring for 30 min at −10° C., another portion of solid $NaNO_2$ (0.149 g, 2.163 mmol) was added. The reaction mixture was then slowly poured into saturated $NaHCO_3$ solution (pH=7) and extracted with DCM (4×200 mL). The combined organic layer was dried over sodium sulfate, concentrated under reduced pressure to afford crude material which was purified by column chromatography using silica gel (100-200 mesh) and 5% EtOAc/hexane as eluent to afford methyl 3-bromothieno[2,3-c]pyridine-2-carboxylate (1.5 g, 5.512 mmol, 31%) as off white solid. LCMS: 271.8 (M+H).

Step 4: Methyl 3-((3-chloro-4-fluorophenyl)amino)thieno[2,3-c]pyridine-2-carboxylate

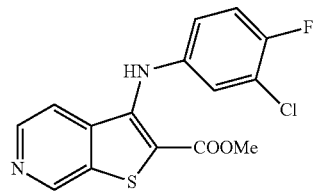 [SMILES: COC(=O)c1sc2cnccc2c1Nc1ccc(F)c(Cl)c1]

To a stirred solution of methyl 3-bromothieno[2,3-c]pyridine-2-carboxylate (0.2 g, 0.735 mmol) in toluene (5 mL) was added 3-chloro-4-fluoro aniline (0.149 g, 1.029 mmol), $Cs_2CO_3$ (0.337 g, 1.102 mmol), BINAP (0.091g, 0.147 mmol) and degassed for 20 min. $Pd_2(dba)_3$ (0.038 g, 0.036 mmol) was then added and the reaction mixture was heated at 100° C. for 16 hr. The reaction mixture was filtered through a bed of Celite® reagent and washed with ethyl acetate. The filtrate was diluted with water (50 mL) and extracted with EtOAc (4×50 mL). The combined organic layer was dried over sodium sulfate, concentrated under reduced pressure to afford crude material which was purified by column chromatography using silica gel (100-200 mesh) and 5% EtOAc/hexane as eluent to afford methyl 3-((3-chloro-4-fluorophenyl)-amino)thieno[2,3-c]pyridine-2-carboxylate (0.1 g, 0.296 mmol, 40%) as pale yellow solid. LCMS: 336.8 (M+H).

Step 5: Methyl 3-((tert-butoxycarbonyl)(3-chloro-4 fluorophenyl)amino)thieno-[2,3-e]pyridine-2-carboxylate

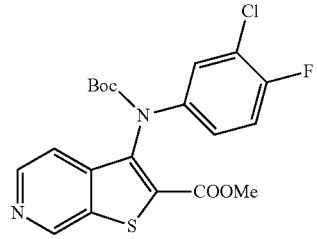 [SMILES: COC(=O)c1sc2cnccc2c1N(C(=O)OC(C)(C)C)c1ccc(F)c(Cl)c1]

To a stirred solution of methyl 3-((3-chloro-4-fluorophenyl)amino)thieno[2,3-c]pyridine-2-carboxylate (0.9 g, 2.678 mmol) in THF(10 mL) was added TEA (0.93 mL, 6.696 mmol) and DMAP (0.196 g, 1.607 mmol) at 0° C. The resulting mixture was stirred for 10 min at 0° C. and then Boc anhydride (1.31 mL, 5.892 mmol) was added dropwise. The reaction mixture was heated at 60° C. for 4 hr. After completion of the reaction, water (100 mL) was added to the reaction mixture and extracted with EtOAc (4×70 mL). The combined organic layer was dried over sodium sulfate, concentrated under reduced pressure to afford the crude material which was purified by column chromatography using silica gel (100-200 mesh) and 15% EtOAc/hexane as eluent to afford methyl 3-((tert-butoxycarbonyl)(3-chloro-4- fluorophenyl)amino)-thieno[2,3-c]pyridine-2 carboxylate (0.8 g, 1.831 mmol, 69%). LCMS: 436.8 (M+H).

Step 6: 3-((teat-Butoxycarbonyl)(3-chloro-4-fluorophenyl)amino)thieno[2,3-c]pyridine-2-carboxylic acid

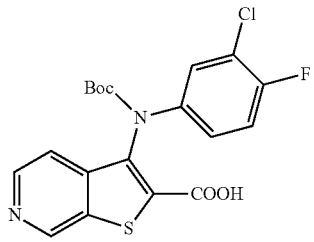

To a stirred solution of methyl 3-((tert-butoxycarbonyl)(3-chloro-4-fluorophenyl)-amino)thieno[2,3-c]pyridine-2 carboxylate (0.8 g, 1.831 mmol) in a mixture of THF:MeOH:H$_2$O (15:9:3 mL) was added LiOH (0.088 g, 3.669 mmol) at 0° C. and resulting mixture was stirred for 16 hr. The reaction mixture was concentrated under reduced pressure and the resulting residue was diluted with water (5 mL) and acidified with 5% citric acid solution (pH=4). The resulting solid precipitate was filtered, washed with water and dried under vacuum to afford 3-((tert-butoxycarbonyl)(3-chloro-4-fluorophenyl)amino)thieno[2,3-c]pyridine-2-carboxylic acid (0.7 g, 1.655 mmol, 90%) as pale yellow solid. LCMS: 423 (M$^r$).

Step 7: teat-Butyl (2-((tert-butoxycarbonyl)amino)thieno[2,3-c]pyridin-3-yl)(3-chloro-4-fluorophenyl)carbamate

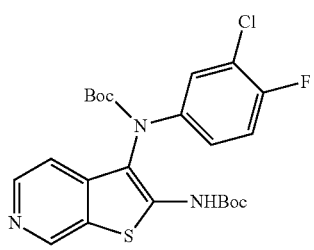 [SMILES: CC(C)(C)OC(=O)Nc1sc2cnccc2c1N(C(=O)OC(C)(C)C)c1ccc(F)c(Cl)c1]

To a stirred solution of 3-((tent-butoxycarbonyl)(3-chloro-4-fluorophenyl) amino)thieno[2,3-c]pyridine-2-carboxylic acid (0.3 g, 0.710 mmol) in tert-BuOH (10 mL) was added DPPA (0.18 mL, 0.853 mmol) and DIPEA (0.13 mL, 0.782 mmol) at 25° C. The resulting reaction mixture was heated to 100° C. for 2 hr and, after completion of the reaction, the mixture was concentrated under reduced pressure to give a residue which was diluted with water (30 mL), neutralized with saturated NaHCO$_3$ solution and extracted with EtOAc (4×70 mL). The combined organic layer was dried over sodium sulfate, concentrated under reduced pressure to afford the crude material which was purified by column chromatography using silica gel (100-200 mesh) and 2% MeOH/DCM as eluent to afford tent-butyl (2-((tert-butoxycarbonyl)amino)thieno[2,3-c]pyridin-3-yl)(3-chloro-4-fluorophenyl)carbamate (0.15 g, 0.303 mmol, 43%) as off white solid. LCMS: 494 (M+H).

Step 8: N$^3$-(3-Chloro-4-fluorophenyl)thieno[2,3-c]pyridine-2,3-diamine

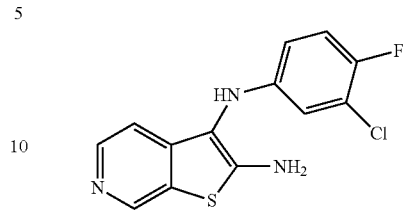

To a stirred solution of tent-butyl (2-((tert-butoxycarbonyl)amino)thieno[2,3-c]pyridin-3-yl)(3-chloro-4-fluorophenyl)carbamate (0.13 g, 0.263 mmol) in 1,4-dioxane (2 mL) was added 4 M dioxane.HCl solution (0.59 mL, 2.373 mmol) at 0° C. The resulting mixture was stirred for 8 hr at 25° C. and, after completion of the reaction, the reaction mass was concentrated under reduced pressure to give residue which was diluted with DCM (70 mL) and basified with liq.NH$_3$. The DCM layer was dried over sodium sulfate, concentrated under reduced pressure to afford crude mass which was purified by column chromatography using silica gel (100-200 mesh) and 2% MeOH/DCM as eluent to afford N$^3$-(3-chloro-4-fluorophenyl)thieno[2,3-c]pyridine-2,3-diamine (0.015 g, 0.051 mmol, 20%) as off white solid. $^1$H-NMR (400 MHz, DMSO-d$_6$): δ 8.66 (s, 1H), 8.13 (d, J=5.4 Hz, 1H), 7.27 (s, 1H), 7.11 (t, J=9.1 Hz, 1H), 6.86 (d, J=5.3 Hz, 1H), 6.72 (bs, 2H), 6.50 (dd, J=6.2 Hz, J'''=2.4 Hz, 1H), 6.42-6.40 (m, 1H); LCMS: 294 (M+H).

Example 18

Synthesis of 3-((3-chlorophenyl)thio)benzo[b]thiophen-2-amine hydrochloride (Compound 125)

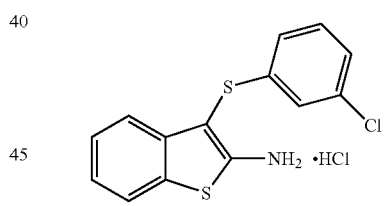

Step 1: 3-Bromo-1-benzothiophene

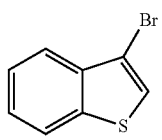

To a solution of benzo[b]thiophene (10 g, 74.516 mmol) in chloroform (75 mL) and acetic acid (75 mL), was stepwise added NBS (16.6 g, 93.268 mmol) for 4 hr at 0° C. and the mixture allowed to stir at room temperature for 48 hr. The progress of the reaction was monitored by TLC and, after completion of reaction, the reaction mass was diluted with chloroform (200 mL) and the resulting mixture was successively washed with a saturated solution of sodium thiosulfate (200 mL), sodium carbonate (200 mL) and brine (150 mL). The extracted organic layer was then dried over sodium sulfate, filtered and evaporated under reduced pressure. The resulting red liquid was then filtered of a pad of silica gel, eluting with hexane to afford 3-bromo-1-benzothiophene (15.87 g, 74.474 mmol, 100%) as yellow oil. The $^1$H NMR and mass was confirmed by reported literature.

Step 2: 3-Bromo-2-nitro-1-benzothiophene

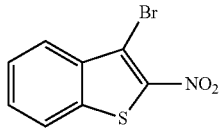 [SMILES: O=[N+]([O-])c1sc2ccccc2c1Br]

Fuming nitric acid (8.6 mL) was dropwise added to a mixture of 3-bromo benzothiophene (3 g, 14.155 mmol) in TFA (7.5 mL) and DCM (15 mL) at 0° C. The reaction was turned greenish, and a yellow solid precipitated. To this reaction mixture was added DCM (10 mL) and the mixture stirred at 0° C. for 30 min. The reaction mass was poured into ice-water (500 mL) and extracted with DCM. The combined organic layers were washed with brine, dried over sodium sulfate and evaporated under reduced pressure to give a yellow solid. The resulting yellow solid was crystallized with DCM and hexane mixture to afford 3-bromo-2-nitro-1-benzothiophene (1.5 g, 5.811 mmol, 41%) as a yellow solid. The $^1$H NMR and mass was confirmed by reported literature.

Step 3: 3-[(3-Chlorophenyl)sulfanyl]-2-nitro-1-benzothiophene

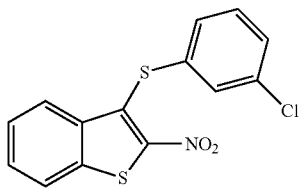 [SMILES: O=[N+]([O-])c1sc2ccccc2c1Sc1cccc(Cl)c1]

3-Chlorothiophenol was added to a solution of sodium hydroxide (0.085 g, 2.139 mmol) in water (2 mL) and dioxane (18 mL) mixture at 0° C. A solution of 3-bromo-2-nitro-1-benzothiophene (0.5 g, 1.945 mmol) in dioxane (2 mL) was then added dropwise and the reaction mixture stirred for 1 h at the same temperature. After completion of the reaction, the reaction mass was diluted with water, extracted with ethyl acetate and washed with brine. The organic layer was dried over sodium sulfate, concentrated under reduced pressure to give residue which was purified by column chromatography using 4% ethyl acetate and hexane mixture on silica gel to afford 3-[(3-chlorophenyl)sulfanyl]-2-nitro-1-benzothiophene (0.375 g, 1.165 mmol, 60%) as yellow solid. $^1$H-NMR (500 MHz, CDCl$_3$): δ 7.83 (d, J=8.3 Hz, 1H), 7.67 (d, J=8.3 Hz, 1H), 7.58-7.55 (m, 1H), 7.38-7.35 (m, 1H), 7.30-7.29 (m, 1H), 7.22-7.21 (m, 1H), 7.20 (s, 1H), 7.18-7.17 (m, 1H).

Step 4: 3-[(3-Chlorophenyl)sulfanyl]-1-benzothiophen-2-amine

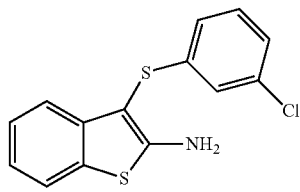

To the solution of 3-[(3-chlorophenyl)sulfanyl]-2-nitro-1-benzothiophene (0.3 g, 0.932 mmol) in ethyl acetate (10 mL) was added activated Pd/C (0.02 g, 10%) under hydrogen gas (balloon) at room temperature and the reaction mass stirred for 12 hr. The reaction mixture was filtered through a Celite® reagent bed, washed with ethyl acetate, the filtrate was distilled off to give a residue. The reside was purified by column chromatography using 6% ethyl acetate and hexane mixture on silica gel to afford 3-[(3-chlorophenyl)sulfanyl]-1-benzothiophen-2-amine (0.15 g, 0.514 mmol, 55%) as reddish viscous liquid which was used in next stage without further purification.

Step 5: 3-[(3-Chlorophenyl)sulfanyl]-1-benzothiophen-2-amine hydrochloride

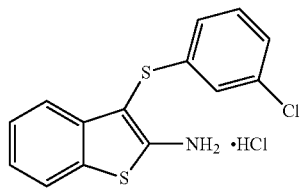 [SMILES: Nc1sc2ccccc2c1Sc1cccc(Cl)c1 ; Cl]

To the solution of 3-[(3-chlorophenyl)sulfanyl]-1-benzothiophen-2-amine (0.15 g, 0.514 mmol) in diethyl ether (5 mL) was added hydrochloride gas absorbed diethyl ether solution (10 mL). The reaction mass was stirred at room temperature for 30 min, a brown solid appeared, the solvent was decanted and the solid dried under vacuum to afford 3-[(3-chlorophenyl)sulfanyl]-1-benzothiophen-2-amine hydrochloride (0.1 g, 0.304, 60%) as light brown solid. $^1$H-NMR (400 MHz, DMSO-d$_6$): δ 7.65 (d, J=7.8 Hz, 1H), 7.24 (t, J=7.9 Hz, 1H), 7.20-7.17 (m, 2H), 7.15-7.12 (m, 1H), 7.05-7.01 (m, 1H), 6.97 (d, J=7.8 Hz, 1H), 6.94-6.93 (m, 1H), 6.45 (bh, 2H); HRMS: 290.9949 (M−H)$^+$.

Example 19

Synthesis of N$^3$-(3-chloro-4-fluorophenyl)-5-phenylbenzo[b]thiophene-2,3-diamine (Compound 134)

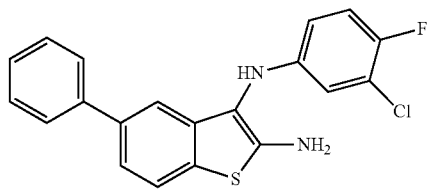 [SMILES: Nc1sc2ccc(-c3ccccc3)cc2c1Nc1ccc(F)c(Cl)c1]

Step 1: 1-Bromo-4-[(2,2-diethoxyethyl)sulfanyl]benzene

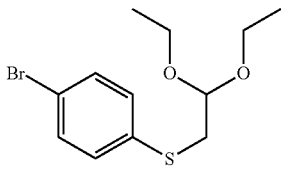 [SMILES: CCOC(CSc1ccc(Br)cc1)OCC]

4-Bromothiophenol (10 g, 52.890 mmol) was dissolved in DMF (25 mL) and potassium carbonate added, followed by a solution of bromoacetaldehyde diethyl acetal (8.9 mL, 68.750 mmol) in DMF (25 mL) at 0° C. The reaction mixture was warmed to room temperature and stirred overnight. The progress of the reaction was monitored by TLC and, after completion of the reaction, the mixture was diluted with water and extracted using ethyl acetate. The combined organic layers were washed with brine, dried over anhydrous sodium sulfate and solvent was evaporated under reduced pressure to dryness to give residue which was purified by column chromatography using hexane as eluent on silica gel to afford 1-bromo-4-[(2,2-diethoxyethyl)sulfanyl]benzene (14 g, 52.288 mmol, 99%) as yellow liquid. The $^1$H NMR and mass was confirmed by reported literature.

Step 2: 5-Bromo-1-benzothiophene

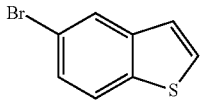

Poly phosphoric acid (28 g) was dissolved in chlorobenzene (25 mL) at 125° C. and a solution of 1-bromo-4-[(2,2-diethoxyethyl)sulfanyl]benzene (14 g, 55.288 mmol) in chlorobenzene (28 mL) was added under nitrogen. The reaction mixture was refluxed at 125° C. overnight. Progress of the reaction was monitored by TLC and, after completion of the reaction, the mixture was diluted with water and extracted using toluene. The combined organic layers were washed with brine, dried over anhydrous sodium sulfate and solvent was evaporated under reduced pressure to give residue which was purified by column chromatography using hexane as eluent on silica gel to afford 5-bromo-1-benzothiophene (5 g, 45.867 mmol, 51%) as white solid. The $^1$H NMR and mass was confirmed by reported literature.

Step 3: 5-Phenyl-1-benzothiophene

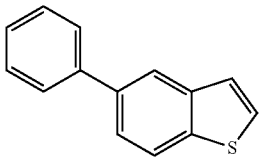 [SMILES: c1ccc(-c2ccc3sccc3c2)cc1]

A solution of 5-bromo-1-benzothiophene (2 g, 9.385 mmol), phenylboronic acid (1.2 g, 9.841 mmol), Pd(PPh$_3$)$_4$, (544 g, 0.471 mmol), potassium carbonate (1.9 g, 13.747 mmol) in toluene and water (20+20 mL) mixture was refluxed at 100° C. for overnight. After completion of the reaction, the mixture was cooled to room temperature, diluted with ethyl acetate, filtered through a Celite® bed, and washed with ethyl acetate. The combined filtrate was washed with water and brine. The organic layer was dried over sodium sulfate and concentrate under reduced pressure to give residue which was purified by column chromatography using hexane as eluent on silica gel to afford 5-phenyl-1-benzothiophene (1.7 g, 8.084 mmol, 86%) as white solid. $^1$H-NMR (400 MHz, CDCl$_3$): δ 7.95 (d, J=1.5 Hz, 1H), 7.86 (dd, J'=8.5 Hz, J"=0.7 Hz, 1H), 7.60-7.58 (m, 2H), 7.52 (dd, J'=8.3 Hz, J"=1.7 Hz, 1H), 7.41-7.37 (m, 3H), 7.32-7.27 (m, 2H).

Step 4: 3-Bromo-5-phenyl-1-benzothiophene

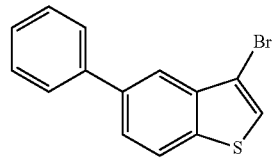 [SMILES: Brc1csc2ccc(-c3ccccc3)cc12]

5-Phenyl-1-benzothiophene (1.5 g, 7.132 mmol) was dissolved in a mixture of chloroform (15 mL) and acetic acid (15 mL) and cooled to 0° C., and NBS (1.6 g, 8.989 mmol) was then added portionwise. The reaction mixture was stirred at room temperature for 48 hr. After completion of the reaction, the mass was quenched by saturated solution of sodium thiosulfate and extracted with chloroform. The combined organic layers were washed with saturated solution of sodium bicarbonate and brine, dried over sodium sulfate and concentrated under reduced pressure to give residue which was purified by column chromatography using hexane as eluent on silica gel to afford 3-bromo-5-phenyl-1-benzothiophene (1.9 g, 6.570 mmol, 92%) as yellow liquid. $^1$H-NMR (500 MHz, CDCl$_3$): δ 8.04 (s, 1H), 7.90 (d, J=8.6 Hz, 1H), 7.70 (dd, J'=8.3 Hz, J"=1.5 Hz, 2H), 7.67 (dd, J'=8.3 Hz, J"=1.5 Hz, 1H), 7.50 (t, J=7.6 Hz, 2H), 7.48 (s, 1H), 7.42-7.39 (m, 1H).

Step 5: 3-Bromo-2-nitro-5-phenyl-1-benzothiophene

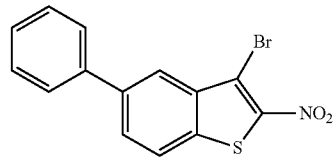 [SMILES: O=[N+]([O-])c1sc2ccc(-c3ccccc3)cc2c1Br]

A solution of 3-bromo-5-phenyl-1-benzothiophene (0.55 g, 1.901 mol) in acetic anhydride (2.28 mL) was cooled to 0° C. and a mixture of fuming nitric acid (0.54 mL) in acetic acid (0.37 mL) was added and the mass stirred for 2 hr. Progress of the reaction was monitored by TLC. After completion of the reaction, the mixture was quenched in ice-cold water, extracted with DCM, dried over anhydrous sodium sulfate and concentrated under reduced pressure to give residue which was purified by column chromatography using hexane as eluent on silica gel to afford 3-bromo-2-nitro-5-phenyl-1-benzothiophene (0.15 g, 0.448 mmol, 34%) as yellow solid. $^1$H-NMR (400 MHz, CDCl$_3$): δ 8.18 (s, 1H), 7.86 (s, 2H), 7.66-7.63 (m, 2H), 7.51-7.47 (m, 2H), 7.43-7.39 (m, 1H).

Step 6: N-(3-Chloro-4-fluorophenyl)-2-nitro-5-phenyl-1-benzothiophen-3-amine

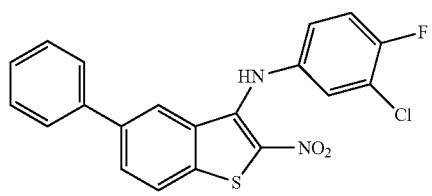

A solution of 3-bromo-2-nitro-5-phenyl-1-benzothiophene (0.07 g, 0.209 mmol) and 3-chloro-4-fluoroaniline (0.061 g, 0.419 mmol) in DMF (1 mL) was heated to 120° C. for 1 hr. After completion of the reaction, the mixture was poured into ice-cold water under stirring, solid precipitated, filtered, washed with water, dried under vacuum and recrystallized with DCM and hexane mixture to afford pure N-(3-chloro-4-fluorophenyl)-2-nitro-5-phenyl-1-benzothiophen-3-amine (0.05 g, 0.125 mmol, 60%) as orange solid. $^1$H-NMR (400 MHz, CDCl$_3$): δ 10.03 (s, 1H), 7.74 (s, 2H), 7.46-7.44 (m, 1H), 7.38-7.35 (m, 2H), 7.33-7.31 (m, 2H), 7.28-7.25 (m, 2H), 7.24-7.22 (m, 2H).

Step 7: N$^3$-(3-Chloro-4-fluorophenyl)-5-phenyl-1-benzothiophene-2,3-diamine (Procedure E)

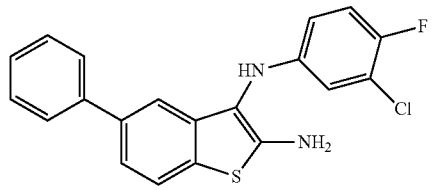

To the solution of N-(3-chloro-4-fluorophenyl)-2-nitro-5-phenyl-1-benzothiophen-3-amine (0.05 g, 0.125 mmol) in methanol (3 mL) was added activated Pd/C (0.005 g, 10%) under hydrogen gas (balloon) at room temperature and the reaction mass stirred for 3 hr. The reaction mixture was filtered through a Celite® bed under nitrogen, washed with methanol, the filtrate was distilled to give residue which was crystallized with a DCM and hexane mixture to afford N$^3$-(3-chloro-4-fluorophenyl)-5-phenyl-1-benzothiophene-2,3-diamine (0.027 g, 0.073 mmol, 58%) as brown solid. $^1$H-NMR (500 MHz, DMSO-d$_6$): δ 7.65 (d, J=8.3 Hz, 1H), 7.50 (d, J=7.4 Hz, 2H), 7.39-7.35 (m, 3H), 7.28-7.23 (m, 2H), 7.18 (s, 1H), 7.07 (t, J=9.0 Hz, 1H), 6.54-6.52 (m, 1H), 6.47-6.44 (m, 1H), 5.94 (bs, 2H); HRMS: 367.0471 [M-H].

Example 20

Synthesis of 2-Amino-3-((3-chloro-4-fluorophenyl)amino)benzo[b]thiophene-6-carbonitrile (Compound 136)

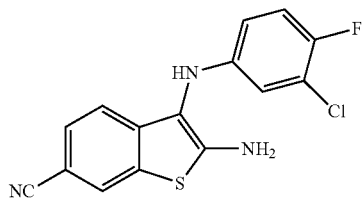

Step 1: 1-Bromo-3-[(2,2-diethoxyethyl)sulfanyl]benzene

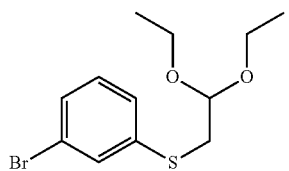 [SMILES: CCOC(CSc1cccc(Br)c1)OCC]

To a stirred solution of 3-bromothiophenol (10.0 g, 52.88 mmol) in DMF (180 mL) was added NaH (3.0 g, 63.45 mmol) portionwise at 0° C. After the addition, the reaction mixture was stirred at room temperature for 30 min. Bromoacetaldehyde dimethylacetal (6.85 mL, 58.17 mmol) was added dropwise and the resulting mixture was stirred at room temperature for 2 hr. The reaction mixture was diluted with EtOAc (250 mL) and washed with cold water and brine solution. The organic layer was dried over anhydrous sodium sulfate, concentrated under reduced pressure to afford the crude material which was purified by column chromatography using silica gel (100-200 mesh) and 2% EtOAc-hexane as eluent to afford 1-bromo-3-(2,2-dimethoxy-ethylsulphanyl)-benzene (11.0 g, 36.038 mmol, 68%) as colorless liquid. GCMS: 277 (m/z).

Step 2: 6-Bromobenzo[b]thiophene and 4-Bromobenzo[b]thiophene

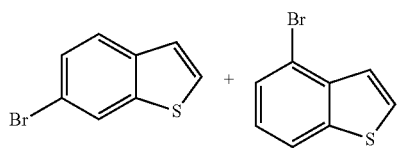

PPA (40.0 g) was combined with chlorobenzene (110 mL) and refluxed for 1 hr. 1-Bromo-3-(2,2-dimethoxy-ethylsulphanyl)-benzene (11.0 g, 36.038 mmol) in chlorobenzene (40 mL) was added dropwise to the refluxing reaction mixture and continued to reflux for 12 hr. The reaction mixture was cooled to room temperature, the top-layer was separated, the bottom layer was diluted with water (200 mL) and then extracted with DCM (2×200 mL). The combined organic layer was dried over anhydrous sodium sulfate, concentrated under reduced pressure to afford the crude material which was purified by column chromatography using silica gel (100-200 mesh) and hexane as eluent to afford a mixture of 6-bromobenzo[b]thiophene and 4-bromo-benzo[b]thiophene (7.0 g, 32.849 mmol, 91%) as pale yellow liquid. GCMS: 213 (m/z).

Step 3: Benzo[b]thiophene-6-carbonitrile

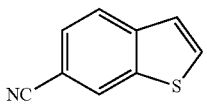 [SMILES: N#Cc1ccc2ccsc2c1]

A mixture of 6-bromobenzo[b]thiophene and 4-bromobenzo[b]thiophene (5.0 g, 23.46 mmol) in DMF (90 mL) was degassed with argon for 15 min. Pd(PPh₃)₄ (1.35 g, 1.173 mmol) was then added and the mixture further degassed for 10 min. Zn(CN)2 (2.75 g, 23.46 mmol) was then added and the mixture refluxed for 3 hr. The mixture was allowed to cool to room temperature and filtered through a pad of Celite® reagent. The filtrate was concentrated, diluted with MTBE (150 mL), washed with cold water, followed by brine. The organic layer was dried over anhydrous sodium sulfate, concentrated under reduced pressure to afford the crude material which was purified by column chromatography using silica gel (100-200 mesh) and 2% EtOAc/hexane as eluent to afford benzo[b]thiophene-6-carbonitrile (1.2 g, 7.537 mmol, 32%) as yellow liquid. ¹H NMR (400 MHz, CDCl₃): δ 8.19 (s, 1H), 7.88 (d, 1H), 7.70 (d, 1H), 7.60-7.56 (m, 1H), 7.41 (d, 1H); GCMS: 159 (m/z).

Step 4: 3-Bromobenzo[b]thiophene-6-carbonitrile

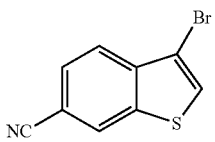

To a stirred solution of benzo[b]thiophene-6-carbonitrile (1.0 g, 6.289 mmol) in CHCl₃ (7 mL) and acetic acid (7 mL) was added NBS (1.34 g, 7.547 mmol) portionwise at 0° C. and the mixture stirred at rt for 48 hr. The reaction mixture was diluted with DCM (60 mL) and washed with saturated solution of sodium thiosulfate solution and NaHCO₃ followed by brine. The organic layer was dried over sodium sulfate, concentrated under reduced pressure to afford the crude material which was purified by column chromatography using silica gel (100-200 mesh) and 2% EtOAc/hexane as eluent to 3-bromobenzo[b]thiophene-6-carbonitrile (0.8 g, 3.359 mmol, 53%) as off white solid. GCMS: 238 (m/z).

Step 5: 3-Bromo-2-nitrobenzo[b]thiophene-6-carbonitrile

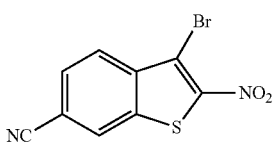 [SMILES: N#Cc1ccc2c(Br)c([N+](=O)[O-])sc2c1]

To a stirred solution of 3-bromobenzo[b]thiophene-6-carbonitrile (0.5 g, 2.10 mmol) in DCM (3 mL) was added trifluoroacetic anhydride (3.87 mL, 27.30 mmol) at 0° C. and the mixture stirred for 30 min. KNO₃ (0.23 g, 2.310 mmol) was then added portionwise at 0° C. and the mixture stirred for a further 30 min. The mixture was diluted with DCM (25 mL) and washed with water and brine solution. The organic layer was dried over sodium sulfate, concentrated under reduced pressure to afford the crude material which was purified by triturating with 50% MTBE and DCM to afford 3-bromo-2-nitro-benzo[b]thiophene-6-carbonitrile (0.25 g, 0.883 mmol, 42%) as yellow solid. LCMS: 281 (M–H).

Step 6: 3-((3-Chloro-4-fluorophenyl)amino)-2-nitrobenzo[b]thiophene-6-carbonitrile

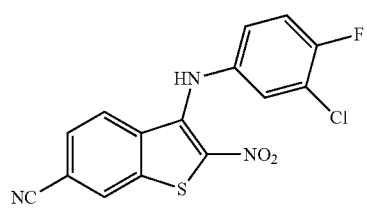

A solution of 3-bromo-2-nitrobenzo[b]thiophene-6-carbonitrile (0.8 g, 2.826 mmol) and 4-fluoro-3-chloro phenyl amine (0.41 g, 2.826 mmol) in DMF (8 mL) was heated at 100° C. in a sealed tube for 12 hr. The mixture was diluted with MTBE (25 mL) and washed with cold water. The organic layer was dried over sodium sulfate, concentrated under reduced pressure to afford the crude material which was purified by triturating with MTBE and pentane to afford 3-(3-chloro-4-fluoro-phenylamino)-2-nitrobenzo[b]thiophene-6-carbonitrile (0.45 g, 1.294 mmol, 46%) as yellow solid. LCMS: 346.2 (M–H).

Step 7: 2-Amino-3-((3-chloro-4-fluorophenyl)amino)benzo[b]thiophene-6-carbonitrile (Procedure F)

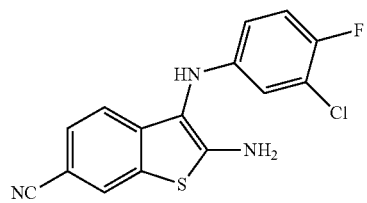 [SMILES: N#Cc1ccc2c(Nc3ccc(F)c(Cl)c3)c([N+](=O)[O-])sc2c1]

To a stirred solution of 3-(3-chloro-4-fluoro-phenylamino)-2-nitro-benzo[b]thiophene-6-carbonitrile (0.2 g, 0.575 mmol) in THF (2 mL) and methanol (2 mL) was added zinc dust (0.075 g, 1.150 mmol) and NH₄Cl (0.062 g, 0.575 mmol) at room temperature and the mixture stirred for 3 hr. The mixture was filtered through a pad of Celite® reagent and washed with ethyl acetate. The filtrate was diluted with EtOAc (30 mL) and washed with water and brine. The organic layer was dried over sodium sulfate, concentrated under reduced pressure to afford the crude material which was purified by triturating with MTBE and pentane to afford 2-amino-3-(3-chloro-4-fluoro-phenylamino)-benzo (b)thiophene-6-carbonitrile (0.08 g, 0.251 mmol, 44%) as pale brown solid.
¹H-NMR (400 MHz, DMSO-d₆): δ 8.11 (s, 1H), 7.47 (d, J=8.3 Hz, 1H), 7.32 (s, 1H), 7.11 (t, J=9.1 Hz, 1H), 7.01 (d, J=8.2 Hz, 1H), 6.63 (bs, 2H), 6.51 (dd, J'=6.2 Hz, J"=2.6 Hz, 1H), 6.43-6.40 (m, 1H); LCMS: 316 (M−H).

Example 21

Synthesis of (3-((3-Chloro-4-fluorophenyl)amino) furo[2,3-c]pyridin-2-yl)-carbamate (Compound 141) (Procedure G)

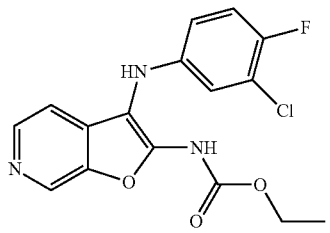 [SMILES: CCOC(=O)Nc1oc2cnccc2c1Nc1ccc(F)c(Cl)c1]

To a stirred solution of N³-(3-chloro-4-fluorophenyl)furo [2,3-c]pyridine-2,3-diamine (1.0 eq) in THF was added pyridine (1.3 eq) followed by ethyl chloroformate (1.1 eq) at 25° C. The reaction mixture was stirred for 3-10 hr at 25° C. and concentrated. The crude material was dissolved in EtOAc, washed thoroughly with water followed by brine, dried over Na₂SO₄ and concentrated. The crude mass was subjected to Prep-TLC/trituration to afford the major desired mono-carbamate (3-((3-chloro-4-fluorophenyl)amino)furo [2,3-c]pyridin-2-yl)carbamate (45-50%) along with traces of di-carbamate ethyl (3-chloro-4-fluorophenyl)(2-((ethoxycarbonyl)amino)furo[2,3-c]pyridin-3-yl)carbamate as solid.

Example 22

Synthesis of Ethyl (3-chloro-4-fluorophenyl)(2-((ethoxycarbonyl)amino)furo-[2,3-c]pyridin-3-yl) carbamate (Compound 142) (Procedure H)

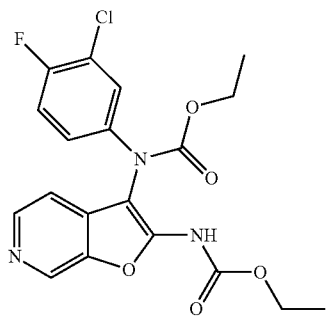 [SMILES: CCOC(=O)Nc1oc2cnccc2c1N(C(=O)OCC)c1ccc(F)c(Cl)c1]

To a stirred solution of N³-(3-chloro-4-fluorophenyl)furo [2,3-c]pyridine-2,3-diamine in THF was added pyridine (10.0 eq) followed by ethyl chloroformate (8.0 eq) at 25° C. Reaction mixture was stirred for 20 hr at 25° C. and concentrated, crude material was dissolved in EtOAc, washed thoroughly with water followed by brine, dried over Na₂SO₄ and concentrated. The crude mass was subjected to Prep-TLC/trituration to afford the desired di-carbamate ethyl (3-chloro-4-fluorophenyl)(2-((ethoxycarbonyl)amino) furo[2,3-c]pyridin-3-yl)carbamate (50-55%) along with mono-carbamate (3(3-chloro-4-fluorophenyl)amino)furo[2, 3-c]pyridin-2-yl)carbamate (20-25%) as solid.

Example 23

Synthesis of N³-(3-chloro-4-fluorophenyl)-7-(2-methylpyridin-4-yl)furo[2,3-c]pyridine-2,3-diamine (Example 158)

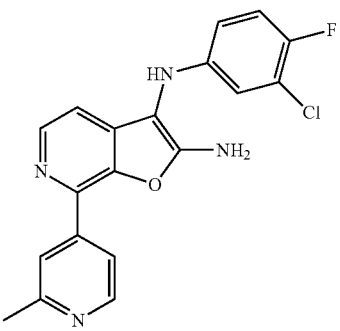 [SMILES: Cc1cc(-c2nccc3c(Nc4ccc(F)c(Cl)c4)c(N)oc23)ccn1]

Step 1: 2-Bromo-3-(methoxymethoxy)pyridine

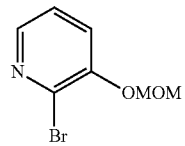

To a stirred solution of 2-bromo-3-hydroxypyridine (50 g, 287.356 mmol) in THF at 0° C. was added t-BuO-K (51.49 g, 459.7 mmol) portion wise. After stirring the reaction mixture for 15 mins, methoxymethyl chloride (34.473 mL, 459.77 mmol) was added to it at 0° C. and the resulting reaction mixture was stirred for 12 h. at 25° C. Reaction mixture was diluted with water and extracted with ethyl acetate (4×500 mL). Organic layer was dried over anhydrous sodium sulfate, concentrated under reduced pressure to afford rude mass which was purified by column chromatography using silica gel (100-200 mesh) and 10% EtOAc-hexane as eluent to afford 2-bromo-3-methoxymethoxy-pyridine (45 g) as pale brown liquid. ¹H-NMR (400 MHz, DMSO-d₆): δ 8.03 (dd, J'=4.5 Hz, J"=1.3 Hz, 1H), 7.60 (dd, J'=8.1 Hz, J"=1.1 Hz, 1H), 7.40 (dd, J'=8.2 Hz, J"=4.5 Hz, 1H), 5.35 (s, 2H), 3.41 (s, 3H).

Step 2: 2-Bromo-3-(methoxymethoxy)isonicotinaldehyde

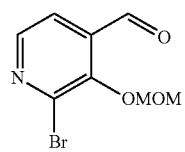

To a stirred solution of 2-Bromo-3-Methoxymethoxypyridine (10.0 g, 45.872 mmol) in anhydrous THF (140 mL) was added LDA (79.5 mL,59.633 mmol, 0.75 M in THF) at −78° C. After stirring for 1 hr at −78° C., ethylformate (5.559 mL, 68.807 mmol) was added to it and stirred for 30 min at −78° C. The cold bath was removed and the reaction mixture was kept at −10° C. and quenched with aq. NH₄Cl solution (50 mL). Reaction mass was extracted with ethyl acetate (3×150 mL), dried over sodium sulfate and was concentrated under reduced pressure to afford crude mass which was passed through a small pad of silica gel (100-200 mesh) using 4% ethylacetate/hexane as eluent to get 2-bromo-3-methoxymethoxy-pyridine-4-carbaldehyde (5.0 g) as pale yellow solid. ¹H-NMR (400 MHz, DMSO-d₆): δ 10.2 (s, 1H), 8.40 (d, J=4.8 Hz, 1H), 7.67 (d, J=4.8 Hz, 1H), 5.25 (s, 2H), 3.55 (s, 3H)).

Step 3: 3-(Methoxymethoxy)-2'-methyl-[2,4'-bipyridine]-4-carbaldehyde

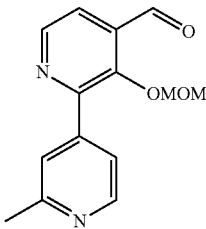

To a stirred solution of 2-bromo-3-methoxymethoxy-pyridine-4-carbaldehyde (8.0 g, 32.52 mmol), 2-methylpyridine-4-boronic acid (4.455 g, 32.52 mmol) and tricyclohexyl phosphine (0.547 g, 1.951 mmol) in dry 1,4-dioxane (500 mL) was added K₃PO₄ (55 mL, 1.27M), MeOH (50 mL) and Pd₂(dba)₃ (0.893 g, 0.976 mmol) under argon atmosphere. The resulting reaction mixture was degassed with argon for 5 mins. then reaction mixture was slowly heated to reflux for about 4 hrs. After completion of reaction the reaction mass was cooled to room temperature, filtered through celite bed, washed with ethyl acetate, filtrate was concentrated under reduced pressure to give crude mass which was purified by column chromatography on silica gel (100-200 mess) using 60% EtOAc/hexane as eluent to afford 3-methoxymethoxy-2'-methyl-[2,4']bipyridinyl-4-carbaldehyde (6.0 g) as brown liquid. ¹H-NMR (400 MHz, DMSO-d₆): δ 10.34 (s, 1H), 8.72 (d, J=4.7 Hz, 1H), 8.58 (d, J=5.1 Hz, 1H), 7.73 (d, J=4.8 Hz, 1H), 7.69 (s, 1H), 7.63 (d, J=4.2 Hz, 1H), 4.96 (s, 2H), 3.20 (s, 3H), 2.56 (s, 3H).

Step 4: 3-Hydroxy-2'-methyl-[2,4'-bipyridine]-4-carbaldehyde

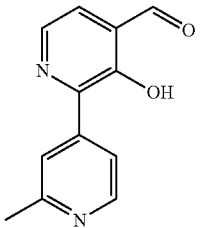 [SMILES: Cc1cc(-c2nccc(C=O)c2O)ccn1]

3-Methoxymethoxy-2'-methyl-[2,4']bipyridinyl-4-carbaldehyde (6.0 g, 65.83 mmol) was taken in DCM (10 mL) under ice bath and 10% TFA-DCM (60 mL) was added slowly, resulting mixture was stirred at 25° C. for 2 hrs. Reaction mixture was cooled under ice bath and basified (pH 10) with potassium carbonate, extracted with ethyl acetate (2×30 mL), aqueous part was neutralized with citric acid and extracted with 10% IPA-DCM (5×50 mL). Combined organic part was dried over sodium sulphate, concentrated under reduced pressure to afford the crude mass which was purified by trituration using mixture of solvents MTBE-pentane to give 3-hydroxy-2'-methyl-[2,4'-bipyridine]-4-carbaldehyde (4.0 g) as brown solid. ¹H-NMR (400 MHz, DMSO-d₆): δ 11.25 (bh, 1H), 10.29 (s, 1H), 8.55 (d, J=5.2 Hz, 1H), 8.42 (d, J=4.7 Hz, 1H), 7.86 (s, 1H), 7.81 (d, J=5.1 Hz, 1H), 7.69 (d, J=4.8 Hz, 1H), 2.55 (s, 3H); LCMS: 315.3 (M+H).

Step 5: 4-(3-Chloro-4-fluorophenyl)imino)methyl)-2'-methyl-[2,4'-bipyridin]-3-ol

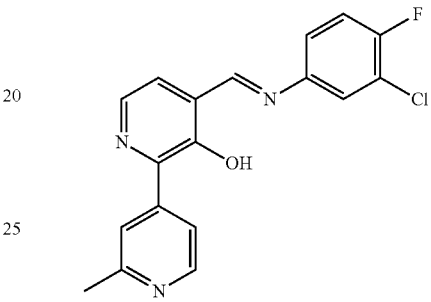

3-Hydroxy-2'-methyl-[2,4']bipyridinyl-4-carbaldehyde (5.0 g, 23.364 mmol) was taken in mixed solvents of TFE (30 mL) and MeCN (30 mL) and added 4-fluoro-3-chlorophenyl amine (3.4 g, 23.364 mmol) at 25° C., resulting mixture was stirred at this temperature for 2 hr. Reaction mixture was concentrated under reduced pressure to give crude mass which was purified by trituration with n-pentane to afford 4-{[3-chloro-4-fluoro-phenylimino]-methyl}-2'-methyl [2,4']bipyridinyl-3-ol (6.0 g). ¹H-NMR (400 MHz, DMSO-d₆): δ 9.22 (s, 1H), 8.78 (d, J=5.9 Hz, 1H), 8.52 (d, J=4.7 Hz, 1H), 8.39 (s, 1H), 8.32 (d, J=5.0 Hz, 1H), 7.95 (dd, J=6.7 Hz, J"=2.3 Hz, 1H), 7.80 (d, .1=4.6 Hz, 1H), 7.65-7.57 (m, 2H), 2.71 (s, 3H); LCMS: 341.9 (M+H).

Step 6: N³-(3-chloro-4-fluorophenyl)-7-(2-methyl-pyridin-4-y0furo[2,3-c]pyridine-2,3-diamine

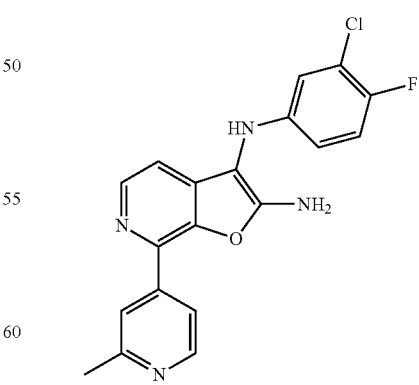

To a stirred solution of 4-{[3-chloro-4-fluoro-phenylimino]-methyl{-2'-methyl-[2,4]bipyridinyl-3-ol (6.0 g, 17.595 mmol) in mixed solvent of DCM (36 mL) and TFE (36 mL) was added TMSCN (8.805 mL, 70.381 mmol) at 25° C. The reaction mixture was stirred for 12 h at 25° C. After completion of reaction the volatiles were removed and crude material was purified by trituration with MTBE/pentane to afford desired product N³-(3-chloro-4-fluorophenyl)-7-(2-methylpyridin-4-yl)furo[2,3-c]pyridine-2,3-diamine (3.0 g) as pale brown solid. ¹H-NMR (400 MHz, CD₃CN): δ 8.65 (s, 1H), 8.29-8.13 (m, 3H), 7.03 (bs, 2H), 6.66 (s, 1H), 6,60 (s, 1H), 5.94 (s, 1H), 5.78 (bs, 2H), 2.66 (s, 3H); LCMS: 369 (M+H).

Example 24

Synthesis of Ethyl (7-((4-carbamoylphenyl)ethynyl)-2-((ethoxycarbonyl) amino)furo[2,3-c]pyridin-3-yl)(3-chloro-4-fluorophenyl)carbamate (Compound 160)

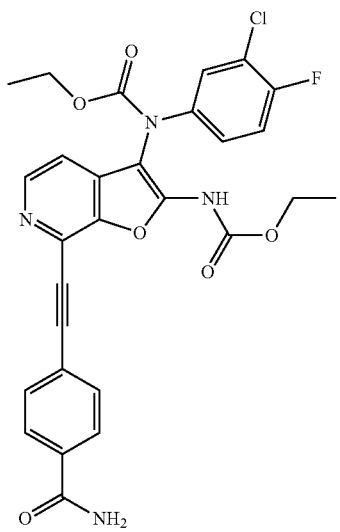 [SMILES: CCOC(=O)Nc1oc2c(C#Cc3ccc(C(N)=O)cc3)nccc2c1N(C(=O)OCC)c1ccc(F)c(Cl)c1]

Step 1: 3-Hydroxy-2-iodopyridine

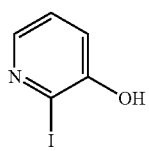

To a stirring solution of 3-hydroxy pyridine (30 g, 315.78 mmol) in water (3000 mL) was added Na₂CO₃ (70 g, 663.15 mmol) followed by Iodine (80 g, 315.78 mmol) in portion wise at 0° C. The reaction mixture was allowed to stir at room temperature for 2 hrs. Reaction mass was acidified with 1N HCl up to pH -4 to get the solid which was filtered off, washed with chilled water followed by MTBE-Hexane to afford desired 3-hydroxy-2-iodopyridine (45 g) as off white solid.

Step 2: 2-Iodo-3-(methoxymethoxy)pyridine

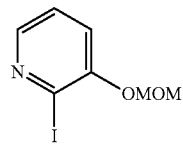

To a stirred solution of 3-hydroxy-2-iodopyridine (10 g, 45.24 mmol) in THF: DMF (10 mL: 20 mL) at 0° C. was added tert-BuO-K (6 g, 54.3 mmol) portion wise. After stirring the reaction mixture for 30 min, methoxymethyl chloride (4 mL, 50 mmol) was added at 0° C. and the resulting mixture was allowed to stir at room temperature for 3 hrs. Reaction mixture was diluted with brine and extracted with EtOAc (3×150 mL). EtOAc part was dried over anhydrous sodium sulfate, concentrated under reduced pressure to afford crude mass which was purified by column chromatography using silica (100-200 mesh) and EtOAc-hexane as eluent to afford 2-iodo-3-(methoxymethoxy)pyridine (6.0 g) as off white solid.

Step 3: 2-Iodo-3-(methoxymethoxy)isonicotinaldehyde

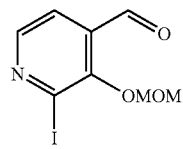

To a stirred solution of 2-iodo-3-(methoxymethoxy)pyridine (4.0 g, 15.094 mmol) in anhydrous THF (60 mL) was added LDA (24.15 mL, 18.113 mmol, 0.75M in THF) drop wise at -78° C. After stirring the reaction mixture for 1 hr at -78° C., DMF (1.74 mL, 22.642 mmol) was added to it and stirred for 15 mins at -78° C. Saturated ammonium chloride solution was added drop wise into the reaction mass at -78° C. and warm-up to room temperature. The resulting quenched mass was extracted with ethyl acetate (2×150 mL). EtOAc part was washed with water followed by brine, dried over sodium sulfate and concentrated under reduced pressure, to afford crude mass which was passed through a pad of silica (100-200 mesh) using 3% EtOAc-hexane as eluent, to afford 2-iodo-3-(methoxymethoxy)-isonicotinaldehyde (2.2 g) as pale yellow solid. ¹H-NMR (400 MHz, DMSO-d₆): δ 10.14 (s, 1H), 8.39 (d, J=4.7 Hz, 1H), 7.60 (d, J=4.8 Hz, 1H), 5,22 (s, 2H), 3.55 (s, 3H).

Step 4: 3-Hydroxy-2-iodoisonicotinaldehyde

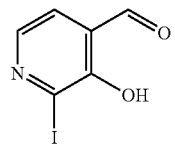

To a stirred solution of 2-iodo-3-(methoxymethoxy)-isonicotinaldehyde (1.2 g, 4.096 mmol) in DCM (3 mL) was added 10% TFA-DCM (10 mL) at 0° C. and stirred at room temperature for 3 hrs. Reaction mass was concentrated under reduced pressure and crude was taken in water (20 mL) and basified (pH-10) with potassium carbonate and extracted with ethyl acetate (2×30 mL), aqueous part was neutralized with citric acid and extracted with 10% IPA-DCM (5×50 mL). Combined organic part was dried over sodium sulphate, concentrated under reduced pressure to afford the crude material which was purified by trituration using MTBE-pentane to afforded 3-hydroxy-2-iodoisonicotinaldehyde (0.75 g) as yellow solid. $^1$H-NMR (400 MHz, DMSO-d$_6$): δ 11.45 (bh, 1H), 10.16 (s, 1H), 8.10 (d, J=3.7 Hz, 1H), 7.53 (d, J=3.4 Hz, 1H); LCMS: 249.5 (M+H).

Step 5: N$^3$-(3-Chloro-4-fluorophenyl)-7-iodofuro[2,3-c]pyridine-2,3-diamine

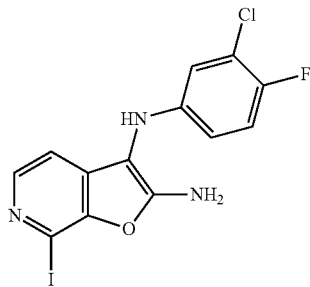 [SMILES: Nc1oc2c(I)nccc2c1Nc1ccc(F)c(Cl)c1]

To a stirred solution of 3-hydroxy-2-iodoisonicotinaldehyde (4.5 g, 18.072 mmol) in dry DCM (70 mL) was added 3-chloro-4-fluoroaniline (2.63 g, 18.072 mmol), TMSCN (11.305 mL, 90.361 mmol) followed by TMSOTf (0.653 mL, 3.614 mmol) and the reaction mass was stirred at room temperature for 5 hr. After completion of the reaction, water was added to the reaction mass and extracted with DCM (2×250 mL). The combined organic layers were washed with water and saturated sodium bicarbonate solution followed by brine, dried over sodium sulphate and evaporated under reduced pressure to afford the crude mass which was purified by trituration with MTBE/pentane to afford the desired compound N$^3$-(3-chloro-4-fluorophenyl)-7-iodofuro[2,3-c]pyridine-2,3-diamine (5.0 g) as brown solid. $^1$H-NMR (400 MHz, DMSO-d$_6$): δ 7.83 (d, J=5.0 Hz, 1H), 7.21 (s, 2H), 7.15-7.09 (m, 2H), 6.83 (d, J=5.0 Hz, 1H), 6.57-6.56 (m, 1H), 6.47-6.45 (m, 1H); LCMS: 404.0 (M+H).

Step 6: Ethyl (3-chloro-4-fluorophenyl)(2-((ethoxycarbonyl)amino)-7-iodofuro [2,3-c]pyridin-3-yl)carbamate

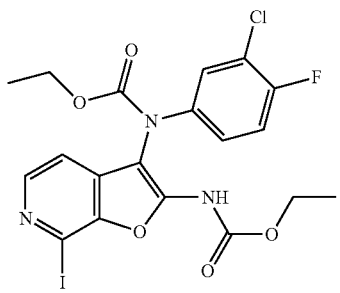 [SMILES: CCOC(=O)Nc1oc2c(I)nccc2c1N(C(=O)OCC)c1ccc(F)c(Cl)c1]

To a stirred solution of N$^3$-(3-chloro-4-fluorophenyl)-7-iodofuro[2,3-c]pyridine-2,3-diamine (5.0 g, 12.407 mmol) in dry THF (50 mL), pyridine (8.011 mL, 99.256 mmol) was added and the reaction mass was stirred for 15 min, then ethylchloroformate (11.811 mL, 124.069 mmol) was added to it. Reaction mass was allowed to stir at room temperature for 4 hrs. After completion of the reaction, the reaction mass was diluted with water and extracted with EtOAc (2×100 mL). The organic layer was washed with water followed by brine, dried over sodium sulphate and evaporated under reduced pressure to afford the crude material which was purified by trituration with MTBE/pentane to afford the desired compound ethyl (3-chloro-4-fluorophenyl)(2-((ethoxycarbonyl)amino)-7-iodofuro[2,3-c]pyridin-3-yl)carbamate (95.5 g) as brown solid. $^1$H-NMR (400 MHz, CD$_3$CN): δ 8.20 (d, J=5.2 Hz, 1H), 7.32 (d, J=5.1 Hz, 1H), 7.10 (t, J=9.0 Hz, 1H), 6.84 (dd, J'=6.2 Hz, J''=2.8 Hz, 1H), 6.75 (dt, J'=8.8 Hz, J''=6.8 Hz, J'''=3.1 Hz, 1H), 6.56 (s, 1H), 4.21 (q, J=7.1 Hz, 4H), 1.17 (t, J=7.1 Hz, 6H); LCMS: 548 (M+H).

Step 7: Ethyl (7-((4-carbamoylphenyl)ethynyl)-2-((ethoxycarbonyl)amino) furo[2,3-c]pyridine-3-yl)(3-chloro-4-fluorophenyl)carbamate

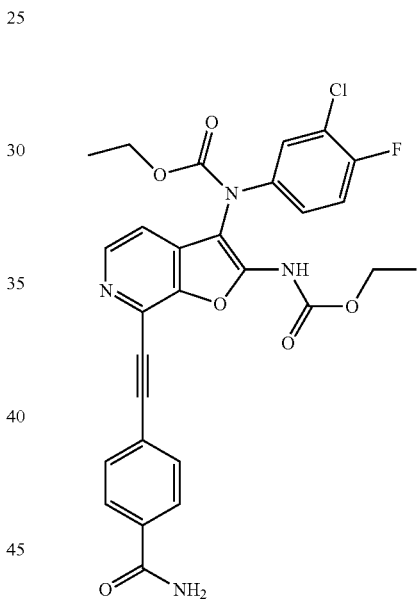

To a stirred solution of ethyl (3-chloro-4-fluorophenyl)(2-((ethoxycarbonyl)amino)-7-iodofuro[2,3-c]pyridin-3-yl)carbamate (0.2 g, 0.366 mmol) in triethylamine (5 mL) and THF (2 mL) was added 4-ethynylbenzamide (0.058 g, 0.402 mmol), CuI (0.003 g, 0.018 mmol), the resulting mass was degassed for 20 mins then PdCl$_2$(PPh$_3$)$_2$ (0.013 g, 0.018 mmol) was added and again degassed for another 10 mins. Reaction mass was heated to 50° C. for 3 hrs. After completion of reaction the reaction mass was cooled to room temperature and filtered through celite bed. Filtrate was concentrated under reduced pressure to give residue which was diluted with water and extracted with ethyl acetate (3×50 mL), EtOAc part was washed with brine, dried over sodium sulfate and concentrated under reduced pressure to afford crude product which was purified by column chromatography on silica (100-200 mesh) using ethyl acetate/hexane as an eluent to afford desired product ethyl (7-((4-carbamoylphenypethynyl)-2-((ethoxycarbonyl)amino)furo[2,3-c]pyridine-3-yl)(3-chloro-4-fluorophenyl)carbamate (60 mg) as brown solid. $^1$H-NMR (400 MHz, DMSO-$d_6$): δ 8.47 (d, J=5.1 Hz, 1H), 8.36 (s, 1H), 8.12 (s, 1H), 7.97 (d, J=8.0 Hz, 2H), 7.76 (d, J=8.0 Hz, 2H), 7.52 (s, 1H), 7.49 (d, J=5.1 Hz, 1H), 7.26 (t, J=9.0 Hz, 1H), 6.82 (dd, J'=6.2 Hz, J"=2.5 Hz, 1H), 6.75-6.71 (m, 1H), 4.18 (q, J=7.0 Hz, 4H), 1.11 (t, J=7.0 Hz, 6H); LCMS: 563.2 (M–H).

Example 25

Synthesis of N'-(3-Chloro-4-fluorophenyl)-5-fluoro-7-(pyridin-4-yl)furo[2,3-c]pyridine-2,3-diamine (Compound 180)

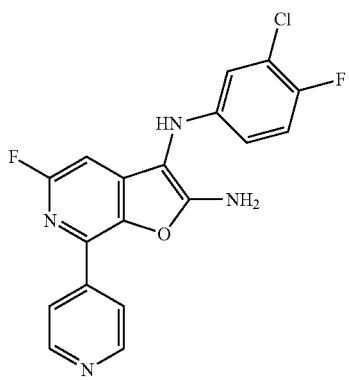 [SMILES: Nc1oc2c(-c3ccncc3)nc(F)cc2c1Nc1ccc(F)c(Cl)c1]

Step 1: 6-Fluoro-3-hydroxy-2-iodopyridine

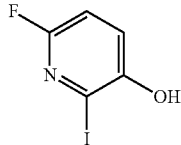

To a stirring solution of 6-fluoro-3-hydroxypyridine (10 g, 88.496 mmol) in THF (300 mL) was added slowly Na$_2$CO$_3$ (19.697 g, 185.841 mmol) in water (300 mL) at 0° C. and stirred for 20 mins. Iodine (22.461 g, 88.496 mmol) was added portion wise at 0° C. and the reaction mass was allowed to stir at room temperature for overnight. Solvent was evaporated; aqueous part was neutralized with 1N HCl, extracted with ethyl acetate. Organic layer was separated, dried over anhydrous Na$_2$SO$_4$ and evaporated under reduce pressure to give crude mass which was triturated with DCM/pentane to get 6-fluoro-3-hydroxy-2-iodopyridine (19.8 g) as a brown solid. $^1$H-NMR (400 MHz, DMSO): δ 10.79 (s, 1H), 7.31-7.27 (m, 1H), 7.03-7.00 (m, 1H); LCMS: 239.8 (M+H).

Step 2: 6-Fluoro-2-iodo-3-(methoxymethoxy)pyridine

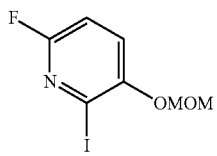

To a stirred solution of 6-fluoro-3-hydroxy-2-iodopyridine (9.0 g, 37.657 mmol) in THF (180 mL) at 0° C. was added tert-BuO—K (6.76 g, 60.251 mmol) portion-wise. After stirring the reaction mixture for 30 min, methoxy methyl chloride (4.55 mL, 60.251 mmol) was added at 0° C. and the resulting mixture was stirred for 2 hr at room temperature. After completion of reaction the reaction mass was diluted with brine and extracted with EtOAc (3×150 mL). The combined organic layers were washed with brine, dried over anhydrous sodium sulfate, concentrated under reduced pressure to afford crude mass (9.6 g) which was purified by column chromatography using silica (100-200 mesh) and 5% EtOAc-Hexane as eluent to afford 6-fluoro-2-iodo-3-(methoxymethoxy)pyridine (8.0 g) as yellow solid. LCMS: 284 (M+H).

Step 3: 6-Fluoro-3-(methoxymethoxy)-2,4'-binyridine

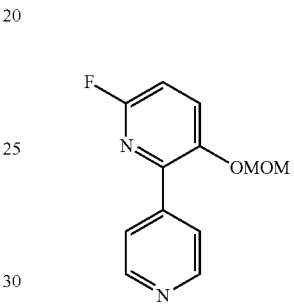

To a stirred solution of 6-fluoro-2-iodo-3-(methoxymethoxy)pyridine (3.5 g, 12.367 mmol) in dioxane (120 mL) was added 4-pyridinylboronic acid (1.67 g, 13.6 mmol), K$_3$PO$_4$ (16.5 mL, 21.02 mmol, 1.27 M solution in water), P(Cy)$_3$ (0.7 g, 2.47 mmol). The reaction mass was degassed for 20 min. with Argon then Pd$_2$(dba)$_3$ (1.13 g, 1.24 mmol) was added and degassed for another 10 min. The resulting mixture was heated to 100° C. for 2 hrs. Reaction mass was cooled to room temperature and filtered through celite bed, filtrate was concentrated under reduced pressure to give crude mass which was purified by column chromatography to afford 6-fluoro-3-(methoxymethoxy)-2,4'-bipyridine (2.8 g) as pale yellow solid. $^1$H-NMR (400 MHz, DMSO): δ 8.69 (d, J=5.0 Hz, 2H), 7.94-7.89 (m, 3H), 7.28 (dd, J'=3.7 Hz, J"=8.9 Hz, 1H), 5.33 (s, 2H), 3.34 (s, 3H); LCMS: 235.2 (M+H).

Step 4: 6-Fluoro-3-(methoxymethoxy)-[2,4'-bipyridine]-4-carbaldehyde

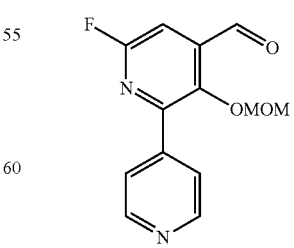

To a stirred solution of 6-fluoro-3-(methoxymethoxy)-2,4'-bipyridine (3.0 g, 12.8 mmol) in anhydrous THF (40.0 mL) was added n-BuLi (7 mL, 14.1 mmol, 2.0 M in hexane)

drop wise at −78° C. After stirring for 1 hr at −78° C., DMF (1.5 mL, 19.2 mmol) was added to it and stirred for 15 mins at −78° C. Saturated ammonium chloride solution was added drop wise to the reaction mass at −78 C and warm-up to room temperature. Reaction mass was extracted with ethyl acetate (2×150 mL), The combined organic layers were washed with water followed by brine, dried over sodium sulfate and concentrated under reduced pressure to afford crude mass 6-fluoro-3-(methoxymethoxy)-[2,4'-bipyridine]-4-carbaldehyde (3.5 µm) which was used as such in the next step.

Step 5: 6-Fluoro-3-hydroxy-[2,4'-bipyridine]-4-carbaldehyde

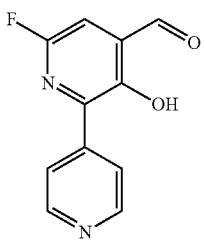 [SMILES: O=Cc1cc(F)nc(-c2ccncc2)c1O]

To a stirred solution of crude 6-fluoro-3-(methoxymethoxy)-[2,4'-bipyridine]-4-carbaldehyde (3.5 g, 13.35 mmol) in DCM (5.0 mL) was added 10% TFA-DCM solution (50.0 mL) at 0° C. Reaction mass was allowed to stir at room temperature for 5 hrs. Evaporated the volatiles, residue was diluted with water (20 mL) and basified (pH-10) with potassium carbonate and extracted with ethyl acetate (2×30 mL), aqueous part was neutralized with citric acid and extracted with 10% IPA-DCM (5×150 mL), combined organic part was dried over sodium sulphate, concentrated under reduced pressure to give crude mass which was purified by trituration using MTBE-pentane to afford 6-fluoro-3-hydroxy-[2,4'-bipyridine]-4-carbaldehyde (1.5 g) as yellow solid. $^1$H-NMR (400 MHz, DMSO): δ 11.15 (bh, 1H), 10.27 (s, 1H), 8.72 (d, J=5.3 Hz, 2H), 8.01 (d, J=4.9 Hz, 2H), 7.49 (d, J=3.6 Hz, 2H).

Step 6: $N^3$-(3-Chloro-4-fluorophenyl)-5-fluoro-7-(pyridin-4-yl)furo[2,3-c]pyridine-2,3-diamine

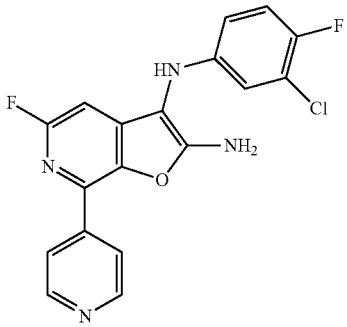 [SMILES: Nc1oc2c(-c3ccncc3)nc(F)cc2c1Nc1ccc(F)c(Cl)c1]

To a stirred solution of 6-fluoro-3-hydroxy-[2,4'-bipyridine]-4-carbaldehyde (0.5 g, 0.23 mmol) in DCM (7 mL) was added 4-fluoro-3-chloroaniline (0.333 g, 0.2.3 mmol), TMS-CN (1.5 mL, 12 mmol) and TMS-OTf (0.08 mL, 0.45 mmol) at 25° C. The resulting reaction mixture was stirred at this temperature for 20 hr. Reaction mass was concentrated and diluted with ethyl acetate (25 mL) and washed with water (2×25 mL) followed by brine solution and dried over sodium sulphate, concentrated under reduce pressure to give crude mass which was taken in DCM (2 mL), and added TMSCN (0.5 mL), TMSOTf (0.02 mL) and the resulting mixture was kept in the refrigerator for 16 hrs. Volatiles were removed and diluted with ethyl acetate (25 mL), washed with water (2×25 mL) followed by brine solution and dried over sodium sulphate, concentrated and purified by trituration using ethyl acetate/DCM to afforded $N^3$-(3-Chloro-4-fluorophenyl)-5-fluoro-7-(pyridin-4-yl)furo[2,3-c]pyridine-2,3-diamine (210 mg) as pale yellow solid. $^1$H-NMR (400 MHz, DMSO-d$_6$): δ 8.76 (d, J=5.8 Hz, 2H), 8.15 (d, J=5.8 Hz, 2H), 7.50 (s, 2H), 7.17-7.12 (m, 2H), 6.63 (dd, J=6.1 Hz, J'''=2.5 Hz, 1H), 6.53-6.49 (m, 2H); LCMS: 373.1 (M+H).

Example 26

Synthesis of $N^3$-(3-Chloro-4-fluorophenyl)-5,7-difluorofuro[2,3-c]pyridine-2,3-diamine (Example 190)

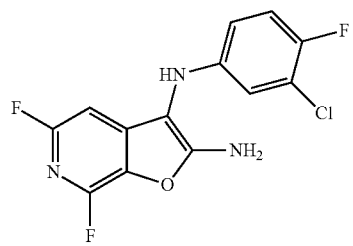

Step 1: 2,6-Difluoro-3-(4,4,5,5-tetramethyl-1,3,2-dioxaborolan-2-yl)pyridine

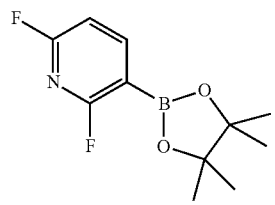 [SMILES: CC1(C)OB(c2ccc(F)nc2F)OC1(C)C]

2,6 Difluoropyridine (5.0 g, 43.44 mmol) was taken in dry THF (60 mL) under Nitrogen atmosphere and cooled to −78° C. then n-BuLi (26.06 mL, 52.1739 mmol 2.0 M in hexane) was added drop-wise over 30 min., followed by B(O$^i$Pr)$_3$ (11.095 mL, 47.785 mmol) at the same temperature and maintained 20 min. Resulting reaction mixture was allowed to warm to room temperature and added pinacol (5.647 g, 47.785 mmol) and acetic acid (4.969 mL, 86.881 mmol). The resulting reaction mixture was stirred at room temperature for 3 h. After completion of reaction, saturated aqueous NH$_4$Cl (100 mL) was poured into reaction mass and extracted with ethyl acetate (3×150 mL). Combined organic layer was washed with saturated aq. NaHCO$_3$ solution (50 mL) followed by brine solution (2×50 mL), dried over anhydrous Na$_2$SO$_4$ and concentrated to afford crude material which was passed through a pad of silica to afford 2,6- difluoro-3-(4,4,5,5-tetramethyl-[1,3,2]dioxaborolan-2-yl)-pyridine (9.0 g) as a brown gummy solid and use as such in next step.

Step 2: 2,6-Difluoro-3-hydroxypyridine

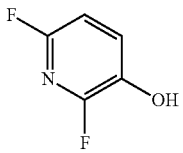

To a stirred solution of sodium perborate tetrahydrate (17.2 g, 112.03 mmol) in water (130 mL) was added THF (130 mL) and 2,6-di fluoro-3-(4,4,5,5-tetramethyl-[1,3,2]dioxaborolan-2-yl)-pyridine (9.0 g, 37.344 mmol) at 0° C. Resulting reaction mixture was stirred at room temperature for 3 h. Reaction mixture was extracted with ethyl acetate (3×150 mL), washed with brine (150 mL) and dried over sodium sulfate and concentrated under reduced pressure to afford crude material which was purified by column chromatography on silica gel (100-200 mesh) using 30% EtOAc-hexane as eluent to afford 2,6-difluoro-3-hydroxypyridine (4.0 g) as white solid. LCMS: 130 (M−H).

Step 3: 2,6-Difluoro-3-(methoxymethoxy)pyridine

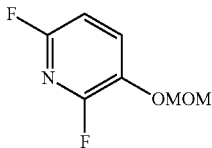

To a stirred solution of 2,6-difluoro-3-hydroxypyridine (4.0 g, 30.534 mmol) in DCM (80 mL) at 0° C. was added DIPEA (10.6 mL, 61.069 mmol), after stirring the reaction mixture for 15 min, methoxy methyl chloride (3.46 mL, 45.802 mmol) was added to it at 0° C. and the resulting mixture was stirred for 3 h at room temperature. Water was added to the reaction mixture and extracted with DCM (2×50 mL). The combined organic part was washed with brine (150 mL) and dried over sodium sulfate and concentrated under reduced pressure to afford crude mass which was purified by column chromatography on silica gel (100-200 mesh silica) using 5% EtOAc-hexane as eluent to afford 2,6-difluoro-3-methoxymethoxy-pyridine (3.2 g) as brown liquid. $^1$H-NMR (400 MHz, DMSO-$d_6$): δ 7.94 (m, 1H), 7.13 (dd, J'=8.5 Hz, J"=2.8 Hz, 1H), 5.27 (s, 2H), 3.41 (s, 3H).

Step 3: 2,6-Difluoro-3-(methoxymethoxy)isonicotinaldehyde

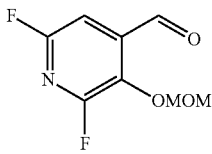

To a stirred solution of 2,6-difluoro-3-methoxymethoxy-pyridine (3.5 g, 20.0 mmol) in anhydrous THF (60 mL) was cooled to −78° C. then added n-BuLi (11 mL, 22 mmol, 2.0 M in hexane) drop-wise maintaining the temperature −78° C. After stirring for 1 h at −78° C., DMF (2.3 mL, 30 mmol) was added and stirred for 30 min at −78° C. Reaction mixture was warm to −10° C. and quenched by adding saturated solution of NH$_4$Cl (30 mL) drop-wise. Reaction mass was extracted with ethyl acetate (3×50 mL), washed with brine, dried over sodium sulfate and concentrated under reduced pressure to afford 2,6-difluoro-3-methoxymethoxy-pyridine-4-carbaldehyde (4.0 g) as a brown liquid which was used as such in the next step.

Step 4: 2,6-Difluoro-3-hydroxyisonicotinaldehyde

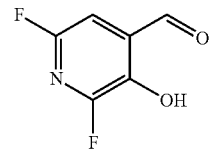

To a stirred solution of 2,6-difluoro-3-methoxymethoxy-pyridine-4-carbaldehyde (4.0 g, 19.704 mmol) in DCM (10 mL) was added 10% TFA-DCM solution (100 mL) at 0° C. and stirred at room temperature for 5 h. Reaction mixture was concentrated, diluted with water and neutralized by solid K$_2$CO$_3$ (pH ~7), extracted with 5% IPA-DCM (3×50 mL). Combined organic layer was washed with water, followed by brine solution, dried over anhydrous Na$_2$SO$_4$ and concentrated under reduce pressure to afford the crude material which was purified by column chromatography on (100-200 mesh silica) using 30% EtOAc-hexane as eluent to afford 2,6-difluoro-3-hydroxyisonicotinaldehyde (1.5 g) as brown liquid. $^1$H-NMR (400 MHz, DMSO-$d_6$): δ 11.45 (bh, 1H), 10.31 (d, J=2.6 Hz, 1H), 7.19 (dd, J'=8.0 Hz, J"=2.6 Hz, 1H).

Step 4: 4-(((3-Chloro-4-fluorophenyl)imino)methyl)-2,6-difluoropyridin-3-ol

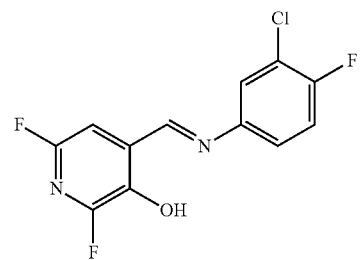 [SMILES: Oc1c(/C=N/c2ccc(F)c(Cl)c2)cc(F)nc1F]

To a stirred solution of 2,6-difluoro-3-hydroxyisonicotinaldehyde (1.0 g, 6.289 mmol) in a mixed solvent [TFE(5 mL):MeCN(5 mL)] was added 4-fluoro-3-chloroaniline (0.915 g, 6.289 mmol) at room temperature, resulting reaction mixture was stirred at room temperature for 2 h. After completion of reaction, the reaction mass was concentrated and triturated with n-pentane to afford 4-(((3-chloro-4-fluorophenyl)imino)methyl)-2,6-difluoropyridin-3-ol (1.3 g) as a yellow solid. $^1$H-NMR (400 MHz, DMSO-$d_6$): δ 11.93 (s, 1H), 9.00 (s, 1H), 7.79 (d, J=6.4 Hz, 1H), 7.57-7.53 (M, 2H), 7.39 (s, 1H).

Step 4: N³-(3-Chloro-4-fluorophenyl)-5,7-difluoro-furo[2,3-c]pyridine-2,3-diamine

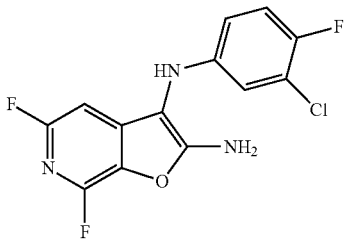

To a stirred solution of 4-(((3-chloro-4-fluorophenyl)imino)methyl)-2,6-difluoropyridin-3-ol (1.3 g, 4.545 mmol) in a mixed solvent [TFE (5 mL):DCM (5 mL)] was added TMSCN (2.95 mL, 23.636 mmol) followed by TMSOTf (0.164 mL, 0.909 mmol) at room temperature and allowed to stir at room temperature for 16 h. Reaction mass was concentrated and residue was taken in DCM, washed with NaHCO₃ solution, followed by brine solution, dried over anhydrous sodium sulfate and concentrated under reduced pressure to give crude material was purified by column chromatography on silica gel (100-200 mesh) 30% EtOAc-hexane as eluent to affordN³-(3-chloro-4-fluorophenyl)-5,7-difluorofuro[2,3-c]pyridine-2,3-diamine (0.4 g) as brown solid. ¹H-NMR (400 MHz, DMSO-d₆): δ 7.46 (s, 2H), 7.16-7.11 (m, 2H), 6.60 (dd, J'=6.2 Hz, J"=2.7 Hz, 1H), 6.48 (dt, J'=8.8 Hz, J"=6.8 Hz, J'''=3.4 Hz, 1H), 6.42 (s, 1H); LCMS: 314 (M+H).

Example 27

Synthesis of 4-(2-Amino-3-((3-chloro-4-fluorophenyl)amino)furo[2,3-c]pyridin-7-yl)-N-methylpicolinamide (Example 195)

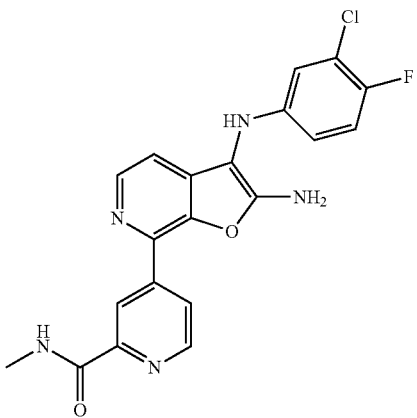 [SMILES: CNC(=O)c1cc(-c2nccc3c(Nc4ccc(F)c(Cl)c4)c(N)oc23)ccn1]

Step 1: 4-Chloro-N-methylpicolinamide

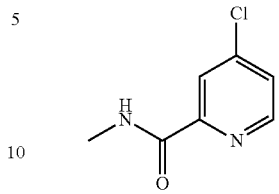

To 4-chloro-pyridine-2-carboxylic acid (5.0 g, 31.847 mmol) was added SOCl₂ (15 mL) and refluxed for 3 h. The volatiles were removed and the reaction mixture was diluted with THF (220 mL), added Et₃N (13.42 mL, 95.541 mmol) and MeNH₂ (19.1 mL, 2M in THF) at 0° C. The reaction mixture was stirred at room temperature for 12 h. After completion of reaction, volatiles were removed to give residue which was diluted with ethyl acetate, washed with saturated solution of sodium bicarbonate. The organic layer was dried over anhydrous Na₂SO₄ and evaporated under reduce pressure to afford 4-chloro-pyridine-2-carboxylic acid methylamide (4.6 g) as brown liquid. ¹H-NMR (400 MHz, DMSO-d₆): δ 8.83 (bs, 1H), 8.62 (d, J=5.2 Hz, 1H), 8.01 (d, J=2.0 Hz, 1H), 7.75 (dd, J'=5.3 Hz, J"=2.0 Hz, 1H), 2.82 (d, J=4.8 Hz, 3H); LCMS: 171 (M+H).

Step 2: N-Methyl-4-(4,4,5,5-tetramethyl-1,3,2-dioxaborolan-2-yl)picolinamide

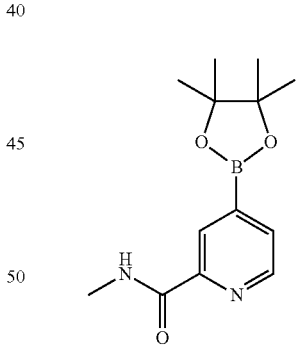

A degassed mixture of 4-chloropyridine-2-carboxylic acid methylamide (4.6 g, 27.059 mmol), bis(pinacolato)diboron (8.246 g, 32.471 mmol), Pd(OAC)₂ (0.243 g, 1.082 mmol), PCy₃ (0.379 g, 1.353 mmol) and potassium acetate (3.983 g, 40.588 mmol) in 1,4-dioxane (215 mL) was heated at 100° C. under nitrogen for 4 h. The reaction mixture was filtered through celite bed and the filtrate was concentrated in vacuum to get crude mass N-methyl-4-(4,4,5,5-tetramethyl-1,3,2-dioxaborolan-2-yl)picolinamide (6.2 g) as pale brown liquid which was used in next step as such without further purification. ¹H-NMR (400 MHz, DMSO-d₆): δ 8.75 (d, J=4.4 Hz, 1H), 8.61 (d, J=4.5 Hz, 1H), 8.20 (s, 1H), 7.71 (d, J=4.4 Hz, 1H), 2.82 (d, J=4.8 Hz, 3H), 1.28 (s, 12H).

Step 3: 4-Formyl-3-(methoxymethoxy)-N-methyl-[2,4'-bipyridine]-2'-carboxamide

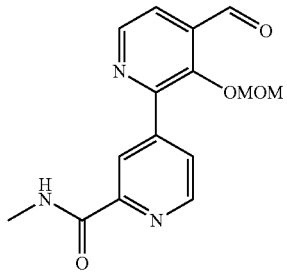

To a stirred solution of 2-bromo-3-methoxymethoxy-pyridine-4-carbaldehyde (5.0 g, 20.325 mmol) in 1,4-dioxane (250 mL) was added crude N-methyl-4-(4,4,5,5-tetramethyl-1,3,2-dioxaborolan-2-yl)picolinamide (3.659 g, 20.325 mmol), $K_3PO_4$ (27.2 mL, 34.553 mmol, 1.27 M in water) and $P(Cy)_3$ (1.14 g, 4.065 mmol). The reaction mixture was degassed for 20 min with Argon then added $Pd_2(dba)_3$ (1.86 g, 2.033 mmol) and again degassed for another 5 min. The reaction mixture was heated to 100° C. for 2 h. After completion of reaction the reaction mixture was cool to room temperature, the volatiles were removed under reduced pressure to afford crude 4-formyl-3-(methoxymethoxy)-N-methyl-[2,4'-bipyridine]-2'-carboxamide (6.3 g), which was forwarded to the next step as such. LCMS: 302 (M+H).

Step 4: 4-Formyl-3-hydroxy-N-methyl-[2,4'-bipyridine]-2'-carboxamide

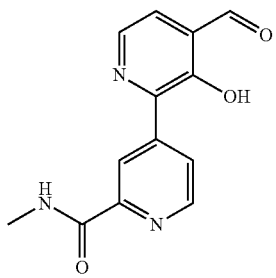 [SMILES: CNC(=O)c1cc(-c2nccc(C=O)c2O)ccn1]

10% TFA-DCM (60 mL) solution was added to crude 4-formyl-3-(methoxymethoxy)-N-methyl-[2,4'-bipyridine]-2'-carboxamide (6.1 g, 20.266 mmol) in DCM (6 mL) at 0° C. After stirring the reaction mixture for 3 h at room temperature, concentrated under reduced pressure, diluted with water and was basified using solid potassium carbonate, washed with ethyl acetate and the aqueous part was acidified to pH-6 using citric acid and extracted with ethyl acetate. The organic layer was washed with brine, dried over anhydrous sodium sulfate and concentrated under reduce pressure to afford crude mass which was purified by trituration using DCM/Et2O/pentane gave pure 4-formyl-3-hydroxy-N-methyl-[2,4'-bipyridine]-2'-carboxamide (2.8 g) as pale brown solid. $^1$H-NMR (400 MHz, DMSO-$d_6$): δ 11.26 (s, 1H), 10.31 (s, 1H), 8.84 (d, J=4.6 Hz, 1H), 8.75 (d, J=5.0 Hz, 1H), 8.67 (s, 1H), 8.51 (d, J=4.7 Hz, 1H), 8.17 (dd, J'=5.0 Hz, J''=1.6 Hz, 1H), 7.76 (d, J=4.8 Hz, 1H), 2.85 (d, J=4.8 Hz, 3H); LCMS: 258.2 (M+H).

Step 5: 4-(2-Amino-3-((3-chloro-4-fluorophenyl)amino)furo[2,3-c]pyridin-7-yl)-N-methylpicolinamide

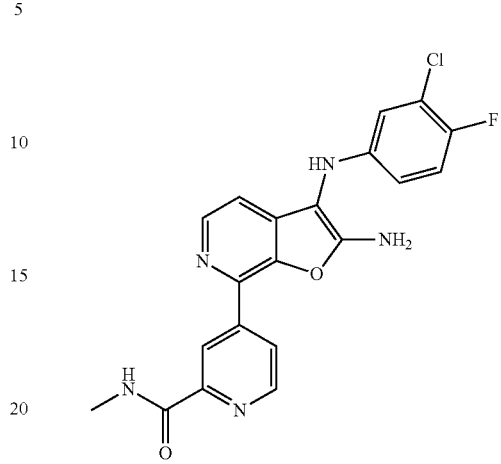

To a stirred solution of 4-formyl-3-hydroxy-N-methyl-[2,4'-bipyridine]-2'-carboxamide (0.5 g, 1.946 mmol) in DCM (6.0 mL) was added 3-chloro-4-fluoroaniline (0.283 g, 1.946 mmol), TMSCN (1.268 mL, 10.117 mmol), TMSOTf (0.071 mL, 0.389 mmol) at room temperature in a sealed tube. The reaction mixture was stirred for 1 hr at 40° C., followed by addition of 10 mmol $NH_4OAc$ buffer (3.0 mL) and stirred for 12 h. The reaction mixture was filtered through a sintered funnel and washed the solid with MTBE/hexane/10-20%EA-hexane to remove trace impurities to get desired compound, 4-(2-amino-3-((3-chloro-4-fluorophenyl)amino)furo[2,3-c]pyridin-7-yl)-N-methylpicolinamide (0.450 g) as orange solid. $^1$H-NMR (400 MHz, DMSO-$d_6$): δ 8.88 (s, 1H), 8.83-8.78 (m, 2H), 8.40 (d, J=4.4 Hz, 1H), 8.25 (d, J=4.9 Hz, 1H), 7.18-7.11 (m, 4H), 6.98 (d, J=4.9 Hz, 1H), 6.62-6.60 (m, 1H), 6.53-6.51 (m, 1H), 2.88 (d, J=4.6 Hz, 3H); LCMS: 412 (M+H).

Example 28

Synthesis of $N^3$-(3-Chloro-4-fluorophenyl)-$N^7,N^7$-diphenylfuro[2,3-e]pyridine-2,3,7-triamine (Example 200)

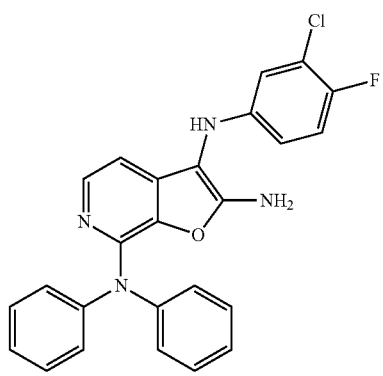 [SMILES: Nc1oc2c(N(c3ccccc3)c3ccccc3)nccc2c1Nc1ccc(F)c(Cl)c1]

Step 1: 3-(Methoxymethoxy)-N,N-diphenylpyridin-2-amine

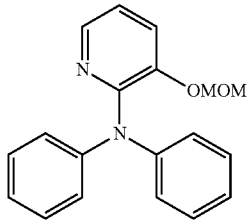

A solution of 2-bromo-3-methoxymethoxy-pyridine (2.0 g, 9.174 mmol), diphenylamine (2.018 g, 11.927 mmol), ter-BuONa (1.763 g, 18.349 mmol) and Dppf (0.305 g, 0.55 mmol) in toluene (27.5 mL) was degassed for 20 min. and in this degassed reaction mixture was added $Pd_2(dba)_3$ (0.168 g, 0.183 mmol). The resulting reaction mixture was again degassed for 10 min. and heated at 80° C. for 16 h. After completion of reaction the reaction mass was filtered through celite bed and the filtrate was evaporated under reduce pressure to obtained crude mass which was purified by column chromatography on silica gel (100-200 mesh) using 20% EtOAc/hexane as eluent to afford (3-methoxymethoxy-pyridin-2-yl)-diphenyl-amine (2.0 g) as brown solid. $^1$H-NMR (400 MHz, DMSO-$d_6$): δ 7.99 (dd, J=4.7 Hz, J''=1.4 Hz, 1H), 7.53 (dd, J'=4.7 Hz, J''=1.4 Hz, 1H),8.1 Hz, J''=1.4 Hz, 1H), 7.26-7.19 (m, 5H), 6.98 (t, J=7.3 Hz, 2H), 6.85 (d, J=7.6 Hz, 4H), 5.01 (s, 2H), 3.01 (s, 3H).

Step 2: 2-(Diphenylamino)-3-(methoxymethoxy) isonicotinaldehyde

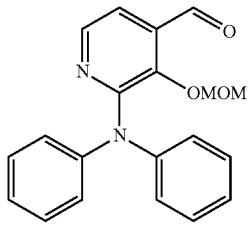

To a stirred solution of (3-methoxymethoxy-pyridin-2-yl)-diphenyl-amine (1.0 g, 3.264 mmol) in THF (13 mL) was added n-BuLi (1.8 mL, 3.6 mmol, 2 Min hexane) drop wise at −78 ° C. After stirring the reaction mixture for 1 h at −78° C., DMF (0.377 mL, 4.896 mmol) was added and stirred for 15 min at −78° C. Reaction mass was quenched with saturated solution of $NH_4Cl$ and extracted with ethyl acetate (2×100 mL). Combined organic layer was washed with brine, dried over anhydrous sodium sulfate, concentrated under reduced pressure to afford crude 2-diphenylamino-3-methoxymethoxy-pyridine-4-carbaldehyde (1.0 g) which was forwarded to the next step without further purification. LCMS: 335 (M+H).

Step 3: 2-(Diphenylamino)-3-hydroxyisonicotinaldehyde

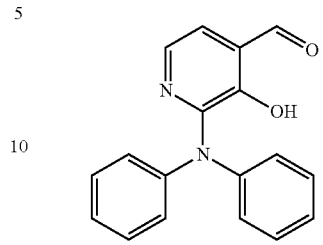

To a stirred solution of crude 2-diphenylamino-3-methoxymethoxy-pyridine-4-carbaldehyde (1.0 g, 2.991 mmol) in DCM (5 mL) was added 10% TFA-DCM (15 mL) at 0° C. After stirring the reaction mixture for 1 h at room temperature, the volatiles were evaporated under reduced pressure. Thus obtained crude was diluted with water (15 mL) and basified up to pH-10 by potassium carbonate and washed with MTBE. The aqueous part was neutralized with citric acid and extracted with 10% IPA-DCM (2×100 mL). The organic layer was separated, dried over anhydrous sodium sulfate, concentrated under reduced pressure to afford 2-diphenylamino-3-hydroxy-pyridine-4-carbaldehyde (0.5 g) as orange solid. $^1$H-NMR (400 MHz, DMSO-$d_6$): δ 10.56 (s, 1H), 10.27 (s, 1H), 8.02 (d, J=4.8 Hz, 1H), 7.42 (d, J=4.9 Hz, 1H), 7.26 (t, J=7.8 Hz, 4H), 7.02 (t, J=7.2 Hz, 2H), 6.90 (d, J=7.9 Hz, 4H); LCMS: 291 (M+H).

Step 4: 4-(((3-Chloro-4-fluorophenyl)imino)methyl)-2-(diphenylamino)pyridin-3-ol

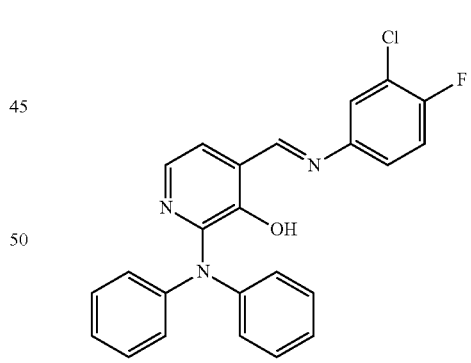

To a solution of 2-diphenylamino-3-hydroxy-pyridine-4-carbaldehyde (0.5 g, 1.722 mmol) in a mixed solvent of triflouroethanol (4 mL) and acetonitrile (4 mL) was added 3-chloro-4-flouroaniline (0.25 g, 1.722 mmol) and the mixture was stirred for 5 h at room temperature. Reaction mass was evaporated to dryness under reduced pressure to afford 4-(((3-chloro-4-fluorophenyl)imino)methyl)-2-(diphenylamino)pyridin-3-ol (0.7 g) as reddish brown liquid. $^1$H-NMR (400 MHz, DMSO-$d_6$): δ 12.74 (s, 1H), 9.06 (s, 1H), 8.02 (d, J=4.9 Hz, 1H), 7.86-7.84 (m, 1H), 7.53-7.49 (m, 2H), 7.47 (d, J=5.0 Hz, 1H), 7.26 (t, J=7.7 Hz, 4H), 7.00 (t, J=7.3 Hz, 2H), 6.89 (d, J=7.9 Hz, 4H).

Step 5: N³-(3-Chloro-4-fluorophenyl)-N⁷,N⁷-diphenylfuro[2,3-c]pyridine-2,3,7-triamine

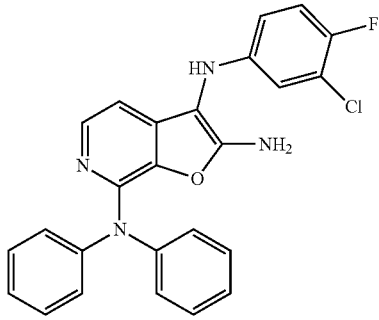 [SMILES: Nc1oc2c(N(c3ccccc3)c3ccccc3)nccc2c1Nc1ccc(F)c(Cl)c1]

To a stirred solution of 4-(((3-chloro-4-fluorophenyl)imino)methyl)-2-(diphenylamino)pyridin-3-ol (0.7 g, 1.675 mmol) in a mixed solvent of trifluoroethanol (5 mL) and dichloromethane (5 mL) was added TMSCN (1.09 mL, 8.711 mmol) at room temperature and stirred for 16 h at ambient temperature. After completion of reaction the solvent was evaporated and thus obtained crude material was purified by column chromatography followed by triturating with ether/pentane to afforded N³-(3-chloro-4-fluorophenyl)-N⁷,N⁷-diphenylfuro[2,3-c]pyridine-2,3,7-triamine (0.15 g) as brown solid. ¹H-NMR (400 MHz, DMSO-$d_6$): δ 7.82 (d, J=5.1 Hz, 1H), 7.27 (t, J=7.8 Hz, 4H), 7.14 (t, J=9.0 Hz, 1H), 7.05-7.01 (m, 3H), 6.93 (d, J=7.8 Hz, 4H), 6.72 (d, J=5.0 Hz, 1H), 6.67 (bs, 2H), 6.59 (dd, J'=6.3 Hz, J''=2.5 Hz, 1H), 6.49-6.44 (m, 1H); LCMS: 445 (M+H).

Example 29

Synthesis of N³-(3-Chlorophenyl)-7-(2-methylpyridin-4-yl)benzo[b]thiophene-2,3-diamine (Compound 248)

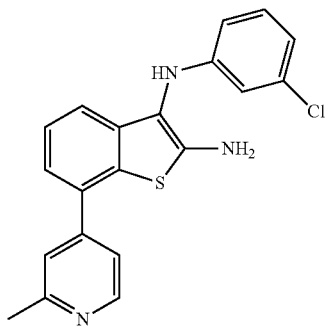 [SMILES: Cc1cc(-c2cccc3c(Nc4cccc(Cl)c4)c(N)sc23)ccn1]

Step 1: (2-Bromophenyl)(2,2-diethoxyethyl)sulfane

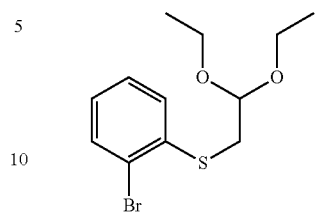

To a stirred suspension of $K_2CO_3$ (9.56 g, 69.17 mmol) in acetone (40 mL) was added 2-bromothiophenol (10.0 g, 53.21 mmol) at 0° C. and stirred the reaction mixture at same temperature for 20-30 min. then added bromoacetaldehyde diethylacetal (11.5 g, 58.33 mmol) drop-wise and stirred the reaction mass at 25° C. for 18 h. The reaction was monitor by tlc and after completion of reaction volatiles were remove under reduce pressure to get concentrated mass which was diluted with water, extracted with ethyl acetate (3×150 mL), combined organic layers were washed with water then brine, dried over anhydrous sodium sulfate, concentrated under reduced pressure to give crude mass which was purified by column chromatography on silica gel using 5% ethyl acetate/hexane mixture as eluent to afford (2-bromophenyl)(2,2-diethoxyethyl)sulfane (15.6 g) as pale yellow oil. ¹H-NMR (400 MHz, CDCl₃): δ 7.49 (d, J=7.8 Hz, 1H), 7.32 (d, J=7.8 Hz, 1H), 7.21 (t, J=7.6 Hz, 1H), 6.98 (t, J=7.6 Hz, 1H), 4.67 (t, J=5.5 Hz, 1H), 3.65 (q, J=6.9 Hz, 2H), 3.52 (q, J=6.8 Hz, 2H), 3.12 (d, J=6.0 Hz, 2H), 1.17 (t, J=6.9 Hz, 6H).

Step 2: 7-Bromobenzo[b]thiophene

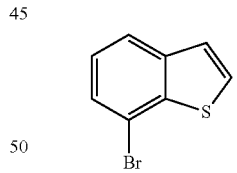

To a stirred solution of PPA (42.22 g) in chlorobenzene (100 mL) was added solution of (2-bromophenyl)(2,2-diethoxyethyl)sulfane (26.2 g, 86.185 mmol) in chlorobenzene (20 mL) drop-wise at 130° C. and allowed the reaction mass to stirred for 4 h. After completion of reaction the reaction mixture was cool down to room temperature and decants the organic layer and keeps it aside. The residue was extracted with toluene (3×100 mL) and combined organic layers were evaporated under reduced pressure to give crude mass which was purified by column chromatography on silica gel using 2% ethyl acetate/hexane as eluent to afford 7-bromobenzo[b]thiophene (12.7 g, 59.62 mmol) as colorless liquid. ¹H-NMR (400 MHz, CDCl₃): δ 7.76 (dd, J'=8.2 Hz, J''=0.9 Hz, 1H), 7.50-7.47 (m, 2H), 7.42 (d, J=5.5 Hz, 1H), 7.23 (t, J=7.8 Hz, 1H).

Step 3: 3,7-Dibromobenzo[b]thiophene

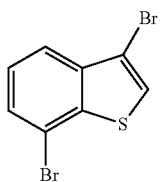

N-Bromosuccinimide (5.73 g. 32.2 mmol) was added slowly into the stirred solution of 7-bromobenzo[b]thiophene (5.28 g, 24.78 mmol) in chloroform (25 mL) and acetic acid (25 mL) at 0° C. The resulting reaction mixture was stirred at 25° C. for 24 h. The reaction was monitor by tic and after completion of reaction the reaction mixture washed with saturated solution of $Na_2S_2O_3$ (20 mL), $NaHCO_3$ (20 mL) and water (10 mL). The organic part was dried over anhydrous sodium sulfate and concentrated under reduce pressure to give crude product which was purified by column chromatography on silica gel using hexane as eluent to afford 3,7-dibromobenzo[b]thiophene (4.7 g, 16.135 mmol) as white solid. $^1$H-NMR (400 MHz, $CDCl_3$): δ 7.80 (dd, J'=8.2 Hz, J"=0.9 Hz, 1H), 7.57 (d, J=7.8 Hz, 1H), 7.52 (s, 1H), 7.36 (t, J=7.8 Hz, 1H).

Step 4: 3,7-Dibromo-2-nitrobenzo[b]thiophene

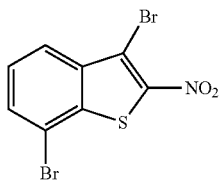 [SMILES: O=[N+]([O-])c1sc2c(Br)cccc2c1Br]

To a stirred solution of 3,7-dibromobenzo[b]thiophene (4.7 g, 16.09 mmol) in acetic anhydride (30 mL) was added fuming $HNO_3$ followed by acetic acid (3.2 g, 53.9 mmol) dropwise at 5-10° C. Reaction mixture was stirred at same temperature for 2 h then quenched with ice-water, the solid was precipitate-out, filtered and washed with water, dried under vacuum to give crude material which was purified by crystallization using DCM/hexane to afford 3,7-dibromo-2-nitrobenzo[b]thiophene (1.63 g, 4.839 mmol), as yellow solid. $^1$H-NMR (400 MHz, $CDCl_3$): δ 8.02 (d, J=8.2 Hz, 1H), 7.79 (d, J=7.8 Hz, 1H), 7.49 (t, J=8.0 Hz, 1H).

Step 4: 7-Bromo-N-(3-chlorophenyl)-2-nitrobenzo[b]thiophen-3-amine

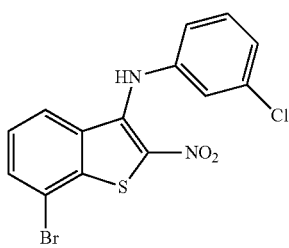 [SMILES: O=[N+]([O-])c1sc2c(Br)cccc2c1Nc1cccc(Cl)c1]

To a stirred solution of 3,7-dibromo-2-nitrobenzo[b]thiophene (0.6 g, 1.78 mmol), in DMF (5 mL) was added 3-chloroaniline (0.681 g, 5.34 mmol) at room temperature. The reaction mixture was stirred at 80° C. for 2 h. After completion of reaction the reaction mass was quenched with ice-water, the solid was precipitate, filtered and washed with water to give wet solid which was dried under hot air oven to afford desired product 7-bromo-N-(3-chlorophenyl)-2-nitrobenzo[b]thiophen-3-amine (0.250 g, 0.652 mmol) as yellow solid. $^1$H-NMR (400 MHz, $CDCl_3$): δ 9.88 (s, 1H), 7.65 (d, J=7.8 Hz, 1H), 7.38-7.29 (m, 3H), 7.18-7.15 (m, 2H), 7.04 (t, J=8.0 Hz, 1H); HRMS: 380.910 (M–H).

Step 5: N-(3-Chlorophenyl)-7-(2-methylpyridin-4-yl)-2-nitrobenzo[b]thiophen-3-amine

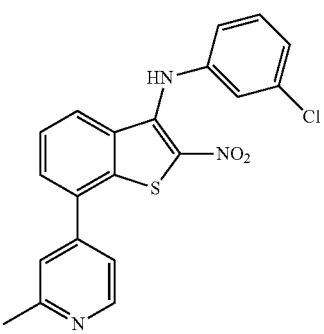

To a stirred solution of 7-bromo-N-(3-chlorophenyl)-2-nitrobenzo[b]thiophen-3-amine (0.25 g, 0.651 mmol) and 2-methyl-4-pyridinylboronic acid (0.116 g, 0.847 mmol) in DMF (5 mL) and $H_2O$ (1 mL) mixture was added $K_3PO_4$ (0.415 g, 1.955 mmol) and $Pd(PPh_3)_4$ (0.075 g, 0.065 mmol, 10 mol %) at room temperature. The resulting reaction mixture was stirred at 100° C. for 2 h, completion of reaction was monitor by tic. After completion of reaction the reaction mass was cooled to room temperature, filtered through celite bed and filtrate was extracted with ethyl acetate (3×20 mL), washed with brine, dried over sodium sulfate, concentrated under reduced pressure to give crude mass which was purified by column chromatography on silica gel using 15% EtOAc/hexane as eluent to afford N-(3-chlorophenyl)-7-(2-methylpyridin-4-yl)-2-nitrobenzo[b]thiophen-3-amine (0.07 g, 0.176 mmol) as reddish solid. $^1$H-NMR (400 MHz, $CDCl_3$): δ 9.93 (s, 1H), 8.67 (d, J=5.3 Hz, 1H), 7.56-7.51 (m, 2H), 7.48 (d, J=5.0 Hz, 1H), 7.40-7.34 (m, 2H), 7.32-7.28 (m, 3H), 7.19 (d, J=7.6 Hz, 1H), 2.75 (s, 3H); HRMS: 396.057 (M+H).

Step 6: $N^3$-(3-Chlorophenyl)-7-(2-methylpyridin-4-yl)benzo[b]thiophene-2,3-diamine

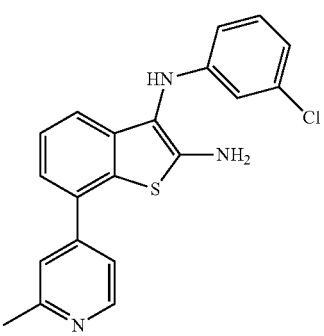 [SMILES: Cc1cc(-c2cccc3c(Nc4cccc(Cl)c4)c([N+](=O)[O-])sc23)ccn1]

To a stirred solution of N-(3-chlorophenyl)-7-(2-methylpyridin-4-yl)-2-nitrobenzorbithiophen-3-amine (0.06 g, 0.152 mmol) in methanol (5 mL) was added activated Pd/C (0.02 g, 10% Pd on charcoal) under nitrogen gas at room temperature then nitrogen gas was replaced by hydrogen gas balloon and continue stirring at ambient temperature for 2 h. After completion of reaction the reaction mixture was filtered through celite bed washed with methanol and filtrate was evaporated under reduce pressure to give crude mass which was purified by trituration using pentane to afford $N^3$-(3-chlorophenyl)-7-(2-methylpyridin-4-yl)benzo[b]thiophene-2,3-diamine (0.02 g, 0.054 mmol, 36%) as off white solid. $^1$H-NMR (400 MHz, DMSO-$d_6$): δ 8.53 (d, J=5.3 Hz, 1H), 7.52 (s, 1H), 7.45 (d, J=4.8 Hz, 1H), 7.40 (s, 1H), 7.25 (t, J=7.7 Hz, 1H), 7.10-7.06 (m, 1H), 7.04-6.99 (m, 2H), 6.55 (d, J=7.8 Hz, 1H), 6.45 (d, J=8.0 Hz, 1H), 6.42 (s, 1H), 5.98 (s, 2H), 2.52 (s, 3H); HRMS: 366.08 (M+H).

Compounds of the invention made according to procedures A-K and Examples 1-29 as described herein are listed below in TABLE 1.

TABLE 1

| No. | Structure | IUPAC Name | $^1$H-NMR (400 MHz) proton shift | LCMS | Proc. |
|---|---|---|---|---|---|
| 1 | 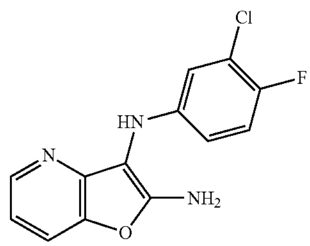 [SMILES: Nc1oc2cccnc2c1Nc1ccc(F)c(Cl)c1] | $N^3$-(3-Chloro-4-fluorophenyl)furo[3,2-b]pyridine-2,3-diamine | DMSO-$d_6$: δ 8.06 (d, J = 4.8 Hz, 1H), 7.52 (d, J = 7.8 Hz, 1H), 7.12-7.07 (m, 2H), 6.85 (dd, J' = 7.7 Hz, J" = 5.2 Hz, 1H), 6.77 (bs, 2H), 6.56-6.55 (m, 1H), 6.51-6.49 (m, 1H) | [M + H] 278.0 | B |
| 2 | 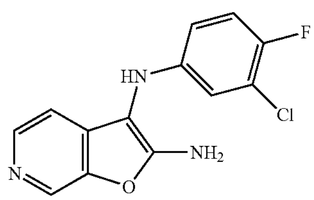 | $N^3$-(3-Chloro-4-fluorophenyl)furo[2,3-c]pyridine-2,3-diamine | DMSO-$d_6$: δ 8.41 (s, 1H), 8.06 (d, J = 5.1 Hz, 1H), 7.15-7.10 (m, 2H), 6.91 (s, 2H), 6.86 (d, J = 5.1 Hz, 1H), 6.56-6.54 (m, 1H), 6.48-6.45 (m, 1H) | [M − H] 276.2 | A |
| 3 | 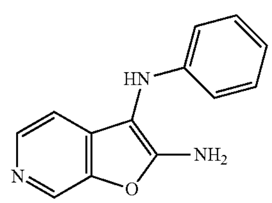 [SMILES: Nc1oc2cnccc2c1Nc1ccccc1] | $N^3$-Phenylfuro[2,3-c]pyridine-2,3-diamine | DMSO-$d_6$: δ 8.39 (s, 1H), 8.03 (d, J = 5.1 Hz, 1H), 7.07 (t, J = 7.7 Hz, 2H), 6.84-6.79 (m, 4H), 6.59 (t, J = 7.3 Hz, 1H), 6.52 (d, J = 7.9 Hz, 2H) | [M − H] 224.0 | A |
| 4 | 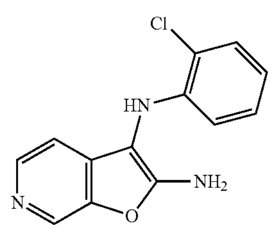 [SMILES: Nc1oc2cnccc2c1Nc1ccccc1Cl] | $N^3$-(2-Chlorophenyl)furo[2,3-c]pyridine-2,3-diamine | DMSO-$d_6$: δ 8.42 (s, 1H), 8.04 (d, J = 5.0 Hz, 1H), 7.30 (d, J = 7.7 Hz, 1H), 7.02 (t, J = 7.7 Hz, 1H), 6.92 (bs, 2H), 6.81 (d, J = 5.0 Hz, 1H), 6.65-6.62 (m, 2H), 6.31 (d, J = 8.1 Hz, 1H). | [M + H] 260.0 | A |
| 5 | 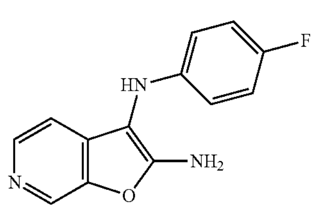 [SMILES: Nc1oc2cnccc2c1Nc1ccc(F)cc1] | $N^3$-(4-Fluorophenyl)furo[2,3-c]pyridine-2,3-diamine | DMSO-$d_6$: δ 8.39 (s, 1H), 8.03 (d, J = 4.9 Hz, 1H), 6.91 (t, J = 8.6 Hz, 2H), 6.84-6.82 (m, 4H), 6.51-6.50 (m, 2H) | [M − H] 242.0 | A |
| 6 | 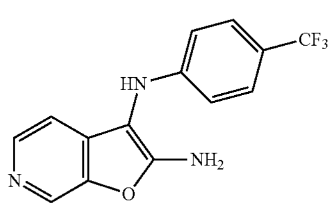 [SMILES: Nc1oc2cnccc2c1Nc1ccc(C(F)(F)F)cc1] | $N^3$-(4-(Trifluoromethyl)phenyl)furo[2,3-c]pyridine-2,3-diamine | DMSO-$d_6$: δ 8.43 (s, 1H), 8.05 (d, J = 5.0 Hz, 1H), 7.56 (s, 1H), 7.40 (d, J = 8.3 Hz, 2H), 7.03 (bs, 2H), 6.87 (d, J = 5.0 Hz, 1H), 6.63 (d, J = 8.2 Hz, 2H) | [M − H] 292.0 | B |

TABLE 1-continued

| No. | Structure | IUPAC Name | $^1$H-NMR (400 MHz) proton shift | LCMS | Proc. |
|---|---|---|---|---|---|
| 7 | 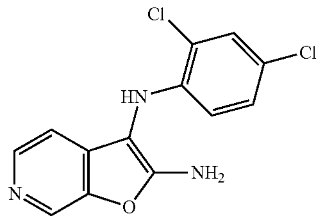 [SMILES: Nc1oc2cnccc2c1Nc1ccc(Cl)cc1Cl] | N$^3$-(2,4-Dichlorophenyl)furo[2,3-c]pyridine-2,3-diamine | DMSO-d$_6$: δ 8.45 (s, 1H), 8.06 (s, 1H), 7.42 (s, 1H), 7.11 (bs, 3H), 6.85 (s, 2H), 6.30 (d, J = 8.9 Hz, 1H) | [M + H] 294.0 | A |
| 8 | 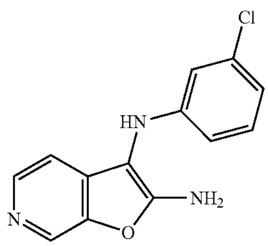 [SMILES: Nc1oc2cnccc2c1Nc1cccc(Cl)c1] | N$^3$-(3-Chlorophenyl)furo[2,3-c]pyridine-2,3-diamine | DMSO-d$_6$: δ 8.41 (s, 1H), 8.06 (d, J = 5.0 Hz, 1H), 7.20 (s, 1H), 7.09 (t, J = 8.2 Hz, 1H), 6.91 (s, 2H), 6.85 (d, J = 5.0 Hz, 1H), 6.61 (d, J = 7.6 Hz, 1H), 6.48 (m, 2H) | [M − H] 258.2 | A |
| 9 | 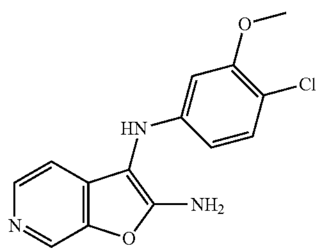 [SMILES: COc1cc(Nc2c(N)oc3cnccc23)ccc1Cl] | N$^3$-(4-Chloro-3-methoxyphenyl)furo[2,3-c]pyridine-2,3-diamine | DMSO-d$_6$: δ 8.42 (s, 1H), 8.06 (d, J = 4.6 Hz, 1H), 7.10 (s, 1H), 7.05 (d, J = 8.6 Hz, 1H), 6.95 (bs, 2H), 6.86 (d, J = 5.0 Hz, 1H), 6.34 (d, J = 1.7 Hz, 1H), 6.04 (dd, J' = 8.4 Hz, J'' = 2.0 Hz, 1H), 3.68 (s, 3H) | [M + H] 290.0 | A |
| 10 | 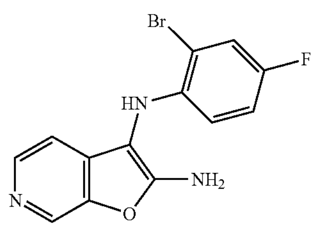 [SMILES: Nc1oc2cnccc2c1Nc1ccc(F)cc1Br] | N$^3$-(2-Bromo-4-fluorophenyl)furo[2,3-c]pyridine-2,3-diamine | DMSO-d$_6$: δ 8.42 (s, 1H), 8.05 (d, J = 4.2 Hz, 1H), 7.44 (dd, J' = 8.2 Hz, J'' = 2.9 Hz, 1H), 6.99-6.95 (m, 3H), 6.80 (d, J = 5.0 Hz, 1H), 6.37 (s, 1H), 6.28 (dd, J' = 9.1 Hz, J'' = 5.3 Hz, 1H) | [M − H] 320.0 | A |
| 11 | 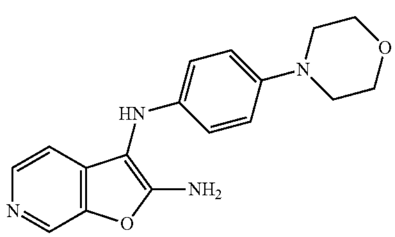 [SMILES: Nc1oc2cnccc2c1Nc1ccc(N2CCOCC2)cc1] | N$^3$-(4-Morpholinophenyl)furo[2,3-c]pyridine-2,3-diamine | DMSO-d$_6$: δ 8.38 (s, 1H), 8.02 (d, J = 4.0 Hz, 1H), 6.81-6.72 (m, 5H), 6.47 (bs, 3H), 3.69 (bs, 4H), 2.89 (bs, 4H) | [M + H] 311.0 | A |
| 12 | 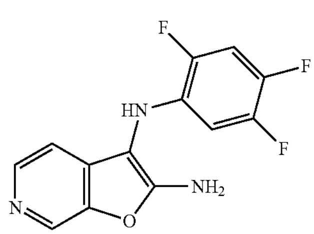 [SMILES: Nc1oc2cnccc2c1Nc1cc(F)c(F)cc1F] | N$^3$-(2,4,5-Trifluorophenyl)furo[2,3-c]pyridine-2,3-diamine | DMSO-d$_6$: δ 8.42 (s, 1H), 8.07 (d, J = 4.9 Hz, 1H), 7.47-7.40 (m, 1H), 7.04 (s, 1H), 6.95 (s, 2H), 6.89 (d, J = 5 Hz, 1H), 6.24-6.17 (m, 1H) | [M + H] 280.0 | A |

TABLE 1-continued

| No. | Structure | IUPAC Name | $^1$H-NMR (400 MHz) proton shift | LCMS | Proc. |
|---|---|---|---|---|---|
| 13 | 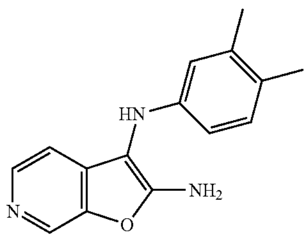 [SMILES: Cc1ccc(Nc2c(N)oc3cnccc23)cc1C] | $N^3$-(3,4-Dimethylphenyl)furo[2,3-c]pyridine-2,3-diamine | DMSO-$d_6$: δ 8.38 (s, 1H), 8.02 (d, J = 5 Hz, 1H), 6.83-6.79 (m, 2H), 6.75 (s, 2H), 6.56 (s, 1H), 6.35 (d, J = 2.1 Hz, 1H), 6.24 (dd, J' = 8.1 Hz, J" = 2.3 Hz, 1H), 2.06 (s, 6H) | [M − H] 252.0 | A |
| 14 | 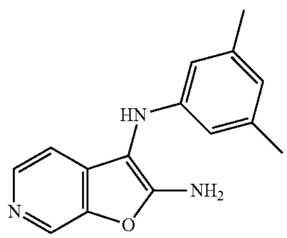 [SMILES: Cc1cc(C)cc(Nc2c(N)oc3cnccc23)c1] | $N^3$-(3,5-Dimethylphenyl)furo[2,3-c]pyridine-2,3-diamine | DMSO-$d_6$: δ 8.39 (s, 1H), 8.04 (d, J = 5.1 Hz, 1H), 6.83 (d, J = 5.1 Hz, 1H), 6.77 (bs, 2H), 6.67 (s, 1H), 6.24 (s, 1H), 6.14 (s, 2H), 2.10 (s, 6H) | [M + H] 254.0 | A |
| 15 | 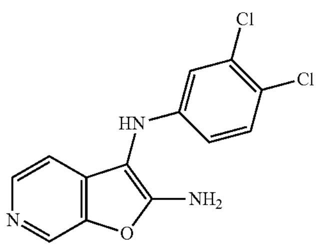 [SMILES: Nc1oc2cnccc2c1Nc1ccc(Cl)c(Cl)c1] | $N^3$-(3,4-Dichlorophenyl)furo[2,3-c]pyridine-2,3-diamine | DMSO-$d_6$: δ 8.41 (s, 1H), 8.06 (d, J = 4.8 Hz, 1H), 7.34 (s, 1H), 7.28 (d, J = 8.8 Hz, 1H), 6.97 (bs, 2H), 6.87 (d, J = 4.9 Hz, 1H), 6.64 (s, 1H), 6.49 (d, J = 8.2 Hz, 1H) | [M − H] 291.8 | A |
| 16 | 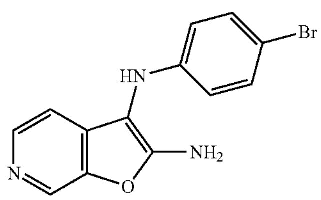 [SMILES: Nc1oc2cnccc2c1Nc1ccc(Br)cc1] | $N^3$-(4-Bromophenyl)furo[2,3-c]pyridine-2,3-diamine | DMSO-$d_6$: δ 8.40 (s, 1H), 8.04 (d, J = 5.0 Hz, 1H), 7.21 (d, J = 8.5 Hz, 2H), 7.08 (s, 1H), 6.88 (bs, 2H), 6.82 (d, J = 5.0 Hz, 1H), 6.47 (d, J = 8.5 Hz, 2H) | [M + H] 304.0 | A |
| 17 | 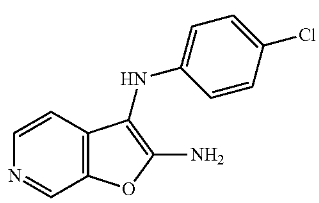 [SMILES: Nc1oc2cnccc2c1Nc1ccc(Cl)cc1] | $N^3$-(4-Chlorophenyl)furo[2,3-c]pyridine-2,3-diamine | DMSO-$d_6$: δ 8.40 (s, 1H), 8.04 (d, J = 5.0 Hz, 1H), 7.10 (d, J = 8.4 Hz, 2H), 7.05 (s, 1H), 6.86 (bs, 2H), 6.82 (d, J = 4.8 Hz, 1H), 6.52 (d, J = 8.4 Hz, 2H) | [M + H] 260.0 | A |
| 18 | 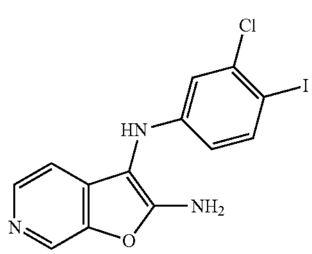 [SMILES: Nc1oc2cnccc2c1Nc1ccc(I)c(Cl)c1] | $N^3$-(3-Chloro-4-iodophenyl)furo[2,3-c]pyridine-2,3-diamine | DMSO-$d_6$: δ 8.41 (s, 1H), 8.06 (d, J = 5.0 Hz, 1H), 7.54 (d, J = 8.6 Hz, 1H), 7.35 (s, 1H), 6.95 (s, 2H), 6.86 (d, J = 4.9 Hz, 1H), 6.67 (bs, 1H), 6.29 (d, J = 6.9 Hz, 1H) | [M − H] 383.8 | A |

TABLE 1-continued

| No. | Structure | IUPAC Name | ¹H-NMR (400 MHz) proton shift | LCMS | Proc. |
|---|---|---|---|---|---|
| 19 | 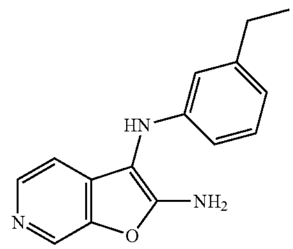 [SMILES: CCc1cccc(Nc2c(N)oc3cnccc23)c1] | $N^3$-(3-Ethylphenyl)furo[2,3-c]pyridine-2,3-diamine | DMSO-$d_6$: δ 8.39 (s, 1H), 8.04 (d, J = 4.6 Hz, 1H), 6.97 (t, 1H), 6.83-6.77 (m, 4H), 6.46-6.40 (m, 2H), 6.38 (m, 1H), 2.43 (merged in DMSO peak, 2H), 1.10 (t, J = 7.3 Hz, 3H) | [M + H] 254.0 | A |
| 20 | 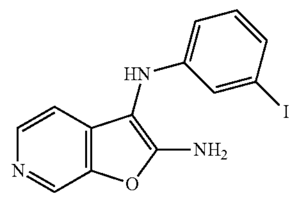 [SMILES: Nc1oc2cnccc2c1Nc1cccc(I)c1] | $N^3$-(3-Iodophenyl)furo[2,3-c]pyridine-2,3-diamine | DMSO-$d_6$: δ 8.40 (s, 1H), 8.06 (d, J = 5.0 Hz, 1H), 7.10 (s, 1H), 6.93-6.84 (m, 6H), 6.50 (d, J = 7.8 Hz, 1H) | [M + H] 351.9 | A |
| 21 | 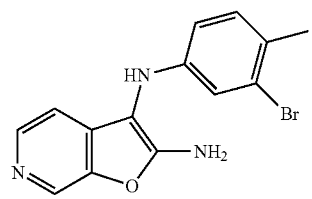 [SMILES: Cc1ccc(Nc2c(N)oc3cnccc23)cc1Br] | $N^3$-(3-Bromo-4-methylphenyl)furo[2,3-c]pyridine-2,3-diamine | DMSO-$d_6$: δ 8.40 (s, 1H), 8.04 (d, J = 5.0 Hz, 1H), 7.03 (d, J = 8.2 Hz, 1H), 6.97 (s, 1H), 6.88 (bs, 2H), 6.83 (d, J = 5.0 Hz, 1H), 6.69 (m, 1H), 6.46-6.43 (m, 1H), 2.18 (s, 3H) | [M − H] 316.0 | A |
| 22 | 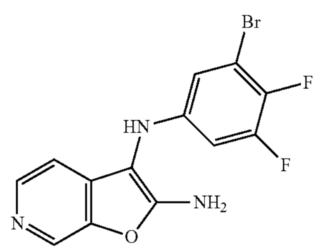 [SMILES: Nc1oc2cnccc2c1Nc1cc(F)c(F)c(Br)c1] | $N^3$-(3-Bromo-4,5-difluorophenyl)furo[2,3-c]pyridine-2,3-diamine | DMSO-$d_6$: δ 8.41 (s, 1H), 8.07 (d, J = 5.0 Hz, 1H), 7.35 (s, 1H), 6.98 (bs, 2H), 6.89 (d, J = 4.9 Hz, 1H), 6.52 (s, 1H), 6.45-6.40 (m, 1H) | [M + H] 340.0 | A |
| 23 | 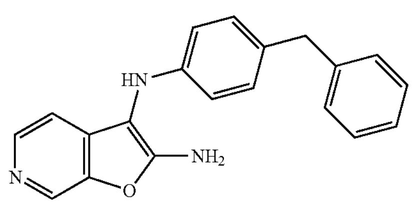 [SMILES: Nc1oc2cnccc2c1Nc1ccc(Cc2ccccc2)cc1] | $N^3$-(4-Benzylphenyl)furo[2,3-c]pyridine-2,3-diamine | DMSO-$d_6$: δ 8.38 (s, 1H), 8.02 (d, J = 5.1 Hz, 1H), 7.27-7.23 (m, 2H), 7.18-7.12 (m, 3H), 6.93 (d, J = 8.2 Hz, 2H), 6.81 (d, J = 5.0 Hz, 1H), 6.75 (bs, 2H), 6.72 (s, 1H), 6.45 (d, J = 8.2 Hz, 2H), 3.76 (s, 2H) | [M + H] 316.2 | A |
| 24 | 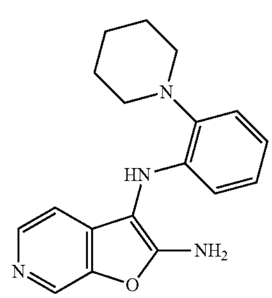 [SMILES: Nc1oc2cnccc2c1Nc1ccccc1N1CCCCC1] | $N^3$-(2-(Piperidin-1-yl)phenyl)furo[2,3-c]pyridine-2,3-diamine | DMSO-$d_6$: δ 8.40 (s, 1H), 8.02 (d, J = 5.1 Hz, 1H), 7.03 (d, J = 7.5 Hz, 1H), 6.84-6.77 (m, 3H), 6.74 (d, J = 5.1 Hz, 1H), 6.61 (t, J = 7.2 Hz, 1H), 6.20 (d, J = 7.8 Hz, 1H), 5.99 (s, 1H), 2.87 (bs, 4H), 1.73-1.69 (m, 4H), 1.54 (bs, 2H) | [M − H] 307.0 | A |

TABLE 1-continued

| No. | Structure | IUPAC Name | ¹H-NMR (400 MHz) proton shift | LCMS | Proc. |
|---|---|---|---|---|---|
| 25 | 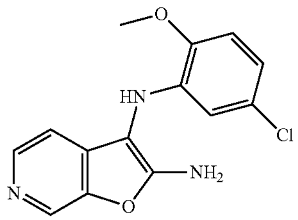 [SMILES: COc1ccc(Cl)cc1Nc1c(N)oc2cnccc12] | $N^3$-(5-Chloro-2-methoxyphenyl)furo[2,3-c]pyridine-2,3-diamine | DMSO-$d_6$: δ 8.42 (s, 1H), 8.06 (d, J = 5.1 Hz, 1H), 6.89-6.87 (m, 3H), 6.82 (d, J = 5.1 Hz, 1H), 6.60 (dd, J' = 8.4 Hz, J" = 2.5 Hz, 1H), 6.55 (s, 1H), 3.06 (d, J = 3.5 Hz, 1H), 3.85 (s, 3H) | [M + H] 290.4 | A |
| 26 | 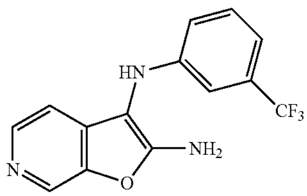 [SMILES: Nc1oc2cnccc2c1Nc1cccc(C(F)(F)F)c1] | $N^3$-(3-(Trifluoromethyl)phenyl)furo[2,3-c]pyridine-2,3-diamine | DMSO-$d_6$: δ 8.42 (s, 1H), 8.06 (d, J = 5.0 Hz, 1H), 7.36 (s, 1H), 7.29 (t, J = 7.9 Hz, 1H), 6.93-6.89 (m, 3H), 6.86 (d, J = 5.1 Hz, 1H), 6.80 (s, 1H), 6.73 (d, J = 8.3 Hz, 1H) | [M + H] 294.2 | A |
| 27 | 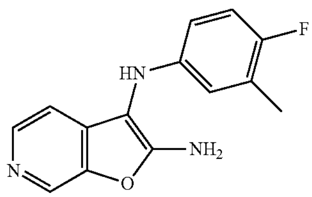 | $N^3$-(4-Fluoro-3-methylphenyl)furo[2,3-c]pyridine-2,3-diamine | DMSO-$d_6$: δ 8.39 (s, 1H), 8.04 (d, J = 5.0 Hz, 1H), 6.86-6.81 (m, 4H), 6.71 (s, 1H), 6.38-6.36 (m, 1H), 6.32-6.29 (m, 1H), 2.09 (s, 3H) | [M + H] 257.8 | A |
| 28 | 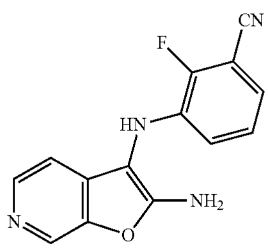 [SMILES: N#Cc1cccc(Nc2c(N)oc3cnccc23)c1F] | 3-((2-Aminofuro[2,3-c]pyridin-3-yl)amino)-2-fluorobenzonitrile | DMSO-$d_6$: δ 8.42 (s, 1H), 8.06 (d, J = 4.8 Hz, 1H), 7.38 (s, 1H), 7.09-6.99 (m, 4H), 6.89 (d, J = 4.6 Hz, 1H), 6.62 (t, J = 7.6 Hz, 1H) | [M + H] 269.0 | A |
| 29 | 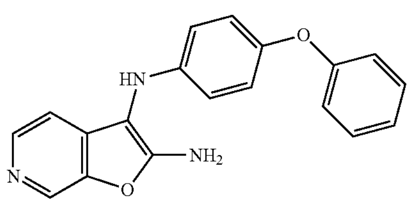 [SMILES: Nc1oc2cnccc2c1Nc1ccc(Oc2ccccc2)cc1] | $N^3$-(4-Phenoxyphenyl)furo[2,3-c]pyridine-2,3-diamine | DMSO-$d_6$: δ 8.38 (s, 1H), 8.05 (d, J = 5.0 Hz, 1H), 7.29 (t, J = 7.7 Hz, 2H), 6.99 (t, J = 7.2 Hz, 1H), 6.87-6.82 (m, 8H), 6.55 (d, J = 8.5 Hz, 2H) | [M − H] 316.1 | A |
| 30 | 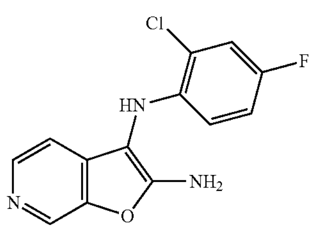 | $N^3$-(2-Chloro-4-fluorophenyl)furo[2,3-c]pyridine-2,3-diamine | DMSO-$d_6$: δ 8.41 (s, 1H), 8.05 (d, J = 5.0 Hz, 1H), 7.30 (dd, J' = 8.5 Hz, J" = 2.8 Hz, 1H), 6.95-6.90 (m, 3H), 6.81 (d, J = 5.1 Hz, 1H), 6.57 (s, 1H), 6.28 (dd, J' = 9.0 Hz, J" = 5.3 Hz, 1H) | [M + H] 278.0 | A |
| 31 | 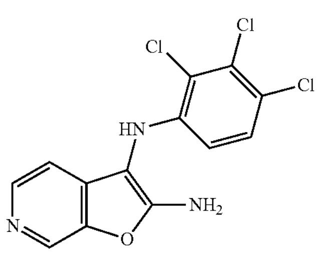 [SMILES: Nc1oc2cnccc2c1Nc1ccc(Cl)c(Cl)c1Cl] | $N^3$-(2,3,4-Trichlorophenyl)furo[2,3-c]pyridine-2,3-diamine | DMSO-$d_6$: δ 8.42 (s, 1H), 8.06 (d, J = 5.0 Hz, 1H), 7.28 (d, J = 9.0 Hz, 1H), 7.11 (s, 1H), 7.01 (bs, 2H), 6.86 (d, J = 5.2 Hz, 1H), 6.29 (d, J = 9.0 Hz, 1H). | [M + H] 327.8 | A |

TABLE 1-continued

| No. | Structure | IUPAC Name | ¹H-NMR (400 MHz) proton shift | LCMS | Proc. |
|---|---|---|---|---|---|
| 32 | 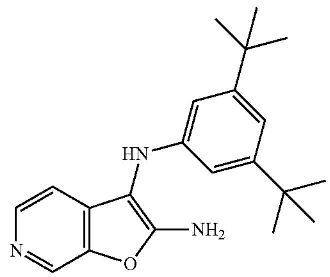 [SMILES: CC(C)(C)c1cc(Nc2c(N)oc3cnccc23)cc(C(C)(C)C)c1] | $N^3$-(3,5-Di-tert-butylphenyl)furo[2,3-c]pyridine-2,3-diamine | DMSO-$d_6$: δ 8.40 (s, 1H), 8.03 (bs, 1H), 6.84 (bs, 1H), 6.72-6.67 (m, 4H), 6.40 (s, 2H), 1.33-1.18 (m, 18H) | [M + H] 338.2 | A |
| 33 | 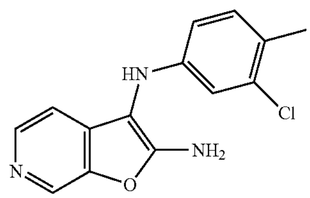 [SMILES: Cc1ccc(Nc2c(N)oc3cnccc23)cc1Cl] | $N^3$-(3-Chloro-4-methylphenyl)furo[2,3-c]pyridine-2,3-diamine | DMSO-$d_6$: δ 8.40 (s, 1H), 8.05 (d, J = 5.0 Hz, 1H), 7.03 (d, J = 8.2 Hz, 1H), 6.97 (s, 1H), 6.86 (bs, 2H), 6.83 (d, J = 5.0 Hz, 1H), 6.50 (s, 1H), 6.42 (d, J = 8.1 Hz, 1H), 2.12 (s, 3H) | [M + H] 274.0 | A |
| 34 | 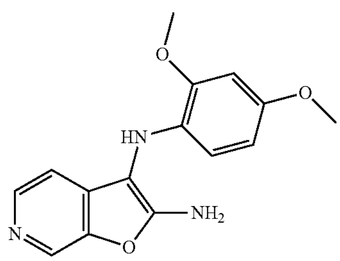 [SMILES: COc1ccc(Nc2c(N)oc3cnccc23)c(OC)c1] | $N^3$-(2,4-Dimethoxyphenyl)furo[2,3-c]pyridine-2,3-diamine | DMSO-$d_6$: δ 8.38 (s, 1H), 8.01 (d, J = 5.0 Hz, 1H), 6.75 (d, J = 5.1 Hz, 1H), 6.72 (bs, 2H), 6.56 (d, J = 2.4 Hz, 1H), 6.26 (dd, J' = 8.6 Hz, J'' = 2.5 Hz, 1H), 6.07 (d, J = 8.5 Hz, 1H), 5.78 (s, 1H), 3.84 (s, 3H), 3.64 (s, 3H) | [M + H] 286.0 | A |
| 35 | 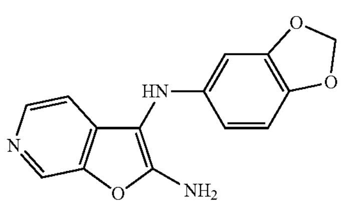 [SMILES: Nc1oc2cnccc2c1Nc1ccc2c(c1)OCO2] | $N^3$-(Benzo[d][1,3]dioxol-5-yl)furo[2,3-c]pyridine-2,3-diamine | DMSO-$d_6$: δ 8.38 (s, 1H), 8.03 (d, J = 4.9 Hz, 1H), 6.83 (d, J = 5.0 Hz, 1H), 6.79 (bs, 2H), 6.65-6.63 (m, 2H), 6.17 (s, 1H), 5.95 (d, J = 8.1 Hz, 1H), 5.83 (s, 2H) | [M + H] 270.0 | A |
| 36 | 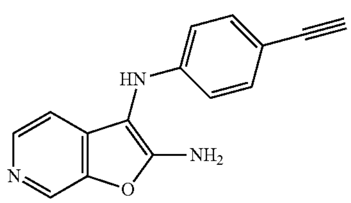 [SMILES: C#Cc1ccc(Nc2c(N)oc3cnccc23)cc1] | $N^3$-(4-Ethynylphenyl)furo[2,3-c]pyridine-2,3-diamine | $CD_3CN$: δ 8.43 (s, 1H), 8.12 (d, J = 5.1 Hz, 1H), 7.25 (d, J = 8.6 Hz, 2H), 6.95 (d, J = 4.9 Hz, 1H), 6.56 (d, J = 8.6 Hz, 2H), 5.87 (s, 1H), 5.36 (s, 2H), 3.18 (s, 1H) | [M + H] 250.0 | A |
| 37 | 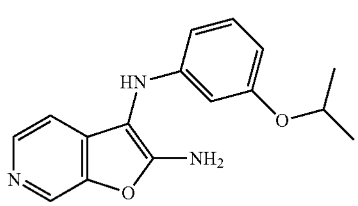 [SMILES: CC(C)Oc1cccc(Nc2c(N)oc3cnccc23)c1] | $N^3$-(3-Isopropoxyphenyl)furo[2,3-c]pyridine-2,3-diamine | DMSO-$d_6$: δ 8.39 (s, 1H), 8.04 (d, J = 5.0 Hz, 1H), 6.95 (t, J = 8.2 Hz, 1H), 6.84-6.80 (m, 4H), 6.14 (dd, J' = 15.2 Hz, J'' = 7.9 Hz, 2H), 6.00 (s, 1H), 4.43-4.37 (m, 1H), 1.18 (d, J = 6 Hz, 6H) | [M + H] 284.2 | A |

TABLE 1-continued

| No. | Structure | IUPAC Name | ¹H-NMR (400 MHz) proton shift | LCMS | Proc. |
|---|---|---|---|---|---|
| 38 | 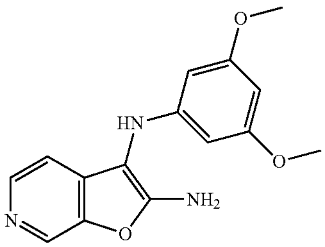 [SMILES: COc1cc(Nc2c(N)oc3cnccc23)cc(OC)c1] | N³-(3,5-Dimethoxyphenyl)furo[2,3-c]pyridine-2,3-diamine | DMSO-d₆: δ 8.39 (s, 1H), 8.05 (d, J = 4.8 Hz, 1H), 6.89 (s, 1H), 6.84 (d, J = 5.0 Hz, 1H), 6.79 (s, 2H), 5.80 (s, 1H), 5.71 (s, 2H), 3.60 (s, 6H) | [M − H] 284.0 | A |
| 39 | 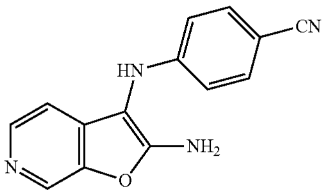 [SMILES: N#Cc1ccc(Nc2c(N)oc3cnccc23)cc1] | 4-((2-Aminofuro[2,3-c]pyridin-3-yl)amino)benzonitrile | DMSO-d₆: δ 8.42 (s, 1H), 8.06 (d, J = 5.1 Hz, 1H), 7.84 (s, 1H), 7.49 (d, J = 8.7 Hz, 2H), 7.01 (s, 2H), 6.84 (d, J = 5.0 Hz, 1H), 6.60 (d, J = 8.3 Hz, 2H) | [M + H] 251.0 | A |
| 40 | 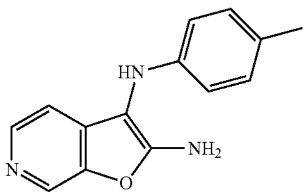 [SMILES: Cc1ccc(Nc2c(N)oc3cnccc23)cc1] | N³-(p-tolyl)Furo[2,3-c]pyridine-2,3-diamine | DMSO-d₆: δ 8.39 (s, 1H), 8.02 (d, J = 5.1 Hz, 1H), 8.88 (d, J = 8.2 Hz, 2H), 6.78 (d, J = 5.0 Hz, 1H), 6.76 (s, 2H), 6.65 (s, 1H), 6.43 (d, J = 8.2 Hz, 2H), 2.15 (s, 3H) | [M + H] 240.0 | A |
| 41 | 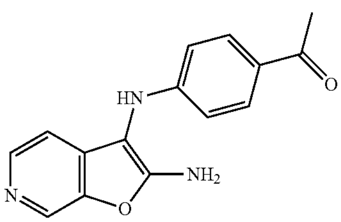 [SMILES: CC(=O)c1ccc(Nc2c(N)oc3cnccc23)cc1] | 1-(4-((2-Aminofuro[2,3-c]pyridin-3-yl)amino)phenyl)ethanone | DMSO-d₆: δ 8.42 (s, 1H), 8.06 (d, J = 5.0 Hz, 1H), 7.75-7.71 (m, 3H), 6.96 (bs, 2H), 6.83 (d, J = 5.0 Hz, 1H), 6.56 (d, J = 8.5 Hz, 2H), 2.40 (s, 3H) | [M + H] 268.2 | A |
| 42 | 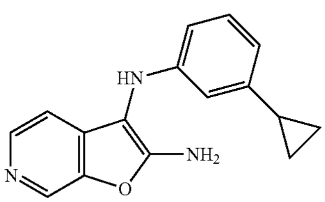 [SMILES: Nc1oc2cnccc2c1Nc1cccc(C2CC2)c1] | N³-(3-Cyclopropylphenyl)furo[2,3-c]pyridine-2,3-diamine | DMSO-d₆: δ 8.39 (s, 1H), 8.03 (d, J = 5.0 Hz, 1H), 6.93 (t, J = 7.6 Hz, 1H), 6.81 (d, J = 5.1 Hz, 1H), 6.76-6.74 (m, 3H), 6.31-6.26 (m, 3H), 1.74-1.71 (m, 1H), 0.85-0.81 (m, 2H), 0.53-0.49 (m, 2H) | [M + H] 266.2 | A |
| 43 | 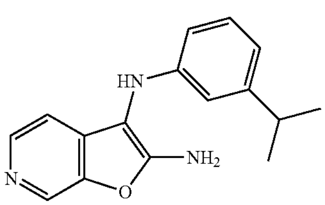 [SMILES: CC(C)c1cccc(Nc2c(N)oc3cnccc23)c1] | N³-(3-Isopropylphenyl)furo[2,3-c]pyridine-2,3-diamine | DMSO-d₆: δ 8.39 (s, 1H), 8.03 (d, J = 5.1 Hz, 1H), 6.97 (t, J = 7.7 Hz, 1H), 6.82 (d, J = 5.1 Hz, 1H), 6.77 (bs, 3H), 6.49-6.46 (m, 2H), 6.28 (d, J = 7.6 Hz, 1H), 2.74-2.67 (m, 1H), 1.12 (d, J = 6.9 Hz, 6H) | [M + H] 268.2 | A |
| 44 | 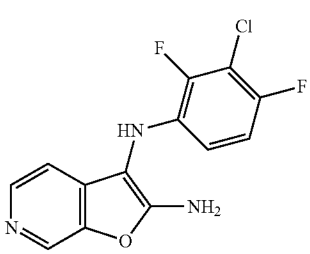 [SMILES: Nc1oc2cnccc2c1Nc1ccc(F)c(Cl)c1F] | N³-(3-Chloro-2,4-difluorophenyl)furo[2,3-c]pyridine-2,3-diamine | DMSO-d₆: δ 8.41 (s, 1H), 8.06 (d, J = 4.9 Hz, 1H), 7.03-6.88 (m, 5H), 6.29-6.23 (m, 1H) | [M + H] 296.0 | A |

TABLE 1-continued

| No. | Structure | IUPAC Name | ¹H-NMR (400 MHz) proton shift | LCMS | Proc. |
|---|---|---|---|---|---|
| 45 | 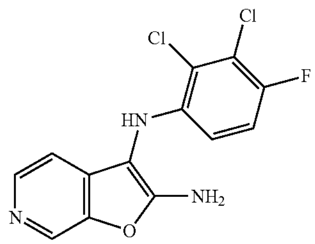 [SMILES: Nc1oc2cnccc2c1Nc1ccc(F)c(Cl)c1Cl] | N³-(2,3-Dichloro-4-fluorophenyl)furo[2,3-c]pyridine-2,3-diamine | DMSO-d₆: δ 8.42 (s, 1H), 8.05 (s, 1H), 7.13 (bs, 1H), 7.00 (s, 2H), 6.87 (s, 2H), 6.27 (s, 1H) | [M + H] 312.0 | A |
| 46 | 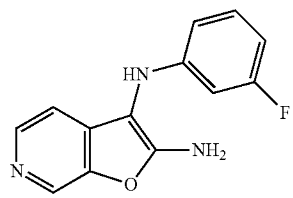 [SMILES: Nc1oc2cnccc2c1Nc1cccc(F)c1] | N³-(3-Fluorophenyl)furo[2,3-c]pyridine-2,3-diamine | DMSO-d₆: δ 8.41 (s, 1H), 8.05 (d, J = 5.0 Hz, 1H), 7.19 (s, 1H), 7.09 (q, J = 7.7 Hz, 1H), 6.88 (s, 2H), 6.85 (d, J = 5.0 Hz, 1H), 6.38-6.35 (m, 2H), 6.22 (d, J = 12.2 Hz, 1H) | [M + H] 244.0 | A |
| 47 | 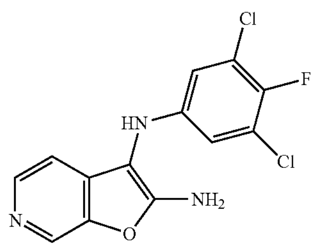 [SMILES: Nc1oc2cnccc2c1Nc1cc(Cl)c(F)c(Cl)c1] | N³-(3,5-Dichloro-4-fluorophenyl)furo[2,3-c]pyridine-2,3-diamine | DMSO-d₆: δ 8.42 (s, 1H), 8.08 (d, J = 5.0 Hz, 1H), 7.36 (s, 1H), 7.01 (bs, 2H), 6.90 (d, J = 5.0 Hz, 1H), 6.55 (d, J = 5.6 Hz, 2H) | [M + H] 312.0 | A |
| 48 | 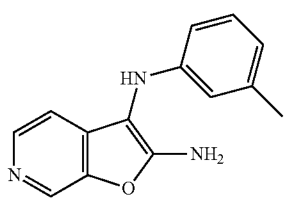 [SMILES: Cc1cccc(Nc2c(N)oc3cnccc23)c1] | N³-(m-tolyl)Furo[2,3-c]pyridine-2,3-diamine | DMSO-d₆): δ 8.40 (s, 1H), 8.04 (d, J = 5.1 Hz, 1H), 6.95 (t, J = 7.7 Hz, 1H), 6.82 (d, J = 5.1 Hz, 1H), 6.80 (bs, 2H), 6.75 (s, 1H), 6.41 (d, J = 7.2 Hz, 1H), 6.35-6.31 (m, 2H), 2.14 (s, 3H) | [M + H] 240.0 | A |
| 49 | 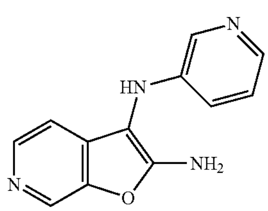 [SMILES: Nc1oc2cnccc2c1Nc1cccnc1] | N³-(Pyridin-3-yl)furo[2,3-c]pyridine-2,3-diamine | DMSO-d₆: δ 8.41 (s, 1H), 8.05 (s, 1H), 7.97 (s, 1H), 7.82 (s, 1H), 7.13 (s, 1H), 7.07 (bs, 1H), 6.93 (bs, 2H), 6.85 (d, J = 3.6 Hz, 1H), 6.74 (d, J = 7.2 Hz, 1H) | [M + H] 227.0 | A |
| 50 | 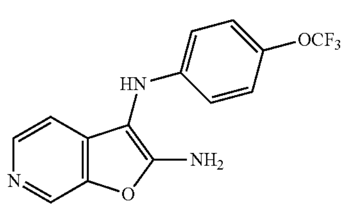 [SMILES: Nc1oc2cnccc2c1Nc1ccc(OC(F)(F)F)cc1] | N³-(4-(Trifluoromethoxy)phenyl)furo[2,3-c]pyridine-2,3-diamine | DMSO-d₆: δ 8.40 (s, 1H), 8.05 (d, J = 4.7 Hz, 1H), 7.13 (s, 1H), 7.07 (d, J = 8.1 Hz, 2H), 6.88 (bs, 2H), 6.85 (d, J = 4.7 Hz, 1H), 6.55 (d, J = 8.5 Hz, 2H) | [M + H] 310.2 | A |
| 51 | 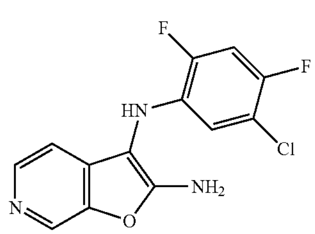 | N³-(5-Chloro-2,4-difluorophenyl)furo[2,3-c]pyridine-2,3-diamine | DMSO-d₆: δ 8.42 (s, 1H), 8.07 (d, J = 5.0 Hz, 1H), 7.46-7.41 (m, 1H), 7.06 (s, 1H), 6.97 (bs, 2H), 6.90 (d, J = 5.0 Hz, 1H), 6.29 (t, J = 8.1 Hz, 1H) | [M + H] 296.0 | A |

TABLE 1-continued

| No. | IUPAC Name | ¹H-NMR (400 MHz) proton shift | LCMS | Proc. |
|---|---|---|---|---|
| 52 | N³-(5-Chloropyridin-3-yl)furo[2,3-c]pyridine-2,3-diamine | DMSO-d₆: δ 8.43 (s, 1H), 8.08 (d, J = 5.1 Hz, 1H), 7.92 (s, 1H), 7.83 (s, 1H), 7.53 (s, 1H), 7.04 (bs, 2H), 6.91 (d, J = 4.9 Hz, 1H), 6.73 (s, 1H) | [M − H] 259.0 | A |
| 53 | N³-([1,1'-Biphenyl]-3-yl)furo[2,3-c]pyridine-2,3-diamine | DMSO-d₆: δ 8.39 (s, 1H), 8.02 (d, J = 5.1 Hz, 1H), 7.62 (d, J = 7.5 Hz, 2H), 7.48 (t, J = 7.6 Hz, 2H), 7.38 (t, J = 7.5 Hz, 1H), 7.08-7.03 (m, 2H), 6.84-6.82 (m, 3H), 6.73 (t, J = 7.3 Hz, 1H), 6.34 (d, J = 8.0 Hz, 1H), 5.80 (s, 1H) | [M + H] 302.2 | A |
| 54 | N³-(2,4-Dimethyl-phenyl)furo[2,3-c]pyridine-2,3-diamine | DMSO-d₆: δ 8.40 (s, 1H), 8.02 (d, J = 5.1 Hz, 1H), 6.84 (s, 1H), 6.78 (d, J = 5.1 Hz, 1H), 6.74 (bs, 2H), 6.68 (d, J = 8.4 Hz, 1H), 6.09 (d, J = 8.1 Hz, 1H), 5.96 (s, 1H), 2.23 (s, 3H), 2.13 (s, 3H) | [M + H] 254.0 | A |
| 55 | N³-(2,5-Dichloro-phenyl)furo[2,3-c]pyridine-2,3-diamine | DMSO-d₆: δ 8.43 (s, 1H), 8.07 (d, J = 5.1 Hz, 1H), 7.33 (d, J = 8.4 Hz, 1H), 7.02 (bs, 2H), 6.99 (s, 1H), 6.86 (d, J = 5.1 Hz, 1H), 6.68 (dd, J' = 8.4 Hz, J'' = 2.4 Hz, 1H), 6.22 (d, J = 2.4 Hz, 1H) | [M + H] 294.0 | A |
| 56 | (2-Amino-3-((3-chloro-4-fluorophenyl)amino)-7-methylfuro[2,3-c]pyridin-4-yl)methanol | DMSO-d₆: δ 7.94 (s, 1H), 7.12 (t, J = 9.0 Hz, 1H), 6.89 (s, 1H), 6.78 (bs, 2H), 6.54 (d, J = 3.7 Hz, 1H), 6.45-6.43 (m, 1H), 4.92 (s, 1H), 4.45 (s, 2H), 2.50 (s, 3H) | [M + H] 322.0 | A |
| 57 | 4-Chloro-N³-(3-chloro-4-fluorophenyl)furo[2,3-c]pyridine-2,3-diamine | DMSO-d₆: δ 8.37 (s, 1H), 8.03 (s, 1H), 7.25 (bs, 2H), 7.11 (t, J = 9.1 Hz, 1H), 7.06 (s, 1H), 6.59-6.57 (m, 1H), 6.47-6.45 (m, 1H) | [M + H] 312.0 | A |
| 58 | N³-(3-Bromo-4-fluorophenyl)furo[2,3-c]pyridine-2,3-diamine | DMSO-d₆: δ 8.41 (s, 1H), 8.06 (d, J = 5.0 Hz, 1H), 7.11-7.07 (m, 2H), 6.91 (bs, 2H), 6.86 (d, J = 5.0 Hz, 1H), 6.70 (dd, J' = 5.8 Hz, J'' = 2.7 Hz, 1H), 6.50 (dt, J' = 8.8 Hz, J'' = 6.8 Hz, J''' = 3.3 Hz, | [M + H] 322.0 | A |

TABLE 1-continued

| No. | Structure | IUPAC Name | ¹H-NMR (400 MHz) proton shift | LCMS | Proc. |
|---|---|---|---|---|---|
| | | | 1H). | | |
| 59 | 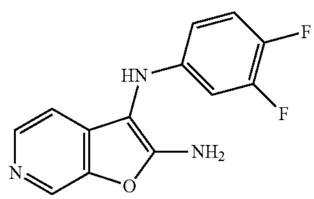 [SMILES: Nc1oc2cnccc2c1Nc1ccc(F)c(F)c1] | N³-(3,4-Difluorophenyl)furo[2,3-c]pyridine-2,3-diamine | DMSO-$d_6$: δ 8.40 (s, 1H), 8.05 (d, J = 5.0 Hz, 1H), 7.16-7.10 (m, 2H), 6.91 (bs, 2H), 6.85 (d, J = 4.9 Hz, 1H), 6.42-6.37 (m, 1H), 6.30 (d, J = 8.5 Hz, 1H) | [−H] 260.0 | A |
| 60 | 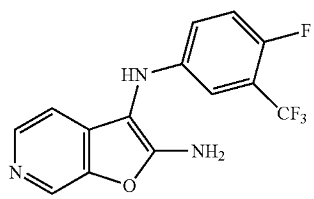 [SMILES: Nc1oc2cnccc2c1Nc1ccc(F)c(C(F)(F)F)c1] | N³-(4-Fluoro-3-(trifluoromethyl)phenyl)furo[2,3-c]pyridine-2,3-diamine | DMSO-$d_6$: δ 8.42 (s, 1H), 8.06 (d, J = 5.0 Hz, 1H), 7.29 (s, 1H), 7.21 (t, J = 9.76 Hz, 1H), 6.95 (bs, 2H), 6.88 (d, J = 5.0 Hz, 1H), 6.80-6.78 (m, 1H), 6.73-6.70 (m, 1H) | [M + H] 312.0 | A |
| 61 | 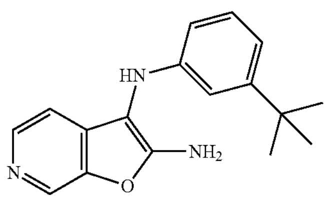 [SMILES: CC(C)(C)c1cccc(Nc2c(N)oc3cnccc23)c1] | N³-(3-(tert-Butyl)phenyl)furo[2,3-c]pyridine-2,3-diamine | DMSO-$d_6$: δ 8.40 (s, 1H), 8.03 (d, J = 5.0 Hz, 1H), 6.98 (t, J = 7.8 Hz, 1H), 6.83-6.78 (m, 4H), 6.67-6.63 (m, 2H), 6.25-6.23 (m, 1H). 1.20 (s, 9H) | [M + H] 282.0 | A |
| 62 | 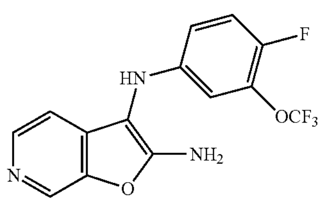 [SMILES: Nc1oc2cnccc2c1Nc1ccc(F)c(OC(F)(F)F)c1] | N³-(4-Fluoro-3-(trifluoromethoxy)phenyl)furo[2,3-c]pyridine-2,3-diamine | DMSO-$d_6$: δ 8.41 (s, 1H), 8.03 (d, J = 5.1 Hz, 1H), 7.22-7.17 (m, 2H), 6.96 (bs, 2H), 6.85 (d, J = 5.1 Hz, 1H), 6.55 (d, J = 5.4 Hz, 1H), 6.47 (dt, J' = 8.8 Hz, J'' = 6.5 Hz, J''' = 3.3 Hz, 1H) | [M + H] 328.2 | A |
| 63 | 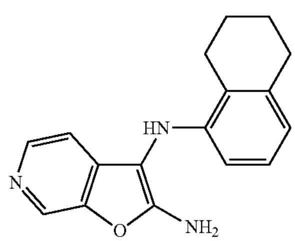 [SMILES: Nc1oc2cnccc2c1Nc1cccc2c1CCCC2] | N³-(5,6,7,8-Tetrahydronaphthalen-1-yl)furo[2,3-c]pyridine-2,3-diamine | DMSO-$d_6$: δ 8.40 (s, 1H), 8.03 (d, J = 5.1 Hz, 1H), 6.81 (d, J = 5.1 Hz, 1H), 6.76-6.74 (m, 3H), 6.37 (d, J = 7.4 Hz, 1H), 6.01-5.99 (m, 2H), 2.67 (t, J = 5.7 Hz, 2H), 2.61 (t, J = 6.2 Hz, 2H), 1.82-1.81 (m, 2H), 1.72-1.70 (m, 2H) | [M + H] 280.0 | A |
| 64 | 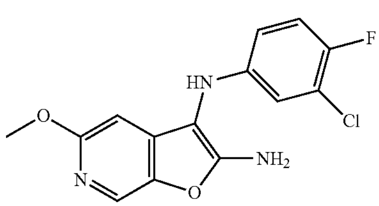 [SMILES: COc1cc2c(Nc3ccc(F)c(Cl)c3)c(N)oc2cn1] | N³-(3-Chloro-4-fluorophenyl)-5-methoxyfuro[2,3-c]pyridine-2,3-diamine | DMSO-$d_6$: δ 7.97 (s, 1H), 7.12 (t, J = 9.1 Hz, 1H), 7.02 (s, 1H), 6.93 (bs, 2H), 6.55 (dd, J' = 6.2 Hz, J'' = 2.6 Hz, 1H), 6.47-6.44 (m, 1H). 6.06 (s, 1H), 3.75 (s, 3H) | [M + H] 308.2 | A |
| 65 | 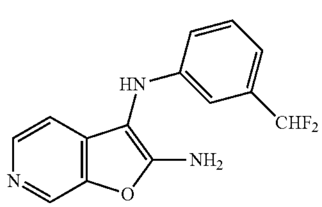 [SMILES: Nc1oc2cnccc2c1Nc1cccc(C(F)F)c1] | N³-(3-(Difluoromethyl)phenyl)furo[2,3-c]pyridine-2,3-diamine | DMSO-$d_6$: δ 8.43 (s, 1H), 8.12 (d, J = 5.1 Hz, 1H), 7.24 (t, J = 7.8 Hz, 1H), 6.95 (d, J = 5.0 Hz, 1H), 7.86 (d, J = 7.4 Hz, 1H), 6.76-6.73 (m, 2H), 6.62 (s, 1H), 5.81 (s, 1H), 5.38 (s, 2H) | [M + H] 276.0 | A |

TABLE 1-continued

| No. | Structure | IUPAC Name | $^1$H-NMR (400 MHz) proton shift | LCMS | Proc. |
| --- | --- | --- | --- | --- | --- |
| 66 | 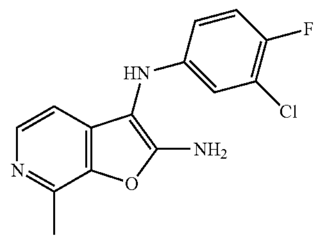 [SMILES: Cc1nccc2c(Nc3ccc(F)c(Cl)c3)c(N)oc12] | N$^3$-(3-Chloro-4-fluorophenyl)-7-methylfuro[2,3-c]pyridine-2,3-diamine | DMSO-d$_6$: δ 7.93 (d, J = 5.1 Hz, 1H), 7.13-7.08 (m, 2H), 6.82 (bs, 2H), 6.71 (d, J = 5.1 Hz, 1H), 6.54 (dd, J' = 6.2 Hz, J" = 2.6 Hz, 1H), 6.48-6.45 (m, 1H), 2.49 (d, J = 2.3 Hz, 3H) | [M + H] 292.0 | A |
| 67 | 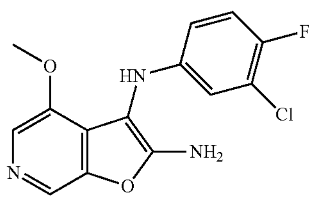 [SMILES: COc1cncc2oc(N)c(Nc3ccc(F)c(Cl)c3)c12] | N$^3$-(3-Chloro-4-fluorophenyl)-4-methoxyfuro[2,3-c]pyridine-2,3-diamine | DMSO-d$_6$: δ 8.18 (s, 1H), 7.86 (s, 1H), 7.09 (t, J = 9.1 Hz, 1H), 6.99 (s, 1H), 6.68 (bs, 2H), 6.54 (dd, J' = 6.1 Hz, J" = 2.5 Hz, 1H), 6.46-6.44 (m, 1H), 3.68 (s, 3H) | [M + H] 308.0 | A |
| 68 | 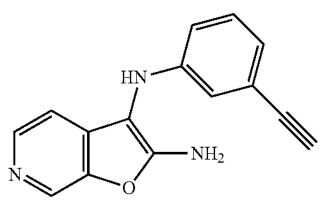 [SMILES: C#Cc1cccc(Nc2c(N)oc3cnccc23)c1] | N$^3$-(3-Ethynylphenyl)furo[2,3-c]pyridine-2,3-diamine | DMSO-d$_6$: δ 8.41 (s, 1H), 8.05 (d, J = 5.0 Hz, 1H), 7.10-7.06 (m, 2H), 6.89 (bs, 2H), 6.84 (d, J = 5.0 Hz, 1H), 6.70 (d, J = 7.4 Hz, 1H), 6.58-6.56 (m, 2H), 3.99 (s, 1H) | [M + H] 250.0 | A |
| 69 | 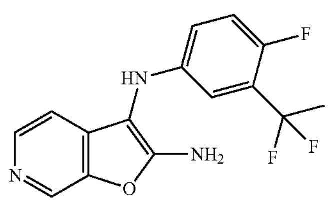 [SMILES: CC(F)(F)c1cc(Nc2c(N)oc3cnccc23)ccc1F] | N$^3$-(3-(1,1-Difluoroethyl)-4-fluorophenyl)furo[2,3-c]pyridine-2,3-diamine | DMSO-d$_6$: δ 8.41 (s, 1H), 8.05 (d, J = 5.0 Hz, 1H), 7.09-7.03 (m, 2H), 6.92 (bs, 2H), 6.86 (d, J = 5.0 Hz, 1H), 6.72 (dd, J' = 6.3 Hz, J" = 2.9 Hz, 1H), 6.55-6.52 (m, 1H), 1.98-1.88 (m, 3H) | [M + H] 308.2 | A |
| 70 | 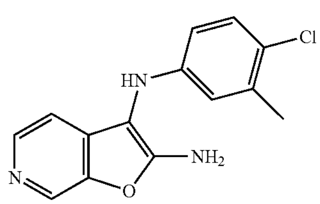 [SMILES: Cc1cc(Nc2c(N)oc3cnccc23)ccc1Cl] | N$^3$-(4-Chloro-3-methylphenyl)furo[2,3-c]pyridine-2,3-diamine | DMSO-d$_6$: δ 8.40 (s, 1H), 8.04 (d, J = 5.0 Hz, 1H), 7.07 (d, J = 8.6 Hz, 1H), 6.95 (s, 1H), 6.84-6.82 (m, 3H), 6.47 (d, J = 2.4 Hz, 1H), 6.35 (dd, J' = 8.6 Hz, J" = 2.6 Hz, 1H), 2.17 (s, 3H) | [M + H] 274.0 | A |
| 71 | 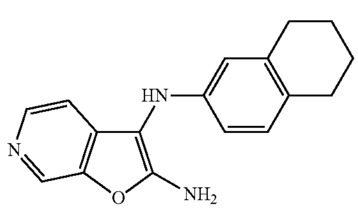 [SMILES: Nc1oc2cnccc2c1Nc1ccc2c(c1)CCCC2] | N$^3$-(5,6,7,8-Tetrahydro-naphthalen-2-yl)furo[2,3-c]pyridine-2,3-diamine | DMSO-d$_6$: δ 8.38 (s, 1H), 8.02 (d, J = 5.0 Hz, 1H), 6.81 (d, J = 5.0 Hz, 1H), 6.76-6.72 (m, 3H), 6.55 (s, 1H), 6.29 (dd, J' = 8.1 Hz, J" = 2.0 Hz, 1H), 6.20 (bs, 1H), 2.55-2.50 (m, 4H), 1.65 (s, 4H) | [M + H] 280.0 | A |
| 72 | 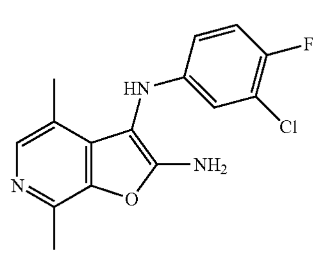 [SMILES: Cc1ncc(C)c2c(Nc3ccc(F)c(Cl)c3)c(N)oc12] | N$^3$-(3-Chloro-4-fluorophenyl)-4,7-dimethyl-furo[2,3-c]pyridine-2,3-diamine | DMSO-d$_6$: δ 7.67 (s, 1H), 7.08 (t, J = 9.0 Hz, 1H), 7.03 (s, 1H), 6.73 (bs, 2H), 6.50-6.48 (m, 1H), 6.42-6.40 (m, 1H), 2.41 (s, 3H), 2.06 (s, 3H) | HRMS [M + H] 306.080 | A |

TABLE 1-continued

| No. | Structure | IUPAC Name | ¹H-NMR (400 MHz) proton shift | LCMS | Proc. |
|---|---|---|---|---|---|
| 73 | 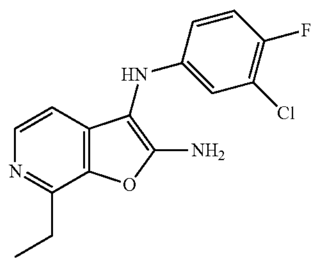 [SMILES: CCc1nccc2c(Nc3ccc(F)c(Cl)c3)c(N)oc12] | N³-(3-Chloro-4-fluorophenyl)-7-ethylfuro[2,3-c]pyridine-2,3-diamine | DMSO-d₆: δ 7.97 (d, J = 5.1 Hz, 1H), 7.14-7.08 (m, 2H), 6.81 (bs, 2H), 6.72 (d, J = 5.1 Hz, 1H), 6.55 (dd, J' = 6.3 Hz, J" = 2.7 Hz, 1H), 6.48-6.44 (m, 1H), 2.86 (q, J = 7.6 Hz, 2H), 1.28 (t, J = 7.6 Hz, 3H) | [M + H] 306.1 | A |
| 74 | 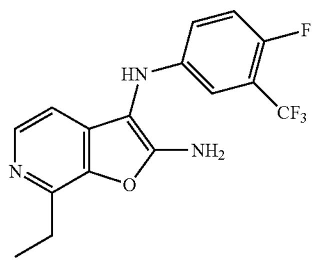 | 7-Ethyl-N³-(4-fluoro-3-(trifluoromethyl)phenyl)furo[2,3-c]pyridine-2,3-diamine | DMSO-d₆: δ 7.97 (d, J = 5.0 Hz, 1H), 7.27 (s, 1H), 7.20 (t, J = 9.8 Hz, 1H), 6.84 (s, 2H), 6.80-6.78 (m, 1H), 6.73-6.69 (m, 2H), 2.86 (q, J = 7.5 Hz, 2H), 1.28 (t, J = 7.5 Hz, 3H) | [M − H] 338.0 | A |
| 75 | 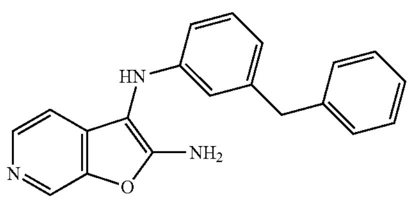 [SMILES: Nc1oc2cnccc2c1Nc1cccc(Cc2ccccc2)c1] | N³-(3-Benzylphenyl)furo[2,3-c]pyridine-2,3-diamine | CD₃CN: δ 8.41 (s, 1H), 8.09 (s, 1H), 7.24-7.18 (m, 5H), 7.03 (s, 1H), 6.89 (s, 1H), 6.57-6.43 (m, 3H), 5.54 (s, 1H), 5.29 (s, 2H), 3.81 (s, 2H) | [M + H] 316.2 | A |
| 76 | 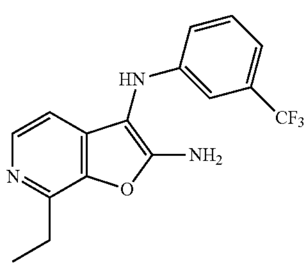 [SMILES: CCc1nccc2c(Nc3cccc(C(F)(F)F)c3)c(N)oc12] | 7-Ethyl-N³-(3-(trifluoromethyl)phenyl)furo[2,3-c]pyridine-2,3-diamine | DMSO-d₆: δ 7.97 (d, J = 5.1 Hz, 1H), 7.35 (s, 1H), 7.28 (t, J = 7.9 Hz, 1H), 6.89 (d, J = 7.6 Hz, 1H), 6.83-6.80 (m, 3H), 6.74-6.71 (m, 2H), 2.86 (q, J = 7.6 Hz, 2H), 1.29 (t, J = 7.6 Hz, 3H) | [M − H] 320.0 | A |
| 77 | 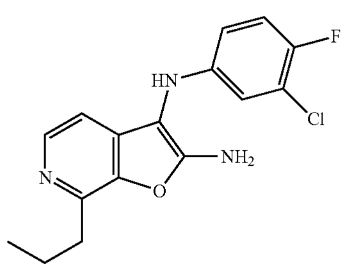 [SMILES: CCCc1nccc2c(Nc3ccc(F)c(Cl)c3)c(N)oc12] | N³-(3-Chloro-4-fluorophenyl)-7-propylfuro[2,3-c]pyridine-2,3-diamine | DMSO-d₆: δ 7.96 (d, J = 5.1 Hz, 1H), 7.14-7.07 (m, 2H), 6.81 (bs, 2H), 6.71 (d, J = 5.1 Hz, 1H), 6.55 (dd, J' = 6.3 Hz, J" = 2.7 Hz, 1H), 6.47-6.44 (m, 1H), 2.81 (t, J = 7.6 Hz, 2H), 1.79-1.71 (m, 2H), 0.94 (t, J = 7.4 Hz, 3H) | [M + H] 320.0 | A |
| 78 | 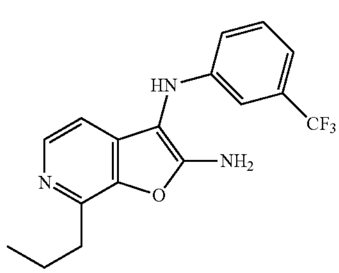 [SMILES: CCCc1nccc2c(Nc3cccc(C(F)(F)F)c3)c(N)oc12] | 7-Propyl-N³-(3-(trifluoromethyl)phenyl)furo[2,3-c]pyridine-2,3-diamine | CD₃CN: δ 8.04 (d, J = 5.1 Hz, 1H), 7.29 (t, J = 8.2 Hz, 1H), 6.97 (d, J = 7.6 Hz, 1H), 6.83-6.80 (m, 3H), 5.91 (s, 1H), 5.30 (s, 2H), 2.89 (t, J = 7.6 Hz, 2H), 1.87-1.78 (m, 2H), 0.98 (t, J = 7.4 Hz, 3H) | [M + H] 336.0 | A |

TABLE 1-continued

| No. | Structure | IUPAC Name | ¹H-NMR (400 MHz) proton shift | LCMS | Proc. |
|---|---|---|---|---|---|
| 79 | 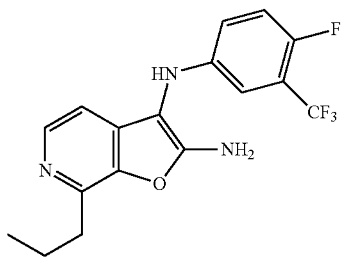 [SMILES: CCCc1nccc2c(Nc3ccc(F)c(C(F)(F)F)c3)c(N)oc12] | N³-(4-Fluoro-3-(trifluoro-methyl)phenyl)-7-propylfuro[2,3-c]pyridine-2,3-diamine | DMSO-$d_6$: δ 7.97 (d, J = 4.8 Hz, 1H), 7.27 (s, 1H), 7.20 (t, J = 9.7 Hz, 1H), 6.85 (s, 2H), 6.80 (s, 1H), 6.73-6.71 (m, 2H), 2.81 (t, J = 7.3 Hz, 2H), 1.79-1.73 (m, 2H), 0.94 (t, J = 7.2 Hz, 3H) | [M + H] 354.4 | A |
| 80 | 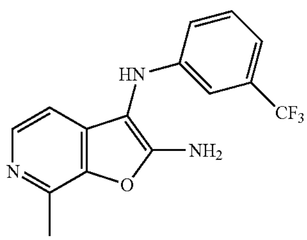 [SMILES: Cc1nccc2c(Nc3cccc(C(F)(F)F)c3)c(N)oc12] | 7-Methyl-N³-(3-(trifluoro-methyl)phenyl)furo[2,3-c]pyridine-2,3-diamine | $CD_3CN$: δ 8.00 (s, 1H), 7.30-7.27 (m, 1H), 6.97 (d, J = 6.8 Hz, 1H), 6.82 (bs, 3H), 5.90 (s, 1H), 5.32 (s, 2H), 2.55 (s, 3H) | [M + H] 308.2 | A |
| 81 | 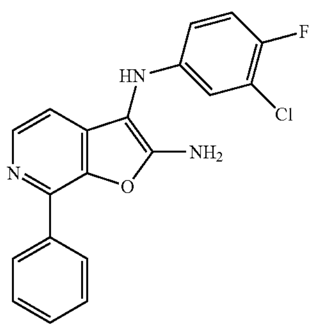 [SMILES: Nc1oc2c(-c3ccccc3)nccc2c1Nc1ccc(F)c(Cl)c1] | N³-(3-Chloro-4-fluorophenyl)-7-phenylfuro[2,3-c]pyridine-2,3-diamine | $CD_3CN$: δ 8.32-8.30 (m, 2H), 8.22 (d, J = 5.0 Hz, 1H), 7.56-7.52 (m, 2H), 7.48-7.44 (m, 1H), 7.03 (t, J = 9.1 Hz, 1H), 6.95 (d, J = 5.0 Hz, 1H), 6.65 (dd, J' = 6.3 Hz, J" = 2.8 Hz, 1H), 6.60-6.56 (m, 1H), 5.71 (s, 1H), 5.42 (s, 2H) | [M + H] 354.0 | A |
| 82 | 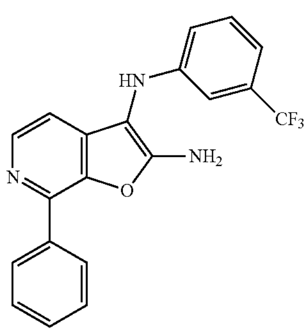 [SMILES: Nc1oc2c(-c3ccccc3)nccc2c1Nc1cccc(C(F)(F)F)c1] | 7-Phenyl-N³-(3-(trifluoro-methyl)phenyl)furo[2,3-c]pyridine-2,3-diamine | $CD_3CN$: δ 8.31 (d, J = 7.5 Hz, 2H), 8.22 (d, J = 4.9 Hz, 1H), 7.55 (t, J = 7.5 Hz, 2H), 7.46 (t, J = 7.2 Hz, 1H), 7.31 (t, J = 8.0 Hz, 1H), 6.99 (d, J = 7.5 Hz, 1H), 6.95 (d, J = 5.0 Hz, 1H), 6.88 (bs, 2H), 5.96 (s, 1H), 5.47 (s, 2H) | [M + H] 370.0 | A |
| 83 | 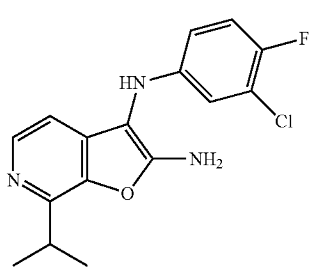 [SMILES: CC(C)c1nccc2c(Nc3ccc(F)c(Cl)c3)c(N)oc12] | N³-(3-Chloro-4-fluorophenyl)-7-isopropyl-furo[2,3-c]pyridine-2,3-diamine | $CD_3CN$: δ 8.05 (d, J = 5.0 Hz, 1H), 7.01 (t, J = 9.1 Hz, 1H), 6.80 (d, J = 5.0 Hz, 1H), 6.61 (dd, J' = 6.3 Hz, J" = 2.8 Hz, 1H), 6.56-6.52 (m, 1H), 5.66 (s, 1H), 5.26 (s, 2H), 3.46-3.39 (m, 1H), 1.34 (d, J = 6.9 Hz, 6H) | [M + H] 320.0 | A |

TABLE 1-continued

| No. | Structure | IUPAC Name | ¹H-NMR (400 MHz) proton shift | LCMS | Proc. |
|---|---|---|---|---|---|
| 84 | 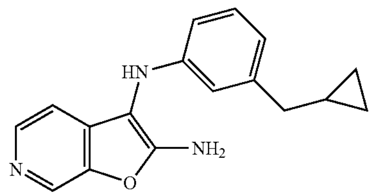 [SMILES: Nc1oc2cnccc2c1Nc1cccc(CC2CC2)c1] | N³-(3-(Cyclopropyl-methyl)phenyl)furo[2,3-c]pyridine-2,3-diamine | CD₃CN: δ 8.42 (s, 1H), 8.11 (d, J = 5.1 Hz, 1H), 7.03 (t, J = 7.8 Hz, 1H), 6.94 (d, J = 5.0 Hz, 1H), 6.61 (d, J = 7.5 Hz, 1H), 6.53 (s, 1H), 6.43 (dd, J' = 8.0 Hz, J" = 1.6 Hz, 1H), 5.52 (s, 1H), 5.30 (s, 2H), 2.38 (d, J = 6.9 Hz, 2H), 0.93-0.86 (m, 1H), 0.44-0.40 (m, 2H), 0.14-0.12 (m, 2H) | [M + H] 280.0 | A |
| 85 | 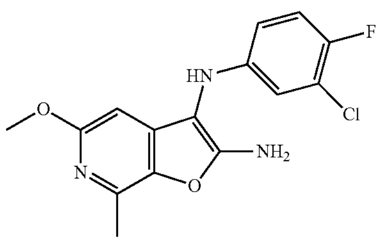 [SMILES: COc1cc2c(Nc3ccc(F)c(Cl)c3)c(N)oc2c(C)n1] | N³-(3-Chloro-4-fluorophenyl)-5-methoxy-7-methylfuro[2,3-c]pyridine-2,3-diamine | DMSO-d₆: δ 7.11 (t, J = 9.1 Hz, 1H), 7.01 (s, 1H), 6.84 (bs, 2H), 6.53 (dd, J' = 6.3 Hz, J" = 2.8 Hz, 1H), 6.47-6.43 (m, 1H), 5.92 (s, 1H), 3.73 (s, 3H), 2.40 (s, 3H) | [M − H] 320.0 | A |
| 86 | 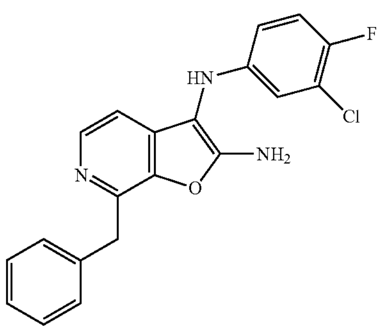 | 7-Benzyl-N³-(3-chloro-4-fluorophenyl)furo[2,3-c]pyridine-2,3-diamine | DMSO-d₆: δ 7.96 (d, J = 5.1 Hz, 1H), 7.32-7.30 (m, 4H), 7.24-7.22 (m, 1H), 7.11-7.06 (m, 2H), 6.77 (bs, 2H), 6.65 (d, J = 5.1 Hz, 1H), 6.56 (dd, J' = 6.2 Hz, J" = 2.5 Hz, 1H), 6.50-6.48 (m, 1H), 4.08 (s, 2H) | [M + H] 368.0 | A |
| 87 | 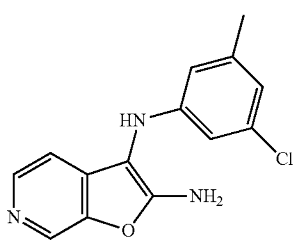 [SMILES: Cc1cc(Cl)cc(Nc2c(N)oc3cnccc23)c1] | N³-(3-Chloro-5-methylphenyl)furo[2,3-c]pyridine-2,3-diamine | DMSO-d₆: δ 8.42 (s, 1H), 8.06 (d, J = 5.0 Hz, 1H), 7.12 (s, 1H), 6.98 (bs, 2H), 6.87 (d, J = 5.0 Hz, 1H), 6.45 (s, 1H), 6.29 (s, 2H), 2.14 (s, 3H) | [M + H] 274.0 | A |
| 88 | 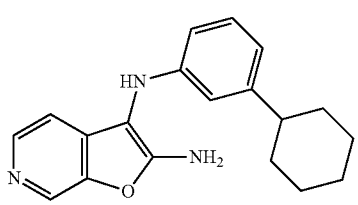 [SMILES: Nc1oc2cnccc2c1Nc1cccc(C2CCCCC2)c1] | N³-(3-Cyclohexyl-phenyl)furo[2,3-c]pyridine-2,3-diamine | DMSO-d₆: δ 8.39 (s, 1H), 8.03 (d, J = 5.1 Hz, 1H), 6.96 (t, J = 7.8 Hz, 1H), 6.83 (d, J = 5.1 Hz, 1H), 6.77 (d, J = 9.1 Hz, 3H), 6.46 (d, J = 7.6 Hz, 1H), 6.42 (s, 1H), 6.30 (dd, J' = 8.0 Hz, J" = 1.5 Hz, 1H), 2.31 (bs, 1H), 173-1.64 (m, 5H), 1.35-1.24 (m, 4H), 1.20-1.15 (m, 1H) | [M + H] 308.0 | A |

TABLE 1-continued

| No. | Structure | IUPAC Name | ¹H-NMR (400 MHz) proton shift | LCMS | Proc. |
|---|---|---|---|---|---|
| 89 | 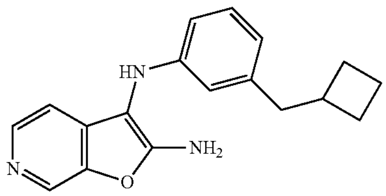 [SMILES: Nc1oc2cnccc2c1Nc1cccc(CC2CCC2)c1] | N³-(3-(Cyclobutylmethyl)phenyl)furo[2,3-c]pyridine-2,3-diamine | CDCl₃: δ 8.52 (s, 1H), 8.20 (d, 1H, J = 5 Hz), 7.08-7.02 (m, 2H), 6.58 (d, 1H, J = 7.2 Hz), 6.45 (d, 1H, J = 7.8 Hz), 6.41 (s, 1H), 4.71 (bs, 1H), 4.51 (bs, 2H), 2.59-2.57 (m, 2H), 2.50-2.45 (m, 1H), 1.98 (m, 2H), 1.82-1.76 (m, 2H), 1.70-1.65 (m, 2H) | [M + H] 294.4 | A |
| 90 | 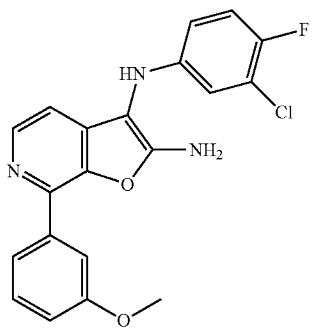 [SMILES: COc1cccc(-c2nccc3c(Nc4ccc(F)c(Cl)c4)c(N)oc23)c1] | N³-(3-Chloro-4-fluorophenyl)-7-(3-methoxyphenyl)furo[2,3-c]pyridine-2,3-diamine | DMSO-d₆: δ 8.16 (d, 1H, J = 5.0 Hz), 7.87 (d, 1H, J = 7.8 Hz), 7.84 (m, 1H), 7.44 (t, 1H, J = 8.0 Hz), 7.15-7.11 (m, 2H), 7.03-7.01 (m, 3H), 6.85 (d, 1H, J = 5.0 Hz), 6.60-6.58 (m, 1H), 6.49 (m, 1H), 3.85 (s, 3H) | [M + H] 384.4 | A |
| 91 | 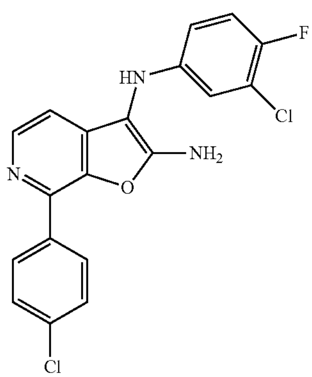 [SMILES: Nc1oc2c(-c3ccc(Cl)cc3)nccc2c1Nc1ccc(F)c(Cl)c1] | N³-(3-Chloro-4-fluorophenyl)-7-(4-chlorophenyl)furo[2,3-c]pyridine-2,3-diamine | DMSO-d₆: δ 8.30 (d, 2H, J = 8.3 Hz), 8.16 (d, 1H, J = 4.9 Hz), 7.60 (d, 2H, J = 8.3 Hz), 7.14-7.11 (m, 2H), 7.04 (s, 2H), 6.87 (d, 1H, J = 4.9 Hz), 6.60 (m, 1H), 6.52 (m, 1H) | [M + H] 388.1 | A |
| 92 | 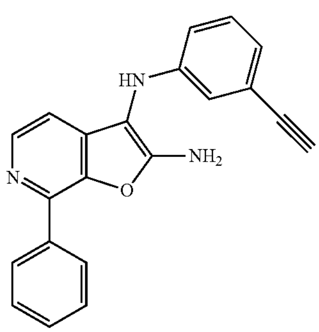 [SMILES: C#Cc1cccc(Nc2c(N)oc3c(-c4ccccc4)nccc23)c1] | N³-(3-Ethynylphenyl)-7-phenylfuro[2,3-c]pyridine-2,3-diamine | DMSO-d₆: δ 8.27 (d, 2H, J = 7.5 Hz), 8.16 (d, 1H, J = 4.8 Hz), 7.54 (t, 2H, J = 7.5 Hz), 7.47-7.45 (m, 1H), 7.11-7.08 (m, 2H), 6.99 (bs, 2H), 6.84 (d, 1H, J = 4.8 Hz), 6.71 (d, 1H, J = 7.2 Hz), 6.63-6.60 (m, 2H), 3.99 (s, 1H) | [M + H] 326.0 | A |
| 93 | 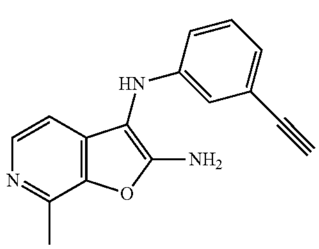 [SMILES: C#Cc1cccc(Nc2c(N)oc3c(C)nccc23)c1] | N³-(3-ethynylphenyl)-7-methylfuro[2,3-c]pyridine-2,3-diamine | CD₃CN: δ 8.0 (d, 1H, J = 5.04 Hz), 7.11 (t, 1H, J = 8.3 Hz), 6.82-6.79 (m, 2H), 6.64 (m, 2H), 5.68 (s, 1H), 5.27 (s, 2H), 3.52 (s, 1H), 2.54 (s, 3H) | [M + H] 264.0 | A |

TABLE 1-continued

| No. | Structure | IUPAC Name | $^1$H-NMR (400 MHz) proton shift | LCMS | Proc. |
|---|---|---|---|---|---|
| 94 | 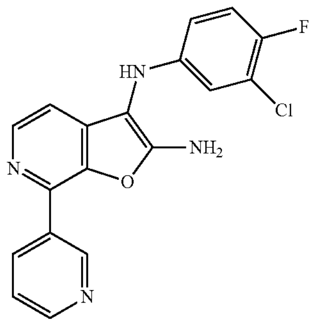 [SMILES: Nc1oc2c(-c3cccnc3)nccc2c1Nc1ccc(F)c(Cl)c1] | N$^3$-(3-Chloro-4-fluorophenyl)-7-(pyridin-3-yl)furo[2,3-c]pyridine-2,3-diamine | CD$_3$CN: δ 9.51 (s, 1H), 8.63 (m, 2H), 8.25 (m, 1H), 7.51 (m, 1H), 7.03-6.99 (m, 2H), 6.66-6.59 (m, 2H), 5.73 (s, 1H), 5.51 (s, 2H) | [M + H] 355.0 | A |
| 95 | 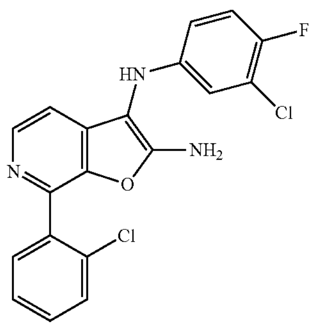 [SMILES: Nc1oc2c(-c3ccccc3Cl)nccc2c1Nc1ccc(F)c(Cl)c1] | N$^3$-(3-Chloro-4-fluorophenyl)-7-(2-chlorophenyl)furo[2,3-e]pyridine-2,3-diamine | DMSO-d$_6$: δ 8.13 (d, J = 5.1 Hz, 1H), 7.61-7.55 (m, 2H), 7.50-7.47 (m, 2H), 7.17-7.13 (m, 2H), 6.95 (bs, 2H), 6.91 (d, J = 5.1 Hz, 1H), 6.59 (dd, J' = 6.2 Hz, J" = 2.6 Hz, 1H), 6.51-6.47 (m, 1H) | [M + H] 388 | A |
| 96 | 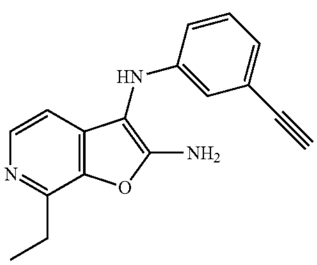 [SMILES: C#Cc1cccc(Nc2c(N)oc3c(CC)nccc23)c1] | 7-Ethyl-N$^3$-(3-ethynylphenyl)furo[2,3-c]pyridine-2,3-diamine | DMSO-d$_6$: δ 7.96 (s, 1H), 7.04 (d, J = 16.0 Hz, 2H), 6.77-6.69 (m, 3H), 6.55 (bs, 2H), 3.98 (s, 1H), 2.86 (s, 2H), 1.28 (s, 3H) | [M + H] 278.1 | A |
| 97 | 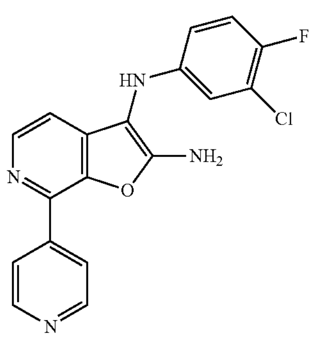 [SMILES: Nc1oc2c(-c3ccncc3)nccc2c1Nc1ccc(F)c(Cl)c1] | N$^3$-(3-Chloro-4-fluorophenyl)-7-(pyridin-4-yl)furo[2,3-c]pyridine-2,3-diamine | DMSO-d$_6$: δ 8.73 (d, J = 6.1 Hz, 2H), 8.27-8.26 (m, 3H), 7.05-7.01 (m, 2H), 6.66 (dd, J' = 6.2 Hz, J" = 2.8 Hz, 1H), 6.60-6.56 (m, 1H), 5.73 (s, 1H), 5.54 (bs, 2H) | [M + H] 355.2 | A |
| 98 | 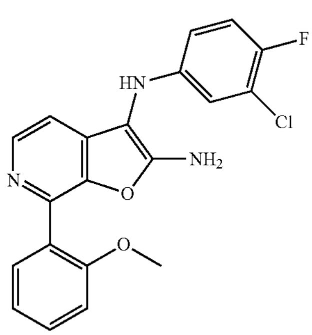 [SMILES: COc1ccccc1-c1nccc2c(Nc3ccc(F)c(Cl)c3)c(N)oc12] | N$^3$-(3-Chloro-4-fluorophenyl)-7-(2-methoxyphenyl)furo[2,3-c]pyridine-2,3-diamine | DMSO-d$_6$: δ 8.09 (d, J = 5.0 Hz, 1H), 7.44-7.37 (m, 2H), 7.17-7.14 (m, 2H), 7.12-7.04 (m, 2H), 6.85-6.82 (m, 3H), 6.58 (dd, J' = 6.2 Hz, J" = 2.5 Hz, 1H), 6.50-6.48 (m, 1H) | [M + H] 384.2 | A |

TABLE 1-continued

| No. | Structure | IUPAC Name | ¹H-NMR (400 MHz) proton shift | LCMS | Proc. |
|---|---|---|---|---|---|
| 99 | 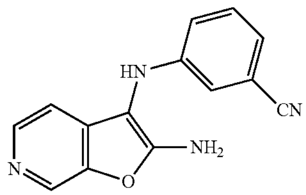 [SMILES: N#Cc1cccc(Nc2c(N)oc3cnccc23)c1] | 3-((2-Aminofuro[2,3-c]pyridin-3-yl)amino)benzonitrile | CD$_3$CN: δ 8.44 (s, 1H), 8.12 (d, J = 4.6 Hz, 1H), 7.27 (t, J = 7.6 Hz, 1H), 7.02 (d, J = 6.9 Hz, 1H), 6.95-6.86 (m, 3H), 5.94 (s, 1H), 5.39 (s, 2H). | [M + H] 251.2 | A |
| 100 | 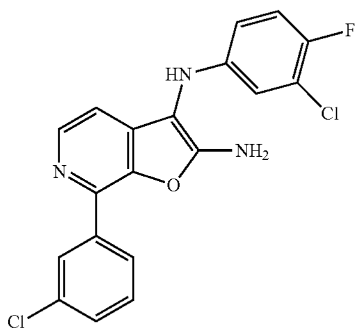 [SMILES: Nc1oc2c(-c3cccc(Cl)c3)nccc2c1Nc1ccc(F)c(Cl)c1] | N$^3$-(3-Chloro-4-fluorophenyl)-7-(3-chlorophenyl)furo[2,3-c]pyridine-2,3-diamine | DMSO-d$_6$: δ 8.28-8.25 (m, 2H), 8.18 (d, J = 4.9 Hz, 1H), 7.59-7.51 (m, 2H), 7.16-7.09 (m, 4H), 6.88 (d, J = 4.9 Hz, 1H), 6.60-6.59 (m, 1H), 6.52-6.50 (m, 1H) | [M + H] 388 | A |
| 101 | 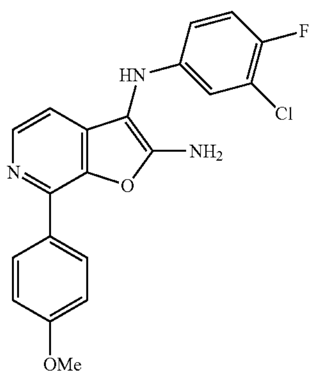 [SMILES: COc1ccc(-c2nccc3c(Nc4ccc(F)c(Cl)c4)c(N)oc23)cc1] | N$^3$-(3-Chloro-4-fluorophenyl)-7-(4-methoxyphenyl)furo[2,3-c]pyridine-2,3-diamine | DMSO-d$_6$: δ 8.24 (d, J = 8.7 Hz, 2H), 8.13 (d, J = 5.0 Hz, 1H), 7.15-7.07 (m, 4H), 6.95 (bs, 2H), 6.80 (d, J = 5.0 Hz, 1H), 6.58 (dd, J' = 6.2 Hz, J" = 2.6 Hz, 1H), 6.52-6.49 (m, 1H), 3.84 (s, 3H) | [M + H] 384 | A |
| 102 | 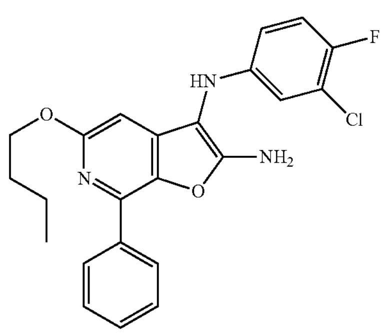 [SMILES: CCCCOc1cc2c(Nc3ccc(F)c(Cl)c3)c(N)oc2c(-c2ccccc2)n1] | 5-Butoxy-N$^3$-(3-chloro-4-fluorophenyl)-7-phenylfuro[2,3-c]pyridine-2,3-diamine | DMSO-d$_6$: δ 8.27 (d, J = 7.5 Hz, 2H), 7.52 (t, J = 7.5 Hz, 2H), 7.43 (t, J = 7.5 Hz, 1H), 7.13 (t, J = 9.1 Hz, 1H), 7.06 (s, 1H), 7.02 (bs, 2H), 6.59 (dd, J' = 6.2 Hz, J" = 2.6 Hz, 1H), 6.52-6.49 (m, 1H), 6.04 (s, 1H), 4.28 (t, J = 6.5 Hz, 2H), 1.72-1.65 (m, 2H), 1.46-1.37 (m, 2H), 0.92 (t, J = 7.4 Hz, 3H) | [M + H] 426.2 | C |
| 103 | 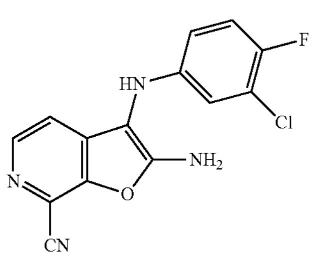 [SMILES: N#Cc1nccc2c(Nc3ccc(F)c(Cl)c3)c(N)oc12] | 2-Amino-3-((3-chloro-4-fluorophenyl)amino)furo[2,3-c]pyridine-7-carbonitrile | CD$_3$CN: δ 8.18 (d, J = 5.1 Hz, 1H), 7.15 (d, J = 5.0 Hz, 1H), 7.03 (t, J = 9.0 Hz, 1H), 6.64-6.62 (m, 1H), 6.56-6.52 (m, 1H), 5.81 (bs, 2H), 5.71 (s, 1H) | [M + H] 303 | A |

TABLE 1-continued

| No. | Structure | IUPAC Name | ¹H-NMR (400 MHz) proton shift | LCMS | Proc. |
|---|---|---|---|---|---|
| 104 | 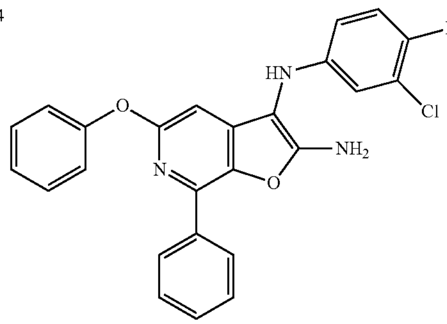 | $N^3$-(3-Chloro-4-fluorophenyl)-5-phenoxy-7-phenylfuro[2,3-c]pyridine-2,3-diamine | DMSO-$d_6$: δ 8.11 (d, J = 6.6 Hz, 2H), 7.47-7.37 (m, 5H), 7.15-7.11 (m, 7H), 6.60 (bs, 1H), 6.52 (bs, 1H), 6.26 (s, 1H) | [M + H] 444.2 | C |
| 105 | 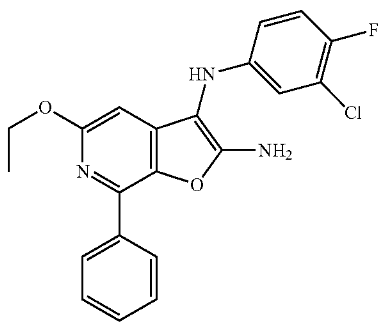 [SMILES: CCOc1cc2c(Nc3ccc(F)c(Cl)c3)c(N)oc2c(-c2ccccc2)n1] | $N^3$-(3-Chloro-4-fluorophenyl)-5-ethoxy-7-phenylfuro[2,3-c]pyridine-2,3-diamine | DMSO-$d_6$: δ 8.27 (d, J = 7.5 Hz, 2H), 7.52 (t, J = 7.4 Hz, 2H), 7.45-7.42 (m, 1H), 7.13 (t, J = 9.1 Hz, 1H), 7.06 (s, 1H), 7.01 (s, 2H), 6.60 (bs, 1H), 6.51-6.49 (m, 1H), 6.03 (s, 1H). 4.34 (q, J = 6.8 Hz, 2H), 1.31 (t, J = 6.9 Hz, 3H) | [M + H] 398.2 | C |
| 106 | 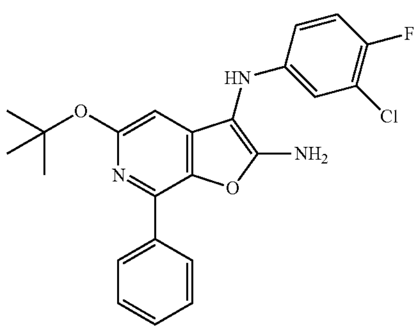 [SMILES: CC(C)(C)Oc1cc2c(Nc3ccc(F)c(Cl)c3)c(N)oc2c(-c2ccccc2)n1] | 5-(tert-Butoxy)-$N^3$-(3-chloro-4-fluorophenyl)-7-phenylfuro[2,3-c]pyridine-2,3-diamine | DMSO-$d_6$: δ 8.24 (d, J = 7.8 Hz, 2H), 7.54 (t, J = 7.4 Hz, 2H), 7.43 (d, J = 7.4 Hz, 1H), 7.13 (t, J = 9.2 Hz, 1H), 7.04 (s, 1H), 6.97 (bs, 2H), 6.60-6.59 (m, 1H), 6.51-6.49 (m, 1H), 5.99 (s, 1H), 1.54 (s, 9H) | [M + H] 426.2 | A |
| 107 | 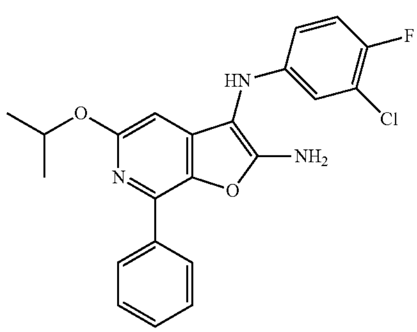 [SMILES: CC(C)Oc1cc2c(Nc3ccc(F)c(Cl)c3)c(N)oc2c(-c2ccccc2)n1] | $N^3$-(3-Chloro-4-fluorophenyl)-5-isopropoxy-7-phenylfuro[2,3-c]pyridine-2,3-diamine | DMSO-$d_6$: δ 8.26 (d, J = 7.7 Hz, 2H), 7.52 (t, J = 7.5 Hz, 2H), 7.43 (t, J = 7.1 Hz, 1H), 7.13 (t, J = 9.1 Hz, 1H), 7.05 (s, 1H), 7.02 (bs, 2H), 6.60 (d, J = 3.9 Hz, 1H), 6.51-6.48 (m, 1H), 5.98 (s, 1H), 5.32-5.26 (m, 1H), 1.29 (d, J = 6.0 Hz, 6H) | [M + H] 412 | A |

TABLE 1-continued

| No. | Structure | IUPAC Name | ¹H-NMR (400 MHz) proton shift | LCMS | Proc. |
|---|---|---|---|---|---|
| 108 | 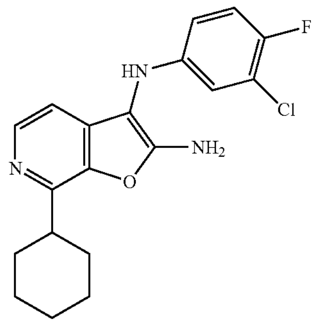 | N³-(3-Chloro-4-fluorophenyl)-7-cyclohexyl-furo[2,3-c]pyridine-2,3-diamine | DMSO-d₆: δ 8.03 (d, J = 5.0 Hz, 1H), 7.01 (t, J = 9.1 Hz, 1H), 6.78 (d, J = 5.0 Hz, 1H), 6.60 (dd, J' = 6.2 Hz, J'' = 2.7 Hz, 1H), 6.55-6.52 (m, 1H), 5.67 (s, 1H), 5.27 (bs, 2H), 3.09 (t, J = 11.6 Hz, 1H), 1.87-1.81 (m, 4H), 1.78-1.73 (m, 3H), 1.51-1.42 (m, 2H), 1.38-1.27 (m, 1H) | [M + H] 360 | A |
| 109 | 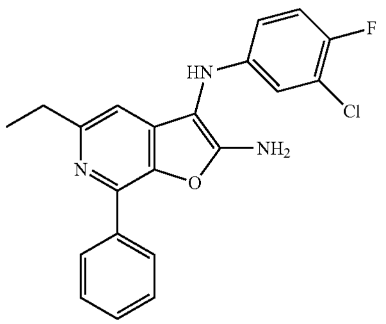 [SMILES: CCc1cc2c(Nc3ccc(F)c(Cl)c3)c(N)oc2c(-c2ccccc2)n1] | N³-(3-Chloro-4-fluorophenyl)-5-ethyl-7-phenylfuro[2,3-c]pyridine-2,3-diamine | CDCl₃: δ 8.24 (d, J = 7.2 Hz, 2H), 7.50 (t, J = 7.1 Hz, 2H), 7.43-7.40 (m, 1H), 6.96 (t, J = 8.6 Hz, 1H), 6.81 (s, 1H), 6.65 (bs 1H), 6.51 (bs, 1H), 4.74 (s, 1H), 4.49 (s, 2H), 2.84 (q, J = 7.7 Hz, 2H), 1.32 (t, J = 7.5 Hz, 3H) | [M + H] 382 | A |
| 110 | 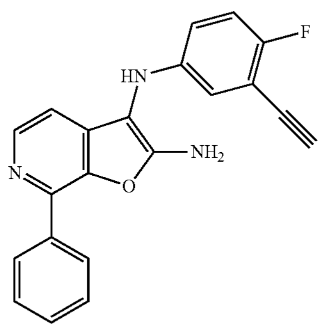 [SMILES: C#Cc1cc(Nc2c(N)oc3c(-c4ccccc4)nccc23)ccc1F] | N³-(3-Ethynyl-4-fluorophenyl)-7-phenylfuro[2,3-c]pyridine-2,3-diamine | DMSO-d₆: δ 8.27 (d, J = 7.4 Hz, 2H), 8.16 (d, J = 5.1 Hz, 1H), 7.53 (t, J = 7.5 Hz, 2H), 7.45 (t, J = 7.3 Hz, 1H), 7.06-7.03 (m, 2H), 7.01-7.00 (m, 2H), 6.85 (d, J = 5.0 Hz, 1H), 6.62-6.56 (m, 2H), 4.33 (s, 1H) | [M + H] 344 | A |
| 111 | 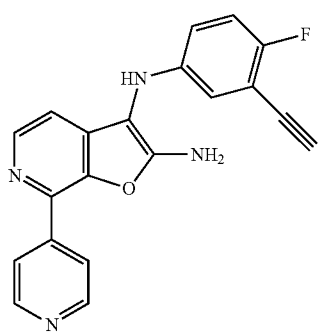 [SMILES: C#Cc1cc(Nc2c(N)oc3c(-c4ccncc4)nccc23)ccc1F] | N³-(3-Ethynyl-4-fluorophenyl)-7-(pyridin-4-yl)furo[2,3-c]pyridine-2,3-diamine | DMSO-d₆: δ 8.74 (d, J = 5.6 Hz, 2H), 8.23-8.21 (m, 3H), 7.12 (bs, 2H), 7.05-7.01 (m, 2H), 6.94 (d, J = 5.1 Hz, 1H), 6.62-6.57 (m, 2H), 4.31 (s, 1H) | [M + H] 345.2 | A |
| 112 | 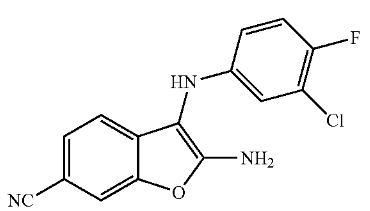 [SMILES: N#Cc1ccc2c(Nc3ccc(F)c(Cl)c3)c(N)oc2c1] | 2-Amino-3-((3-chloro-4-fluorophenyl)amino)benzofuran-6-carbonitrile | DMSO-d₆: δ 7.75 (s, 1H), 7.39 (d, J = 8.1 Hz, 1H), 7.14-7.10 (m, 2H), 6.96 (bs, 2H), 6.92 (d, J = 8.0 Hz, 1H), 6.56 (dd, J' = 6.3 Hz, J'' = 2.7 Hz, 1H), 6.47 (dt, J' = 8.8 Hz, J'' = 6.6 Hz, J''' = 3.2 Hz, 1H) | [M − H] 300 | A, B |

TABLE 1-continued

| No. | Structure | IUPAC Name | ¹H-NMR (400 MHz) proton shift | LCMS | Proc. |
|---|---|---|---|---|---|
| 113 | 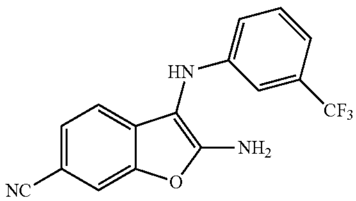 [SMILES: N#Cc1ccc2c(Nc3cccc(C(F)(F)F)c3)c(N)oc2c1] | 2-Amino-3-((3-(trifluoro-methyl)phenyl)amino)benzofuran-6-carbonitrile | CD$_3$CN: δ 7.60 (s, 1H), 7.39 (d, J = 7.4 Hz, 1H), 7.29 (s, 1H), 7.05 (d, J = 7.6 Hz, 1H), 6.98 (d, J = 6.8 Hz, 1H), 6.84 (bs, 2H), 5.93 (s, 1H), 5.39 (bs, 2H) | [M − H] 316 | A, B |
| 114 | 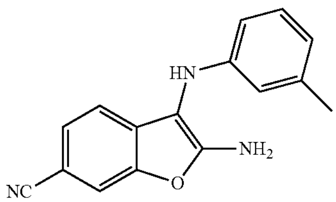 [SMILES: Cc1cccc(Nc2c(N)oc3cc(C#N)ccc23)c1] | 2-Amino-3-(m-tolylamino)benzofuran-6-carbonitrile | DMSO-d$_6$: δ 7.73 (s, 1H), 7.37 (d, J = 7.9 Hz, 1H), 6.95 (t, J = 7.8 Hz, 1H), 6.89 (d, J = 8.0 Hz, 1H), 6.83 (s, 2H), 6.80 (s, 1H), 6.42 (d, J = 7.4 Hz, 1H), 6.35-6.31 (m, 2H), 2.14 (s, 3H) | [M − H] 262 | A, B |
| 115 | 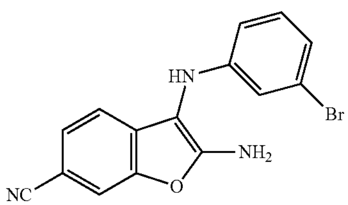 [SMILES: N#Cc1ccc2c(Nc3cccc(Br)c3)c(N)oc2c1] | 2-Amino-3-((3-bromophenyl)amino)benzofuran-6-carbonitrile | CD$_3$CN: δ 7.59 (s, 1H), 7.38 (dd, J' = 8.1 Hz, J" = 1.1 Hz, 1H), 7.06-7.02 (m, 2H), 6.83 (dd, J' = 7.8 Hz, J" = 0.9 Hz, 1H), 6.72 (t, J = 2.0 Hz, 1H), 6.60 (dd, J' = 8.2 Hz, J" = 2.2 Hz, 1H), 5.78 (s, 1H), 5.37 (bs, 2H) | [M − H] 326 | A, B |
| 116 | 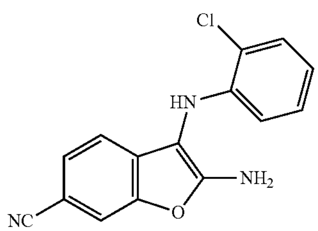 [SMILES: N#Cc1ccc2c(Nc3ccccc3Cl)c(N)oc2c1] | 2-Amino-3-((2-chlorophenyl)amino)benzofuran-6-carbonitrile | CD$_3$CN: δ 7.60 (s, 1H), 7.36 (dd, J' = 22.0 Hz, J" = 7.8 Hz, 2H), 7.03-7.02 (m, 2H), 6.69 (t, J = 7.2 Hz, 1H), 6.42 (d, J = 7.9 Hz, 1H), 5.82 (s, 1H), 5.42 (bs, 2H) | [M − H] 282 | A, B |
| 117 | 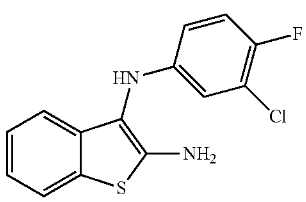 [SMILES: Nc1sc2ccccc2c1Nc1ccc(F)c(Cl)c1] | N³-(3-Chloro-4-fluorophenyl)benzo[b]thiophene-2,3-diamine | (500 MHz, DMSO-d$_6$): δ 7.56 (d, J = 7.5 Hz, 1H), 7.22 (s, 1H), 7.11-7.06 (m, 2H), 6.97-6.94 (m, 2H), 6.48-6.46 (m, 1H), 6.44-6.41 (m, 1H), 5.85 (bs, 2H) | [M + H] 293.0 | B, E |
| 118 | 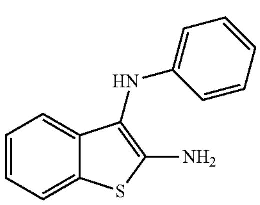 [SMILES: Nc1sc2ccccc2c1Nc1ccccc1] | N³-Phenylbenzo[b]thiophene-2,3-diamine | (500 MHz, DMSO-d$_6$): δ 7.55 (d, J = 7.5 Hz, 1H), 7.07 (t, J = 7.2 Hz, 1H), 7.03-6.98 (m, 3H), 6.94 (t, J = 7.2 Hz, 2H), 6.53 (t, J = 7.3 Hz, 1H), 6.47 (d, J = 7.6 Hz, 2H), 5.70 (bs, 2H) | [M + H] 240.1 | B, E |
| 119 | 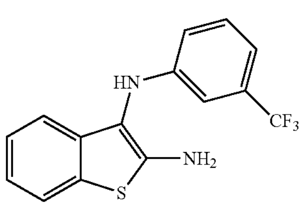 [SMILES: Nc1sc2ccccc2c1Nc1cccc(C(F)(F)F)c1] | N³-(3-(Trifluoro-methyl)phenyl)benzo[b]thiophene-2,3-diamine | (500 MHz, DMSO-d$_6$): δ 7.57 (d, J = 8.0 Hz, 1H), 7.49 (s, 1H), 7.23 (t, J = 8.0 Hz, 1H), 7.09 (t, J = 7.0 Hz, 1H), 6.97-6.93 (m, 2H), 6.83 (d, J = 7.3 Hz, 1H), 6.76 (bs, 1H), 6.67 (d, J = 8.0 Hz, 1H), 5.87 (bs, 2H) | [M + H] 309.1 | B, E |

TABLE 1-continued

| No. | Structure | IUPAC Name | $^1$H-NMR (400 MHz) proton shift | LCMS | Proc. |
|---|---|---|---|---|---|
| 120 | 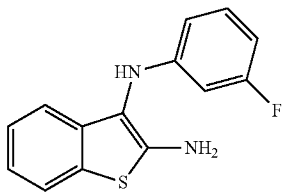 [SMILES: Nc1sc2ccccc2c1Nc1cccc(F)c1] | $N^3$-(3-Fluorophenyl)benzo[b]thiophene-2,3-diamine | CDCl$_3$: δ 7.59 (d, J = 7.8 Hz, 1H), 7.25-7.21 (m, 2H), 7.15-7.06 (m, 2H), 6.46-6.41 (m, 2H), 6.32-6.28 (m, 1H), 5.08 (s, 1H), 4.14 (bs, 2H) | [M + H] 259.1 | B, E |
| 121 | 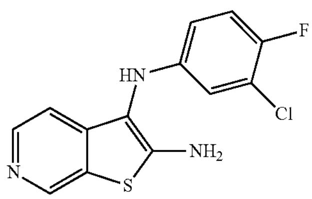 [SMILES: Nc1sc2cnccc2c1Nc1ccc(F)c(Cl)c1] | $N^3$-(3-Chloro-4-fluorophenyl)thieno[2,3-c]pyridine-2,3-diamine | DMSO-d$_6$: δ 8.66 (s, 1H), 8.13 (d, J = 5.4 Hz, 1H), 7.27 (s, 1H), 7.11 (t, J = 9.1 Hz, 1H), 6.86 (d, J = 5.3 Hz, 1H), 6.72 (bs, 2H), 6.50 (dd, J' = 6.2 Hz, J" = 2.4 Hz, 1H), 6.42-6.40 (m, 1H) | [M + H] 294 | D |
| 122 | 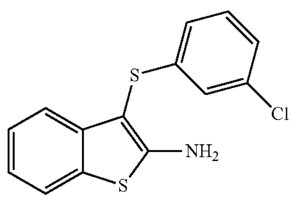 [SMILES: Nc1sc2ccccc2c1Sc1cccc(Cl)c1] | 3-((3-Chlorophenyl)thio)benzo[b]thiophen-2-amine | (500 MHz, CDCl$_3$): δ 7.61 (d, J = 7.7 Hz, 1H), 7.47 (d, J = 8.0 Hz, 1H), 7.27 (dd, J' = 14.7 Hz, J" = 7.0 Hz, 1H), 7.16 (t, J = 7.7 Hz, 1H), 7.11-7.04 (m, 3H), 6.92 (d, J = 7.1 Hz, 1H), 4.83 (bs, 2H) | [M + H] 292 | E, K |
| 123 | 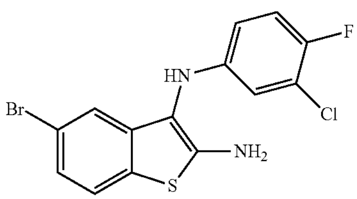 | 5-Bromo-$N^3$-(3-chloro-4-fluorophenyl)benzo[b]thiophene-2,3-diamine | (500 MHz, DMSO-d$_6$): δ 7.53 (d, J = 8.3 Hz, 1H), 7.24 (s, 1H), 7.10 (d, J = 9.2 Hz, 1H), 7.07 (dd, J' = 8.3 Hz, J" = 1.8 Hz, 1H), 7.03 (d, J = 1.8 Hz, 1H), 6.47 (dd, J' = 6.5 Hz, J" = 2.8 Hz, 1H), 6.40 (dt, J' = 8.9 Hz, J" = 3.4 Hz, 1H), 6.14 (bs, 2H) | [M + H] 370.9 | E |
| 124 | 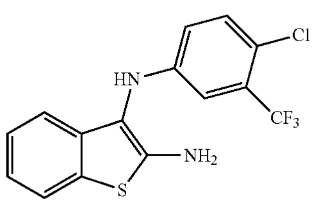 [SMILES: Nc1sc2ccccc2c1Nc1ccc(Cl)c(C(F)(F)F)c1] | $N^3$-(4-Chloro-3-(trifluoromethyl)phenyl)benzo[b]thiophene-2,3-diamine | (500 MHz, DMSO-d$_6$): δ 7.67 (s, 1H), 7.56 (d, J = 7.7 Hz, 1H), 7.30 (d, J = 8.6 Hz, 1H), 7.10 (t, J = 7.5 Hz, 1H), 6.97-6.93 (m, 3H), 6.58 (d, J = 7.8 Hz, 1H), 5.94 (bs, 2H) | [M + H] 343 | E |
| 125 | 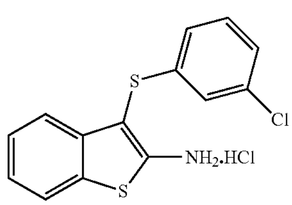 | 3-((3-Chlorophenyl)thio)benzo[b]thiophen-2-amine hydrochloride | DMSO-d$_6$: δ 7.65 (d, J = 7.8 Hz, 1H), 7.24 (t, J = 7.9 Hz, 1H), 7.20-7.17 (m, 2H), 7.15-7.12 (m, 1H), 7.05-7.01 (m, 1H), 6.97 (d, J = 7.8 Hz, 1H), 6.94-6.93 (m, 1H), 6.45 (bh, 2H) | [M − HCl] 290.9 | E, K |
| 126 | 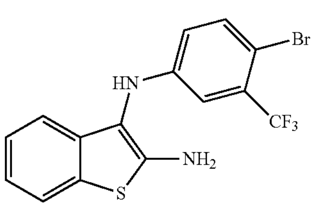 [SMILES: Nc1sc2ccccc2c1Nc1ccc(Br)c(C(F)(F)F)c1] | $N^3$-(4-Bromo-3-(trifluoromethyl)phenyl)benzo[b]thiophene-2,3-diamine | (500 MHz, DMSO-d$_6$): δ 7.68 (s, 1H), 7.56 (d, J = 7.8 Hz, 1H), 7.44 (d, J = 8.9 Hz, 1H), 7.10 (dd, J' = 8.0 Hz, J" = 0.85 Hz, 1H), 6.97-6.93 (m, 3H), 6.50 (d, J = 7.2 Hz, 1H), 5.94 (bs, 2H) | [M − H] 384.9 | E |

TABLE 1-continued

| No. | Structure | IUPAC Name | $^1$H-NMR (400 MHz) proton shift | LCMS | Proc. |
|---|---|---|---|---|---|
| 127 | 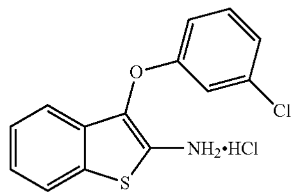 | 3-(3-Chlorophenoxy)benzo[b]thiophen-2-amine hydrochloride | DMSO-$d_6$: δ 7.63 (d, J = 8.1 Hz, 1H), 7.31 (t, J = 8.1 Hz, 1H), 7.13 (t, J = 7.5 Hz, 1H), 7.07-7.00 (m, 2H), 6.92-6.85 (m, 3H), 5.66 (bh, 2H) | [M − HCl] 276 | E, K |
| 128 | 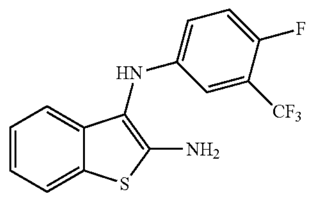 [SMILES: Nc1sc2ccccc2c1Nc1ccc(F)c(C(F)(F)F)c1] | $N^3$-(4-Fluoro-3-(trifluoromethyl)phenyl)benzo[b]thiophene-2,3-diamine | (500 MHz, DMSO-$d_6$): δ 7.57 (d, J = 7.5 Hz, 1H), 7.42 (s, 1H), 7.18-7.09 (m, 2H), 6.97-6.94 (m, 2H), 6.75 (dd, J' = 6.0 Hz, J" = 2.6 Hz, 1H), 6.65-6.62 (m, 1H), 5.89 (bs, 2H) | [M + H] 327.1 | E |
| 129 | 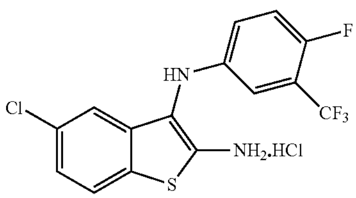 | 5-Chloro-$N^3$-(3-chloro-4-fluorophenyl)benzo[b]thiophene-2,3-diamine hydrochloride | (500 MHz, DMSO-$d_6$): δ 7.59 (d, J = 8.3 Hz, 1H), 7.09 (t, J = 9.2 Hz, 1H), 6.94 (d, J = 8.3 Hz, 1H), 6.88 (s, 1H), 6.49-6.48 (m, 1H), 6.41-6.39 (m, 1H), 4.67 (bh, 4H) | [M + Cl] 360.9 | E |
| 130 | 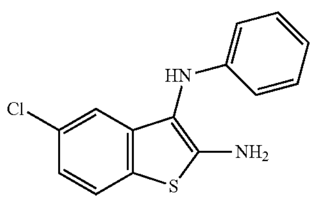 [SMILES: Nc1sc2ccc(Cl)cc2c1Nc1ccccc1] | 5-Chloro-$N^3$-phenylbenzo[b]thiophene-2,3-diamine | (500 MHz, DMSO-$d_6$): δ 7.58 (d, J = 8.3 Hz, 1H), 7.03 (t, J = 7.3 Hz, 2H), 6.99 (s, 1H), 6.93 (d, J = 8.3 Hz, 1H), 6.85 (s, 1H), 6.56 (t, J = 7.6 Hz, 1H), 6.46 (d, J = 8.3 Hz, 2H), 6.00 (bs, 2H) | [M + H] 275 | E |
| 131 | 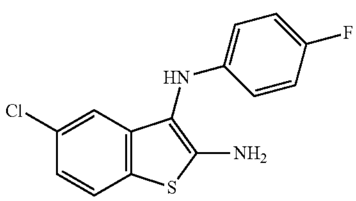 [SMILES: Nc1sc2ccc(Cl)cc2c1Nc1ccc(F)cc1] | 5-Chloro-$N^3$-(4-fluorophenyl)benzo[b]thiophene-2,3-diamine | (500 MHz, DMSO-$d_6$): δ 7.57 (d, J = 8.3 Hz, 1H), 6.97 (s, 1H), 6.93 (d, J = 8.3 Hz, 1H), 6.90-6.86 (m, 3H), 6.44 (dd, J' = 8.6 Hz, J" = 4.6 Hz, 2H), 6.03 (bs, 2H) | [M + H] 293 | E |
| 132 | 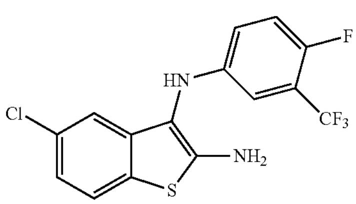 | 5-Chloro-$N^3$-(4-fluoro-3-(trifluoromethyl)phenyl)benzo[b]thiophene-2,3-diamine | (500 MHz, DMSO-$d_6$): δ 7.59 (d, J = 8.3 Hz, 1H), 7.44 (s, 1H), 7.17 (t, J = 9.8 Hz, 1H), 6.95 (d, J = 8.3 Hz, 1H), 6.90 (s, 1H), 6.76-6.75 (m, 1H), 6.63-6.61 (m, 1H), 6.18 (bs, 2H) | [M − H] 359 | E |
| 133 | 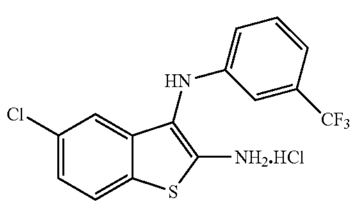 | 5-Chloro-$N^3$-(3-(trifluoromethyl)phenyl)benzo[b]thiophene-2,3-diamine hydrochloride | (500 MHz, DMSO-$d_6$, salt free): δ 7.60 (d, J = 8.2 Hz, 1H), 7.51 (s, 1H), 7.25 (t, J = 7.8 Hz, 1H), 6.95 (d, J = 8.3 Hz, 1H), 6.88-6.85 (m, 2H), 6.75 (s, 1H), 6.65 (d, J = 8.3 Hz, 1H), 6.17 (bs, 2H) | [M − H] 341 | E |

TABLE 1-continued

| No. | Structure | IUPAC Name | $^1$H-NMR (400 MHz) proton shift | LCMS | Proc. |
|---|---|---|---|---|---|
| 134 | 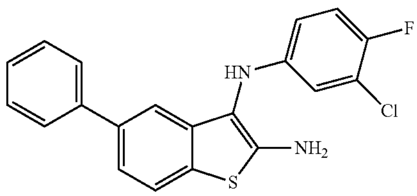 [SMILES: Nc1sc2ccc(-c3ccccc3)cc2c1Nc1ccc(F)c(Cl)c1] | N$^3$-(3-Chloro-4-fluorophenyl)-5-phenylbenzo[b]thiophene-2,3-diamine | (500 MHz, DMSO-d$_6$): δ 7.65 (d, J = 8.3 Hz, 1H), 7.50 (d, J = 7.4 Hz, 2H), 7.39-7.35 (m, 3H), 7.28-7.23 (m, 2H), 7.18 (s, 1H), 7.07 (t, J = 9.0 Hz, 1H), 6.54-6.52 (m, 1H), 6.47-6.44 (m, 1H), 5.94 (bs, 2H) | [M − H] 367 | E |
| 135 | 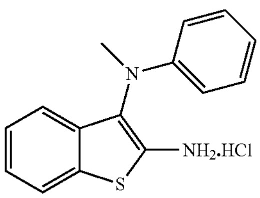 | N$^3$-Methyl-N$^3$-phenylbenzo[b]thiophene-2,3-diamine hydrochloride | DMSO-d$_6$, salt free: δ 7.58 (d, J = 9.8 Hz, 1H), 7.12-7.03 (m, 3H), 6.95 (t, J = 7.6 Hz, 1H), 6,76 (dd, J' = 7.8 Hz, J" = 0.5 Hz, 1H), 6.60 (td, J' = 8.3 Hz, J" = 1.0 Hz, 1H), 6.54-6.51 (m, 2H), 5.99 (bs, 2H), 3.18 (s, 3H) | [M + H] 255.1 | E |
| 136 | 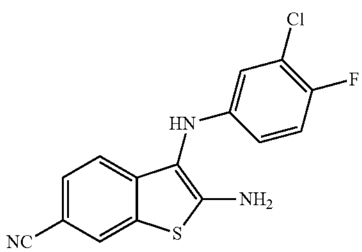 [SMILES: N#Cc1ccc2c(Nc3ccc(F)c(Cl)c3)c(N)sc2c1] | 2-Amino-3-((3-chloro-4-fluorophenyl)amino)benzo[b]thiophene-6-carbonitrile | DMSO-d$_6$: δ 8.11 (s, 1H), 7.47 (d, J = 8.3 Hz, 1H), 7.32 (s, 1H), 7.11 (t, J = 9.1 Hz, 1H), 7.01 (d, J = 8.2 Hz, 1H), 6.63 (bs, 2H), 6.51 (dd, J' = 6.2 Hz, J" = 2.6 Hz, 1H), 6.43-6.40 (m, 1H) | [M − H] 316 | E, F |
| 137 | 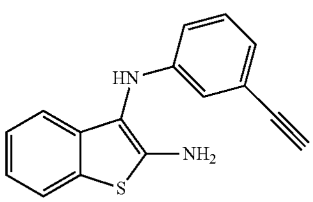 [SMILES: C#Cc1cccc(Nc2c(N)sc3ccccc23)c1] | N$^3$-(3-Ethynyl-phenyl)-1-benzothiophene-2,3-diamine | (500 MHz, DMSO-d$_6$): δ 7.56 (d, J = 7.7 Hz, 1H), 7.19 (s, 1H), 7.08 (d, J = 7.7 Hz, 1H), 7.05-7.02 (m, 1H), 6.94 (dd, J' = 13.1 Hz, J" = 7.3 Hz, 2H), 6.64 (d, J = 7.4 Hz, 1H), 6.54 (d, J = 8.0 Hz, 1H), 6.47 (s, 1H), 5.80 (bs, 2H), 3.93 (s, 1H) | [M + H] 265.1 | E, F |
| 138 | 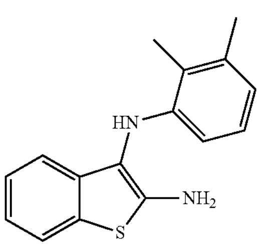 [SMILES: Cc1cccc(Nc2c(N)sc3ccccc23)c1C] | N$^3$-(2,3-Dimethyl-phenyl)-1-benzothiophene-2,3-diamine | (500 MHz, DMSO-d$_6$): δ 7.55 (d, J = 7.6 Hz, 1H), 7.05 (t, J = 7.3 Hz, 1H), 6.93 (t, J = 6.9 Hz, 1H), 6.86 (d, J = 7.6 Hz, 1H), 6.66 (t, J = 7.6 Hz, 1H), 6.42 (d, J = 7.4 Hz, 1H), 6.19 (s, 1H), 5.91 (d, J = 7.9 Hz, 1H), 5.69 (bs, 2H), 2.19 (d, J = 4.3 Hz, 6H) | [M + H] 269.1 | E |
| 139 | 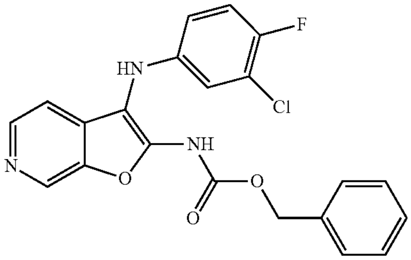 [SMILES: O=C(Nc1oc2cnccc2c1Nc1ccc(F)c(Cl)c1)OCc1ccccc1] | Benzyl (3-((3-chloro-4-fluorophenyl)amino)furo[2,3-c]pyridin-2-yl)carbamate | DMSO-d$_6$: δ 10.39 (s, 1H), 8.85 (s, 1H), 8.35 (d, J = 8.5 Hz, 1H), 7.80 (s, 1H), 7.33 (bs, 6H), 7.15 (t, J = 9.0 Hz, 1H), 6.73 (d, J = 3.2 Hz, 1H), 6.61 (s, 1H), 5.12 (s, 2H) | [M − H] 410 | G |

TABLE 1-continued

| No. | Structure | IUPAC Name | $^1$H-NMR (400 MHz) proton shift | LCMS | Proc. |
|---|---|---|---|---|---|
| 140 | 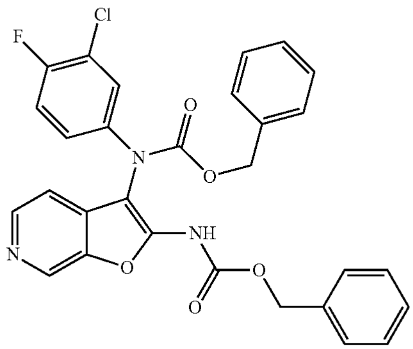 [SMILES: O=C(Nc1oc2cnccc2c1N(C(=O)OCc1ccccc1)c1ccc(F)c(Cl)c1)OCc1ccccc1] | Benzyl (2-(((benzyloxy)carbonyl)amino)furo[2,3-c]pyridin-3-yl)(3-chloro-4-fluorophenyl)carbamate | DMSO-d$_6$: δ 8.96 (s, 1H), 8.39-8.36 (m, 2H), 7.45-7.15 (m, 12 H), 6.75 (s, 1H), 6.62 (s, 1H), 5.20 (s, 4H) | [M + H] 546 | H |
| 141 | 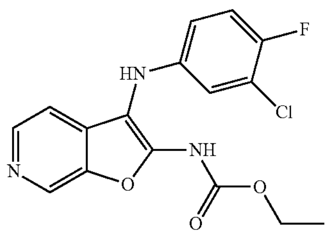 [SMILES: CCOC(=O)Nc1oc2cnccc2c1Nc1ccc(F)c(Cl)c1] | Ethyl (3-((3-chloro-4-fluorophenyl)amino)furo[2,3-c]pyridin-2-yl)carbamate | DMSO-d$_6$: δ 10.19 (s, 1H), 8.83 (s, 1H), 8.34 (d, J = 5.0 Hz, 1H), 7.75 (s, 1H), 7.31 (d, J = 5.2 Hz, 1H), 7.18 (t, J = 9.1 hz, 1H), 6.73-6.71 (m, 1H), 6.63-6.60 (m, 1H), 4.07 (q, J = 7.0 Hz, 2H), 1.14 (t, J = 7.0 Hz, 3H) | [M + H] 350 | G |
| 142 | 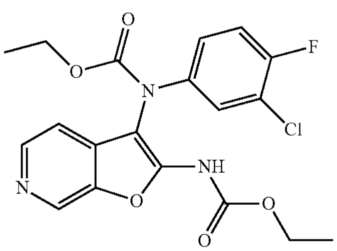 [SMILES: CCOC(=O)Nc1oc2cnccc2c1N(C(=O)OCC)c1ccc(F)c(Cl)c1] | Ethyl (3-chloro-4-fluorophenyl)(2-((ethoxycarbonyl)amino)furo[2,3-c]pyridin-3-yl)carbamate | DMSO-d$_6$: δ 8.97 (s, 1H), 8.42 (d, J = 5.2 Hz, 1H), 8.28 (s, 1H), 7.42 (d, J = 5.1 Hz, 1H), 7.25 (t, J = 9.1 Hz, 1H), 6.77 (dd, J' = 2.7 Hz, J'' = 6.2 Hz, 1H), 6.70-6.78 (m, 1H), 4.15 (q, J = 7.1 Hz, 4H), 1.08 (t, J = 7.1 Hz, 6H) | [M + H] 422.2 | H |
| 143 | 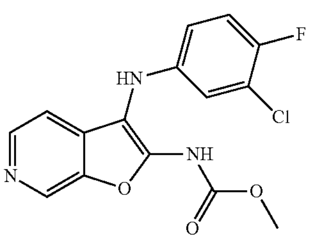 [SMILES: COC(=O)Nc1oc2cnccc2c1Nc1ccc(F)c(Cl)c1] | Methyl (3-((3-chloro-4-fluorophenyl)amino)furo[2,3-c]pyridin-2-yl)carbamate | DMSO-d$_6$: δ 10.24 (s, 1H), 8.85 (s, 1H), 8.34 (d, J = 5.1 Hz, 1H), 7.77 (s, 1H), 7.31 (d, J = 5.1 Hz, 1H), 7.19 (t, J = 9.1 Hz, 1H), 6.73-6.71 (m, 1H), 6.62-6.60 (m, 1H), 3.63 (s, 3H) | [M + H] 336 | G |
| 144 | 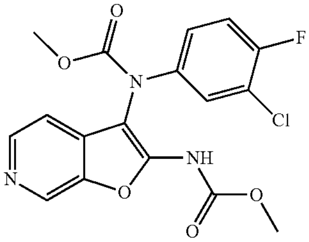 [SMILES: COC(=O)Nc1oc2cnccc2c1N(C(=O)OC)c1ccc(F)c(Cl)c1] | Methyl (3-chloro-4-fluorophenyl)(2-((methoxycarbonyl)amino)furo[2,3-c]pyridin-3-yl)carbamate | DMSO-d$_6$: δ 8.97 (s, 1H), 8.42 (d, J = 5.0 Hz, 1H), 8.23 (s, 1H), 7.39 (d, J = 4.8 Hz, 1H), 7.24 (t, J = 8.8 Hz, 1H), 6.79-6.78 (m, 1H), 6.68-6.66 (m, 1H), 3.69 (s, 6H) | [M + H] 394 | H |

TABLE 1-continued

| No. | Structure | IUPAC Name | ¹H-NMR (400 MHz) proton shift | LCMS | Proc. |
|---|---|---|---|---|---|
| 145 | 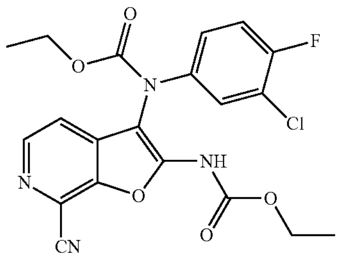 [SMILES: CCOC(=O)Nc1oc2c(C#N)nccc2c1N(C(=O)OCC)c1ccc(F)c(Cl)c1] | Ethyl (3-chloro-4-fluorophenyl)(7-cyano-2-((ethoxycarbonyl)amino)furo[2,3-c]pyridin-3-yl)carbamate | DMSO-d$_6$: δ 8.50 (d, J = 5.1 Hz, 1H), 7.63 (d, J = 5.1 Hz, 1H), 7.11 (t, J = 9 Hz, 1H), 6.84 (dd, J' = 6.3 Hz, J" = 2.8 Hz, 1H), 6.75 (dt, J' = 8.9 Hz, J" = 6.8 Hz, J''' = 3.7 Hz, 1H), 6.64 (s, 1H), 4.19 (q, J = 7.1 Hz, 4H), 1.15 (t, J = 7.1 Hz, 6H) | [M + H] 447 | H |
| 146 | 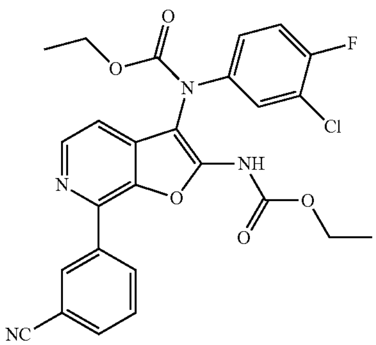 [SMILES: CCOC(=O)Nc1oc2c(-c3cccc(C#N)c3)nccc2c1N(C(=O)OCC)c1ccc(F)c(Cl)c1] | Ethyl (3-chloro-4-fluorophenyl)(7-(3-cyanophenyl)-2-((ethoxycarbonyl)amino)furo[2,3-c]pyridin-3-yl)carbamate | DMSO-d$_6$: δ 8.60-8.56 (m, 3H), 8.35 (s, 1H), 8.00 (d, J = 7.5 Hz, 1H), 7.83 (t, J = 7.8 Hz, 1H), 7.50 (d, J = 4.6 Hz, 1H), 7.26 (t, J = 9.6 Hz, 1H), 6.83 (bs, 1H), 6.75 (bs, 1H), 4.17 (q, J = 6.7 Hz, 4H), 1.10 (t, J = 6.8 Hz, 6H) | [M + H] 523.2 | H |
| 147 | 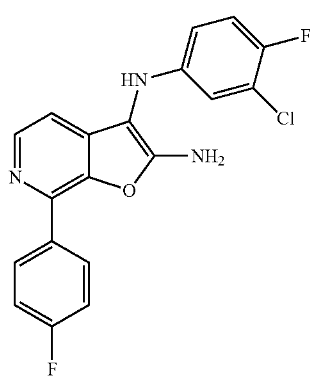 [SMILES: Nc1oc2c(-c3ccc(F)cc3)nccc2c1Nc1ccc(F)c(Cl)c1] | N³-(3-Chloro-4-fluorophenyl)-7-(4-fluorophenyl)furo[2,3-c]pyridine-2,3-diamine | DMSO-d$_6$: δ 8.30 (dd, J' 8.2 Hz, J" = 5.8 Hz, 2H), 8.15 (d, J = 5.2 Hz, 1H), 7.38 (t, J = 8.8 Hz, 2H), 7.17-7.11 (m, 4H), 6.87 (d, J = 5.1 Hz, 1H), 6.59 (dd, J' 6.2 Hz, J" = 2.87 Hz, 1H), 6.52-6.50 (m, 1H) | [M + H] 371.8 | A |
| 148 | 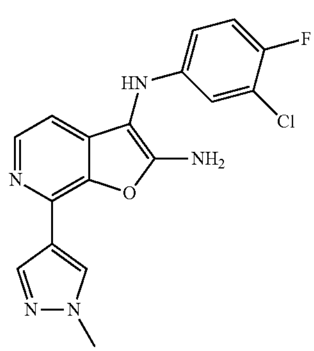 [SMILES: Cn1cc(-c2nccc3c(Nc4ccc(F)c(Cl)c4)c(N)oc23)cn1] | N³-(3-Chloro-4-fluorophenyl)-7-(1-methyl-1H-pyrazol-4-yl)furo[2,3-c]pyridine-2,3-diamine | DMSO-d$_6$: δ 8.30 (s, 1H), 8.12 (s, 1H), 8.02 (s, 1H), 7.12 (bs, 2H), 6.90 (bs, 2H) 6.72 (s, 1H), 6.57 (s, 1H), 6.49 (s, 1H), 3.94 (s, 3H) | [M + H] 358 | A |

TABLE 1-continued

| No. | Structure | IUPAC Name | ¹H-NMR (400 MHz) proton shift | LCMS | Proc. |
|---|---|---|---|---|---|
| 149 | 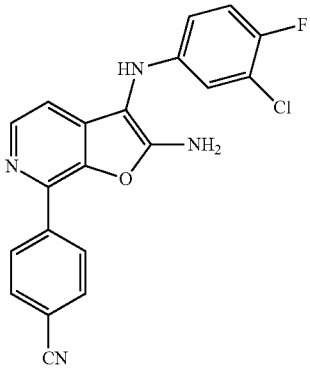 [SMILES: N#Cc1ccc(-c2nccc3c(Nc4ccc(F)c(Cl)c4)c(N)oc23)cc1] | 4-(2-Amino-3-((3-chloro-4-fluorophenyl)amino)furo[2,3-c]pyridin-7-yl)benzonitrile | DMSO-d₆: δ 8.46 (d, J = 8.2 Hz, 2H), 8.21 (d, J = 4.9 Hz, 1H), 8.01 (d, J = 8.2 Hz, 2H), 7.17-7.11 (m, 4H), 6.93 (d, J = 4.9 Hz, 1H), 6.60-6.59 (m, 1H), 6.52-6.50 (m, 1H) | [M + H] 379 | C |
| 151 | 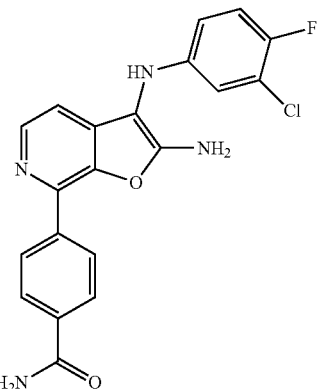 | 4-(2-Amino-3-((3-chloro-4-fluorophenyl)amino)furo[2,3-c]pyridin-7-yl)benzamide | CDCN₃: δ 8.42 (d, J = 8.3 Hz, 2H), 8.25 (d, J = 5.0 Hz, 1H), 7.97 (d, J = 8.4 Hz, 2H), 7.03 (t, J = 9.0 Hz, 1H), 6.98 (d, J = 5.0 Hz, 1H), 6.85 (bs, 1H), 6.66 (dd, J' = 6.3 Hz, J" = 2.8 Hz, 1H), 6.58 (dt, J' 8.8 Hz, J" = 6.7 Hz, J'" = 3.3 Hz, 1H), 6.05 (bs, 1H), 5.72 (s, 1H), 5.46 (s, 2H), | [M + H] 397 | C |
| 152 | 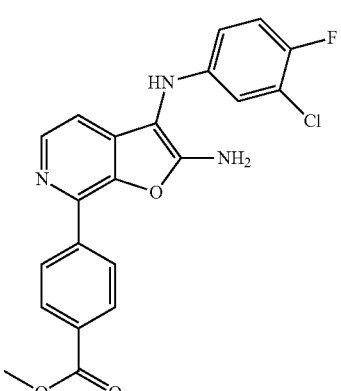 | Methyl 4-(2-amino-3-((3-chloro-4-fluorophenyl)amino)furo[2,3-c]pyridin-7-yl)benzoate | DMSO-d₆: δ 8.42 (d, J = 8.4 Hz, 2H), 8.21 (d, J = 5.0 Hz, 1H), 8.10 (d, J = 8.4 Hz, 2H), 7.16-7.08 (m, 4H), 6.91 (d, J = 5.0 Hz, 1H), 6.60 (dd, J' = 6.2 Hz, J" = 2.6 Hz, 1H), 6.53-6.50 (m, 1H), 3.90 (s, 3H) | [M + H] 412 | C |
| 153 | 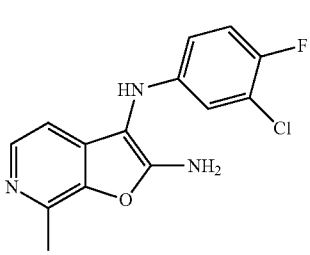 | N³-(3-Chloro-4-fluorophenyl)-7-iodofuro[2,3-c]pyridine-2,3-diamine | DMSO-d₆: δ 7.83 (d, J = 5.0 Hz, 1H), 7.21 (s, 2H), 7.15-7.09 (m, 2H), 6.83 (d, J = 5.0 Hz, 1H), 6.57-6.56 (m, 1H), 6.47-6.45 (m, 1H) | [M + H] 403.8 | C |

TABLE 1-continued

| No. | Structure | IUPAC Name | ¹H-NMR (400 MHz) proton shift | LCMS | Proc. |
|---|---|---|---|---|---|
| 154 | 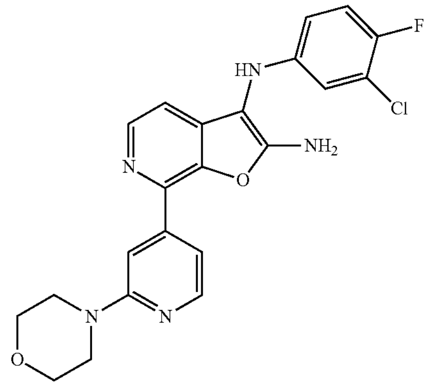 [SMILES: Nc1oc2c(-c3ccnc(N4CCOCC4)c3)nccc2c1Nc1ccc(F)c(Cl)c1] | N³-(3-Chloro-4-fluorophenyl)-7-(2-morpholino-pyridin-4-yl)furo[2,3-c]pyridine-2,3-diamine | DMSO-d₆: δ 8.31 (d, J = 4.6 Hz, 1H), 8.18 (d, J = 4.7 Hz, 1H), 7.59 (s, 1H), 7.51 (s, 1H), 7.37 (bs, 2H), 7.20 (s, 1H), 7.14 (t, J = 8.7 Hz, 1H), 6.95 (d, J = 4.3 Hz, 1H), 6.61 (s, 1H), 6.53 (bs, 1H), 3.75 (s, 4H), 3.53 (s, 4H) | [M + H] 440 | A |
| 155 | 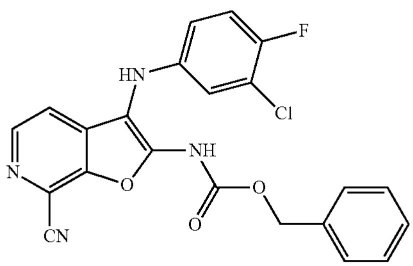 [SMILES: N#Cc1nccc2c(Nc3ccc(F)c(Cl)c3)c(NC(=O)OCc3ccccc3)oc12] | Benzyl (3-((3-chloro-4-fluorophenyl)amino)-7-cyanofuro[2,3-c]pyridin-2-yl)carbamate | CD₃CN: δ 8.42 (d, J = 5.1 Hz, 1H), 8.37 (bh, 1H), 7.50 (d, J = 5.1 Hz, 1H), 7.37 (bs, 5H), 7.05 (t, J = 9.0 Hz, 1H), 6.75 (dd, J' = 6.2 Hz, J'' = 2.7 Hz, 1H), 6.64 (dt, J' = 8.8 Hz, J'' = 6.6 Hz, J''' = 3.2 Hz, 1H), 6.32 (s, 1H), 5.18 (s, 2H) | [M − H] 435.2 | G |
| 156 | 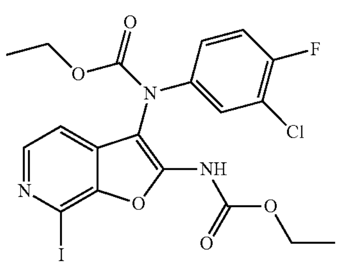 [SMILES: CCOC(=O)Nc1oc2c(I)nccc2c1N(C(=O)OCC)c1ccc(F)c(Cl)c1] | Ethyl (3-chloro-4-fluorophenyl)(2-((ethoxy-carbonyl)amino)-7-iodofuro[2,3-c]pyridin-3-yl)carbamate | CD₃CN: δ 8.20 (d, J = 5.2 Hz, 1H), 7.32 (d, J = 5.1 Hz, 1H), 7.10 (t, J = 9.0 Hz, 1H), 6.84 (dd, J' = 6.2 Hz, J'' = 2.8 Hz, 1H), 6.75 (dt, J' = 8.8 Hz, J'' = 6.8 Hz, J''' = 3.1 Hz, 1H), 6.56 (s, 1H), 4.21 (q, J = 7.1 Hz, 4H), 1.17 (t, J = 7.1 Hz, 6H) | [M − H] 546.1 | H |
| 157 | 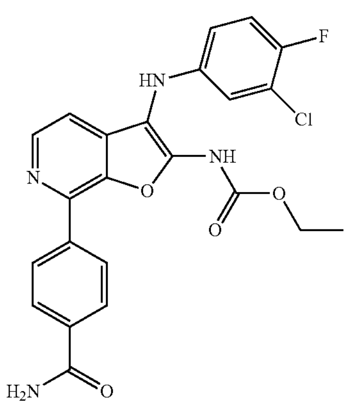 [SMILES: CCOC(=O)Nc1oc2c(-c3ccc(C(N)=O)cc3)nccc2c1Nc1ccc(F)c(Cl)c1] | Ethyl (7-(4-carbamoyl-phenyl)-3-((3-chloro-4-fluorophenyl)amino)furo[2,3-c]pyridin-2-yl)carbamate | DMSO-d₆: δ 10.34 (s, 1H), 8.47 (d, J = 4.7 Hz, 1H), 8.38 (d, J = 7.8 Hz, 2H), 8.10-8.05 (m, 3H), 7.79 (s, 1H), 7.47 (s, 1H), 7.34 (d, J = 4.5 Hz, 1H), 7.19 (t, J = 9.0 Hz, 1H), 6.77 (bs, 1H), 6.66 (bs, 1H), 4.10 (q, J = 6.8 Hz, 2H), 1.16 (t, J = 6.8 Hz, 3H) | [M + H] 469 | G |

TABLE 1-continued

| No. | Structure | IUPAC Name | ¹H-NMR (400 MHz) proton shift | LCMS | Proc. |
|---|---|---|---|---|---|
| 158 | 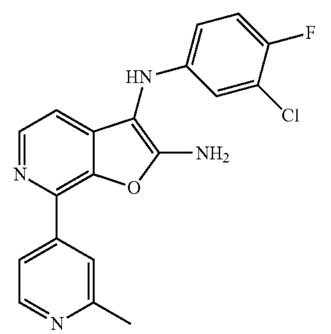 [SMILES: Cc1cc(-c2nccc3c(Nc4ccc(F)c(Cl)c4)c(N)oc23)ccn1] | N³-(3-Chloro-4-fluorophenyl)-7-(2-methylpyridin-4-yl)furo[2,3-c]pyridine-2,3-diamine | CD$_3$CN: δ 8.65 (s, 1H), 8.29-8.13 (m, 3H), 7.03 (bs, 2H), 6.66 (s, 1H), 6.60 (s, 1H), 5.94 (s, 1H), 5.78 (bs, 2H), 2.66 (s, 3H) | [M + H] 369 | A |
| 159 | 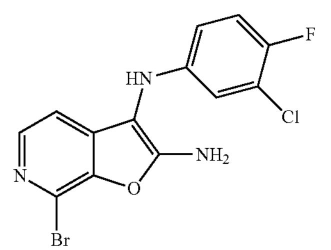 [SMILES: Nc1oc2c(Br)nccc2c1Nc1ccc(F)c(Cl)c1] | 7-Bromo-N³-(3-chloro-4-fluorophenyl)furo[2,3-c]pyridine-2,3-diamine | DMSO-d$_6$: δ 7.85 (d, J = 5.1 Hz, 1H), 7.26 (bs, 2H), 7.16 (s, 1H), 7.12 (t, J = 9.1 Hz, 1H), 6.88 (d, J = 5.1 Hz, 1H), 6.58 (dd, J' = 6.3 Hz, J" = 2.7 Hz, 1H), 6.48 (dt, J' = 8.9 Hz, J" = 6.8 Hz, J'" = 3.4 Hz, 1H) | [M + H] 356 | A |
| 160 | 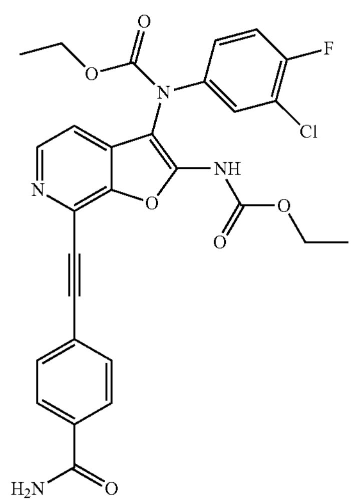 [SMILES: CCOC(=O)Nc1oc2c(C#Cc3ccc(C(N)=O)cc3)nccc2c1N(C(=O)OCC)c1ccc(F)c(Cl)c1] | Ethyl (7-((4-carbamoylphenyl)ethynyl)-2-((ethoxycarbonyl)amino)furo[2,3-c]pyridin-3-yl)(3-chloro-4-fluorophenyl)carbamate | DMSO-d$_6$: δ 8.47 (d, J = 5.1 Hz, 1H), 8.36 (s, 1H), 8.12 (s, 1H), 7.97 (d, J = 8.0 Hz, 2H), 7.76 (d, J = 8.0 Hz, 2H), 7.52 (s, 1H), 7.49 (d, J = 5.1 Hz, 1H), 7.26 (t, J = 9.0 Hz, 1H), 6.82 (dd, J' = 6.2 Hz, J" = 2.5 Hz, 1H), 6.75-6.71 (m, 1H), 4.18 (q, J = 7.0 Hz, 4H), 1.11 (t, J = 7.0 Hz, 6H) | [M − H] 563.2 | H |
| 161 | 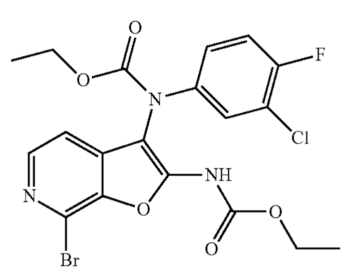 [SMILES: CCOC(=O)Nc1oc2c(Br)nccc2c1N(C(=O)OCC)c1ccc(F)c(Cl)c1] | Ethyl (7-bromo-2-((ethoxycarbonyl)amino)furo[2,3-c]pyridin-3-yl)(3-chloro-4-fluorophenyl)carbamate | DMSO-d$_6$: δ 8.38 (s, 1H), 8.24 (d, J = 5.0 Hz, 1H), 7.48 (d, J = 5.2 Hz, 1H), 7.25 (t, J = 9.1 Hz, 1H), 6.82-6.81 (m, 1H), 6.73-6.71 (m, 1H), 4.17 (q, J = 7.0 Hz, 4H), 1.10 (t, J = 7.0 Hz, 6H) | [M + H] 502.2 | H |

TABLE 1-continued

| No. | Structure | IUPAC Name | ¹H-NMR (400 MHz) proton shift | LCMS | Proc. |
|---|---|---|---|---|---|
| 162 | 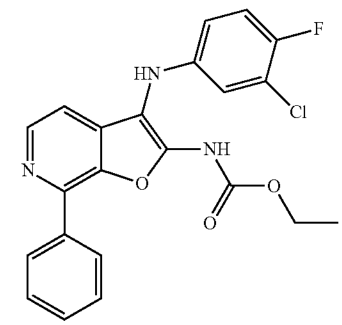 [SMILES: CCOC(=O)Nc1oc2c(-c3ccccc3)nccc2c1Nc1ccc(F)c(Cl)c1] | Ethyl (3-((3-chloro-4-fluorophenyl)amino)-7-phenylfuro[2,3-c]pyridin-2-yl)carbamate | DMSO-$d_6$: δ 1.04 (s, 1H), 8.44 (d, J = 4.8 Hz, 1H), 8.31 (d, J = 7.6 Hz, 2H), 7.78 (s, 1H), 7.58 (t, J = 7.3 Hz, 2H), 7.52-7.50 (m, 1H), 7.30 (d, J = 4.9 Hz, 1H), 7.19 (t, J = 8.9 Hz, 1H), 6.67-6.76 (m, 1H), 6.66-6.64 (m, 1H), 4.10 (q, J = 6.9 Hz, 2H), 1.15 (t, J = 6.9 Hz, 3H) | [M + H] 426 | G |
| 163 | 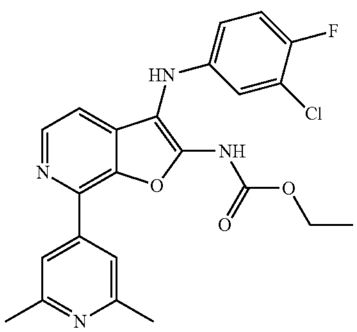 [SMILES: CCOC(=O)Nc1oc2c(-c3cc(C)nc(C)c3)nccc2c1Nc1ccc(F)c(Cl)c1] | Ethyl (3-((3-chloro-4-fluorophenyl)amino)-7-(2,6-dimethyl-pyridin-4-yl)furo[2,3-c]pyridin-2-yl)carbamate | CD$_3$CN: δ 8.42 (d, J = 5.0 Hz, 1H), 7.95 (s, 2H), 7.27 (d, J = 5.1 Hz, 1H), 7.06 (t, J = 9.0 Hz, 1H), 6.77 (dd, J' = 6.2 Hz, J'' = 2.9 Hz, 1H), 6.69-6.65 (m, 1H), 6.32 (s, 1H), 4.18 (q, J = 7.0 Hz, 2H), 2.57 (s, 6H), 1.23 (t, J = 7.0 Hz, 3H) | [M + H] 455 | G |
| 164 | 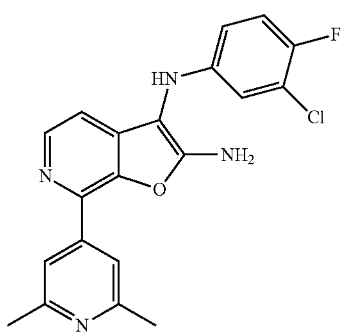 [SMILES: Cc1cc(-c2nccc3c(Nc4ccc(F)c(Cl)c4)c(N)oc23)cc(C)n1] | N³-(3-Chloro-4-fluorophenyl)-7-(2,6-dimethyl-pyridin-4-yl)furo[2,3-c]pyridine-2,3-diamine | DMSO-$d_6$: δ 8.19 (d, J = 5.0 Hz, 1H), 7.88 (s, 2H), 7.16-7.12 (m, 4H), 6.92 (d, J = 4.9 Hz, 1H), 6.60 (dd, J' = 6.1 Hz, J'' = 2.4 Hz, 1H), 6.52-6.49 (m, 1H), 2.53 (s, 6H) | [M + H] 383 | A |
| 165 | 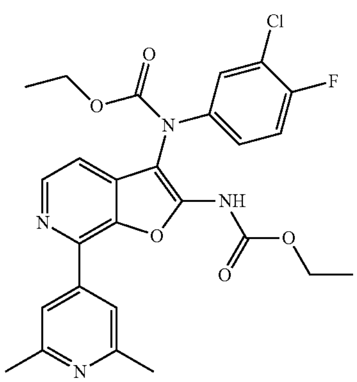 [SMILES: CCOC(=O)Nc1oc2c(-c3cc(C)nc(C)c3)nccc2c1N(C(=O)OCC)c1ccc(F)c(Cl)c1] | Ethyl (3-chloro-4-fluorophenyl)(7-(2,6-dimethyl-pyridin-4-yl)-2-((ethoxy-carbonyl)amino)furo[2,3-c]pyridin-3-yl)carbamate | CD$_3$CN: δ 8.50 (d, J = 5.0 Hz, 1H), 7.92 (s, 2H), 7.39 (d, J = 4.9 Hz, 1H), 7.09 (t, J = 9.0 Hz, 1H), 6.85-6.84 (m, 1H), 6.76-6.74 (m, 1H), 6.54 (s, 1H), 4.19 (q, J = 7.1 Hz, 4H), 2.57 (s, 6H), 1.14 (t, J = 7.1 Hz, 6H) | [M + H] 527 | H |

TABLE 1-continued

| No. | Structure | IUPAC Name | ¹H-NMR (400 MHz) proton shift | LCMS | Proc. |
|---|---|---|---|---|---|
| 166 | 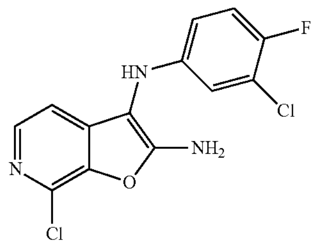 [SMILES: Nc1oc2c(Cl)nccc2c1Nc1ccc(F)c(Cl)c1] | 7-Chloro-N3-(3-chloro-4-fluorophenyl)furo[2,3-c]pyridine-2,3-diamine | DMSO-d$_6$: δ 7.87 (d, J = 5.1 Hz, 1H), 7.25 (s, 2H), 7.16-7.10 (m, 2H), 6.88 (d, J = 5.1 Hz, 1H), 6.59 (dd, J' = 6.2 Hz, J" = 2.6 Hz, 1H), 6.48 (dt, J' = 8.8 Hz, J" = 6.7 Hz, J'" = 3.4 Hz, 1H) | [M + H] 312 | A |
| 167 | 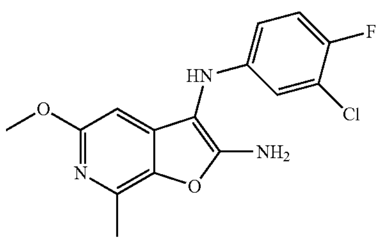 | N³-(3-Chloro-4-fluorophenyl)-7-iodo-5-methoxyfuro[2,3-c]pyridine-2,3-diamine | DMSO-d$_6$: δ 7.23 (s, 2H), 7.14-7.09 (m, 2H), 6.56-6.55 (m, 1H), 6.46-6.43 (m, 1H), 6.03 (s, 1H), 3.74 (s, 3H) | [M + H] 434 | A |
| 169 | 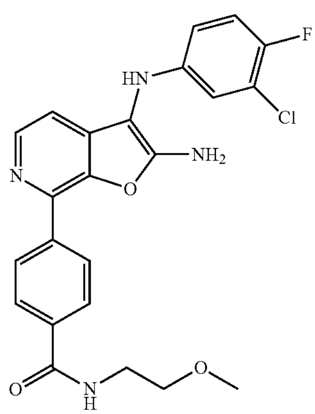 [SMILES: COCCNC(=O)c1ccc(-c2nccc3c(Nc4ccc(F)c(Cl)c4)c(N)oc23)cc1] | 4-(2-Amino-3-((3-chloro-4-fluorophenyl)amino)furo[2,3-c]pyridin-7-yl)-N-(2-methoxyethyl)benzamide | CD$_3$CN: δ 8.11 (d, J = 8.2 Hz, 2H), 8.06-8.03 (m, 3H), 7.26 (bs, 1H), 7.16 (d, J = 6.2 Hz, 1H), 7.08 (t, J = 9.0 Hz, 1H), 6.70 (dd, J' = 6.1 Hz, J" = 2.6 Hz, 1H), 6.65-6.60 (m, 3H), 5.88 (s, 1H), 3.59-3.54 (m, 4H), 3.35 (s, 3H) | [M + H] 455 | A |
| 170 | 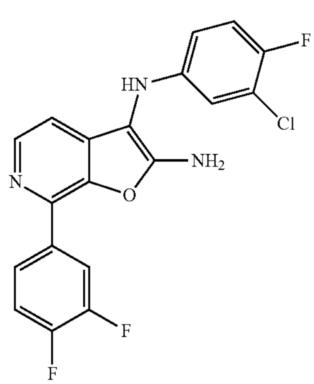 [SMILES: Nc1oc2c(-c3ccc(F)c(F)c3)nccc2c1Nc1ccc(F)c(Cl)c1] | N³-(3-chloro-4-fluorophenyl)-7-(3,4-difluorophenyl)furo[2,3-c]pyridine-2,3-diamine | DMSO-d$_6$: δ 8.26 (t, J = 10.4 Hz, 1H), 8.17 (d, J = 5.2 Hz, 2H), 7.62 (q, J = 9.3 Hz, 1H), 7.16-7.11 (m, 4H), 6.89 (d, J = 5.0 Hz, 1H), 6.60 (dd, J' = 6.2 Hz, J" = 2.6 Hz, 1H), 6.53-6.50 (m, 1H), | [M + H] 390 | A |

TABLE 1-continued

| No. | Structure | IUPAC Name | ¹H-NMR (400 MHz) proton shift | LCMS | Proc. |
|---|---|---|---|---|---|
| 171 | 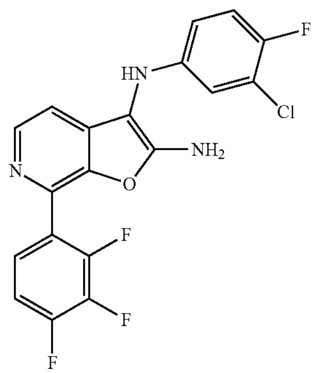 [SMILES: Nc1oc2c(-c3ccc(F)c(F)c3F)nccc2c1Nc1ccc(F)c(Cl)c1] | N³-(3-Chloro-4-fluorophenyl)-7-(2,3,4-trifluorophenyl)furo[2,3-c]pyridine-2,3-diamine | DMSO-$d_6$: δ 8.17 (d, J = 5.1 Hz, 1H), 7.63-7.57 (m, 1H), 7.50 (q, J = 8.5 Hz, 1H), 7.15-7.11 (m, 2H), 7.07 (s, 2H), 6.94 (d, J = 5.0 Hz, 1H), 6.59 (dd, J' = 6.2 Hz, J" = 2.7 Hz, 1H), 6.51-6.48 (m, 1H) | [M + H] 408 | A |
| 172 | 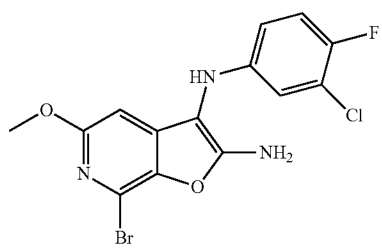 [SMILES: COc1cc2c(Nc3ccc(F)c(Cl)c3)c(N)oc2c(Br)n1] | 7-Bromo-N³-(3-chloro-4-fluorophenyl)-5-methoxy-furo[2,3-c]pyridine-2,3-diamine | DMSO-$d_6$: δ 7.27 (s, 2H), 7.14-7.08 (m, 2H), 6.57 (dd, J' = 6.3 Hz, J" = 2.7 Hz, 1H), 6.46 (dt, J' = 8.7 Hz, J" = 6.6 Hz, J''' = 3.5 Hz, 1H), 6.08 (s, 1H), 3.75 (s, 3H) | [M + H] 386 | A |
| 173 | 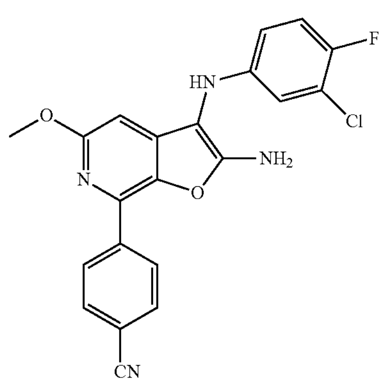 [SMILES: COc1cc2c(Nc3ccc(F)c(Cl)c3)c(N)oc2c(-c2ccc(C#N)cc2)n1] | 4-(2-Amino-3-((3-chloro-4-fluorophenyl)amino)-5-methoxyfuro[2,3-c]pyridin-7-yl)benzonitrile | DMSO-$d_6$: δ 8.47 (d, J = 8.2 Hz, 2H), 8.01 (d, J = 8.2 Hz, 2H), 7.18-7.09 (m, 4H), 6.61-6.59 (m, 1H), 6.51-6.48 (m, 1H), 6.14 (s, 1H), 3.88 (s, 3H) | [M + H] 409 | A |
| 174 | 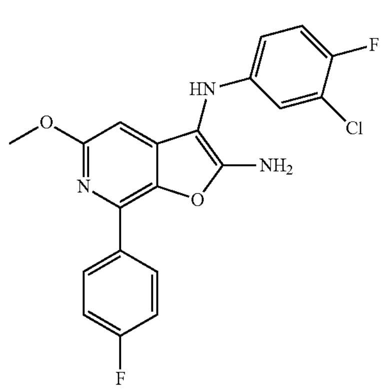 [SMILES: COc1cc2c(Nc3ccc(F)c(Cl)c3)c(N)oc2c(-c2ccc(F)cc2)n1] | N³-(3-chloro-4-fluorophenyl)-7-(4-fluorophenyl)-5-methoxy-furo[2,3-c]pyridine-2,3-diamine | DMSO-$d_6$: δ 8.34 (dd, J' = 8.2 Hz, J" = 5.6 Hz, 2H), 7.37 (t, J = 8.8 Hz, 2H), 7.15-7.05 (m, 4H), 6.59-6.57 (m, 1H), 6.50-6.48 (m, 1H), 6.07 (s, 1H), 3.87 (s, 3H) | [M + H] 402 | A |

TABLE 1-continued

| No. | Structure | IUPAC Name | ¹H-NMR (400 MHz) proton shift | LCMS | Proc. |
|---|---|---|---|---|---|
| 175 | 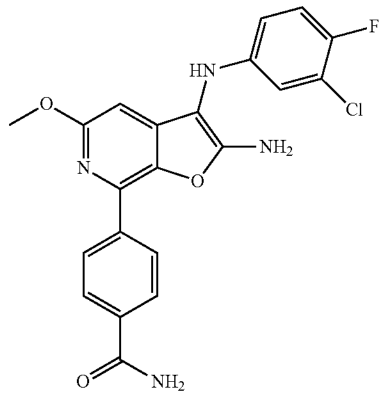 [SMILES: COc1cc2c(Nc3ccc(F)c(Cl)c3)c(N)oc2c(-c2ccc(C(N)=O)cc2)n1] | 4-(2-amino-3-((3-chloro-4-fluorophenyl)amino)-5-methoxyfuro[2,3-c]pyridin-7-yl)benzamide | DMSO-d$_6$: δ 8.36 (d, J = 8.3 Hz, 2H), 8.06 (s, 1H), 8.01 (d, J = 8.3 Hz, 2H), 7.45 (s, 1H), 7.15-7.08 (m, 4H), 6.59 (dd, J' = 6.1 Hz, J" = 2.6 Hz, 1H), 6.51-6.49 (m, 1H), 6.11 (s, 1H), 3.89 (s, 3H) | [M + H] 427 | A |
| 176 | 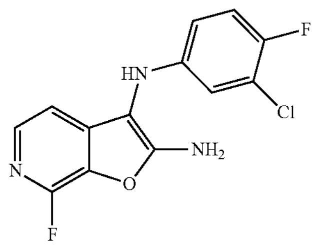 [SMILES: Nc1oc2c(F)nccc2c1Nc1ccc(F)c(Cl)c1] | N$^3$-(3-chloro-4-fluorophenyl)-7-fluorofuro[2,3-c]pyridine-2,3-diamine | DMSO-d$_6$: δ 7.66 (d, J = 5.2 Hz, 1H), 7.15-7.11 (m, 4H), 6.83 (dd, J' = 5.1 Hz, J" = 2.6 Hz, 1H), 6.58 (dd, J' = 6.2 Hz, J" = 2.6 Hz, 1H), 6.48 (dt, J' = 8.9 Hz, J" = 6.7 Hz, J'" = 3.4 Hz, 1H) | [M + H] 296 | C |
| 177 | 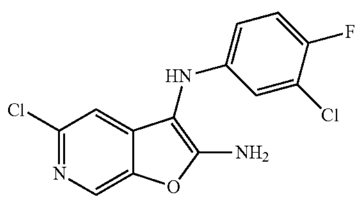 [SMILES: Nc1oc2cnc(Cl)cc2c1Nc1ccc(F)c(Cl)c1] | 5-Chloro-N3-(3-chloro-4-fluorophenyl)furo[2,3-c]pyridine-2,3-diamine | DMSO-d$_6$: δ 8.20 (s, 1H), 7.27 (s, 2H), 7.13 (t, J = 9.0 Hz, 1H), 7.08 (s, 1H), 6.77 (s, 1H), 6.58-6.57 (m, 1H), 6.47-6.45 (m, 1H) | [M + H] 311.8 | A |
| 178 | 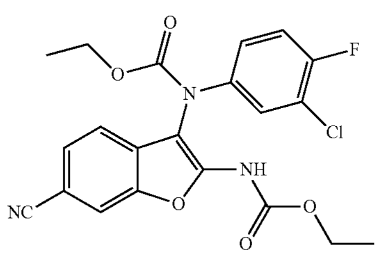 [SMILES: CCOC(=O)Nc1oc2cc(C#N)ccc2c1N(C(=O)OCC)c1ccc(F)c(Cl)c1] | Ethyl (3-chloro-4-fluorophenyl)(6-cyano-2-((ethoxycarbonyl)amino)benzofuran-3-yl)carbamate | DMSO-d$_6$: δ 8.28 (s, 2H), 7.70 (d, J = 7.4 Hz, 1H), 7.55 (d, J = 8.2 Hz, 1H), 7.23 (t, J = 9.4 Hz, 1H), 6.78 (bs, 1H), 6.71 (bs, 1H), 4.16-4.14 (m, 4H), 1.09 (bs, 6H) | [M − H] 444 | H |
| 179 | 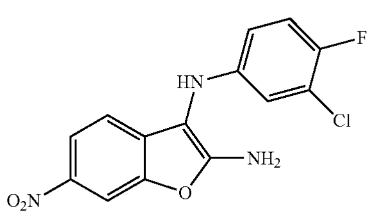 [SMILES: Nc1oc2cc([N+](=O)[O-])ccc2c1Nc1ccc(F)c(Cl)c1] | N$^3$-(3-chloro-4-fluorophenyl)-6-nitrobenzofuran-2,3-diamine | DMSO-d$_6$: δ 8.11 (d, J = 1.9 Hz, 1H), 7.98 (dd, J' = 8.6 Hz, J" = 1.9 Hz, 1H), 7.35 (bs, 2H), 7.19 (s, 1H), 7.13 (t, J = 9.0 Hz, 1H), 6.92 (d, J = 8.6 Hz, 1H), 6.59 (dd, J' = 6.2 Hz, J" = 2.7 Hz, 1H), 6.49 (dt, J' = 8.9 Hz, J" = 6.7 Hz, J'" = 3.5 Hz, 1H), | [M − H] 320 | B |

TABLE 1-continued

| No. | Structure | IUPAC Name | ¹H-NMR (400 MHz) proton shift | LCMS | Proc. |
|---|---|---|---|---|---|
| 180 | 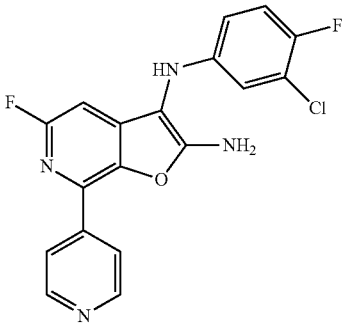 | N³-(3-Chloro-4-fluorophenyl)-5-fluoro-7-(pyridin-4-yl)furo[2,3-c]pyridine-2,3-diamine | DMSO-$d_6$: δ 8.76 (d, J = 5.8 Hz, 2H), 8.15 (d, J = 5.8 Hz, 2H), 7.50 (s, 2H), 7.17-7.12 (m, 2H), 6.63 (dd, J' = 6.1 Hz, J" = 2.5 Hz, 1H), 6.53-6.49 (m, 2H) | [M + H] 373.2 | C |
| 181 | 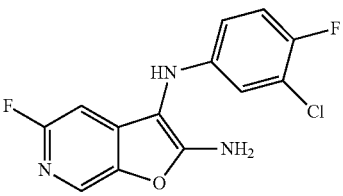 | N³-(3-Chloro-4-fluorophenyl)-5-fluorofuro[2,3-c]pyridine-2,3-diamine | DMSO-$d_6$: δ 7.99 (s, 1H), 7.24 (s, 2H), 7.15-7.10 (m, 2H), 6.58-6.57 (m, 1H), 6.47-6.45 (m, 1H), 6.38 (s, 1H) | [M + H] 296.2 | C |
| 182 | 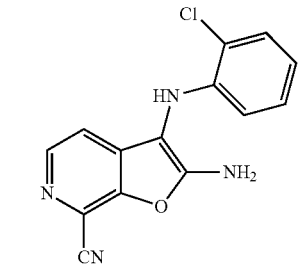 [SMILES: N#Cc1nccc2c(Nc3ccccc3Cl)c(N)oc12] | 2-Amino-3-((2-chlorophenyl)amino)furo[2,3-c]pyridine-7-carbonitrile | DMSO-$d_6$: δ 8.14 (d, J = 5.1 Hz, 1H), 7.61 (s, 2H), 7.31 (d, J = 7.89 Hz, 1H), 7.05-7.01 (m, 2H), 6.73 (s, 1H), 6.66 (t, J = 7.5 Hz, 1H), 6.35 (d, J = 8.1 Hz, 1H) | [M + H] 285 | A |
| 183 | 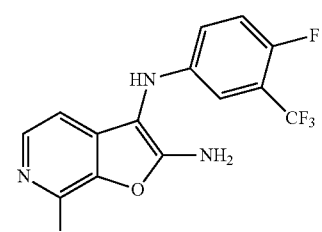 | 2-Amino-3-((4-fluoro-3-(trifluoromethyl)phenyl)amino)furo[2,3-c]pyridine-7-carbonitrile | DMSO-$d_6$: δ 8.15 (d, J = 5.1 Hz, 1H), 7.63 (s, 2H), 7.38 (s, 1H), 7.22 (t, J = 9.6 Hz, 1H), 7.11 (d, J = 4.8 Hz, 1H), 6.84 (s, 1H), 6.76-6.73 (m, 1H) | [M − H] 335 | A |
| 184 | 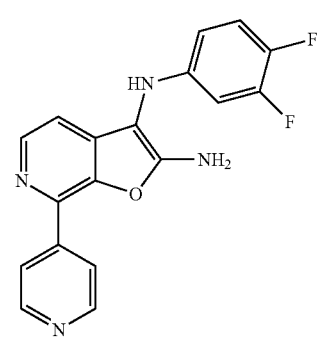 [SMILES: Nc1oc2c(-c3ccncc3)nccc2c1Nc1ccc(F)c(F)c1] | N³-(3,4-difluorophenyl)-7-(pyridin-4-yl)furo[2,3-c]pyridine-2,3-diamine | CD₃CN: δ 8.72 (s, 2H), 8.26 (s, 3H), 7.07-7.03 (m, 2H), 6.47-6.40 (m, 2H), 5.74 (s, 1H), 5.55 (s, 2H) | [M + H] 339 | A |

TABLE 1-continued

| No. | Structure | IUPAC Name | ¹H-NMR (400 MHz) proton shift | LCMS | Proc. |
|---|---|---|---|---|---|
| 185 | 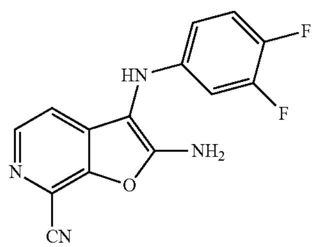 [SMILES: N#Cc1nccc2c(Nc3ccc(F)c(F)c3)c(N)oc12] | 2-Amino-3-((3,4-difluorophenyl)amino)furo[2,3-c]pyridine-7-carbonitrile | DMSO-$d_6$: δ 8.14 (d, J = 5.2 Hz, 1H), 7.59 (s, 2H), 7.18-7.10 (m, 2H), 7.07 (d, J = 5.1 Hz, 1H), 6.48-6.43 (m, 1H), 6.34-6.32 (m, 1H) | [M + H] 287.1 | A |
| 186 | 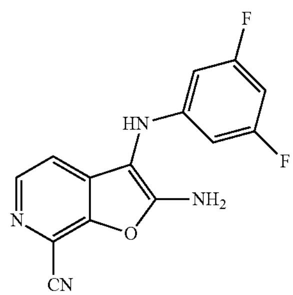 [SMILES: N#Cc1nccc2c(Nc3cc(F)cc(F)c3)c(N)oc12] | 2-Amino-3-((3,5-difluorophenyl)amino)furo[2,3-c]pyridine-7-carbonitrile | DMSO-$d_6$: δ 8.16 (d, J = 5.1 Hz, 1H), 7.64 (s, 2H), 7.59 (s, 1H), 7.10 (d, J = 5.4 Hz, 1H), 6.37-6.32 (m, 1H), 6.18-6.15 (m, 2H) | [M − H] 285.1 | A |
| 187 | 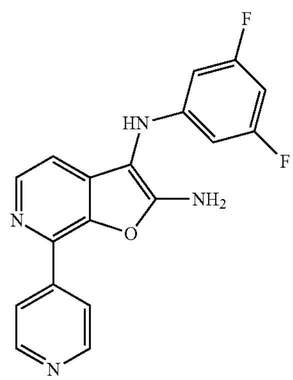 [SMILES: Nc1oc2c(-c3ccncc3)nccc2c1Nc1cc(F)cc(F)c1] | $N^3$-(3,5-Difluorophenyl)-7-(pyridin-4-yl)furo[2,3-c]pyridine-2,3-diamine | DMSO-$d_6$: δ 8.75 (d, J = 4.3 Hz, 2H), 8.23 (d, J = 3.7 Hz, 3H), 7.60 (s, 1H), 7.22 (s, 2H), 6.96 (d, J = 4.4 Hz, 1H), 6.34 (t, J = 9.4 Hz, 1H), 6.16 (d, J = 9.3 Hz, 2H) | [M + H] 339.1 | A |
| 188 | 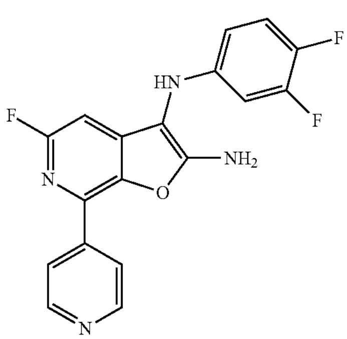 [SMILES: Nc1oc2c(-c3ccncc3)nc(F)cc2c1Nc1ccc(F)c(F)c1] | $N^3$-(3,4-Difluorophenyl)-5-fluoro-7-(pyridin-4-yl)furo[2,3-c]pyridine-2,3-diamine | DMSO-$d_6$: δ 8.76 (d, J = 4.8 Hz, 2H), 8.14 (d, J = 4.9 Hz, 2H), 7.48 (s, 2H), 7.16-7.11 (m, 2H), 6.51-6.47 (m, 2H), 6.36-6.34 (m, 1H) | [M + H] 357.2 | C |
| 189 | 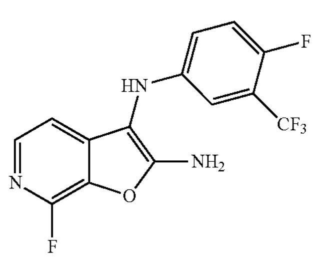 [SMILES: Nc1oc2c(F)nccc2c1Nc1ccc(F)c(C(F)(F)F)c1] | 7-Fluoro-$N^3$-(4-fluoro-3-(trifluoromethyl)phenyl)furo[2,3-c]pyridine-2,3-diamine | DMSO-$d_6$: δ 7.67 (d, J = 4.9 Hz, 1H), 7.34 (s, 1H), 7.24-7.18 (m, 3H), 6.85-6.82 (m, 2H), 6.74-6.71 (m, 1H) | [M − H] 328.2 | C |

TABLE 1-continued

| No. | Structure | IUPAC Name | ¹H-NMR (400 MHz) proton shift | LCMS | Proc. |
|---|---|---|---|---|---|
| 190 | 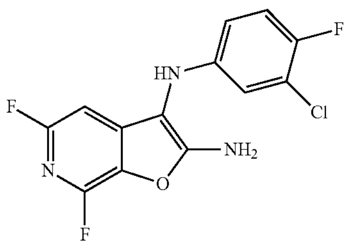 [SMILES: Nc1oc2c(F)nc(F)cc2c1Nc1ccc(F)c(Cl)c1] | N³-(3-Chloro-4-fluorophenyl)-5,7-difluoro-furo[2,3-c]pyridine-2,3-diamine | DMSO-d₆: δ 7.46 (s, 2H), 7.16-7.11 (m, 2H), 6.60 (dd, J' = 6.2 Hz, J" = 2.7 Hz, 1H), 6.48 (dt, J' = 8.8 Hz, J" = 6.8 Hz, J'" = 3.4 Hz, 1H), 6.42 (s, 1H) | [M + H] 314 | C |
| 191 | 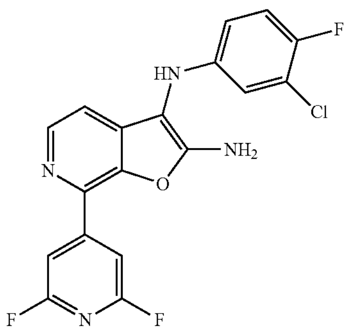 [SMILES: Nc1oc2c(-c3cc(F)nc(F)c3)nccc2c1Nc1ccc(F)c(Cl)c1] | N³-(3-Chloro-4-fluorophenyl)-7-(2,6-difluoro-pyridin-4-yl)furo[2,3-c]pyridine-2,3-diamine | DMSO-d₆: δ 8.23 (d, J = 4.9 Hz, 1H), 7.93 (s, 2H), 7.31 (bs, 2H), 7.19 (s, 1H), 7.14 (t, J = 9.1 Hz, 1H), 7.01 (d, J = 4.9 Hz, 1H), 6.60 (dd, , J' = 6.1 Hz, J" = 2.3 Hz, 1H), 6.52-6.50 (m, 1H) | [M + H] 391 | C |
| 192 | 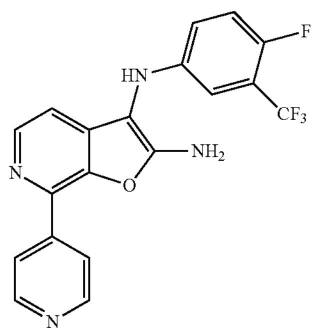 [SMILES: Nc1oc2c(-c3ccncc3)nccc2c1Nc1ccc(F)c(C(F)(F)F)c1] | N³-(4-Fluoro-3-(trifluoro-methyl)phenyl)-7-(pyridin-4-yl)furo[2,3-c]pyridine-2,3-diamine | DMSO-d₆: δ 8.75 (d, J = 5.1 Hz, 2H), 8.23 (bs, 3H), 7.36 (s, 1H), 7.24-7.20 (m, 3H), 6.97 (d, J = 4.7 Hz, 1H), 6.84 (bs, 1H), 6.77-6.75 (m, 1H) | [M + H] 389 | A |
| 193 | 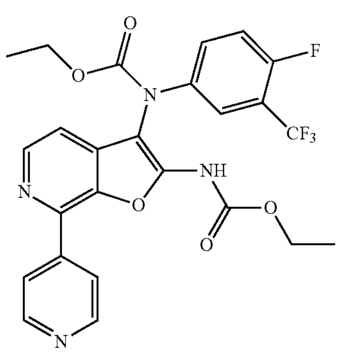 [SMILES: CCOC(=O)Nc1oc2c(-c3ccncc3)nccc2c1N(C(=O)OCC)c1ccc(F)c(C(F)(F)F)c1] | Ethyl (2-((ethoxy-carbonyl)amino)-7-(pyridin-4-yl)furo[2,3-c]pyridin-3-yl)(4-fluoro-3-(trifluoro-methyl)phenyl)carbamate | DMSO-d₆: δ 8.82 (bs, 2H), 8.60 (d, J = 5.1 Hz, 1H), 8.54 (s, 1H), 8.24 (s, 2H), 7.56 (d, J = 5.1 Hz, 1H), 7.36 (t, J = 9.5 Hz, 1H), 7.05-7.02 (m, 2H), 4.16 (q, J = 7.1 Hz, 4H), 1.07 (t, J = 7.1 Hz, 6H) | [M + H] 533.2 | H |
| 194 | 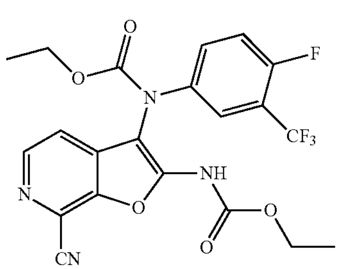 [SMILES: CCOC(=O)Nc1oc2c(C#N)nccc2c1N(C(=O)OCC)c1ccc(F)c(C(F)(F)F)c1] | Ethyl (7-cyano-2-((ethoxy-carbonyl)amino)furo[2,3-c]pyridin-3-yl)(4-fluoro-3-(trifluoro-methyl)phenyl)carbamate | CD₃CN: δ 8.50 (d, J = 5.1 Hz, 1H), 7.62 (d, J = 5.1 Hz, 1H), 7.18 (t, J = 10.0 Hz, 1H), 7.03-7.01 (m, 2H), 6.76 (s, 1H), 4.19 (q, J = 7.1 Hz, 4H), 1.14 (t, J = 7.1 Hz, 6H) | [M − H] 479.2 | H |

| No. | Structure | IUPAC Name | ¹H-NMR (400 MHz) proton shift | LCMS | Proc. |
|---|---|---|---|---|---|
| 195 | 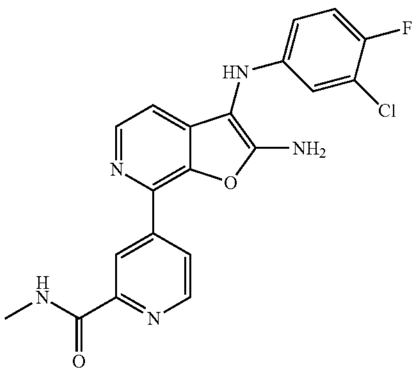 [SMILES: CNC(=O)c1cc(-c2nccc3c(Nc4ccc(F)c(Cl)c4)c(N)oc23)ccn1] | 4-(2-Amino-3-((3-chloro-4-fluorophenyl)amino)furo[2,3-c]pyridin-7-yl)-N-methyl-picolinamide | DMSO-$d_6$: δ 8.88 (s, 1H), 8.83-8.78 (m, 2H), 8.40 (d, J = 4.4 Hz, 1H), 8.25 (d, J = 4.9 Hz, 1H), 7.18-7.11 (m, 4H), 6.98 (d, J = 4.9 Hz, 1H), 6.62-6.60 (m, 1H), 6.53-6.51 (m, 1H), 2.88 (d, J = 4.6 Hz, 3H) | [M + H] 412 | J |
| 196 | 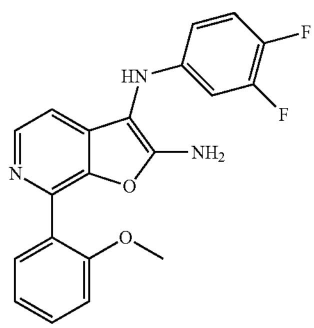 [SMILES: COc1ccccc1-c1nccc2c(Nc3ccc(F)c(F)c3)c(N)oc12] | $N^3$-(3,4-Difluoro-phenyl)-7-(2-methoxy-phenyl)furo[2,3-c]pyridine-2,3-diamine | DMSO-$d_6$: δ 8.09 (d, J = 5.1 Hz, 1H), 7.44 (t, J = 7.7 Hz, 1H), 7.38 (d, J = 7.4 Hz, 1H), 7.17-7.11 (m, 3H), 7.06 (t, J = 7.4 Hz, 1H), 6.84-6.82 (m, 3H), 6.44-6.40 (m, 1H), 6.32-6.30 (m, 1H), 3.76 (s, 3H) | [M + H] 368.1 | A |
| 197 | 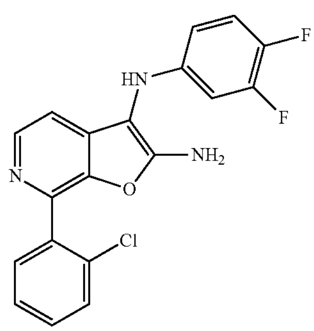 [SMILES: Nc1oc2c(-c3ccccc3Cl)nccc2c1Nc1ccc(F)c(F)c1] | 7-(2-Chlorophenyl)-$N^3$-(3,4-difluorophenyl)furo[2,3-c]pyridine-2,3-diamine | DMSO-$d_6$: δ 8.13 (d, J = 5.1 Hz, 1H), 7.61-.55 (m, 2H), 7.52-7.45 (m, 2H), 7.18-7.11 (m, 2H), 6.96 (bs, 2H), 6.90 (d, J = 5.0 Hz, 1H), 6.46-6.41 (m, 1H), 6.33-6.31 (m, 1H) | [M + H] 372 | A |
| 198 | 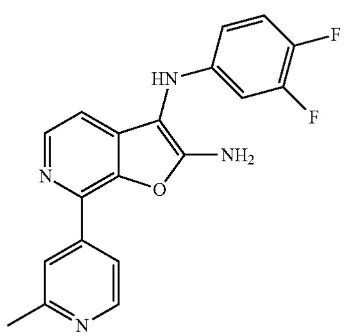 | $N^3$-(3,4-Difluoro-phenyl)-7-(2-methylpyridin-4-yl)furo[2,3-c]pyridine-2,3-diamine | DMSO-$d_6$: δ 8.60 (d, J = 5.0 Hz, 1H), 8.20 (d, J = 5.0 Hz, 1H), 8.09 (s, 1H), 8.03 (d, J = 4.8 Hz, 1H), 7.17-7.10 (m, 4H), 6.93 (d, J = 5.0 Hz, 1H), 6.47-6.42 (m, 1H), 6.34-6.32 (m, 1H), 2.58 (s, 3H) | [M + H] 353.1 | A |

TABLE 1-continued

| No. | Structure | IUPAC Name | ¹H-NMR (400 MHz) proton shift | LCMS | Proc. |
|---|---|---|---|---|---|
| 199 | 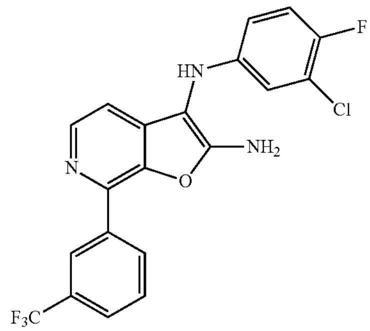 [SMILES: Nc1oc2c(-c3cccc(C(F)(F)F)c3)nccc2c1Nc1ccc(F)c(Cl)c1] | N³-(3-Chloro-4-fluorophenyl)-7-(3-(trifluoromethyl)phenyl)furo[2,3-c]pyridine-2,3-diamine | DMSO-d₆: δ 8.60-8.57 (m, 2H), 8.21 (d, J = 5.0 Hz, 1H), 7.84-7.77 (m, 2H), 7.17-7.12 (m, 4H), 6.92 (d, J = 5.0 Hz, 1H), 6.61 (dd, J' = 6.3 Hz, J" = 2.6 Hz, 1H), 6.51 (dt, J' = 8.9 Hz, J" = 6.7 Hz, J''' = 3.5 Hz, 1H) | [M + H] 422 | A, C |
| 200 | 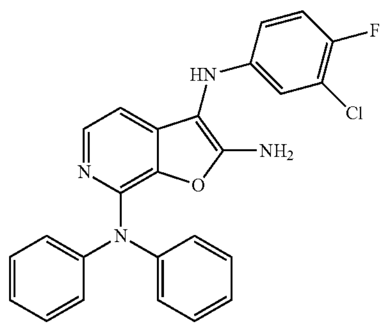 [SMILES: Nc1oc2c(N(c3ccccc3)c3ccccc3)nccc2c1Nc1ccc(F)c(Cl)c1] | N³-(3-Chloro-4-fluorophenyl)-N7,N7-diphenylfuro[2,3-c]pyridine-2,3,7-triamine | DMSO-d₆: δ 7.82 (d, J = 5.1 Hz, 1H), 7.27 (t, J = 7.8 Hz, 4H), 7.14 (t, J = 9.0 Hz, 1H), 7.05-7.01 (m, 3H), 6.93 (d, J = 7.8 Hz, 4H), 6.72 (d, J = 5.0 Hz, 1H), 6.67 (bs, 2H), 6.59 (dd, J' = 6.3 Hz, J" = 2.5 Hz, 1H), 6.49-6.44 (m, 1H) | [M + H] 445 | A |
| 201 | 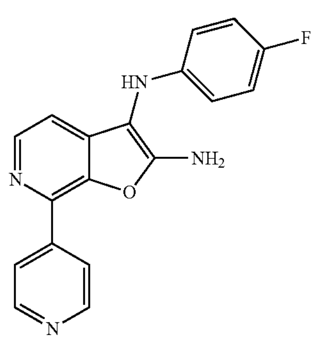 [SMILES: Nc1oc2c(-c3ccncc3)nccc2c1Nc1ccc(F)cc1] | N³-(4-Fluorophenyl)-7-(pyridin-4-yl)furo[2,3-c]pyridine-2,3-diamine | CD₃CN: δ 8.73 (d, J = 5.3 Hz, 2H), 8.27-8.24 (m, 3H), 7.01 (d, J = 4.8 Hz, 1H), 6.90 (t, J = 8.7 Hz, 2H), 6.62-6.59 (m, 2H), 5.58 (s, 1H), 5.49 (bs, 2H) | [M + H] 321.2 | A |
| 202 | 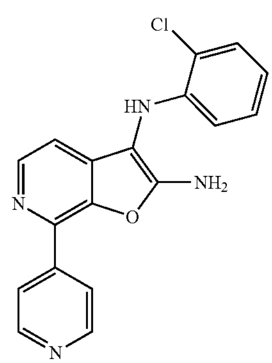 [SMILES: Nc1oc2c(-c3ccncc3)nccc2c1Nc1ccccc1Cl] | N³-(2-Chlorophenyl)-7-(pyridin-4-yl)furo[2,3-c]pyridine-2,3-diamine | CD₃CN: δ 8.78 (d, J = 6.2 Hz, 2H), 8.29-8.25 (m, 3H), 7.35 (d, J = 9.0 Hz, 1H), 7.07-7.04 (m, 2H), 6.72 (t, J = 6.7 Hz, 1H), 6.49 (d, J = 7.0 Hz, 1H), 5.89 (s, 1H), 5.83 (bs, 2H), | [M + H] 337 | A |

TABLE 1-continued

| No. | Structure | IUPAC Name | ¹H-NMR (400 MHz) proton shift | LCMS | Proc. |
|---|---|---|---|---|---|
| 203 | 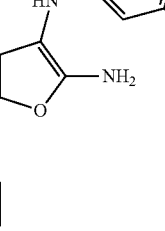 | 7-(Pyridin-4-yl)-N³-(3-(trifluoromethyl)phenyl)furo[2,3-c]pyridine-2,3-diamine | DMSO-$d_6$: δ 8.75 (d, J = 4.9 Hz, 2H), 8.24-8.21 (m, 3H), 7.44 (s, 1H), 7.30 (t, J = 7.8 Hz, 1H), 7.19 (bs, 2H), 6.96-6.90 (m, 2H), 6.84 (s, 1H), 6.77 (d, J = 7.5 Hz, 1H) | [M + H] 371 | A |
| 204 | 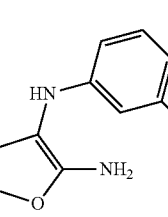 | N³-(3-Chloro-4-fluorophenyl)-7-(naphthalen-1-yl)furo[2,3-c]pyridine-2,3-diamine | $CD_3CN$: δ 8.30 (d, J = 5.1 Hz, 1H), 8.04-7.99 (m, 2H), 7.92 (d, J = 8.4 Hz, 1H), 7.74 (d, J = 6.8 Hz, 1H), 7.64 (t, J = 7.7 Hz, 1H), 7.56 (t, J = 7.5 Hz, 1H), 7.48 (t, J = 7.3 Hz, 1H), 7.07-7.03 (m, 2H), 6.71 (dd, J' = 6.1 Hz, J" = 2.6 Hz, 1H), 6.64-6.61 (m, 1H), 5.75 (s, 1H), 5.26 (s, 2H) | [M + H] 404 | A |
| 205 | 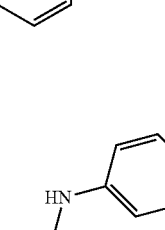 | N³-(4-fluoro-3-(trifluoromethyl)phenyl)-7-(2-methylpyridin-4-yl)furo[2,3-c]pyridine-2,3-diamine | $CD_3CN$: δ 8.73 (d, J = 5.7 Hz, 1H), 8.34 (s, 1H), 8.31-8.27 (m, 2H), 7.13-7.09 (m, 2H), 6.87-6.85 (m, 2H), 6.00 (bs, 3H), 2.75 (s, 3H) | [M + H] 403 | A |
| 206 | 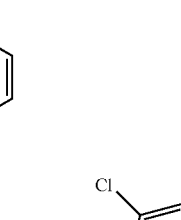 | N³-(2-chlorophenyl)-7-(2-methylpyridin-4-yl)furo[2,3-c]pyridine-2,3-diamine | $CD_3CN$: δ 8.75 (d, J = 5.4 Hz, 1H), 8.40-8.28 (m, 3H), 7.36 (d, J = 7.9 Hz, 1H), 7.14 (d, J = 5.0 Hz, 1H), 7.06 (t, J = 7.3 Hz, 1H), 6.73 (t, J = 7.3 Hz, 1H), 6.48 (d, J = 8.0 Hz, 1H), 6.09 (bs, 2H), 5.93 (s, 1H), 2.78 (s, 3H) | [M + H] 351 | A |

TABLE 1-continued

| No. | Structure | IUPAC Name | ¹H-NMR (400 MHz) proton shift | LCMS | Proc. |
|---|---|---|---|---|---|
| 207 | 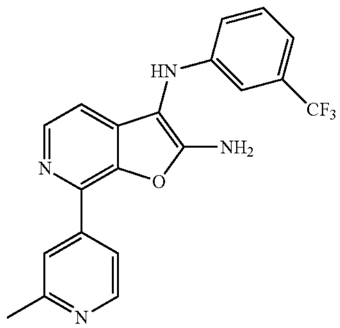 [SMILES: Cc1cc(-c2nccc3c(Nc4cccc(C(F)(F)F)c4)c(N)oc23)ccn1] | 7-(2-methylpyridin-4-yl)-N³-(3-(trifluoromethyl)phenyl)furo[2,3-c]pyridine-2,3-diamine | DMSO-$d_6$: δ 8.76 (d, J = 5.2 Hz, 1H), 8.22 (d, J = 5.6 Hz, 1H), 8.10-7.95 (m, 4H), 7.58 (s, 1H), 7.33 (t, J = 7.7 Hz, 1H), 7.08 (d, J = 5.4 Hz, 1H), 6.96 (d, J = 7.4 Hz, 1H), 6.87 (s, 1H), 6.81 (d, J = 8.0 Hz, 1H), 2.66 (s, 3H) | [M + H] 385.1 | A |
| 208 | 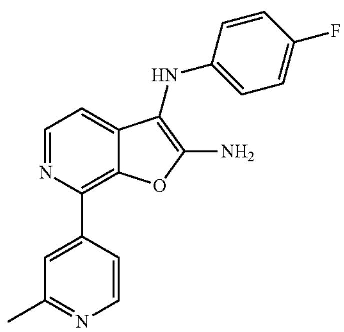 [SMILES: Cc1cc(-c2nccc3c(Nc4ccc(F)cc4)c(N)oc23)ccn1] | N³-(4-fluorophenyl)-7-(2-methylpyridin-4-yl)furo[2,3-c]pyridine-2,3-diamine | CD$_3$CN: δ 8.74 (d, J = 5.7 Hz, 1H), 8.34 (s, 1H), 8.30 (d, J = 5.6 Hz, 1H), 8.26 (d, J = 5.6 Hz, 1H), 7.12 (d, J = 5.4 Hz, 1H), 6.92 (t, J = 8.8 Hz, 2H), 6.63 (dd, J' = 8.9 Hz, J" = 4.5 Hz, 2H), 6.09 (bs, 2H), 5.71 (bs, 1H), 2.76 (s, 3H) | [M + H] 335.2 | A |
| 209 | 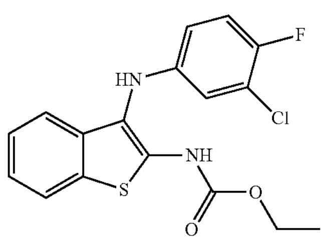 [SMILES: CCOC(=O)Nc1sc2ccccc2c1Nc1ccc(F)c(Cl)c1] | Ethyl (3-((3-chloro-4-fluorophenyl)amino)benzo[b]thiophen-2-yl)carbamate | (500 MHz, DMSO-$d_6$: δ 10.21 (s, 1H), 7.81 (d, J = 7.6 Hz, 1H), 7.54 (s, 1H), 7.27-7.21 (m, 3H), 7.10 (t, J = 9.0 Hz, 1H), 6.51-6.50 (m, 1H), 6.39-6.37 (m, 1H), 4.13 (q, J = 7.0 Hz, 2H), 1.19 (t, J = 7.0 Hz, 3H) | [M + H] 365.05 | G |
| 210 | 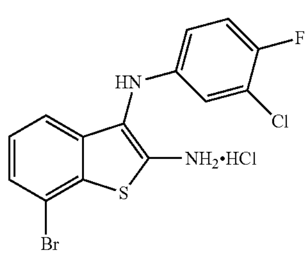 | 7-Bromo-N³-(3-chloro-4-fluorophenyl)benzo[b]thiophene-2,3-diamine hydrochloride | (500 MHz, DMSO-$d_6$: δ 7.32 (s, 1H), 7.16 (d, J = 7.8 Hz, 1H), 7.09-7.06 (m, 2H), 6.95 (d, J = 7.5 Hz, 1H), 6.47-6.46 (m, 1H), 6.42-6.39 (m, 1H), 6.16 (s, 2H) | [M + H] 370.9 | E, I |
| 211 | 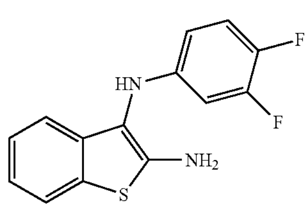 [SMILES: Nc1sc2ccccc2c1Nc1ccc(F)c(F)c1] | N³-(3,4-Difluorophenyl)benzo[b]thiophene-2,3-diamine | (500 MHz, CDCl$_3$: δ 7.59 (d, J = 7.4 Hz, 1H), 7.25-7.12 (m, 3H), 6.96-6.91 (m, 1H), 6.41-6.37 (m, 1H), 6.34-6.31 (m, 1H), 4.95 (s, 1H), 4.15 (s, 2H) | [M − H] 275.04 | E |

TABLE 1-continued

| No. | Structure | IUPAC Name | ¹H-NMR (400 MHz) proton shift | LCMS | Proc. |
|---|---|---|---|---|---|
| 212 | 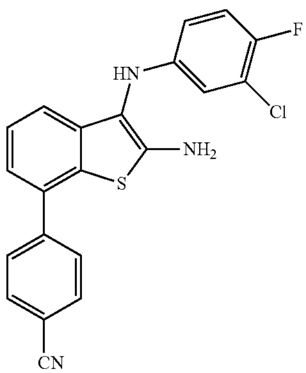 [SMILES: N#Cc1ccc(-c2cccc3c(Nc4ccc(F)c(Cl)c4)c(N)sc23)cc1] | 4-(2-Amino-3-((3-chloro-4-fluorophenyl)amino)benzo[b]thiophen-7-yl)benzonitrile | DMSO-$d_6$: δ 7.96 (d, J = 8.2 Hz, 2H), 7.84 (d, J = 8.7 Hz, 2H), 7.31 (s, 1H), 7.26 (t, J = 7.6 Hz, 1H), 7.11-7.06 (m, 2H), 7.02 (dd, J' = 7.8 Hz, J" = 0.9 Hz, 1H), 6.49 (dd, J' = 6.0 Hz, J" = 2.7 Hz, 1H), 6.43 (dt, J' = 8.7 Hz, J" = 6.8 Hz, J''' = 3.7 Hz, 1H), 6.00 (s, 2H) | [M − H] 392.04 | I |
| 213 | 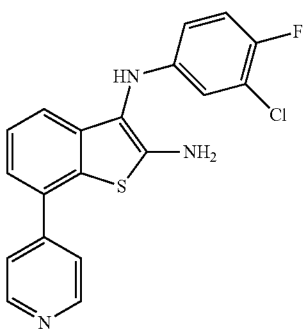 [SMILES: Nc1sc2c(-c3ccncc3)cccc2c1Nc1ccc(F)c(Cl)c1] | $N^3$-(3-Chloro-4-fluorophenyl)-7-(pyridin-4-yl)benzo[b]thiophene-2,3-diamine | DMSO-$d_6$: δ 8.68 (d, J = 5.9 Hz, 2H), 7.65 (d, J = 5.9 Hz, 2H), 7.32 (s, 1H), 7.27 (t, J = 7.6 Hz, 1H), 7.12-7.08 (m, 2H), 7.03 (d, J = 7.8 Hz, 1H), 6.50 (dd, J' = 6.0 Hz, J" = 2.3 Hz, 1H), 6.45-6.42 (m, 1H), 6.01 (s, 2H) | [M + H] 370.05 | I |
| 214 | 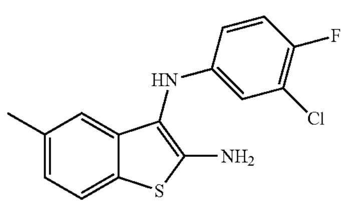 [SMILES: Cc1ccc2sc(N)c(Nc3ccc(F)c(Cl)c3)c2c1] | $N^3$-(3-Chloro-4-fluorophenyl)-5-methylbenzo[b]thiophene-2,3-diamine | DMSO-$d_6$: δ 7.42 (d, J = 8.7 Hz, 1H), 7.20 (s, 1H), 7.07 (t, J = 8.9 Hz, 1H), 6.79-6.77 (m, 2H), 6.45 (dd, J' = 6.4 Hz, J" = 2.7 Hz, 1H), 6.42-6.38 (m, 1H), 5.80 (s, 2H), 2.22 (s, 3H) | [M + H] 307.04 | E |
| 215 | 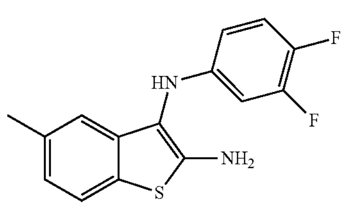 [SMILES: Cc1ccc2sc(N)c(Nc3ccc(F)c(F)c3)c2c1] | $N^3$-(3,4-difluorophenyl)-5-methylbenzo[b]thiophene-2,3-diamine | DMSO-$d_6$: δ 7.42 (d, J = 8.7 Hz, 1H), 7.21 (s, 1H), 7.10-7.03 (m, 1H), 6.79-6.76 (m, 2H), 6.32-6.27 (m, 1H), 6.24-6.21 (m, 1H), 5.78 (s, 2H), 2.22 (s, 3H) | [M + H] 291.07 | E |
| 216 | 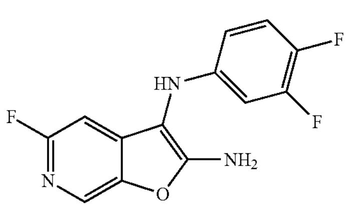 [SMILES: Nc1oc2cnc(F)cc2c1Nc1ccc(F)c(F)c1] | $N^3$-(3,4-difluorophenyl)-5-fluorofuro[2,3-c]pyridine-2,3-diamine | DMSO-$d_6$: δ 7.99 (s, 1H), 7.23 9s, 2H), 7.17-7.10 (m, 2H), 6.45-6.39 (m, 1H), 6.37 (s, 1H), 6.30-6.28 (m, 1H) | [M + H] 280.2 | C |

TABLE 1-continued

| No. | Structure | IUPAC Name | ¹H-NMR (400 MHz) proton shift | LCMS | Proc. |
|---|---|---|---|---|---|
| 217 | 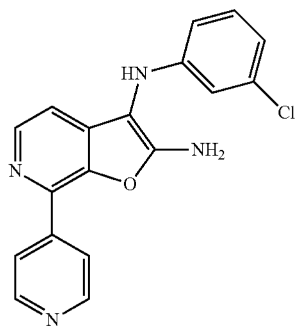 [SMILES: Nc1oc2c(-c3ccncc3)nccc2c1Nc1cccc(Cl)c1] | N³-(3-Chlorophenyl)-7-(pyridin-4-yl)furo[2,3-c]pyridine-2,3-diamine | CD$_3$CN: δ 8.73 (d, J = 5.9 Hz, 2H), 8.27-8.25 (m, 3H), 7.12 (t, J = 8.3 Hz, 1H), 7.04 (d, J = 5.0 Hz, 1H), 6.70 (d, J = 7.8 Hz, 1H), 6.60-6.58 (m, 2H), 5.82 (s, 1H), 5.56 (bs, 2H), | [M + H] 337 | A |
| 218 | 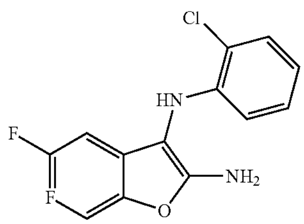 | N³-(2-Chlorophenyl)-5-fluorofuro[2,3-c]pyridine-2,3-diamine | DMSO-d$_6$: δ 8.00 (s, 1H), 7.30 (d, J = 7.8 Hz, 1H), 7.23 (s, 2H), 7.04 (t, J = 7.5 Hz, 1H), 6.67-6.62 (m, 2H), 6.34-6.32 (m, 2H), | [M + H] 278 | C |
| 219 | 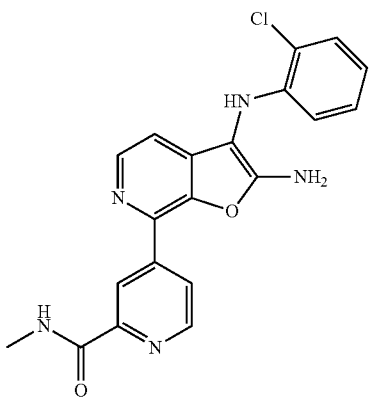 [SMILES: CNC(=O)c1cc(-c2nccc3c(Nc4ccccc4Cl)c(N)oc23)ccn1] | 4-(2-Amino-3-((2-chlorophenyl)amino)furo[2,3-c]pyridin-7-yl)-N-methyl-picolinamide | DMSO-d$_6$: δ 8.88 (s, 1H), 8.85 (d, J = 4.8 Hz, 1H), 8.79 (d, J = 5.1 Hz, 1H), 8.41-8.39 (m, 1H), 8.24 (d, J = 5.0 1H), 7.32 (d, J = 7.7 Hz, 1H), 7.22 (bs, 2H), 7.03 (t, J = 7.7 Hz, 1H), 6.93 (d, J = 5.0 Hz, 1H), 6.71 (s, 1H), 6.65 (t, J = 7.5 Hz, 1H), 6.38 (d, J = 7.8 Hz, 1H), 2.88 (d, J = 4.8 Hz, 3H) | [M + H] 394.2 | J |
| 220 | 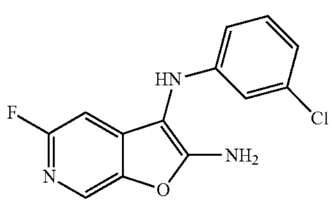 [SMILES: Nc1oc2cnc(F)cc2c1Nc1cccc(Cl)c1] | N³-(3-Chlorophenyl)-5-fluorofuro[2,3-c]pyridine-2,3-diamine | DMSO-d$_6$: δ 8.00 (s, 1H), 7.24 (s, 2H), 7.20 (s, 1H), 7.09 (t, J = 8.0 Hz, 1H), 6.62 (d, J = 7.4 Hz, 1H), 6.49-6.46 (m, 2H), 6.37 (s, 1H), | [M + H] 278.1 | C |
| 221 | 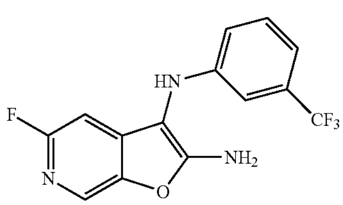 [SMILES: Nc1oc2cnc(F)cc2c1Nc1cccc(C(F)(F)F)c1] | 5-Fluoro-N³-(3-(trifluoromethyl)phenyl)furo[2,3-c]pyridine-2,3-diamine | CD$_3$CN: δ 7.97 (s, 1H), 7.30 (t, J = 7.8 Hz, 1H), 6.99 (d, J = 7.6 Hz, 1H), 6.83 (d, J = 7.8 Hz, 2H), 6.47 (s, 1H), 5.89 (s, 1H), 5.61 (s, 2H) | [M + H] 311.7 | C |
| 222 | 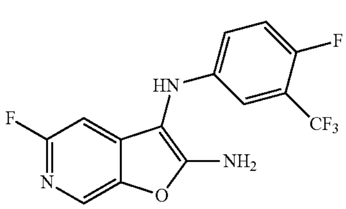 | 5-Fluoro-N-(4-fluoro-3-(trifluoromethyl)phenyl)furo[2,3-c]pyridine-2,3-diamine | DMSO-d$_6$: δ 8.00 (s, 1H), 7.29-7.19 (m, 4H), 6.81-6.80 (m, 1H), 6.72-6.70 (m, 1H), 6.42 (s, 1H) | [M + H] 330 | C |

TABLE 1-continued

| No. | Structure | IUPAC Name | $^1$H-NMR (400 MHz) proton shift | LCMS | Proc. |
|---|---|---|---|---|---|
| 223 | 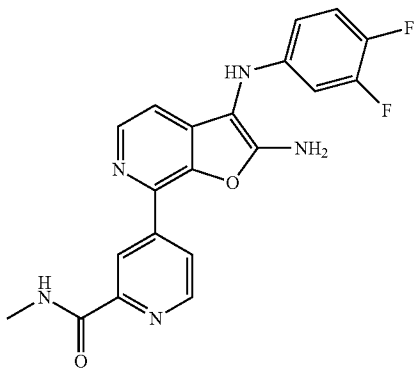 [SMILES: CNC(=O)c1cc(-c2nccc3c(Nc4ccc(F)c(F)c4)c(N)oc23)ccn1] | 4-(2-Amino-3-((3,4-difluorophenyl)amino)furo[2,3-c]pyridin-7-yl)-N-methyl-picolinamide | DMSO-$d_6$: δ 8.86 (s, 2H), 8.80 (d, J = 4.8 Hz, 1H), 8.38 (d, J = 3.9 Hz, 1H), 8.24 (d, J = 4.6 Hz, 1H), 7.27-7.13 (m, 4H), 6.97 (d, J = 4.6 Hz, 1H), 6.46 (dd, J' = 12.4 Hz, J" = 6.2 Hz, 1H), 6.35 (d, J = 7.6 Hz, 1H), 2.87 (d, J = 4.2 Hz, 3H) | [M + H] 396.2 | J |
| 224 | 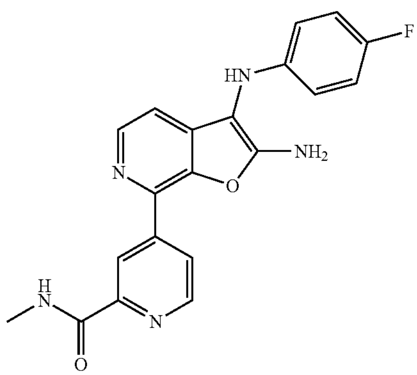 [SMILES: CNC(=O)c1cc(-c2nccc3c(Nc4ccc(F)cc4)c(N)oc23)ccn1] | 4-(2-Amino-3-((4-fluorophenyl)amino)furo[2,3-c]pyridin-7-yl)-N-methyl-picolinamide | DMSO-$d_6$: δ 8.86 (s, 2H), 8.80 (d, J = 4.9 Hz, 1H), 8.39 (d, J = 4.0 Hz, 1H), 8.23 (d, J = 5.0 Hz, 1H), 7.19 (bs, 1H), 6.95-6.92 (m, 4H), 6.56-6.53 (m, 2H), 2.87 (d, J = 4.5 Hz, 3H) | [M + H] 378 | J |
| 225 | 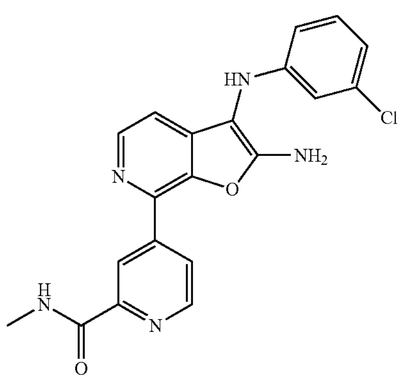 [SMILES: CNC(=O)c1cc(-c2nccc3c(Nc4cccc(Cl)c4)c(N)oc23)ccn1] | 4-(2-Amino-3-((3-chlorophenyl)amino)furo[2,3-c]pyridin-7-yl)-N-methyl-picolinamide | DMSO-$d_6$: δ 8.93 (s, 2H), 8.63 (s, 1H), 8.35 (bs, 2H), 8.24-8.20 (m, 2H), 7.46 (s, 1H), 7.16-7.09 (m, 2H), 6.69 (d, J = 7.0 Hz, 1H), 6.59-6.57 (m, 2H), 2.88 (d, J = 3.8 Hz, 3H) | [M + H] 394.2 | J |
| 226 | 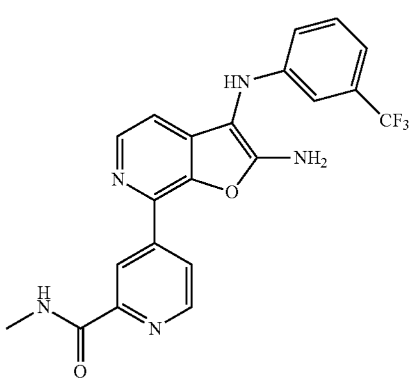 [SMILES: CNC(=O)c1cc(-c2nccc3c(Nc4cccc(C(F)(F)F)c4)c(N)oc23)ccn1] | 4-(2-Amino-3-((3-(trifluoromethyl)phenyl)amino)furo[2,3-c]pyridin-7-yl)-N-methyl-picolinamide | DMSO-$d_6$: δ 8.91 (d, J 2H), 8.76 (s, 1H), 8.30 (d, J = 4.2 Hz, 1H), 8.23 (d, J = 5.5 Hz, 1H), 7.95 (bh, 2H), 7.57 (s, 1H), 7.33 (t, J = 7.9 Hz, 1H), 7.07 (d, J = 5.4 Hz, 1H), 6.95 (d, J = 7.6 Hz, 1H), 6.88 (s, 1H, 6.81 (d, J = 8.2 Hz, 1H), 2.88 (d, J = 4.5 Hz, 3H) | [M + H] 428 | J |

TABLE 1-continued

| No. | Structure | IUPAC Name | $^1$H-NMR (400 MHz) proton shift | LCMS | Proc. |
|---|---|---|---|---|---|
| 227 | 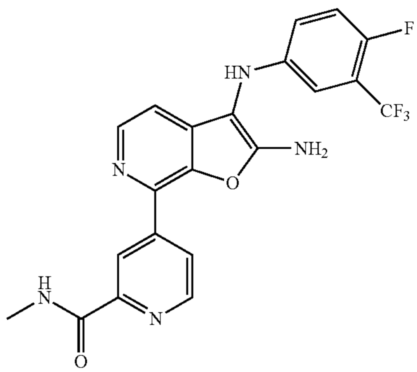 [SMILES: CNC(=O)c1cc(-c2nccc3c(Nc4ccc(F)c(C(F)(F)F)c4)c(N)oc23)ccn1] | 4-(2-amino-3-((4-fluoro-3-(trifluoromethyl)phenyl)amino)furo[2,3-c]pyridin-7-yl)-N-methylpicolinamide | DMSO-d$_6$: δ 8.96 (s, 2H), 8.63 (bs, 3H), 8.19 (s, 2H), 7.60 (s, 1H), 7.27 (t, J = 8.8 Hz, 1H), 7.17 (d, J = 4.4 Hz, 1H), 6.91 (s, 1H), 6.86 (s, 1H), 2.88 (s, 3H) | [M + H] 445.9 | J |
| 228 | 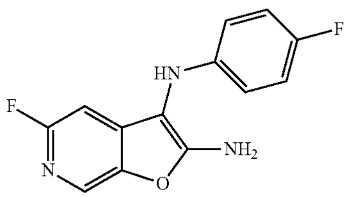 [SMILES: Nc1oc2cnc(F)cc2c1Nc1ccc(F)cc1] | 5-Fluoro-N$^3$-(4-fluorophenyl)furo[2,3-c]pyridine-2,3-diamine | DMSO-d$_6$: δ 7.98 (s, 1H), 7.17 (s, 2H), 6.93 (t, J = 8.5 Hz, 2H), 6.82 (s, 1H), 6.51-6.49 (m, 2H), 6.31 (s, 1H) | [M + H] 262.1 | C |
| 229 | 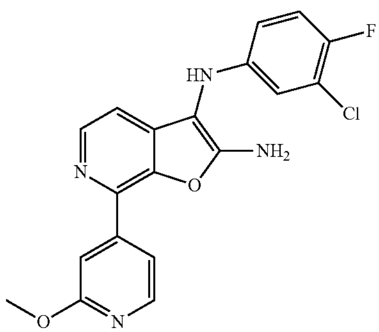 [SMILES: COc1cc(-c2nccc3c(Nc4ccc(F)c(Cl)c4)c(N)oc23)ccn1] | N$^3$-(3-Chloro-4-fluorophenyl)-7-(2-methoxypyridin-4-yl)furo[2,3-c]pyridine-2,3-diamine | DMSO-d$_6$: δ 8.32 (d, J = 5.4 Hz, 1H), 8.20 (d, J = 5.0 Hz, 1H), 7.85 (d, J = 5.3 Hz, 1H), 7.66 (s, 1H), 7.15-7.11 (m, 4H), 6.93 (d, J = 5.0 Hz, 1H), 6.60 (dd, J' = 6.2 Hz, J" = 2.5 Hz, 1H), 6.52-6.49 (m, 1H), 3.93 (s, 3H) | [M − H] 385.2 | A |
| 230 | 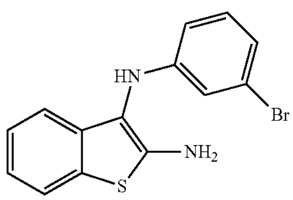 [SMILES: Nc1sc2ccccc2c1Nc1cccc(Br)c1] | N$^3$-(3-Bromophenyl)benzo[b]thiophene-2,3-diamine | (500 MHz, DMSO-d$_6$): δ 7.56 (d, J = 7.7 Hz, 1H), 7.31 (s, 1H), 7.10 (t, J = 7.0 Hz, 1H), 6.98-6.93 (m, 3H), 6.67 (d, J = 7.7 Hz, 1H), 6.56 (s, 1H), 6.47 (d, J = 8.0 Hz, 1H), 5.84 (s, 2H) | [M − H] 316.97 | E |
| 231 | 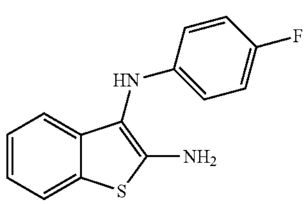 [SMILES: Nc1sc2ccccc2c1Nc1ccc(F)cc1] | N$^3$-(4-Fluorophenyl)benzo[b]thiophene-2,3-diamine | (500 MHz, DMSO-d$_6$): δ 7.55 (d, J = 7.7 Hz, 1H), 7.08 (t, J = 7.2 Hz, 1H), 6.96-6.94 (m, 3H), 6.86 (t, 8.2 Hz, 2H), 6.44 (bs, 2H), 5.74 (s, 2H), | [M + H] 259.07 | E |
| 232 | 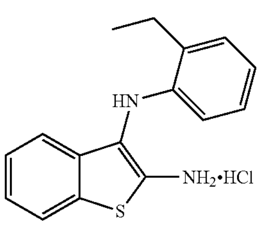 | N$^3$-(2-Ethylphenyl)benzo[b]thiophene-2,3-diamine hydrochloride | (500 MHz, DMSO-d$_6$): δ 7.58 (d, J = 8.1 Hz, 1H), 7.06 (t, J = 7.9 Hz, 1H), 7.00-6.94 (m, 2H), 6.87 (d, J = 7.8 Hz, 1H), 6.78 (d, J = 7.7 Hz, 1H), 6.53 (t, J = 7.3 Hz, 1H), 6.04 (d, J = 7.4 Hz, 1H), 2.69 (q, J = 7.5 Hz, 2H), 1.24 (t, J = 7.5 Hz, 3H) | [M + H] 269.11 | E |

TABLE 1-continued

| No. | Structure | IUPAC Name | $^1$H-NMR (400 MHz) proton shift | LCMS | Proc. |
|---|---|---|---|---|---|
| 233 | 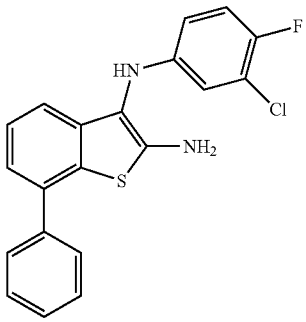 [SMILES: Nc1sc2c(-c3ccccc3)cccc2c1Nc1ccc(F)c(Cl)c1] | N$^3$-(3-Chloro-4-fluorophenyl)-7-phenylbenzo[b]thiophene-2,3-diamine | (500 MHz, DMSO-d$_6$): δ 7.63 (d, J = 7.4 Hz, 2H), 7.49 (t, J = 7.5 Hz, 2H), 7.41 (t, J = 7.5 Hz, 1H), 7.30 (s, 1H), 7.22 (t, J = 7.6 Hz, 1H), 7.09 (t, J = 9.0 Hz, 1H), 7.01 (d, J = 7.3 Hz, 1H), 6.96 (d, J = 7.6 Hz, 1H), 6.52-6.50 (m, 1H), 6.46-6.41 (m, 1H), 5.91 (s, 2H) | [M + H] 369.06 | I, E |
| 234 | 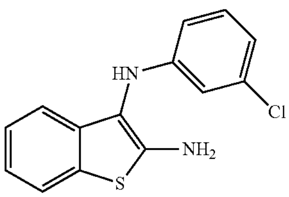 [SMILES: Nc1sc2ccccc2c1Nc1cccc(Cl)c1] | N$^3$-(3-Chlorophenyl)benzo[b]thiophene-2,3-diamine | (400 MHz, DMSO-d$_6$): δ 7.58 (dd, J' = 7.8 Hz, J" = 0.8 Hz, 1H), 7.35 (s, 1H), 7.12 (t, J = 7.6 Hz, 1H), 7.05 (t, J = 7.9 Hz, 1H), 7.00-6.95 (m, 2H), 6.58-6.56 (m, 1H), 6.47-6.45 (m, 1H), 6.42-6.43 (m, 1H), 5.88 (s, 2H) | [M + H] 275.04 | E |
| 235 | 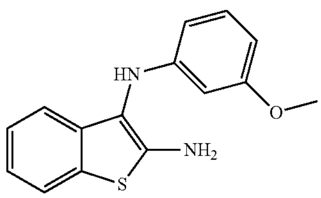 [SMILES: COc1cccc(Nc2c(N)sc3ccccc23)c1] | N$^3$-(3-Methoxyphenyl)benzo[b]thiophene-2,3-diamine | (500 MHz, DMSO-d$_6$): δ 7.55 (d, J = 8.1 Hz, 1H), 7.08 (t, J = 7.5 Hz, 1H), 7.01 (s, 1H), 6.96-6.90 (m, 3H), 6.14 (d, J = 7.8 Hz, 1H), 6.09 (d, J = 8.0 Hz, 1H), 6.03 (s, 1H), 5.70 (s, 2H), 3.58 (s, 3H) | [M + H] 271.09 | E |
| 236 | 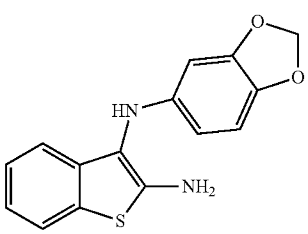 [SMILES: Nc1sc2ccccc2c1Nc1ccc2c(c1)OCO2] | N$^3$-(benzo[d][1,3]dioxol-5-yl)benzo[b]thiophene-2,3-diamine | (500 MHz, DMSO-d$_6$): δ 7.54 (d, J = 7.6 Hz, 1H), 7.08 (t, J = 7.2 Hz, 1H), 6.96-6.92 (m, 2H), 6.79 (s, 1H), 6.59 (d, J = 8.2 Hz, 1H), 6.10 (d, J = 2.5 Hz, 1H), 5.90 (dd, J' = 8.4 Hz, J" = 2.2 Hz, 1H), 5.78 (s, 2H), 5.70 (s, 2H) | [M + H] 285.06 | E |
| 237 | 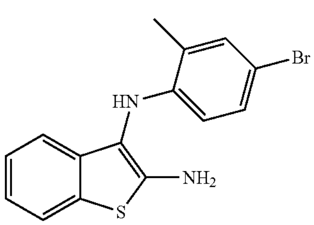 [SMILES: Cc1cc(Br)ccc1Nc1c(N)sc2ccccc12] | N$^3$-(4-Bromo-2-methylphenyl)benzo[b]thiophene-2,3-diamine | (500 MHz, DMSO-d$_6$): δ 7.56 (d, J = 7.7 Hz, 1H), 7.15 (s, 1H), 7.07 (t, J = 7.5 Hz, 1H), 6.94-6.93 (m, 2H), 6.85 (d, J = 7.7 Hz, 1H), 6.44 (s, 1H), 5.94 (d, J = 8.6 Hz, 1H), 5.82 (s, 2H), 2.27 (s, 3H) | [M + H] 333.01 | E |
| 238 | 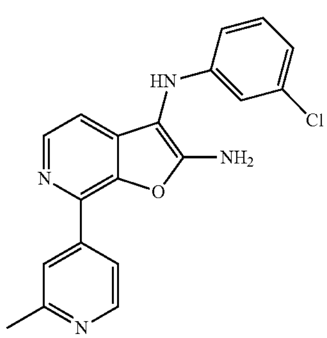 [SMILES: Cc1cc(-c2nccc3c(Nc4cccc(Cl)c4)c(N)oc23)ccn1] | N$^3$-(3-Chlorophenyl)-7-(2-methylpyridin-4-yl)furo[2,3-c]pyridine-2,3-diamine | CD$_3$CN: δ 8.72 (d, J = 5.6 Hz, 1H), 8.33 (s, 1H), 8.28 (d, J = 5.4 Hz, 2H), 7.15-7.10 (m, 2H), 6.72 (d, J = 8.8 Hz, 1H), 6.60 (d, J = 6.7 Hz, 2H), 6.00-5.97 (m, 3H), 2.74 (s, 3H) | [M + H] 351 | A |

TABLE 1-continued

| No. | Structure | IUPAC Name | $^1$H-NMR (400 MHz) proton shift | LCMS | Proc. |
|---|---|---|---|---|---|
| 239 | 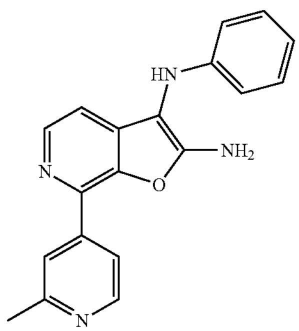 [SMILES: Cc1cc(-c2nccc3c(Nc4ccccc4)c(N)oc23)ccn1] | 7-(2-Methylpyridin-4-yl)-N$^3$-phenylfuro[2,3-c]pyridine-2,3-diamine | CD$_3$CN: δ 8.73 (d, J = 5.7 Hz, 1H), 8.32 (s, 1H), 8.28-8.25 (m, 2H), 7.15 (t, J = 7.8 Hz, 2H), 7.11 (d, J = 5.5 Hz, 1H), 6.73 (t, J = 7.3 Hz, 1H), 6.64 (d, J = 8.0 Hz, 2H), 6.05 (s, 2H), 5.75 (s, 1H), 2.75 (s, 3H) | [M + H] 317.2 | A |
| 240 | 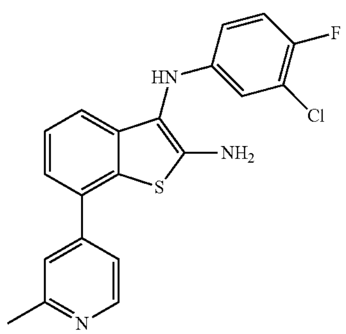 | N$^3$-(3-Chloro-4-fluorophenyl)-7-(2-methylpyridin-4-yl)benzo[b]thiophene-2,3-diamine | DMSO-d$_6$: δ 8.53 (d, J = 5.3 Hz, 1H), 7.52 (s, 1H), 7.44 (d, J = 4.4 Hz, 1H), 7.30 (s, 1H), 7.25 (t, J = 7.7 Hz, 1H), 7.11-7.06 (m, 2H), 7.01 (d, J = 7.6 Hz, 1H), 6.49 (dd, J' = 6.3 Hz, J'' = 2.6 Hz, 1H), 6.43 (dt, J' = 8.8 Hz, J'' = 6.0 Hz, J''' = 3.4 Hz, 1H), 5.99 (s, 2H), 2.51 (s, 3H) | [M + H] 384.07 | I |
| 241 | 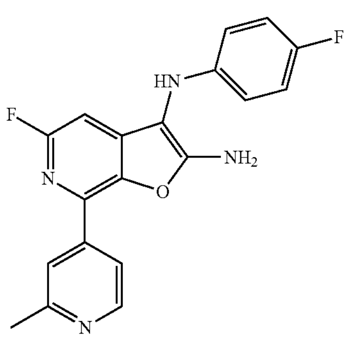 [SMILES: Cc1cc(-c2nc(F)cc3c(Nc4ccc(F)cc4)c(N)oc23)ccn1] | 5-Fluoro-N$^3$-(4-fluorophenyl)-7-(2-methylpyridin-4-yl)furo[2,3-c]pyridine-2,3-diamine | DMSO-d$_6$: δ 8.61 (d, J = 5.2 Hz, 1H), 8.00 (s, 1H), 7.96 (d, J = 5.2 Hz, 1H), 7.41 (s, 2H), 6.94 (t, J = 8.7 Hz, 2H), 6.89 (s, 1H), 6.56-6.63 (m, 2H), 6.40 (d, J = 2.2 Hz, 1H), 2.58 (s, 3H) | [M + H] 353.1 | C |
| 242 | 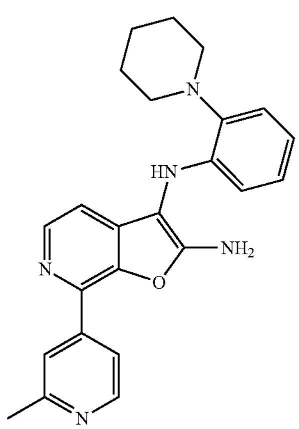 [SMILES: Cc1cc(-c2nccc3c(Nc4ccccc4N4CCCCC4)c(N)oc23)ccn1] | 7-(2-Methylpyridin-4-yl)-N$^3$-(2-(piperidin-1-yl)phenyl)furo[2,3-c]pyridine-2,3-diamine | CD$_3$CN: δ 8.60 (d, J = 5.1 Hz, 1H), 8.22 (d, J = 5.0 Hz, 1H), 8.15 (s, 1H), 8.08 (d, J = 5.3 Hz, 1H), 7.11 (d, J = 7.8 Hz, 1H), 6.92 (d, J = 5.0 Hz, 1H), 6.84 (t, J = 6.9 Hz, 1H), 6.69 (t, J = 7.1 Hz, 1H), 6.36 (d, J = 7.8 Hz, 1H), 6.03 (s, 1H), 5.46 (d, J = 2H), 2.93 (bs, 4H), 2.62 (s, 3H), 1.78-1.74 (m, 4H), 1.62-1.59 (m, 2H) | [M + H] 399.9 | A |

TABLE 1-continued

| No. | Structure | IUPAC Name | ¹H-NMR (400 MHz) proton shift | LCMS | Proc. |
|---|---|---|---|---|---|
| 243 | 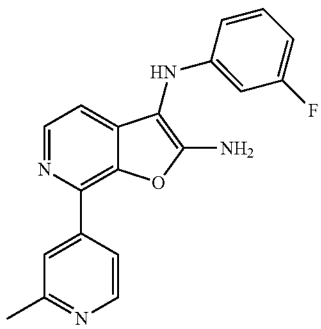 [SMILES: Cc1cc(-c2nccc3c(Nc4cccc(F)c4)c(N)oc23)ccn1] | N³-(3-Fluorophenyl)-7-(2-methylpyridin-4-yl)furo[2,3-c]pyridine-2,3-diamine | CD₃CN: δ 8.74 (d, J = 5.6 Hz, 1H), 8.35 (s, 1H), 8.31-8.27 (m, 2H), 7.17-7.12 (m, 2H), 6.51-6.43 (m, 2H), 6.35 (dt, J' = 12.0 Hz, J" = 4.4 Hz, J'" = 2.4 Hz, 1H), 6.06 (bs, 2H), 5.99 (s, 1H), 2.75 (s, 3H) | [M + H] 335.1 | A |
| 244 | 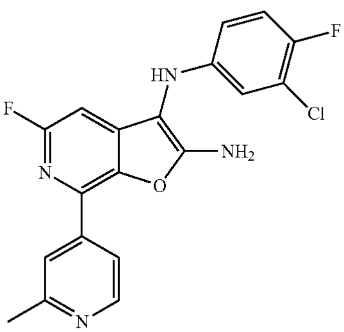 [SMILES: Cc1cc(-c2nc(F)cc3c(Nc4ccc(F)c(Cl)c4)c(N)oc23)ccn1] | N³-(3-Chloro-4-fluorophenyl)-5-fluoro-7-(2-methylpyridin-4-yl)furo[2,3-c]pyridine-2,3-diamine | DMSO-d₆: δ 8.84 (d, J = 5.2 Hz, 1H), 8.39 (s, 1H), 8.32 (bs, 1H), 7.64 (s, 2H), 7.20 (s, 1H), 7.15 (t, 9.1 Hz, 1H), 6.62 (dd, J' = 6.2 Hz, J" = 2.6 Hz, 1H), 6.60 (s, 1H), 6.56-6.52 (m, 1H), 2.74 (s, 3H) | [M + H] 387.1 | C |
| 245 | 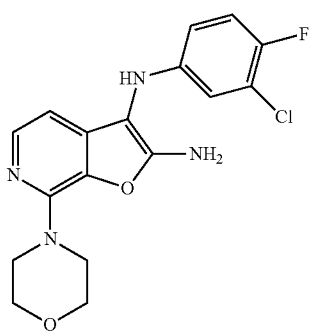 [SMILES: Nc1oc2c(N3CCOCC3)nccc2c1Nc1ccc(F)c(Cl)c1] | N³-(3-Chloro-4-fluorophenyl)-7-morpholino-furo[2,3-c]pyridine-2,3-diamine | DMSO-d₆: δ 7.68 (d, J = 5.2 Hz, 1H), 7.11 (t, J = 9.0 Hz, 1H), 7.05 (s, 1H), 6.59 (s, 2H), 6.53 (dd, J' = 6.0 Hz, J" = 2.0 Hz, 1H), 6.48-6.45 (m, 1H), 6.41 (d, J = 4.8 Hz, 1H), 3.75 (d, J = 4.4 Hz, 4H), 3.61 (d, J = 4.4 Hz, 4H) | [M + H] 363.2 | A |
| 246 | 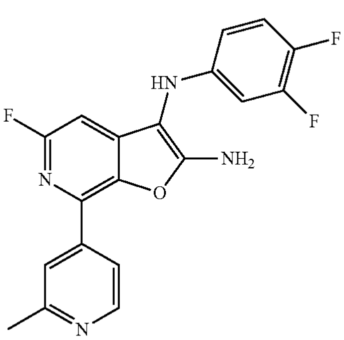 [SMILES: Cc1cc(-c2nc(F)cc3c(Nc4ccc(F)c(F)c4)c(N)oc23)ccn1] | N³-(3,4-Difluorophenyl)-5-fluoro-7-(2-methylpyridin-4-yl)furo[2,3-c]pyridine-2,3-diamine | DMSO-d₆: δ 8.61 (d, J = 5.0 Hz, 1H), 7.99 (s, 1H), 7.96 (d, J = 4.8 Hz, 1H), 7.47 (s, 2H), 7.17-7.11 (m, 2H), 6.50-6.46 (m, 2H), 6.36-6.33 (m, 1H), 2.59 (s, 3H) | [M + H] 371.2 | C |

TABLE 1-continued

| No. | Structure | IUPAC Name | ¹H-NMR (400 MHz) proton shift | LCMS | Proc. |
|---|---|---|---|---|---|
| 247 | 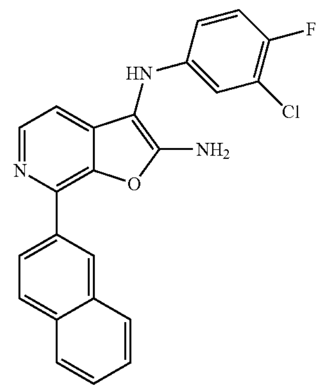 [SMILES: Nc1oc2c(-c3ccc4ccccc4c3)nccc2c1Nc1ccc(F)c(Cl)c1] | N³-(3-Chloro-4-fluorophenyl)-7-(naphthalen-2-yl)furo[2,3-c]pyridine-2,3-diamine | DMSO-d₆: δ 8.84 (s, 1H), 8.44 (d, J = 8.5 Hz, 1H), 8.23 (d, J = 5.0 Hz, 1H), 8.07-8.05 (m, 2H), 8.00-7.97 (m, 1H), 7.60-7.57 (m, 2H), 7.19 (s, 1H), 7.15 (t, J = 9.1 Hz, 1H), 7.08 (bs, 2H), 6.90 (d, J = 4.9 Hz, 1H), 6.63-61 (m, 1H), 6.54-6.52 (m, 1H) | [M + H] 404 | A |
| 248 | 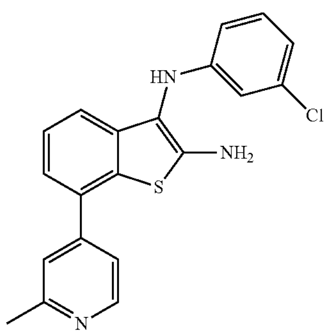 | N³-(3-Chlorophenyl)-7-(2-methylpyridin-4-yl)benzo[b]thiophene-2,3-diamine | DMSO-d₆: δ 8.53 (d, J = 5.3 Hz, 1H), 7.52 (s, 1H), 7.45 (d, J = 4.8 Hz, 1H), 7.40 (s, 1H), 7.25 (t, J = 7.7 Hz, 1H), 7.10-7.06 (m, 1H), 7.04-6.99 (m, 2H), 6.55 (d, J = 7.8 Hz, 1H), 6.45 (d, J = 8.0 Hz, 1H), 6.42 (s, 1H), 5.98 (s, 2H), 2.52 (s, 3H) | [M + H] 366.08 | A |
| 249 | 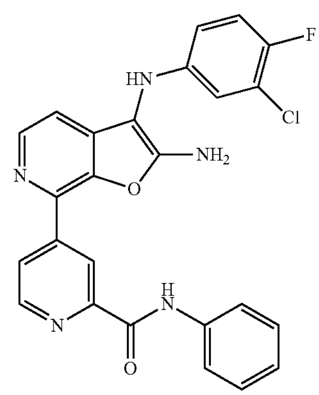 [SMILES: Nc1oc2c(-c3ccnc(C(=O)Nc4ccccc4)c3)nccc2c1Nc1ccc(F)c(Cl)c1] | 4-(2-Amino-3-((3-chloro-4-fluorophenyl)amino)furo[2,3-c]pyridin-7-yl)-N-phenyl-picolinamide | DMSO-d₆: δ 10.72 (s, 1H), 9.01 (s, 1H), 8.91 (d, J = 5.2 Hz, 1H), 8.48 (dd, J' = 5.1 Hz, J'' = 1.5 Hz, 1H), 8.27 (d, J = 5.0 Hz, 1H), 7.95 (d, J = 7.7 Hz, 2H), 7.39 (t, J = 8.0 Hz, 2H), 7.25 (bs, 2H), 7.20 (s, 1H), 7.17-7.12 (m, 2H), 7.00 (d, J = 5.0 Hz, 1H), 6.62 (dd, J' = 6.3 Hz, J'' = 2.7 Hz, 1H), 6.55-6.52 (m, 1H) | [M + H] 474.2 | J |
| 250 | 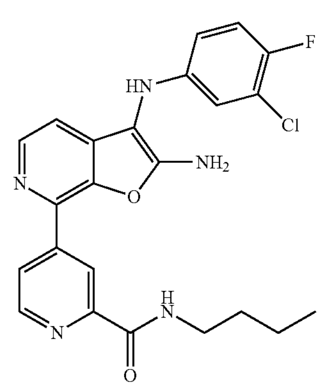 [SMILES: CCCCNC(=O)c1cc(-c2nccc3c(Nc4ccc(F)c(Cl)c4)c(N)oc23)ccn1] | 4-(2-Amino-3-((3-chloro-4-fluorophenyl)amino)furo[2,3-c]pyridin-7-yl)-N-butyl-picolinamide | DMSO-d₆: δ 8.87-8.83 (m, 2H), 8.80 (d, J = 5.0 Hz, 1H), 8.39 (d, J = 4.2 Hz, 1H), 8.25 (d, J = 5.0 Hz, 1H), 7.26 (bs, 2H), 7.19 (s, 1H), 7.14 (t, J = 9.1 Hz, 1H), 6.98 (d, J = 4.9 Hz, 1H), 6.61 (dd, J' = 6.6 Hz, J'' = 2.8 Hz, 1H), 6.53-6.51 (m, 1H), 3.37-3.32 (m, 2H, merged with DMSO water), 1.57-1.52 (m, 2H), 1.36-1.31 (m, 2H), 0.91 (t, J = 7.3 Hz, 3H) | [M + H] 454.4 | J |

TABLE 1-continued

| No. | Structure | IUPAC Name | $^1$H-NMR (400 MHz) proton shift | LCMS | Proc. |
|---|---|---|---|---|---|
| 251 | 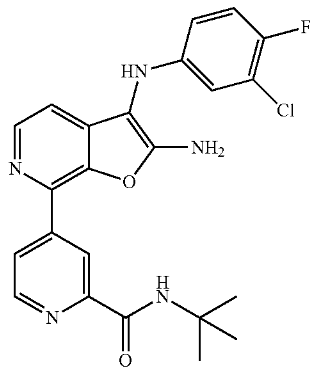 [SMILES: CC(C)(C)NC(=O)c1cc(-c2nccc3c(Nc4ccc(F)c(Cl)c4)c(N)oc23)ccn1] | 4-(2-Amino-3-((3-chloro-4-fluorophenyl)amino)furo[2,3-c]pyridin-7-yl)-N-(tert-butyl)picolinamide | DMSO-$d_6$: δ 8.82 (d, J = 4.4 Hz, 2H), 8.35 (d, J = 4.2 Hz, 1H), 8.23 (d, J = 5.4 Hz, 1H), 8.15 (s, 1H), 7.62 (bs, 2H), 7.25 (s, 1H), 7.15 (t, J = 9.1 Hz, 1H), 7.02 (d, J = 5.3 Hz, 1H), 6.63 (dd, J' = 6.2 Hz, J" = 2.5 Hz, 1H), 6.56-6.53 (m, 1H), 1.45 (s, 9H) | [M + H] 454.3 | J |
| 252 | 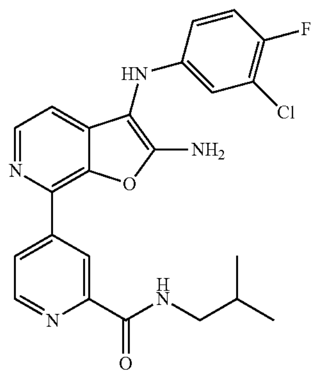 [SMILES: CC(C)CNC(=O)c1cc(-c2nccc3c(Nc4ccc(F)c(Cl)c4)c(N)oc23)ccn1] | 4-(2-Amino-3-((3-chloro-4-fluorophenyl)amino)furo[2,3-c]pyridin-7-yl)-N-isobutyl-picolinamide | DMSO-$d_6$: δ 8.89 (s, 1H), 8.85-8.79 (m, 2H), 8.41 (d, J = 3.8 Hz, 1H), 8.25 (d, J = 4.9 Hz, 1H), 7.20-7.18 (m, 3H), 7.14 (t, J = 9.1 Hz, 1H), 6.98 (d, J = 4.9 Hz, 1H), 6.62-6.61 (m, 1H), 6.53-6.51 (m, 1H), 3.18 (t, J = 6.3 Hz, 2H), 1.95-1.88 (m, 1H), 0.91 (d, J = 6.6 Hz, 3H) | [M + H] 454.3 | J |
| 253 | 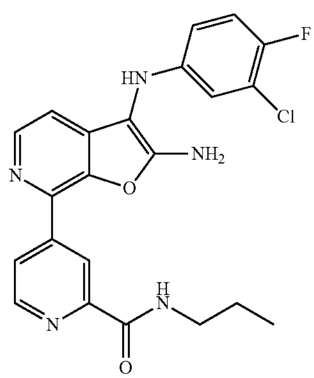 [SMILES: CCCNC(=O)c1cc(-c2nccc3c(Nc4ccc(F)c(Cl)c4)c(N)oc23)ccn1] | 4-(2-Amino-3-((3-chloro-4-fluorophenyl)amino)furo[2,3-c]pyridin-7-yl)-N-propyl-picolinamide | $CD_3CN$: δ 8.83-8.81 (m, 2H), 8.26 (s, 1H), 8.21 (dd, J' = 5.0 Hz, J" = 1.7 Hz, 1H), 8.14 (d, J = 5.9 Hz, 1H), 7.15 (d, J = 5.8 Hz, 1H), 7.06 (t, J = 9.0 Hz, 1H), 6.68 (dd, J' = 6.2 Hz, J" = 2.8 Hz, 1H), 6.63-6.60 (m, 1H), 6.43 (s, 2H), 5.83 (s, 1H), 3.40 (q, J = 6.8 Hz, 2H), 1.64 (sextet, J = 7.3 Hz, 2H), 0.96 (t, J = 7.4 Hz, 3H) | [M + H] 440.3 | J |
| 254 | 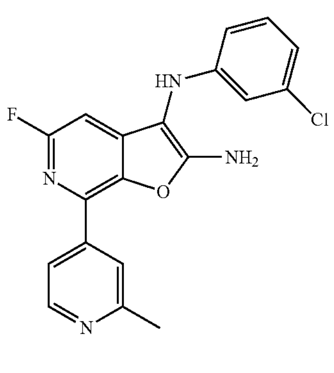 [SMILES: Cc1cc(-c2nc(F)cc3c(Nc4cccc(Cl)c4)c(N)oc23)ccn1] | N$^3$-(3-Ahlorophenyl)-5-fluoro-7-(2-methylpyridin-4-yl)furo[2,3-c]pyridine-2,3-diamine | DMSO-$d_6$: δ 8.62 (d, J = 5.2 Hz, 1H), 8.00 (s, 1H), 7.96 (d, J = 5.0 Hz, 1H), 7.49 (s, 2H), 7.27 (s, 1H), 7.11 (t, J = 8.0 Hz, 1H), 6.64 (d, J = 1.2 Hz, 1H), 6.55-6.50 (m, 2H), 6.47 (s, 1H), 2.59 (s, 3H) | [M + H] 369 | C |

TABLE 1-continued

| No. | Structure | IUPAC Name | $^1$H-NMR (400 MHz) proton shift | LCMS | Proc. |
|---|---|---|---|---|---|
| 256 | 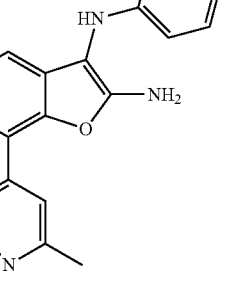 | $N^3$-(2,4-Difluorophenyl)-7-(2-methylpyridin-4-yl)furo[2,3-c]pyridine-2,3-diamine | DMSO-$d_6$: δ 8.60 (d, J = 4.8 Hz, 1H), 8.19 (d, J = 4.8 Hz, 1H), 8.09 (s, 1H), 8.03 (d, J = 5.2 Hz, 1H), 7.18-7.11 (m, 3H), 6.93 (d, J = 4.8 Hz, 1H), 6.79-6.75 (m, 2H), 6.37-6.31 (m, 1H), 2.59 (s, 3H) | [M + H] 353 | A |
| 257 | 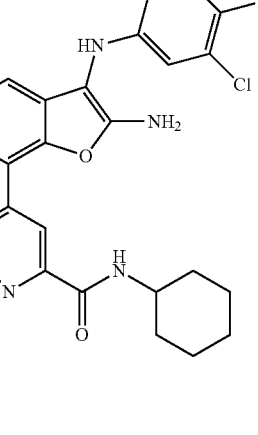 | 4-(2-Amino-3-((3-chloro-4-fluorophenyl)amino)furo[2,3-c]pyridin-7-yl)-N-cyclohexylpicolinamide | DMSO-$d_6$: δ 8.88 (s, 1H), 8.79 (d, J = 5.1 Hz, 1H), 8.52 (d, J = 8.6 Hz, 1H), 8.40 (dd, J' = 5.0 Hz, J" = 1.3 Hz, 1H), 8.25 (d, J = 5.0 Hz, 1H), 7.22 (s, 2H), 7.18 (s, 1H), 7.14 (t, J = 9.0 Hz, 1H), 6.98 (d, J = 5.0 Hz, 1H), 6.61 (dd, J' = 6.2 Hz, J" = 2.6 Hz, 1H), 6.54-6.51 (m, 1H), 3.84-3.82 (m, 1H), 1.85-1.82 (m, 2H), 1.75-1.72 (m, 2H), 1.62-1.59 (m, 1H), 1.48-1.30 (m, 4H), 1.21-1.15 (m, 1H) | [M + H] 480.2 | J |
| 258 | 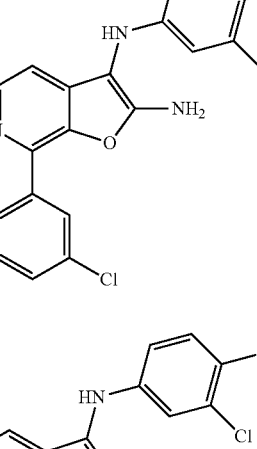 | $N^3$-(3-Chloro-4-fluorophenyl)-7-(3,5-dichlorophenyl)furo[2,3-c]pyridine-2,3-diamine | DMSO-$d_6$: δ 8.28 (d, J = 1.6 Hz, 2H), 8.18 (d, J = 5.0 Hz, 1H), 7.71 (s, 1H), 7.19-7.11 (m, 4H), 6.92 (d, J = 5.0 Hz, 1H), 6.60 (dd, J' = 6.2 Hz, J" = 2.5 Hz, 1H), 6.52-6.50 (m, 1H) | [M + H] 422 | A |
| 259 | 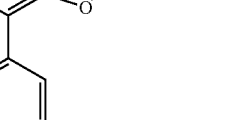 | 7-(2-(tert-Butyl)pyridin-4-yl)-$N^3$-(3-chloro-4-fluorophenyl)furo[2,3-c]pyridine-2,3-diamine | DMSO-$d_6$: δ 8.67 (d, J = 4.9 Hz, 1H), 8.24 (s, 1H), 8.22 (d, J = 4.9 Hz, 1H), 8.03 (d, J = 4.3 Hz, 1H), 7.18-7.11 (m, 4H), 6.94 (d, J = 4.9 Hz, 1H), 6.60-6.59 (m, 1H), 6.52-6.50 (m, 1H), 1.40 (s, 9H) | [M + H] 411 | A |

TABLE 1-continued

| No. | Structure | IUPAC Name | ¹H-NMR (400 MHz) proton shift | LCMS | Proc. |
|---|---|---|---|---|---|
| 260 | 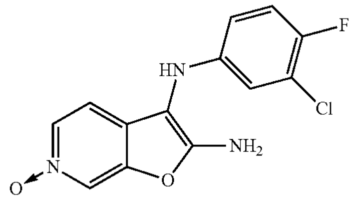 [SMILES: Nc1oc2c[n+]([O-])ccc2c1Nc1ccc(F)c(Cl)c1] | 2-Amino-3-((3-chloro-4-fluorophenyl)amino)furo[2,3-c]pyridine 6-oxide | DMSO-$d_6$: δ 8.43 (s, 1H), 7.83 (d, J = 6.4 Hz, 1H), 7.14 (t, J = 9.0 Hz, 2H), 6.99 (s, 2H), 6.77 (d, J = 6.5 Hz, 1H), 6.58 (dd, J' = 6.1 Hz, J" = 2.5 Hz, 1H), 6.50-6.47 (m, 1H) | [M + H] 294.1 | A |
| 261 | 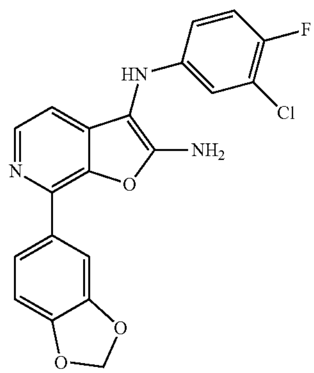 [SMILES: Nc1oc2c(-c3ccc4c(c3)OCO4)nccc2c1Nc1ccc(F)c(Cl)c1] | 7-(Benzo[d][1,3]dioxol-5-yl)-$N^3$-(3-chloro-4-fluorophenyl)furo[2,3-c]pyridine-2,3-diamine | DMSO-$d_6$: δ 8.11 (d, J = 5.2 Hz, 1H), 7.85 (d, J = 8.0 Hz, 1H), 7.80 (s, 1H), 7.15-7.13 (m, 2H), 7.07 (d, J = 8.8 Hz, 1H), 7.01 (s, 2H), 6.81 (d, J = 5.2 Hz, 1H), 6.58 (dd, J' = 6.0 Hz, J" = 2.4 Hz, 1H), 6.52-6.48 (m, 1H), 6.11 (s, 2H) | [M + H] 398.1 | A |
| 262 | 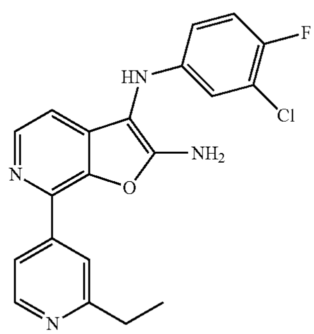 [SMILES: CCc1cc(-c2nccc3c(Nc4ccc(F)c(Cl)c4)c(N)oc23)ccn1] | $N^3$-(3-Chloro-4-fluorophenyl)-7-(2-ethylpyridin-4-yl)furo[2,3-c]pyridine-2,3-diamine | CD$_3$CN: δ 8.69 (d, J = 5.4 Hz, 1H), 8.20 (d, J = 5.5 Hz, 1H), 8.15 (s, 1H), 8.09 (d, J = 5.3 Hz, 1H), 7.11 (d, J = 5.4 Hz, 1H), 7.05 (t, J = 9.0 Hz, 1H), 6.66 (dd, J' = 6.2 Hz, 1H), 6.60 (dt, J' = 8.8 Hz, J" = 6.5 Hz, J'" = 3.3 Hz, 1H), 6.04 (s, 2H), 5.80 (s, 1H), 2.98 (q, J = 7.6 Hz, 2H), 1.38 (t, J = 7.6 Hz, 3H) | [M + H] 382.8 | J |
| 263 | 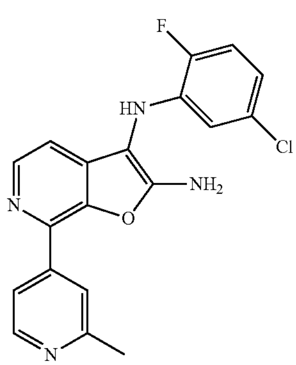 [SMILES: Cc1cc(-c2nccc3c(Nc4cc(Cl)ccc4F)c(N)oc23)ccn1] | $N^3$-(5-Chloro-2-fluorophenyl)-7-(2-methylpyridin-4-yl)furo[2,3-c]pyridine-2,3-diamine | DMSO-$d_6$: δ 8.61 (d, J = 5.2 Hz, 1H), 8.22 (d, J = 4.8 Hz, 1H), 8.10 (s, 1H), 8.04 (d, J = 4.8 Hz, 1H), 7.22 (d, J = 8.4 Hz, 2H), 7.15 (t, J = 10.2 Hz, 2H), 6.97 (d, J = 5.2 Hz, 1H), 6.64-6.62 (M, 1H), 6.29 (d, J = 6.0 Hz, 1H), 2.59 (s, 3H) | [M + H] 369.2 | A |

TABLE 1-continued

| No. | Structure | IUPAC Name | ¹H-NMR (400 MHz) proton shift | LCMS | Proc. |
|---|---|---|---|---|---|
| 264 | 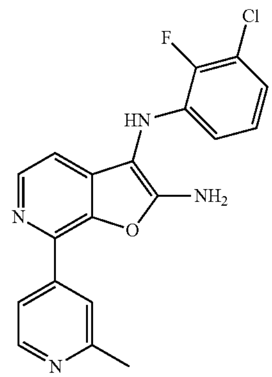 [SMILES: Cc1cc(-c2nccc3c(Nc4cccc(Cl)c4F)c(N)oc23)ccn1] | N³-(3-Chloro-2-fluorophenyl)-7-(2-methylpyridin-4-yl)furo[2,3-c]pyridine-2,3-diamine | DMSO-d$_6$: δ 8.61 (d, J = 4.8 Hz, 1H), 8.20 (d, J = 5.2 Hz, 1H), 8.09 (s, 1H), 8.03 (d, J = 5.2 Hz, 1H), 7.18 (s, 3H), 6.96 (d, J = 5.2 Hz, 1H), 6.88 (t, J = 7.6 Hz, 1H), 6.74 (t, J = 6.8 Hz, 1H), 6.32 (t, J = 7.2 Hz, 1H), 2.67 (s, 3H) | [M + H] 369.1 | A |
| 265 | 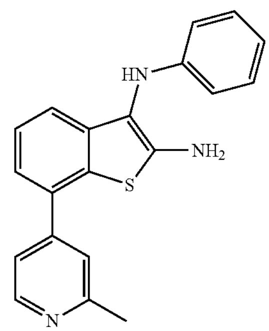 [SMILES: Cc1cc(-c2cccc3c(Nc4ccccc4)c(N)sc23)ccn1] | 7-(2-Methylpyridin-4-yl)-N³-phenylbenzo[b]thiophene-2,3-diamine | DMSO-d$_6$: δ 8.52 (d, J = 5.0 Hz, 1H), 7.51 (s, 1H), 7.45-7.43 (m, 1H), 7.22 (t, J = 7.6 Hz, 1H), 7.08-7.00 (m, 5H), 6.54 (t, J = 7.3 Hz, 1H), 6.49 (d, J = 7.8 Hz, 2H), 5.85 (s, 2H), 2.51 (s, 3H) | [M + H] 332.12 | I, E |
| 266 | 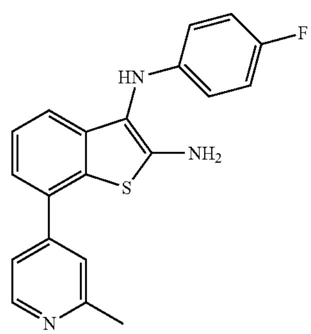 [SMILES: Cc1cc(-c2cccc3c(Nc4ccc(F)cc4)c(N)sc23)ccn1] | N³-(4-Fluorophenyl)-7-(2-methylpyridin-4-yl)benzo[b]thiophene-2,3-diamine | DMSO-d$_6$: δ 8.53 (d, J = 5.2 Hz, 1H), 7.51 (s, 1H), 7.44 (d, J = 4.6 Hz, 1H), 7.23 (t, J = 7.6 Hz, 1H), 7.08-7.06 (m, 2H), 6.99 (d, J = 7.8 Hz, 1H), 6.87 (t, J = 8.8 Hz, 2H), 6.46 (dd, J' = 8.7 Hz, J" = 4.6 Hz, 2H), 5.90 (s, 2H), 2.51 (s, 3H) | [M + H] 350.11 | I, E |
| 267 | 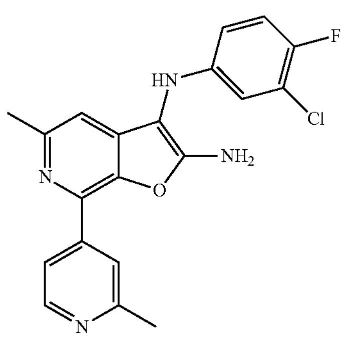 [SMILES: Cc1cc(-c2nc(C)cc3c(Nc4ccc(F)c(Cl)c4)c(N)oc23)ccn1] | N³-(3-Chloro-4-fluorophenyl)-5-methyl-7-(2-methylpyridin-4-yl)furo[2,3-c]pyridine-2,3-diamine | DMSO-d$_6$: δ 8.58 (d, J = 5.0 Hz, 1H), 8.06 (s, 1H), 8.01 (d, J = 4.6 Hz, 1H), 7.15-7.12 (m, 2H), 7.07 (s, 2H), 6.78 (s, 1H), 6.59 (dd, J' = 6.2 Hz, J" = 2.4 Hz, 1H), 6.50-6.48 (m, 1H), 2.58 (s, 3H), 2.45 (s, 3H) | [M + H] 383.1 | A |

TABLE 1-continued

| No. | Structure | IUPAC Name | ¹H-NMR (400 MHz) proton shift | LCMS | Proc. |
|---|---|---|---|---|---|
| 268 | 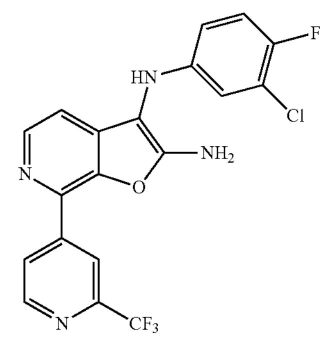 [SMILES: Nc1oc2c(-c3ccnc(C(F)(F)F)c3)nccc2c1Nc1ccc(F)c(Cl)c1] | N³-(3-Chloro-4-fluorophenyl)-7-(2-(trifluoromethyl)pyridin-4-yl)furo[2,3-c]pyridine-2,3-diamine | DMSO-$d_6$: δ 8.95 (d, J = 5.1 Hz, 1H), 8.64 (s, 1H), 8.55 (d, J = 4.8 Hz, 1H), 8.26 (d, J = 5.0 Hz, 1H), 7.28 (s, 2H), 7.19 (s, 1H), 7.14 (t, J = 9.1 Hz, 2H), 7.01 (d, J = 5.0 Hz, 1H), 6.61 (dd, J' = 6.2 Hz, J" = 2.6 Hz, 1H) | [M + H] 423.2 | J |
| 269 | 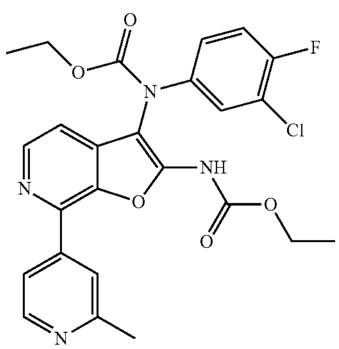 [SMILES: CCOC(=O)Nc1oc2c(-c3ccnc(C)c3)nccc2c1N(C(=O)OCC)c1ccc(F)c(Cl)c1] | Ethyl (3-chloro-4-fluorophenyl)(2-((ethoxycarbonyl)amino)-7-(2-methylpyridin-4-yl)furo[2,3-c]pyridin-3-yl)carbamate | DMSO-$d_6$: δ 8.67 (d, J = 5.2 Hz, 1H), 8.57 (d, J = 4.8 Hz, 1H), 8.35 (s, 1H), 8.07 (s, 1H), 8.02 (d, J = 5.2 Hz, 1H), 7.53 (d, J = 4.8 Hz, 1H), 7.26 (t, J = 9.0 Hz, 1H), 6.83 (dd, J' = 6.2 Hz, J" = 2.8 Hz, 1H), 6.76-6.73 (m, 1H), 4.17 (q, J = 6.9 Hz, 4H), 2.60 (s, 3H), 1.10 (t, J = 7.0 Hz, 6H) | [M + H] 513.2 | H |
| 271 | 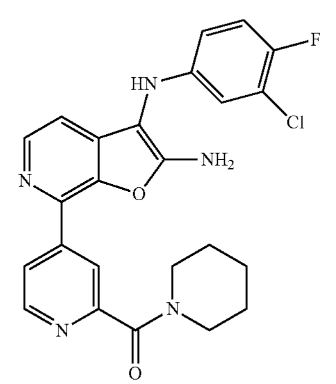 [SMILES: Nc1oc2c(-c3ccnc(C(=O)N4CCCCC4)c3)nccc2c1Nc1ccc(F)c(Cl)c1] | (4-(2-Amino-3-((3-chloro-4-fluorophenyl)amino)furo[2,3-c]pyridin-7-yl)pyridin-2-yl)(piperidin-1-yl)methanone | DMSO-$d_6$: δ 8.87 (d, J = 5.2 Hz, 1H), 8.06-8.03 (m, 2H), 7.94 (d, J = 4.4 Hz, 1H), 7.21 (d, J = 6.4 Hz, 1H), 7.08 (t, J = 9.2 Hz, 1H), 6.91 (s, 2H), 6.69 (dd, J' = 6.0 Hz, J" = 2.8 Hz, 1H), 6.63 (dt, J' = 8.6 Hz, J" = 7.0 Hz, J'" = 3.4 Hz, 1H), 5.90 (s, 1H), 3.71 (t, J = 5.2 Hz, 2H), 3.40 (t, J = 5.2 Hz, 2H), 1.71-1.66 (m, 4H), 1.57-1.55 (m, 2H) | [M + H] 466.1 | J |
| 272 | 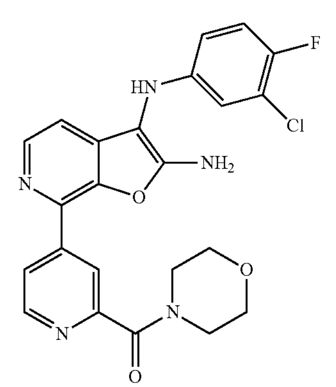 [SMILES: Nc1oc2c(-c3ccnc(C(=O)N4CCOCC4)c3)nccc2c1Nc1ccc(F)c(Cl)c1] | (4-(2-Amino-3-((3-chloro-4-fluorophenyl)amino)furo[2,3-c]pyridin-7-yl)pyridin-2-yl)(morpholino)methanone | DMSO-$d_6$: δ 8.75 (d, J = 5.2 Hz, 1H), 8.40 (s, 1H), 8.33 (d, J = 5.0 Hz, 1H), 8.23 (d, J = 5.0 Hz, 1H), 7.22 (s, 2H), 7.18 (s, 1H), 7.14 (t, J = 9.1 Hz, 1H), 6.97 (d, J = 5.0 Hz, 1H), 6.60 (dd, J' = 6.2 Hz, J" = 2.6 Hz, 1H), 6.51 (dt, J' = 8.8 Hz, J" = 6.6 Hz, J'" = 3.2 Hz, 1H), 3.70 (s, 4H), 3.59 (d, J = 4.1 Hz, 2H), 3.50 (d, J = 4.1 Hz, 2H) | [M + H] 468.3 | J |

TABLE 1-continued

| No. | Structure | IUPAC Name | $^1$H-NMR (400 MHz) proton shift | LCMS | Proc. |
|---|---|---|---|---|---|
| 273 | 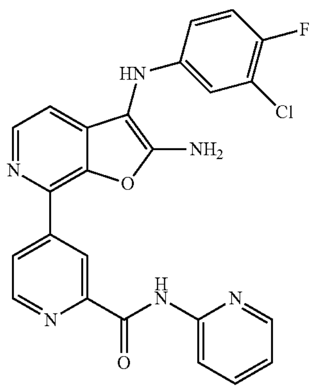 [SMILES: Nc1oc2c(-c3ccnc(C(=O)Nc4ccccn4)c3)nccc2c1Nc1ccc(F)c(Cl)c1] | 4-(2-Amino-3-((3-chloro-4-fluorophenyl)amino)furo[2,3-c]pyridin-7-yl)-N-(pyridin-2-yl)picolinamide | DMSO-$d_6$: δ 10.51 (s, 1H), 9.05 (s, 1H), 8.93 (d, J = 5.1 Hz, 1H), 8.54 (d, J = 5.1 Hz, 1H), 8.43 (d, J = 4.2 Hz, 1H), 8.33 (d, J = 8.3 Hz, 1H), 8.28 (d, J = 5.0 Hz, 1H), 7.94 (t, J = 7.9 Hz, 1H), 7.31 (bs, 2H), 7.25-7.21 (m, 2H), 7.15 (t, J = 9.1 Hz, 1H), 7.01 (d, J = 5.1 Hz, 1H), 6.62 (dd, J' = 6.2 Hz, J" = 2.6 Hz, 1H), 6.55-6.52 (m, 1H) | [M + H] 475.3 | J |
| 274 | 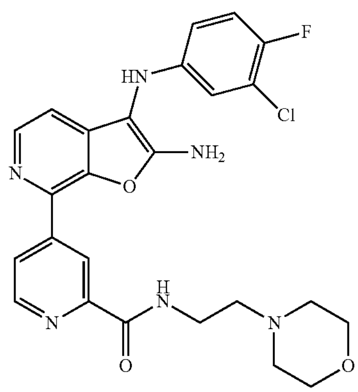 [SMILES: Nc1oc2c(-c3ccnc(C(=O)NCCN4CCOCC4)c3)nccc2c1Nc1ccc(F)c(Cl)c1] | 4-(2-Amino-3-((3-chloro-4-fluorophenyl)amino)furo[2,3-c]pyridin-7-yl)-N-(2-morpholinoethyl)picolinamide | CD$_3$CN: δ 9.01 (s, 1H), 8.74 (d, J = 5.0 Hz, 1H), 8.46-8.44 (m, 1H), 8.41 (bs, 1H), 8.19 (d, J = 4.9 Hz, 1H), 7.05-7.01 (m, 2H), 6.66 (dd, J' = 6.3 Hz, J" = 2.7 Hz, 1H), 6.59 (dt, J' = 8.8 Hz, J" = 6.7 Hz, J'" = 3.1 Hz, 1H), 5.74 (s, 1H), 5.61 (s, 2H), 3.67 (t, J = 4.4 Hz, 4H), 3.59-3.54 (m, 2H), 2.64-2.63 (m, 2H), 2.53 (s, 4H) | [M + H] 511.2 | J |
| 275 | 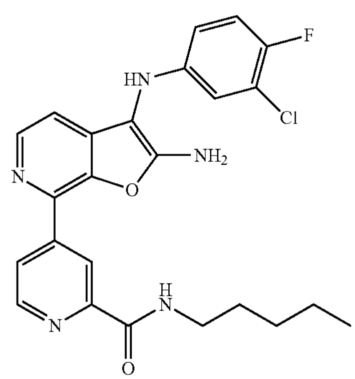 [SMILES: CCCCCNC(=O)c1cc(-c2nccc3c(Nc4ccc(F)c(Cl)c4)c(N)oc23)ccn1] | 4-(2-Amino-3-((3-chloro-4-fluorophenyl)amino)furo[2,3-c]pyridin-7-yl)-N-pentyl-picolinamide | CD$_3$CN: δ 8.90 (s, 1H), 8.77 (d, J = 5.2 Hz, 1H), 8.33-8.32 (m, 1H), 8.24-8.20 (m, 2H), 7.10-7.02 (m, 2H), 6.67 (dd, J' = 6.0 Hz, J" = 2.6 Hz, 1H), 6.60 (dt, J' = 8.8 Hz, J" = 6.4 Hz, J'" = 3.2 Hz, 1H), 6.01 (s, 2H), 5.78 (s, 1H), 3.42 (q, J = 6.8 Hz, 2H), 1.65-1.61 (m, 2H), 1.38-1.36 (m, 4H), 0.91 (t, J = 6.8 Hz, 3H) | [M + H] 468.2 | J |
| 276 | 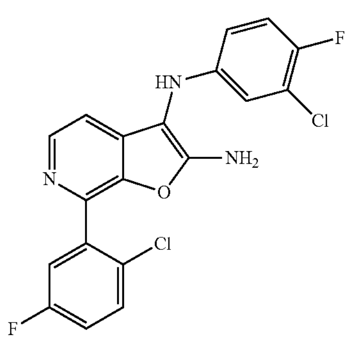 [SMILES: Nc1oc2c(-c3cc(F)ccc3Cl)nccc2c1Nc1ccc(F)c(Cl)c1] | N$^3$-(3-Chloro-4-fluorophenyl)-7-(2-chloro-5-fluorophenyl)furo[2,3-c]pyridine-2,3-diamine | CD$_3$CN: δ 8.22 (d, J = 4.8 Hz, 1H), 7.60-7.57 (m, 1H), 7.36 (d, J = 6.5 Hz, 1H), 7.27-7.23 (m, 1H), 7.06-7.02 (m, 2H), 6.65-6.64 (m, 1H), 6.58-6.56 (m, 1H), 5.73 (s, 1H), 5.40 (s, 2H) | [M + H] 406.1 | A |

| No. | Structure | IUPAC Name | ¹H-NMR (400 MHz) proton shift | LCMS | Proc. |
|---|---|---|---|---|---|
| 277 | 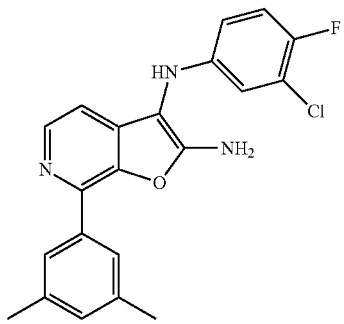 [SMILES: Cc1cc(C)cc(-c2nccc3c(Nc4ccc(F)c(Cl)c4)c(N)oc23)c1] | N³-(3-Chloro-4-fluorophenyl)-7-(3,5-dimethylphenyl)furo[2,3-c]pyridine-2,3-diamine | DMSO-d₆: δ 8.12 9 (d, J = 5.1 Hz, 1H), 7.23-7.21 (m, 2H), 7.17-7.12 (m, 3H), 6.93 (bs, 2H), 6.87 (d, J = 5.0 Hz, 1H), 6.61-6.59 (m, 1H), 6.51-6.48 (m, 1H), 2.32 (s, 3H), 2.16 (s, 3H) | [M + H] 381.8 | A |
| 278 | 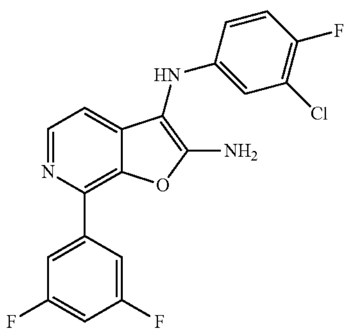 [SMILES: Nc1oc2c(-c3cc(F)cc(F)c3)nccc2c1Nc1ccc(F)c(Cl)c1] | N³-(3-Chloro-4-fluorophenyl)-7-(3,5-difluorophenyl)furo[2,3-c]pyridine-2,3-diamine | CD₃CN: δ 8.22 (d, J = 4.7 Hz, 1H), 8.01 (d, J = 8.8 Hz, 2H), 7.05-6.99 (m, 3H), 6.67-6.64 (m, 1H), 6.59-6.57 (m, 1H), 5.73 (s, 1H), 5.59 (s, 2H) | [M + H] 390.2 | A |
| 279 | 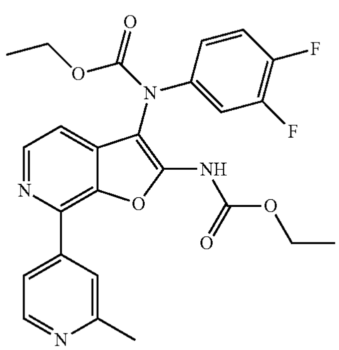 [SMILES: CCOC(=O)Nc1oc2c(-c3ccnc(C)c3)nccc2c1N(C(=O)OCC)c1ccc(F)c(F)c1] | Ethyl (3,4-difluorophenyl)(2-((ethoxycarbonyl)amino)-7-(2-methylpyridin-4-yl)furo[2,3-c]pyridin-3-yl)carbamate | DMSO-d₆: δ 8.72 (bs, 1H), 8.57 (d, J = 4.8 Hz, 1H), 8.33 (s, 1H), 8.09 (s, 1H), 8.03 (s, 1H), 7.51 (d, J = 4.8 Hz, 1H), 7.30-7.23 (m, 1H), 6.70-6.66 (m, 1H), 6.56-6.54 (m, 1H), 4.17 (q, J = 7.1 Hz, 4H), 2.60 (s, 3H), 1.09 (t, J = 7.0 Hz, 6H) | [M + H] 497.3 | H |
| 280 | 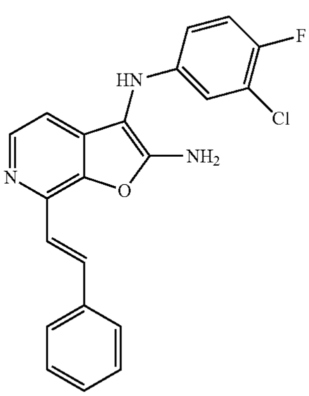 [SMILES: Nc1oc2c(/C=C/c3ccccc3)nccc2c1Nc1ccc(F)c(Cl)c1] | N³-(3-Chloro-4-fluorophenyl)-7-styrylfuro[2,3-c]pyridine-2,3-diamine | DMSO-d₆: δ 8.08 (d, J = 5.2 Hz, 1H), 7.81 (d, J = 16.0 Hz, 1H), 7.67 (d, J = 7.6 Hz, 2H), 7.45-7.39 (m, 3H), 7.34 (t, J = 7.2 Hz, 1H), 7.13 (t, J = 8.8 Hz, 2H), 6.98 (s, 2H), 6.78 (d, J = 5.2 Hz, 1H), 6.58 (dd, J' = 6.0 Hz, J" = 2.6 Hz, 1H), 6.50 (dt, J' = 8.8 Hz, J" = 6.8 Hz, J" = 3.6 Hz, 1H), | [M + H] 380.2 | A |

TABLE 1-continued

| No. | Structure | IUPAC Name | $^1$H-NMR (400 MHz) proton shift | LCMS | Proc. |
|---|---|---|---|---|---|
| 281 | 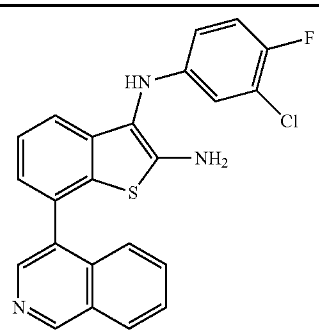 | N$^3$-(3-Chloro-4-fluorophenyl)-7-(isoquinolin-4-yl)benzo[b]thiophene-2,3-diamine | DMSO-d$_6$: δ 9.38 (s, 1H), 8.53 (s, 1H), 8.22 (d, J = 5.3 Hz, 1H), 7.71 (s, 2H), 7.58 (s, 1H), 7.32-7.29 (m, 2H), 7.13-7.07 (m, 2H), 7.03 (d, J = 6.9 Hz, 1H), 6.57-6.56 (m, 1H), 6.48-6.46 (m, 1H), 5.89 (s, 2H), | [M + H] 420.07 | I |

TABLE 2. is a non-exhaustive list of compounds of the invention that can be made using according the procedures described herein.

TABLE 2

| No. | Structure | IUPAC Name | M + 1 |
|---|---|---|---|
| 301 | 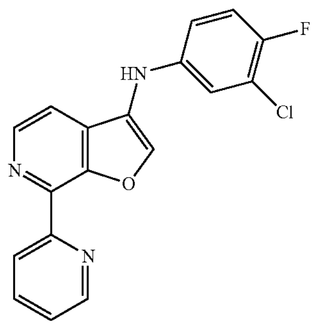 [SMILES: Fc1ccc(Nc2coc3c(-c4ccccn4)nccc23)cc1Cl] | N$^3$-(3-Chloro-4-fluorophenyl)-7-(pyridin-2-yl)furo[2,3-c]pyridine-2,3-diamine | 355.76 |
| 302 | 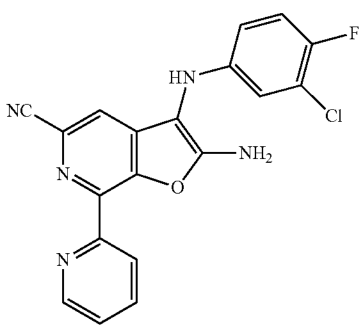 [SMILES: N#Cc1cc2c(Nc3ccc(F)c(Cl)c3)c(N)oc2c(-c2ccccn2)n1] | 2-Amino-3-((3-chloro-4-fluorophenyl)amino)-7-(pyridine-2-yl)furo[2,3-c]pyridine-5-carbonitrile | 380.06 |
| 303 | 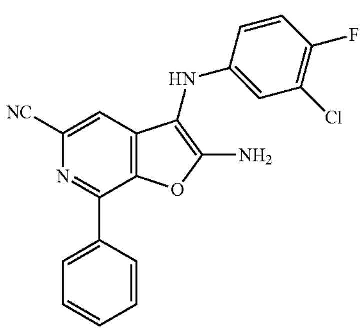 [SMILES: N#Cc1cc2c(Nc3ccc(F)c(Cl)c3)c(N)oc2c(-c2ccccc2)n1] | 2-Amino-3-((3-chloro-4-fluorophenyl)amino)-7-phenylfuro[2,3-c]pyridine-5-carbonitrile | 379.07 |

TABLE 2-continued

| No. | Structure | IUPAC Name | M + 1 |
|---|---|---|---|
| 304 | 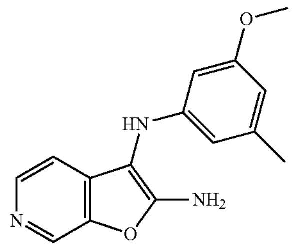 [SMILES: COc1cc(C)cc(Nc2c(N)oc3cnccc23)c1] | N³-(3-Methoxy-5-methylphenyl)furo[2,3-c]pyridine-2,3-diamine | 270.29 |
| 305 | 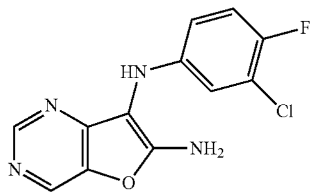 [SMILES: Nc1oc2cncnc2c1Nc1ccc(F)c(Cl)c1] | N⁷-(3-Chloro-4-fluorophenyl)furo[3,2-d]pyrimidine-6,7-diamine | 279.67 |
| 306 | 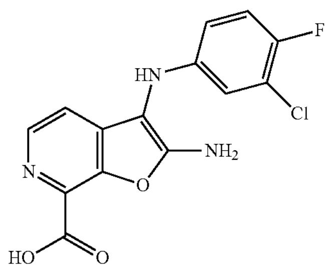 [SMILES: Nc1oc2c(C(=O)O)nccc2c1Nc1ccc(F)c(Cl)c1] | 2-Amino-3-((3-chloro-4-fluorophenyl)amino)furo[2,3-c]pyridine-7-carboxylic acid | 322.69 |
| 307 | 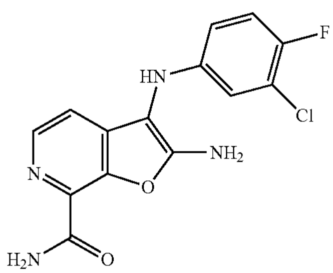 [SMILES: NC(=O)c1nccc2c(Nc3ccc(F)c(Cl)c3)c(N)oc12] | 2-Amino-3-((3-chloro-4-fluorophenyl)amino)furo[2,3-c]pyridine-7-carboxamide | 321.70 |
| 308 | 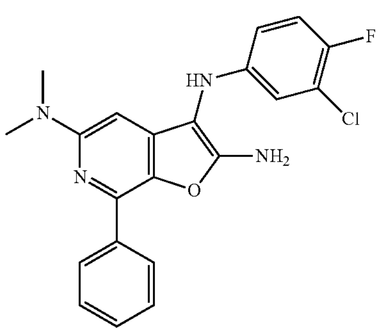 [SMILES: CN(C)c1cc2c(Nc3ccc(F)c(Cl)c3)c(N)oc2c(-c2ccccc2)n1] | N³-(3-Chloro-4-fluorophenyl)-N5,N5-dimethyl-7-phenylfuro[2,3-c]pyridine-2,3,5-triamine | 397.84 |
| 309 | 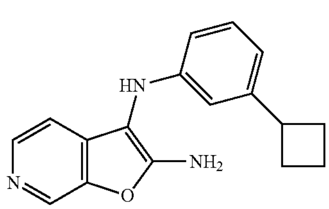 [SMILES: Nc1oc2cnccc2c1Nc1cccc(C2CCC2)c1] | N³-(3-Cyclobutylphenyl)furo[2,3-c]pyridine-2,3-diamine | 280.33 |

| No. | Structure | IUPAC Name | M + 1 |
|---|---|---|---|
| 310 | 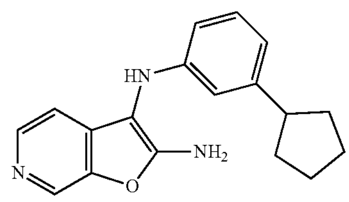 [SMILES: Nc1oc2cnccc2c1Nc1cccc(C2CCCC2)c1] | N³-(3-Cyclopentylphenyl)furo[2,3-c]pyridine-2,3-diamine | 294.36 |
| 311 | 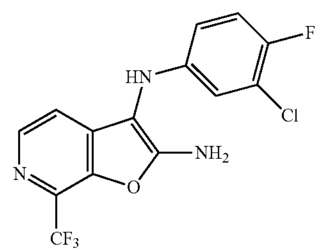 [SMILES: Nc1oc2c(C(F)(F)F)nccc2c1Nc1ccc(F)c(Cl)c1] | N³-(3-Chloro-4-fluorophenyl)-7-(trifluoromethyl)furo[2,3-c]pyridine-2,3-diamine | 346.67 |
| 312 | 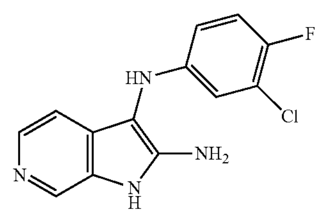 [SMILES: Nc1[nH]c2cnccc2c1Nc1ccc(F)c(Cl)c1] | N³-(3-Chloro-4-fluorophenyl)-1H-pyrrolo[2,3-c]pyridine-2,3-diamine | 276.68 |
| 313 | 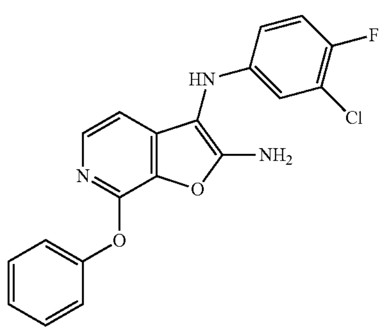 [SMILES: Nc1oc2c(Oc3ccccc3)nccc2c1Nc1ccc(F)c(Cl)c1] | N³-(3-Chloro-4-fluorophenyl)-7-phenoxyfuro[2,3-c]pyridine-2,3-diamine | 370.07 |
| 314 | 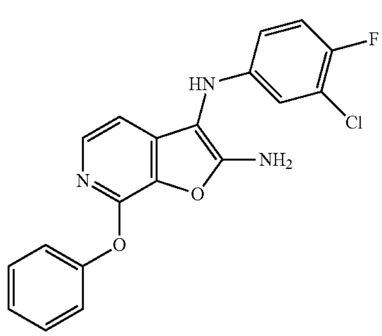 [SMILES: Nc1oc2c(Oc3ccccc3)nccc2c1Nc1ccc(F)c(Cl)c1] | N³-(3-Chloro-4-fluorophenyl)-7-(pyridine-2-yloxy)furo[2,3-c]pyridine-2,3-diamine | 371.06 |

TABLE 2-continued

| No. | Structure | IUPAC Name | M + 1 |
|---|---|---|---|
| 315 | 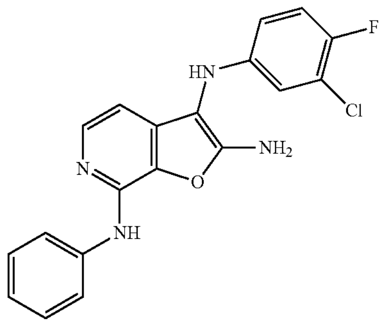 [SMILES: Nc1oc2c(Nc3ccccc3)nccc2c1Nc1ccc(F)c(Cl)c1] | $N^3$-(3-Chloro-4-fluorophenyl)-$N^7$-phenylfuro[2,3-c]pyridine-2,3,7-triamine | 369.08 |
| 316 | 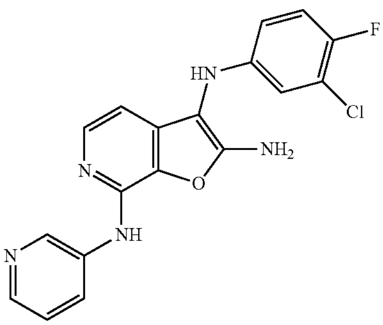 [SMILES: Nc1oc2c(Nc3cccnc3)nccc2c1Nc1ccc(F)c(Cl)c1] | $N^3$-(3-Chloro-4-fluorophenyl)-$N^7$-(pyridine-3-yl)furo[2,3-c]pyridine-2,3,7-triamine | 370.08 |
| 317 | 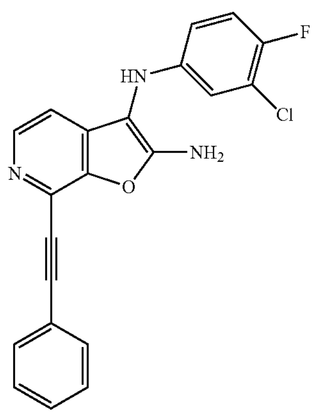 [SMILES: Nc1oc2c(C#Cc3ccccc3)nccc2c1Nc1ccc(F)c(Cl)c1] | $N^3$-(3-Chloro-4-fluorophenyl)-7-(phenylethynyl)furo[2,3-c]pyridine-2,3-diamine | 378.07 |
| 318 | 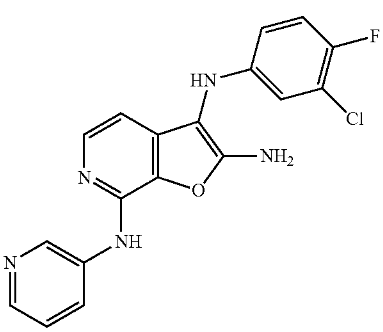 [SMILES: Nc1oc2c(Nc3cccnc3)nccc2c1Nc1ccc(F)c(Cl)c1] | $N^3$-(3-Chloro-4-fluorophenyl)-$N^7$-(pyridine-3-yl)furo[2,3-c]pyridine-2,3,7-triamine | 370.08 |

TABLE 2-continued

| No. | Structure | IUPAC Name | M + 1 |
|---|---|---|---|
| 319 | 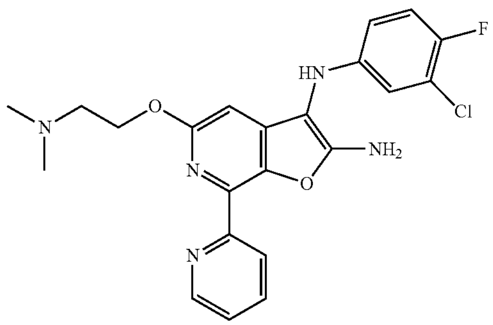 [SMILES: CN(C)CCOc1cc2c(Nc3ccc(F)c(Cl)c3)c(N)oc2c(-c2ccccn2)n1] | N³-(3-Chloro-4-fluorophenyl)-5-(2-(dimethylamino)ethoxy)-7-(pyridine-2-yl)furo[2,3-c]pyridine-2,3-diamine | 442.14 |
| 320 | 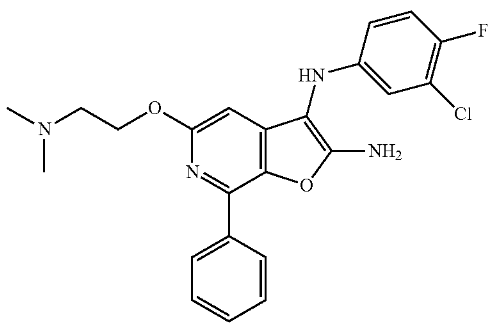 [SMILES: CN(C)CCOc1cc2c(Nc3ccc(F)c(Cl)c3)c(N)oc2c(-c2ccccc2)n1] | N³-(3-Chloro-4-fluorophenyl)-5-(3-dimethylamino)ethoxy)-7-phenylfuro[2,3-c]pyridine-2,3-diamine | 441.14 |
| 321 | 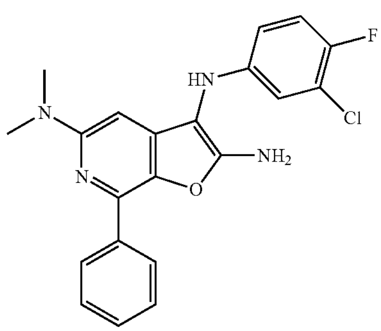 [SMILES: CN(C)c1cc2c(Nc3ccc(F)c(Cl)c3)c(N)oc2c(-c2ccccc2)n1] | N³-(3-Chloro-4-fluorophenyl)-N⁵,N⁵-dimethyl-7-phenylfuro[2,3-c]pyridine-2,3,5-triamine | 397.12 |
| 322 | 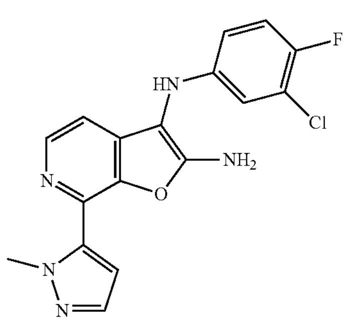 [SMILES: Cn1nccc1-c1nccc2c(Nc3ccc(F)c(Cl)c3)c(N)oc12] | N³-(3-Chloro-4-fluorophenyl)-7-(1-methyl-1H-pyrazol-5-yl)furo[2,3-c]pyridine-2,3-diamine | 358.08 |

TABLE 2-continued

| No. | Structure | IUPAC Name | M + 1 |
|---|---|---|---|
| 323 | 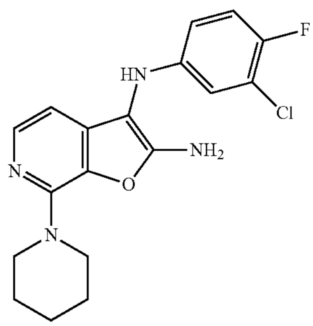 [SMILES: Nc1oc2c(N3CCCCC3)nccc2c1Nc1ccc(F)c(Cl)c1] | N³-(3-Chloro-4-fluorophenyl)-7-(piperidin-1-yl)furo[2,3-c]pyridine-2,3-diamine | 361.12 |
| 324 | 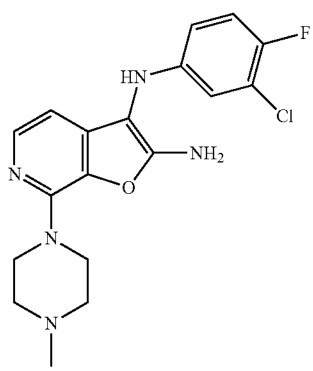 [SMILES: CN1CCN(c2nccc3c(Nc4ccc(F)c(Cl)c4)c(N)oc23)CC1] | N³-(3-Chloro-4-fluorophenyl)-7-(4-methylpiperazin-1-yl)furo[2,3-c]pyridine-2,3-diamine | 376.13 |
| 325 | 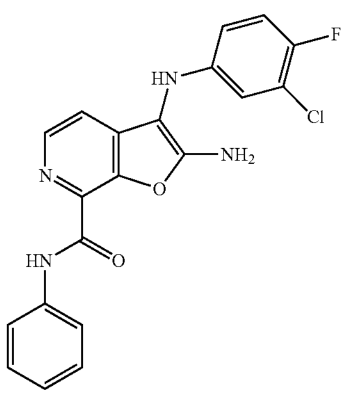 [SMILES: Nc1oc2c(C(=O)Nc3ccccc3)nccc2c1Nc1ccc(F)c(Cl)c1] | 2-Amino-3-((3-chloro-4-fluorophenyl)amino)-N-phenylfuro[2,3-c]pyridine-7-carboxamide | 397.08 |
| 326 | 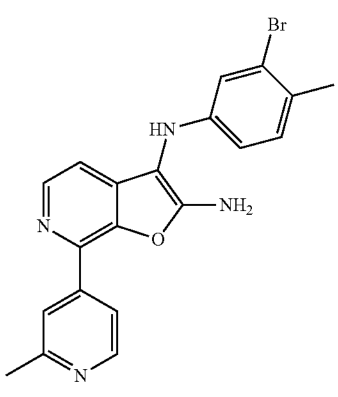 | N³-(3-Bromo-4-methylphenyl)-7-(2-methylpyridin-4-yl)furo[2,3-c]pyridine-2,3-diamine | 409.06 |

| No. | Structure | IUPAC Name | M + 1 |
|---|---|---|---|
| 327 | 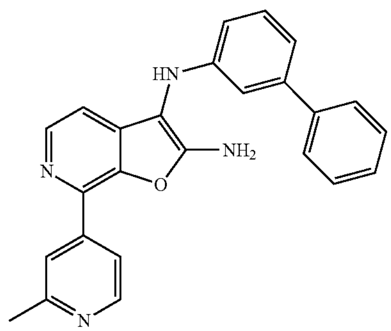 [SMILES: Cc1cc(-c2nccc3c(Nc4cccc(-c5ccccc5)c4)c(N)oc23)ccn1] | N³-([1,1'-Biphenyl]-3-yl)-7-(2-methylpyridin-4-yl)furo[2,3-c]pyridine-2,3-diamine | 393.17 |
| 328 | 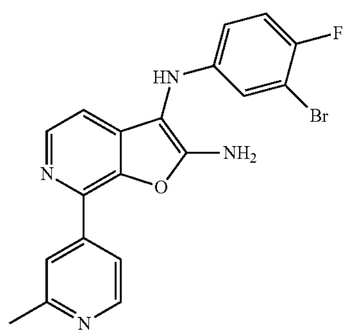 [SMILES: Cc1cc(-c2nccc3c(Nc4ccc(F)c(Br)c4)c(N)oc23)ccn1] | N³-(3-Bromo-4-fluorophenyl)-7-(2-methylpyridin-4-yl)furo[2,3-c]pyridine-2,3-diamine | 413.04 |
| 329 | 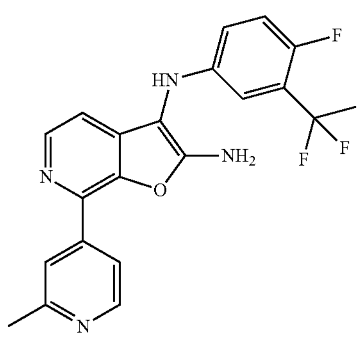 [SMILES: Cc1cc(-c2nccc3c(Nc4ccc(F)c(C(C)(F)F)c4)c(N)oc23)ccn1] | N³-(3-(1,1-Difluoroethyl)-4-fluorophenyl)-7-(2-methylpyridin-4-yl)furo[2,3-c]pyridine-2,3-diamine | 399.14 |
| 330 | 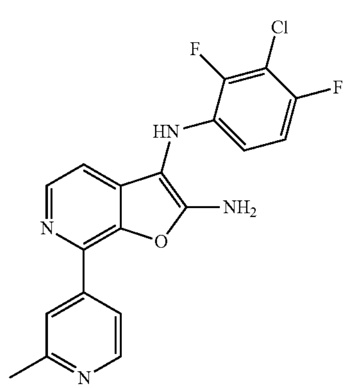 [SMILES: Cc1cc(-c2nccc3c(Nc4ccc(F)c(Cl)c4F)c(N)oc23)ccn1] | N³-(3-Chloro-2,4-difluorophenyl)-7-(2-methylpyridin-4-yl)furo[2,3-c]pyridine-2,3-diamine | 387.08 |

TABLE 2-continued

| No. | Structure | IUPAC Name | M + 1 |
|---|---|---|---|
| 331 | 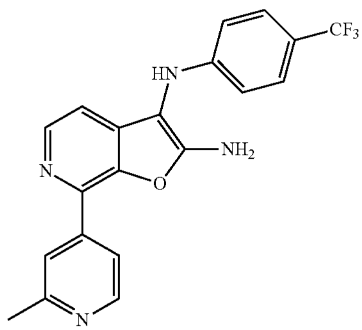 [SMILES: Cc1cc(-c2nccc3c(Nc4ccc(C(F)(F)F)cc4)c(N)oc23)ccn1] | 7-(2-Methylpyridin-4-yl)-N³-(4-(trifluoromethyl)phenyl)furo[2,3-c]pyridine-2,3-diamine | 385.12 |
| 332 | 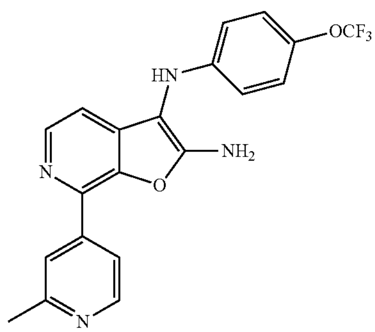 [SMILES: Cc1cc(-c2nccc3c(Nc4ccc(OC(F)(F)F)cc4)c(N)oc23)ccn1] | 7-(2-Methylpyridin-4-yl)-N³-(4-(trifluoromethoxy)phenyl)furo[2,3-c]pyridine-2,3-diamine | 401.12 |
| 333 | 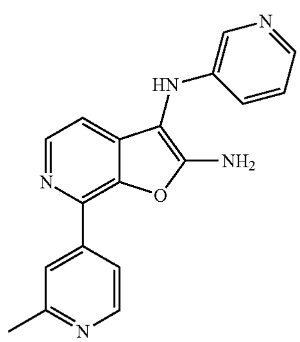 [SMILES: Cc1cc(-c2nccc3c(Nc4cccnc4)c(N)oc23)ccn1] | 7-(2-Methylpyridin-4-yl)-N³-(pyridin-3-yl)furo[2,3-c]pyridine-2,3-diamine | 318.13 |
| 334 | 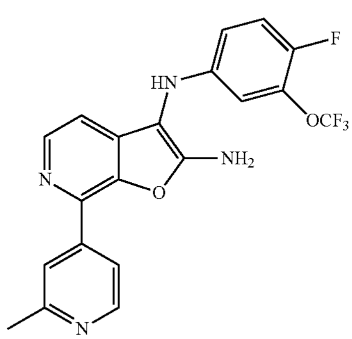 [SMILES: Cc1cc(-c2nccc3c(Nc4ccc(F)c(OC(F)(F)F)c4)c(N)oc23)ccn1] | N³-(4-Fluoro-3-(trifluoromethoxy)phenyl)-7-(2-methylpyridin-4-yl)furo[2,3-c]pyridine-2,3-diamine | 419.11 |

TABLE 2-continued

| No. | Structure | IUPAC Name | M + 1 |
|---|---|---|---|
| 335 | 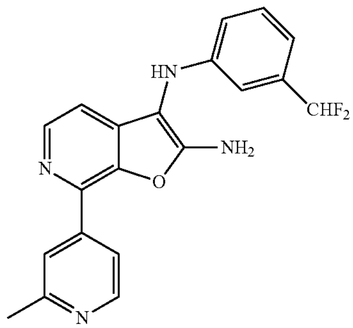 [SMILES: Cc1cc(-c2nccc3c(Nc4cccc(C(F)F)c4)c(N)oc23)ccn1] | N³-(3-(Difluoromethyl)phenyl)-7-(2-methylpyridin-4-yl)furo[2,3-c]pyridine-2,3-diamine | 367.13 |
| 336 | 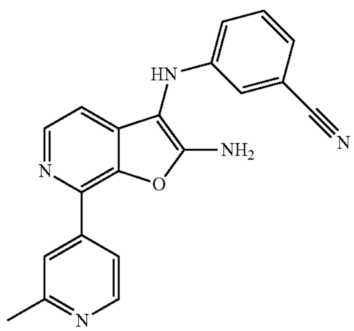 [SMILES: Cc1cc(-c2nccc3c(Nc4cccc(C#N)c4)c(N)oc23)ccn1] | 3-((2-Amino-7-(2-methylpyridin-4-yl)furo[2,3-c]pyridin-3-yl)amino)benzonitrile | 342.13 |
| 337 | 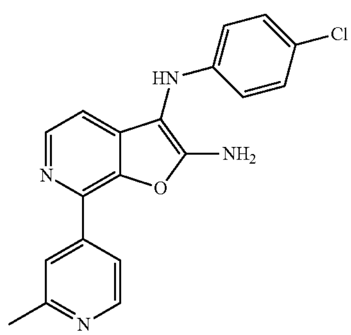 [SMILES: Cc1cc(-c2nccc3c(Nc4ccc(Cl)cc4)c(N)oc23)ccn1] | N³-(4-Chlorophenyl)-7-(2-methylpyridin-4-yl)furo[2,3-c]pyridine-2,3-diamine | 351.10 |
| 338 | 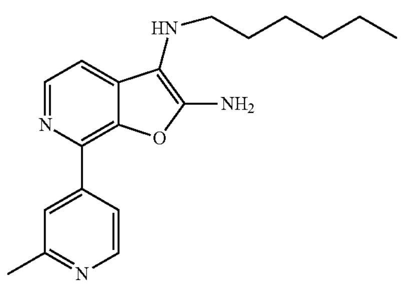 [SMILES: CCCCCCNc1c(N)oc2c(-c3ccnc(C)c3)nccc12] | N³-Hexyl-7-(2-methylpyridin-4-yl)furo[2,3-c]pyridine-2,3-diamine | 325.20 |

TABLE 2-continued

| No. | Structure | IUPAC Name | M + 1 |
|---|---|---|---|
| 339 | 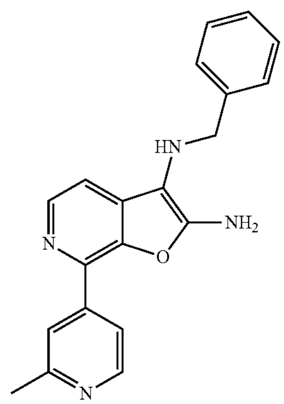 [SMILES: Cc1cc(-c2nccc3c(NCc4ccccc4)c(N)oc23)ccn1] | N³-Benzyl-7-(2-methylpyridin-4-yl)furo[2,3-c]pyridine-2,3-diamine | 331.15 |
| 340 | 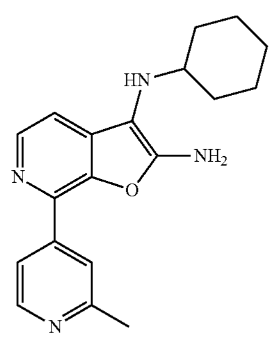 [SMILES: Cc1cc(-c2nccc3c(NC4CCCCC4)c(N)oc23)ccn1] | N³-Cyclohexyl-7-(2-methylpyridin-4-yl)furo[2,3-c]pyridine-2,3-diamine | 323.18 |
| 341 | 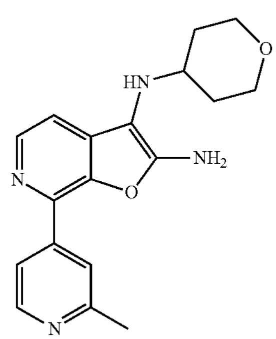 [SMILES: Cc1cc(-c2nccc3c(NC4CCOCC4)c(N)oc23)ccn1] | 7-(2-Methylpyridin-4-yl)-N³-(tetrahydro-2H-pyran-4-yl)furo[2,3-c]pyridine-2,3-diamine | 325.16 |
| 342 | 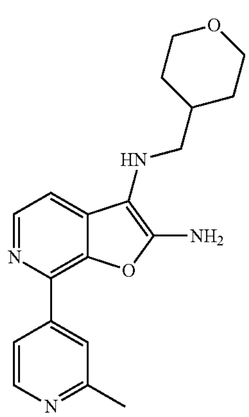 [SMILES: Cc1cc(-c2nccc3c(NCC4CCOCC4)c(N)oc23)ccn1] | 7-(2-Methylpyridin-4-yl)-N³-((tetrahydro-2H-pyran-4-yl)methyl)furo[2,3-c]pyridine-2,3-diamine | 339.18 |

TABLE 2-continued

| No. | Structure | IUPAC Name | M + 1 |
|---|---|---|---|
| 343 | 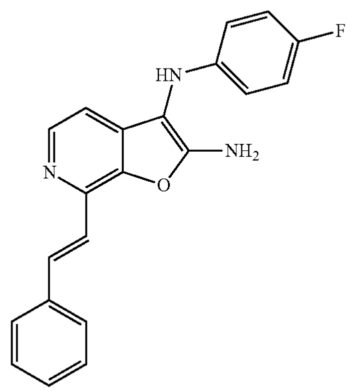 [SMILES: Nc1oc2c(/C=C/c3ccccc3)nccc2c1Nc1ccc(F)cc1] | (E)-N³-(4-Fluorophenyl)-7-styrylfuro[2,3-c]pyridine-2,3-diamine | 346.13 |
| 344 | 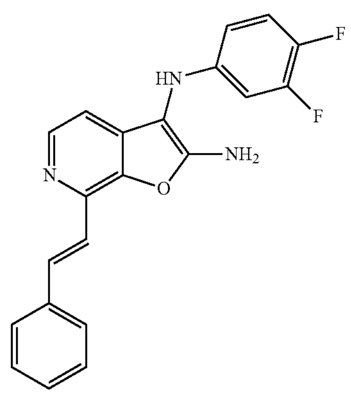 [SMILES: Nc1oc2c(/C=C/c3ccccc3)nccc2c1Nc1ccc(F)c(F)c1] | (E)-N³-(3,4-Difluorophenyl)-7-styrylfuro[2,3-c]pyridine-2,3-diamine | 364.12 |
| 345 | 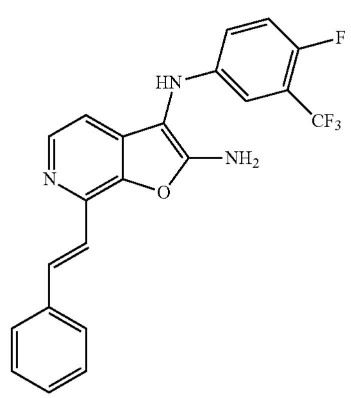 [SMILES: Nc1oc2c(/C=C/c3ccccc3)nccc2c1Nc1ccc(F)c(C(F)(F)F)c1] | (E)-N³-(4-Fluoro-3-(trifluoromethyl)phenyl)-7-styrylfuro[2,3-c]pyridine-2,3-diamine | 414.12 |
| 346 | 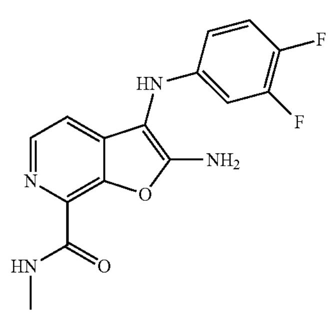 [SMILES: CNC(=O)c1nccc2c(Nc3ccc(F)c(F)c3)c(N)oc12] | 2-Amino-3-((3,4-difluorophenyl)amino)-N-methylfuro[2,3-c]pyridine-7-carboxamide | 319.10 |

TABLE 2-continued

| No. | Structure | IUPAC Name | M + 1 |
|---|---|---|---|
| 347 | 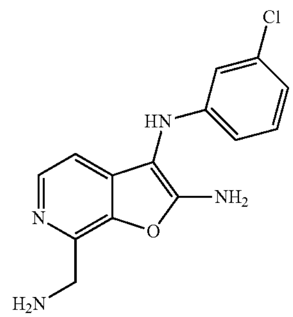 [SMILES: NCc1nccc2c(Nc3cccc(Cl)c3)c(N)oc12] | 7-(Aminomethyl)-N³-(3-chlorophenyl)furo[2,3-c]pyridine-2,3-diamine | 289.08 |
| 348 | 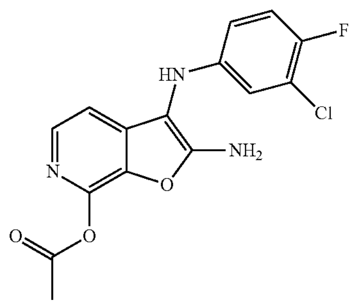 [SMILES: CC(=O)Oc1nccc2c(Nc3ccc(F)c(Cl)c3)c(N)oc12] | 2-Amino-3-((3-chloro-4-fluorophenyl)amino)furo[2,3-c]pyridin-7-yl acetate | 336.05 |
| 349 | 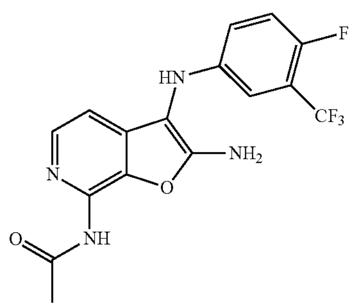 [SMILES: CC(=O)Nc1nccc2c(Nc3ccc(F)c(C(F)(F)F)c3)c(N)oc12] | N-(2-Amino-3-((3-chloro-4-fluorophenyl)amino)furo[2,3-c]pyridin-7-yl)acetamide | 335.07 |
| 350 | 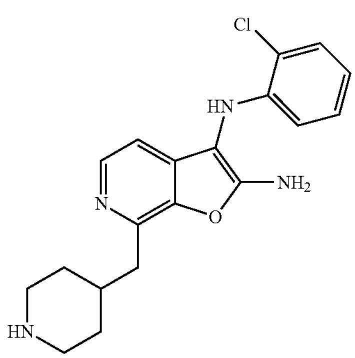 [SMILES: Nc1oc2c(CC3CCNCC3)nccc2c1Nc1ccccc1Cl] | N³-(2-Chlorophenyl)-7-(piperidin-4-ylmethyl)furo[2,3-c]pyridine-2,3-diamine | 357.14 |
| 351 | 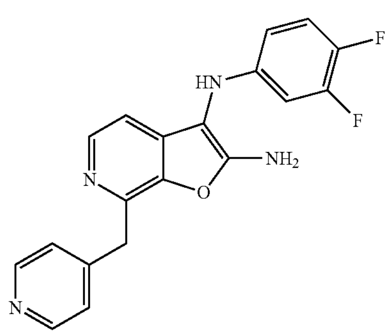 [SMILES: Nc1oc2c(Cc3ccncc3)nccc2c1Nc1ccc(F)c(F)c1] | N³-(3,4-Difluorophenyl)-7-(pyridin-4-ylmethyl)furo[2,3-c]pyridine-2,3-diamine | 353.12 |

TABLE 2-continued

| No. | Structure | IUPAC Name | M + 1 |
|---|---|---|---|
| 352 | 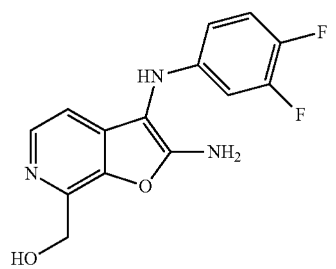 [SMILES: Nc1oc2c(CO)nccc2c1Nc1ccc(F)c(F)c1] | (2-Amino-3-((3,4-difluorophenyl)amino)furo[2,3-c]pyridin-7-yl)methanol | 292.08 |
| 353 | 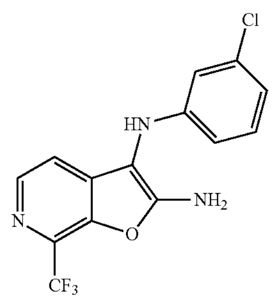 [SMILES: Nc1oc2c(C(F)(F)F)nccc2c1Nc1cccc(Cl)c1] | $N^3$-(3-Chlorophenyl)-7-(trifluoromethyl)furo[2,3-c]pyridine-2,3-diamine | 328.04 |
| 354 | 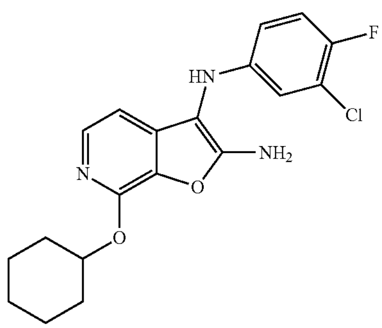 [SMILES: Nc1oc2c(OC3CCCCC3)nccc2c1Nc1ccc(F)c(Cl)c1] | $N^3$-(3-Chloro-4-fluorophenyl)-7-(cyclohexyloxy)furo[2,3-c]pyridine-2,3-diamine | 376.12 |
| 355 | 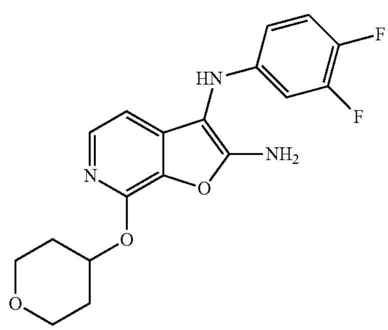 [SMILES: Nc1oc2c(OC3CCOCC3)nccc2c1Nc1ccc(F)c(F)c1] | $N^3$-(3,4-Difluorophenyl)-7-((tetrahydro-2H-pyran-4-yl)oxy)furo[2,3-c]pyridine-2,3-diamine | 362.13 |
| 356 | 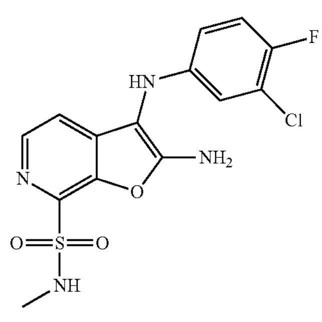 [SMILES: CNS(=O)(=O)c1nccc2c(Nc3ccc(F)c(Cl)c3)c(N)oc12] | 2-Amino-3-((3-chloro-4-fluorophenyl)amino)-N-methylfuro[2,3-c]pyridine-7-sulfonamide | 371.03 |

| No. | Structure | IUPAC Name | M + 1 |
|---|---|---|---|
| 357 | 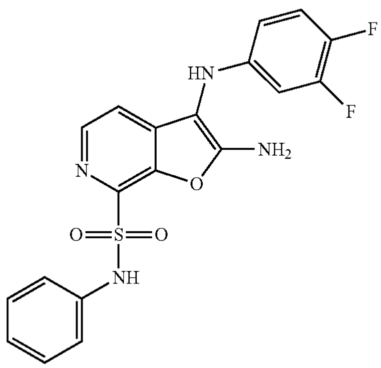 [SMILES: Nc1oc2c(S(=O)(=O)Nc3ccccc3)nccc2c1Nc1ccc(F)c(F)c1] | 2-Amino-3-((3,4-difluorophenyl)amino)-N-phenylfuro[2,3-c]pyridine-7-sulfonamide | 417.08 |
| 358 | 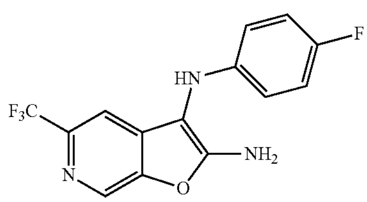 [SMILES: Nc1oc2cnc(C(F)(F)F)cc2c1Nc1ccc(F)cc1] | N³-(4-Fluorophenyl)-5-(trifluoromethyl)furo[2,3-c]pyridine-2,3-diamine | 312.07 |
| 359 | 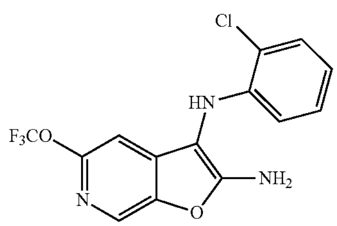 [SMILES: Nc1oc2cnc(OC(F)(F)F)cc2c1Nc1ccccc1Cl] | N³-(2-Chlorophenyl)-5-(trifluoromethoxy)furo[2,3-c]pyridine-2,3-diamine | 344.04 |
| 360 | 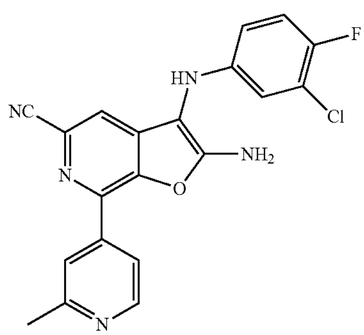 [SMILES: Cc1cc(-c2nc(C#N)cc3c(Nc4ccc(F)c(Cl)c4)c(N)oc23)ccn1] | 2-Amino-3-((3-chloro-4-fluorophenyl)amino)-7-(2-methylpyridin-4-yl)furo[2,3-c]pyridine-5-carbonitrile | 394.08 |
| 361 | 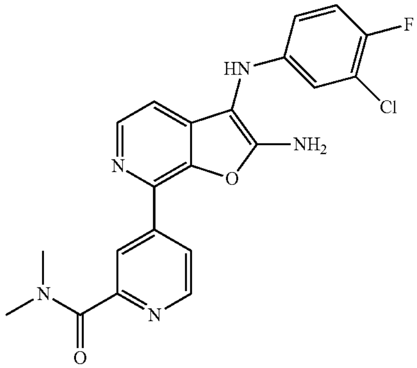 [SMILES: CN(C)C(=O)c1cc(-c2nccc3c(Nc4ccc(F)c(Cl)c4)c(N)oc23)ccn1] | 4-(2-Amino-3-((3-chloro-4-fluorophenyl)amino)furo[2,3-c]pyridin-7-yl)-N,N-dimethylpicolinamide | 426.11 |

TABLE 2-continued

| No. | Structure | IUPAC Name | M + 1 |
|---|---|---|---|
| 362 | 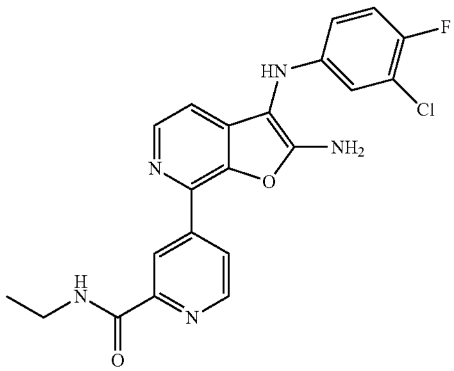 [SMILES: CCNC(=O)c1cc(-c2nccc3c(Nc4ccc(F)c(Cl)c4)c(N)oc23)ccn1] | 4-(2-Amino-3-((3-chloro-4-fluorophenyl)amino)furo[2,3-c]pyridin-7-yl)-N-ethylpicolinamide | 426.11 |
| 363 | 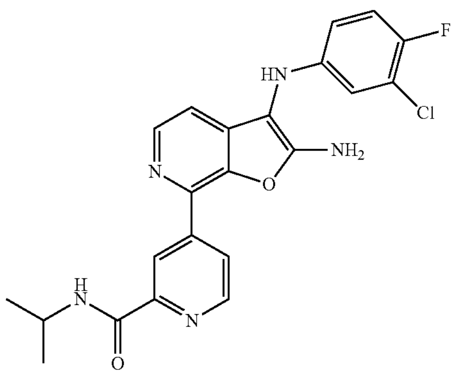 [SMILES: CC(C)NC(=O)c1cc(-c2nccc3c(Nc4ccc(F)c(Cl)c4)c(N)oc23)ccn1] | 4-(2-Amino-3-((3-chloro-4-fluorophenyl)amino)furo[2,3-c]pyridin-7-yl)-N-isopropylpicolinamide | 440.12 |
| 364 | 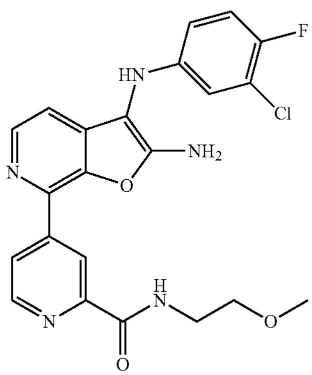 | 4-(2-Amino-3-((3-chloro-4-fluorophenyl)amino)furo[2,3-c]pyridin-7-yl)-N-(2-methoxyethyl)picolinamide | 456.12 |
| 365 | 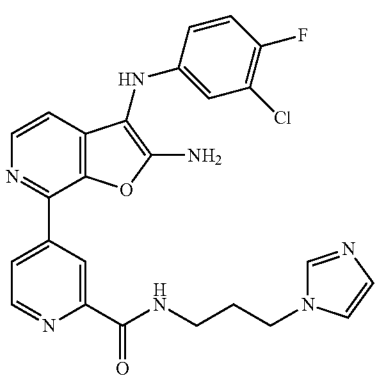 [SMILES: Nc1oc2c(-c3ccnc(C(=O)NCCCn4ccnc4)c3)nccc2c1Nc1ccc(F)c(Cl)c1] | N-(3-(1H-Imidazol-1-yl)propyl)-4-(2-amino-3-((3-chloro-4-fluorophenyl)amino)furo[2,3-c]pyridin-7-yl)picolinamide | 506.15 |

TABLE 2-continued

| No. | Structure | IUPAC Name | M + 1 |
|---|---|---|---|
| 366 | 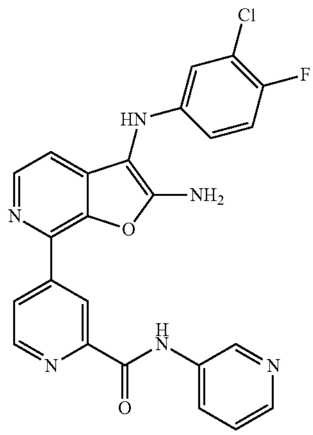 [SMILES: Nc1oc2c(-c3ccnc(C(=O)Nc4cccnc4)c3)nccc2c1Nc1ccc(F)c(Cl)c1] | 4-(2-Amino-3-((3-chloro-4-fluorophenyl)amino)furo[2,3-c]pyridin-7-yl)-N-(pyridin-3-yl)picolinamide | 475.10 |
| 367 | 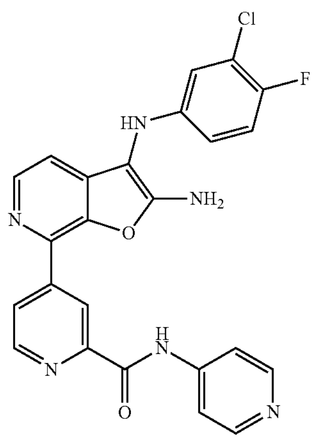 [SMILES: Nc1oc2c(-c3ccnc(C(=O)Nc4ccncc4)c3)nccc2c1Nc1ccc(F)c(Cl)c1] | 4-(2-Amino-3-((3-chloro-4-fluorophenyl)amino)furo[2,3-c]pyridin-7-yl)-N-(pyridin-4-yl)picolinamide | 475.10 |
| 368 | 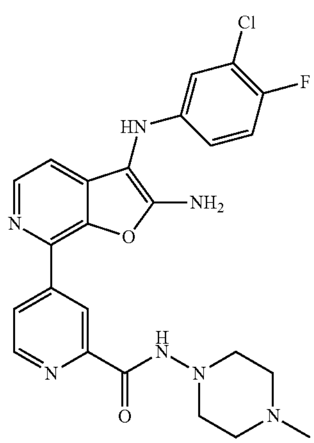 [SMILES: CN1CCN(NC(=O)c2cc(-c3nccc4c(Nc5ccc(F)c(Cl)c5)c(N)oc34)ccn2)CC1] | 4-(2-Amino-3-((3-chloro-4-fluorophenyl)amino)furo[2,3-c]pyridin-7-yl)-N-(4-methylpiperazin-1-yl)picolinamide | 496.16 |
| 369 | 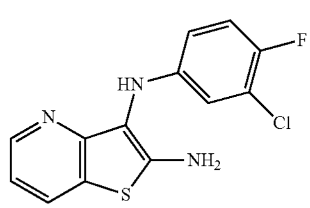 [SMILES: Nc1sc2cccnc2c1Nc1ccc(F)c(Cl)c1] | $N^3$-(3-Chloro-4-fluorophenyl)thieno[3,2-b]pyridine-2,3-diamine | 294.02 |

TABLE 2-continued

| No. | Structure | IUPAC Name | M + 1 |
|---|---|---|---|
| 370 | 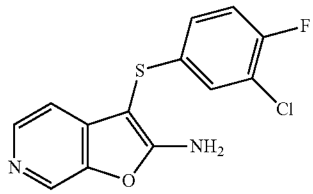 | 3-((3-Chloro-4-fluorophenyl)thio)furo[2,3-c]pyridin-2-amine | 295.0 |
| 371 | 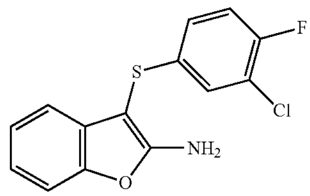 [SMILES: Nc1oc2ccccc2c1Sc1ccc(F)c(Cl)c1] | 3-((3-Chloro-4-fluorophenyl)thio)benzofuran-2-amine | 294.0 |
| 372 | 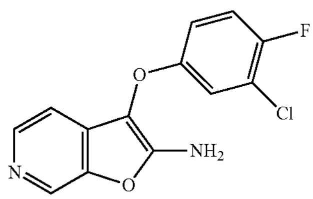 | 3-(3-Chloro-4-fluorophenoxy)furo[2,3-c]pyridin-2-amine | 279.0 |
| 373 | 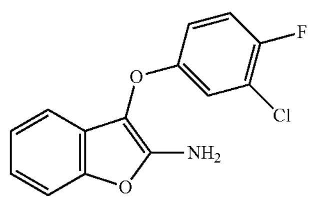 [SMILES: Nc1oc2ccccc2c1Oc1ccc(F)c(Cl)c1] | 3-(3-Chloro-4-fluorophenoxy)benzofuran-2-amine | 278.0 |
| 374 | 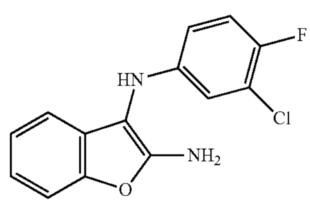 [SMILES: Nc1oc2ccccc2c1Nc1ccc(F)c(Cl)c1] | N3-(3-Chloro-4-fluorophenyl)benzofuran-2,3-diamine | 277.05 |
| 375 | 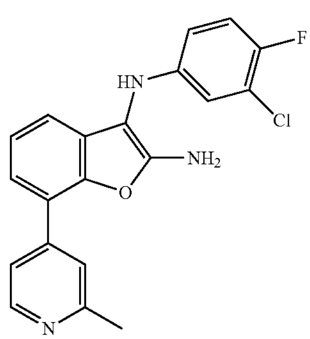 [SMILES: Cc1cc(-c2cccc3c(Nc4ccc(F)c(Cl)c4)c(N)oc23)ccn1] | N3-(3-Chloro-4-fluorophenyl)-7-(2-methylpyridin-4-yl)benzofuran-2,3-diamine | 368.09 |

TABLE 2-continued

| No. | Structure | IUPAC Name | M + 1 |
|---|---|---|---|
| 376 | 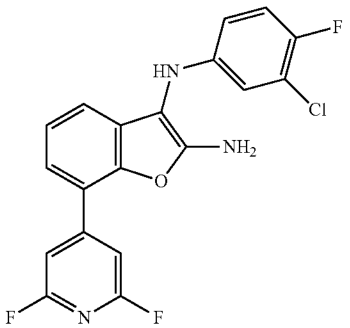 | N3-(3-Chloro-4-fluorophenyl)-7-(2,6-difluoropyridin-4-yl)benzofuran-2,3-diamine | 390.06 |
| 377 | 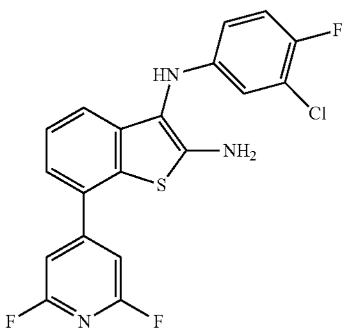 [SMILES: Nc1sc2c(-c3cc(F)nc(F)c3)cccc2c1Nc1ccc(F)c(Cl)c1] | N3-(3-Chloro-4-fluorophenyl)-7-(2,6-difluoropyridin-4-yl)benzo[b]thiophene-2,3-diamine | 406.03 |
| 378 | 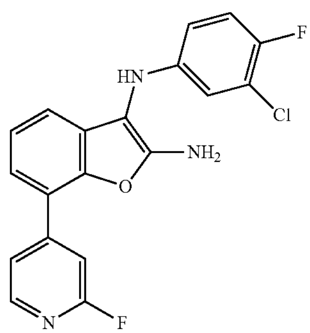 [SMILES: Nc1oc2c(-c3ccnc(F)c3)cccc2c1Nc1ccc(F)c(Cl)c1] | N3-(3-Chloro-4-fluorophenyl)-7-(2-fluoropyridin-4-yl)benzofuran-2,3-diamine | 372.07 |
| 379 | 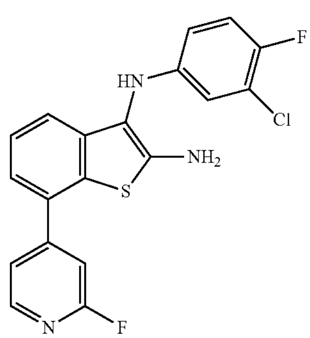 | N3-(3-Chloro-4-fluorophenyl)-7-(2-fluoropyridin-4-yl)benzo[b]thiophene-2,3-diamine | 388.04 |

TABLE 2-continued

| No. | Structure | IUPAC Name | M + 1 |
|---|---|---|---|
| 380 | 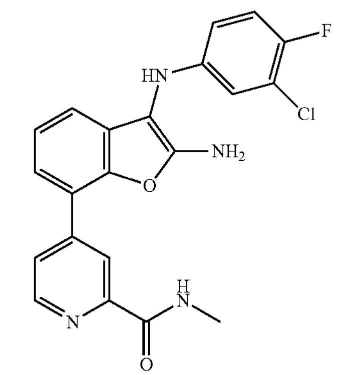 [SMILES: CNC(=O)c1cc(-c2cccc3c(Nc4ccc(F)c(Cl)c4)c(N)oc23)ccn1] | 4-(2-Amino-3-((3-chloro-4-fluorophenyl)amino)benzofuran-7-yl)-N-methylpicolinamide | 411.10 |
| 381 | 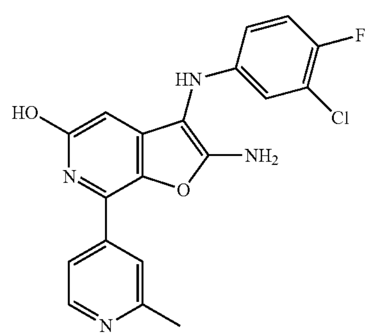 [SMILES: Cc1cc(-c2nc(O)cc3c(Nc4ccc(F)c(Cl)c4)c(N)oc23)ccn1] | 2-Amino-3-((3-chloro-4-fluorophenyl)amino)-7-(2-methylpyridin-4-yl)furo[2,3-c]pyridin-5-ol | 385.08 |
| 382 | 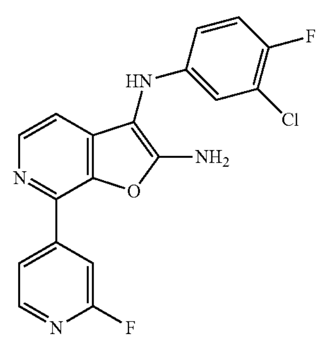 [SMILES: Nc1oc2c(-c3ccnc(F)c3)nccc2c1Nc1ccc(F)c(Cl)c1] | $N^3$-(3-Chloro-4-fluorophenyl)-7-(2-fluoropyridin-4-yl)benzofuran-2,3-diamine | 373.06 |
| 383 | 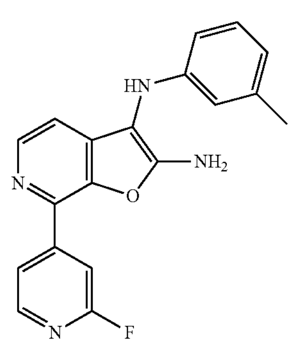 [SMILES: Cc1cccc(Nc2c(N)oc3c(-c4ccnc(F)c4)nccc23)c1] | N3-(3-chlorophenyl)-7-(2-fluoropyridin-4-yl)furo[2,3-c]pyridine-2,3-diamine | 255.07 |

TABLE 2-continued

| No. | Structure | IUPAC Name | M + 1 |
|---|---|---|---|
| 384 | 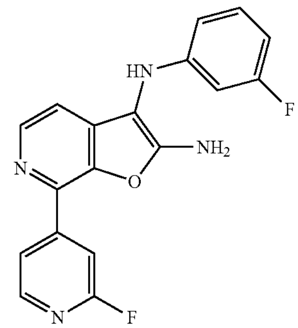 [SMILES: Nc1oc2c(-c3ccnc(F)c3)nccc2c1Nc1cccc(F)c1] | N3-(3-Fluorophenyl)-7-(2-fluoropyridin-4-yl)furo[2,3-c]pyridine-2,3-diamine | 339.10 |
| 385 | 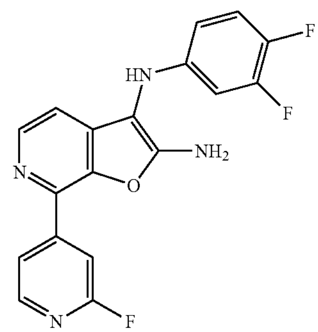 [SMILES: Nc1oc2c(-c3ccnc(F)c3)nccc2c1Nc1ccc(F)c(F)c1] | N3-(3,4-Difluorophenyl)-7-(2-fluoropyridin-4-yl)furo[2,3-c]pyridine-2,3-diamine | 357.09 |
| 386 | 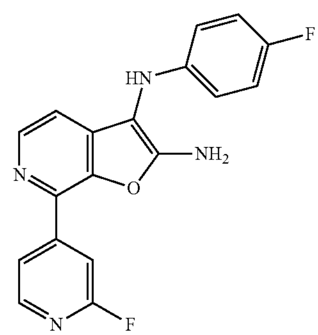 [SMILES: Nc1oc2c(-c3ccnc(F)c3)nccc2c1Nc1ccc(F)cc1] | N3-(4-Fluorophenyl)-7-(2-fluoropyridin-4-yl)furo[2,3-c]pyridine-2,3-diamine | 339.10 |
| 387 | 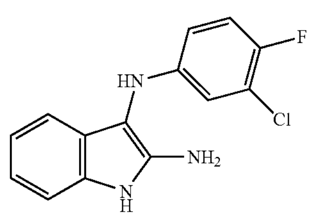 [SMILES: Nc1[nH]c2ccccc2c1Nc1ccc(F)c(Cl)c1] | N3-(3-Chloro-4-fluorophenyl)-1H-indole-2,3-diamine | 276.07 |
| 388 | 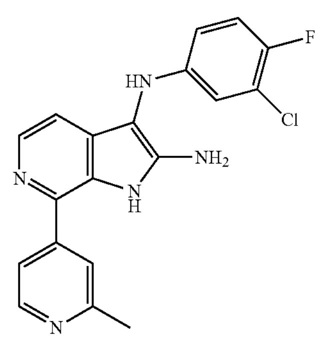 [SMILES: Cc1cc(-c2nccc3c(Nc4ccc(F)c(Cl)c4)c(N)[nH]c23)ccn1] | N3-(3-Chloro-4-fluorophenyl)-7-(2-methylpyridin-4-yl)-1H-pyrrolo[2,3-c]pyridine-2,3-diamine | 368.10 |

TABLE 2-continued

| No. | Structure | IUPAC Name | M + 1 |
|---|---|---|---|
| 389 | 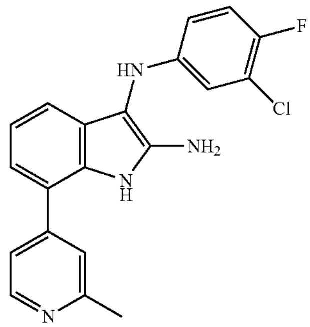 [SMILES: Cc1cc(-c2cccc3c(Nc4ccc(F)c(Cl)c4)c(N)[nH]c23)ccn1] | N3-(3-Chloro-4-fluorophenyl)-7-(2-methylpyridin-4-yl)-1H-indole-2,3-diamine | 367.11 |
| 390 | 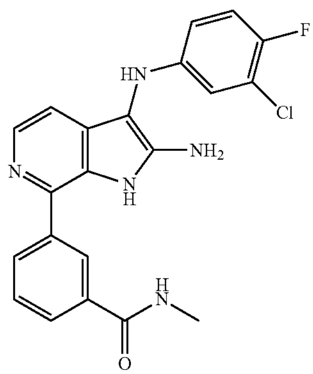 [SMILES: CNC(=O)c1cccc(-c2nccc3c(Nc4ccc(F)c(Cl)c4)c(N)[nH]c23)c1] | 4-(2-Amino-3-((3-chloro-4-fluorophenyl)amino)-1H-pyrrolo[2,3-c]pyridin-7-yl)-N-methylpicolinamide | 411.11 |
| 391 | 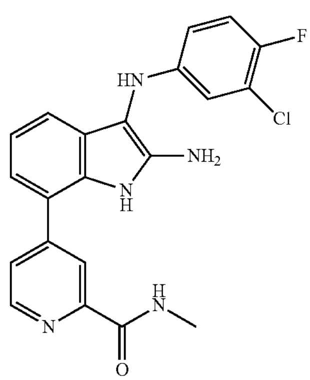 [SMILES: CNC(=O)c1cc(-c2cccc3c(Nc4ccc(F)c(Cl)c4)c(N)[nH]c23)ccn1] | 4-(2-Amino-3-((3-chloro-4-fluorophenyl)amino)-1H-indol-7-yl)-N-methylpicolinamide | 410.11 |
| 392 | 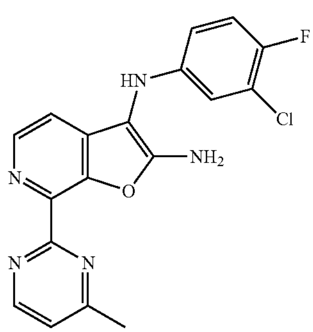 [SMILES: Cc1ccnc(-c2nccc3c(Nc4ccc(F)c(Cl)c4)c(N)oc23)n1] | N3-(3-Chloro-4-fluorophenyl)-7-(4-methylpyrimidin-2-yl)furo[2,3-c]pyridine-2,3-diamine | 370.08 |

TABLE 2-continued

| No. | Structure | IUPAC Name | M + 1 |
|---|---|---|---|
| 393 | 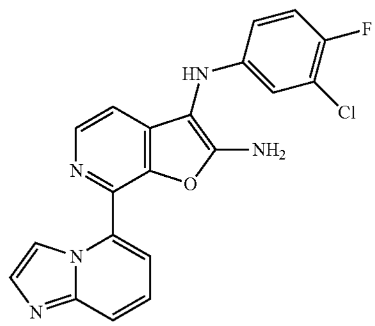 [SMILES: Nc1oc2c(-c3cccc4nccn34)nccc2c1Nc1ccc(F)c(Cl)c1] | N3-(3-Chloro-4-fluorophenyl)-7-(imidazo[1,2-a]pyridin-5-yl)furo[2,3-c]pyridine-2,3-diamine | 394.08 |
| 394 | 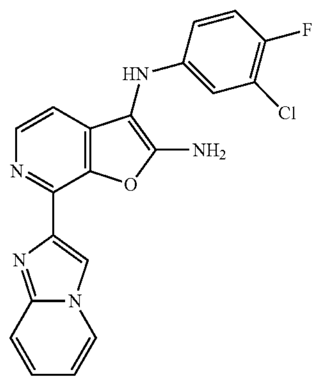 [SMILES: Nc1oc2c(-c3cn4ccccc4n3)nccc2c1Nc1ccc(F)c(Cl)c1] | N3-(3-Chloro-4-fluorophenyl)-7-(imidazo[1,2-a]pyridin-2-yl)furo[2,3-c]pyridine-2,3-diamine | 394.08 |
| 395 | 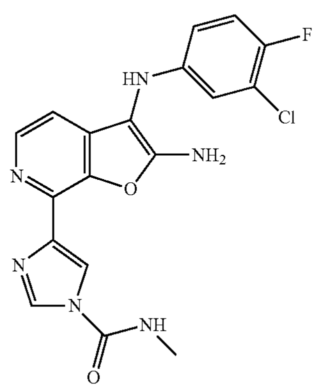 [SMILES: CNC(=O)n1cnc(-c2nccc3c(Nc4ccc(F)c(Cl)c4)c(N)oc23)c1] | 4-(2-Amino-3-((3-chloro-4-fluorophenyl)amino)furo[2,3-c]pyridin-7-yl)-N-methyl-1H-imidazole-1-carboxamide | 401.09 |
| 396 | 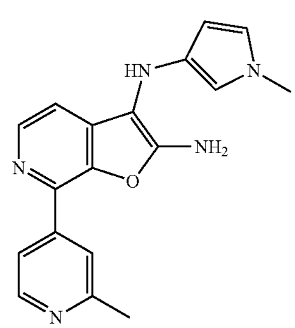 [SMILES: Cc1cc(-c2nccc3c(Nc4ccn(C)c4)c(N)oc23)ccn1] | N3-(1-Methyl-1H-pyrrol-3-yl)-7-(2-methylpyridin-4-yl)furo[2,3-c]pyridine-2,3-diamine | 320.15 |

TABLE 2-continued

| No. | Structure | IUPAC Name | M + 1 |
|---|---|---|---|
| 397 | 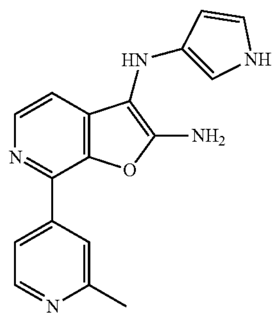 [SMILES: Cc1cc(-c2nccc3c(Nc4cc[nH]c4)c(N)oc23)ccn1] | 7-(2-Methylpyridin-4-yl)-N3-(1H-pyrrol-3-yl)furo[2,3-c]pyridine-2,3-diamine | 306.13 |
| 398 | 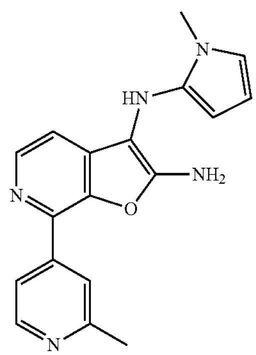 [SMILES: Cc1cc(-c2nccc3c(Nc4cccn4C)c(N)oc23)ccn1] | N3-(1-Methyl-1H-pyrrol-2-yl)-7-(2-methylpyridin-4-yl)furo[2,3-c]pyridine-2,3-diamine | 320.15 |
| 399 | 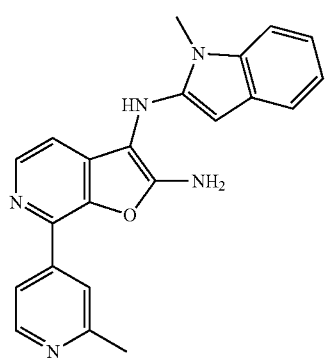 [SMILES: Cc1cc(-c2nccc3c(Nc4cc5ccccc5n4C)c(N)oc23)ccn1] | N3-(1-Methyl-1H-indol-2-yl)-7-(2-methylpyridin-4-yl)furo[2,3-c]pyridine-2,3-diamine | 370.16 |
| 400 | 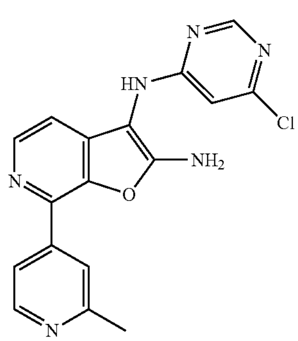 [SMILES: Cc1cc(-c2nccc3c(Nc4cc(Cl)ncn4)c(N)oc23)ccn1] | N3-(6-Chloropyrimidin-4-yl)-7-(2-methylpyridin-4-yl)furo[2,3-c]pyridine-2,3-diamine | 353.09 |

TABLE 2-continued

| No. | Structure | IUPAC Name | M + 1 |
|---|---|---|---|
| 401 | 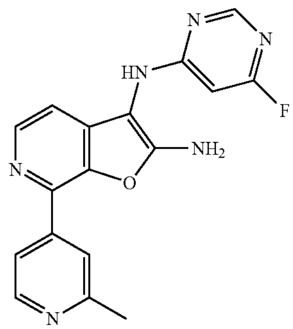 [SMILES: Cc1cc(-c2nccc3c(Nc4cc(F)ncn4)c(N)oc23)ccn1] | N3-(6-Fluoropyrimidin-4-yl)-7-(2-methylpyridin-4-yl)furo[2,3-c]pyridine-2,3-diamine | 337.12 |
| 402 | 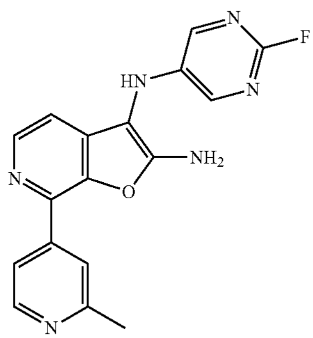 [SMILES: Cc1cc(-c2nccc3c(Nc4cnc(F)nc4)c(N)oc23)ccn1] | N3-(2-Fluoropyrimidin-5-yl)-7-(2-methylpyridin-4-yl)furo[2,3-c]pyridine-2,3-diamine | 337.12 |
| 403 | 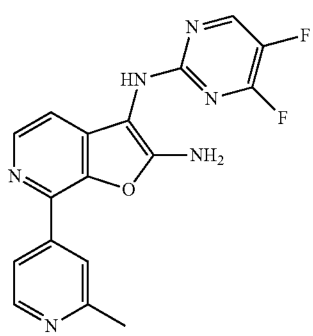 [SMILES: Cc1cc(-c2nccc3c(Nc4ncc(F)c(F)n4)c(N)oc23)ccn1] | N3-(4,5-difluoropyrimidin-2-yl)-7-(2-methylpyridin-4-yl)furo[2,3-c]pyridine-2,3-diamine | 355.11 |
| 404 | 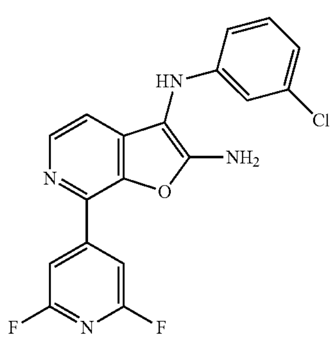 [SMILES: Nc1oc2c(-c3cc(F)nc(F)c3)nccc2c1Nc1cccc(Cl)c1] | N$^3$-(3-Chlorophenyl)-7-(2,6-difluoropyridin-4-yl)furo[2,3-c]pyridine-2,3-diamine | 373.06 |

| No. | Structure | IUPAC Name | M + 1 |
|---|---|---|---|
| 405 | 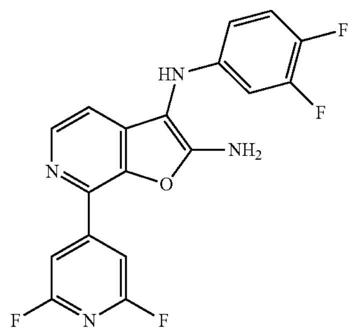 [SMILES: Nc1oc2c(-c3cc(F)nc(F)c3)nccc2c1Nc1ccc(F)c(F)c1] | N3-(3,4-Difluorophenyl)-7-(2,6-difluoropyridin-4-yl)furo[2,3-c]pyridine-2,3-diamine | 375.08 |
| 406 | 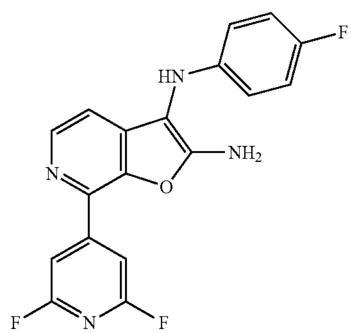 [SMILES: Nc1oc2c(-c3cc(F)nc(F)c3)nccc2c1Nc1ccc(F)cc1] | 7-(2,6-Difluoropyridin-4-yl)-N3-(4-fluorophenyl)furo[2,3-c]pyridine-2,3-diamine | 357.09 |
| 407 | 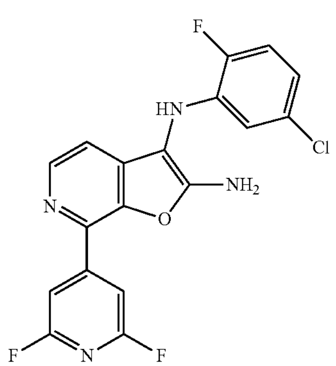 [SMILES: Nc1oc2c(-c3cc(F)nc(F)c3)nccc2c1Nc1cc(Cl)ccc1F] | N3-(5-chloro-2-fluorophenyl)-7-(2,6-difluoropyridin-4-yl)furo[2,3-c]pyridine-2,3-diamine | 391.05 |
| 408 | 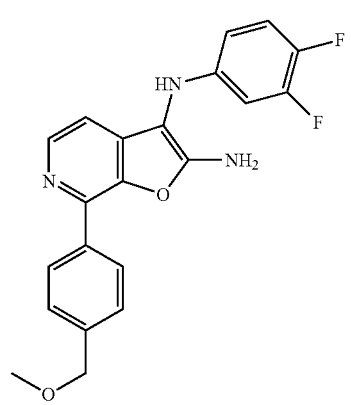 [SMILES: COCc1ccc(-c2nccc3c(Nc4ccc(F)c(F)c4)c(N)oc23)cc1] | N3-(3,4-Difluorophenyl)-7-(4-(methoxymethyl)phenyl)furo[2,3-c]pyridine-2,3-diamine | 382.13 |

| No. | Structure | IUPAC Name | M + 1 |
|---|---|---|---|
| 409 | 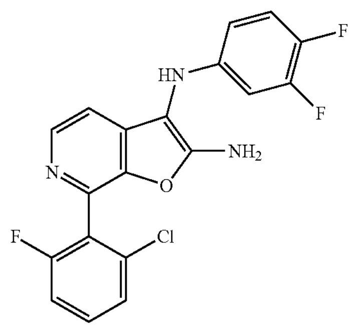 [SMILES: Nc1oc2c(-c3c(F)cccc3Cl)nccc2c1Nc1ccc(F)c(F)c1] | 7-(2-Chloro-6-fluorophenyl)-N3-(3,4-difluorophenyl)furo[2,3-c]pyridine-2,3-diamine | 403.06 |
| 410 | 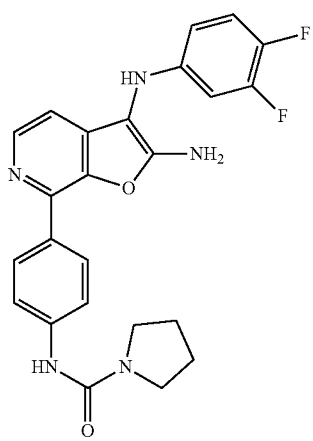 [SMILES: Nc1oc2c(-c3ccc(NC(=O)N4CCCC4)cc3)nccc2c1Nc1ccc(F)c(F)c1] | N-(4-(2-Amino-3-((3,4-difluorophenyl)amino)furo[2,3-c]pyridin-7-yl)phenyl)pyrrolidine-1-carboxamide | 450.17 |
| 411 | 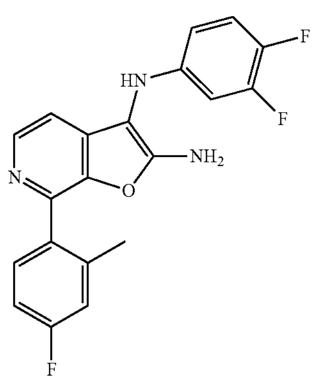 [SMILES: Cc1cc(F)ccc1-c1nccc2c(Nc3ccc(F)c(F)c3)c(N)oc12] | N3-(3,4-Difluorophenyl)-7-(4-fluoro-2-methylphenyl)furo[2,3-c]pyridine-2,3-diamine | 370.11 |
| 412 | 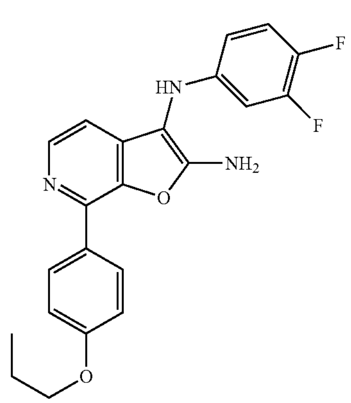 [SMILES: CCCOc1ccc(-c2nccc3c(Nc4ccc(F)c(F)c4)c(N)oc23)cc1] | N3-(3,4-Difluorophenyl)-7-(4-propoxyphenyl)furo[2,3-c]pyridine-2,3-diamine | 396.15 |

TABLE 2-continued

| No. | Structure | IUPAC Name | M + 1 |
|---|---|---|---|
| 413 | 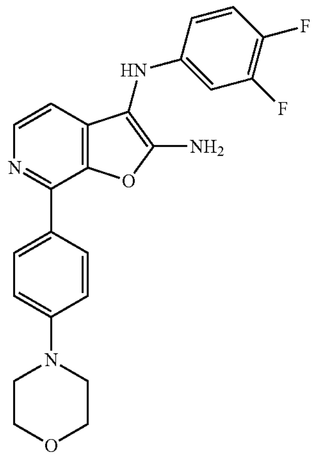 [SMILES: Nc1oc2c(-c3ccc(N4CCOCC4)cc3)nccc2c1Nc1ccc(F)c(F)c1] | N3-(3,4-Difluorophenyl)-7-(4-morpholinophenyl)furo[2,3-c]pyridine-2,3-diamine | 423.16 |
| 414 | 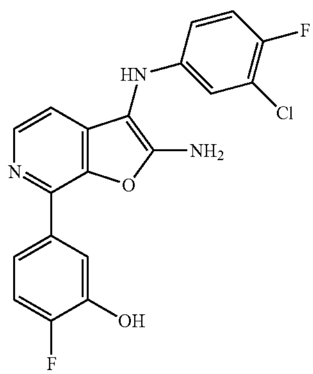 [SMILES: Nc1oc2c(-c3ccc(F)c(O)c3)nccc2c1Nc1ccc(F)c(Cl)c1] | 5-(2-Amino-3-((3-chloro-4-fluorophenyl)amino)furo[2,3-c]pyridin-7-yl)-2-fluorophenol | 388.06 |
| 415 | 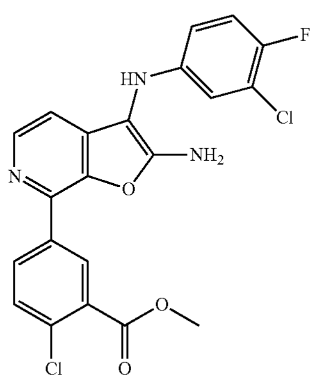 [SMILES: COC(=O)c1cc(-c2nccc3c(Nc4ccc(F)c(Cl)c4)c(N)oc23)ccc1Cl] | Methyl 5-(2-amino-3-((3-chloro-4-fluorophenyl)amino)furo[2,3-c]pyridin-7-yl)-2-chlorobenzoate | 446.04 |
| 416 | 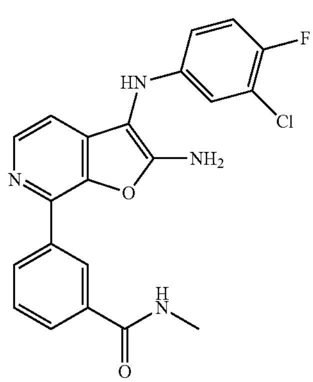 [SMILES: CNC(=O)c1cccc(-c2nccc3c(Nc4ccc(F)c(Cl)c4)c(N)oc23)c1] | 3-(2-Amino-3-((3-chloro-4-fluorophenyl)amino)furo[2,3-c]pyridin-7-yl)-N-methylbenzamide | 411.10 |

TABLE 2-continued

| No. | Structure | IUPAC Name | M + 1 |
|---|---|---|---|
| 417 | 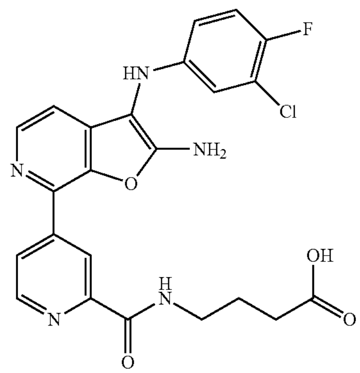 [SMILES: Nc1oc2c(-c3ccnc(C(=O)NCCCC(=O)O)c3)nccc2c1Nc1ccc(F)c(Cl)c1] | 4-(4-(2-Amino-3-((3-chloro-4-fluorophenyl)amino)furo[2,3-c]pyridin-7-yl)picolinamido)butanoic acid | 484.11 |
| 418 | 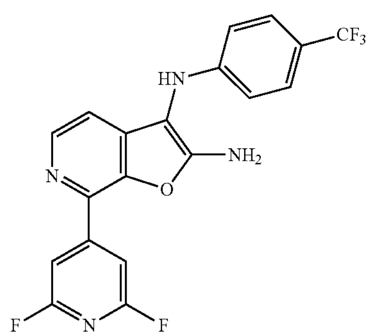 [SMILES: Nc1oc2c(-c3cc(F)nc(F)c3)nccc2c1Nc1ccc(C(F)(F)F)cc1] | 7-(2,6-Difluoropyridin-4-yl)-$N^3$-(4-(trifluoromethyl)phenyl)furo[2,3-c]pyridine-2,3-diamine | 407.09 |
| 419 | 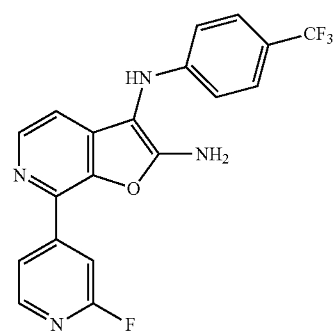 [SMILES: Nc1oc2c(-c3ccnc(F)c3)nccc2c1Nc1ccc(C(F)(F)F)cc1] | 7-(2-Fluoropyridin-4-yl)-$N^3$-(4-(trifluoromethyl)phenyl)furo[2,3-c]pyridine-2,3-diamine | 389.10 |
| 420 | 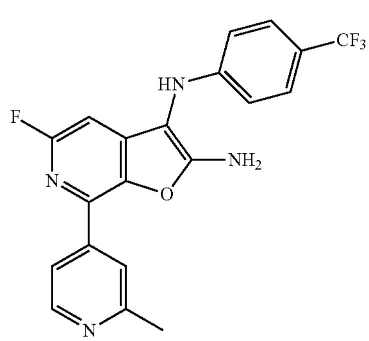 [SMILES: Cc1cc(-c2nc(F)cc3c(Nc4ccc(C(F)(F)F)cc4)c(N)oc23)ccn1] | 5-Fluoro-7-(2-methylpyridin-4-yl)-N3-(4-(trifluoromethyl)phenyl)furo[2,3-c]pyridine-2,3-diamine | 403.11 |

TABLE 2-continued

| No. | Structure | IUPAC Name | M + 1 |
|---|---|---|---|
| 421 | 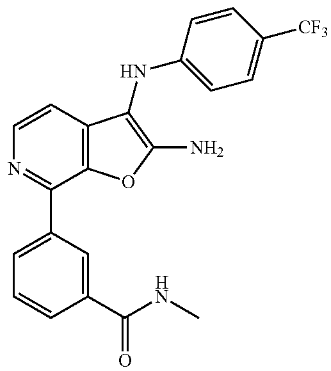 [SMILES: CNC(=O)c1cccc(-c2nccc3c(Nc4ccc(C(F)(F)F)cc4)c(N)oc23)c1] | 4-(2-Amino-3-((4-(trifluoromethyl)phenyl)amino)furo[2,3-c]pyridin-7-yl)-N-methylpicolinamide | 428.13 |
| 422 | 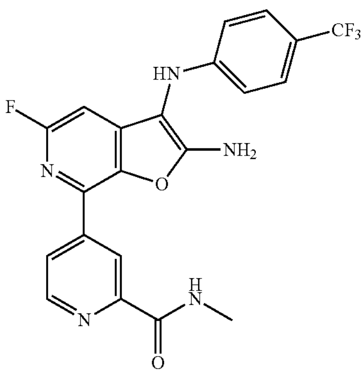 [SMILES: CNC(=O)c1cc(-c2nc(F)cc3c(Nc4ccc(C(F)(F)F)cc4)c(N)oc23)ccn1] | 4-(2-Amino-5-fluoro-3-((4-(trifluoromethyl)phenyl)amino)furo[2,3-c]pyridin-7-yl)-N-methylpicolinamide | 446.12 |
| 423 | 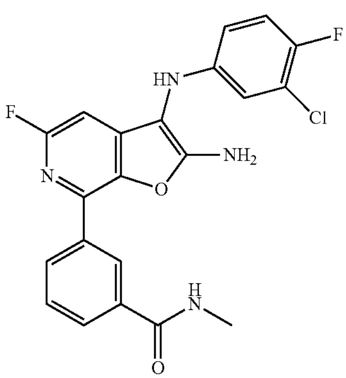 [SMILES: CNC(=O)c1cccc(-c2nc(F)cc3c(Nc4ccc(F)c(Cl)c4)c(N)oc23)c1] | 4-(2-Amino-3-((3-chloro-4-fluorophenyl)amino)-5-fluorofuro[2,3-c]pyridin-7-yl)-N-methylpicolinamide | 430.08 |
| 424 | 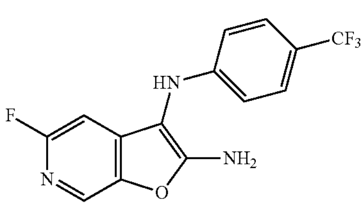 [SMILES: Nc1oc2cnc(F)cc2c1Nc1ccc(C(F)(F)F)cc1] | 5-Fluoro-$N^3$-(4-(trifluoromethyl)phenyl)furo[2,3-c]pyridine-2,3-diamine | 312.07 |
| 425 | 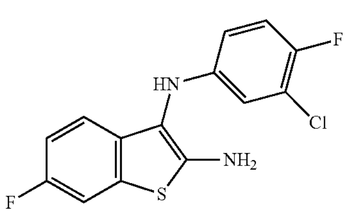 [SMILES: Nc1sc2cc(F)ccc2c1Nc1ccc(F)c(Cl)c1] | $N^3$-(3-Chloro-4-fluorophenyl)-6-fluorobenzo[b]thiophene-2,3-diamine | 311.02 |

TABLE 2-continued

| No. | Structure | IUPAC Name | M + 1 |
|---|---|---|---|
| 426 | 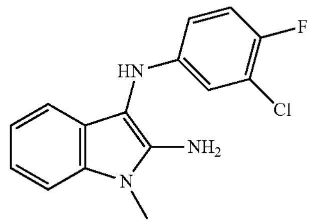 [SMILES: Cn1c(N)c(Nc2ccc(F)c(Cl)c2)c2ccccc21] | N³-(3-Chloro-4-fluorophenyl)-1-methyl-1H-indole-2,3-diamine | 290.08 |
| 427 | 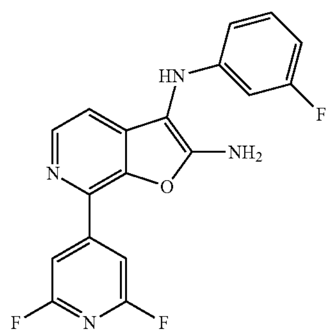 [SMILES: Nc1oc2c(-c3cc(F)nc(F)c3)nccc2c1Nc1cccc(F)c1] | 7-(2,6-difluoropyridin-4-yl)-N3-(3-fluorophenyl)furo[2,3-c]pyridine-2,3-diamine | 357.1 |
| 428 | 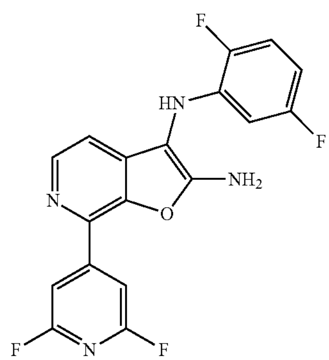 [SMILES: Nc1oc2c(-c3cc(F)nc(F)c3)nccc2c1Nc1cc(F)ccc1F] | N³-(2,5-Ddifluorophenyl)-7-(2,6-difluoropyridin-4-yl)furo[2,3-c]pyridine-2,3-diamine | 375.09 |
| 429 | 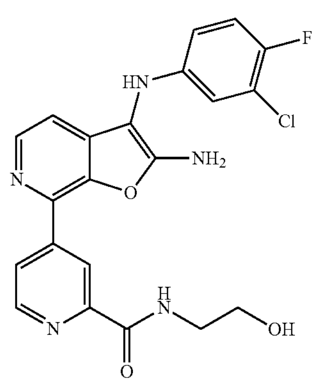 [SMILES: Nc1oc2c(-c3ccnc(C(=O)NCCO)c3)nccc2c1Nc1ccc(F)c(Cl)c1] | 4-(2-Amino-3-((3-chloro-4-fluorophenyl)amino)furo[2,3-c]pyridin-7-yl)-N-(2-hydroxyethyl)picolinamide | 442.11 |

TABLE 2-continued

| No. | Structure | IUPAC Name | M + 1 |
|---|---|---|---|
| 430 | 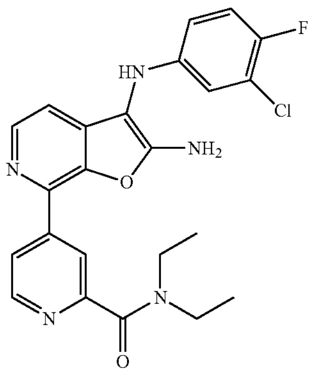 [SMILES: CCN(CC)C(=O)c1cc(-c2nccc3c(Nc4ccc(F)c(Cl)c4)c(N)oc23)ccn1] | 4-(2-Amino-3-((3-chloro-4-fluorophenyl)amino)furo[2,3-c]pyridin-7-yl)-N,N-diethylpicolinamide | 454.14 |
| 431 | 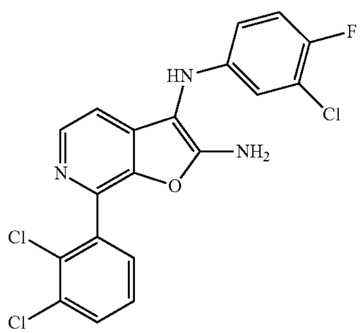 [SMILES: Nc1oc2c(-c3cccc(Cl)c3Cl)nccc2c1Nc1ccc(F)c(Cl)c1] | $N^3$-(3-Chloro-4-fluorophenyl)-7-(2,3-dichlorophenyl)furo[2,3-c]pyridine-2,3-diamine | 422.00 |
| 432 | 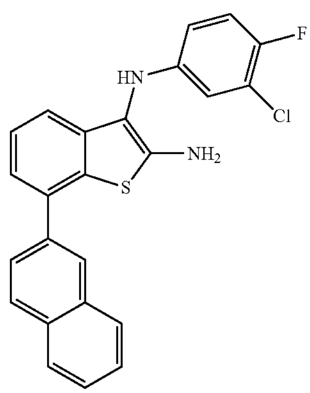 [SMILES: Nc1sc2c(-c3ccc4ccccc4c3)cccc2c1Nc1ccc(F)c(Cl)c1] | $N^3$-(3-Chloro-4-fluorophenyl)-7-(naphthalen-2-yl)benzo[b]thiophene-2,3-diamine | 419.08 |

One of skill in the art will recognize that the compounds of the invention may be made as described herein and by methods known in the art.

Example 30

A. In-vitro IDO1 Enzyme (Indoleamine 2,3-dioxygenase) Assay

Human indoleamine 2,3-dioxygenase1 (hIDO1) catalyzes the oxidative cleavage of the pyrrole ring of the indole nucleus of tryptophan to yield N-formylkynurenine which can be converted to kynurenine (KYN) by deformylation. hIDO1 with an N-terminal His tag, expressed and purified from *E. coli* cells was procured from either Enzo Life-Sciences, NY, USA). Unless otherwise stated, all materials were procured from Sigma Aldrich, Mo., USA.

The assay monitoring the conversion of L-tryptophan to KYN was carried out as follows. hIDO1 (10 nM) was incubated with tryptophan (30 μM) in the presence of ascorbic acid (20 mM), methylene blue (10 μM) and catalase (100 μg/mL) in potassium phosphate buffer (50 mM; pH 6.5) at 37C for 30 min. The reaction was terminated with 30% trichloroacetic acid (TCA) and further incubated at 65C for 15 min to fully convert N-formylkynurenine to KYN. The reaction mixture was then centrifuged to remove sediments and the KYN in the supernatant was estimated by UV-visible absorption spectroscopy at 360 nm using a Waters HPLC system fitted with a C-18 column or by LC/MS/MS. See, Sono, 1980, J. Biol. Chem., 255:1339-1345, which is herein incorporated by reference.

Percent inhibition at each concentration of test compounds was determined by estimating the decrease in KYN with reference to the reaction control with 1% DMSO vehicle. Data were analyzed using nonlinear regression to generate IC50 values using Graph Pad Prism® 5. The test compounds inhibit IDO1 activity and reduce the levels of kynurenine pathway metabolite KYN as shown below in Table 3.

B. HeLa Cell Based IDO1 (Indoleamine 2,3-dioxygenase) Assay

HeLa cells were obtained from ATCC and maintained in DMEM supplemented with sodium bicarbonate (2.1 g/L), HEPES (4.1 g/L), L-glutamine (2 mM), non-essential amino acid (84 mg/L) and fetal bovine serum (10% FBS) and maintained at 95% humidity and 5% $CO_2$ in a 37° C. incubator. Unless otherwise stated, all materials were procured from Sigma. Upon incubation with gamma-interferon (IFNγ), HeLa cells express IDO1, which catalyzes the formation of N-formyl kynurenine from tryptophan present in growth medium. The assay was performed as follows:

Cells were plated in medium (300 µL) at a density of 0.1 million per well of a 48 well plate and hIDO1 was induced by overnight treatment with IFNγ (50 ng/mL) (Peprotech, USA). The following day, cells were washed to remove IFNγ and were incubated with specific concentrations of test compounds (typically 10 µM to 1 nM, final volume 300 µL) in Hanks Balanced Salt Solution (HBSS) containing 80 µM L-tryptophan. Following incubation, supernatant (150 µL) was transferred to a 96 well plate into which 30%TCA (30 µ) was added and the contents further incubated at 65° C. for 15 min to fully convert N-formylkynurenine to kynurenine. The reaction mixture was then centrifuged to remove sediments and the KYN in the supernatant was estimated by UV-visible absorption spectroscopy at 360 nm using a Waters HPLC system fitted with a C-18 column. (Xiangdong Liu et al. Blood 2010, Vol-117, 3520-30; Sono described above).

Percent inhibition at each concentration of test compounds was determined by estimating the decrease in KYN with reference to the reaction control with 1% DMSO vehicle. Data were analyzed using nonlinear regression to generate IC50 values using Graph Pad Prism® 5. The test compounds inhibit IDO1 and reduce kynurenine pathway metabolite KYN (Table 3).

TABLE 3

A: IC50 < 200 nM; B: IC50 = 200 to 1000 nM; C: IC50 > 1000 nM.
Enz = IDO1 Enzyme assay, Cell = HeLa cell assay

| No. | Enz (IC$_{50}$ IDO1) | Cell |
|---|---|---|
| 1 | A | |
| 2 | A | A |
| 3 | B | A |
| 4 | C | A |
| 5 | B | A |
| 6 | C | |
| 7 | C | |
| 8 | B | A |
| 9 | C | B |
| 10 | C | B |
| 11 | C | |
| 12 | C | |
| 13 | B | A |
| 14 | B | A |
| 15 | B | B |
| 16 | C | B |
| 17 | C | |
| 18 | C | |
| 19 | B | B |
| 20 | A | A |
| 21 | B | A |
| 22 | C | B |
| 23 | C | |
| 24 | C | |
| 25 | C | B |
| 26 | A | A |
| 27 | A | A |
| 28 | C | |
| 29 | C | |
| 30 | C | |
| 31 | C | |
| 32 | C | |
| 33 | A | A |
| 34 | C | |
| 35 | B | A |
| 36 | C | |
| 37 | C | |
| 38 | C | |
| 39 | C | |
| 40 | C | A |
| 41 | C | |
| 42 | A | A |
| 43 | B | A |
| 44 | B | A |
| 45 | C | |
| 46 | B | A |
| 47 | C | B |
| 48 | A | A |
| 49 | C | |
| 50 | C | |
| 51 | C | A |
| 52 | C | |
| 53 | C | |
| 54 | C | |
| 55 | C | A |
| 56 | C | |
| 57 | C | |
| 58 | A | A |
| 59 | B | A |
| 60 | A | A |
| 61 | C | |
| 62 | B | A |
| 63 | C | |
| 64 | A | A |
| 65 | A | A |
| 66 | A | A |
| 67 | C | A |
| 68 | B | A |
| 69 | B | A |
| 70 | B | A |
| 71 | C | A |
| 72 | B | B |
| 73 | A | A |
| 74 | A | A |
| 75 | C | |
| 76 | A | A |
| 77 | A | A |
| 78 | A | A |
| 79 | A | A |
| 80 | A | A |
| 81 | A | A |
| 82 | A | A |
| 83 | A | A |
| 84 | C | B |
| 85 | A | A |
| 86 | A | A |
| 87 | B | B |
| 88 | C | |
| 89 | C | |
| 90 | A | A |
| 91 | A | A |
| 92 | A | A |
| 93 | B | A |
| 94 | A | A |
| 95 | A | A |
| 96 | A | A |
| 97 | A | A |
| 98 | A | A |
| 99 | C | A |
| 100 | A | A |

TABLE 3-continued

A: IC50 < 200 nM; B: IC50 = 200 to 1000 nM; C: IC50 > 1000 nM.
Enz = IDO1 Enzyme assay, Cell = HeLa cell assay

| No. | Enz | Cell |
|---|---|---|
| 101 | A | A |
| 102 | C | C |
| 103 | A | A |
| 104 | C |   |
| 105 | B | C |
| 106 | C | C |
| 107 | C |   |
| 108 | A | A |
| 109 | B | B |
| 110 | A | A |
| 111 | A | A |
| 112 | A | A |
| 113 | A | A |
| 114 | B | A |
| 115 | A | A |
| 116 | C | B |
| 117 | A | A |
| 118 | B | A |
| 119 | A | A |
| 120 | A | A |
| 121 | C |   |
| 122 | C |   |
| 123 | A | B |
| 124 | A | A |
| 125 | C |   |
| 126 | B | B |
| 127 | C |   |
| 128 | A |   |
| 129 | B |   |
| 130 | B | B |
| 131 | B | B |
| 132 | B | B |
| 133 | B | B |
| 134 | C |   |
| 135 | C |   |
| 136 | C |   |
| 137 | B | A |
| 138 | C | B |
| 139 | C | C |
| 140 | C |   |
| 141 | C |   |
| 142 | C |   |
| 143 | C |   |
| 144 | C |   |
| 145 | C |   |
| 146 | C |   |
| 147 | A | A |
| 148 | A | A |
| 149 | A | A |
| 151 | A | A |
| 152 | A | A |
| 153 | A | A |
| 154 | A | A |
| 155 | C |   |
| 156 | C |   |
| 157 | C |   |
| 158 | A | A |
| 159 | A | A |
| 160 | C |   |
| 161 | C |   |
| 162 | C |   |
| 163 | C |   |
| 164 | A | A |
| 165 | C |   |
| 166 | A | A |
| 167 | A | A |
| 169 | A | A |
| 170 | A | A |
| 171 | A |   |
| 172 | A | A |
| 173 | A | A |
| 174 | A | B |
| 175 | A | A |
| 176 | A | A |
| 177 | A | A |
| 179 | A | A |
| 180 | A | A |
| 181 | A | A |
| 182 | A | A |
| 183 | A | A |
| 184 | A | A |
| 185 | B | A |
| 186 | C | C |
| 187 | B | A |
| 188 | A | A |
| 189 | A | A |
| 190 | A | A |
| 191 | A | A |
| 192 | A | A |
| 193 | C |   |
| 194 | C |   |
| 195 | A | A |
| 196 | B | A |
| 197 | A | A |
| 198 | A | A |
| 199 | A | A |
| 200 | B | A |
| 201 | A | A |
| 202 | A | A |
| 203 | A | A |
| 204 | A | A |
| 205 | A | A |
| 206 | A | A |
| 207 | A | A |
| 208 | A | A |
| 209 | C |   |
| 210 | A | B |
| 211 | A | A |
| 212 | A | A |
| 213 | A | A |
| 214 | B | A |
| 215 | B | A |
| 216 | A | A |
| 217 | A | A |
| 218 | B | A |
| 219 | A | A |
| 220 | A | A |
| 221 | A | A |
| 222 | A | A |
| 223 | A | A |
| 224 | A | A |
| 225 | A | A |
| 226 | A | A |
| 227 | A | A |
| 228 | A | A |
| 229 | A | A |
| 230 | A | A |
| 231 | B | B |
| 232 | C | C |
| 233 | A | A |
| 234 | A | A |
| 235 | B | A |
| 236 | A | A |
| 237 | C | B |
| 238 | A | A |
| 239 | A | A |
| 240 | A | A |
| 241 | A | A |
| 242 | C |   |
| 243 | A | A |
| 244 | A | A |
| 245 | A | A |
| 246 | A | A |
| 247 | A | A |
| 248 | A | A |
| 249 | A | B |

TABLE 3-continued

A: IC50 < 200 nM; B: IC50 = 200 to 1000 nM; C: IC50 > 1000 nM.
Enz = IDO1 Enzyme assay, Cell = HeLa cell assay

| No. | IC$_{50}$ (IDO1) Enz | Cell |
|---|---|---|
| 250 | A | A |
| 251 | A | A |
| 252 | A | A |
| 253 | A | A |
| 254 | A | A |
| 256 | A | A |
| 257 | A | A |
| 258 | A | B |
| 259 | A | B |
| 260 | B | B |
| 261 | A | A |
| 262 | A | A |
| 263 | A | A |
| 264 | B | A |
| 265 | A | |
| 266 | A | |
| 267 | A | A |
| 268 | A | A |
| 269 | C | C |
| 271 | A | A |
| 272 | A | A |
| 273 | A | A |
| 274 | A | A |
| 275 | A | B |
| 276 | A | A |
| 277 | A | A |
| 278 | A | A |
| 279 | C | C |
| 280 | A | A |

C. CHO-K1 Cell Based TDO (Tryptophan 2,3-dioxygenase) Assay

Human TDO (hTDO)-transfected CHO-K1 cells were used to identify test compounds that inhibit TDO activity and reduce Kynurenine production. CHO-K1 cells (ATCC) were cultured in DMEM supplemented with sodium bicarbonate (2.1 g/L), HEPES (4.1 g/L), L-glutamine (2 mM), non-essential amino acid (84 mg/L) and fetal bovine serum (10%) and maintained at 95% humidity and 5% CO$_2$ in a 37° C. incubator. The TDO gene (TDO2) (Accession number NM_005651.1) was purchased from Origene (USA) and stably expressed in CHO-K1 cells using the expression vector pcDNA4/Myc-HisB Hygro (Life Technologies, USA). TDO-expressing clones were identified based on the kynurenine production by the cells. Expanded clones were used for assay as described below. Unless otherwise stated, all materials were procured from Sigma.

hTDO transfected CHO-K1 cells (0.05 million/well) were seeded in a 96-well plate and maintained overnight in DMEM containing 10% FBS (200 µL) at 95% humidity and 5% CO$_2$ in a 37° C. incubator. The following day, cells were washed and incubated with test compounds (typically 31 µM to 10 nM, final volume 150 µL) in Hanks Balanced Salt Solution (HBSS) containing 80 µM L-tryptophan for 2 hours. Supernatant (150 µL) from the cells was treated with 30% TCA (30nL) to precipitate proteins. Supernatants were further incubated at 65° C. for 15 min to convert N-formylkynurenine to kynurenine. KYN in the supernatant was measured by LC/MS/MS using an API4000 mass spectrometer (Applied Biosystems) coupled to a Shimadzu Prominence LC system fitted with a C18 column.

Percent inhibition of the test compounds was determined by measuring the decrease in KYN as compared to the reaction control (DMSO vehicle). IC$_{50}$ values were calculated using Graph Pad Prism® 5 as described above. Compounds inhibited TDO activity in cell culture system and reduced the levels of kynurenine metabolite KYN as shown below in Table 4.

TABLE 4

A: IC50 < 500 nM; B: IC50 = 500 to 2000 nM;
C: IC50 > 2000 nM hTDO cellular assay

| No. | IC$_{50}$ (TDO) |
|---|---|
| 2 | B |
| 3 | A |
| 4 | C |
| 5 | B |
| 6 | B |
| 7 | C |
| 8 | B |
| 9 | B |
| 10 | C |
| 11 | C |
| 12 | C |
| 13 | B |
| 14 | B |
| 15 | B |
| 16 | B |
| 17 | B |
| 18 | B |
| 19 | C |
| 20 | B |
| 21 | B |
| 22 | C |
| 23 | B |
| 24 | C |
| 25 | B |
| 26 | B |
| 27 | B |
| 28 | C |
| 29 | C |
| 30 | B |
| 31 | C |
| 32 | B |
| 33 | B |
| 34 | C |
| 35 | B |
| 36 | B |
| 37 | C |
| 39 | B |
| 40 | B |
| 41 | B |
| 42 | C |
| 43 | C |
| 44 | B |
| 45 | C |
| 46 | B |
| 47 | B |
| 49 | B |
| 50 | B |
| 51 | C |
| 52 | B |
| 53 | C |
| 54 | B |
| 55 | C |
| 56 | C |
| 57 | B |
| 58 | A |
| 59 | B |
| 60 | B |
| 61 | C |
| 62 | C |
| 63 | C |
| 64 | B |
| 65 | B |
| 66 | A |
| 67 | B |
| 68 | B |
| 69 | C |
| 70 | B |
| 71 | C |
| 72 | B |

TABLE 4-continued

A: IC50 < 500 nM; B: IC50 = 500 to 2000 nM;
C: IC50 > 2000 nM hTDO cellular assay

| No. | IC$_{50}$ (TDO) |
|---|---|
| 73 | A |
| 74 | C |
| 75 | C |
| 76 | B |
| 77 | C |
| 78 | C |
| 79 | B |
| 80 | C |
| 81 | A |
| 82 | C |
| 83 | B |
| 84 | C |
| 85 | B |
| 87 | B |
| 88 | B |
| 89 | C |
| 90 | B |
| 93 | B |
| 94 | A |
| 95 | A |
| 96 | B |
| 97 | A |
| 98 | B |
| 99 | C |
| 100 | C |
| 102 | C |
| 103 | A |
| 104 | C |
| 105 | C |
| 106 | B |
| 107 | C |
| 108 | B |
| 109 | C |
| 110 | B |
| 111 | B |
| 113 | B |
| 114 | C |
| 115 | A |
| 116 | C |
| 117 | A |
| 118 | A |
| 119 | C |
| 120 | A |
| 121 | C |
| 122 | C |
| 123 | C |
| 124 | C |
| 125 | C |
| 126 | C |
| 127 | C |
| 128 | C |
| 129 | C |
| 130 | C |
| 131 | B |
| 132 | C |
| 133 | B |
| 135 | C |
| 136 | C |
| 137 | C |
| 138 | B |
| 139 | B |
| 141 | C |
| 142 | C |
| 143 | C |
| 144 | C |
| 145 | C |
| 146 | C |
| 147 | B |
| 148 | B |
| 149 | B |
| 151 | B |
| 152 | B |
| 153 | A |
| 154 | C |
| 155 | B |
| 156 | C |
| 157 | C |
| 158 | B |
| 159 | A |
| 160 | C |
| 161 | C |
| 162 | C |
| 163 | C |
| 164 | C |
| 165 | C |
| 166 | A |
| 167 | C |
| 172 | C |
| 173 | C |
| 174 | B |
| 175 | C |
| 176 | A |
| 177 | B |
| 179 | B |
| 180 | B |
| 181 | A |
| 182 | C |
| 183 | B |
| 184 | A |
| 185 | A |
| 186 | B |
| 187 | A |
| 188 | B |
| 189 | B |
| 190 | B |
| 191 | B |
| 192 | B |
| 193 | C |
| 194 | C |
| 195 | B |
| 196 | A |
| 197 | A |
| 198 | A |
| 199 | C |
| 200 | C |
| 201 | A |
| 202 | B |
| 203 | B |
| 204 | A |
| 205 | B |
| 206 | B |
| 207 | B |
| 208 | A |
| 209 | C |
| 210 | B |
| 211 | A |
| 213 | B |
| 214 | C |
| 215 | C |
| 216 | A |
| 217 | A |
| 218 | B |
| 219 | B |
| 220 | A |
| 221 | B |
| 222 | A |
| 223 | B |
| 224 | A |
| 225 | B |
| 226 | C |
| 227 | C |
| 228 | A |
| 229 | B |
| 230 | B |
| 231 | C |
| 232 | C |
| 233 | C |
| 234 | A |
| 235 | A |
| 236 | C |

TABLE 4-continued

A: IC50 < 500 nM; B: IC50 = 500 to 2000 nM;
C: IC50 > 2000 nM hTDO cellular assay

| No. | IC$_{50}$ (TDO) |
|---|---|
| 237 | C |
| 238 | B |
| 239 | A |
| 240 | C |
| 241 | A |
| 242 | C |
| 243 | A |
| 244 | B |
| 245 | B |
| 246 | B |
| 247 | C |
| 248 | B |
| 249 | C |
| 250 | C |
| 251 | C |
| 252 | C |
| 253 | C |
| 254 | B |
| 256 | A |
| 257 | C |
| 258 | C |
| 259 | C |
| 260 | B |
| 261 | B |
| 262 | B |
| 263 | C |
| 264 | C |
| 265 | B |
| 266 | B |
| 267 | C |
| 268 | C |
| 269 | C |
| 271 | B |
| 272 | B |
| 273 | C |
| 274 | B |
| 275 | C |
| 276 | B |
| 277 | B |
| 278 | B |
| 279 | C |
| 280 | B |
| 281 | C |

D. In-vitro IDO2 Enzyme (Indoleamine 2,3-dioxygenase2) Assay

Human indoleamine 2,3-dioxygenase-2 (hIDO2) catalyzes the oxidative cleavage of the pyrrole ring of the indole nucleus of tryptophan to yield N-formylkynurenine which can be converted to kynurenine (KYN) by deformylation. hIDO2 with an C-terminal His tag (Sino Biological Inc (China)) was expressed in E. coli cells and the protein was purified using standard methods well known in the art. Unless otherwise stated, all materials were procured from Sigma Aldrich, Mo., USA.

The assay monitoring the conversion of L-tryptophan to KYN was carried out as follows. hIDO$_2$ (160 nM) was incubated with tryptophan (5000 04) in the presence of ascorbic acid (20 mM), methylene blue (10 04) and catalase (100 µg/mL) in potassium phosphate buffer (100 mM; pH 7.5) at 37 degrees C. for 30 min. The reaction was terminated with 30% trichloroacetic acid (TCA) and further incubated at 65 degrees C. for 15 min to fully convert N-formylkynurenine to KYN. The reaction mixture was then centrifuged to remove sediments, and the KYN in the supernatant was measured by UV-visible absorption spectroscopy at 360 nm using a Waters HPLC system fitted with a C-18 column or by LC/MS/MS (C. J. D Austin et. Al, Amino Acid 2009, 565-578).

Percent inhibition at each concentration of test compounds was determined by determining the decrease in KYN with reference to the reaction control with 1% DMSO vehicle. Data were analyzed using nonlinear regression to generate IC50 values using Graph Pad Prism® 5. Compounds 2 and 184 were tested as described above. Compounds 2 and 184 inhibit IDO2 activity with an IC50 less than 1 uM and reduced the levels of kynurenine pathway metabolite KYN (Table 5).

TABLE 5A

IC50 < 1000 nM; B: IC50 = 1000 to 2000 nM; C: IC50 > 2000 nM
IDO2 Enzyme assay

| No. | IC50 values IDO2 |
|---|---|
| 2 | A |
| 184 | A |

As described herein in example 30 and TABLES 3-5, the compounds of the invention inhibit one or more of IDO1 or IDO2 or TDO.

Example 31

Reduction of LPS Induced Plasma Kynurenine Levels in C57BL/6 Mice

Inflammatory mediators such as Lipopolysaccharides (LPS) and Interferon-gamma (TFNg) arc well-established inducers of IDO1 expression. Intraperitoneal (i.p.) administration of bacterial lipopolysaccharide (LPS) induces peak IDO1 activity in a variety of tissues within one day after LPS administration resulting in the production and release of kynurenine into the bloodstream (Takikawa, O., et al. (1986) J. Biol. Chem. 261:3648-53; Yoshida, H., et al. (1998) Cell 94:739-750). LPS-injected mice have been used as models to study IDO1 expression and activity. Three-eight fed C57 BL/6 mice (age 7-8 weeks, weight: about 20-22 g) were injected intrapritoneally with bacterial lipopolysaccharide (LPS; 26:B6 Sigma) at a concentration of 6 mg/kg. Animals were then housed in normal condition for 20 hours at which time the test compounds were administered orally in formulation containing 30% polyethylene glycol 400 (PEG 400) and 20% propylene glycol (PG) in normal saline (Dosing volume 10mL/kg). Blood was drawn through retrorbital bleeds into a tube containing 100 mM EDTA for plasma collection at the following times: just prior to LPS treatment, just prior to test compound dosing (0 hr) and then at 2 hr, 4 hr, 6 hr, 8 hr, 24 hr and 48 hr post-test compound dosing. Plasma KYN and drug levels were determined by LC/MS/MS using an API4000 mass spectrometer (Applied Biosystems) coupled to a Shimadzu Prominence LC system fitted with a C18 column.

Compounds were tested as described above and the data is shown in TABLE 6. In vivo pharmacodynamic studies with LPS-injected mouse model show that the compounds of the invention inhibit the activity of IDO1 and reduce plasma kynurenine metabolite, KYN levels in vivo.

TABLE 6

A > 50%, B > 25% < 50%, C < 25%

| No. | activity | Formulation in NS |
|-----|----------|-------------------|
| 2 | A | 30% PEG & 30% PG |
| 26 | A | 25% DACM & 37.5% PG |
| 58 | A | 30% PEG & 20% PG |
| 59 | A | 40% PEG, 20% PG & 10% DACM |
| 92 | A | 30% PEG & 20% PG |
| 95 | B | 30% PEG & 30% PG |
| 96 | A | 30% PEG & 20% PG |
| 97 | A | 30% PEG & 20% PG |
| 101 | A | 30% PEG & 20% PG |
| 103 | A | 30% PEG & 30% PG |
| 117 | B | 30% PEG & 20% PG |
| 121 | C | 40% PEG & 20% PG |
| 140 | A | 30% PEG & 30% PG |
| 142 | A | 30% PEG & 30% PG |
| 147 | A | 10% CrEL, 10% EtOH & 20% PG |
| 149 | A | 10% CrEL, 10% EtOH & 20% PG |
| 154 | A | 15% CrEL, & 15% EtOH |
| 158 | A | 30% PEG & 20% PG |
| 164 | A | 30% PEG & 20% PG |
| 166 | A | 30% PEG & 20% PG |
| 169 | A | 10% CrEL, 10% EtOH & 20% PG |
| 170 | B | 40% PEG, 20% PG & 10% DACM |
| 171 | A | 40% PEG, 20% PG & 10% DACM |
| 171 | A | 40% PEG, 20% PG & 10% DACM |
| 177 | A | 40% PEG, 20% PG & 10% DACM |
| 180 | A | 40% PEG, 20% PG & 10% DACM |
| 181 | A | 40% PEG, 20% PG & 10% DACM |
| 183 | A | 15% CrEL & 15% EtOH |
| 184 | A | 30% PEG & 20% PG |
| 188 | A | 30% PEG & 20% PG |
| 190 | B | 30% PEG & 20% PG |
| 192 | A | 40% PEG & 20% PG |
| 198 | A | 40% PEG & 20% PG |
| 204 | B | 40% PEG & 20% PG |
| 207 | A | 40% PEG & 20% PG |
| 208 | A | 40% PEG & 20% PG |
| 213 | B | 40% PEG & 20% PG |
| 234 | B | 30% PEG & 20% PG |
| 240 | A | 30% PEG & 20% PG |

Example 32

A. In Vivo Testing of KYN Pathway Inhibitors for Antitumor Activity

Tumor volume reduction by the test compounds was evaluated in a syngeneic CT26/Balb/C tumor model as described below. Balb/c mice were purchased from Vivo Bio Tech, Hyderabad, India, and housed in sterile conditions using an individually ventilated caging system manufactured by Citizen Industries Limited, Ahmedabad, India. Mice were quarantined for at least 7 days before experimentation.

Mouse colorectal tumor forming cells, CT-26 cells (ATCC, USA), were cultured in DMEM and 10% FBS medium supplemented with 1x non-essential amino acid (HiMedia) in an incubator maintained at 37QC with 95% humidity and 5% $CO_2$. One million ($1 \times 10^6$) live syngeneic CT-26 cells suspended in 0.2 ml of 1x FBS were injected subcutaneously in the right flank of each Balb/c mouse (age 6-8 weeks, weight: about 18-20 g) on day 1 under anesthesia. Eight to ten mice were used per experimental group. Subcutaneous cells formed localized tumors. Animals were visually inspected twice a day. Tumor measurements were initiated 7 days post injection using Vernier calipers. Tumor sizes at day 7 ranged typically from 80-150 mm³. Tumor dimensions were subsequently measured every 3 to 4 days and tumor volume was determined. Assuming tumors to be ellipsoid, tumor volume was calculated using the formula:

$$V = (D \times d \times d)/2$$

Where D is longest diameter in mm, and d is shortest diameter in mm.

When the average tumor volume in the mice reached 100-120 mm³, tumor bearing mice were randomized for treatment with either test compound or vehicle alone. Test compounds were formulated generally in normal saline comprising Polyethylene Glycol (PEG400), Propylene glycol (PG) and Dimethyl Acetamide (DACM) at pH 4.5-5.0 and dosed orally at ranges 40-75 mg/kg (dose volume—5 mL/kg) twice a day. Solutions of the compounds were prepared immediately before dosing the animals. In general, tumor volume was measured at various times post-dosing from day 1 to day 34.

A non-limiting example is provided. Tumor bearing mice were dosed orally twice a day at 40 mg/kg body weight with either vehicle control or test compound 2 formulated in 30% Polyethylene Glycol (PEG-400), 20% Propylene glycol (PG) in normal saline. Tumors were measured and tumor volumes were determined at 1, 4, 6, 9, 11, and 14 days after the first dose as described above. Animals were sacrificed on day 14. Tumor and blood samples were harvested for further analysis. Just prior to animal sacrifice, blood was drawn retro-orbitally into a tube containing 0.2% EDTA for plasma collection. The harvested tumors were weighed and snap frozen in liquid nitrogen immediately. Plasma KYN concentrations are measured for pharmacokinetic analysis using LC/MS/MS using an API4000 mass spectrometer (Applied Biosystems) coupled to a Shimadzu Prominence LC system fitted with a C18 column.

Compound 2 significantly decreased tumor growth in compound 2-treated animal over 14 days compared to control vehicle-treated animals (FIG. 1(*a*)). Similarly, mice dosed with compounds 97, 166 and 184 reduced tumor growth by 26%-38% (FIG. 1(*b*)-1(*d*)) compared to control animals. Plasma KYN levels were reduced by 40-50% in the compound treated animals compared to control animals (data not shown).

B. Combination Therapy with Chemotherapy

Test compounds were evaluated in mice syngeneic tumor models described above for usefulness in combination therapy with a chemotheraputic agent, Doxorubicin (DOXO, Sterling Biotech, India).

Tumor bearing Balb/c mice as described earlier were randomized to receive vehicle alone, test compound alone, DOXO alone, or test compound in combination with DOXO. Animals in DOXO treated arm were injected intraperitoneally on day 1 with DOXO formulated in normal saline (7.5 mg/kg). Five days later, the animals were dosed twice a day orally with either a test compound or vehicle alone during the test period till the end of the experiment. A second smaller dose of DOXO at 3 or 4 mg/Kg was administered to the DOXO-treated animals about 3 weeks after the first DOXO dose. Tumor volume was measured in animals as described above.

Non-limiting examples follow. Test compound 97 was formulated in 40% PEG, 20% PG, 10% DACM in normal saline. From day 5 after the first DOXO dose was administered till the end of the study period on day 35, the animals were dosed twice a day orally with compound 97 (75 mg/kg). Three weeks later, the DOXO-treated animals were injected i.p. with a second dose of DOXO (3 mg/kg). Tumor volume was monitored as described above. Tumor tissues and final blood samples were harvested from the mice 4 hours after the final test compound dose. Tumor samples were weighed and snap frozen as described previously.

Figure 2:
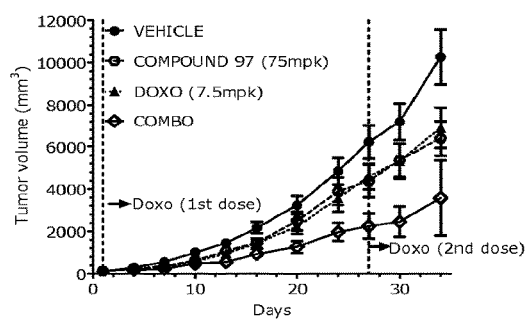
FIG. 2(a). Shows the mean tumor growth rate of CT-26 cells in Balb/c mice when dosed orally BID with test compound 184 (50 mg/kg in 40% PEG400+20% PG+10% DACM in NS) and vehicle either alone or in combination with Doxorubicin (DOXO).
FIG. 2(b). Shows the mean tumor growth rate of CT-26 tumor cells in Balb/c mice when dosed orally BID with test compound 97 (75 mg/kg in 40% PEG400+20% PG+10% DACM in NS) and vehicle either alone or in combination with DOXO.
Figure 2:
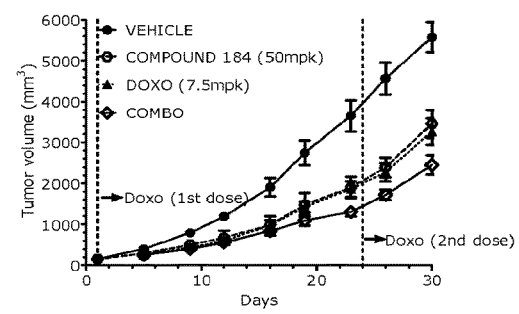

Animals treated with combination of compound 97 and DOXO showed greater reduction in tumor volume than that achieved by DOXO or by test compound alone (FIG. 2(a)).

Similarly, a second set of experiments was conducted with test compound 184 formulated in 40% PEG, 20% PG, 10% DACM in normal saline. As described above, animals were dosed with test compound 184 at 50 mg/kg twice a day orally during the study period. Animals treated with a combination of compound 184 and DOXO showed greater reduction in tumor volume than that achieved by DOXO or by the test compound alone (FIG. 2(b)). Thus, the time of tumor progression is reduced by treatment with compounds of the invention.

C. Tissue Penetration Assays i. Tumor penetration in mice: Tumor penetration of test compounds and KYN levels in tumor and plasma of treated animals were determined in a syngeneic CT26/Balb/C tumor model. Briefly, three to four tumor bearing Balb/c mice (tumor size=150-200 mm$^3$) were dosed twice a day orally for 4 days with test compound (for e.g., compound 2) at 50 mg/kg formulated in carboxymethyl cellulose (CMC). A vehicle control was included along with the test compounds. Blood samples were collected by retro-orbital bleed or terminal cardiac bleed into tubes containing heparin just before the final dose and at two hours after the final dose. Animals were sacrificed two hours post-final dose. Tumors were harvested and weighed immediately. Tumors were then snap frozen in liquid nitrogen, pulverized and dissolved in homogenization buffer (chilled acetonitrile/water/formic acid (10:90:0.1 v/v/v) to extract test compounds and kynurenine, KYN.

Plasma and tumor tissue KYN levels were reduced in test compound treated animals compared to control vehicle-treated animals (TABLE 7). For example, compounds 2 and 97 each reduced tumor KYN levels by 81%. At 2 hours post-dosing, the plasma KYN levels were reduced by 62% and 67% respectively in the animals treated with compound 2 or 97 compared to the control animals dosed with vehicle alone. The concentration of test compounds in the tumor tissue extracts is determined by LC/MS/MS using an API 4000 or AP15500 Qtrap mass spectrometer.

TABLE 7

| No | Dose (mg/kg) | % KYN drop Plasma | % KYN drop Tumor |
|---|---|---|---|
| 2 | 50 | A | A |
| 142 | 50 | A | A |
| 26 | 20 | B | A |
| 97 | 50 | A | A |
| 98 | 50 | C | C |
| 103 | 50 | B | C |
| 145 | 50 | B | C |
| 154 | 50 | A | B |
| 158 | 50 | A | A |
| 164 | 50 | B | B |
| 166 | 50 | B | B |
| 181 | 50 | B | C |
| 183 | 50 | B | C |
| 180 | 50 | C | B |
| 184 | 50 | A | A |
| 188 | 50 | B | A |
| 190 | 50 | B | A |
| 195 | 50 | A | A |
| 198 | 50 | A | A |
| 204 | 50 | A | A | ii. Brain penetration in rats: Early and accurate prediction of drug penetration of the blood brain barrier is vital for the development of drugs targeting the central nervous system. Accordingly, ability of the compounds of the invention to penetrate the blood brain barrier was tested according to the methods well established in the art (Giorgetti et al., (2010) JPET 333:748-757, 2010). Briefly, Sprague-Dawley rats (n=3 per time point studied) were administered a single intravenous dose of the test compounds 2 or 97 formulated in 40% PEG and 20% PG at 10 mg/kg. Three rats were used for each of the following time points post-dosing: 0.5 hr, 1.5 hr and 3.0 hrs. First, blood was collected during deep anesthesia in heparinized tubes, and then animals were sacrificed and their brains were harvested. The brains were then pulverized in liquid nitrogen and homogenized in fixed volumes of ice cold homogenization buffer (10% Acetonitrile, 0.1% formic acid in water). Plasma was separated from blood using standard procedures. Plasma and brain concentrations of test compounds 2 and 97 were determined by LC/MS/MS using an API 4000 or AP15500 Qtrap mass spectrometer. Brain/Plasma ratio of test compounds 2 and 97 were determined after normalizing brain weight and buffer volume.

Compound 2 and 97 are capable of penetrating blood brain barrier to enter the brain tissue (TABLE 8). Accordingly, the compounds of the invention are useful for treating kynurenine pathway- and/or IDO1- and/or IDO2- and/or TDO-associated brain diseases.

TABLE 8

| No. | Time (hr) | Ratio of Drug Concentration (Brain:Plasma) |
|---|---|---|
| 2 | 0.5 | 9.8:1 |
|  | 1.5 | 10.7:1 |
|  | 3.0 | 6.0:1 |
| 97 | 0.5 | 0.67:1 |
|  | 1.5 | 0.47:1 |
|  | 3.0 | 0.64:1 |

Example 33

Induction of T-cell Proliferation

Conceptually, a reduction in the immune suppressive effects of kynurenine pathway metabolites or one or more of IDO1 or IDO2 or TDO enzymes may result in increased numbers or reactivity of tumor specific immune cells. Further, inhibition of one or more of IDO1 or IDO2 or TDO enzymes may further increase the number or reactivity of tumor reactive immune cells when combined with other therapeutics, for example chemotherapeutics (e.g., doxorubicin) and/or immune modulators (e.g., anti-CTLA4 and/or anti-PD-L1 and /or anti-PD1 antibody). In animal models described below, it may also be possible to directly and/or indirectly measure the number and/or activity of tumor reactive immune cells. Methods for measuring the number and/or activity of tumor reactive immune cells are well established and can be performed using techniques familiar to those skilled in the art (Current Protocols in Immunology, vol 4, Coligan, J. E., et al; Immunotherapy of Cancer, Human Press, 2006, Disis, M. L. and references therein). The following experiment addresses the ability of the compounds of the invention to induce T-cell proliferation and reduce the immunosuppressive effects of kynurenine pathway metabolites or the activity o one or more of IDO1 or IDO2 or TDO enzymes.

Effect of Kynurenine Pathway Inhibitors on T-cell Proliferation that is Suppressed by IDO1-expressing Dendritic Cells Monocytes are collected from human peripheral blood mononuclear cells by leukophoresis. Monocytes are then seeded at a density of $1\times10^6$ cells/well in a 96 well plate, using RPMI 1640 medium supplemented with 10% FBS and 2 mM L-glutamine (all from Invitrogen). Adherent cells are retained on the plate after overnight culture at 37° C. Adherent monocytes are then stimulated for 5-7 days with 100 ng/ml GM-CSF (PeproTech) and (250 ng/ml L4 (PeproTech), followed by activation with 0.5 ug/ml LPS from Salmonella typhimurium (Sigma) and 50 ng/mL IFN gamma (R&D systems) for additional 2 days to induce dendritic cell maturation.

After dendritic cell activation, the medium is replaced with completed RPMI 1640 supplemented with 100-200 U/ml L-2 (ProSpec-Tany Technogene) and 100 ng/mL anti-$CD_3$ antibody (PharMingen), T-cells (~3 times.$10^5$ cells/well), and serial dilutions of test compounds. After incubation for 2 more days, T-cell proliferation are measured by BrdU incorporation assay, using a colorimetric Cell Proliferation ELISA kit per manufacturer's instruction (Roche Molecular Biochemicals). Cells are continuously cultured for 16-18 hours in the presence of 10 uM BrdU labeling solution. The FixDenat solution is removed and 100 ul/well ant-BrdU-POD antibody conjugate working solution was added. The reaction is carried out at room temperature. The antibody conjugate is then removed and cells were rinsed 3 times with 200 ul/well washing solution. Finally, 100 ul/well of substrate solution is added and the results are obtained using a microreader (Spectra Max Plus, Molecular Devices) during color development. Multiple readings at various time points are obtained to ensure that the data is within the linear range. The data is routinely obtained from replicated experiment, and appropriate controls are included. (Terness P, et al. (2002) J. Exp. Med. 196(4):447-57; and Hwu P, et al. (2000) J. Immunol. 164(7):3596-9).

Example 34

In Vivo TDO Assay

The ability of test compounds to inhibit TDO activity in vivo in tumors can be determined using P815 mouse tumor model (Uyttenhove C, et al. (2003) Nat Med 9:1269-1274; Pilotte L, et al. PNAS 2012). Briefly, P815 tumor cells are transfected with TDO cDNA. TDO-expressing tumor cells are injected i.p. into naïve syngenic DBA/2 mice (Harlan, USA) resulting in tumor growth. Tumor volumes are measured as described above. When the average tumor volumes in the mice reach 100-120 $mm^3$, tumor bearing mice are randomized for treatment with either test compound or vehicle alone. Test compounds are formulated generally in normal saline comprising Polyethylene Glycol (PEG400), Propylene Glycol (PG) and Dimethyl Acetamide (DACM) at pH 4.5-5.0 and dosed orally at ranges 40-75 mg/kg (dose volume-5 mL/kg) twice a day. Solutions of the compounds are prepared immediately before dosing the animals. In general, tumor volume is measured at various times post-dosing from day 1 to day 34. The reduction in tumor progression and plasma Kyn levels are determined as described above.

Liver and tumor tissue homogenates are obtained from the mice treated with either a test compound or vehicle. Assays for hepatic and tumor TDO activity are carried out using L-Trp as substrate as previously described (Pilotte L, et al. PNAS 2012), with activity expressed as µmol of KYN formed per hour per gram of wet liver weight. Briefly, dry pellets of liver and tumor tissues are lysed in 50 mM potassium phosphate buffer (pH 7.5). 150 mM KCL, 250 mM sucrose, 1 mM L-Tryptophan, 10 uM bovine hemin and protease inhibitors (complete EDTA free, Roche Applied Science). The extract is first centrifuged at 4 degree C. for 5 min at 700×g and the supernatant is centrifuged at 20,000×g for 15 min. The buffer of the clarified extract is then exchanged over 50 mM potassium phosphate buffer (H 7.5) using a HiTrap desalting column (GE Healthcare), and aliquots are frozen in liquid nitrogen and kept at −80 C until further use.

TDO activity is measured as follows: The reaction mixture contain (final concentration) 50 mM potassium phosphate buffer (pH 7.5), protease inhibitors, 20 mM ascorbic acid, 10 uM methylene blue, 500 units/ml catalase (bovine liver, Sigma), and L-Tryptophan in the presence or absence of test compounds. The reaction is initiated by addition of 100 µl of cell/tissue extract to 100 µl of reaction mixture prewarmed at 37 C. The reaction is conducted at 37 C for 10, 30, 60 min and stopped by the addition of 40 µl of TCA 30% (wt/vol). To convert N-formylkynurenine to kynurenine, the reaction mixture is mixed with 125 µl of 2% (wt/vol) 4-(Dimethylamino) benzaldehyde in acetic acid and incubated for 10 min at room temperature. The reaction mixture is then centrifuged to remove sediments and the supernatant was monitored by LC/MS/MS using a API4000 mass spectrometer (Applied Biosystems) coupled to a Shimadzu Prominence LC system fitted with a Cl 8 column. Percent inhibition at each concentration of test compounds is determined by estimating the decrease in KYN. Data are analyzed using nonlinear regression to generate $IC_{50}$ values using Graph Pad Prism® 5.

Example 35

In Vivo Testing of Inhibitors in LPS-induced Depressive-like Behaviors in Mice Model Increased levels of Kynurenine pathway metabolites, independent of immune activation or IDO1 activation, are capable of inducing depressive-like behaviors in mice administered with increasing doses of exogenous L-Kynurenine. LPS administration is known to activate IDO1 and culminate in depressive-like behavioral syndrome. Depressive behavior of mice in LPS injected mice has been characterized by increased duration of immobility in both the forced swim and tail suspension tests. Compounds of the invention reduce plasma KYN levels (Examples 31 and 32; Tables 6 and 7). The ability of the compounds of the invention to reduce depressive-like behavior are tested in mice injected with LPS that show increased KYN levels and increased IDO1 and/or TDO activity following procedures well known in the art (O'Connor et al. Mol. Psychiatry. 2009 May; 14(5): 511-522; Porsolt, R. D. Rev Neurosci. 2000;11 (1):53-8).

Behavioral Experiments—Locomotor Activity

The effects of LPS on locomotor activity (LMA) is assessed in mice individually placed in a clean, novel cage similar to the home cage, but devoid of bedding or litter. The cage is divided into four virtual quandrants, and the LMA is measured by counting the number of line crossings and rearings over a 5 min period. Counting is done by a well-trained observer who is blinded to the treatments.

Behavioral experiments—Forced Swim Test

The forced swim test (FST) is conducted according to methods well established and known in the art (Porsolt, R. D. Rev Neurosci. 2000; 11(1):53-8). Briefly, each mouse is placed individual in a cylinder (diameter 23 cm; height 31 cm) containing 15 cm of water maintained at 23+/−1 degree C. The water is changed between testing sessions. Mice are placed into the water for 6 min and then returned to their home cage. During the test, the mice are video recorded from above, and the duration of immobility is determined over the last 5 min of the test using the mobility function of the "Observer Basic" software (Nolus, Netherlands). Briefly, the mice arc recognized in contrast from their background and tracked in 2 different dimensions as the surface arc of the detectable object (mouse) moves within the predefined arena. Mobility is defined as the displacement of detectable surface area (mouse) over time and is averaged over 3 sample intervals to reduce error generated by sharp movements or missing frames in the digital record. Program analysis settings can be: Sampling rate=3/s; detection method=substration with low threshold of 20 and high threshold of 255 and minimum detectable object size of 200 pixels; image filtering=2 pixel erosion and dilation; mobility threshold of 20% with 3 interval averaging. It is well understood that other settings can be used by those of skill in the art.

Behavioral Experiments—Tail Suspension Test

The mice are taken from their home cage and a small piece of adhesive tape is placed approximately 2 cm from the tip of the tail. A single hole is punched in the tape and the mice are hung individually for a period of 10 min on a hook connected to a strain gauge. A computerized system for processing the force exerted on the guage (Mouse Tail Suspension Package, MED-TSS-MS, Med Associates, St. Albans, Vt.) automatcally collected and analyzed the movements of each individual mouse. The time of immobility is determined after establishing a threshold of each individual mouse that is set precisely at the activity level that would exclude all movements and only encompass immobility. Time below the threshold indicates the time of immobility. Program analysis settings can be: integration=on; resolution=0.1; gain=4; start rigger=20.

Behavioral data are analyzed using a one-way (treatment), two-way (pretreatment X treatment) or a three-way (pretreatment X treatment X time) ANOVA with repeated measurement on the time factor where appropriate, followed by a post-hoc pairwise multiple comparison procedure using the Fisher's LSD method, if the interaction is significant.

Example 36

In Vivo Testing of the Inhibitors in Human Immunodeficiency Virus-1 (HIV-1) Encephalitis Model Inhbition of IDO1 is known to enhance the elimination of HIV-1 virus infected macrophages in the central nervous system in animal models of a Human Immunodeffiency Virus-1 (HIV-1) Encephalities (Potula et al. Blood. (2005) 106: 2382-2390). The ability of the test compounds to eliminate infected HIV-1 macrophages effectively in the nervous system can be tested using such well-established models.

Cell Isolation and Viral Infection

Monocytes and PBL can be obtained by counter current centrifugal elutriation of leukopheresis packs from Dulbecco's Modified Eagle's Medium (DMEM, Sigma-Aldrich) supplemented with 10% heat-inactivated pooled human serum, 1% glutamine, 50 ug/ml gentamycin, l0ug/m1 Ciproflaxin (Sigma), and 1000 U/ml highly purified recombinant human macrophage colony-stimulating factor. After 7 days in culture, MDM are infected with HIV-1ADA at multiplicity of infection of 0.01.

Hu-PBL-NOD/SCID HIVE Mice 4 week old male NOD/C.B-17 SCID mice can be purchased from a resource such as Jackson Laboratory (Bar Harbor, Minn., USA). Animals are maintained in sterile microisolator cages under pathogen-free conditions. All animals are injected i.p. with rat anti-$CD_{122}$ (0.25 mg/mouse) 3 days before PBL transplantation ad two with rabbit asialo-GM1 antibodies (0.2 mg/mouse) (Wako) one day before and three days after PBL injection ($20 \times 10^6$ cells/mouse). HIV-1ADA infected MDM ($3 \times 10^5$ cells in 10 ul) are injected intracranially (i.c.) eight days following PBL reconstitution generating hu-PBL-NOD/SCID HIVE mice. Immediately following the intracranial injection of HIV-1 infected MDM the hu-NOD/SCID mice are subcutaneously (s.c.) implanted with control (vehicle) or compound pellets (14-28 day slow release, Innovative research). Experiments are desiged to confirm the induction of virus-specific CTLs in hu-NOD/SCID mice by tetramer staining and neuropathic analyses of MDM elimination from the brain tissue. Then, experiments are designed to analyze human lymphocyte reconstitution, humoral responses, and neuropathological alterations. In these experiments, animals are bled on day 7 and sacrificed at 14 and 21 days after i.c. injection of human MDM. Blood collected in EDTA-containing tubes is used for flow-cytometry and plasma is used for detection of HIV-1 p24 using ELISA (Beckman Coulter). HIV-1 specific antibodies are detected by Western blot tests according to the manufacturer's instructions (Cambridge Biotech HIV-1 Western Blot kit, Calypte Biomedical). Similar amount of virus-specific antibodies are detected in control and compound-treated animals. A total of 3 independent experiments can be performed using 3 different human leukocyte donors.

FACScan of Peripheral Blood and Spleen in hu PBL-NOD/SCID HIVE Mice

Two-color FACS analysis can be performed on peripheral blood at weeks 1-3 and splenocytes at weeks 2 and 3 after i.c. injection of human MDM. Cells are incubated with fluorochrome-conjugated monoclonal antibodies (mAbs) to CD4, CD, CD56, CD3, IFN-gamma (Bioscience) for 30 mins at 4 degrees C. To evaluate the cellular response, IFN-gamma intracellular staining is performed in combination with anti-human $CD_8$ and FITC-conjugated anti-mouse $CD_{45}$ to exclude murine cells. To determine the antigen-specific CTL, allophycocyainn-conjugated tetramer staining for HIV-$1_{gag}$ (p17(aa77-85) SLYNTVATL, SL-9) and HIV-$1_{pol}$ [(a476-485) ILKEPVHGV, L-9] is performed on phytohemaglutinin/IL-2 (PHA/IL2)-stimulated splenocytes. Cells are stained following the recommendation of the NIH/NIAID, National Tetramer Core Facilities. Data are analyzed with a FACS Calibor using CellQuest Software (Becton Dickinson Immunocytometry System).

Histopathology and Image Analyses

Brain tissues are collected at days 14 and 21 after i.c. injection of MDM, fixed in 4% phosphate-buffered paraformaldehyde and embedded I paraffin or frozen at −80 degrees C. for later use. Coronal sections from the embedded blocks are cut in order to identify the injection site. For each mouse, 30-100 (5 um thick) serial sections are cut from the human MDM injection site and 3-7 slides (10 sections apart) are analyzed. Brain sections are deparaffinized with xylene ad hydrated in gradient alcohols. Immunohistochemical staining follows a basic indirect protocol, using antigen retrieval by heating to 95 degree C. in 0.01 mol/L citrate buffer for 30 mi for antigen retrieval. To identify human cells in mouse brains, mAb to Vimentin (1:50, clone 3B4, Dako Corp.), which identifies all human leukocytes is used. Human MDM ad $CD_{8+}$lymphocytes are detected with $CD_{68}$ (1:50 dilution, clone KP 1) and $CD_8$ (1:50 dilution, clone 144B) antibodies respectively. Virus-infected cells are labeled with mAb to HIV-$1_p24$ (1:10, clone Kal-1, all from DAKO). Reactive murine microglial cells are detected with Iba-1 antibody (1:500, Wako). Expression of human IDO1 (huIDO1) and/or human TDO (huTDO) are visualized with Abs obtained from Enzo Lifesciences (USA) and Abcam (USA). Primary antibodies are detected with appropriate biotinylated secondary antibodies and visualized with aviden-biotin complexes (Vectastain Elite ABC kit, Vector Laboratories) or horseradish-peroxidase (HRP)-coupled dextran polymer (EnVision, DAKO). Immunostained sections are counterstained with Mayer's hemotoxylin. Sections from which primary antibody is deleted or irrelevant IgG isotype is incorporated serves as controls. Two independent observers in a blinded fashion count the numbers of $CD^{8+}$ lymphocytes, $CD^{68+}$ MDM, and $HV-1_{p24}$ cells in each section form each mouse. Light microscopic examination is performed with a Nikon Eclipse 800 microscope (Nikon Instruments Inc.). Semi-quantitative analysis for Ibal (percentage of area occupied by immunostaining) is carried out by computer-assisted image analysis (Image-Pro®Plus, Media Cybernetics).

Data is analyzed using Prism (Graph Pad) with Student t-test for comparisons and ANOVA. P values<0.5 are considered significant. (Potula et al. Blood Oct. 1, 2005, vol: 106(7) 2382-2390).

Example 37

Increased levels of IDO1 and kynurenine pathway metabolites has been observed in the autopsy brain slices brains of Alzheimer's disease subjects (Bonda et al. Redox Rep. 2010; 15(4): 161-168) and circulating antibodies to the kynurenine metabolites have also been identified (Duleu et al. International Journal of Alzheimer's Disease, vol. 2010, Article ID 501541, 6 pages, 2010. doi:10.4061/2010/501541). The ability of the test compounds to reduce the kynurenine pathway metabolites in the brains by inhibiting kynurenine pathway or one or more of IDO1 or IDO2 or TDO is tested used animal models of Alzheimer's disease.

Various Alzheimer's disease mouse models animals (for example, B6; 129-Psen1tm1Mpm Tg(APPSwe,tauP301L) 1Lfa/Mmjax, B6C3-Tg(APPswe, PSEN1dE9)$_{85}$Dbo/Mmjax, B6.Cg-Tg(APPswe,PSEN1dE9)85Dbo/Mmjax, B6.129-Tg(APPSw)40Btla/Mmjax, B6.Cg-Nos2tm1Lau Tg(Thy1APPSwDutIowa)BWevn/Mmjax) can be purchased from Jackson Laboratories, USA. As an non-limiting example, B6; 129-Psen1tm1Mpm Tg(APPSwe, tauP301L) 1Lfa/Mmjax mice are purchased and housed in sterile conditions as described before. The mice develop neurofibrillary tangles in the hippocampus after about 6 months and in the rest of the cortex subsequently. Cognitive deficits in the mice are manifested about 4 months of age although no neuronal loss has been reported in these mice.

Mice about 6 moths of age are randomized to be dosed in a single intravenous dose of either a vehicle control or a test compound formulated in PEG and PG in normal saline at 10 mg/kg as described in earlier examples. In one set of experiments, the ability of the compounds to penetrate blood brain barrier and reduce plasma kynurenine metabolites by the test compounds tested. Three mice are used for each of the following time points post-dosing: 0.5 hr, 1.5 hr and 3.0 hrs. Brain and plasma drug and KYN levels are determined in the animals as described previously. Presence and reduction of circulating antibodies to kynurenine pathway metabolites is determined (Duleu et al. International Journal of Alzheimer's Disease, vol. 2010, Article ID 501541, 6 pages, 2010. doi:10.4061/2010/501541).

In a second set of experiments, effect of test compounds on the cognitive function of the mice is tested. Test compound and vehicle control treated animals are dosed orally twice as day as previously described for 8 days and subjected to behavioral tests that arc well known in the art (Choi et al. J. Neurochem. 2013, 124(1) 59-68).

Briefly, spatial learning and memory is assessed using the Morris Water Maze, as previously described (McKee et al. Brain Res. 2008, 1207, 225-236) in mice treated with either a test compound or a vehicle control. Briefly, a circular plastic pool is filled with water (22° C.) that is colored with non-toxic white paint to obscure the location of a submerged platform. Three visual cues are placed around the tank to orient the mice, with the platform remaining in a fixed location. The platform location is kept constant for each mouse during training, and it is 1.5 cm beneath the surface of the water. On each day, training consisted of five trials. For each trial, the mouse is placed into the pool facing the wall from one of four randomly varied start positions and allowed to swim until finding the platform. If a mouse fails to find the platform within 60 s, the mouse is manually guided to the hidden platform and allowed to stay on the platform for 30 s. Probe trials for retention of spatial training are conducted 1.5 and 24 h after the last training trial. During the probe trials, the platform is removed and mice are free to swim in the pool for 60 s. Mice are monitored with a camera mounted on the ceiling directly over the pool and recorded for subsequent analysis. The escape latency to cross the platform location, the number of platform location crosses, and path length are recorded. The ability of the test compound to improve cognitive function and reduce plasma and brain kynurenine metabolite levels is determined.

Example 38

Identification of Metabolites of the Test Compounds

Prodrugs and metabolites of a compound may be identified using routine techniques known in the art. See, e.g., Bertolini et al., J. Med. Chem., 40, 2011-2016 (1997); Shan, et al., J. Pharm. Sci., 86 (7), 765-767; Bagshawe, Drug Dev. Res., 34, 220-230 (1995); Bodor, Advances in Drug Res., 13, 224-331 (1984); Bundgaard, Design of Prodrugs (Elsevier Press 1985); Larsen, Design and Application of Prodrugs, Drug Design and Development (Krogsgaard-Larsen et al., eds., Harwood Academic Publishers, 1991); Dear et al., J. Chromatogr. B, 748, 281-293 (2000); Spraul et al., J. Pharmaceutical & Biomedical Analysis, 10, 601-605 (1992); and Prox et al., Xenobiol., 3, 103-112 (1992).

Metabolites of test compounds are identified by in vitro incubations with liver microsomes, liver S9 fractions and hepatocytes using either cold or $^{14}C$-labeled compounds. They arc identified using HPLC based on retention times, MS and MS/MS fragmentation times and NMR analysis.

A. Liver Microsomes

Test compounds are incubated with pooled liver microsomes from mouse. Incubations are carried out at 37 degrees C. in a shaking water bath. The incubation mixtures consist of: 0.1 M Potassium Phosphate buffer, pH 7.4, 0.5 mM NADPH, 0.5 mg/ml liver microsomal protein, and 20 uM of a test compound. After 5 mins pre-incubation at 37 degree C., to incubations are initiated with the addition of the test compound and NADPH. After 60 mins, the mixtures are quenched by adding one volume of cold acetonitrile. The samples are vortexed and centrifuged for 10 mins at 14000 rpm. Aliquots of the supernatant (200 ul) are taken for LC/MS/MS analysis.

B. Liver S9 Fractions

The test compounds are incubated at 37 degree C. with pooled liver S9 fractions taken from humans in a shaking water bath. The incubation mixtures consist of: 0.1M Potassium Phosphate buffer, pH 7.4, 0.5 mM NADPH, 0.5 mg/ml liver microsomal protein, and 20 uM of a test compound. After 5 mins pre-incubation at 37 degree C., to incubations are initiated with the addition of the test compound and NADPH. After 2 hours, the mixtures are quenched by adding one volume of cold acetonitrile. The samples are vortexed and centrifuged for 10 mins at 14000 rpm. Aliquots of the supernatant (200 ul) are taken for LC/MS/MS analysis.

C. Hepatocytes

A test compound is incubated with pooled hepatocytes from mice at concentrations of 3 uM to 30 uM. The incubation mixtures are prepared by adding 4.5 ul/ml of 0.67 and 6.7 uM of $^{14}$C-labeled compound stock solutions in acetonitrile for 3 uM to 30 uM incubations respectively at an appropriate amount of incubation medium (2 to 5 ml) containing a $10^6$ cells/ml. All samples are incubated at 37 degrees C. for 3 hours in an incubatr under 5% $CO_2$ atmosphere on an orbital shaker. The mixtures are quenched by adding one volume of cold acetonitrile. The samples are vortexed and centrifuged for 10 mins at 14000 rpm. Radioactivity in 20 ul of supernatant is measured by liquid scintillation and 20 ul of the suprnatents is injected into HPLC for metabolite profiling.

Metabolites of test compounds can also also identified from in vivo urine, bile, feces and plasma samples from mammals including humans using $^{14}$C-labeled test compounds. A representative study is described below.

Six mice arc dosed orally with a $^{14}$C-labeled test compound with a target dose of 100 mg/kg, 100 uCi/kg. The dosing solutions are prepared in 50 mM citrate buffer the night before dosing and stored at RT in the dark. Bile, urine and feces are obtained over intervals through 48 hours post-dose. Blood is drawn before dosing and at 0.5, 1, 2, 4, 8, 12, 24 and 48 hours post dosing. Plasma is prepared from blood samples by centrifuging for 15 min at 1000 g.

A. Bile

A representative pooled bile sample is prepared by combining 5% portion of volume of each bile sample/mouse collected over 48 hours. The pooled bile sample is diluted 1:1 (vol:vol) by addition of water to bile. The diluted bile is centrifuged for 10 min at 14000. Supernatants (20 ul aliquot) are analyzed by LC/MS/MS for the metabolite identification.

B. Urine

A representative pooled urine sample is prepard by combining 20% portion of volume of each urine sample/mouse collected over 48 hours. The pooled urine sample is diluted 1:1 (vol:vol) by addition of water to bile. The diluted bile is centrifuged for 10 min at 14600. Supernatants (30 ul aliquot) are analyzed by LC/MS/MS for the metabolite identification.

C. Plasma

Two pooled samples (1 h and 4 h) are prepared by combining equal volumes of plasma samples from each mouse that are collected for each time point. The pooled samples are each extracted once with 5 ml acetonitrile/methanol (50:50 by volume) and twice additionally with 3 ml acetonitrile/ethanol. After extraction with organic solvents, the extracted samples are centrifuged at 4000 rpm for 10 min at 5 degree C. and the supernatants from each centrifugation step are combined. The supernatants are evaporated to dryness at RT under $N_2$ gas. The dried residues are reconstituted in 350 ul of the mobile phase of 80%/20% water containing acetonitrile. The samples are centrifuged again at 14000 rpm for 10 mins at 5 degrees C. 100 ul of supernatants are injected into LC/MS/MS for metabolite identification.

D. Feces

A representative pooled feces sample is prepared by combining 5% portion of volume of each feces sample/mouse collected over 48 hours. The pooled feces sample (1 ml) is extracted with 2 m of methanol/acetonitrile (50:50 vol/vol). The mixtures are vortexed, sonicated for and centrifuged at 4000 rpm for 15 min. Supernatants are collected and the pellets are extracted two more times with methanol/acetonitrile/water (1:1:1 v/v/v) and the supematents are combined and evaporated to dryness under N2. The dried residues are suspended in 0.5 ml methanol/water 1:1 (v/v) and centrifuged for 10 min at 14000 rpm. Supernatents (60 ul aliquot) are analyzed by LC/MS/MS for the metabolite identification.

Without wishing to be bound to the above exemplar, it is to be understood that in the methods described herein, the individual components of a co-administration, combination can be administered by any suitable means, contemporaneously, simultaneously, sequentially, separately , alternation or in a single pharmaceutical formulation. Where the co-administered compounds or compositions are administered in separate dosage forms, dosage levels, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

All publications cited in this specification are incorporated herein by reference. While the invention has been described with reference to particular embodiments, it will be appreciated that modifications can be made without departing from the spirit of the invention. Such modifications are intended to fall within the scope of the appended claims.

What is claimed is:
1. A compound of formula (I):

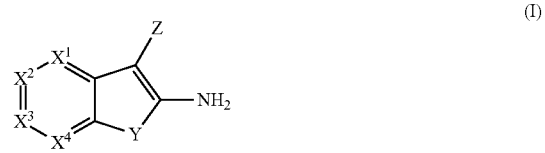

wherein:
  $X^1$ is $CR^1$;
  $X^2$ is $CR^2$;
  $X^3$ is N;
  $X^4$ is $CR^4$;
  Y is O,
  Z is $NR^5R^6$;
  $R^1$, $R^2$ and $R^4$ are independently selected from the group consisting of H, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, mono or bicyclic optionally substituted $C_6$-$C_{14}$ aryl, mono or bicycle optionally substituted heteroaryl, optionally substituted (aryl)alkyl, (alkoxy)carbonyl, (alkyl)amido, (alkyl)amino, optionally substituted mono or bicyclic cycloalkyl, optionally substituted mono or bicycle heterocyclyl, aminoalkyl, alkylcarboxyl, (alkyl)carboxyamido, optionally substituted (aryl)amino, hydroxyl, halogen, $C_1$-$C_6$ haloalkyl, optionally substituted heterocyclyl(alkyl)-, optionally substituted heteroaryl(alkyl), hydroxyalkyl, perfluoroalkyl, optionally substituted aryloxy, optionally substituted heteroaryloxy, optionally substituted $C_3$-$C_8$ cycloalkoxy, $N(R^7)_2$, CN, $NO_2$, $CO_2H$, $CONR^AR^B$, $S(O)_nR^7$, and optionally substituted heterocyclyloxy having 1 to 2 heteroatoms selected from the group consisting of O, $S(O)_n$, and $NR^7$;

n is 0 to 2;

$R^A$ and $R^B$ are independently selected from the group consisting of H, optionally substituted $C_1$-$C_6$ alkyl, optionally substituted mono or bicyclic $C_6$-$C_{14}$ aryl, optionally substituted mono or bicyclic heteroaryl, optionally substituted (aryl)alkyl, optionally substituted mono or bicyclic $C_3$-$C_8$ cycloalkyl, optionally substituted mono or bicyclic heterocyclyl, $C_1$-$C_6$ haloalkyl, optionally substituted heterocyclyl(alakyl), optionally substituted heteroaryl(alkyl), hydroxyalkyl, and perfluoroalkyl;

$R^5$ is selected from the group consisting of optionally substituted $C_1$-$C_6$ alkyl, optionally substituted mono or bicyclic $C_6$-$C_{14}$ aryl, optionally substituted (aryl)alkyl, optionally substituted mono or bicyclic cycloalkyl, optionally substituted mono or bicyclic heterocyclyl, $C_1$-$C_6$ haloalkyl, optionally substituted heterocyclyl(alkyl), optionally substituted heteroaryl(alkyl), hydroxyalkyl, and perfluoroalkyl;

$R^6$ is H; and $R^7$ is H, $C_1$-$C_6$ alkyl, mono or bicyclic $C_6$-$C_{14}$ aryl, mono or bicyclic heteroaryl, (aryl)alkyl, (alkoxy)carbonyl, (alkyl)amido, (alkyl)amino, mono or bicyclic cycloalkyl, mono or bicyclic heterocyclyl, alkylcarboxyl, heterocyclyl(alkyl), heteroaryl(alkyl), hydroxyalkyl, perfluoroalkyl, aryloxy, heteroaryloxy, $C_3$-$C_6$ cycloalkoxy, or heterocyclyloxy having 1 to 2 heteroatoms selected from the group consisting of O, $S(O)_n$, and $NR^A$;

or a pharmaceutically acceptable salt thereof.

2. The compound according to claim 1, wherein $R^1$ is H, halogen, CN, $C_1$-$C_6$ hydroxyalkyl, $C_1$-$C_6$ alkoxy, or $C_1$-$C_6$ alkyl.

3. The compound according to claim 1, wherein $R^2$ is H, halogen, hydroxyl, CN, $N(R^7)_2$, mono or bicycle optionally substituted $C_6$-$C_{14}$ aryl, optionally substituted $C_1$-$C_6$ alkoxy, optionally substituted $C_1$-$C_6$ alkyl, or optionally substituted aryloxy.

4. The compound according to claim 1, wherein $R^4$ is H, optionally substituted $C_1$-$C_6$ alkyl, optionally substituted $C_2$-$C_6$ alkenyl, optionally substituted $C_2$-$C_6$ alkynyl, mono or bicycle optionally substituted $C_6$-$C_{14}$ aryl, mono or bicyclic optionally substituted heteroaryl, optionally substituted (aryl)alkyl, optionally substituted mono or bicyclic cycloalkyl, optionally substituted mono or bicyclic heterocyclyl, halogen, optionally substituted heterocyclyl(alkyl)-, optionally substituted heteroaryl(alkyl) or CN.

5. The compound according to claim 4, wherein $R^4$ is optionally substituted $C_1$-$C_6$ alkyl, optionally substituted $C_2$-$C_6$ alkenyl, optionally substituted $C_2$-$C_6$ alkynyl, optionally substituted (aryl)alkyl, halogen, optionally substituted heterocyclyl(alkyl)-, optionally substituted heteroaryl(alkyl) or CN.

6. The compound according to claim 1, wherein $R^5$ is optionally substituted phenyl.

7. The compound according to claim 6, wherein $R^5$ is:

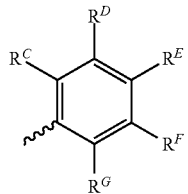

wherein, $R^C$ to $R^G$ are independently selected from the group consisting of H, halogen, $C_1$-$C_6$ haloalkyl, $C_1$-$C_6$ alkoxy, heterocycle, optionally substituted $C_1$-$C_6$ alkyl, $C_3$-$C_8$ cycloalkyl, CN, —O(aryl), $C_2$-$C_6$ alkynyl, $C(O)C_1$-$C_6$ alkyl, —O—$C_1$-$C_6$ haloalkyl, and optionally substituted aryl.

8. The compound according to claim 1, wherein $R^5$ is optionally substituted heteroaryl.

9. The compound according to claim 8, wherein $R^5$ is pyridine optionally substituted with one or more halogen.

10. The compound according to claim 1, wherein $R^5$ is benzo[d]dioxolane or tetrahydronaphthalene.

11. The compound according to claim 1, selected from the group consisting of:

$N^3$-(3-Chloro-4-fluorophenyl)furo[2,3-c]pyridine-2,3-diamine, $N^3$-Phenylfuro[2,3-c]pyridine-2,3-diamine, $N^3$-(2-Chlorophenyl)furo[2,3-c]pyridine-2,3-diamine, $N^3$-(4-Fluorophenyl)furo[2,3-c]pyridine-2,3-diamine, $N^3$-(4-(Trifluoromethyl)phenyl)furo[2,3-c]pyridine-2,3-diamine, $N^3$-(2,4-Dichlorophenyl)furo[2,3-c]pyridine-2,3-diamine, $N^3$-(3-Chlorophenyl)furo[2,3-c]pyridine-2,3-diamine, $N^3$-(4-Chloro-3-methoxyphenyl)furo[2,3-c]pyridine-2,3-diamine, $N^3$-(2-Bromo-4-fluorophenyl)furo[2,3-c]pyridine-2,3-diamine, $N^3$-(4-Morpholinophenyl)furo[2,3-c]pyridine-2,3-diamine, $N^3$-(2,4,5-Trifluorophenyl)furo[2,3-c]pyridine-2,3-diamine, $N^3$-(2,4,5-Trifluorophenyl)furo[2,3-c]pyridine-2,3-diamine, $N^3$-(3,4-Dimethylphenyl)furo[2,3-c]pyridine-2,3-diamine, $N^3$-(3,5-Dimethylphenyl)furo[2,3-c]pyridine-2,3-diamine, $N^3$-(3,4-Dichlorophenyl)furo[2,3-c]pyridine-2,3-diamine, $N^3$-(4-Bromophenyl)furo[2,3-c]pyridine-2,3-diamine, $N^3$-(4-Chloropheny)furo[2,3-c]pyridine-2,3-diamine, $N^3$-(3-Chloro-4-iodophenyl)furo[2,3-c]pyridine-2,3-diamine, $N^3$-(3-Ethylpheny)furo[2,3-c]pyridine-2,3-diamine, $N^3$-(3-Iodophenyl)furo[2,3-c]pyridine-2,3-diamine, $N^3$-(3-Bromo-4-methylphenyl)furo[2,3-c]pyridine-2,3-diamine, $N^3$-(3-Bromo-4,5-difluorophenyl)furo[2,3-c]pyridine-2,3-diamine, $N^3$-(4-Benzylphenyl)furo[2,3-c]pyridine-2,3-c diamine, $N^3$-(2-(Piperidin-1-yl)phenyl)furo[2,3-c]pyridine-2,3-diamine,
$N^3$-(5-Chloro-2-methoxyphenyl)furo[2,3-c]pyridine-2,3-diamine,
$N^3$-(3-(Trifluoromethyl)phenyl)furo[2,3-c]pyridine-2,3-diamine,
$N^3$-(4-Fluoro-3-methylphenyl)furo[2,3-c]pyridine-2,3-diamine,
3-((2-Aminofuro[2,3-c]pyridin-3-yl)amino)-2-fluorobenzonitrile,
$N^3$-(4-Phenoxyphenyl)furo[2,3-c]pyridine-2,3-diamine,
$N^3$-(2-Chloro-4-fluorophenyl)furo[2,3-c]pyridine-2,3-diamine,
$N^3$-(2,3,4-Trichlorophenyl)furo[2,3-c]pyridine-2,3-diamine,
$N^3$-(3,5-Di-tert-butylphenyl)furo[2,3-c]pyridine-2,3-diamine,
$N^3$-(3-Chloro-4-methylphenyl)furo[2,3-c]pyridine-2,3-diamine,
$N^3$-(2,4-Dimethoxyphenyl)furo[2,3-c]pyridine-2,3-diamine,
$N^3$-(4-Ethynylphenyl)furo[2,3-c]pyridine-2,3-diamine,
$N^3$-(3,5-Dimethoxyphenyl)furo[2,3-c]pyridine-2,3-diamine,
4-((2-Aminofuro[2,3-c]pyridin-3-yl)amino)benzonitrile,
$N^3$-(p-tolyl)Furo[2,3-c]pyridine-2,3-diamine,
1-(4-((2-Aminofuro[2,3-c]pyridin-3-yl)amino)phenyl)ethanone,
$N^3$-(3-Cyclopropylphenyl)furo[2,3-c]pyridine-2,3-diamine,
$N^3$-(3-Isopropylphenyl)furo[2,3-c]pyridine-2,3-diamine,
$N^3$-(3-Chloro-2,4-difluorophenyl)furo[2,3-c]pyridine-2,3-diamine,
$N^3$-(2,3-Dichloro-4-fluorophenyl)furo[2,3-c]pyridine-2,3-diamine,
$N^3$-(3-Fluorophenyl)furo[2,3-c]pyridine-2,3-diamine,
$N^3$-(3,5-Dichloro-4-fluorophenyl)furo[2,3-c]pyridine-2,3-diamine,
$N^3$-(m-tolyl)Furo[2,3-c]pyridine-2,3-diamine,
$N^3$-(4-(Trifluoromethoxy)phenyl)furo[2,3-c]pyridine-2,3-diamine,
$N^3$-(5-Chloro-2,4-difluorophenyl)furo[2,3-c]pyridine-2,3-diamine,
$N^3$-([1,1'-Biphenyl]-3-yl)furo[2,3-c]pyridine-2,3-diamine,
$N^3$-(2,4-Dimethylphenyl)furo[2,3-c]pyridine-2,3-diamine,
$N^3$-(2,5-Dichlorophenyl)furo[2,3-c]pyridine-2,3-diamine,
(2-Amino-3-((3-chloro-4-fluorophenyl)amino)-7-methylfuro[2,3-c]pyridin-4-yl)methanol,
4-Chloro-$N^3$-(3-chloro-4-fluorophenyl)furo[2,3-c]pyridine-2,3-diamine,
$N^3$-(3-Bromo-4-fluorophenyl)furo[2,3-c]pyridine-2,3-diamine,
$N^3$-(3,4-Difluorophenyl)furo[2,3-c]pyridine-2,3-diamine,
$N^3$-(4-Fluoro-3-(trifluoromethyl)phenyl)furo[2,3-c]pyridine-2,3-diamine,
$N^3$-(3-(tert-Butyl)phenyl)furo[2,3-c]pyridine-2,3-diamine,
$N^3$-(4-Fluoro-3-(trifluoromethoxy)phenyl)furo[2,3-c]pyridine-2,3-diamine,
$N^3$-(5,6,7,8-Tetrahydronaphthalen-1-yl)furo[2,3-c]pyridine-2,3-diamine,
$N^3$-(3-Chloro-4-fluorophenyl)-5-methoxyfuro[2,3-c]pyridine-2,3-diamine,
$N^3$-(3-(Difluoromethyl)phenyl)furo[2,3-c]pyridine-2,3-diamine,
$N^3$-(3-Chloro-4-fluorophenyl)-7-methylfuro[2,3-c]pyridine-2,3-diamine,
$N^3$-(3-Chloro-4-fluorophenyl)-4-methoxyfuro[2,3-c]pyridine-2,3-diamine,
$N^3$-(3-Ethynylphenyl)furo[2,3-c]pyridine 2,3diamine,
$N^3$-(3-(1,1-Difluoroethyl)-4-fluorophenyl)furo [2,3-c]pyridine-2,3-diamine,
$N^3$-(4-Chloro-3-methylphenyl)furo[2,3-c]pyridine-2,3-diamine,
$N^3$-(5,6,7,8-Tetrahydronaphthalen-2-yl)furo[2,3-c]-pyridine-2,3-diamine,
$N^3$-(3-Chloro-4-fluorophenyl)-4,7-dimethylfuro[2,3-c]pyridine-2,3-diamine,
$N^3$-(3-Chloro-4-fluorophenyl)-7-ethylfuro[2,3-c]pyridine-2,3-diamine,
7-Ethyl-$N^3$-(4-fluoro-3-(trifluoromethyl)phenyl)furo[2,3-c]pyridine-2,3-diamine,
$N^3$-(3-Benzylphenyl)furo[2,3-c]pyridine-2,3-diamine,
7-Ethyl-$N^3$-(3-(trifluoromethy)pheny)furo[2,3-c]pyridine-2,3-diamine
$N^3$-(3-Chloro-4-fluorophenyl)-7-propylfuro[2,3-c]pyridine-2,3-diamine,
7-Propyl-$N^3$-(3-(trifluoromethyl)phenyl)furo[2,3-c]pyridine-2,3-diamine,
$N^3$-(4-Fluoro-3-(trifluoromethyl)phenyl)-7-propylfuro[2,3-c]pyridine-2,3-diamine,
7-Methyl-$N^3$-(3-(trifluoromethyl)phenyl)furo[2,3-c]pyridine-2,3-diamine,
$N^3$-(3-Chloro-4-fluorophenyl)-7-phenylfuro[2,3-c]pyridine-2,3-diamine,
7-Phenyl-$N^3$-(3-(trifluoromethyl)phenyl)furo[2,3-c]pyridine-2,3-diamine,
$N^3$-(3-Chloro-4-fluorophenyl)-7-isopropylfuro[2,3-c]pyridine-2,3-diamine,
$N^3$-(3-(Cyclopropylmethyl)phenyl)furo[2,3-c]pyridine-2,3-diamine,
$N^3$-(3-Chloro-4fluorophenyl)-5-methoxy-7-methylfuro[2,3-c]pyridine-2,3-diamine,
7-Benzyl-$N^3$-(3-chloro-4-fluorophenyl)furo[2,3-c]pyridine-2,3-diamine,
$N^3$-(3-Chloro-5-methylphenyl)furo[2,3-c]pyridine-2,3-diamine,
$N^3$-(3-Cyclohexylphenyl)furo[2,3-c]pyridine-2,3-diamine,
$N^3$-(3-(Cyclobutylmethyl)phenyl)furo[2,3-c]pyridine-2,3-diamine,
$N^3$-(3-Chloro-4-fluorophenyl)-7-(3-methoxyphenyl)furo[2,3-c]pyridine-2,3-diamine,
$N^3$-(3-Chloro-4-fluorophenyl)-7-(4-chlorophenyl)furo[2,3-c]pyridine-2,3-diamine,
$N^3$-(3-Ethynylpheny)-7-phenylfuro[2,3-c]pyridine-2,3-diamine,
$N^3$-(3-ethynylphenyl)-7-methylfuro[2,3-c]pyridine-2,3-diamine,
$N^3$-(3-Chloro-4-fluorophenyl)-7-(pyridin-3-yl)furo[2,3-c]pyridine-2,3-diamine,
$N^3$-(3-Chloro-4-fluorophenyl)-7-(2-chlorophenyl)furo[2,3-c]pyridine-2,3-diamine,
7-Ethyl-$N^3$-(3-ethynylphenyl)furo[2,3-c]pyridine-2,3-diamine,
$N^3$-(3-Chloro-4-fluoropheny)-7-(pyridin-4-yl)furo[2,3-c]pyridine-2,3-diamine,
$N^3$-(3-Chloro-4-fluorophenyl)-7-(2-methoxyphenyl)furo[2,3-c]pyridine-2,3-diamine,
3-((2-Aminofuro[2,3-c]pyridin-3-yl)amino)benzonitrile, N³-(3-Chloro-4-fluorophenyl)-7-(3-chlorophenyl)furo[2,3-c]pyridine-2,3-diamine,
N³-(3-Chloro-4-fluorophenyl)-7-(4-methoxyphenyl)furo[2,3-c]pyridine-2,3-diamine,
5-Butoxy-N³-(3-chloro-4-fluorophenyl)-7-phenylfuro[2,3-c]pyridine-2,3-diamine,
2-Amino-3-((3-chloro-4-fluorophenyl)amino)furo[2,3-c]pyridine-7-carbonitrile,
N³-(3-Chloro-4-fluorophenyl)-5-phenoxy-7-phenylfuro[2,3-c]pyridine-2,3-diamine,
N³-(3-Chloro-4-fluorophenyl)-5-ethoxy-7-phenylfuro[2,3-c]pyridine-2,3-diamine,
5-(tert-Butoxy)-N³-(3-chloro-4-fluorophenyl)-7-phenylfuro[2,3-c]pyridine-2,3-diamine,
N³-(3-Chloro-4-fluorophenyl)-5-isopropoxy-7-phenylfuro[2,3-c]pyridine-2,3-diamine,
N³-(3-Chloro-4-fluorophenyl)-7-cyclohexylfuro[2,3-c]pyridine-2,3-diamine,
N³-(3-Chloro-4-fluorophenyl)-5-ethyl-7-phenylfuro[2,3-]pyridine-2,3-diamine,
N³-(3-Ethynyl-4-fluorophenyl)-7-phenylfuro[2,3-c]pyridine-2,3-diamine,
N³-(3-Ethynyl-4-fluorophenyl)-7-(pyridin-4-yl)furo[2,3-c]pyridine-2,3-diamine,
N³-(3-Chloro-4-fluorophenyl)-7-(pyridin-2-yl)furo[2,3-c]pyridine-2,3-diamine,
2-Amino-3-((3-chloro-4-fluorophenyl)amino)-7-(pyridine-2-yl)furo[2,3-c]pyridine-5-carbonitrile,
2-Amino-3-((3-chloro-4-fluorophenyl)amino)-7-phenylfuro[2,3-c]pyridine-5-carbonitrile,
N³-(3-Methoxy-5-methylphenyl)furo[2,3-c]pyridine-2,3-diamine,
2-Amino-3-((3-chloro-4-fluorophenyl)amino)furo[2,3-c]pyridine-7-carboxylic acid,
2-Amino-3-((3-chloro-4-fluorophenyl)amino)furo[2,3-c]pyridine-7-carboxamide,
N³-(3-Chloro-4-fluorophenyl)-N5, N5-dimethyl-7-phenylfuro[2,3-c]pyridine-2,3,5-triamine,
N³-(3-Cyclobutylphenyl)furo[2,3-c]pyridine-2,3-diamine,
N³-(3-Cyclopentylphenyl)furo[2,3-c]pyridine-2,3-diamine,
N³-(3-Chloro-4-fluorophenyl)-7-(trifluoromethyl)furo[2,3-c]pyridine-2,3-diamine,
N³-(3-Chloro-4-fluorophenyl)-7-phenoxyfuro[2,3-c]pyridine-2,3-diamine,
N³-(3-Chloro-4-fluorophenyl)-7-(pyridine-2-yloxy)furo[2,3-c]pyridine diamine,
N³-(3-Chloro-4-fluorophenyl)-N⁷-phenylfuro[2,3-c]pyridine-2,3,7-triamine,
N³-(3-Chloro-4-fluorophenyl)-N⁷-(pyridine-3-yl)furo[2,3-c]pyridine-2,3,7-triamine,
N³-(3-Chloro-4-fluorophenyl)-7-(phenylethynyl)furo[2,3-c]-pyridine-2,3-diamine,
N³-(3-Chloro-4-fluorophenyl)-5-(2-(dimethylamino)ethoxy)-7-(pyridine-2-yl)furo[2,3-c]pyridine-2,3-diamine,
N³-(3-Chloro-4-fluorophenyl)-5-(3-dimethylamino)ethoxy)-7-phenylfuro[2,3-c]pyridine-2,3-diamine,
N³-(3-Chloro-4-fluorophenyl)-7-(1-methyl-1H-pyrazol-5-yl)furo[2,3-c]pyridine-2,3-diamine,
N³-(3-Chloro-4-fluorophenyl)-7-(piperidin-1-yl)furo[2,3-c]pyridine-2,3-diamine,
N³-(3-Chloro-4-fluorophenyl)-7-(4-methylpiperazin-1-yl)furo[2,3-c]pyridine-2,3-diamine,
2-Amino-3-((3-chloro-4-fluorophenyl)amino)-N-phenylfuro[2,3-c]pyridine-7-carboxamide,
N³-(3-Chloro-4-fluorophenyl)-7-(4-fluorophenyl)furo[2,3-c]pyridine-2,3-diamine,
N³-(3-Chloro-4-fluorophenyl)-7-(1-methyl-1H-pyrazol-4-yl)furo[2,3-c]pyridine-2,3-diamine,
4-(2-Amino-3-((3-chloro-4-fluorophenyl)amino)furo[2,3-c]pyridin-7-yl)benzonitrile,
4-(2-Amino-3-((3-chloro-4-fluorophenyl)amino)furo[2,3-c]pyridin-7-yl)benzamide,
Methyl 4-(2-amino-3-((3-chloro-4-fluorophenyl)amino)furo[2,3-c]pyridin-7-yl)benzoate,
N³-(3-Chloro-4-fluorophenyl)-7-iodofuro[2,3-c]pyridine-2,3-diamine,
N³-(3-Chloro-4-fluorophenyl)-7-(2-morpholinopyridin-4-yl)furo[2,3-c]pyridine-2,3-diamine,
N³-(3-Chloro-4-fluorophenyl)-7-(2-methylpyridin-4-yl)furo[2,3-c]pyridine-2,3-diamine,
7-Bromo-N³-(3-chloro-4-fluorophenyl)furo[2,3-c]pyridine-2,3-diamine,
N³-(3-Chloro-4-fluorophenyl)-7-(2,6-dimethylpyridin-4-yl)furo[2,3-c]pyridine-2,3-diamine,
7-Chloro-N3-(3-chloro-4-fluorophenyl)furo[2,3-c]pyridine-2,3-diamine,
N³-(3-Chloro-4-fluorophenyl)-7-iodo-5-methoxyfuro[2,3-c]pyridine-2,3-diamine,
4-(2-Amino-3-((3-chloro-4-fluorophenyl)amino)furo[2,3-c]pyridin-7-yl)-N-(2-methoxyethyl)benzamide,
N³-(3-chloro-4-fluorophenyl)-7-(3,4-difluorophenyl)furo[2,3-c]pyridine-2,3-diamine,
N³-(3-Chloro-4-fluorophenyl)-7-(2,3,4-trifluorophenyl)furo[2,3-c]pyridine-2,3-diamine,
7-Bromo-N³-(3-chloro-4-fluorophenyl)-5-methoxyfuro[2,3-c]pyridine-2,3-diamine,
4-(2-Amino-3-((3-chloro-4-fluoropheny)amino)-5-methoxyfuro[2,3-c]pyridin-7-yl)benzonitrile,
N³-(3-chloro-4-fluorophenyl)-7-(4-fluorophenyl)-5-methoxyfuro[2,3-c]pyridine-2,3-diamine,
4-(2-amino-3-((3-chloro-4-fluorophenyl)amino)-5-methoxyfuro[2,3-c]pyridin-7-yl)benzamide,
N³-(3-chloro-4-fluorophenyl)-7-fluorofuro[2,3-c]pyridine-2,3-diamine,
5-Chloro-N³-(3-chloro-4-fluorophenyl)furo[2,3-c]pyridine-2,3-diamine,
N³-(3-Chloro-4-fluorophenyl)-5-fluoro-7-(pyridin-4-yl)furo[2,3-c]pyridine-2,3-diamine,
N³-(3-chloro-4-fluorophenyl)-5-fluorofuro[2,3-c]pyridine-2,3-diamine,
2-Amino-3-((2-chlorophenyl)amino)furo[2,3-c]pyridine-7-carbonitrile,
2-Amino-3-((4-fluoro-3-(trifluoromethyl)phenyl)amino)furo[2,3-c]pyridine-7-carbonitrile,
N³(3,4-difluorophenyl)-7-(pyridin-4-yl)furo[2,3-c]pyridine-2,3-diamine,
2-Amino-3-((3,4-difluorophenyl)amino)furo[2,3-c]pyridine-7-carbonitrile,
2-Amino-3-((3,5-difluorophenyl)amino)furo[2,3-c]pyridine-7-carbonitrile,
N³-(3,5-Difluorophenyl)-7-(pyridin-4-yl)furo[2,3-c]pyridine-2,3-diamine,
N³-(3,4-Difluorophenyl)-5-fluoro-7-(pyridin-4-yl)furo[2,3-c]pyridine-2,3-diamine,
7-Fluoro-N³-(4-fluoro-3-(trifluoromethyl)phenyl)furo[2,3-c]pyridine-2,3-diamine,
N³-(3-Chloro-4-fluorophenyl)-5,7-difluorofuro[2,3-c]pyridine-2,3-diamine,
N³-(3-Chloro-4-fluorophenyl)-7-(2,6-difluoropyridin-4-yl)furo[2,3-c]pyridine-2,3-diamine, N³-(4-Fluoro-3-(trifluoromethyl)phenyl)-7-(pyridin-4-yl)furo[2,3-c]pyridine-2,3-diamine,
4-(2-Amino-3-((3-chloro-4-fluorophenyl)amino)furo[2,3-c]pyridin-7-yl)-N-methylpicolinamide,
N³-(3,4-Difluorophenyl)-7-(2-methoxyphenyl)furo[2,3-c]pyridine-2,3-diamine,
7-(2-Chlorophenyl)-N³-(3,4-difluorophenyl)furo[2,3-c]pyridine-2,3-diamine,
N³-(3,4-Difluorophenyl)-7-(2methylpyridin-4-yl)furo[2,3-c]pyridine-2,3-diamine,
N³-(3-Chloro-4-fluorophenyl)-7-(3-(trifluoromethyl)phenyl)furo[2,3-c]pyridine-2,3-diamine,
N³-(3-Chloro-4-fluorophenyl)-N7,N7-diphenylfuro[2,3-c]pyridine-2,3,7-triamine,
N³-(4-Fluorophenyl)-7-(pyridin-4-yl)furo[2,3-c]pyridine-2,3-diamine,
N³-(2-Chlorophenyl)-7-(pyridin-4-yl)furo[2,3-c]pyridine-2,3-diamine,
7-(Pyridin-4-yl)-N³-(3-trifluoromethyl)phenyl)furo[2,3-c]pyridine-2,3-diamine,
N³-(3-Chloro-4-fluorophenyl)-7-(naphthalen-1-yl)furo[2,3-c]pyridne-2,3-diamine,
N³-(4-fluoro-3-trifluoromethyl)phenyl)-7-(2-methylpyridin-4-yl)furo[2,3-c]pyridine-2,3-diamine,
N³-(2-chlorophenyl)-7-(2-methylpyridin-4-yl)furo[2,3-c]pyridine-2,3-diamine,
7-(2-methylpyridin-4-yl)-N³-(3-(trifluoromethyl)phenyl)furo[2,3-c]pyridine-2,3-diamine,
N³-(4-fluorophenyl)-7-(2-methylpyridin-4-yl)furo[2,3-c]pyridine-2,3-diamine,
N³-(3,4-difluorophenyl)-5-fluorofuro[2,3-c]pyridine-2,3-diamine,
N³-(3-Chlorophenyl)-7-(pyridin-4-yl)furo[2,3-c]pyridine-2,3-diamine,
N³-(2-Chlorophenyl)-5-fluorofuro[2,3-c]pyridine-2,3-diamine,
4-(2-Amino-3-((2-chlorophenyl)amino)furo[2,3-c]pyridin-7-yl)-N-methylpicolinamide,
N³-(3-Chlorophenyl)-5-fuorofuro[2,3-c]pyridine-2,3-diamine,
5-Fluoro-N³-(3-(trifluoromethyl)phenyl)furo[2,3-c]pyridine-2,3-diamine,
5-Fluoro-N³-(4-fluoro-3-(trifluoromethyl)phenyl)furo[2,3-c]pyridine-2,3-diamine,
4-(2-Amino-3-((3,4-difluorophenyl)amino)furo[2,3-c]pyridin-7-yl)-N-methylpicolinamide,
4-(2-Amino-3-((4-fluorophenyl)amino)furo[2,3-c]pyridin-7-yl)-N-methylpicolinamide,
4-(2-Amino-3-((3-chlorophenyl)amino)furo[2,3-c]pyridin-7-yl)-N-methylpicolinamide,
4-(2-Amino-3-((3-(trifluoromethyl)phenyl)amino)furo[2,3-c]pyridin-7-yl)-N-methylpicolinamde,
4-(2-amino-3-((4-fluoro-3-(trifluoromethyl)phenyl)amino)furo[2,3-c]pyridin-7-yl)-N-methypicolinamide,
5-Fluoro-N³-(4-fluorophenyl)furo[2,3-c]pyridine-2,3-diamine,
N³-(3-Chloro-4-fluorophenyl)-7-(2-methoxypyridin-4-yl)furo[2,3-c]pyridine-2,3-diamine,
N³-(3-Chlorophenyl)-7-(2-methylpyridin-4-yl)furo[2,3-c]pyridine-2,3-diamine,
7-(2-Methylpyridin-4-yl)-N3-phenylfuro[2,3-c]pyridine-2,3-diamine,
5-Fluoro-N³-(4-fluorophenyl)-7-(2-methylpyridin-4-yl)furo[2,3]pyridne-2,3-diamine,
7-(2-Methylpyridin-4-yl)-N³-(2-(piperidin-1-yl)phenyl)furo[2,3-c]pyridine-2,3-diamine,
N³-(3-Fluorophenyl)-7-(2-methylpyridin-4-yl)furo[2,3-c]pyridine-2,3-diamine,
N³-(3-Chloro-4-fluorophenyl)-5-fluoro-7-(2-methylpyridin-4-yl)furo[2,3-c]pyridine-2,3-diamine,
N³-(3-Chloro-4-fluorophenyl)-7-morpholinofuro[2,3-c]pyridine-2,3-diamine,
N³-(3,4-Difluorophenyl)-5-fluoro-7-(2-methylpyridin-4-yl)furo[2,3-c]pyridine-2,3-diamine,
N³-(3-Chloro-4-fluorophenyl)-7-(naphthalen-2-yl)furo[2,3-c]pyridine-2,3-diamine,
4-(2-Amino-3-((3-chloro-4-fluorophenyl)amino)furo[2,3-c]pyridin-7-yl)-N-phenylpicolinamide,
4-(2-Amino-3-((3-chloro-4-fluorophenyl)amino)furo[2,3-c]pyridin-7-yl)-N-butylpicolinamide,
4-(2-Amino-3-((3-chloro-4-fluorophenyl)amino)furo[2,3-c]pyridin-7-yl)-N-(tert-butyl)picolinamide,
4-(2-Amino-3-((3-chloro-4-fluorophenyl)amino)furo[2,3-c]pyridin-7-yl)-N-isobutylpicolinamide,
4-(2-Amino-3-((3-chloro-4-fluorophenyl)amino)furo[2,3-c]pyridin-7-yl)-N-propylpicolinamide,
N³-(3-Chlorophenyl)-5-fuoro-7-(2-methylpyridin-4-yl)furo[2,3-c]pyridine-2,3-diamine,
N³-(2,4-Difluorophenyl)-7-(2-methylpyridin-4-yl)furo[2,3-c]pyridine-2,3-diamine,
4-(2-Amino-3-((3-chloro-4-fluorophenyl)amino)furo[2,3-c]pyridin-7-yl)-N-cyclohexylpicolinamide,
N³-(3-Chloro-4-fluorophenyl)-7-(3,5-dichlorophenyl)furo[2,3-c]pyridine-2,3-diamine,
7-(2-(tert-Butyl)pyridin-4-yl)-N³-(3-chloro-4-fluorophenyl)furo[2,3-c]pyridine-2,3-diamine,
7-(Benzo[d][1,3]dioxol-5-yl)-N3-(3-chloro-4-fluorophenyl)furo[2,3-c]pyridine-2,3-diamine,
N³-(3-Chloro-4-fluorophenyl)-7-(2-ethylpyridin-4-yl)furo[2,3-c]pyridine-2,3-diamine,
N³-(5-Chloro-2-fluorophenyl)-7-(2-methylpyridin-4-yl)furo[2,3-c]pyridine-2,3-diamine,
N³-(3-Chloro-2-fluorophenyl)-7-(2-methylpyridin-4-yl)furo[2,3-c]pyridine-2,3-diamine
N³-(3-Chloro-4-fluorophenyl)-5-methyl-7-(2-methylpyridin-4-yl)furo[2,3-c]pyridine-2,3-diamine,
N³-(3-Chloro-4-fluorophnenyl)-7-(2-(trifluoromethyl)pyridin-4-yl)furo[2,3-c]pyridine-2,3-diamine,
(4-(2-Amino-3-((3-chloro-4-fluorophenyl)amino)furo[2,3-c]pyridin-7-yl)pyridin-2-yl)(piperidin-1-yl)methanone,
(4-(2-Amino-3-((3-chloro-4-fluorophenyl)amino)furo[2,3-c]pyridin-7-yl)pyridin-2-yl)(morpholino)methanone,
4-(2-Amino-3-((3-chloro-4-fluorophenyl)amino)furo[2,3-c]pyridin-7-yl)-N-(pyridin-2-yl)picolinamide, 4-(2-Amino-3-((3-chloro-4-fluorophenyl)amino)furo[2,3-c]pyridin-7-yl)-N-(2-morpholinoethy)picolinamide,
4-(2-Amino-3-((3-chloro-4-flurophenyl)amino)furo[2,3-c]pyridin-7-yl)-N-pentylpicolinamide,
N³-(3-Chloro-4-fluorophenyl)-7-(2-chloro-5-fluorophenyl)furo[2,3-c]pyridine-2,3-diamine,
N³-(3-Chloro-4-fluorophenyl)-7-(3,5-dimethylphenyl)furo[2,3-c]pyridine-2,3-diamine,
N³-(3-Chloro-4-fluorophenyl)-7-(3,5-difluorophenyl)furo[2,3-c]pyridine-2,3-diamine,
N³-(3-Chloro-4-fluorophenyl)-7-styrylfuro[2,3-c]pyridine-2,3-diamine,
N³-(3-Bromo-4-methylphenyl)-7-(2-methylpyridin-4-yl)furo[2,3-c]pyridine-2,3-diamine,
N³-([1,1'-Biphenyl]-3-yl)-7-(2-methylpyridin-4-yl)furo[2,3-c]pyridine-2,3-diamine,
N³-(3-Bromo-4-fluorophenyl)-7-(2-methylpyridin-4-yl)furo[2,3-c]pyridine-2,3-diamine, N³-((3-(1,1-Difluoroethyl)-4-fluorophenyl)-7-(2-methylpyridin-4-yl)furo[2,3-c]pyridine-2,3-diamine,
N³-(3-Chloro-2,4-difluorophenyl)-7-(2-methylpyridin-4-yl)furo[2,3-c]pyridine-2,3-diamine,
7-(2-Methylpyridin-4-yl)-N³-(4-(trifluoromethyl)phenyl)furo[2,3-c]pyridine-2,3-diamine,
7-(2-Methylpyridin-4-yl)-N³-(4-(trifluoromethoxy)phenyl)furo[2,3-c]pyridine-2,3-diamine,
N³-(4-Fluoro-3-(trifluoromethoxy)phenyl)-7-(2-methylpyridin-4-yl)furo[2,3-c]pyridine-2,3-diamine,
N³-(3-(Difluoromethyl)phenyl)-7-(2-methylpyridin-4-yl)furo[2,3-c]pyridine-2,3-diamine,
3-((2-Amino-7-(2-methylpyridin-4-yl)furo[2,3-c]pyridin-3-yl)amino)benzonitrile,
N³-(4-Chlorophenyl-7-(2-methylpyridin-4-yl)furo[2,3-c]pyridine-2,3-diamine,
N³-Hexyl-7-(2-methylpyridin-4-yl)furo[2,3-c]pyridine-2,3-diamine,
N³-Benzyl-7-(2-methylpyridin-4-yl)furo[2,3-c]pyridine-2,3-diamine,
N³-Cyclohexyl-7-(2-methylpyridin-4-yl)furo[2,3-c]pyridine-2,3-diamine,
7-(2-Methylpyridin-4-yl)-N³-(tetrahydro-2H-pyran-4-yl)furo[2,3-c]pyridine-2,3-diamine,
7-(2-Methylpyridin-4-yl)-N³-((tetrahydro-2H-pyran-4-yl)methyl)furo[2,3-c]pyridine-2,3-diamine,
(E)-N³-(4-Fluorophenyl)-7-styrylfuro[2,3-c]pyridine-2,3-diamine,
(E)-N³-(3,4-Difluorophenyl)-7-styrylfuro[2,3-c]pyridine-2,3-diamine,
(E)-N³-(4-Fluoro-3-(trifluoromethyl)phenyl)-7-styrylfuro[2,3-c]pyridine-2,3-diamine,
2-Amino-3-((3,4-difluorophenyl)amino)-N-methylfuro[2,3-c]pyridine-7-carboxamide,
7-(Aminomethyl)-N³-(3-chlorophenyl)furo[2,3-c]pyridine-2,3-diamine,
2-Amino-3-((3-chloro-4-fluorophenyl)amino)furo[2,3-c]pyridin-7-yl acetate,
N-(2-Amino-3-((3-chloro-4-fluorophenyl)amino)furo[2,3-c]pyridin-7-yl)acetamide,
N³-(2-Chlorophenyl)-7-(piperidin-4-ylmethyl)furo[2,3-c]pyridine-2,3-diamine,
N³-(3,4-Difluorophenyl)7-(pyridin-4-ylmethyl)furo[2,3-c]pyridine-2,3-diamine,
(2-Amino-3-((3,4-difluorophenyl)amino)furo[2,3-c]pyridin-7-yl)methanol,
N³-(3-Chlorophenyl)-7-(trifluoromethyl)furo[2,3-c]pyridine-2,3-diamine,
N³-(3-Chloro-4-fluorophenyl)-7-(cyclohexyloxy)furo[2,3-c]pyridine-2,3-diamine,
N³-(3,4-Difluorophenyl)-7-((tetrahydro-2H-pyran-4-yl)oxy)furo[2,3-c]pyridine-2,3-diamine,
2-Amino-3-((3-chloro-4-fluorophenyl)amino)-N-methylfuro[2,3-c]pyridine-7-sulfonamide,
2-Amino-3-((3,4-difluorophenyl)amino)-N-phenylfuro[2,3-c]pyridine-7-sulfonamide,
N³-(4-Fluorophenyl)-5-(trifluoromethyl)furo[2,3-c]pyridine-2,3-diamine,
N³-(2-Chlorophenyl)-5-(trifluoromethoxy)furo[2,3-c]pyridine-2,3-diamine,
2-Amino-3-((3-chloro-4-fluorophenyl)amino)-7-(2-methylpyridin-4-yl)furo[2,3-c]pyridine-5-carbonitrile,
4-(2-Amino-3-((3-chloro-4-fluorophenyl)amino)furo[2,3-c]pyridin-7-yl)-N,N-dimethylpicolinamide,
4-(2-Amino-3-((3-chloro-4-fluorophenyl)amino)furo[2,3-c]pyridin-7-yl)-N-ethylpicolinamide,
4-(2-Amino-3-((3-chloro-4-fluorophenyl)amino)furo[2,3-c]pyridin-7-yl)-N-isopropylpicolinamide,
4-(2-Amino-3-((3-chloro-4-fluorophenyl)amino)furo[2,3-c]pyridin-7-yl)-N-(2-methoxyethyl)picolinamide,
N-(3-(1H-Imidazol-1-yl)propyl)-4-(2-amino-3-((3-chloro-4-fluorophenyl)amino)furo[2,3-c]pyridin-7-yl)picolinamide,
4-(2-Amino-3-((3-chloro-4-fluorophenyl)amino)furo[2,3-c]pyridin-7-yl)-N-(pyridin-3-yl)picolinamide,
4-(2-Amino-3-((3-chloro-4-fluorophenyl)amino)furo[2,3-c]pyridin-7-yl)-N-(pyridin-4-yl)picolinamide,
4-(2-Amino-3-((3-chloro-4-fluorophenyl)amino)furo[2,3-c]pyridin-7-yl)-N-(4-methylpiperazin-1-yl)picolinamide,
2-Amino-3-((3-chloro-4-fluorophenyl)amino)-7-(2-methylpyridin-4-yl)furo[2,3-c]pyridin-5-ol,
N³-(3-chlorophenyl)-7-(2-fluoropyridin-4-yl)furo[2,3-c]pyridine-2,3-diamine,
N³-(3-Fluorophenyl)-7-(2-fluoropyridin-4-yl)furo[2,3-c]pyridine-2,3-diamine,
N³-(3,4-Difluorophenyl)-7-(2-fluoropyridin-4-yl)furo[2,3-c]pryidine-2,3-diamine,
N³-(4-Fluorophenyl)-7-(2-fluoropyridin-4-yl)furo[2,3-c]pyridine-2,3-diamine,
N³-(3-Chloro-4-fluorophenyl)-7-(4-methylpyrimidin-2-yl)furo[2,3-c]pyridine-2,3-diamine,
N³-(3-Chloro-4-fluorophenyl)-7-(imidazo[1,2-a]pyridin-5-yl)furo[2,3-c]pyridine-2,3-diamine,
N³-(3-Chloro-4-fluorophenyl)-7-(imidazo[1,2-a]pyridin-2-yl)furo[2,3-c]pyridine-2,3-diamine,
4-(2-Amino-3-((3-chloro-4-fluorophenyl)amino)furo[2,3-c]pyridin-7-yl)-N-methyl-1H-imidazole-1-carboxamide,
N³-(3-Chlorophenyl)-7-(2,6-difluoropyridin-4-yl)furo[2,3-c]pyridine-2,3-diamine,
N³-(3,4-Difluorophenyl)-7-(2,6-difluoropyridin-4-yl)furo[2,3-c]pyridine-2,3-diamine,
7-(2,6-Difluoropyridin-4-yl)-N3-(4-fluorophenyl)furo[2,3-c]pyridine-2,3-diamine,
N³-(5-chloro-2-fluorophenyl)-7-(2,6-difluoropyridin-4-yl)furo[2,3-c]pyridine-2,3-diamine,
N³-(3,4-Difluorophenyl)-7-(4-(methoxymethyl)phenyl)furo[2,3-c]pyridine-2,3-diamine,
7-(2-Chloro-6-fluorophenyl)-N3-(3,4-difluorophenyl)furo[2,3-c]pyridine-2,3-diamine,
N-(4-(2-Amino-3-((3,4-difluorophenyl)amino)furo[2,3-c]pyridin-7-yl)phenyl)pyrrolidine-1 carboxamide,
N³-(3,4-Difluorophenyl)-7-(4-fluoro-2-methylphenyl)furo[2,3-c]pyridine-2,3-diamine,
N³-(3,4-Difluorophenyl)-7-(4-propoxyphenyl)furo[2,3-c]pyridine-2,3-diamine,
N³-(3,4-Difluorophenyl)-7-(4-morpholinophenyl)furo[2,3-c]pyridine-2,3-diamine,
5-(2-Amino-3-((3-chloro-4-fluorophenyl)amino)furo[2,3-c]pyridin-7-yl)-2-fluorophenol,
Methyl 5-(2-amino-3-((3-chloro-4-fluorophenyl)amino)furo[2,3-c]pyridin-7-yl)-2-chlorobenzoate,
3-(2-Amino-3-((3-chloro-4-fluorophenyl)amino)furo[2,3-c]pyridin-7-yl)-N-methylbenzamide,
4-(4-(2-Amino-3-((3-chloro-4-fluorophenyl)amino)furo[2,3-c]pyridin-7-yl)picolinamido)butanoic acid,
7-(2,6-Difluoropyridin-4-yl)-N³-(4-(trifluoromethyl)phenyl)furo[2,3-c]pyridine-2,3-diamine,
7-(2-Fluoropyridin-4-yl)-N³-(4-(trifluoromethyl)phenyl)furo[2,3-c]pyridine-2,3-diamine,
5-Fluoro-7-(2-methylpyridin-4-yl)-N3-(4-(trifluoromethyl)phenyl)furo[2,3-c]pyridine-2,3diamine, 4-(2-Amino-3-((4-(trifluoromethyl)phenyl)amino)furo[2,3-c]pyridin-7-yl)-N-methylpicolinamide, 4-(2-Amino-5-fluoro-3-((4-(trifluoromethyl)phenyl)amino)furo[2,3-c]pyridin-7-yl)-N-methylpicolinamide, 4-(2-Amino-3-((3-chloro-4-fluorophenyl)amino)-5-fluorofuro[2,3-c]pyridin-7-yl)-N-methylpicolinamide, 5-Fluoro-$N^3$-(4-(trifluoromethyl)phenyl)furo[2,3-c]pyridine-2,3-diamine, 7-(2,6-Difluoropyridin-4-yl)-$N^3$-(3-fluorophenyl)furo[2,3-c]pyridine-2,3-diamine, $N^3$-(2,5-Difluorophenyl)-7-(2,6-difluoropyridin-4-yl)furo[2,3-c]pyridine-2,3-diamine, 4-(2-Amino-3-((3-chloro-4-fluorophenyl)amino)furo[2,3-c]pyridin-7-yl)-N-(2-hydroxyethy)picolinamide, 4-(2-Amino-3-((3-chloro-4-fluorophenyl)amino)furo[2,3-c]pyridin-7-yl)-N,N diethylpicolinamide, and $N^3$-(3-Chloro-4-fluorophenyl)-7-(2,3-dichlorophenyl)furo[2,3-c]pyridine-2,3-diamine, or a pharmaceutically acceptable salt thereof.

12. A pharmaceutical composition, comprising a compound of claim 1, or a pharmaceutically acceptable salt thereof, and a pharmaceutically acceptable carrier.

\* \* \* \* \*

UNITED STATES PATENT AND TRADEMARK OFFICE
CERTIFICATE OF CORRECTION

PATENT NO. : 10,294,212 B2
APPLICATION NO. : 15/724596
DATED : May 21, 2019
INVENTOR(S) : Monali Banerjee et al.

It is certified that error appears in the above-identified patent and that said Letters Patent is hereby corrected as shown below:

In the Claims

At Column 419, Line 26, Claim 1 "heterocyclyl(alakyl)" should be replaced with "heterocyclyl(alkyl)."

At Column 420, Line 58, Claim 11 "N3-(4-Chloropheny)" should be replaced with "N3-(4-Chlorophenyl)."

At Column 420, Line 61, Claim 11 "N3-(3-Ethylpheny)" should be replaced with "N3-(3-Ethylphenyl)."

At Column 422, Line 21, Claim 11 "7-Ethyl-N3-(3-(trifluoromethy)pheny)" should be replaced with "7-Ethyl-N3-(3-(trifluoromethyl)phenyl)."

At Column 422, Line 63, Claim 11 "N3-(3-Chloro-4-fluoropheny)" should be replaced with "N3-(3-Chloro-4-fluorophenyl)."

At Column 423, Lines 19-20, Claim 11 "phenylfuro[2,3-]pyridine" should be replaced with "phenylfuro[2,3-c]pyridine."

At Column 424, Line 34, Claim 11 "4-(2-Amino-3-((3-chloro-4-fluoropheny)" should be replaced with "4-(2-Amino-3-((3-chloro-4-fluorophenyl)."

At Column 429, Line 14, Claim 11 "N-(2-hydroxyethy)" should be replaced with "N-(2-hydroxyethyl)."

Signed and Sealed this
Thirteenth Day of August, 2019

Andrei Iancu
*Director of the United States Patent and Trademark Office*